United States Patent
Olhava et al.

(10) Patent No.: US 9,096,634 B2
(45) Date of Patent: *Aug. 4, 2015

(54) SUBSTITUTED PURINE AND 7-DEAZAPURINE COMPOUNDS

(71) Applicant: Epizyme, Inc., Cambridge, MA (US)

(72) Inventors: Edward J. Olhava, Newton, MA (US); Richard Chesworth, Concord, MA (US); Kevin W. Kuntz, Woburn, MA (US); Victoria M. Richon, Wellesley, MA (US); Roy M. Pollock, Medford, MA (US); Scott R. Daigle, Newburyport, MA (US)

(73) Assignee: Epizyme, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/055,510

(22) Filed: Oct. 16, 2013

(65) Prior Publication Data

US 2014/0051654 A1 Feb. 20, 2014

Related U.S. Application Data

(63) Continuation of application No. 13/310,157, filed on Dec. 2, 2011, now Pat. No. 8,580,762.

(60) Provisional application No. 61/419,661, filed on Dec. 3, 2010.

(51) Int. Cl.
C07H 19/16 (2006.01)
C07H 19/14 (2006.01)
C07D 473/34 (2006.01)
C07D 487/04 (2006.01)

(52) U.S. Cl.
CPC ............. *C07H 19/16* (2013.01); *C07D 473/34* (2013.01); *C07D 487/04* (2013.01); *C07H 19/14* (2013.01)

(58) Field of Classification Search
None
See application file for complete search history.

(56) References Cited

U.S. PATENT DOCUMENTS

| 7,576,069 B2 | 8/2009 | Rieger et al. | |
| 8,580,762 B2 * | 11/2013 | Olhava et al. | 514/46 |
| 2004/0147464 A1 | 7/2004 | Roberts et al. | |
| 2006/0040889 A1 | 2/2006 | Rieger et al. | |
| 2006/0189636 A1 | 8/2006 | Critchley et al. | |
| 2006/0235037 A1 | 10/2006 | Purandare et al. | |
| 2007/0191293 A1 | 8/2007 | Langston et al. | |
| 2008/0064653 A1 | 3/2008 | Li et al. | |
| 2008/0132525 A1 | 6/2008 | Wahhab et al. | |
| 2009/0105476 A1 | 4/2009 | Fairhurst et al. | |
| 2010/0144655 A1 | 6/2010 | Chen et al. | |
| 2012/0122895 A1 | 5/2012 | Jiang et al. | |
| 2015/0011495 A1 | 1/2015 | Olhava et al. | |

FOREIGN PATENT DOCUMENTS

| CN | 102066372 A | 5/2011 |
| EP | 1138688 A1 | 10/2001 |
| EP | 2208721 A1 | 7/2010 |
| WO | WO-0172764 A1 | 10/2001 |
| WO | WO-0177075 A2 | 10/2001 |
| WO | WO-02100152 A2 | 12/2002 |
| WO | WO-03074083 A1 | 9/2003 |
| WO | WO-2004007512 A2 | 1/2004 |
| WO | WO-2004022572 A1 | 3/2004 |
| WO | WO-2006015357 A2 | 2/2006 |
| WO | WO 2006/028618 A1 | 3/2006 |
| WO | WO-2006078752 A2 | 7/2006 |
| WO | WO-2006113615 A2 | 10/2006 |
| WO | WO-2007100304 A1 | 9/2007 |
| WO | WO-2008124150 A1 | 10/2008 |
| WO | WO-2009089425 A1 | 7/2009 |
| WO | WO-2010027005 A1 | 3/2010 |
| WO | WO-2010048149 A2 | 4/2010 |
| WO | WO-2012075492 A2 | 6/2012 |
| WO | WO-2012075500 A2 | 6/2012 |
| WO | WO-2012082436 A2 | 6/2012 |

OTHER PUBLICATIONS

Daigle et al. "Selective Killing of Mixed Lineage Leukemia Cells by a Potent Small-Molecule DOT1L Inhibitor." *Cancer Cell*. 20(2011):53-65.

Gao and Liu, "DOT1: A distinct class of histone lysine methyltransferase", *Hereditas*, 29(12):1449-1454 (2007).

* cited by examiner

*Primary Examiner* — Traviss C McIntosh, III

(74) *Attorney, Agent, or Firm* — Cooley LLP; Heidi A. Erlacher; Lian Ouyang

(57) ABSTRACT

The present invention relates to substituted purine and 7-deazapurine compounds. The present invention also relates to pharmaceutical compositions containing these compounds and methods of treating disorders in which DOT1-mediated protein methylation plays a part, such as cancer and neurological disorders, by administering these compounds and pharmaceutical compositions to subjects in need thereof.

20 Claims, 3 Drawing Sheets

SUBSTITUTED PURINE AND 7-DEAZAPURINE COMPOUNDS

CROSS-REFERENCE TO RELATED APPLICATION

This application is a continuation of U.S. application Ser. No. 13/310,157, filed Dec. 2, 2011, now allowed, which claims priority to, and the benefit of, U.S. provisional application No. 61/419,661, filed Dec. 3, 2010, the contents of each of which are incorporated herein by reference in their entireties.

BACKGROUND OF THE INVENTION

In eukaryotic cells, DNA is packaged with histones to form chromatin. Approximately 150 base pairs of DNA are wrapped twice around an octamer of histones (two each of histones 2A, 2B, 3, and 4) to form a nucleosome, the basic unit of chromatin. Changes in the ordered structure of chromatin can lead to alterations in transcription of associated genes. This process is highly controlled because changes in gene expression patterns can profoundly affect fundamental cellular processes such as differentiation, proliferation, and apoptosis. Control of changes in chromatin structure (and hence of transcription) is mediated by covalent modifications to histones, most notably of their N-terminal tails. These modifications are often referred to as epigenetic because they can lead to heritable changes in gene expression, but do not affect the sequence of the DNA itself. Covalent modifications (for example, methylation, acetylation, phosphorylation, and ubiquitination) of the side chains of amino acids are enzymatically mediated.

The selective addition of methyl groups to specific amino acid sites on histones is controlled by the action of a unique family of enzymes known as histone methyltransferases (HMTs). The level of expression of a particular gene is influenced by the presence or absence of a methyl group at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species and still other enzymes can remove these species to provide temporal control of gene expression.

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion. Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease) and cardiovascular diseases. Therefore, selectively modulating the aberrant action of epigenetic enzymes holds great promise for the treatment of a range of diseases.

There is an ongoing need for new agents which modulate the aberrant action of epigenetic enzymes. The present invention provides compounds that meet this need.

SUMMARY OF THE INVENTION

The invention provides compounds useful for modulating the aberrant action of epigenetic enzymes. The present invention also provides pharmaceutically acceptable salts, esters, and/or N-oxides, of these compounds.

In one aspect, the present invention features a substituted purine or 7-deazapurine compound of Formula (I) below or a pharmaceutically acceptable salt or ester thereof

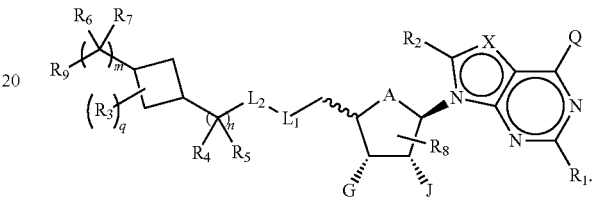

(I)

In this formula,
A is O or $CH_2$;
each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

Q is H, $NH_2$, $NHR_b$, $NR_bR_c$, $R_b$, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

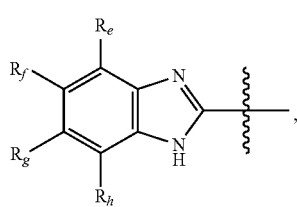,

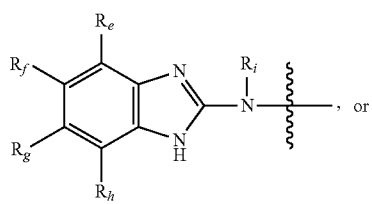, or

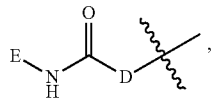, in which each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_i$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

q is 0, 1, 2, 3, or 4;
m is 0, 1, or 2; and
n is 0, 1, or 2.

One subset of the compounds of Formula (I) includes those of Formula (II):

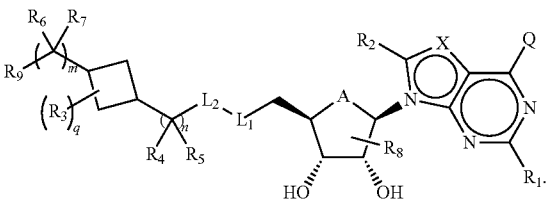

(II)

Another subset of the compounds of Formula (I) includes those of Formula (IIIa), (IIIb) or (IIIc):

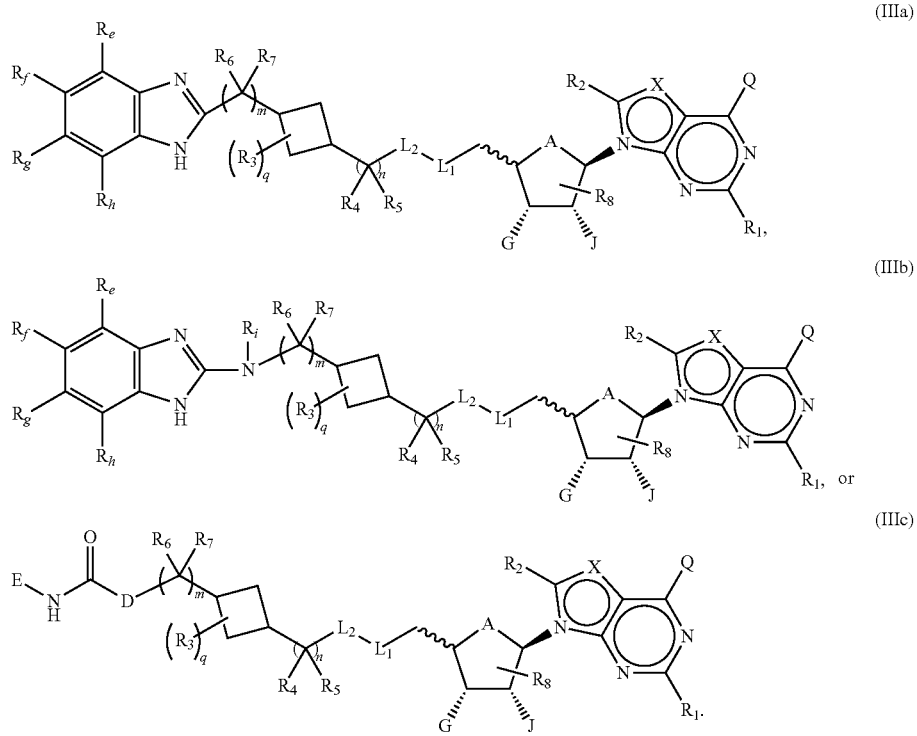

The compounds of Formulae (I), (II), (IIIa), (IIIb), (IIIc) and (IV) can include one or more of the following features.

The sum of m and n is at least 1.

m is 1 or 2 and n is O.

m is 2 and n is O.

A is $CH_2$.

A is O.

$L_1$ is N(Y).

$L_1$ is SO or $SO_2$.

Y is $R_d$.

$R_d$ is $C_1$-$C_6$ alkyl.

$L_2$ is absent.

At least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-Pr, t-Bu, and $CF_3$).

$R_i$ is H or $C_1$-$C_6$ alkyl.

$R_9$ is

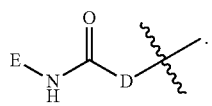

D is O.

D is $NR_j$, e.g., NH.

D is $CR_jR_k$, e.g., $CH_2$, $CHCH_3$, or $C(CH_3)_2$.

E is -$M_3$-$T_3$, in which $M_3$ is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl.

$T_3$ is phenyl optionally substituted with one or more substituents selected from the group consisting of halo, hydroxyl, carboxyl, cyano, nitro, $C_1$-$C_6$ alkyl, $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl, and $C_6$-$C_{10}$ aryloxyl, and $C_7$-$C_{14}$ alkylaryl.

X is N.

X is $CR_x$, e.g., CH.

Q is $NH_2$ or $NHR_b$, in which $R_b$ is -$M_1$-$T_1$, $M_1$ being a bond or $C_1$-$C_6$ alkyl linker and $T_1$ being $C_3$-$C_8$ cycloalkyl.

Q is H.

$R_9$ is

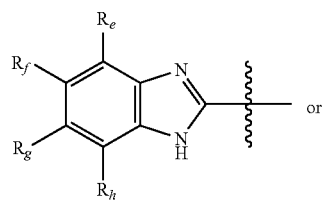

-continued

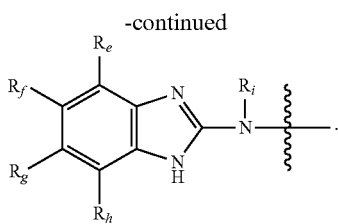

At least one of $R_e$, $R_f$, $R_g$, and $R_h$ is selected from the group consisting of F, Cl, $CF_3$, $OCF_3$, $SO_2CF_3$, $C_1$-$C_4$ alkyl, and $C_1$-$C_4$ alkoxyl.

$R_1$, $R_2$, $R_3$, $R_4$, $R_5$, $R_6$, $R_7$, and $R_8$ are each H.

The invention also relates to a compound of Formula (IV) or its N-oxide or a pharmaceutically acceptable salt thereof:

(IV)

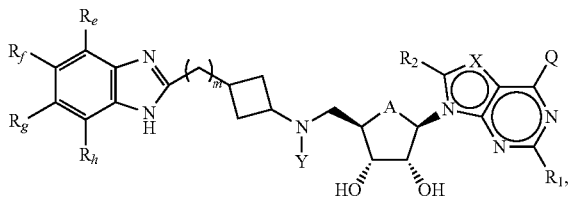

wherein, A is O or $CH_2$;

Q is H, $NH_2$, $NHR_b$, $NR_bR_c$, OH, $R_b$, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

Y is H, $R_d$, $SO_2R_d$, or $COR_d$, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$ and $R_2$ independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

each of $R_e$, $R_f$, $R_g$, and $R_h$ independently is -$M_2$-$T_2$, in which $M_2$ is a bond, $SO_2$, SO, S, CO, $CO_2$, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, and m is 0, 1, or 2.

For example, A is O. In certain compounds of Formula (IV), A is O and m is 2.

In certain compounds of Formula (IV), X is N.

For example, in certain compounds, Q is $NH_2$ or $NHR_b$, in which $R_b$ is -$M_1$-$T_1$, $M_1$ being a bond or $C_1$-$C_6$ alkyl linker and $T_1$ being $C_3$-$C_8$ cycloalkyl For example, in certain compounds of Formula (IV), $R_1$ and $R_2$ are each H.

In certain compounds of Formula (IV), Y is $R_d$. For example, $R_d$ is $C_1$-$C_6$ alkyl optionally substituted with $C_3$-$C_8$ cycloalkyl or halo. For example, $R_d$ is $C_3$-$C_8$ cycloalkyl optionally substituted with $C_1$-$C_6$ alkyl or halo.

The invention also relates to a compound of Formula (IV), wherein at least one of $R_e$, $R_f$, $R_g$, and $R_h$ is halo, $C_1$-$C_6$ alkoxyl optionally substituted with one or more halo; $C_1$-$C_6$ alkylsulfonyl optionally substituted with one or more halo; $C_1$-$C_6$ alkyl optionally substituted with one or more substituents selected from CN, halo, $C_3$-$C_8$ cycloalkyl, hydroxy, and $C_1$-$C_6$ alkoxyl; $C_3$-$C_8$ cycloalkyl optionally substituted with one or more $C_1$-$C_6$ alkyl or CN; or 4 to 8-membered heterocycloalkyl optionally substituted with one or more substituents selected from CN, halo, hydroxy, $C_1$-$C_6$ alkyl and $C_1$-$C_6$ alkoxyl. For example, the compound of Formula (IV) has at least one of $R_e$, $R_f$, $R_g$, and $R_h$ selected from F; Cl; Br; $CF_3$; $OCF_3$; $SO_2CF_3$; oxetanyl optionally substituted with one or more substituents selected from CN, halo, hydroxy, $C_1$-$C_6$ alkyl and $C_1$-$C_6$ alkoxyl; $C_3$-$C_8$ cycloalkyl optionally substituted with one or more substituents selected from $C_1$-$C_4$ alkyl; and $C_1$-$C_4$ alkyl optionally substituted with one or more substituents selected from halo, $C_3$-$C_8$ cycloalkyl, hydroxy and $C_1$-$C_6$ alkoxyl.

For example, the invention relates to compounds of Formula (IV) where at least one of $R_f$ and $R_g$ is alkyl, optionally substituted with hydroxyl. For example, the invention relates to compounds where at least one of $R_f$ and $R_g$ is t-butyl substituted with hydroxyl.

The invention relates to a compound selected from Compounds 1-140. The invention also relates to a salt of a compound selected from Compounds 1-140. The invention also relates to an N-oxide of compound selected from Compounds 1-140. The invention also relates to a salt of an N-oxide of compound selected from Compounds 1-140. For example, the invention relates to a compound selected from Compounds 1-7, 9-109, and 111-140.

The invention also relates to a pharmaceutical composition of a therapeutically effective amount of a compound of Formula (IV) and a pharmaceutically acceptable carrier.

The invention also relates to a pharmaceutical composition of a therapeutically effective amount of a salt of a compound of Formula (IV) and a pharmaceutically acceptable carrier.

The invention also relates to a pharmaceutical composition of a therapeutically effective amount of a hydrate of a compound of Formula (IV) and a pharmaceutically acceptable carrier.

The invention also relates to a pharmaceutical composition of a therapeutically effective amount of a compound selected from Compounds 1-140 and a pharmaceutically acceptable carrier. The invention also relates to a pharmaceutical composition of a therapeutically effective amount of a salt of a compound selected from Compounds 1-140 and a pharmaceutically acceptable carrier. The invention also relates to a pharmaceutical composition of a therapeutically effective amount of an N-oxide of a compound selected from Compounds 1-140 and a pharmaceutically acceptable carrier. The invention also relates to a pharmaceutical composition of a therapeutically effective amount of an N-oxide of salt of a compound selected from Compounds 1-140 and a pharmaceutically acceptable carrier. The invention also relates to a pharmaceutical composition of a therapeutically effective amount of a hydrate of a compound selected from Compounds 1-140 and a pharmaceutically acceptable carrier.

The present invention provides pharmaceutical compositions comprising one or more compounds of Formula (I), (II), (IIIa), (IIIb), (IIIc) or (IV), and one or more pharmaceutically acceptable carriers.

The present invention provides methods of treating or preventing cancer. The present invention provides methods of treating cancer. The present invention also provides methods of preventing cancer. The method includes administering to a subject in need thereof a therapeutically effective amount of the compound of Formula (I), (II), (IIIa), (IIIb), or (IIIc). The cancer can be a hematological cancer. Preferably, the cancer is leukemia. More preferably, the cancer is acute myeloid leukemia, acute lymphocytic leukemia or mixed lineage leukemia.

The present invention provides methods of treating or preventing a disease or disorder mediated by translocation of a gene on chromosome 11q23. The present invention provides methods of treating a disease or disorder mediated by translocation of a gene on chromosome 11q23. The present invention also provides methods of preventing a disease or disorder mediated by translocation of a gene on chromosome 11q23. The method includes administering to a subject in need thereof a therapeutically effective amount of the compound of Formula (I), (II), (IIIa), (IIIb), (IIIc) or (IV).

The present invention provides methods of treating or preventing a disease or disorder in which DOT1-mediated protein methylation plays a part or a disease or disorder mediated by DOT1-mediated protein methylation. The present invention provides methods of treating a disease or disorder in which DOT1-mediated protein methylation plays a part or a disease or disorder mediated by DOT1-mediated protein methylation. The present invention also provides methods of preventing a disease or disorder in which DOT1-mediated protein methylation plays a part or a disease or disorder mediated by DOT1-mediated protein methylation. The method includes administering to a subject in need thereof a therapeutically effective amount of the compound of Formula (I), (II), (IIIa), (IIIb), (IIIc) or (IV).

The present invention provides methods of inhibiting DOT1L activity in a cell. The method includes contacting the cell with an effective amount of one or more of the compound of Formula (I), (II), (IIIa), (IIIb), (IIIc) or (IV).

Still another aspect of the invention relates to a method of reducing the level of Histone H3 Lysine residue 79 (H3-K79) methylation in a cell. The method includes contacting a cell with a compound of the present invention. Such method can be used to ameliorate any condition which is caused by or potentiated by the activity of DOT1 through H3-K79 methylation.

The present invention relates to use of the compounds disclosed herein in preparation of a medicament for treating or preventing cancer. The use includes a compound of Formula (I), (II), (IIIa), (IIIb), (IIIc) or (IV) for administration to a subject in need thereof in a therapeutically effective amount. The cancer can be a hematological cancer. Preferably, the cancer is leukemia. More preferably, the cancer is acute myeloid leukemia, acute lymphocytic leukemia or mixed lineage leukemia.

The present invention provides use of the compounds disclosed herein in preparation of a medicament for treating or preventing a disease or disorder mediated by translocation of a gene on chromosome 11q23. The use includes a compound of Formula (I), (II), (IIIa), (IIIb), (IIIc) or (IV) for administration to a subject in need thereof in a therapeutically effective amount.

The present invention provides use of the compounds disclosed herein in preparation of a medicament for treating or preventing a disease or disorder in which DOT1-mediated protein methylation plays a part or a disease or disorder mediated by DOT1-mediated protein methylation. The use includes a compound of Formula (I), (II), (IIIa), (IIIb), (IIIc) or (IV) for administration to a subject in need thereof in a therapeutically effective amount.

The present invention provides use of the compounds disclosed herein for inhibiting DOT1L activity in a cell. The use includes contacting the cell with an effective amount of one or more of the compound of Formula (I), (II), (IIIa), (IIIb), (IIIc) or (IV).

Still another aspect of the invention relates to a use of the compounds disclosed herein for reducing the level of Histone H3 Lysine residue 79 (H3-K79) methylation in a cell. The use includes contacting a cell with a compound of the present invention. Such use can ameliorate any condition which is caused by or potentiated by the activity of DOT1 through H3-K79 methylation.

In the formulae presented herein, the variables can be selected from the respective groups of chemical moieties later defined in the detailed description.

In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use in modulating an epigenetic enzyme. In certain embodiments, the compounds of the present invention are useful for treating, preventing, or reducing the risk of cancer or for the manufacture of a medicament for treating, preventing, or reducing the risk of cancer. Accordingly, the compounds or the formulations can be administered, for example, via oral, parenteral, otic, ophthalmic, nasal, or topical routes, to provide an effective amount of the compound to the mammal.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION OF THE INVENTION

Figure 1:
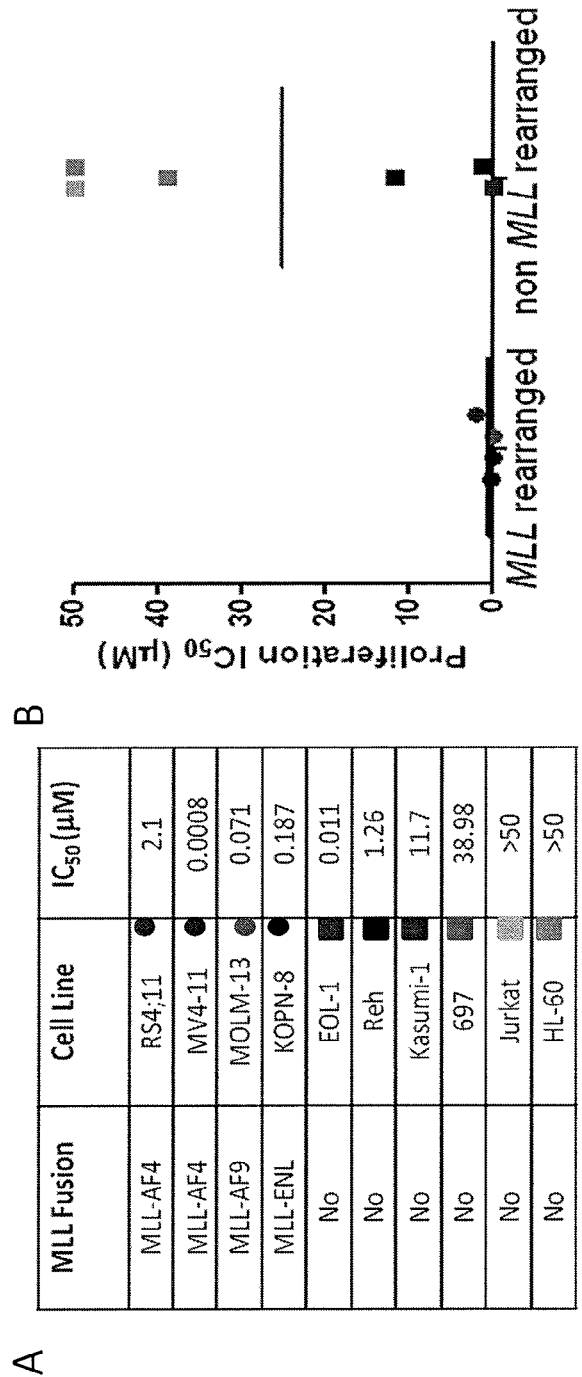
FIGS. 1A and 1B are respectively a table and a plot demonstrating the potency and selectivity of the anti-proliferative activity of Compound 2 using a panel of MLL-rearranged and non-MLL-rearranged human leukemia cell lines. The cell lines used in the study are listed in FIG. 1A

The present invention provides a family of compounds that can be used to selectively modulate the aberrant action of an epigenetic enzyme. Further, the compounds can be used to treat or prevent a disease state in a mammal caused or mediated by aberrant action of an epigenetic enzyme. The present invention includes pharmaceutically acceptable salts, esters, tautomers, and N-oxides of these compounds.

The present invention provides novel substituted purine and 7-deazapurine compounds, synthetic methods for making the compounds, pharmaceutical compositions containing them and various uses of the compounds.

1. SUBSTITUTED PURINE COMPOUNDS AND SUBSTITUTED 7-DEAZAPURINE COMPOUNDS

The present invention provides the compounds of Formula (I):

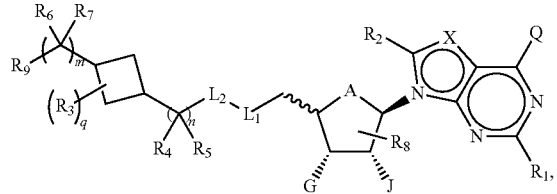

or a pharmaceutically acceptable salt or ester thereof, wherein:
A is O or $CH_2$;
each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;
Q is H, $NH_2$, $NHR_b$, $NR_bR_c$, $R_b$, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
$L_1$ is N(Y), S, SO, or $SO_2$;
$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

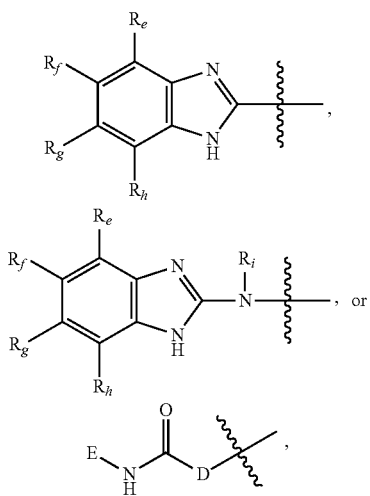

in which each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_t$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

q is 0, 1, 2, 3, or 4;
m is 0, 1, or 2; and
n is 0, 1, or 2.
For example, the sum of in and n is at least 1.
For example, m is 1 or 2 and n is 0.
For example, m is 2 and n is 0
For example, A is $CH_2$.
For example, A is O.
For example, $L_1$ is N(Y).
For example, $L_1$ is SO or $SO_2$.
For example, Y is $R_d$.
For example, $R_d$ is $C_1$-$C_6$ alkyl.
For example, $L_2$ is absent.
For example, each of G and J independently is $OR_a$.
For example, $R_a$ is H.
For example, $R_9$ is

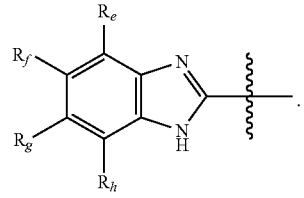

For example, $R_9$ is

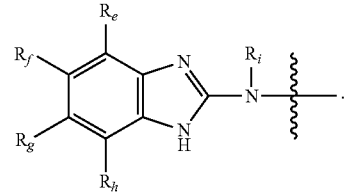

For example, at least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-propyl, n-butyl, and $CF_3$).

For example, R, is H or $C_1$-$C_6$ alkyl (e.g., methyl, ethyl, n-propyl, i-propyl, n-butyl, s-butyl, t-butyl, n-pentyl, s-pentyl and n-hexyl).
For example,
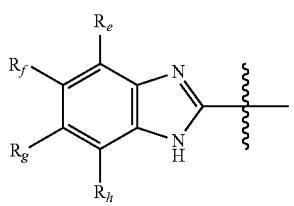
is unsubstituted benzimidazolyl or one of the following groups:
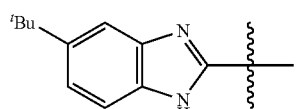
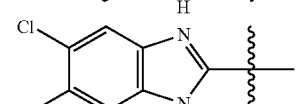
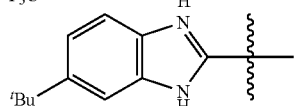
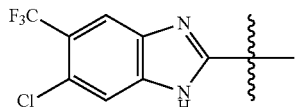
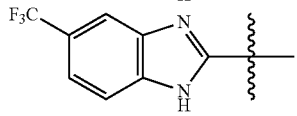
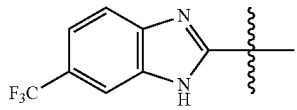
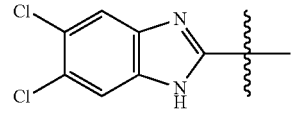
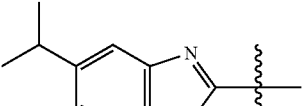
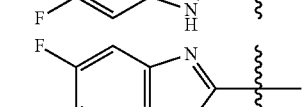
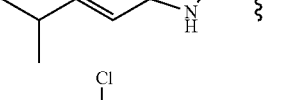
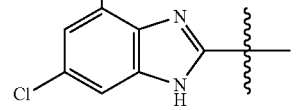
-continued
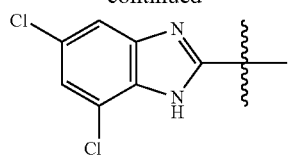
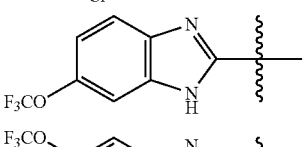
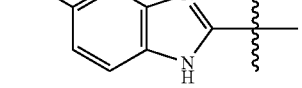
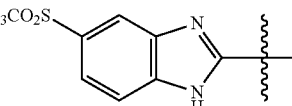
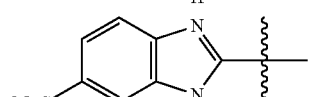
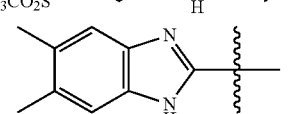
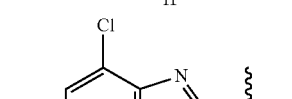
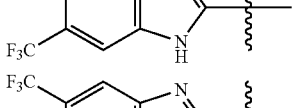
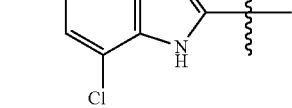
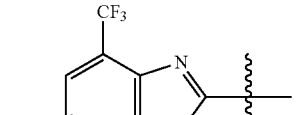
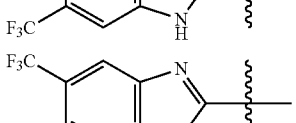
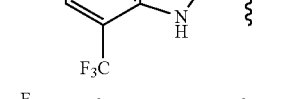
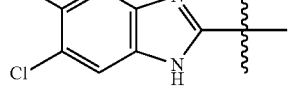
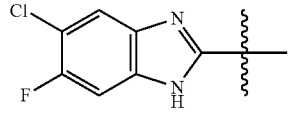
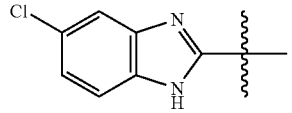

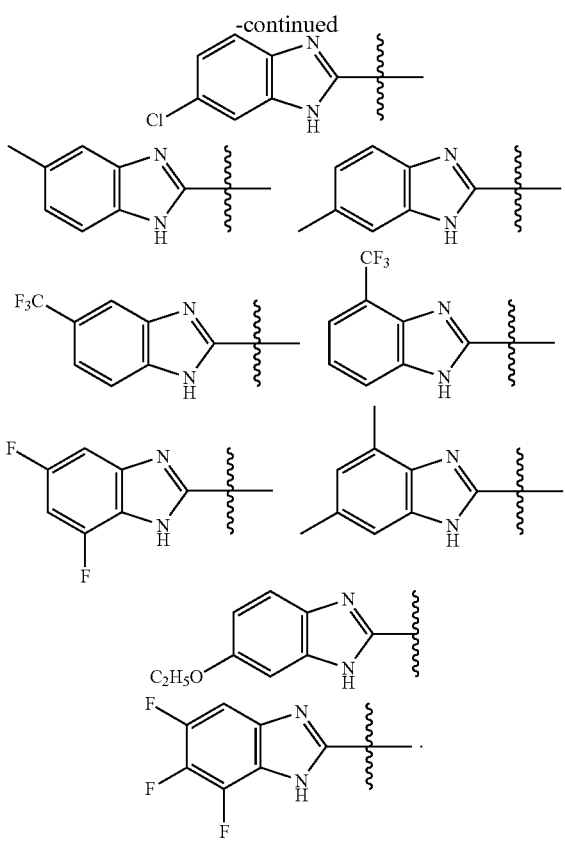

For example, $R_9$ is

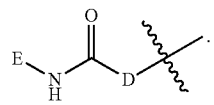

For example, D is O.
For example, D is $NR_j$.
For example, $R_j$ is H.
For example, D is $CR_jR_k$.
For example, each of $R_j$ and $R_k$ is H.
For example, E is -$M_3$-$T_3$, in which $M_3$ is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl.

For example, $T_3$ is phenyl optionally substituted with one or more substituents selected from the group consisting of halo, hydroxyl, carboxyl, cyano, nitro, $C_1$-$C_6$ alkyl (e.g., methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl.

For example, E is

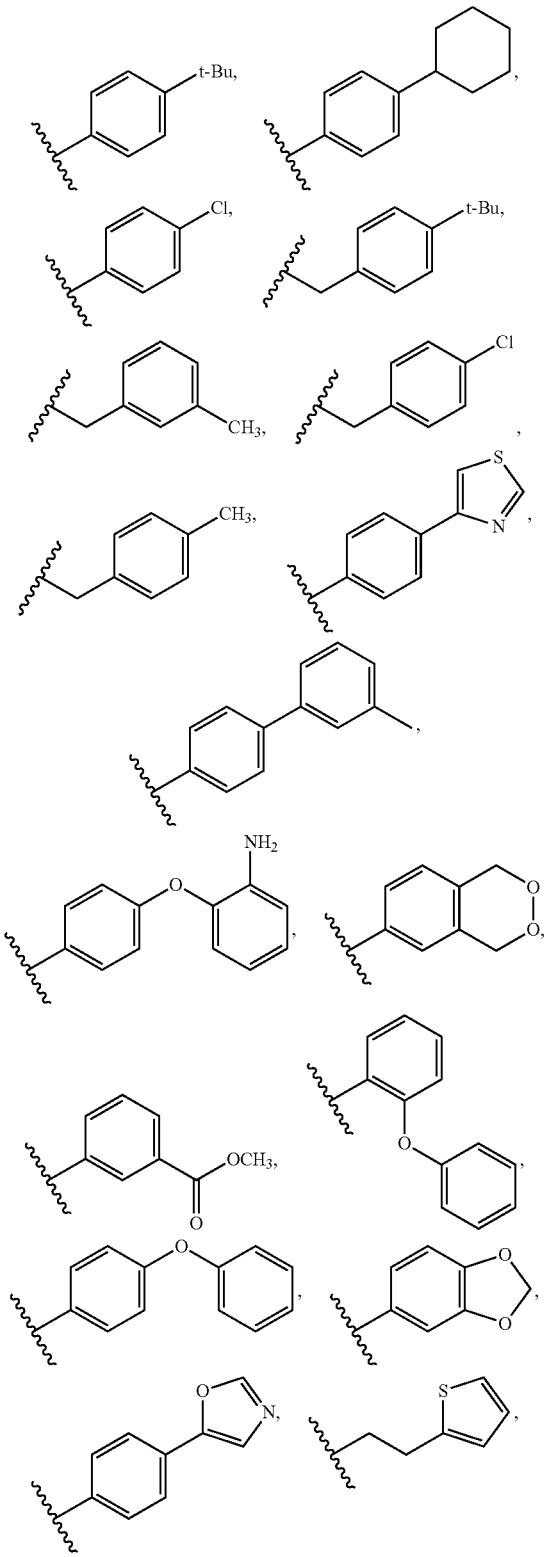

-continued

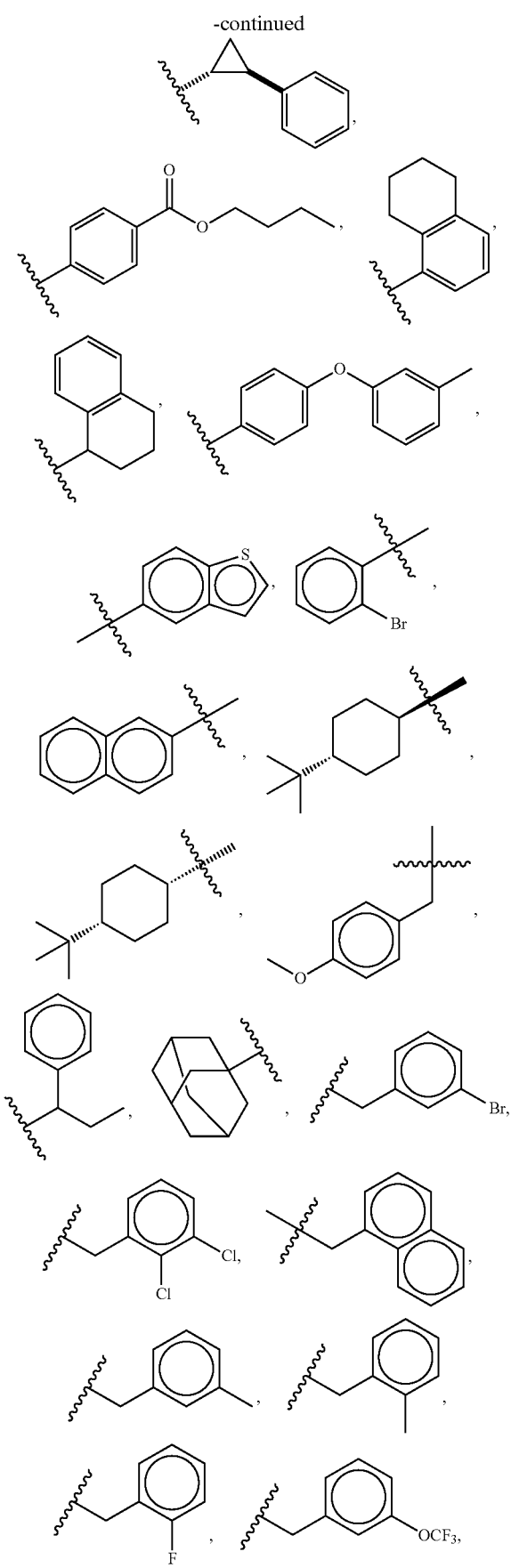

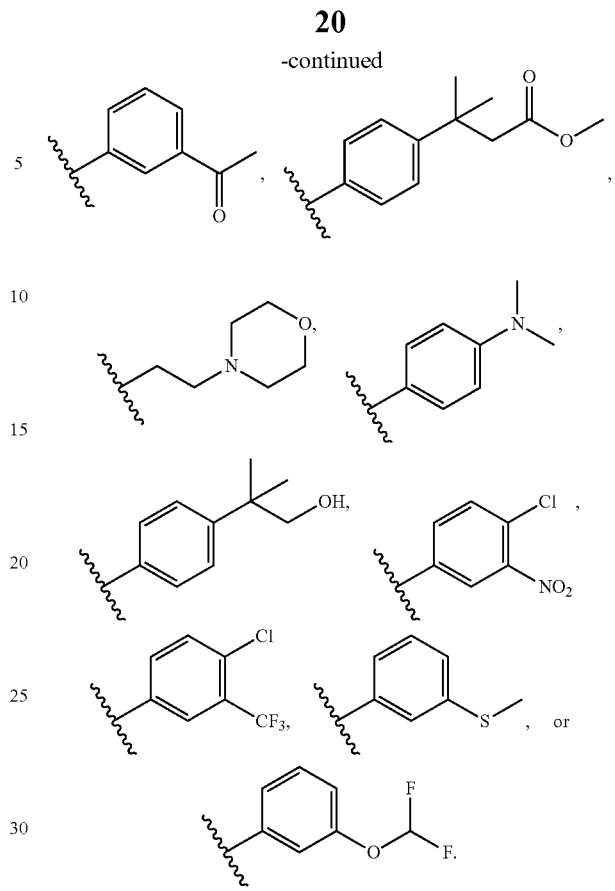

For example, X is N.
For example, X is $CR_x$.
For example, X is CH.
For example, Q is $NH_2$ or $NHR_b$, in which $R_b$ is $-M_1-T_1$, $M_1$ being a bond or $C_1$-$C_6$ alkyl linker and $T_1$ being $C_3$-$C_8$ cycloalkyl.
For example, Q is H.
For example, $R_1$, $R_2$, $R_3$, $R_4$, $R_5$, $R_6$, $R_7$, and $R_8$ are each H.
For example, when $R_8$ is halo and is attached to the same carbon atom as J, then J is not hydroxyl.
For example, when $R_8$ is halo and is attached to the same carbon atom as G, then G is not hydroxyl.
For example, $T_2$ is not halo when $M_2$ is $SO_2$, SO, S, CO or O.
For example, $T_2$ is a 4-8 membered heterocycloalkyl which is bound to $M_2$ via a heteroatom.
For example, $T_2$ is a 4-8 membered heterocycloalkyl which is bound to $M_2$ via a N atom.
For example, $T_2$ is a 4-8 membered heterocycloalkyl which is bound to $M_2$ via a C atom.
The present invention provides the compounds of Formula (II):

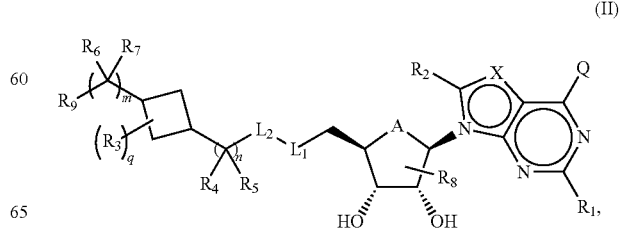

(II)

or a pharmaceutically acceptable salt or ester thereof, wherein:

A is O or CH$_2$;

Q is H, NH$_2$, NHR$_b$, NR$_b$R$_c$, R$_b$, or OR$_b$, in which each of R$_b$ and R$_c$ independently is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 7-membered heterocycloalkyl, 5 to 10-membered heteroaryl, or -M$_1$-T$_1$ in which M$_1$ is a bond or C$_1$-C$_6$ alkyl linker optionally substituted with halo, cyano, hydroxyl, or C$_1$-C$_6$ alkoxyl and T$_1$ is C$_3$-C$_8$ cycloalkyl, C$_6$-C$_{10}$ aryl, 4 to 6-membered heterocycloalkyl, or 5 to 10-membered heteroaryl, or R$_b$ and R$_c$, together with the N atom to which they attach, form 4 to 7-membered heterocycloalkyl having 0 or 1 additional heteroatoms to the N atom optionally substituted with C$_1$-C$_6$ alkyl, C$_2$-C$_6$ alkenyl, C$_2$-C$_6$ alkynyl, halo, hydroxyl, carboxyl, C(O)OH, C(O)O—C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl, and each of R$_b$, R$_c$, and T$_1$ is optionally substituted with one or more substituents selected from the group consisting of C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

X is N or CR$_x$, in which R$_x$ is H, halo, hydroxyl, carboxyl, cyano, or R$_{S1}$, R$_{S1}$ being amino, C$_1$-C$_6$ alkoxyl, C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 6-membered heterocycloalkyl, or 5 to 6-membered heteroaryl, and R$_{S1}$ being optionally substituted with one or more substituents selected from the group consisting of halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

L$_1$ is N(Y), S, SO, or SO$_2$;

L$_2$ is CO or absent when L$_1$ is N(Y) or L$_2$ is absent when L$_1$ is S, SO, or SO$_2$, in which Y is H, R$_d$, SO$_2$R$_d$, or COR$_d$ when L$_2$ is absent, or Y is H or R$_d$ when L$_2$ is CO, R$_d$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 6-membered heterocycloalkyl, or 5 to 6-membered heteroaryl, and R$_d$ being optionally substituted with one or more substituents selected from the group consisting of C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, C$_1$-C$_6$ alkylsulfonyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl and with C$_3$-C$_8$ cycloalkyl, C$_6$-C$_{10}$ aryl, 4 to 6-membered heterocycloalkyl, or 5 to 6-membered heteroaryl further optionally substituted with C$_1$-C$_6$ alkyl, C$_2$-C$_6$ alkenyl, C$_2$-C$_6$ alkynyl, halo, hydroxyl, carboxyl, C(O)OH, C(O)O—C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl;

each of R$_1$, R$_2$, R$_3$, R$_4$, R$_5$, R$_6$, and R$_7$, independently, is H, halo, hydroxyl, carboxyl, cyano, R$_{S2}$, R$_{S2}$ being amino, C$_1$-C$_6$ alkoxyl, C$_1$-C$_6$ alkyl, C$_2$-C$_6$ alkenyl, or C$_2$-C$_6$ alkynyl, and each R$_{S2}$ being optionally substituted with one or more substituents selected from the group consisting of halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

R$_8$ is H, halo or R$_{S3}$, R$_{S3}$ being C$_1$-C$_6$ alkyl, C$_2$-C$_6$ alkenyl, or C$_2$-C$_6$ alkynyl, and R$_{S3}$ being optionally substituted with one or more substituents selected from the group consisting of halo, hydroxyl, carboxyl, cyano amino, C$_1$-C$_6$ alkoxyl, mono-C$_1$-C$_6$ alkylamino, di-C$_1$-C$_6$ alkylamino, and C$_3$-C$_8$ cycloalkyl;

R$_9$ is

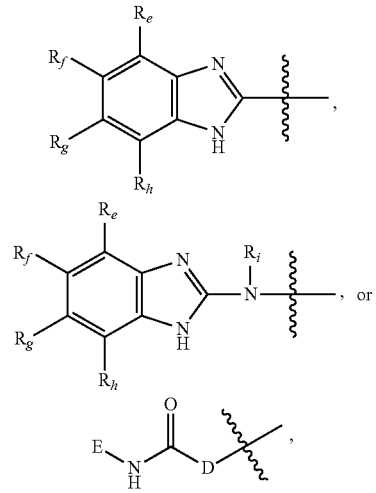

in which each of R$_e$, R$_f$, R$_g$, and R$_h$, independently is -M$_2$-T$_2$, in which M$_2$ is a bond, SO$_2$, SO, S, CO, CO$_2$, O, O—C$_1$-C$_4$ alkyl linker, C$_1$-C$_4$ alkyl linker, NH, or N(R$_t$), R$_t$ being C$_1$-C$_6$ alkyl, and T$_2$ is H, halo, or R$_{S4}$, R$_{S4}$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 8-membered heterocycloalkyl, or 5 to 10-membered heteroaryl, and each of O—C$_1$-C$_4$ alkyl linker, C$_1$-C$_4$ alkyl linker, R$_t$, and R$_{S4}$ being optionally substituted with one or more substituents selected from the group consisting of halo, hydroxyl, carboxyl, cyano, C$_1$-C$_6$ alkyl, C$_2$-C$_6$ alkenyl, C$_2$-C$_6$ alkynyl, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl, R$_t$ is H or C$_1$-C$_6$ alkyl optionally substituted with one or more substituents selected from the group consisting of halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl, D is O, NR$_j$, or CR$_j$R$_k$, each of R$_j$ and R$_k$ independently being H or C$_1$-C$_6$ alkyl, or R$_j$ and R$_k$ taken together, with the carbon atom to which they are attached, form a C$_3$-C$_{10}$ cycloalkyl ring, and E is -M$_3$-T$_3$, M$_3$ being a bond or C$_1$-C$_6$ alkyl linker optionally substituted with halo or cyano, T$_3$ being C$_3$-C$_{10}$ cycloalkyl, C$_6$-C$_{10}$ aryl, 5 to 10-membered heteroaryl, or 4 to 10-membered heterocycloalkyl, and T$_3$ being optionally substituted with one or more substituents selected from the group consisting of halo, hydroxyl, thiol, carboxyl, cyano, nitro, C$_1$-C$_6$ alkyl, C$_2$-C$_6$ alkenyl, C$_2$-C$_6$ alkynyl, C$_1$-C$_6$ alkoxyl, C$_1$-C$_6$ haloalkyl, C$_1$-C$_6$ haloalkoxyl, C$_1$-C$_6$ alkylthio, C$_1$-C$_6$ alkylsulfonyl, C$_1$-C$_6$ haloalkylsulfonyl, C$_1$-C$_6$ alkylcarbonyl, C$_1$-C$_6$ alkoxycarbonyl, oxo, amino, mono-C$_1$-C$_6$ alkylamino, di-C$_1$-C$_6$ alkylamino, C$_3$-C$_8$ cycloalkyl, C$_4$-C$_{12}$ alkylcycloalkyl, C$_6$-C$_{10}$ aryl, C$_6$-C$_{10}$ aryloxyl, C$_7$-C$_{14}$ alkylaryl, C$_6$-C$_{10}$ aminoaryloxyl, C$_6$-C$_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

q is 0, 1, 2, 3, or 4;
m is 0, 1, or 2; and
n is 0, 1, or 2.

For example, the sum of m and n is at least 1.
For example, m is 1 or 2 and n is 0.
For example, m is 2 and n is 0
For example, A is $CH_2$.
For example, A is O.
For example, $L_1$ is N(Y).
For example, $L_1$ is SO or $SO_2$.
For example, Y is $R_d$.
For example, $R_d$ is $C_1$-$C_6$ alkyl.
For example, $L_2$ is absent.
For example, $R_9$ is

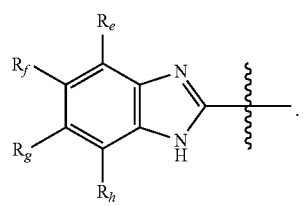

For example, $R_9$ is

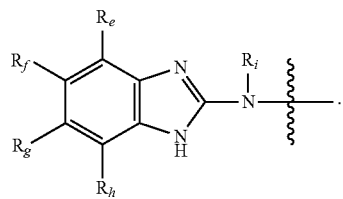

For example, at least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-propyl, n-butyl, and $CF_3$).

For example, $R_i$ is H or $C_1$-$C_6$ alkyl (e.g., methyl, ethyl, n-propyl, i-propyl, n-butyl, s-butyl, t-butyl, n-pentyl, s-pentyl or n-hexyl).

For example,

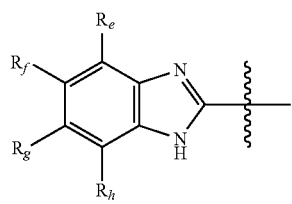

is unsubstituted benzimidazolyl or one of the following groups:

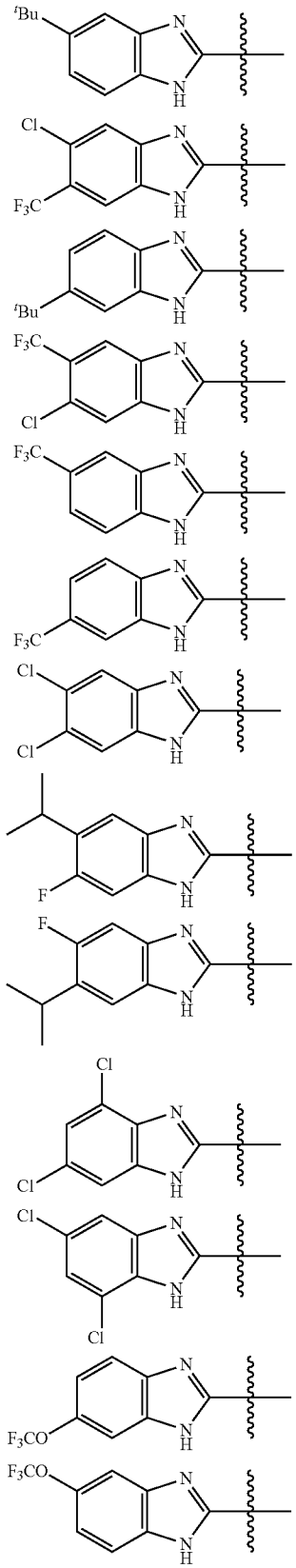

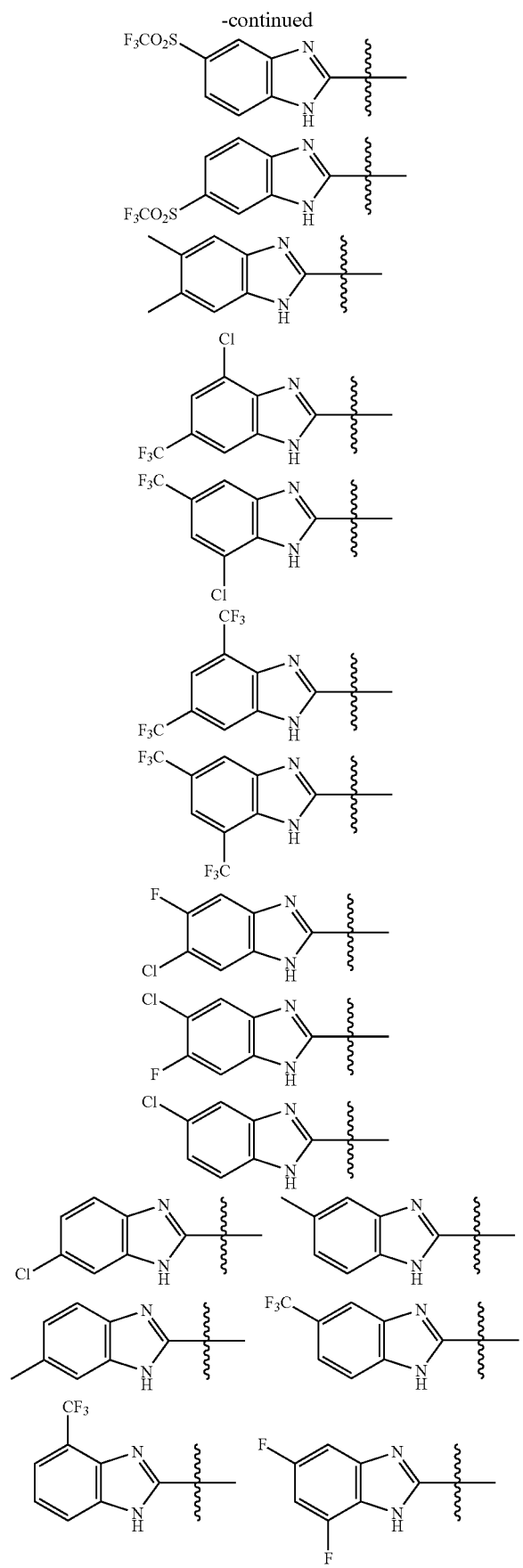

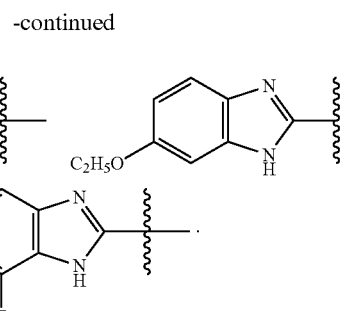

For example, $R_9$ is

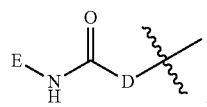

For example, D is O.

For example, D is $NR_j$.

For example, $R_j$ is H.

For example, D is $CR_jR_k$.

For example, each of $R_j$ and $R_k$ is H.

For example, E is $-M_3-T_3$, in which $M_3$ is a bond or $C_1-C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1-C_6$ alkyl, $C_2-C_6$ alkenyl, $C_2-C_6$ alkynyl, $C_1-C_6$ alkoxyl, $C_1-C_6$ haloalkyl, $C_1-C_6$ haloalkoxyl, $C_1-C_6$ alkylthio, $C_1-C_6$ alkylsulfonyl, $C_1-C_6$ alkylcarbonyl, $C_1-C_6$ alkoxycarbonyl, oxo, amino, mono-$C_1-C_6$ alkylamino, di-$C_1-C_6$ alkylamino, $C_3-C_8$ cycloalkyl, $C_4-C_{12}$ alkylcycloalkyl, $C_6-C_{10}$ aryl, $C_6-C_{10}$ aryloxyl, $C_7-C_{14}$ alkylaryl, $C_6-C_{10}$ aminoaryloxyl, $C_6-C_{10}$ arylthio, 4 to 6-membered heterocycloalkyl optionally substituted with $C_1-C_4$ alkyl, 5 to 6-membered heteroaryl optionally substituted with $C_1-C_4$ alkyl, and $C_1-C_6$ alkyl that is substituted with hydroxy, $C_1-C_6$ alkoxycarbonyl, $C_3-C_8$ cycloalkyl, $C_6-C_{10}$ aryl, 4 to 6-membered heterocycloalkyl, or 5 to 6-membered heteroaryl.

For example, $T_3$ is phenyl optionally substituted with one or more substituents selected from the group consisting of halo, hydroxyl, carboxyl, cyano, nitro, $C_1-C_6$ alkyl (e.g., methyl, ethyl, n-propyl, i-propyl, n-butyl, s-butyl, t-butyl, n-pentyl, s-pentyl and n-hexyl), $C_1-C_6$ alkoxyl, $C_1-C_6$ haloalkyl, $C_1-C_6$ haloalkoxyl, $C_1-C_6$ alkylsulfonyl, $C_6-C_{10}$ aryl (e.g., phenyl or naphthyl), and $C_6-C_{10}$ aryloxyl, and $C_7-C_{14}$ alkylaryl.

For example, E is

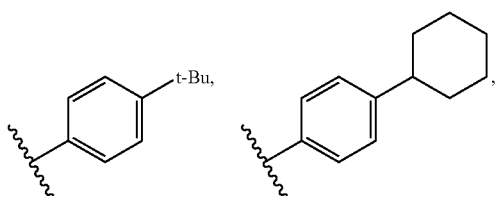

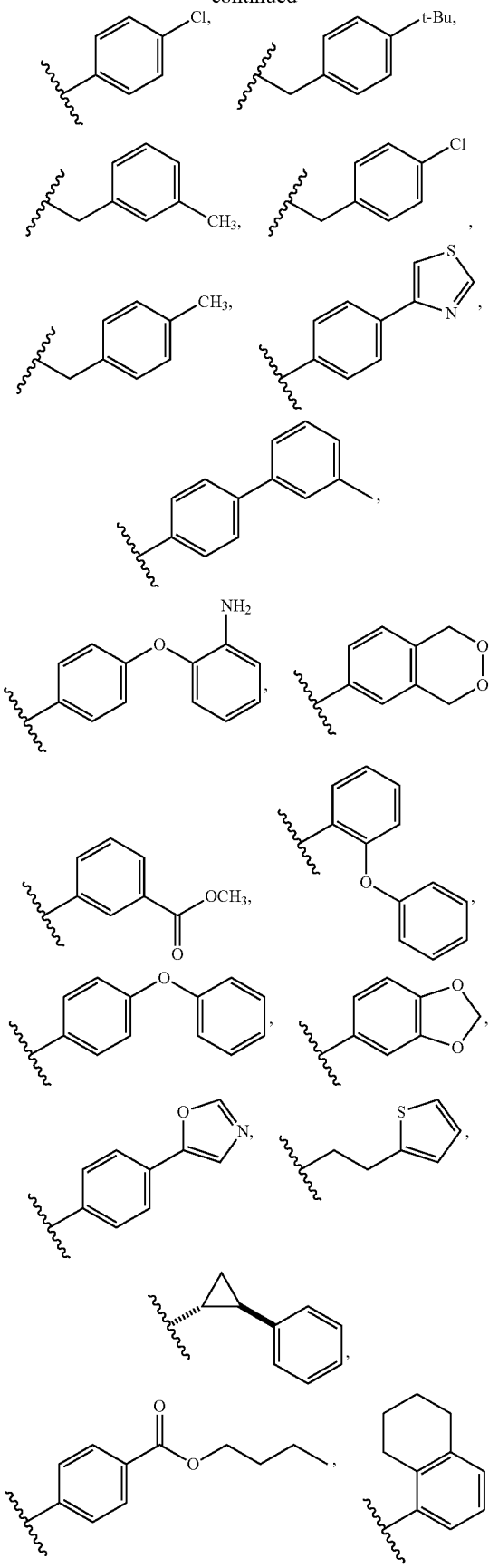
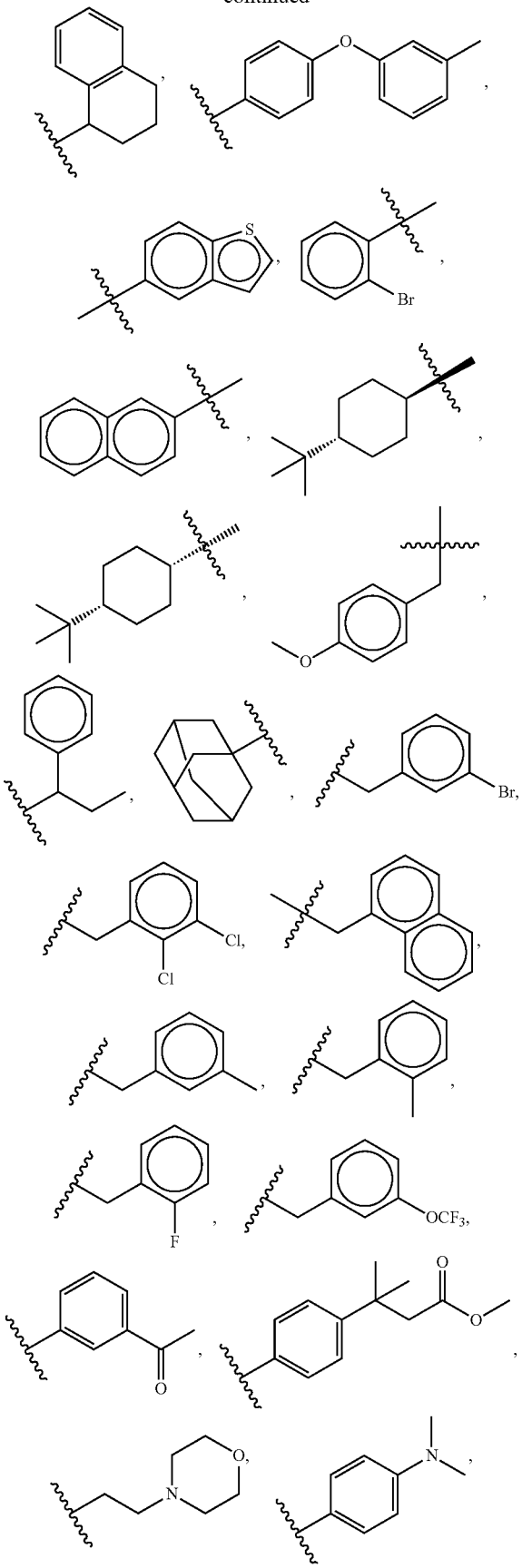

-continued

[chemical structures: 4-(2-hydroxy-1,1-dimethylethyl)phenyl; 4-chloro-3-nitrophenyl; 4-chloro-3-(trifluoromethyl)phenyl; 3-(methylthio)phenyl; 3-(difluoromethoxy)phenyl]

For example, X is N.
For example, X is $CR_x$.
For example, X is CH.
For example, Q is $NH_2$ or $NHR_b$, in which $R_b$ is $-M_1-T_1$, $M_1$ being a bond or $C_1-C_6$ alkyl linker and $T_1$ being $C_3-C_8$ cycloalkyl.
For example, Q is H.
For example, $R_1$, $R_2$, $R_3$, $R_4$, $R_5$, $R_6$, $R_7$, and $R_8$ are each H.
For example, when $R_8$ is halo and is attached to the same carbon atom as J, then J is not hydroxyl.
For example, when $R_8$ is halo and is attached to the same carbon atom as G, then G is not hydroxyl.
For example, $T_2$ is not halo when $M_2$ is $SO_2$, SO, S, CO or O.
For example, $T_2$ is a 4-8 membered heterocycloalkyl which is bound to $M_2$ via a heteroatom.
For example, $T_2$ is a 4-8 membered heterocycloalkyl which is bound to $M_2$ via a N atom.
For example, $T_2$ is a 4-8 membered heterocycloalkyl which is bound to $M_2$ via a C atom.

The present invention provides the compounds of Formula (IIIa) or (IIIb):

A is O or $CH_2$;
each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

Q is H, $NH_2$, $NHR_b$, $NR_bR_c$, $R_b$, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or $-M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the (IIIa)

[chemical structure of Formula IIIa]

(IIIb)

[chemical structure of Formula IIIb]

or a pharmaceutically acceptable salt or ester thereof, wherein:

group consisting of halo, hydroxyl, carboxyl, cyano, $C_1$-$C_6$ alkoxyl, amino, mono-$C_1$-$C_6$ alkylamino, di-$C_1$-

$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_t$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

q is 0, 1, 2, 3, or 4;

m is 0, 1, or 2; and n is 0, 1, or 2.

For example, the sum of m and n is at least 1.

For example, in is 1 or 2 and n is O.

For example, m is 2 and n is 0

For example, A is $CH_2$.

For example, A is O.

For example, $L_1$ is N(Y).

For example, $L_1$ is SO or $SO_2$.

For example, Y is $R_d$.

For example, $R_d$ is $C_1$-$C_6$ alkyl.

For example, $L_2$ is absent.

For example, each of G and J independently is $OR_a$.

For example, $R_a$ is H.

For example, at least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-propyl, n-butyl, and $CF_3$).

For example, R, is H or $C_1$-$C_6$ alkyl (e.g., methyl, ethyl, n-propyl, i-propyl, n-butyl, s-butyl, t-butyl, n-pentyl, s-pentyl and n-hexyl).

For example,

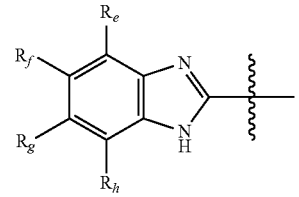

is unsubstituted benzimidazolyl or one of the following groups:

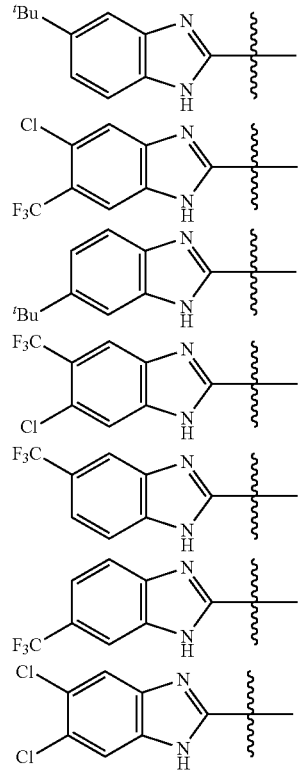

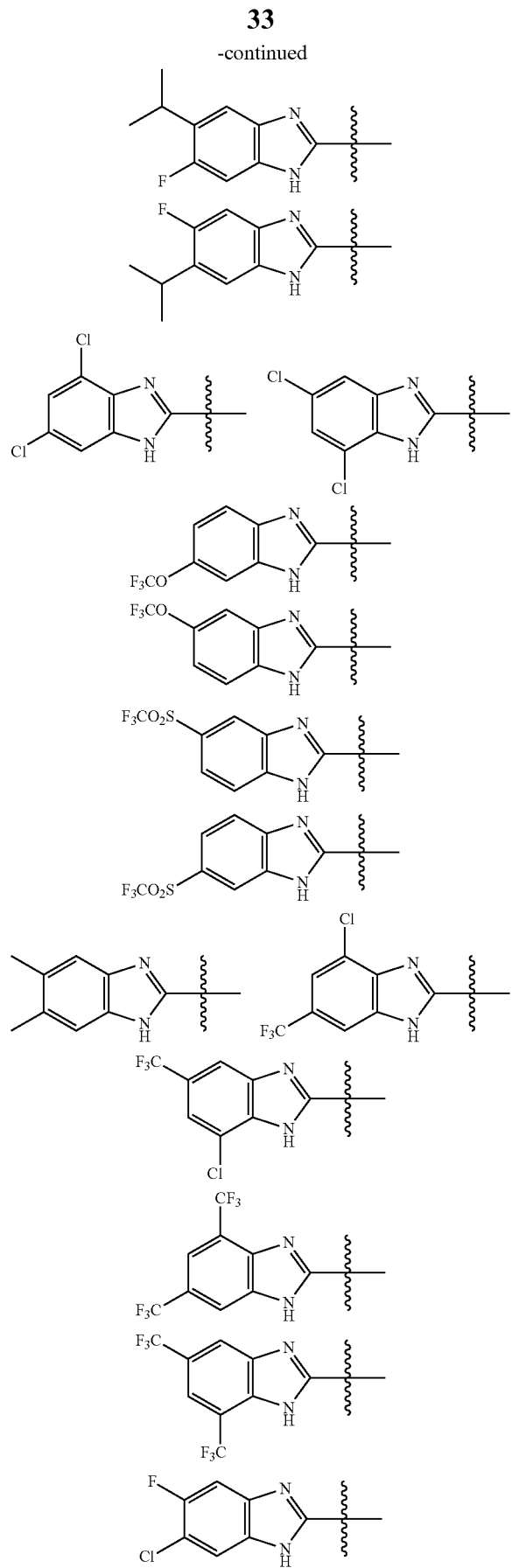
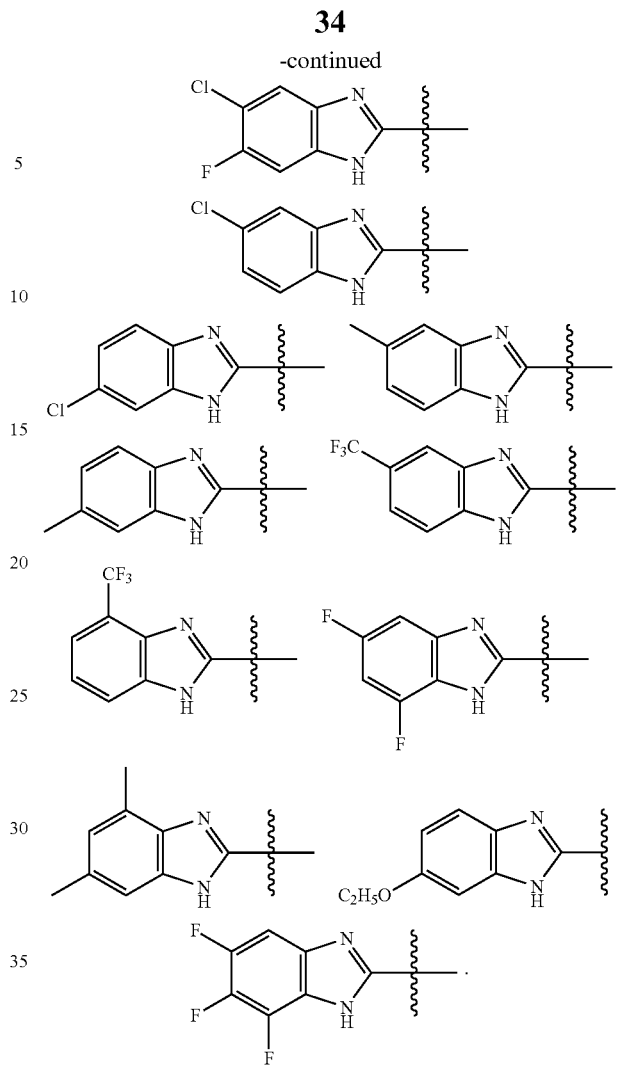

For example, X is N.

For example, X is $CR_x$.

For example, X is CH.

For example, Q is $NH_2$ or $NHR_b$, in which $R_b$ is $-M_1-T_1$, $M_1$ being a bond or $C_1$-$C_6$ alkyl linker and $T_1$ being $C_3$-$C_8$ cycloalkyl.

For example, Q is H.

For example, $R_1$, $R_2$, $R_3$, $R_4$, $R_5$, $R_6$, $R_7$, and $R_9$ are each H.

For example, when $R_8$ is halo and is attached to the same carbon atom as J, then J is not hydroxyl.

For example, when $R_8$ is halo and is attached to the same carbon atom as G, then G is not hydroxyl.

For example, $T_2$ is not halo when $M_2$ is $SO_2$, SO, S, CO or O.

For example, $T_2$ is a 4-8 membered heterocycloalkyl which is bound to $M_2$ via a heteroatom.

For example, $T_2$ is a 4-8 membered heterocycloalkyl which is bound to $M_2$ via a N atom.

For example, $T_2$ is a 4-8 membered heterocycloalkyl which is bound to $M_2$ via a C atom.

The present invention provides the compounds of Formula (IIIc):

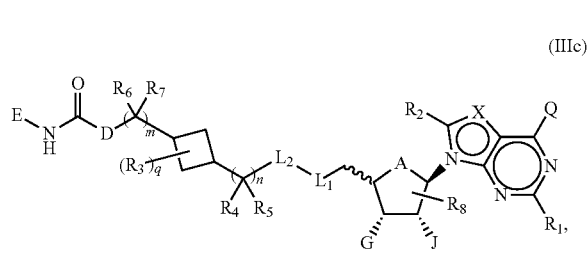

(IIIc)

or a pharmaceutically acceptable salt or ester thereof, wherein:
- A is O or $CH_2$;
- each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;
- Q is H, $NH_2$, $NHR_b$, $NR_bR_c$, $R_b$, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
- X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamine, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
- $L_1$ is N(Y), S, SO, or $SO_2$;
- $L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_6$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamine, $C_3$-$C_8$ cycloalkyl, $C_6$-$C_{10}$ aryl, 4 to 6-membered heterocycloalkyl, or 5 to 6-membered heteroaryl;
- each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
- $R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;
- D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring;
- E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;
- q is 0, 1, 2, 3, or 4;
- m is 0, 1, or 2; and
- n is 0, 1, or 2.
- For example, the sum of m and n is at least 1.
- For example, m is 1 or 2 and n is O.
- For example, m is 2 and n is 0
- For example, A is $CH_2$.
- For example, A is O.
- For example, $L_1$ is N(Y).
- For example, $L_1$ is SO or $SO_2$.
- For example, Y is $R_d$.
- For example, $R_d$ is $C_1$-$C_6$ alkyl.
- For example, $L_2$ is absent.
- For example, each of G and J independently is $OR_a$.

For example, $R_a$ is H.
For example, D is O.
For example, D is $NR_j$.
For example, $R_j$ is H.
For example, D is $CR_jR_k$.
For example, each of $R_j$ and $R_k$ is H.
For example, E is -$M_3$-$T_3$, in which $M_3$ is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl.

For example, $T_3$ is phenyl optionally substituted with one or more substituents selected from the group consisting of halo, hydroxyl, carboxyl, cyano, nitro, $C_1$-$C_6$ alkyl (e.g., methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl.

For example, E is

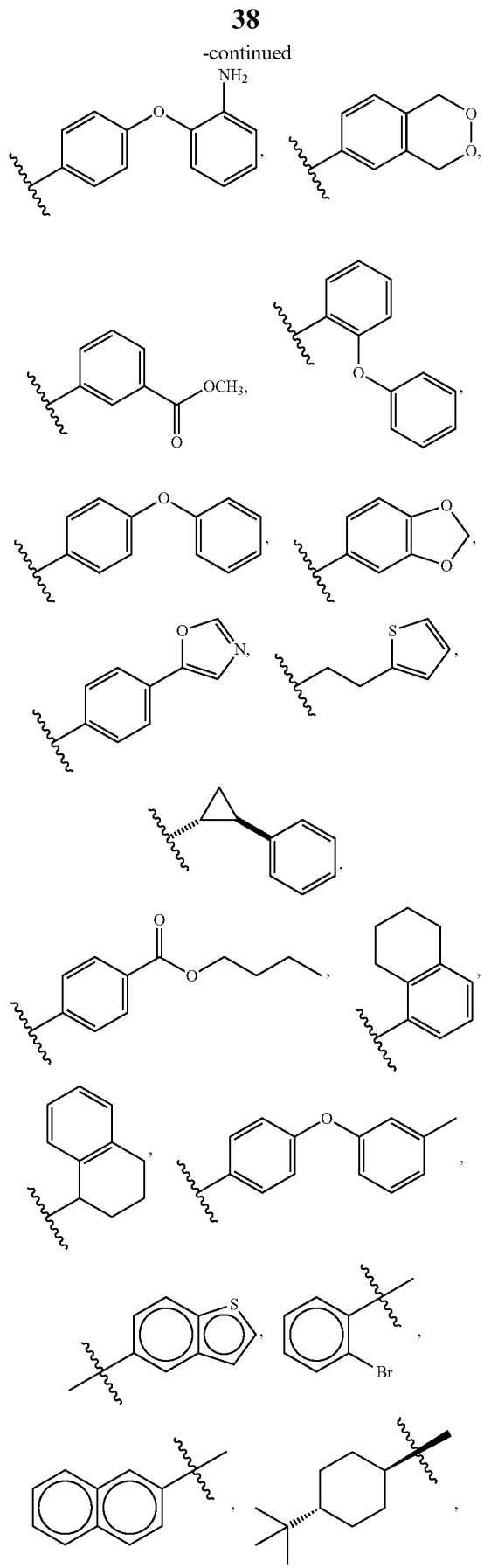

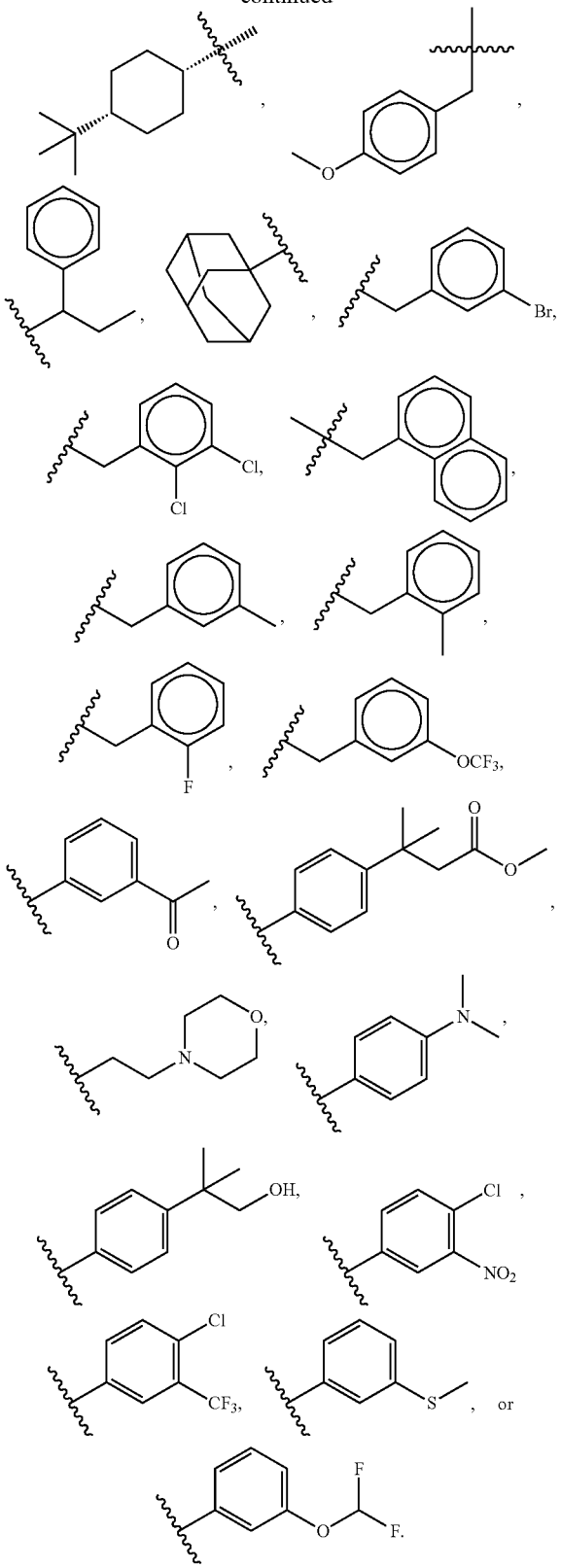

For example, X is N.
For example, X is CR$_x$.
For example, X is CH.

For example, Q is NH$_2$ or NHR$_b$, in which R$_b$ is -M$_1$-T$_1$, M$_1$ being a bond or C$_1$-C$_6$ alkyl linker and T$_1$ being C$_3$-C$_8$ cycloalkyl.

For example, Q is H.

For example, R$_1$, R$_2$, R$_3$, R$_4$, R$_5$, R$_6$, R$_7$, and R$_8$ are each H.

For example, when R$_8$ is halo and is attached to the same carbon atom as J, then J is not hydroxyl.

For example, when R$_8$ is halo and is attached to the same carbon atom as G, then G is not hydroxyl.

For example, T$_2$ is not halo when M$_2$ is SO$_2$, SO, S, CO or O.

For example, T$_2$ is a 4-8 membered heterocycloalkyl which is bound to M$_2$ via a heteroatom.

For example, T$_2$ is a 4-8 membered heterocycloalkyl which is bound to M$_2$ via a N atom.

For example, T$_2$ is a 4-8 membered heterocycloalkyl which is bound to M$_2$ via a C atom.

The invention also relates to a compound of Formula (IV) or its N-oxide or a pharmaceutically acceptable salt thereof:

(IV)

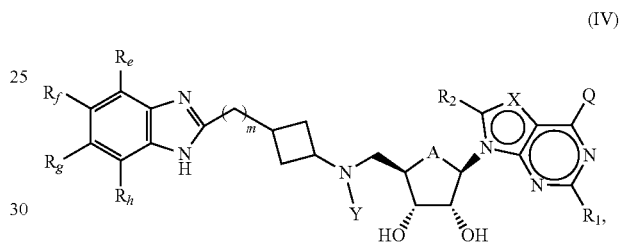

wherein A is O or CH$_2$;

Q is H, NH$_2$, NHR$_b$, NR$_b$R$_c$, OH, R$_b$, or OR$_b$, in which each of R$_b$ and R$_c$ independently is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 7-membered heterocycloalkyl, 5 to 10-membered heteroaryl, or -M$_1$-T$_1$ in which M$_1$ is a bond or C$_1$-C$_6$ alkyl linker optionally substituted with halo, cyano, hydroxyl or C$_1$-C$_6$ alkoxyl and T$_1$ is C$_3$-C$_8$ cycloalkyl, C$_6$-C$_{10}$ aryl, 4 to 6-membered heterocycloalkyl, or 5 to 10-membered heteroaryl, or R$_b$ and R$_c$, together with the N atom to which they attach, form 4 to 7-membered heterocycloalkyl having 0 or 1 additional heteroatoms to the N atom optionally substituted with C$_1$-C$_6$ alkyl, C$_2$-C$_6$ alkenyl, C$_2$-C$_6$ alkynyl, halo, hydroxyl, carboxyl, C(O)OH, C(O)O—C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl, and each of R$_b$, R$_c$, and T$_1$ is optionally substituted with one or more substituents selected from C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

X is N or CR$_x$, in which R$_x$ is H, halo, hydroxyl, carboxyl, cyano, or R$_{S1}$, R$_{S1}$ being amino, C$_1$-C$_6$ alkoxyl, C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 6-membered heterocycloalkyl, or 5 to 6-membered heteroaryl, and R$_{S1}$ being optionally substituted with one or more substituents selected from halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

Y is H, $R_d$, $SO_2R_d$, or $COR_d$, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$ and $R_2$ independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, and m is 0, 1, or 2.

For example, A is O. In certain compounds of Formula (IV), A is O and m is 2.

In certain compounds of Formula (IV), X is N.

For example, in certain compounds, Q is $NH_2$ or $NHR_b$, in which $R_b$ is -$M_1$-$T_1$, $M_1$ being a bond or $C_1$-$C_6$ alkyl linker and $T_1$ being $C_3$-$C_8$ cycloalkyl For example, in certain compounds of Formula (IV), $R_1$ and $R_2$ are each H.

In certain compounds of Formula (IV), Y is $R_d$. For example, $R_d$ is $C_1$-$C_6$ alkyl optionally substituted with $C_3$-$C_8$ cycloalkyl or halo. For example, $R_d$ is $C_3$-$C_8$ cycloalkyl optionally substituted with $C_1$-$C_6$ alkyl or halo.

The invention also relates to a compound of Formula (IV), wherein at least one of $R_e$, $R_f$, $R_g$, and $R_h$, is halo, $C_1$-$C_6$ alkoxyl optionally substituted with one or more halo; $C_1$-$C_6$ alkylsulfonyl optionally substituted with one or more halo; $C_1$-$C_6$ alkyl optionally substituted with one or more substituents selected from CN, halo, $C_3$-$C_8$ cycloalkyl, hydroxy, and $C_1$-$C_6$ alkoxyl; $C_3$-$C_8$ cycloalkyl optionally substituted with one or more $C_1$-$C_6$ alkyl or CN; or 4 to 8-membered heterocycloalkyl optionally substituted with one or more substituents selected from CN, halo, hydroxy, $C_1$-$C_6$ alkyl and $C_1$-$C_6$ alkoxyl. For example, the compound of Formula (IV) has at least one of $R_e$, $R_f$, $R_g$, and $R_h$, selected from F; Cl; Br; $CF_3$; $OCF_3$; $SO_2CF_3$; oxetanyl optionally substituted with one or more substituents selected from CN, halo, hydroxy, $C_1$-$C_6$ alkyl and $C_1$-$C_6$ alkoxyl; $C_3$-$C_8$ cycloalkyl optionally substituted with one or more substituents selected from $C_1$-$C_4$ alkyl; and $C_1$-$C_4$ alkyl optionally substituted with one or more substituents selected from halo, $C_3$-$C_8$ cycloalkyl, hydroxy and $C_1$-$C_6$ alkoxyl.

For example, the invention relates to compounds of Formula (IV) where at least one of $R_f$ and $R_g$ is alkyl, optionally substituted with hydroxyl. For example, the invention relates to compounds where at least one of $R_f$ and $R_g$ is t-butyl substituted with hydroxyl.

The invention relates to a compound selected from Compounds 1-140. The invention also relates to a salt of a compound selected from Compounds 1-140. The invention also relates to an N-oxide of compound selected from Compounds 1-140. The invention also relates to a salt of an N-oxide of compound selected from Compounds 1-140. For example, the invention relates to a compound selected from Compounds 1-7, 9-109, and 111-140.

The invention also relates to a pharmaceutical composition of a therapeutically effective amount of a compound of Formula (IV) and a pharmaceutically acceptable carrier.

The invention also relates to a pharmaceutical composition of a therapeutically effective amount of a salt of a compound of Formula (IV) and a pharmaceutically acceptable carrier.

The invention also relates to a pharmaceutical composition of a therapeutically effective amount of a hydrate of a compound of Formula (IV) and a pharmaceutically acceptable carrier.

The invention also relates to a pharmaceutical composition of a therapeutically effective amount of a compound selected from Compounds 1-140 and a pharmaceutically acceptable carrier. The invention also relates to a pharmaceutical composition of a therapeutically effective amount of a salt of a compound selected from Compounds 1-140 and a pharmaceutically acceptable carrier. The invention also relates to a pharmaceutical composition of a therapeutically effective amount of an N-oxide of a compound selected from Compounds 1-140 and a pharmaceutically acceptable carrier. The invention also relates to a pharmaceutical composition of a therapeutically effective amount of an N-oxide of salt of a compound selected from Compounds 1-140 and a pharmaceutically acceptable carrier. The invention also relates to a pharmaceutical composition of a therapeutically effective amount of a hydrate of a compound selected from Compounds 1-140 and a pharmaceutically acceptable carrier.

The present invention provides pharmaceutical a composition comprising one or more compounds of Formula (I), (II), (IIIa), (IIIb), or (IIIc), and one or more pharmaceutically acceptable carriers.

The invention also relates to a pharmaceutical composition of a therapeutically effective amount of a salt of a compound of Formula (I), (II), (IIIa), (IIIb), or (IIIc) and a pharmaceutically acceptable carrier.

The invention also relates to a pharmaceutical composition of a therapeutically effective amount of a hydrate of a compound of Formula (I), (II), (IIIa), (IIIb), or (IIIc) and a pharmaceutically acceptable carrier.

The present invention provides methods of treating or preventing cancer. The present invention provides methods of treating cancer. The present invention also provides methods of preventing cancer. The method includes administering to a subject in need thereof a therapeutically effective amount of the compound of Formula (I), (II), (IIIa), (IIIb), or (IIIc). The cancer can be a hematological cancer. Preferably, the cancer is leukemia. More preferably, the cancer is acute myeloid leukemia, acute lymphocytic leukemia or mixed lineage leukemia.

The present invention provides methods of treating or preventing a disease or disorder mediated by translocation of a gene on chromosome 11 q23. The present invention provides methods of treating a disease or disorder mediated by translocation of a gene on chromosome 11q23. The present invention also provides methods of preventing a disease or disorder mediated by translocation of a gene on chromosome 11 q23. The method includes administering to a subject in need thereof a therapeutically effective amount of the compound of Formula (I), (II), (IIIa), (IIIb), (IIIc) or (IV).

The present invention provides methods of treating or preventing a disease or disorder in which DOT1-mediated protein methylation plays a part or a disease or disorder mediated by DOT1-mediated protein methylation. The present invention provides methods of treating a disease or disorder in which DOT1-mediated protein methylation plays a part or a disease or disorder mediated by DOT1-mediated protein methylation. The present invention also provides methods of preventing a disease or disorder in which DOT1-mediated protein methylation plays a part or a disease or disorder mediated by DOT1-mediated protein methylation. The method includes administering to a subject in need thereof a therapeutically effective amount of the compound of Formula (I), (II), (IIIa), (IIIb), (IIIc) or (IV).

The present invention provides methods of inhibiting DOT1L activity in a cell. The method includes contacting the cell with an effective amount of one or more of the compound of Formula (I), (II), (IIIa), (IIIb), (IIIc) or (IV).

Still another aspect of the invention relates to a method of reducing the level of Histone H3 Lysine residue 79 (H3-K79) methylation in a cell. The method includes contacting a cell with a compound of the present invention. Such method can be used to ameliorate any condition which is caused by or potentiated by the activity of DOT1 through H3-K79 methylation.

The present invention relates to use of the compounds disclosed herein in preparation of a medicament for treating or preventing cancer. The use includes a compound of Formula (I), (II), (IIIa), (IIIb), (IIIc) or (IV) for administration to a subject in need thereof in a therapeutically effective amount. The cancer can be a hematological cancer. Preferably, the cancer is leukemia. More preferably, the cancer is acute myeloid leukemia, acute lymphocytic leukemia or mixed lineage leukemia.

The present invention provides use of the compounds disclosed herein in preparation of a medicament for treating or preventing a disease or disorder mediated by translocation of a gene on chromosome 11q23. The use includes a compound of Formula (I), (II), (IIIa), (IIIb), (IIIc) or (IV) for administration to a subject in need thereof in a therapeutically effective amount.

The present invention provides use of the compounds disclosed herein in preparation of a medicament for treating or preventing a disease or disorder in which DOT1-mediated protein methylation plays a part or a disease or disorder mediated by DOT1-mediated protein methylation. The use includes a compound of Formula (I), (II), (IIIa), (IIIb), (IIIc) or (IV) for administration to a subject in need thereof in a therapeutically effective amount.

The present invention provides use of the compounds disclosed herein for inhibiting DOT1L activity in a cell. The use includes contacting the cell with an effective amount of one or more of the compound of Formula (I), (II), (IIIa), (IIIb), (IIIc) or (IV).

Still another aspect of the invention relates to a use of the compounds disclosed herein for reducing the level of Histone H3 Lysine residue 79 (H3-K79) methylation in a cell. The use includes contacting a cell with a compound of the present invention. Such use can ameliorate any condition which is caused by or potentiated by the activity of DOT1 through H3-K79 methylation.

In the formulae presented herein, the variables can be selected from the respective groups of chemical moieties later defined in the detailed description.

In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use in modulating an epigenetic enzyme. In certain embodiments, the compounds of the present invention are useful for treating, preventing, or reducing the risk of cancer or for the manufacture of a medicament for treating, preventing, or reducing the risk of cancer. Accordingly, the compounds or the formulations can be administered, for example, via oral, parenteral, otic, ophthalmic, nasal, or topical routes, to provide an effective amount of the compound to the mammal.

Representative compounds of the present invention include compounds listed in Table 1.

TABLE 1

| Cmpd No. | Structure | Chemical Name | Data (MS or NMR) |
|---|---|---|---|
| 1 | 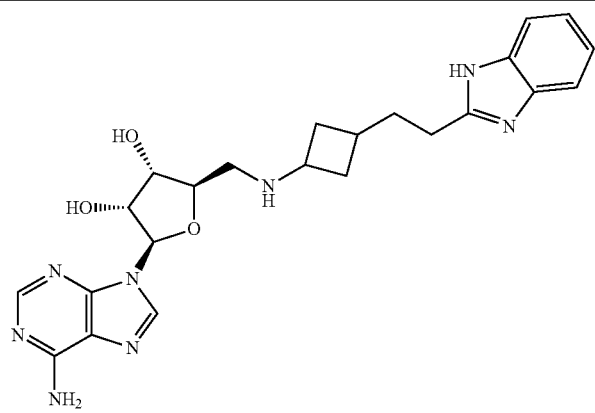 | (2R,3S,4R,5R)-2-(((3-(2-(1H-benzo[d]imidazol-2-yl)ethyl)cyclobutyl)amino)methyl)-5-(6-amino-9H-purin-9-yl)tetrahydrofuran-3,4-diol | |

TABLE 1-continued

| Cmpd No. | Structure | Chemical Name | Data (MS or NMR) |
|---|---|---|---|
| 2 | 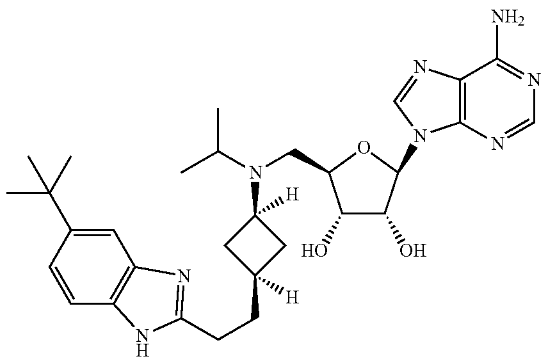 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1] | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol | 563.4 (M + H)+ |
| 3 | 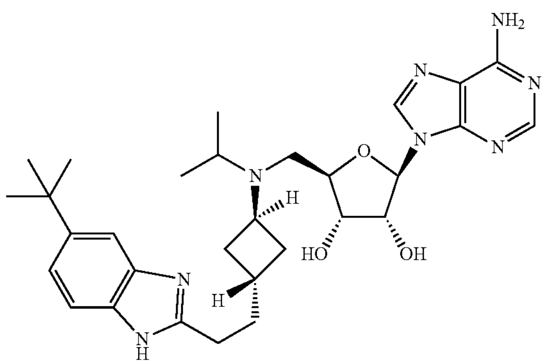 [SMILES: CC(C)N(C[C@H]1O[C@@H](n2cnc3c(N)ncnc32)[C@H](O)[C@@H]1O)[C@H]1C[C@H](CCc2nc3cc(C(C)(C)C)ccc3[nH]2)C1] | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(isopropyl)amino)methyl)tetrahydrofuran-3,4-diol | 563.5 (M + H)+ |
| 4 | 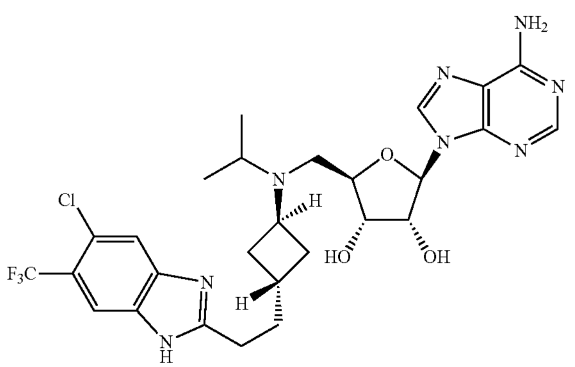 [SMILES: CC(C)N(C[C@H]1O[C@@H](n2cnc3c(N)ncnc32)[C@H](O)[C@@H]1O)[C@H]1C[C@H](CCc2nc3cc(Cl)c(C(F)(F)F)cc3[nH]2)C1] | (2R,3R,4S,5R)-2-(6-amino-9H-purin-9-yl)-5-((((1s,3R)-3-(2-(5-chloro-6-(trifluoromethyl)-1H-benzo[d]imidazol-2-yl)ethyl)cyclobutyl)(isopropyl)amino)methyl)tetrahydrofuran-3,4-diol | 609.2 (M + H)+ |
| 5 | 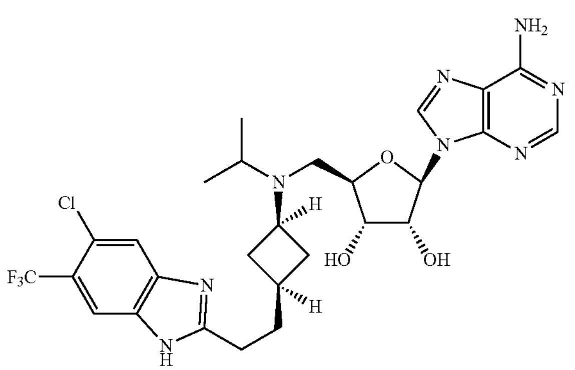 [SMILES: CC(C)N(C[C@H]1O[C@@H](n2cnc3c(N)ncnc32)[C@H](O)[C@@H]1O)[C@H]1C[C@@H](CCc2nc3cc(Cl)c(C(F)(F)F)cc3[nH]2)C1] | (2R,3R,4S,5R)-2-(6-amino-9H-purin-9-yl)-5-((((1r,3S)-3-(2-(5-chloro-6-(trifluoromethyl)-1H-benzo[d]imidazol-2-yl)ethyl)cyclobutyl)(isopropyl)amino)methyl)tetrahydrofuran-3,4-diol | 609.2 (M + H)+ |

TABLE 1-continued

| Cmpd No. | Structure | Chemical Name | Data (MS or NMR) |
|---|---|---|---|
| 6 | 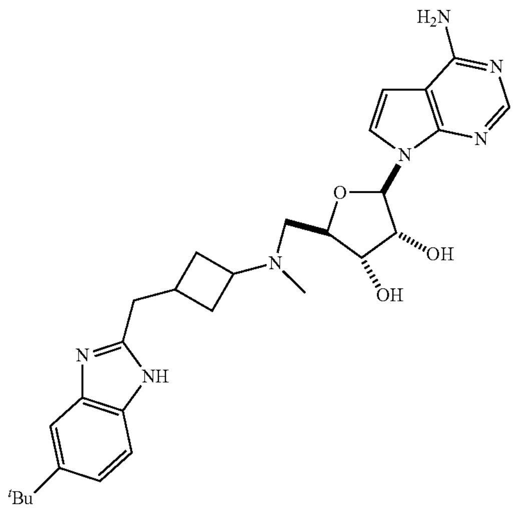 | (2R,3R,4S,5R)-2-(4-amino-7H-pyrrolo[2,3-d]pyrimidin-7-yl)-5-(((3-((5-(tert-butyl)-1H-benzo[d]imidazol-2-yl)methyl)cyclobutyl)(methyl)amino)meth-ly)tetrahydrofuran-3,4-diol | 520.4 (M + H)+ |
| 7 | 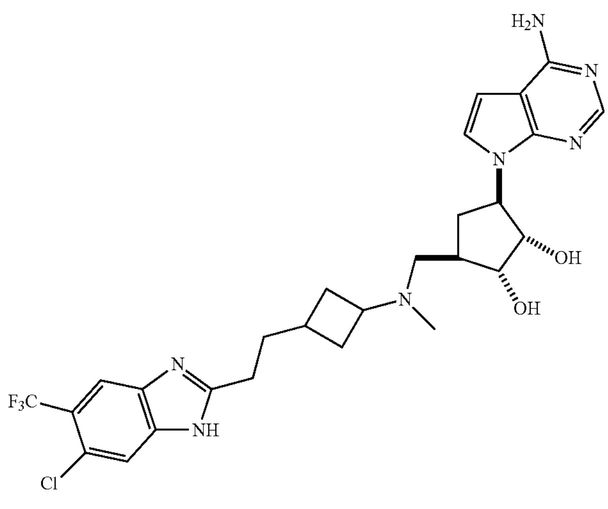 | (1R,2S,3R,5R)-3-(4-amino-7H-pyrrolo[2,3-d]pyrimidin-7-yl)-5-(((3-(2-(6-chloro-5-(trifluoromethyl)-1H-benzo[d]imidazol-2-yl)ethyl)cyclobutyl)(methyl)amino)methyl)cyclopentane-1,2-diol | 579.7 (M + H)+ |
| 8 | 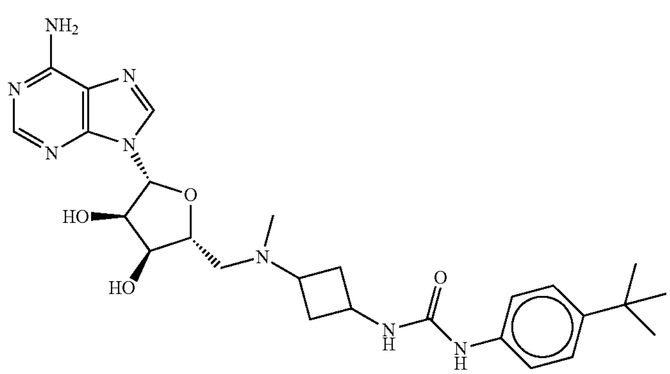 | 1-(3-((((2R,3S,4R,5R)-5-(6-amino-9H-purin-9-yl)-3,4-dihydroxytetrahydrofuran-2-yl)methyl)(methyl)amino)cyclobutyl)-3-(4-tert-butylphenyl)urea | 525.5 (M + H)+ |

TABLE 1-continued

| Cmpd No. | Structure | Chemical Name | Data (MS or NMR) |
|---|---|---|---|
| 9 | 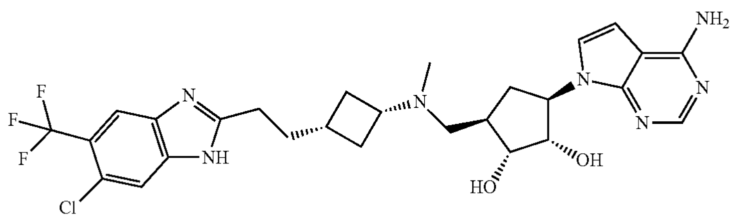 [SMILES: CN(C[C@H]1C[C@@H](n2ccc3c(N)ncnc32)[C@H](O)[C@@H]1O)[C@H]1C[C@@H](CCc2nc3cc(C(F)(F)F)c(Cl)cc3[nH]2)C1] | (1R,2S,3R,5R)-3-(4-amino-7H-pyrrolo[2,3-d]pyrimidin-7-yl)-5-((((1r,3S)-3-(2-(6-chloro-5-(trifluoromethyl)-1H-benzo[d]imidazol-2-yl)ethyl)cyclobutyl)(methyl)amino)methyl)cyclopentane-1,2-diol | 578.3 (M + H)$^+$ |
| 10 | 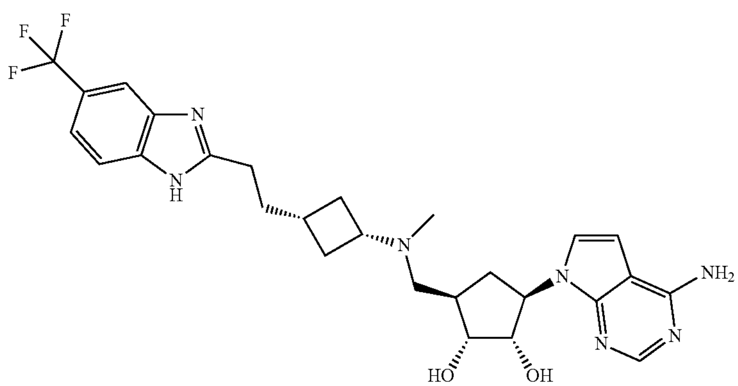 [SMILES: CN(C[C@H]1C[C@@H](n2ccc3c(N)ncnc32)[C@H](O)[C@@H]1O)[C@H]1C[C@@H](CCc2nc3cc(C(F)(F)F)ccc3[nH]2)C1] | (1R,2S,3R,5R)-3-(4-amino-7H-pyrrolo[2,3-d]pyrimidin-7-yl)-5-((methyl((1r,3S)-3-(2-(5-(trifluoromethyl)-1H-benzo[d]imidazol-2-yl)ethyl)cyclobutyl)amino)methyl)cyclopentane-1,2-diol | 544.3 (M + H)$^+$ |
| 11 | 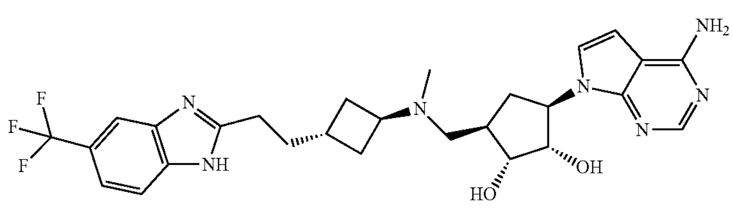 [SMILES: CN(C[C@H]1C[C@@H](n2ccc3c(N)ncnc32)[C@H](O)[C@@H]1O)[C@H]1C[C@H](CCc2nc3cc(C(F)(F)F)ccc3[nH]2)C1] | (1R,2S,3R,5R)-3-(4-amino-7H-pyrrolo[2,3-d]pyrimidin-7-yl)-5-((methyl((1s,3R)-3-(2-(5-(trifluoromethyl)-1H-benzo[d]imidazol-2-yl)ethyl)cyclobutyl)amino)methyl)cyclopentane-1,2-diol | 544.3 (M + H)$^+$ |
| 12 | 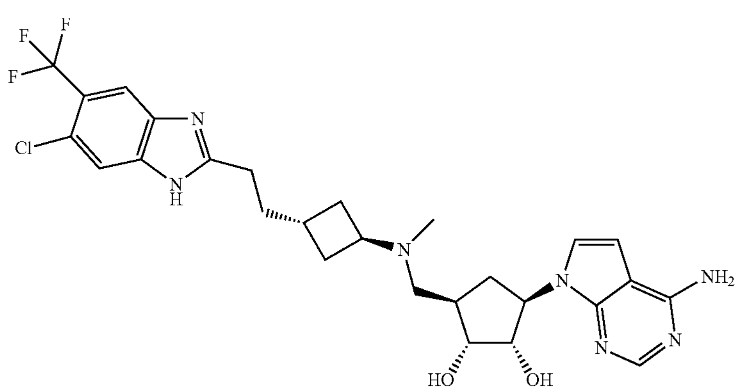 [SMILES: CN(C[C@H]1C[C@@H](n2ccc3c(N)ncnc32)[C@H](O)[C@@H]1O)[C@H]1C[C@H](CCc2nc3cc(C(F)(F)F)c(Cl)cc3[nH]2)C1] | (1R,2S,3R,5R)-3-(4-amino-7H-pyrrolo[2,3-d]pyrimidin-7-yl)-5-((((1s,3R)-3-(2-(6-chloro-5-(trifluoromethyl)-1H-benzo[d]imidazol-2-yl)ethyl)cyclobutyl)(methyl)amino)methyl)cyclopentane-1,2-diol | 578.3 (M + H)$^+$ |

TABLE 1-continued

| Cmpd No. | Structure | Chemical Name | Data (MS or NMR) |
|---|---|---|---|
| 13 | 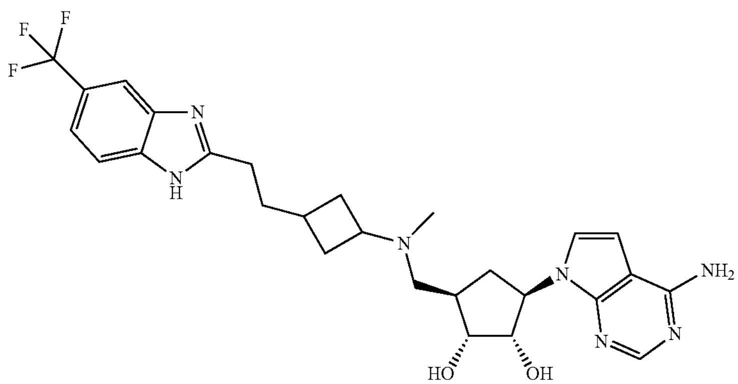 [SMILES: CN(C[C@H]1C[C@@H](n2ccc3c(N)ncnc32)[C@H](O)[C@@H]1O)C1CC(CCc2nc3cc(C(F)(F)F)ccc3[nH]2)C1] | (1R,2S,3R,5R)-3-(4-amino-7H-pyrrolo[2,3-d]pyrimidin-7-yl)-5-((methyl(3-(2-(5-(trifluoromethyl)-1H-benzo[d]imidazol-2-yl)ethyl)cyclobutyl)amino)methyl)cyclopentane-1,2-diol | 544.5 (M + H)+ |
| 14 | 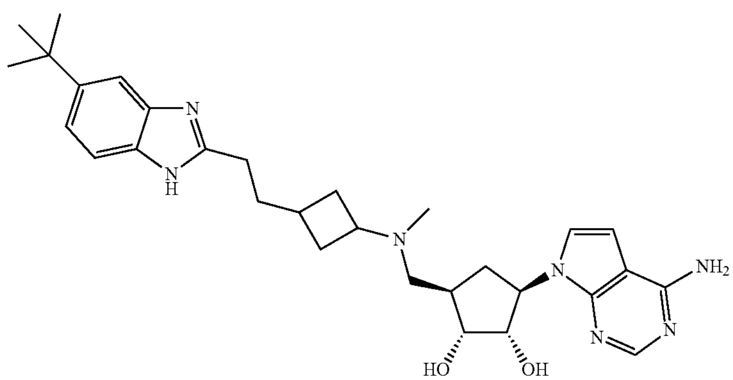 [SMILES: CN(C[C@H]1C[C@@H](n2ccc3c(N)ncnc32)[C@H](O)[C@@H]1O)C1CC(CCc2nc3cc(C(C)(C)C)ccc3[nH]2)C1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(methyl)amino)methyl)cyclopentane-1,2-diol | 532.3 (M + H)+ |
| 15 | 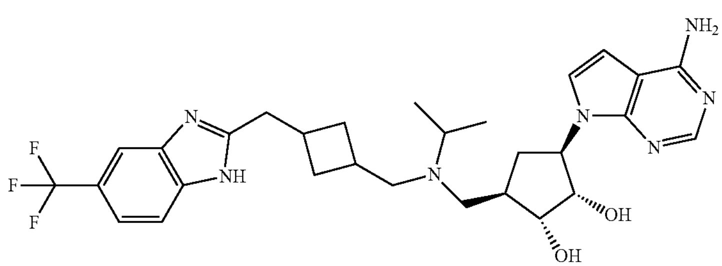 [SMILES: CC(C)N(CC1CC(Cc2nc3cc(C(F)(F)F)ccc3[nH]2)C1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-((isopropyl((3-((5-(trifluoromethyl)-1H-benzo[d]imidazol-2-yl)methyl)cyclobutyl)methyl)amino)methyl)cyclopentane-1,2-diol | 572.4 (M + H)+ |
| 16 | 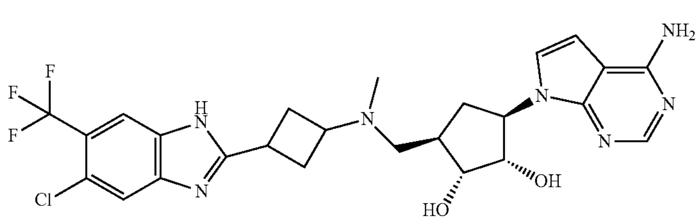 [SMILES: CN(C[C@H]1C[C@@H](n2ccc3c(N)ncnc32)[C@H](O)[C@@H]1O)C1CC(c2nc3cc(Cl)c(C(F)(F)F)cc3[nH]2)C1] | (1R,2S,3R,5R)-3-(4-amino-7H-pyrrolo[2,3-d]pyrimidin-7-yl)-5-(((3-(5-chloro-6-(trifluoromethyl)-1H-benzo[d]imidazol-2-yl)cyclobutyl)(methyl)amino)methyl)cyclopentane-1,2-diol | 550.3 (M + H)+ |

TABLE 1-continued

| Cmpd No. | Structure | Chemical Name | Data (MS or NMR) |
|---|---|---|---|
| 17 | 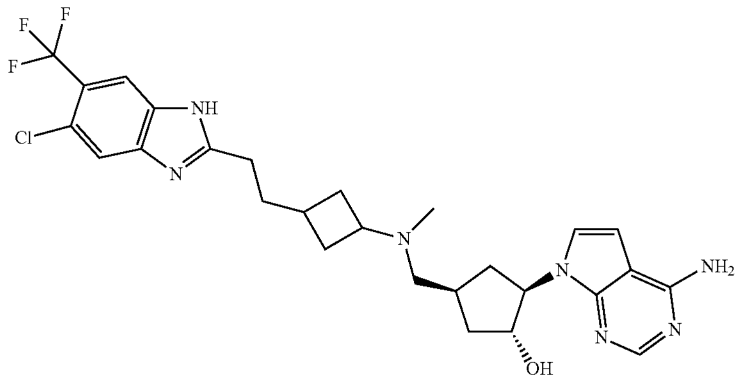 [SMILES: CN(C[C@@H]1C[C@@H](O)[C@H](n2ccc3c(N)ncnc32)C1)C1CC(CCc2nc3cc(Cl)c(C(F)(F)F)cc3[nH]2)C1] | (1R,2R,4S)-2-(4-amino-7H-pyrrolo[2,3-d]pyrimidin-7-yl)-4-(((3-(2-(5-chloro-6-(trifluoromethyl)-1H-benzo[d]imidazol-2-yl)ethyl)cyclobutyl)(methyl)amino)methyl)cyclopentanol | 562.3 (M + H)+ |
| 18 | 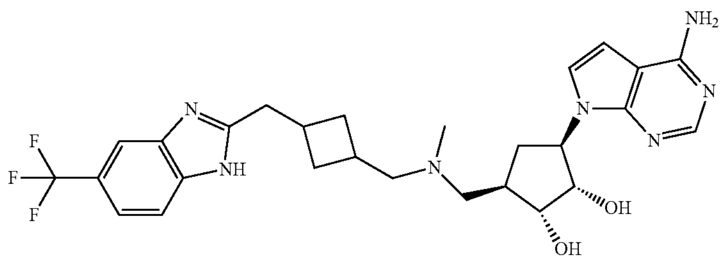 [SMILES: CN(CC1CC(Cc2nc3cc(C(F)(F)F)ccc3[nH]2)C1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-((methyl((3-((5-(trifluoromethyl)-1H-benzo[d]imidazol-2-yl])methyl)cyclobutyl)methyl)amino)methyl)cyclopentane-1,2-diol | 544 (M + H)+ |
| 19 | 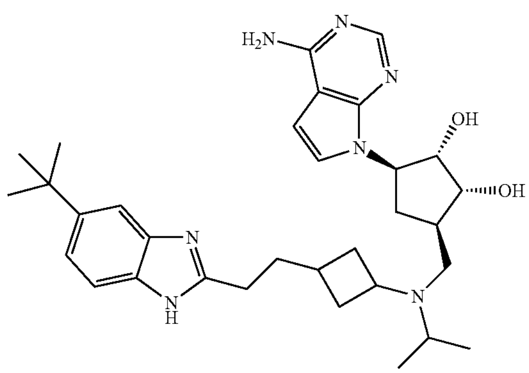 [SMILES: CC(C)N(C[C@H]1C[C@@H](n2ccc3c(N)ncnc32)[C@H](O)[C@@H]1O)C1CC(CCc2nc3cc(C(C)(C)C)ccc3[nH]2)C1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(isopropyl)amino)methyl)cyclopentane-1,2-diol | NMR data |
| 20 | 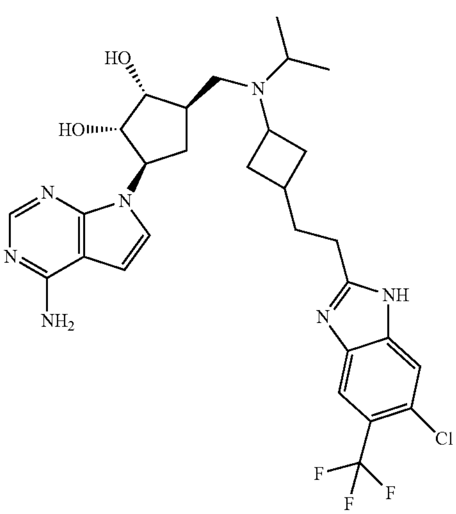 [SMILES: CC(C)N(C[C@H]1C[C@@H](n2ccc3c(N)ncnc32)[C@H](O)[C@@H]1O)C1CC(CCc2nc3cc(C(F)(F)F)c(Cl)cc3[nH]2)C1] | (1R,2S,3R,5R)-3-(4-amino-7H-pyrrolo[2,3-d]pyrimidin-7-yl)-5-(((3-(2-(6-chloro-5-(trifluoromethyl)-1H-benzo[d]imidazol-2-yl)ethyl)cyclobutyl)(isopropyl)amino)methyl)cyclopentane-1,2-diol | NMR data |

TABLE 1-continued

| Cmpd No. | Structure | Chemical Name | Data (MS or NMR) |
|---|---|---|---|
| 21 | 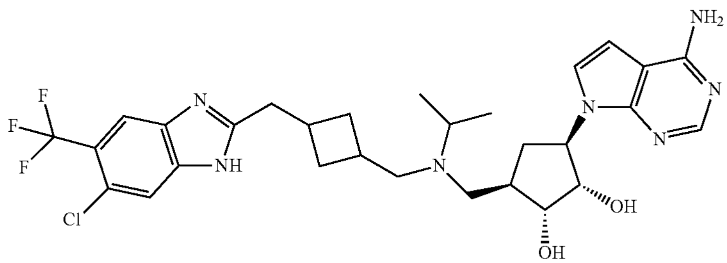 [SMILES: CC(C)N(CC1CC(Cc2nc3cc(C(F)(F)F)c(Cl)cc3[nH]2)C1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-((((3-((6-chloro-5-(trifluoromethyl)-1H-benzo[d]imidazol-2-yl)methyl)cyclobutyl)methyl)(isopropyl)amino)methyl)cyclopentane-1,2-diol | 606.3 (M + H)+ |
| 22 | 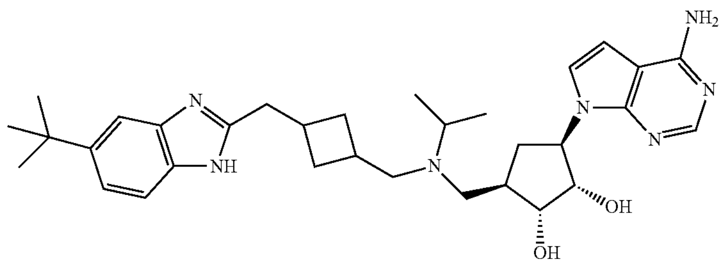 [SMILES: CC(C)N(CC1CC(Cc2nc3cc(C(C)(C)C)ccc3[nH]2)C1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-((((3-((5-(tert-butyl)-1H-benzo[d]imidazol-2-yl)methyl)cyclobutyl)methyl)(isopropyl)amino)methyl)cyclopentane-1,2-diol | 560.4 (M + H)+ |
| 23 | 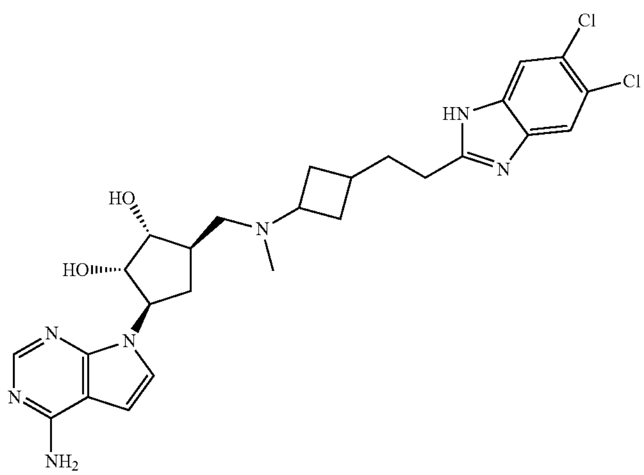 [SMILES: CN(C[C@H]1C[C@@H](n2ccc3c(N)ncnc32)[C@H](O)[C@@H]1O)C1CC(CCc2nc3cc(Cl)c(Cl)cc3[nH]2)C1] | (1R,2S,3R,5R)-3-(4-amino-7H-pyrrolo[2,3-d]pyrimidin-7-yl)-5-(((3-(2-(5,6-dichloro-1H-benzo[d]imidazol-2-yl)ethyl)cyclobutyl)(methyl)amino)methyl)cyclopentane-1,2-diol | NMR data |
| 24 | 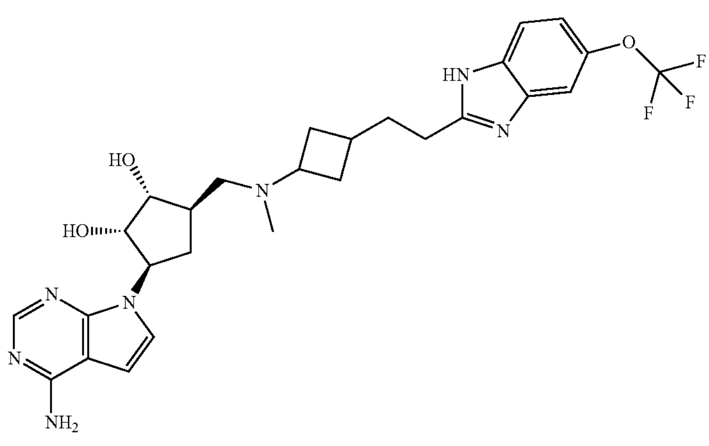 [SMILES: CN(C[C@H]1C[C@@H](n2ccc3c(N)ncnc32)[C@H](O)[C@@H]1O)C1CC(CCc2nc3cc(OC(F)(F)F)ccc3[nH]2)C1] | (1R,2S,3R,5R)-3-(4-amino-7H-pyrrolo[2,3-d]pyrimidin-7-yl)-5-((methyl(3-(2-(5-(trifluoromethoxy)-1H-benzo[d]imidazol-2-yl)ethyl)cyclobutyl)amino)methyl)cyclopentane-1,2-diol | 558.2 (M + H)+ |

TABLE 1-continued

| Cmpd No. | Structure | Chemical Name | Data (MS or NMR) |
|---|---|---|---|
| 25 | 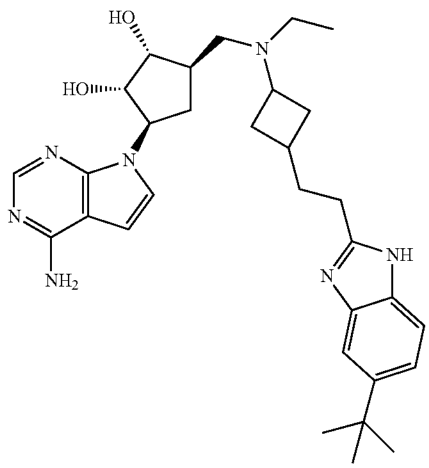 [SMILES: CCN(C[C@H]1C[C@@H](n2ccc3c(N)ncnc32)[C@H](O)[C@@H]1O)C1CC(CCc2nc3cc(C(C)(C)C)ccc3[nH]2)C1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(ethyl)amino)methyl)cyclopentane-1,2-diol | 546.3 (M + H)+ |
| 26 | 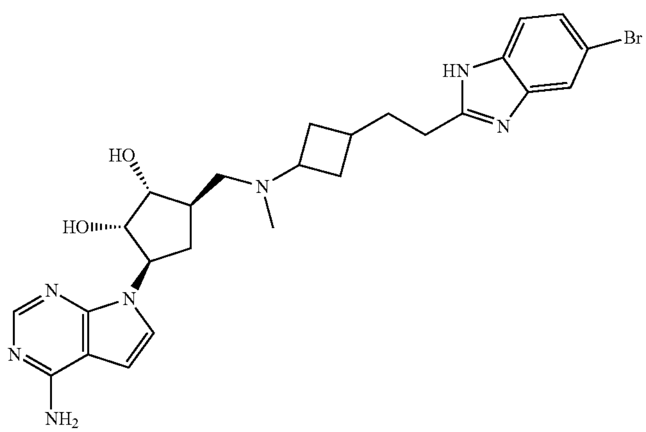 | (1R,2S,3R,5R)-3-(4-amino-7H-pyrrolo[2,3-d]pyrimidin-7-yl)-5-(((3-(2-(5-bromo-1H-benzo[d]imidazol-2-yl)ethyl)cyclobutyl)(methyl)amino)methyl)cyclopentane-1,2-diol | 554.1 (M + H)+ |
| 27 | 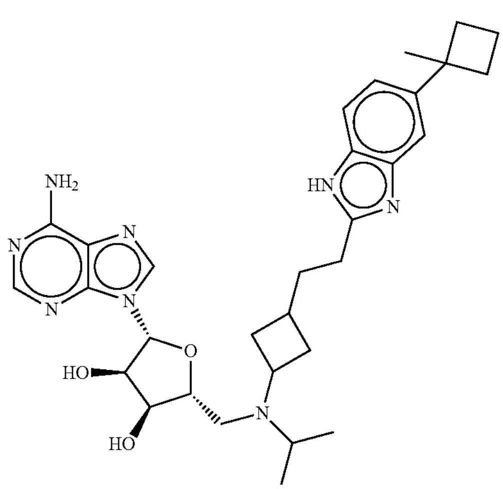 | (2R,3R,4S,5R)-2-(6-amino-9H-purin-9-yl)-5-((isopropyl(3-(2-(5-(1-methylcyclobutyl)-1H-benzo[d]imidazol-2-yl)ethyl)cyclobutyl)amino)methyl)tetrahydrofuran-3,4-diol | 575.5 (M + H)+ |

TABLE 1-continued

| Cmpd No. | Structure | Chemical Name | Data (MS or NMR) |
|---|---|---|---|
| 28 | 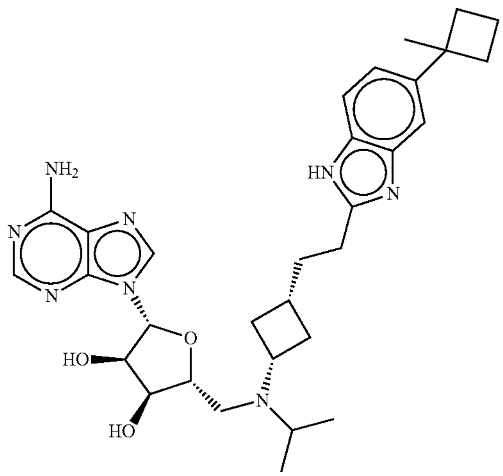 | (2R,3R,4S,5R)-2-(6-amino-9H-purin-9-yl)-5-((isopropyl((1r,3S)-3-(2-(5-(1-methylcyclobutyl)-1H-benzo[d]imidazol-2-yl)ethyl)cyclobutyl)amino)methyl)tetrahydrofuran-3,4-diol | 575.5 (M + H)+ |
| 29 | 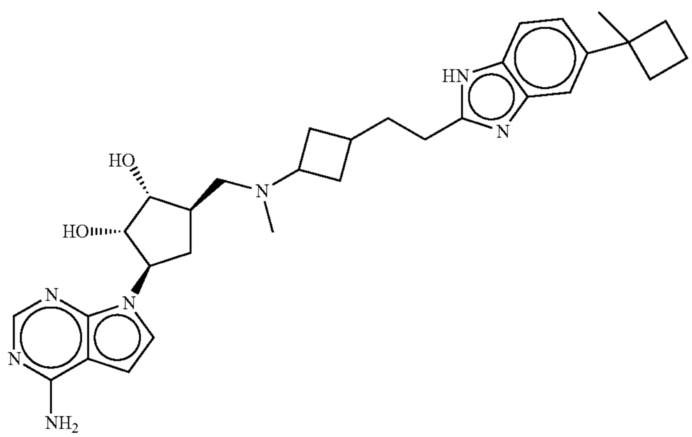 | (1R,2S,3R,5R)-3-(4-amino-7H-pyrrolo[2,3-d]pyrimidin-7-yl)-5-((methyl(3-(2-(5-(1-methylcyclobutyl)-1H-benzo[d]imidazol-2-yl)ethyl)cyclobutyl)amino)methyl)cyclopentane-1,2-diol | 544.4 (M + H)+ |
| 30 | 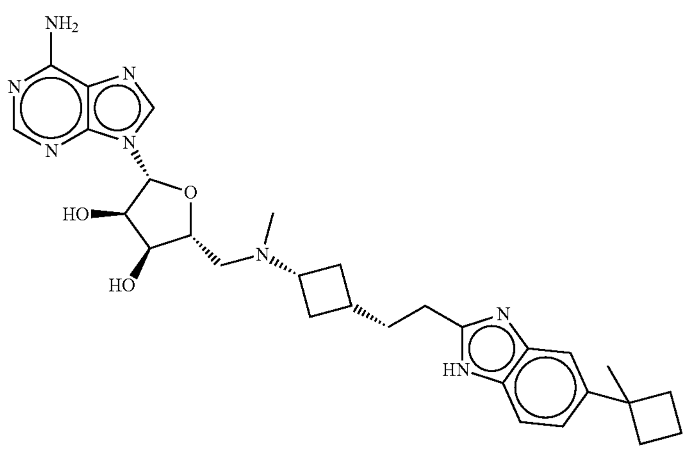 | (2R,3R,4S,5R)-2-(6-amino-9H-purin-9-yl)-5-((methyl((1r,3S)-3-(2-(5-(1-methylcyclobutyl)-1H-benzo[d]imidazol-2-yl)ethyl)cyclobutyl)amino)methyl)tetrahydrofuran-3,4-diol | 547.6 (M + H)+ |

TABLE 1-continued

| Cmpd No. | Structure | Chemical Name | Data (MS or NMR) |
|---|---|---|---|
| 31 | 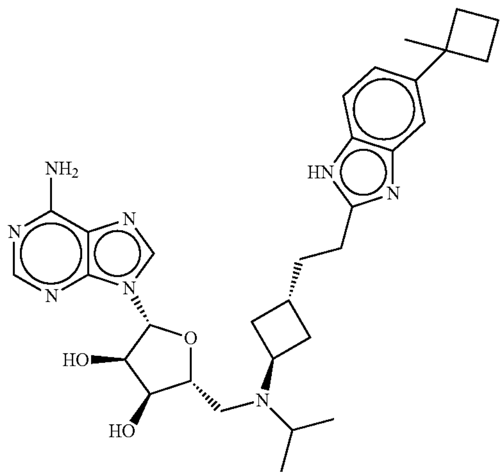 | (2R,3R,4S,5R)-2-(6-amino-9H-purin-9-yl)-5-((isopropyl((1s,3R)-3-(2-(5-(1-methylcyclobutyl)-1H-benzo[d]imidazol-2-yl)ethyl)cyclobutyl)amino)methyl)tetrahydrofuran-3,4-diol | 575.6 (M + H)+ |
| 32 | 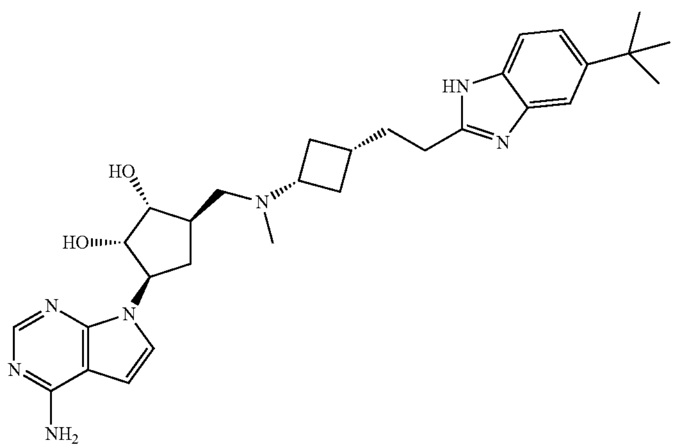 [SMILES: CN(C[C@H]1C[C@@H](n2ccc3c(N)ncnc32)[C@H](O)[C@@H]1O)[C@H]1C[C@@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(methyl)amino)methyl)cyclopentane-1,2-diol | 532.4 (M + H)+ |
| 33 | 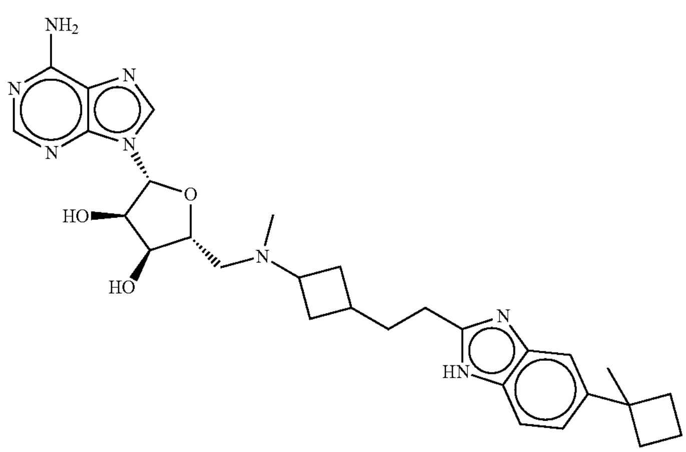 | (2R,3R,4S,5R)-2-(6-amino-9H-purin-9-yl)-5-((methyl(3-(2-(5-(1-methylcyclobutyl)-1H-benzo[d]imidazol-2-yl)ethyl)cyclobutyl)amino)methyl)tetrahydrofuran-3,4-diol | 547.3 (M + H)+ |

TABLE 1-continued

| Cmpd No. | Structure | Chemical Name | Data (MS or NMR) |
|---|---|---|---|
| 34 | 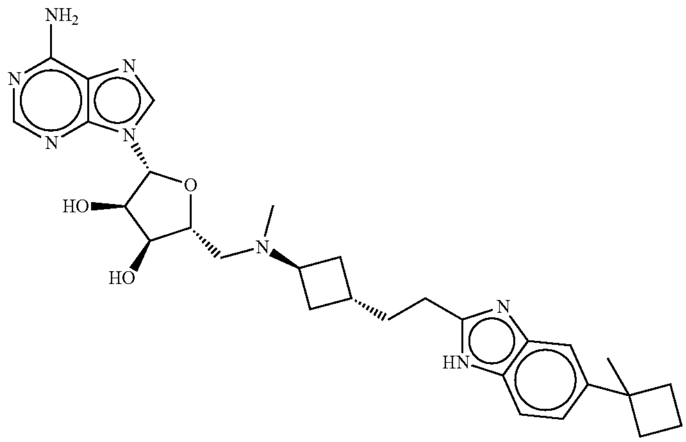 | (2R,3R,4S,5R)-2-(6-amino-9H-purin-9-yl)-5-((methyl((1s,3R)-3-(2-(5-(1-methylcyclobutyl)-1H-benzo[d]imidazol-2-yl)ethyl)cyclobutyl)amino)methyl)tetrahydrofuran-3,4-diol | 547.5 (M + H)+ |
| 35 | 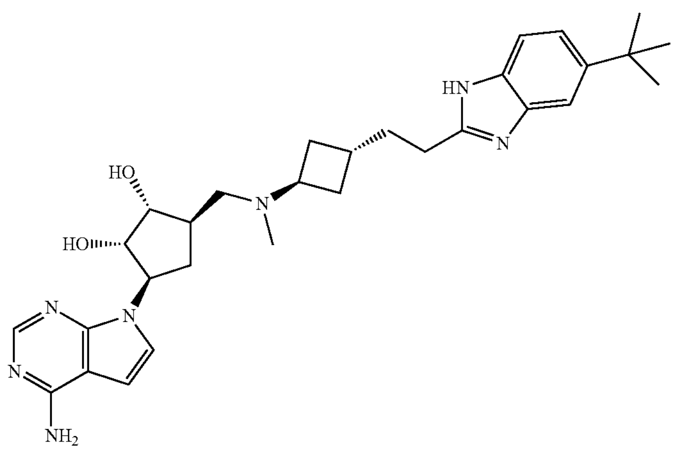 [SMILES: CN(C[C@H]1C[C@@H](n2ccc3c(N)ncnc32)[C@H](O)[C@@H]1O)[C@H]1C[C@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(methyl)amino)methyl)cyclopentane-1,2-diol | NMR data |
| 36 | 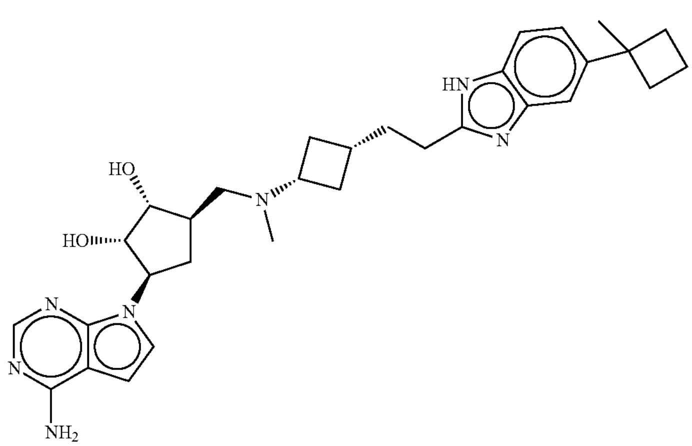 | (1R,2S,3R,5R)-3-(4-amino-7H-pyrrolo[2,3-d]pyrimidin-7-yl)-5-((methyl((1r,3S)-3-(2-(5-(1-methylcyclobutyl)-1H-benzo[d]imidazol-2-yl)ethyl)cyclobutyl)amino)methyl)cyclopentane-1,2-diol | 544.4 (M + H)+ |

TABLE 1-continued

| Cmpd No. | Structure | Chemical Name | Data (MS or NMR) |
|---|---|---|---|
| 37 | 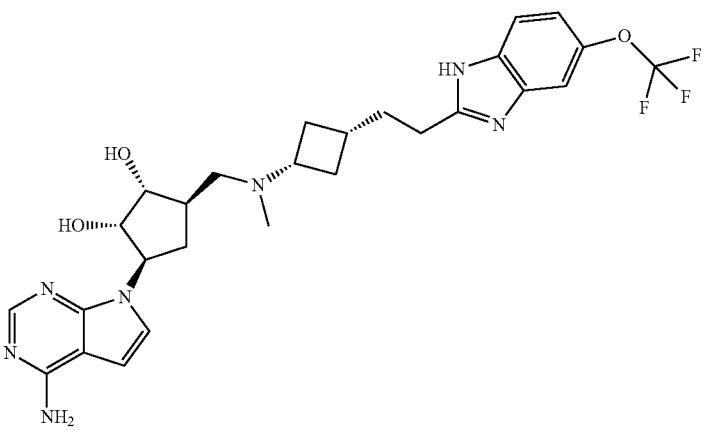 [SMILES: CN(C[C@H]1C[C@@H](n2ccc3c(N)ncnc32)[C@H](O)[C@@H]1O)[C@H]1C[C@@H](CCc2nc3cc(OC(F)(F)F)ccc3[nH]2)C1] | (1R,2S,3R,5R)-3-(4-amino-7H-pyrrolo[2,3-d]pyrimidin-7-yl)-5-((methyl((1r,3S)-3-(2-(5-(trifluoromethoxy)-1H-benzo[d]imidazol-2-yl)ethyl)cyclobutyl)amino)methyl)cyclopentane-1,2-diol | 558.3 (M + H)+ |
| 38 | 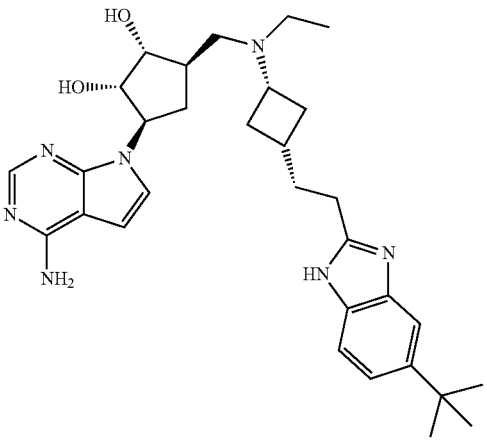 | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(ethyl)amino)methyl)cyclopentane-1,2-diol | 546.3 (M + H)+ |
| 39 | 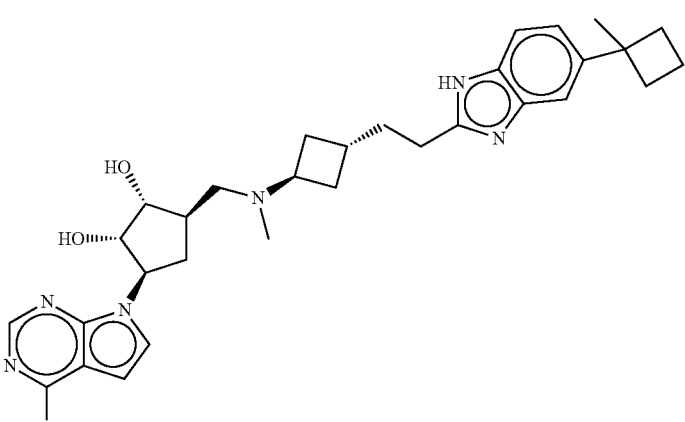 | (1R,2S,3R,5R)-3-(4-amino-7H-pyrrolo[2,3-d]pyrimidin-7-yl)-5-((methyl((1s,3R)-3-(2-(5-(1-methylcyclobutyl)-1H-benzo[d]imidazol-2-yl)ethyl)cyclobutyl)amino)methyl)cyclopentane-1,2-diol | 544.3 (M + H)+ |

TABLE 1-continued

| Cmpd No. | Structure | Chemical Name | Data (MS or NMR) |
|---|---|---|---|
| 40 | 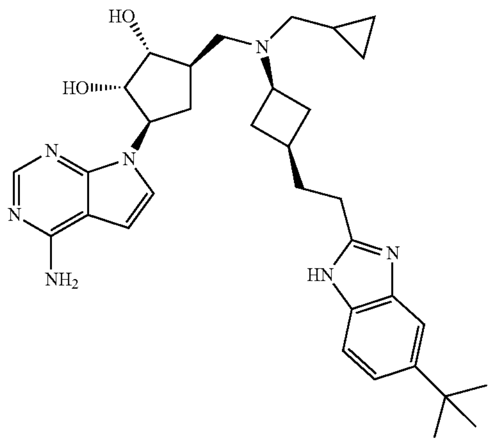 [SMILES: CC(C)(C)c1ccc2[nH]c(CC[C@H]3C[C@@H](N(CC4CC4)C[C@H]4C[C@@H](n5ccc6c(N)ncnc65)[C@H](O)[C@@H]4O)C3)nc2c1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(cyclopropylmethyl)amino)methyl)cyclopentane-1,2-diol | NMR data |
| 41 | 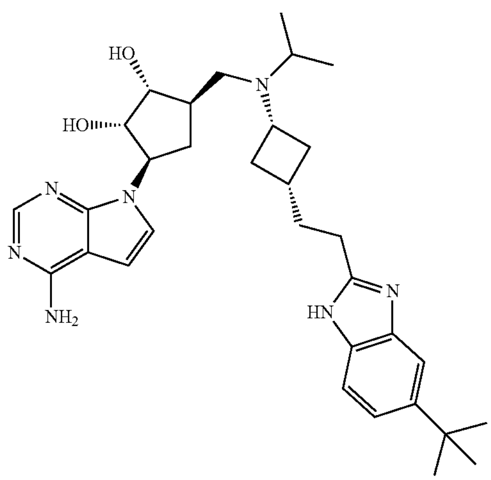 [SMILES: CC(C)N(C[C@H]1C[C@@H](n2ccc3c(N)ncnc32)[C@H](O)[C@@H]1O)[C@H]1C[C@@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(isopropyl)amino)methyl)cyclopentane-1,2-diol | NMR data |
| 42 | 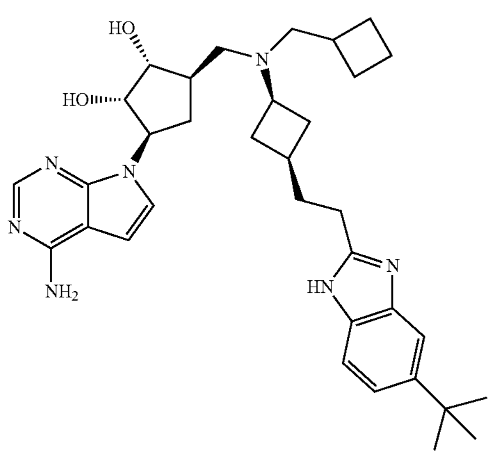 [SMILES: CC(C)(C)c1ccc2[nH]c(CC[C@H]3C[C@@H](N(CC4CCC4)C[C@H]4C[C@@H](n5ccc6c(N)ncnc65)[C@H](O)[C@@H]4O)C3)nc2c1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(cyclobutylmethyl)amino)methyl)cyclopentane-1,2-diol | 586.3 (M + H)+ |

TABLE 1-continued

| Cmpd No. | Structure | Chemical Name | Data (MS or NMR) |
|---|---|---|---|
| 43 | 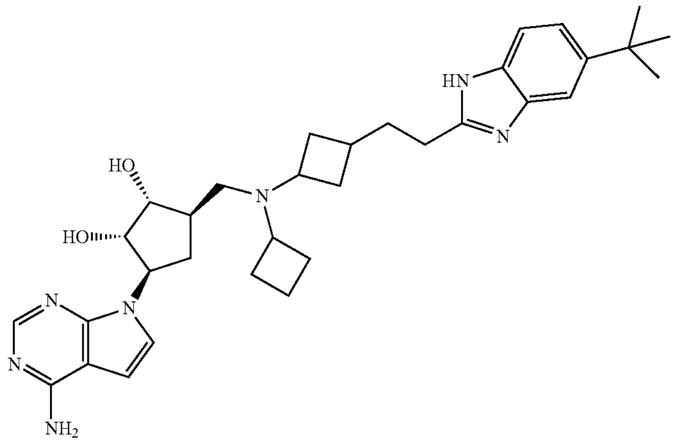 [SMILES: CC(C)(C)c1ccc2[nH]c(CCC3CC(N(C[C@H]4C[C@@H](n5ccc6c(N)ncnc65)[C@H](O)[C@@H]4O)C4CCC4)C3)nc2c1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(cyclobutyl)amino)methyl)cyclopentane-1,2-diol | 572.2 (M + H)+ |
| 44 | 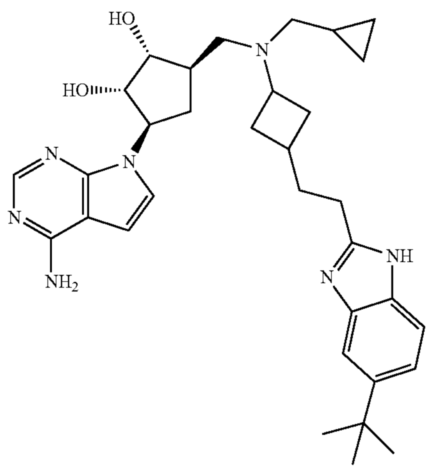 [SMILES: CC(C)(C)c1ccc2[nH]c(CCC3CC(N(CC4CC4)C[C@H]4C[C@@H](n5ccc6c(N)ncnc65)[C@H](O)[C@@H]4O)C3)nc2c1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(cyclopropylmethyl)amino)methyl)cyclopentane-1,2-diol | 572.6 (M + H)+ |
| 45 | 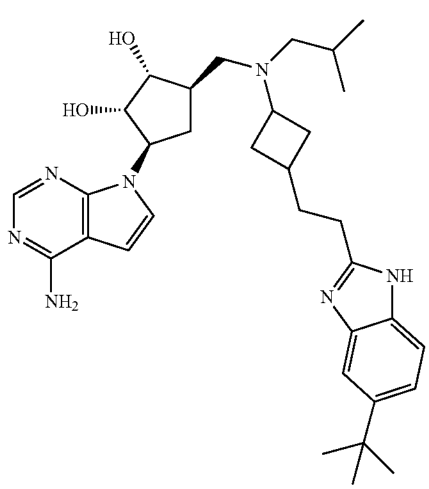 [SMILES: CC(C)CN(C[C@H]1C[C@@H](n2ccc3c(N)ncnc32)[C@H](O)[C@@H]1O)C1CC(CCc2nc3cc(C(C)(C)C)ccc3[nH]2)C1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(isobutyl)amino)methyl)cyclopentane-1,2-diol | 574.6 (M + H)+ |

TABLE 1-continued

| Cmpd No. | Structure | Chemical Name | Data (MS or NMR) |
|---|---|---|---|
| 46 | 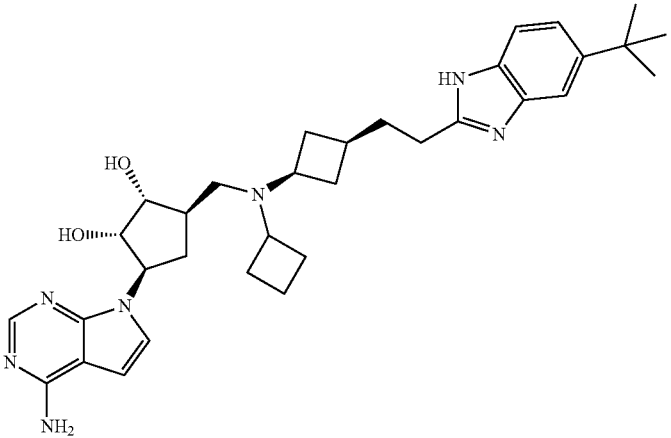 [SMILES: CC(C)(C)c1ccc2[nH]c(CC[C@H]3C[C@@H](N(C[C@H]4C[C@@H](n5ccc6c(N)ncnc65)[C@H](O)[C@@H]4O)C4CCC4)C3)nc2c1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(cyclobutyl)amino)methyl)cyclopentane-1,2-diol | 572.6 (M + H)+ |
| 47 | 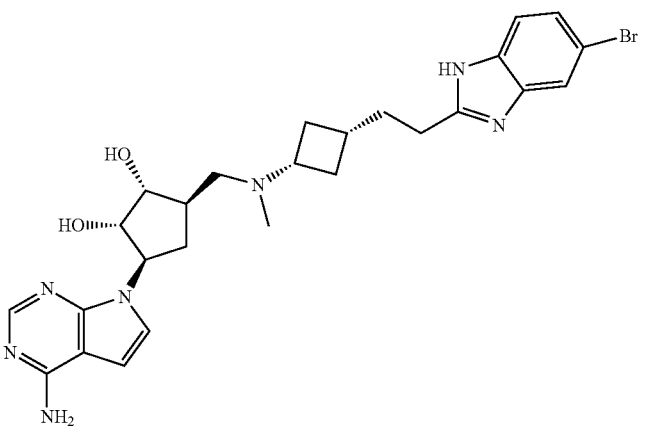 [SMILES: CN(C[C@H]1C[C@@H](n2ccc3c(N)ncnc32)[C@H](O)[C@@H]1O)[C@H]1C[C@@H](CCc2nc3cc(Br)ccc3[nH]2)C1] | (1R,2S,3R,5R)-3-(4-amino-7H-pyrrolo[2,3-d]pyrimidin-7-yl)-5-(((((1r,3S)-3-(2-(5-bromo-1H-benzo[d]imidazol-2-yl)ethyl)cyclobutyl)(methyl)amino)methyl)cyclopentane-1,2-diol | 556.0 (M + H)+ |
| 48 | 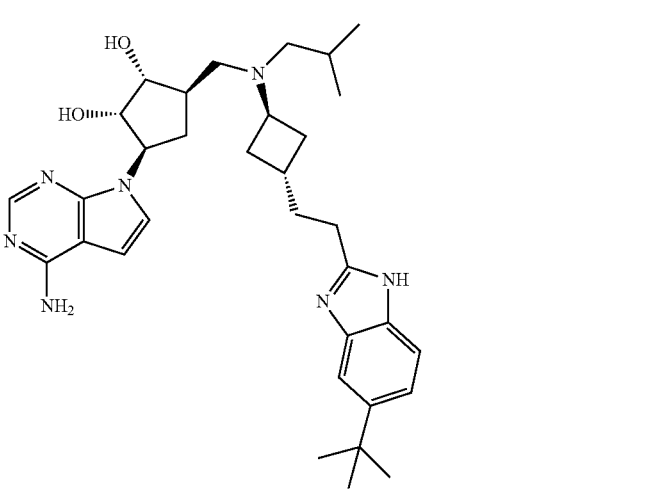 [SMILES: CC(C)CN(C[C@H]1C[C@@H](n2ccc3c(N)ncnc32)[C@H](O)[C@@H]1O)[C@H]1C[C@H](CCc2nc3cc(C(C)(C)C)ccc3[nH]2)C1] | (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(isobutyl)amino)methyl)cyclopentane-1,2-diol | 572.3 (M + H)+ |

TABLE 1-continued

| Cmpd No. | Structure | Chemical Name | Data (MS or NMR) |
|---|---|---|---|
| 49 | 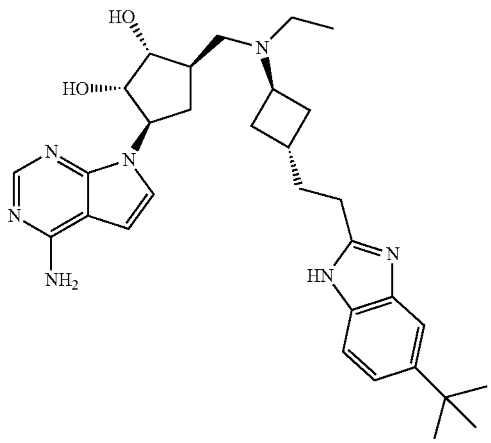 [SMILES: CCN(C[C@H]1C[C@@H](n2ccc3c(N)ncnc32)[C@H](O)[C@@H]1O)[C@H]1C[C@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(ethyl)amino)methyl)cyclopentane-1,2-diol | 546.3 (M + H)+ |
| 50 | 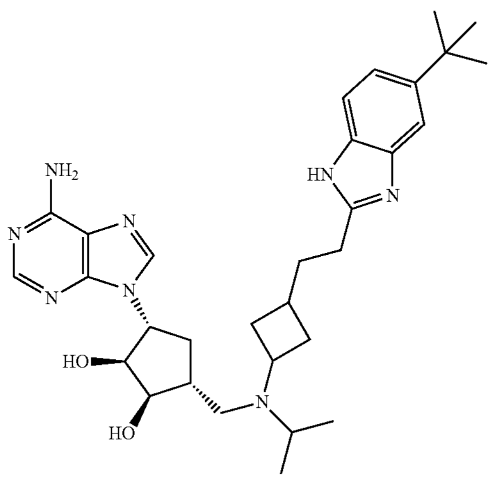 [SMILES: CC(C)N(C[C@H]1C[C@@H](n2cnc3c(N)ncnc32)[C@H](O)[C@@H]1O)C1CC(CCc2nc3cc(C(C)(C)C)ccc3[nH]2)C1] | (1R,2S,3R,5R)-3-(6-amino-9H-purin-9-yl)-5-(((3-(2-(5-(tert-butyl)-1H-benzo[d]imidazol-2-yl)ethyl)cyclobutyl)(isopropyl)amino)methyl)cyclopentane-1,2-diol | 561.4 (M + H)+ |
| 51 | 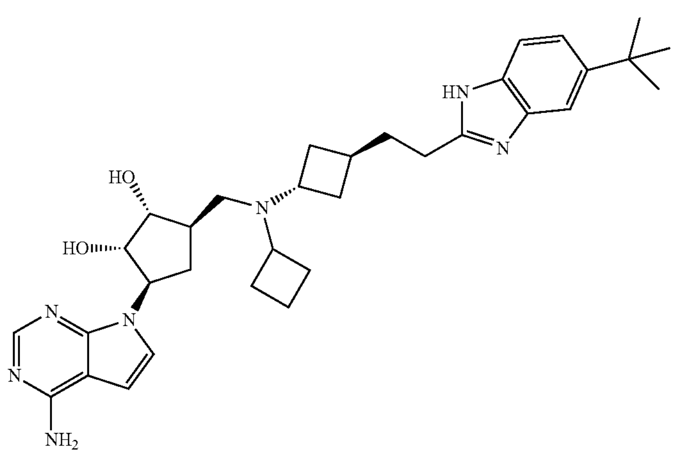 [SMILES: CC(C)(C)c1ccc2[nH]c(CC[C@H]3C[C@H](N(C[C@H]4C[C@@H](n5ccc6c(N)ncnc65)[C@H](O)[C@@H]4O)C4CCC4)C3)nc2c1] | (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(cyclobutyl)amino)methyl)cyclopentane-1,2-diol | 572.7 (M + H)+ |

TABLE 1-continued

| Cmpd No. | Structure | Chemical Name | Data (MS or NMR) |
|---|---|---|---|
| 52 | 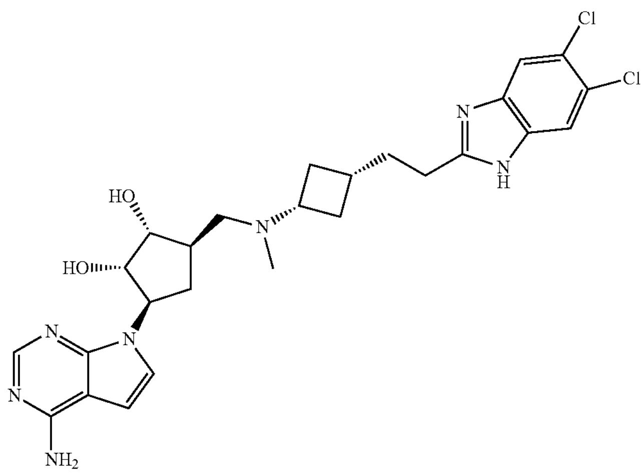 [SMILES: CN(C[C@H]1C[C@@H](n2ccc3c(N)ncnc32)[C@H](O)[C@@H]1O)[C@H]1C[C@@H](CCc2nc3cc(Cl)c(Cl)cc3[nH]2)C1] | (1R,2S,3R,5R)-3-(4-amino-7H-pyrrolo[2,3-d]pyrimidin-7-yl)-5-((((1r,3S)-3-(2-(5,6-dichloro-1H-benzo[d]imidazol-2-yl)ethyl)cyclobutyl)(methyl)amino)methyl)cyclopentane-1,2-diol | NMR data |
| 53 | 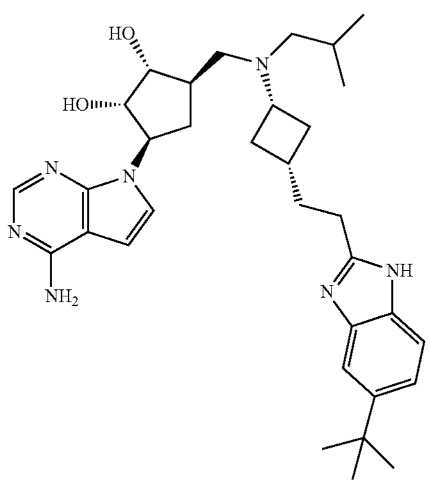 [SMILES: CC(C)CN(C[C@H]1C[C@@H](n2ccc3c(N)ncnc32)[C@H](O)[C@@H]1O)[C@H]1C[C@@H](CCc2nc3cc(C(C)(C)C)ccc3[nH]2)C1] | (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(isobutyl)amino)methyl)cyclopentane-1,2-diol | 572.3 (M − H)⁻ |
| 54 | 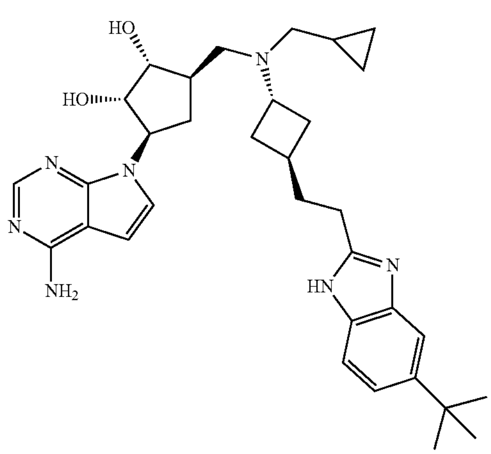 [SMILES: CC(C)(C)c1ccc2[nH]c(CC[C@H]3C[C@H](N(CC4CC4)C[C@H]4C[C@@H](n5ccc6c(N)ncnc65)[C@H](O)[C@@H]4O)C3)nc2c1] | (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(cyclopropylmethyl)amino)methyl)cyclopentane-1,2-diol | NMR data |

TABLE 1-continued

| Cmpd No. | Structure | Chemical Name | Data (MS or NMR) |
|---|---|---|---|
| 55 | 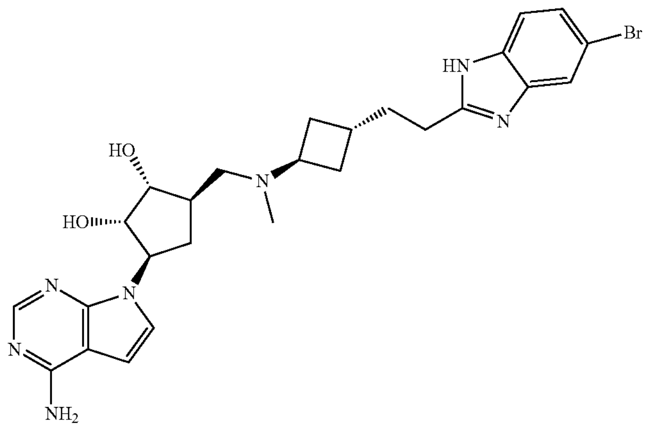 [SMILES: CN(C[C@H]1C[C@@H](n2ccc3c(N)ncnc32)[C@H](O)[C@@H]1O)[C@H]1C[C@H](CCc2nc3cc(Br)ccc3[nH]2)C1] | (1R,2S,3R,5R)-3-(4-amino-7H-pyrrolo[2,3-d]pyrimidin-7-yl)-5-((((1s,3R)-3-(2-(5-bromo-1H-benzo[d]imidazol-2-yl)ethyl)cyclobutyl)(methyl)amino)methyl)cyclopentane-1,2-diol | NMR data |
| 56 | 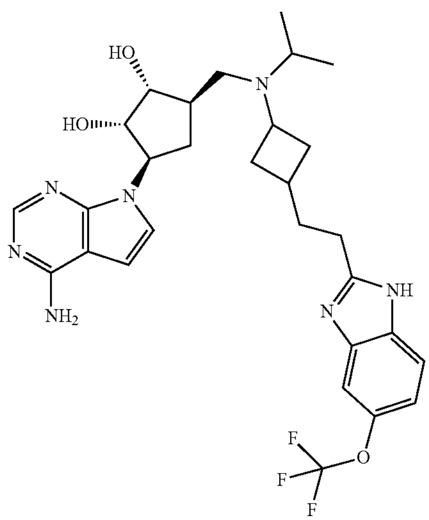 [SMILES: CC(C)N(C[C@H]1C[C@@H](n2ccc3c(N)ncnc32)[C@H](O)[C@@H]1O)C1CC(CCc2nc3cc(OC(F)(F)F)ccc3[nH]2)C1] | (1R,2S,3R,5R)-3-(4-amino-7H-pyrrolo[2,3-d]pyrimidin-7-yl)-5-((isopropyl(3-(2-(5-(trifluoromethoxy)-1H-benzo[d]imidazol-2-yl)ethyl)cyclobutyl)amino)methyl)cyclopentane-1,2-diol | 588.2 (M + H)+ |
| 57 | 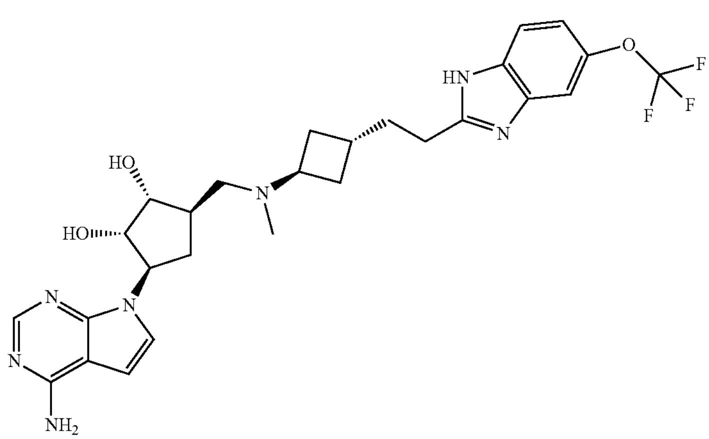 [SMILES: CN(C[C@H]1C[C@@H](n2ccc3c(N)ncnc32)[C@H](O)[C@@H]1O)[C@H]1C[C@H](CCc2nc3cc(OC(F)(F)F)ccc3[nH]2)C1] | (1R,2S,3R,5R)-3-(4-amino-7H-pyrrolo[2,3-d]pyrimidin-7-yl)-5-((methyl((1s,3R)-3-(2-(5-(trifluoromethoxy)-1H-benzo[d]imidazol-2-yl)ethyl)cyclobutyl)amino)methyl)cyclopentane-1,2-diol | 560.1 (M + H)+ |

| Cmpd No. | Structure | Chemical Name | Data (MS or NMR) |
|---|---|---|---|
| 58 | 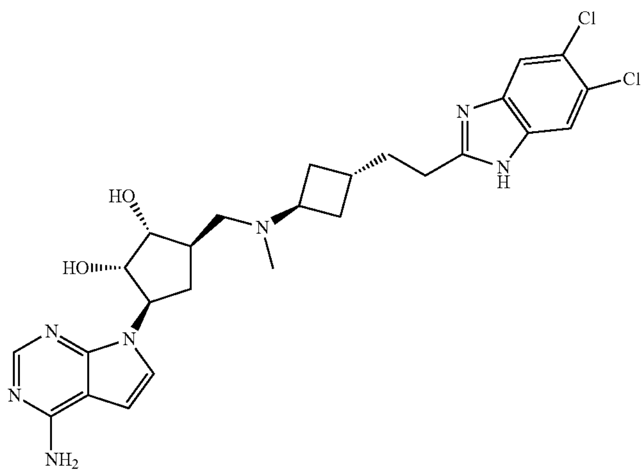 [SMILES: CN(C[C@H]1C[C@@H](n2ccc3c(N)ncnc32)[C@H](O)[C@@H]1O)[C@H]1C[C@H](CCc2nc3cc(Cl)c(Cl)cc3[nH]2)C1] | (1R,2S,3R,5R)-3-(4-amino-7H-pyrrolo[2,3-d]pyrimidin-7-yl)-5-((((1s,3R)-3-(2-(5,6-dichloro-1H-benzo[d]imidazol-2-yl)ethyl)cyclobutyl)(methyl)amino)methyl)cyclopentane-1,2-diol | NMR data |
| 59 | 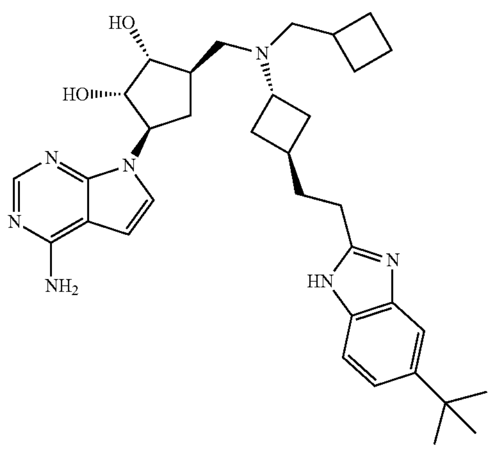 [SMILES: CC(C)(C)c1ccc2[nH]c(CC[C@H]3C[C@H](N(CC4CCC4)C[C@H]4C[C@@H](n5ccc6c(N)ncnc65)[C@H](O)[C@@H]4O)C3)nc2c1] | (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(cyclobutylmethyl)amino)methyl)cyclopentane-1,2-diol | 586.4 (M + H)+ |
| 60 | 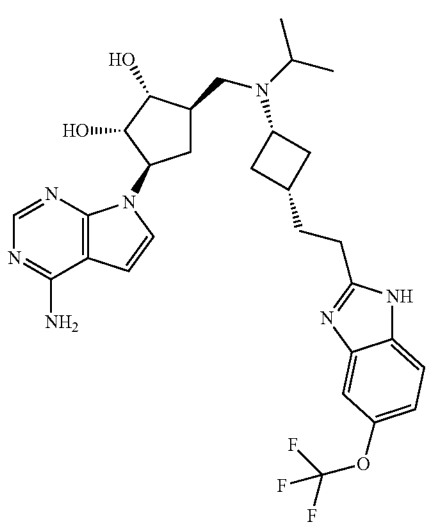 [SMILES: CC(C)N(C[C@H]1C[C@@H](n2ccc3c(N)ncnc32)[C@H](O)[C@@H]1O)[C@H]1C[C@@H](CCc2nc3cc(OC(F)(F)F)ccc3[nH]2)C1] | (1R,2S,3R,5R)-3-(4-amino-7H-pyrrolo[2,3-d]pyrimidin-7-yl)-5-((isopropyl((1r,3S)-3-(2-(5-(trifluoromethoxy)-1H-benzo[d]imidazol-2-yl)ethyl)cyclobutyl)amino)methyl)cyclopentane-1,2-diol | 588.2 (M + H)+ |

TABLE 1-continued

| Cmpd No. | Structure | Chemical Name | Data (MS or NMR) |
|---|---|---|---|
| 61 | 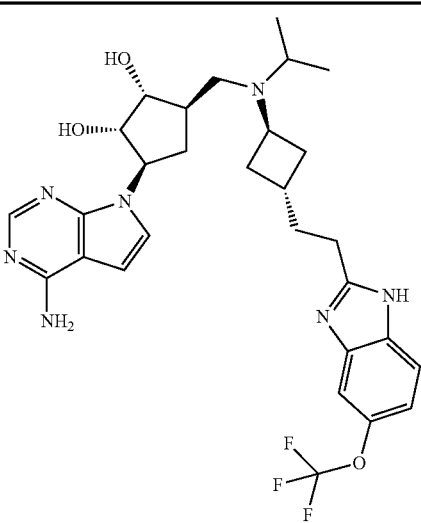 | (1R,2S,3R,5R)-3-(4-amino-7H-pyrrolo[2,3-d]pyrimidin-7-yl)-5-((isopropyl((1s,3R)-3-(2-(5-(trifluoromethoxy)-1H-benzo[d]imidazol-2-yl)ethyl)cyclobutyl)amino)methyl)cyclopentane-1,2-diol | 588.7 (M + H)+ |
| 62 | 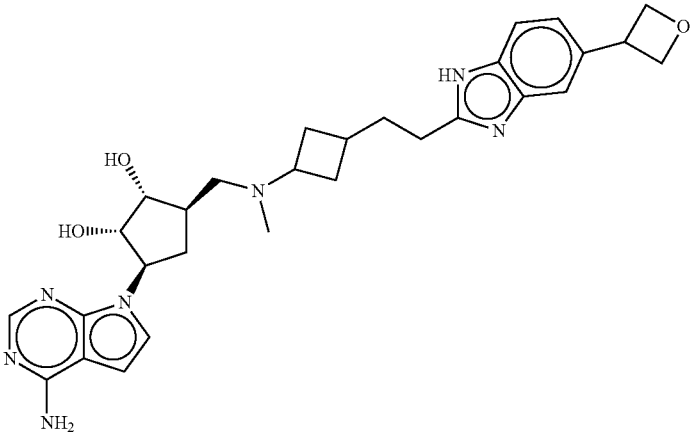 | (1R,2S,3R,5R)-3-(4-amino-7H-pyrrolo[2,3-d]pyrimidin-7-yl)-5-((methyl(3-(2-(5-(oxetan-3-yl)-1H-benzo[d]imidazol-2-yl)ethyl)cyclobutyl)amino)methyl)cyclopentane-1,2-diol | NMR data |
| 63 | 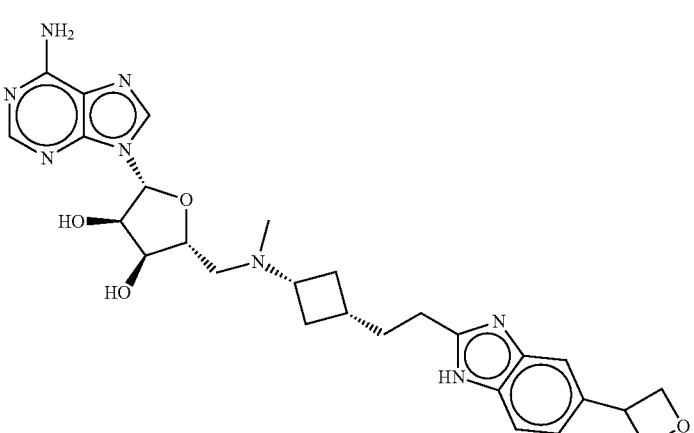 | (2R,3R,4S,5R)-2-(6-amino-9H-purin-9-yl)-5-((methyl((1r,3S)-3-(2-(5-(oxetan-3-yl)-1H-benzo[d]imidazol-2-yl)ethyl)cyclobutyl)amino)methyl)tetrahydrofuran-3,4-diol | 535.4 (M + H)+ |

TABLE 1-continued

| Cmpd No. | Structure | Chemical Name | Data (MS or NMR) |
|---|---|---|---|
| 64 | 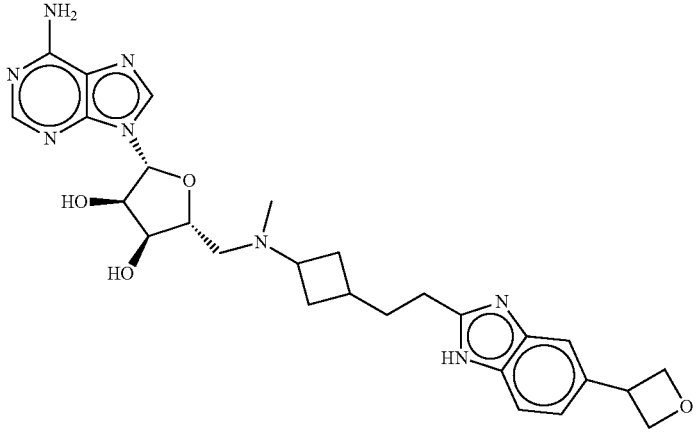 | (2R,3R,4S,5R)-2-(6-amino-9H-purin-9-yl)-5-((methyl(3-(2-(5-(oxetan-3-yl)-1H-benzo[d]imidazol-2-yl)ethyl)cyclobutyl)amino)methyl)tetrahydrofuran-3,4-diol | 535.3 (M + H)+ |
| 65 | 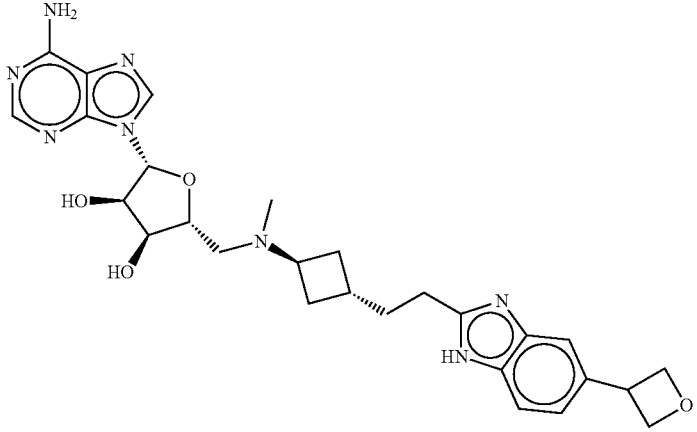 | (2R,3R,4S,5R)-2-(6-amino-9H-purin-9-yl)-5-((methyl((1s,3R)-3-(2-(5-(oxetan-3-yl)-1H-benzo[d]imidazol-2-yl)ethyl)cyclobutyl)amino)methyl)tetrahydrofuran-3,4-diol | 535.4 (M + H)+ |
| 66 | 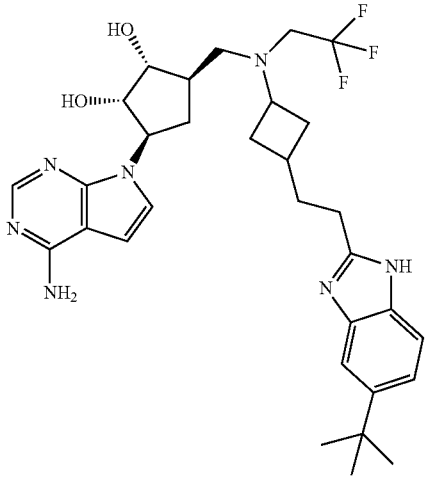 [SMILES: CC(C)(C)c1ccc2[nH]c(CCC3CC(N(C[C@H]4C[C@@H](n5ccc6c(N)ncnc65)[C@H](O)[C@@H]4O)CC(F)(F)F)C3)nc2c1] | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(2,2,2-trifluoroethyl)amino)methyl)cyclopentane-1,2-diol | 600.2 (M + H)+ |

TABLE 1-continued

| Cmpd No. | Structure | Chemical Name | Data (MS or NMR) |
|---|---|---|---|
| 67 | 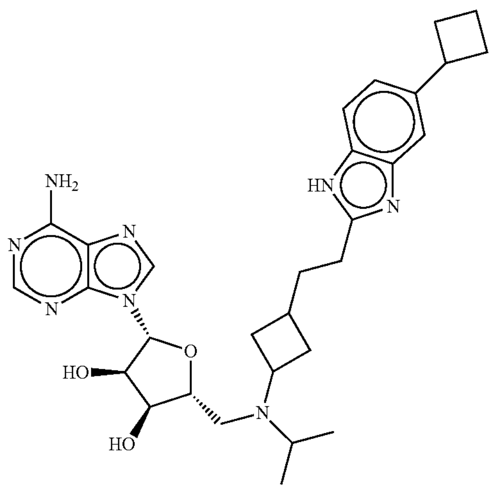 | (2R,3R,4S,5R)-2-(6-amino-9H-purin-9-yl)-5-(((3-(2-(5-cyclobutyl-1H-benzo[d]imidazol-2-yl)ethyl)cyclobutyl)(isopropyl)amino)methyl)tetrahydrofuran-3,4-diol | 561.5 (M + H)+ |
| 68 | 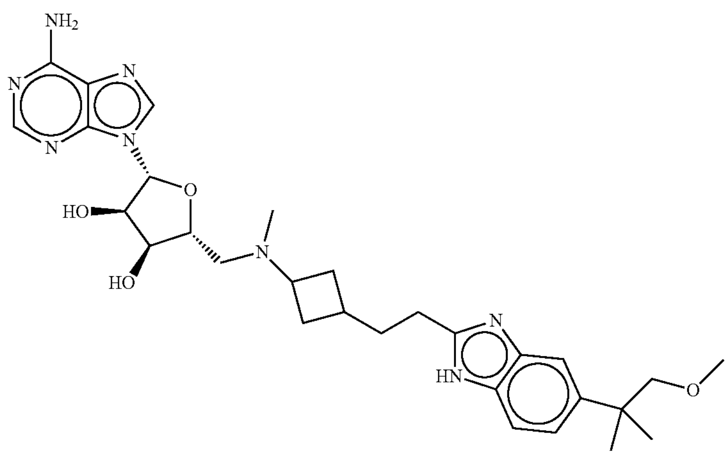 | (2R,3R,4S,5R)-2-(6-amino-9H-purin-9-yl)-5-(((3-(2-(5-(1-methoxy-2-methylpropan-2-yl)-1H-benzo[d]imidazol-2-yl)ethyl)cyclobutyl)(methyl)amino)methyl)tetrahydrofuran-3,4-diol | 565.4 (M + H)+ |
| 69 | 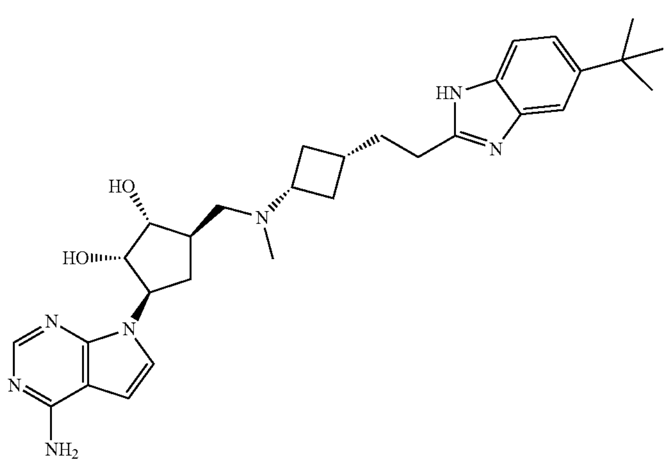 [SMILES: CN(C[C@H]1C[C@@H](n2ccc3c(N)ncnc32)[C@H](O)[C@@H]1O)[C@H]1C[C@@H](CCc2nc3cc(C(C)(C)C)ccc3[nH]2)C1] | (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(methyl)amino)methyl)cyclopentane-1,2-diol | 532.3 (M + H)+ |

TABLE 1-continued

| Cmpd No. | Structure | Chemical Name | Data (MS or NMR) |
|---|---|---|---|
| 70 | 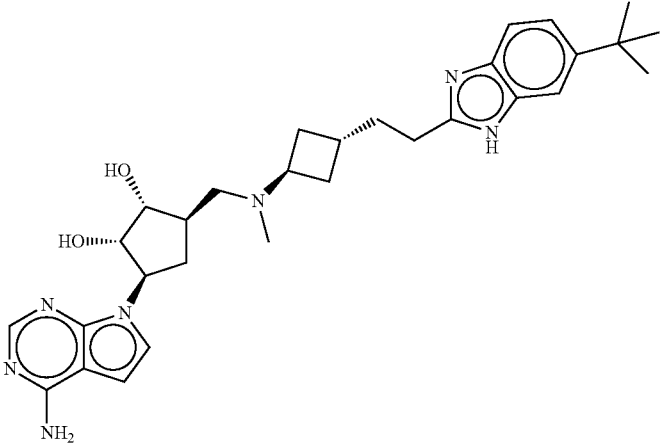 | (1R,2S,3R,5R)-3-(4-amino-7H-pyrrolo[2,3-d]pyrimidin-7-yl)-5-((((1s,3R)-3-(2-(6-(tert-butyl)-1H-benzo[d]imidazol-2-yl)ethyl)cyclobutyl)(methyl)amino)methyl)cyclopentane-1,2-diol | 532.3 (M + H)+ |
| 71 | 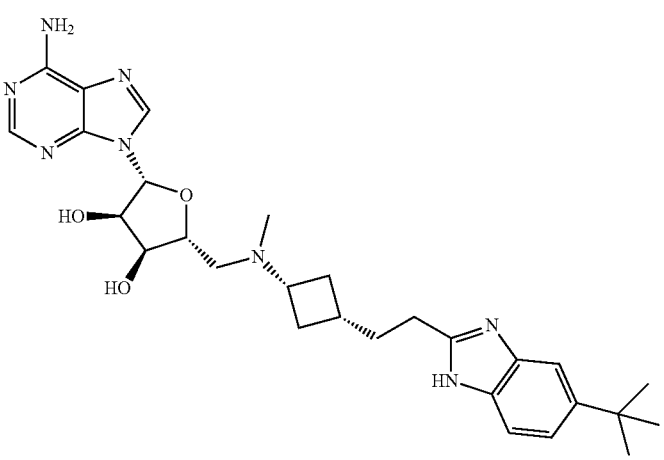 [SMILES: CN(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1] | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(methyl)amino)methyl)tetrahydrofuran-3,4-diol | 535.3 (M + H)+ |
| 72 | 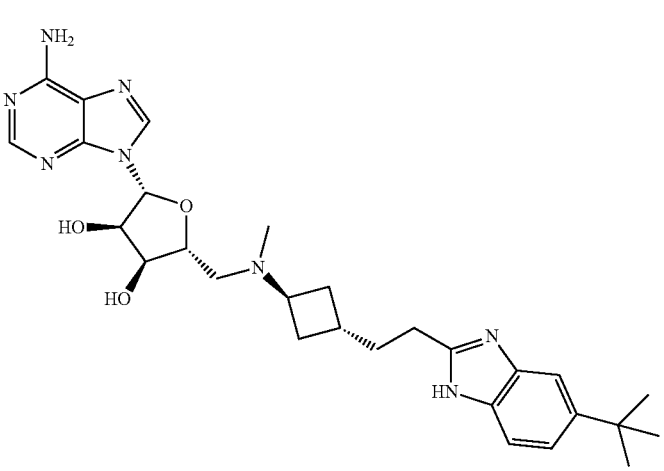 [SMILES: CN(C[C@H]1O[C@@H](n2cnc3c(N)ncnc32)[C@H](O)[C@@H]1O)[C@H]1C[C@H](CCc2nc3cc(C(C)(C)C)ccc3[nH]2)C1] | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(methyl)amino)methyl)tetrahydrofuran-3,4-diol | 535.3 (M + H)+ |

TABLE 1-continued

| Cmpd No. | Structure | Chemical Name | Data (MS or NMR) |
|---|---|---|---|
| 73 | 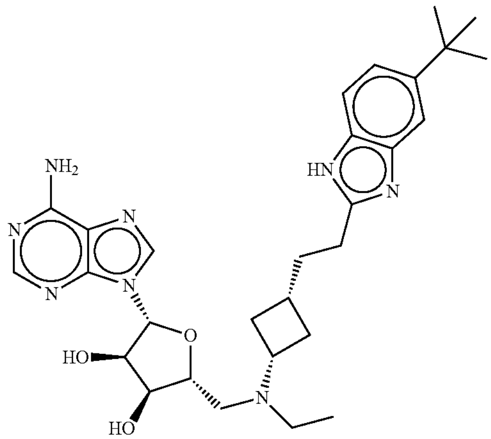 | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(ethyl)amino)methyl)tetrahydrofuran-3,4-diol | 549.3 (M + H)+ |
| 74 | 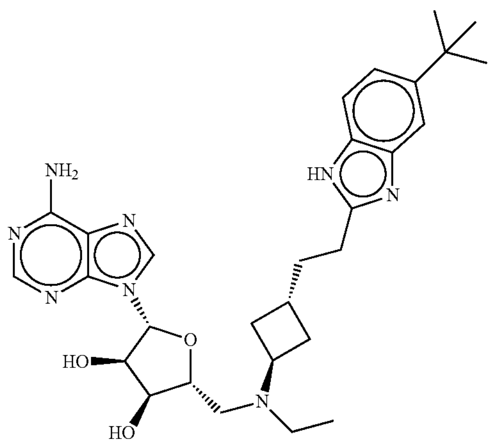 | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(ethyl)amino)methyl)tetrahydrofuran-3,4-diol | 549.3 (M + H)+ |
| 75 | 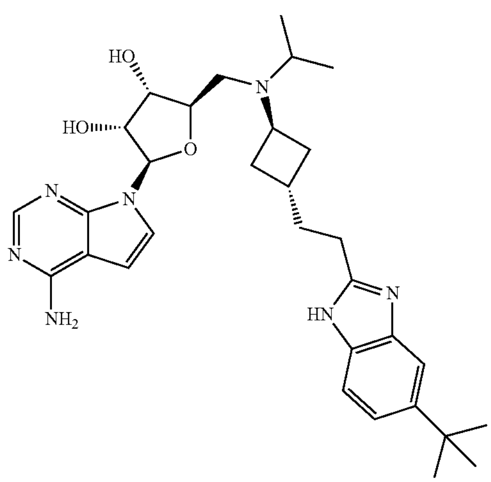 [SMILES: CC(C)N(C[C@H]1O[C@@H](n2ccc3c(N)ncnc32)[C@H](O)[C@@H]1O)[C@H]1C[C@H](CCc2nc3cc(C(C)(C)C)ccc3[nH]2)C1] | (2R,3R,4S,5R)-2-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(isopropyl)amino)methyl)tetrahydrofuran-3,4-diol | 562.5 (M + H)+ |

TABLE 1-continued

| Cmpd No. | Structure | Chemical Name | Data (MS or NMR) |
|---|---|---|---|
| 76 | 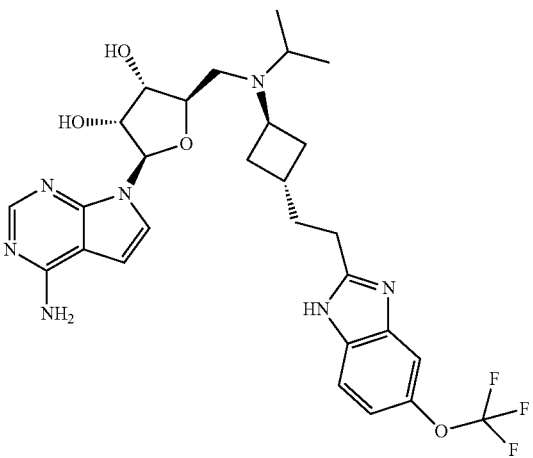 [SMILES: CC(C)N(C[C@H]1O[C@@H](n2ccc3c(N)ncnc32)[C@H](O)[C@@H]1O)[C@H]1C[C@H](CCc2nc3cc(OC(F)(F)F)ccc3[nH]2)C1] | (2R,3R,4S,5R)-2-(4-amino-7H-pyrrolo[2,3-d]pyrimidin-7-yl)-5-((isopropyl((1s,3R)-3-(2-(5-(trifluoromethoxy)-1H-benzo[d]imidazol-2-yl)ethyl)cyclobutyl)amino)methyl)tetrahydrofuran-3,4-diol | 590.3 (M + H)+ |
| 77 | 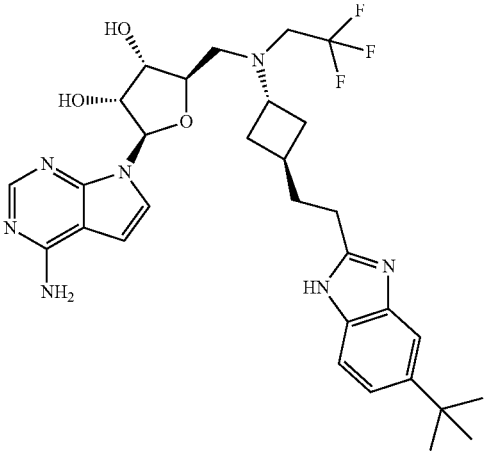 [SMILES: CC(C)(C)c1ccc2[nH]c(CC[C@H]3C[C@H](N(C[C@H]4O[C@@H](n5ccc6c(N)ncnc65)[C@H](O)[C@@H]4O)CC(F)(F)F)C3)nc2c1] | (2R,3R,4S,5R)-2-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol | 602.3 (M + H)+ |
| 78 | 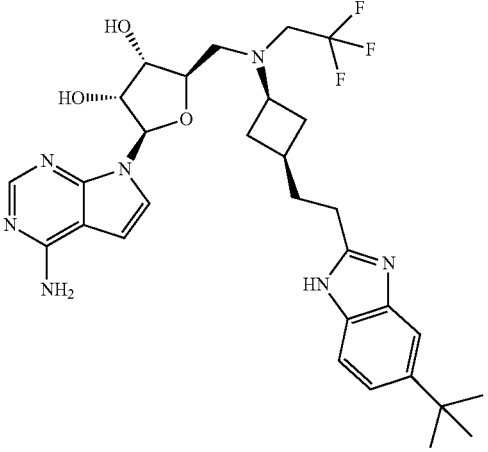 [SMILES: CC(C)(C)c1ccc2[nH]c(CC[C@H]3C[C@@H](N(C[C@H]4O[C@@H](n5ccc6c(N)ncnc65)[C@H](O)[C@@H]4O)CC(F)(F)F)C3)nc2c1] | (2R,3R,4S,5R)-2-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol | 602.3 (M + H)+ |

TABLE 1-continued

| Cmpd No. | Structure | Chemical Name | Data (MS or NMR) |
|---|---|---|---|
| 79 | 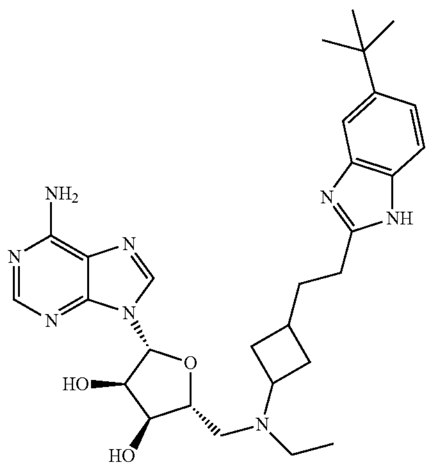 [SMILES: CCN(C[C@H]1O[C@@H](n2cnc3c(N)ncnc32)[C@H](O)[C@@H]1O)C1CC(CCc2nc3cc(C(C)(C)C)ccc3[nH]2)C1] | (2R,3R,4S,5R)-2-(6-amino-9H-purin-9-yl)-5-(((3-(2-(5-(tert-butyl)-1H-benzo[d]imidazol-2-yl)ethyl)cyclobutyl)(ethyl)amino)methyl)tetrahydrofuran-3,4-diol | 549.3 (M + H)+ |
| 80 | 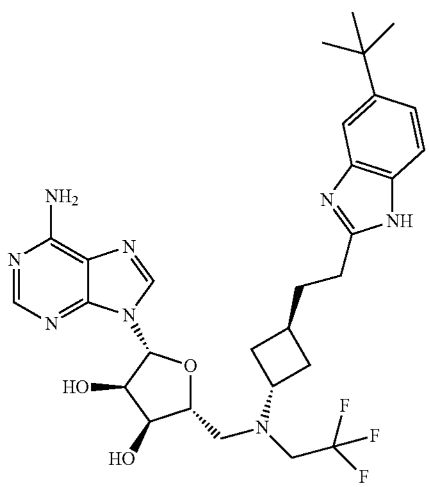 [SMILES: CC(C)(C)c1ccc2[nH]c(CC[C@H]3C[C@H](N(C[C@H]4O[C@@H](n5cnc6c(N)ncnc65)[C@H](O)[C@@H]4O)CC(F)(F)F)C3)nc2c1] | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol | 603.3 (M + H)+ |
| 81 | 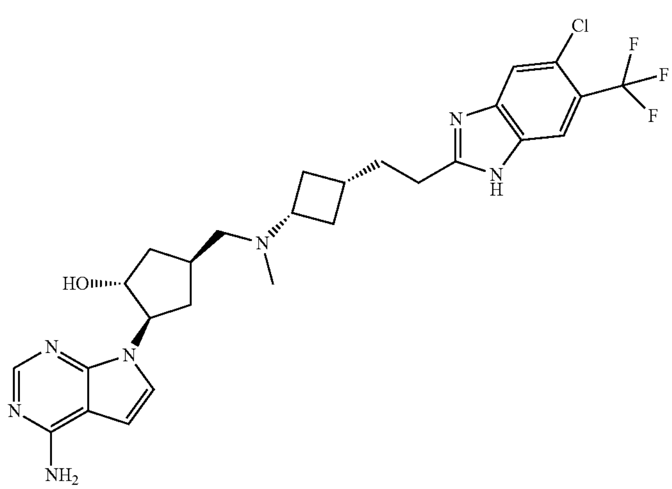 [SMILES: CN(C[C@@H]1C[C@@H](O)[C@H](n2ccc3c(N)ncnc32)C1)[C@H]1C[C@@H](CCc2nc3cc(Cl)c(C(F)(F)F)cc3[nH]2)C1] | (1R,2R,4S)-2-(4-amino-7H-pyrrolo[2,3-d]pyrimidin-7-yl)-4-((((1r,3R)-3-(2-(5-chloro-6-(trifluoromethyl)-1H-benzo[d]imidazol-2-yl)ethyl)cyclobutyl)(methyl)amino)methyl)cyclopentanol | 562.3 (M + H)+ |

TABLE 1-continued

| Cmpd No. | Structure | Chemical Name | Data (MS or NMR) |
|---|---|---|---|
| 82 | 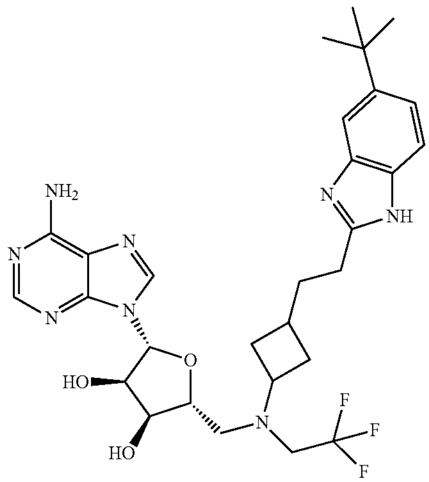 [SMILES: CC(C)(C)c1ccc2[nH]c(CCC3CC(N(C[C@H]4O[C@@H](n5cnc6c(N)ncnc65)[C@H](O)[C@@H]4O)CC(F)(F)F)C3)nc2c1] | (2R,3R,4S,5R)-2-(6-amino-9H-purin-9-yl)-5-(((3-(2-(5-(tert-butyl)-1H-benzo[d]imidazol-2-yl)ethyl)cyclobutyl)(2,2,2-trifluoroethyl)amino)methyl)tetrahydrofuran-3,4-diol | 603.3 (M + H)+ |
| 83 | 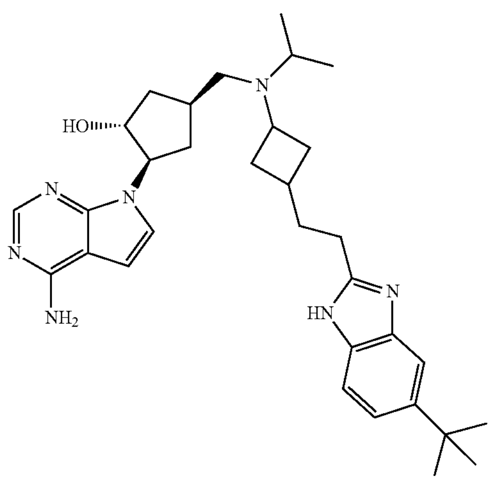 [SMILES: CC(C)N(C[C@@H]1C[C@@H](O)[C@H](n2ccc3c(N)ncnc32)C1)C1CC(CCc2nc3cc(C(C)(C)C)ccc3[nH]2)C1] | (1R,2R,4S)-2-(4-amino-7H-pyrrolo[2,3-d]pyrimidin-7-yl)-4-(((3-(2-(5-(tert-butyl)-1H-benzo[d]imidazol-2-yl)ethyl)cyclobutyl)(isopropyl)amino)methyl)cyclopentanol | 544.5 (M + H)+ |
| 84 | 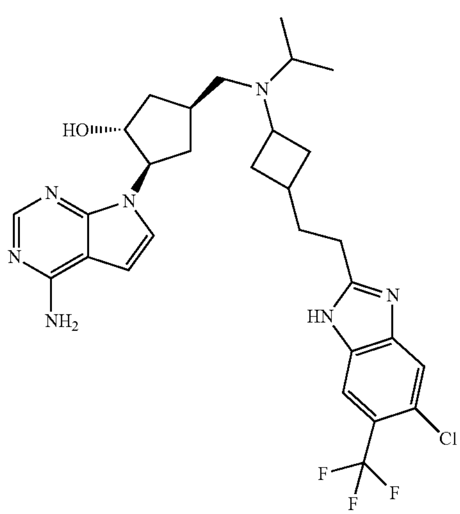 [SMILES: CC(C)N(C[C@@H]1C[C@@H](O)[C@H](n2ccc3c(N)ncnc32)C1)C1CC(CCc2nc3cc(Cl)c(C(F)(F)F)cc3[nH]2)C1] | (1R,2R,4S)-2-(4-amino-7H-pyrrolo[2,3-d]pyrimidin-7-yl)-4-(((3-(2-(5-chloro-6-(trifluoromethyl)-1H-benzo[d]imidazol-2-yl)ethyl)cyclobutyl)(isopropyl)amino)methyl)cyclopentanol | 590.3 (M + H)+ |

TABLE 1-continued

| Cmpd No. | Structure | Chemical Name | Data (MS or NMR) |
|---|---|---|---|
| 85 | 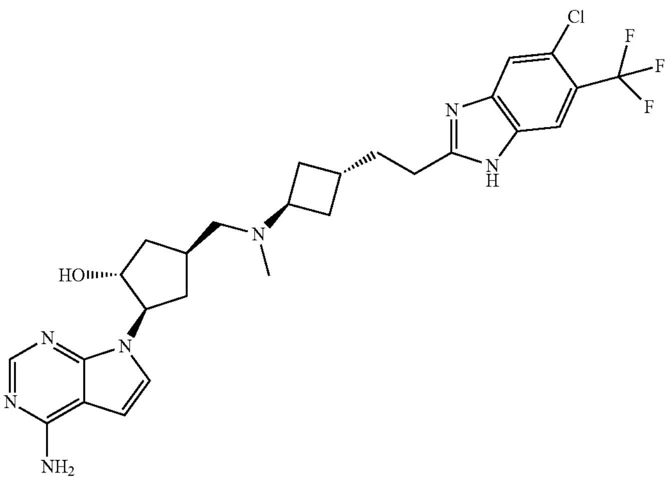 [SMILES: CN(C[C@@H]1C[C@@H](O)[C@H](n2ccc3c(N)ncnc32)C1)[C@H]1C[C@H](CCc2nc3cc(Cl)c(C(F)(F)F)cc3[nH]2)C1] | (1R,2R,4S)-2-(4-amino-7H-pyrrolo[2,3-d]pyrimidin-7-yl)-4-((((1s,3S)-3-(2-(5-chloro-6-(trifluoromethyl)-1H-benzo[d]imidazol-2-yl)ethyl)cyclobutyl)(methyl)amino)methyl)cyclopentanol | 562.3 (M + H)+ |
| 86 | 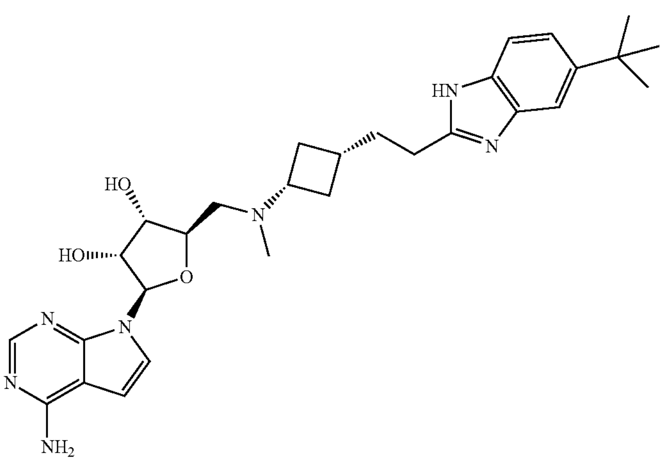 [SMILES: CN(C[C@H]1O[C@@H](n2ccc3c(N)ncnc32)[C@H](O)[C@@H]1O)[C@H]1C[C@@H](CCc2nc3cc(C(C)(C)C)ccc3[nH]2)C1] | (2R,3R,4S,5R)-2-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(methyl)amino)methyl)tetrahydrofuran-3,4-diol | 534.3 (M + H)+ |
| 87 | 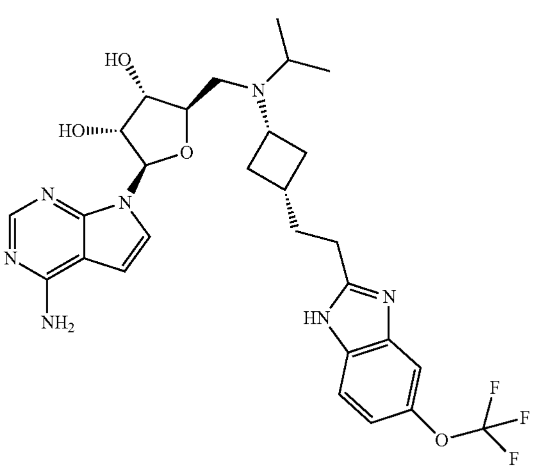 [SMILES: CC(C)N(C[C@H]1O[C@@H](n2ccc3c(N)ncnc32)[C@H](O)[C@@H]1O)[C@H]1C[C@@H](CCc2nc3cc(OC(F)(F)F)ccc3[nH]2)C1] | (2R,3R,4S,5R)-2-(4-amino-7H-pyrrolo[2,3-d]pyrimidin-7-yl)-5-((isopropyl((1r,3S)-3-(2-(5-(trifluoromethoxy)-1H-benzo[d]imidazol-2-yl)ethyl)cyclobutyl)amino)methyl)tetrahydrofuran-3,4-diol | 590.3 (M + H)+ |

TABLE 1-continued

| Cmpd No. | Structure | Chemical Name | Data (MS or NMR) |
|---|---|---|---|
| 88 | 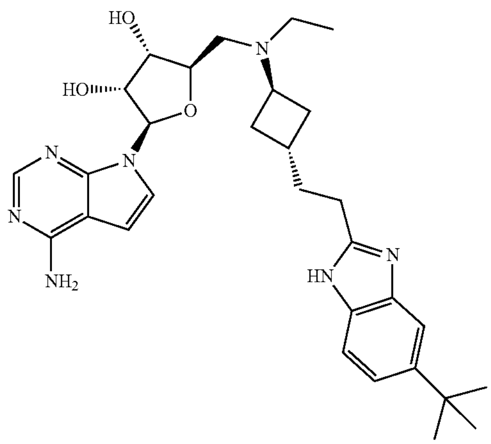 [SMILES: CCN(C[C@H]1O[C@@H](n2ccc3c(N)ncnc32)[C@H](O)[C@@H]1O)[C@H]1C[C@H](CCc2nc3cc(C(C)(C)C)ccc3[nH]2)C1] | (2R,3R,4S,5R)-2-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(ethyl)amino)methyl)tetrahydrofuran-3,4-diol | 548.3 (M + H)+ |
| 89 | 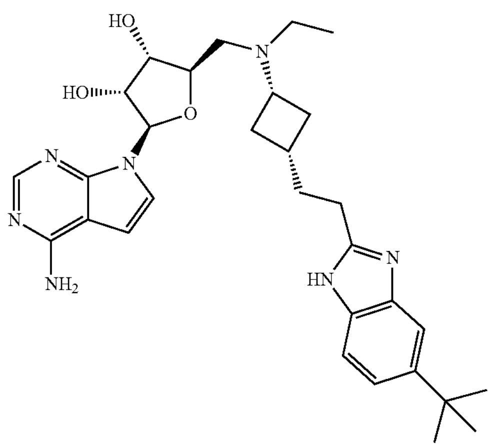 | (2R,3R,4S,5R)-2-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(ethyl)amino)methyl)tetrahydrofuran-3,4-diol | 548.3 (M + H)+ |
| 90 | 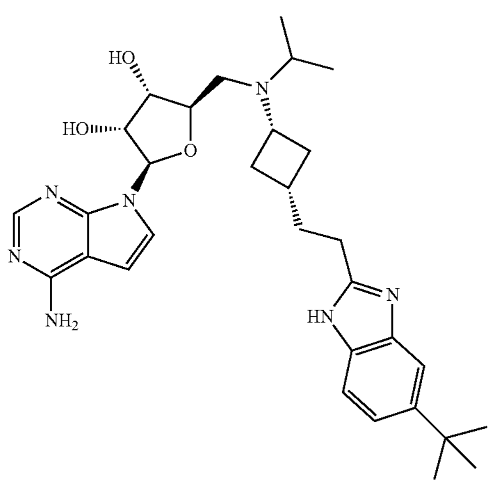 | (2R,3R,4S,5R)-2-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol | 562.5 (M + H)+ |

TABLE 1-continued

| Cmpd No. | Structure | Chemical Name | Data (MS or NMR) |
|---|---|---|---|
| 91 | 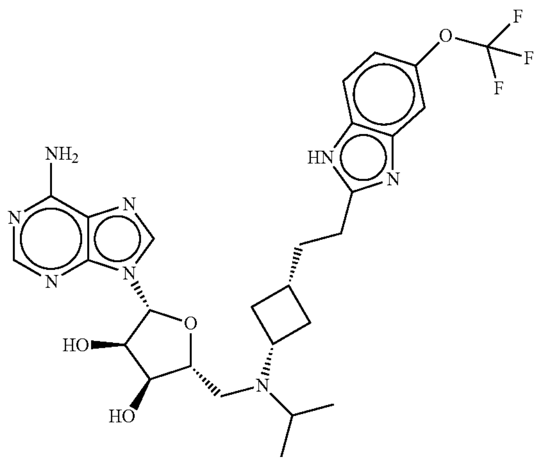 | (2R,3R,4S,5R)-2-(6-amino-9H-purin-9-yl)-5-((isopropyl((1r,3S)-3-(2-(5-(trifluoromethoxy)-1H-benzo[d]imidazol-2-yl)ethyl)cyclobutyl)amino)methyl)tetrahydrofuran-3,4-diol | 591.2 (M + H)+ |
| 92 | 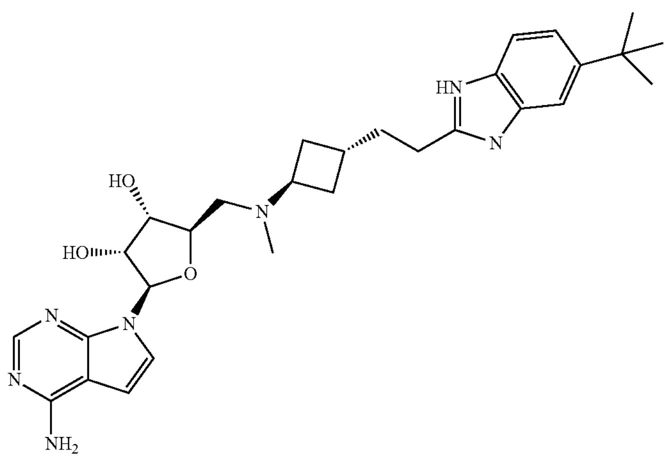 [SMILES: CN(C[C@H]1O[C@@H](n2ccc3c(N)ncnc32)[C@H](O)[C@@H]1O)[C@H]1C[C@H](CCc2nc3ccc(C(C)(C)C)cc3[nH]2)C1] | (2R,3R,4S,5R)-2-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(methyl)amino)methyl)tetrahydrofuran-3,4-diol | 534.3 (M + H)+ |
| 93 | 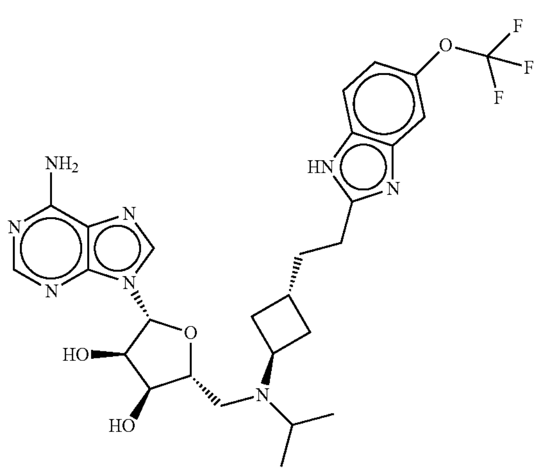 | (2R,3R,4S,5R)-2-(6-amino-9H-purin-9-yl)-5-((isopropyl((1s,3R)-3-(2-(5-(trifluoromethoxy)-1H-benzo[d]imidazol-2-yl)ethyl)cyclobutyl)amino)methyl)tetrahydrofuran-3,4-diol | 591.3 (M + H)+ |

TABLE 1-continued

| Cmpd No. | Structure | Chemical Name | Data (MS or NMR) |
|---|---|---|---|
| 94 | 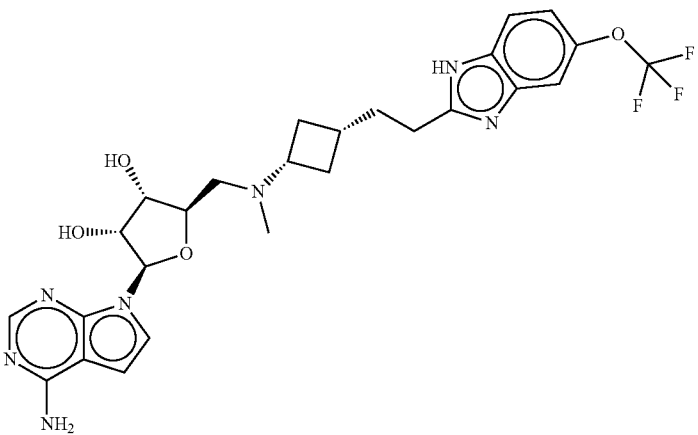 | (2R,3R,4S,5R)-2-(4-amino-7H-pyrrolo[2,3-d]pyrimidin-7-yl)-5-((methyl((1r,3S)-3-(2-(5-(trifluoromethoxy)-1H-benzo[d]imidazol-2-yl)ethyl)cyclobutyl)amino)methyl)tetrahydrofuran-3,4-diol | 562.2 (M + H)+ |
| 95 | 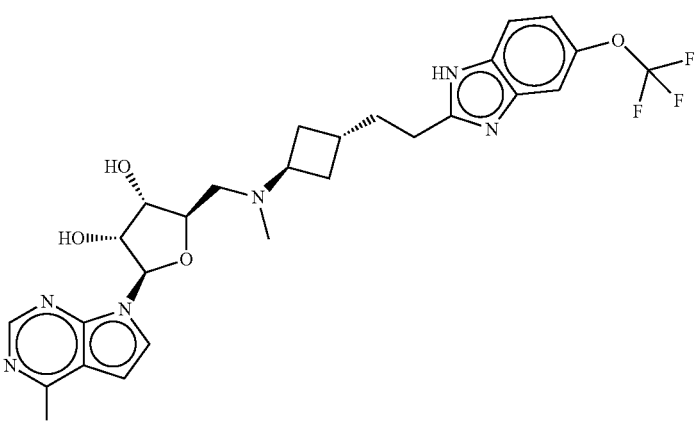 | (2R,3R,4S,5R)-2-(4-amino-7H-pyrrolo[2,3-d]pyrimidin-7-yl)-5-((methyl((1s,3R)-3-(2-(5-(trifluoromethoxy)-1H-benzo[d]imidazol-2-yl)ethyl)cyclobutyl)amino)methyl)tetrahydrofuran-3,4-diol | 562.3 (M + H)+ |
| 96 | 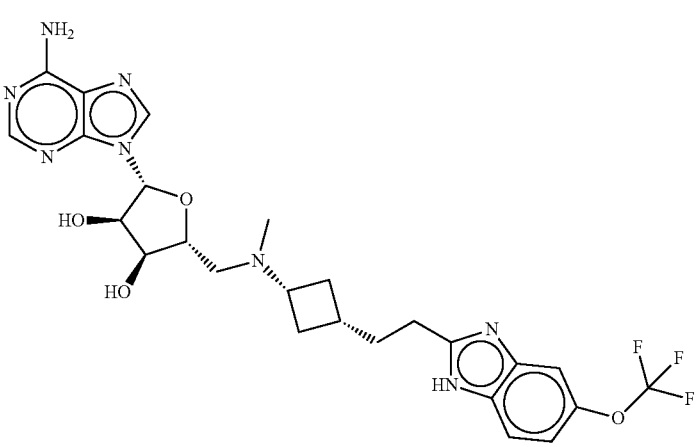 | (2R,3R,4S,5R)-2-(6-amino)-9H-purin-9-yl)-5-((methyl((1r,3S)-3-(2-(5-(trifluoromethoxy)-1H-benzo[d]imidazol-2-yl)ethyl)cyclobutyl)amino)methyl)tetrahydrofuran-3,4-diol | 563.3 (M + H)+ |

TABLE 1-continued

| Cmpd No. | Structure | Chemical Name | Data (MS or NMR) |
|---|---|---|---|
| 97 | 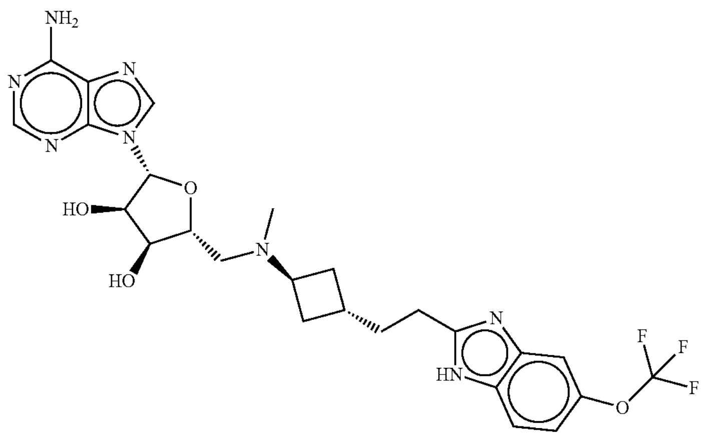 | (2R,3R,4S,5R)-2-(6-amino-9H-purin-9-yl)-5-((methyl((1s,3R)-3-(2-(5-(trifluoromethoxy)-1H-benzo[d]imidazol-2-yl)ethyl)cyclobutyl)amino)methyl)tetrahydrofuran-3,4-diol | 563.3 (M + H)+ |
| 98 | 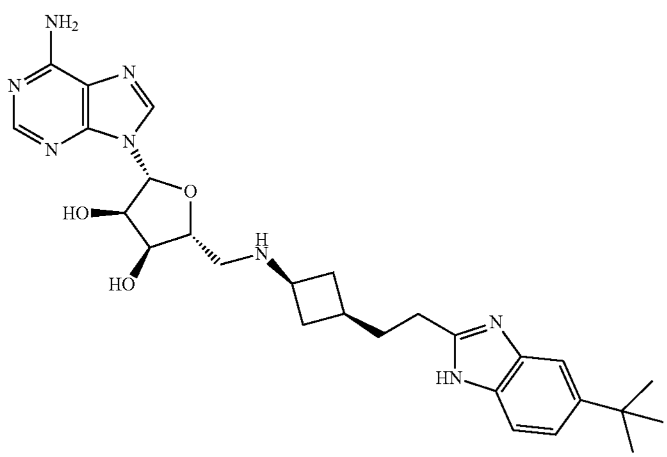 [SMILES: CC(C)(C)c1ccc2[nH]c(CC[C@H]3C[C@@H](NC[C@H]4O[C@@H](n5cnc6c(N)ncnc65)[C@H](O)[C@@H]4O)C3)nc2c1] | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)amino)methyl)tetrahydrofuran-3,4-diol | 521.3 (M + H)+ |
| 99 | 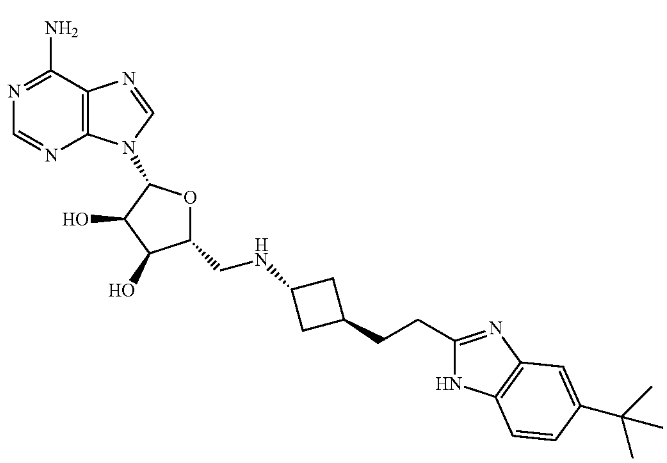 [SMILES: CC(C)(C)c1ccc2[nH]c(CC[C@H]3C[C@H](NC[C@H]4O[C@@H](n5cnc6c(N)ncnc65)[C@H](O)[C@@H]4O)C3)nc2c1] | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)amino)methyl)tetrahydrofuran-3,4-diol | 521.3 (M + H)+ |

TABLE 1-continued

| Cmpd No. | Structure | Chemical Name | Data (MS or NMR) |
|---|---|---|---|
| 100 | 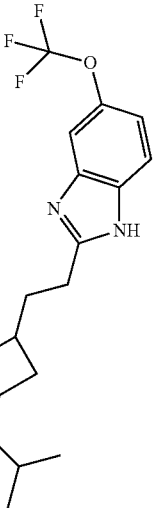 | (2R,3R,4S,5R)-2-(6-amino-9H-purin-9-yl)-5-((isopropyl(3-(2-(5-(trifluoromethoxy)-1H-benzo[d]imidazol-2-yl)ethyl)cyclobutyl)amino)methyl)tetrahydrofuran-3,4-diol | 591.3 (M + H)+ |
| 101 | 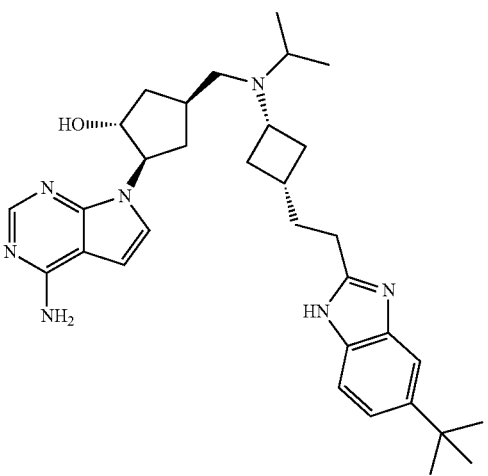 [SMILES: CC(C)N(C[C@@H]1C[C@@H](O)[C@H](n2ccc3c(N)ncnc32)C1)[C@H]1C[C@@H](CCc2nc3cc(C(C)(C)C)ccc3[nH]2)C1] | (1R,2R,4S)-2-(4-amino-7H-pyrrolo[2,3-d]pyrimidin-7-yl)-4-((((1r,3R)-3-(2-(5-(tert-butyl)-1H-benzo[d]imidazol-2-yl)ethyl)cyclobutyl)(isopropyl)amino)methyl)cyclopentanol | 544.1 (M + H)+ |
| 102 | 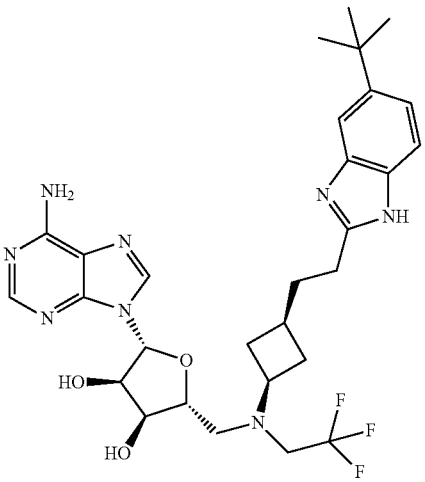 [SMILES: CC(C)(C)c1ccc2[nH]c(CC[C@H]3C[C@@H](N(C[C@H]4O[C@@H](n5cnc6c(N)ncnc65)[C@H](O)[C@@H]4O)CC(F)(F)F)C3)nc2c1] | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol | 603.3 (M + H)+ |

TABLE 1-continued

| Cmpd No. | Structure | Chemical Name | Data (MS or NMR) |
|---|---|---|---|
| 103 | 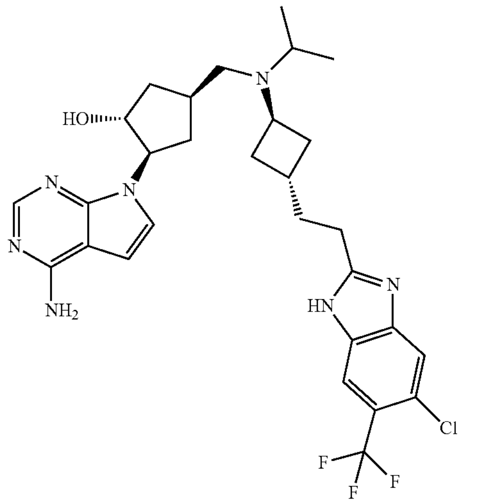 [SMILES: CC(C)N(C[C@@H]1C[C@@H](O)[C@H](n2ccc3c(N)ncnc32)C1)[C@H]1C[C@H](CCc2nc3cc(Cl)c(C(F)(F)F)cc3[nH]2)C1] | (1R,2R,4S)-2-(4-amino-7H-pyrrolo[2,3-d]pyrimidin-7-yl)-4-((((1s,3S)-3-(2-(5-chloro-6-(trifluoromethyl)-1H-benzo[d]imidazol-2-yl)ethyl)cyclobutyl)(isopropyl)amino)methyl)cyclopentanol | 589.9 (M + H)+ |
| 104 | 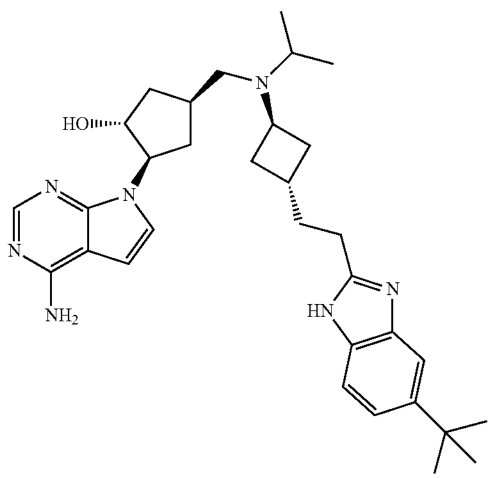 [SMILES: CC(C)N(C[C@@H]1C[C@@H](O)[C@H](n2ccc3c(N)ncnc32)C1)[C@H]1C[C@H](CCc2nc3cc(C(C)(C)C)ccc3[nH]2)C1] | (1R,2R,4S)-2-(4-amino-7H-pyrrolo[2,3-d]pyrimidin-7-yl)-4-((((1s,3S)-3-(2-(5-(tert-butyl)-1H-benzo[d]imidazol-2-yl)ethyl)cyclobutyl)(isopropyl)amino)methyl)cyclopentanol | 544.1 (M + H)+ |
| 105 | 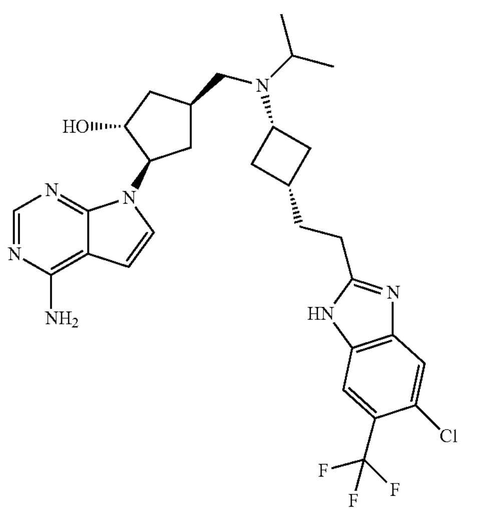 [SMILES: CC(C)N(C[C@@H]1C[C@@H](O)[C@H](n2ccc3c(N)ncnc32)C1)[C@H]1C[C@@H](CCc2nc3cc(Cl)c(C(F)(F)F)cc3[nH]2)C1] | (1R,2R,4S)-2-(4-amino-7H-pyrrolo[2,3-d]pyrimidin-7-yl)-4-((((1r,3R)-3-(2-(5-chloro-6-(trifluoromethyl)-1H-benzo[d]imidazol-2-yl)ethyl)cyclobutyl)(isopropyl)amino)methyl)cyclopentanol | 589.9 (M + H)+ |

TABLE 1-continued

| Cmpd No. | Structure | Chemical Name | Data (MS or NMR) |
|---|---|---|---|
| 106 | 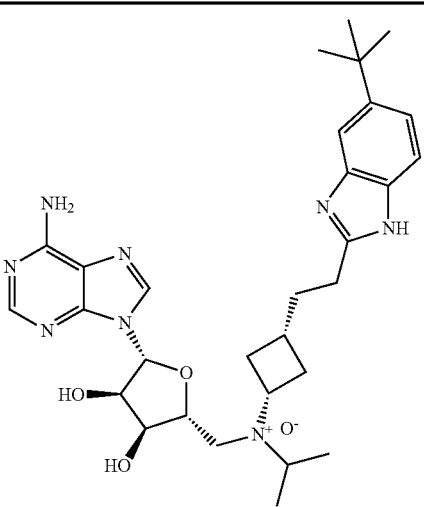 | (1r,3S)-N-((((2R,3S,4R,5R)-5-(6-amino-9H-purin-9-yl)-3,4-dihydroxytetrahydrofuran-2-yl)methyl)-3-(2-(5-(tert-butyl)-1H-benzo[d]imidazol-2-yl)ethyl)-N-isopropylcyclobutanamine oxide | 579.4 (M + H)+ |
| 107 | 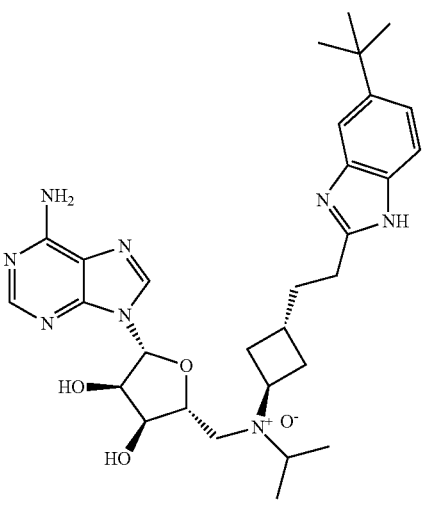 | (R,1s,3R)-N-((((2R,3S,4R,5R)-5-(6-amino-9H-purin-9-yl)-3,4-dihydroxytetrahydrofuran-2-yl)methyl)-3-(2-(5-(tert-butyl)-1H-benzo[d]imidazol-2-yl)ethyl)-N-isopropylcyclobutanamine oxide | 579.4 (M + H)+ |
| 108 | 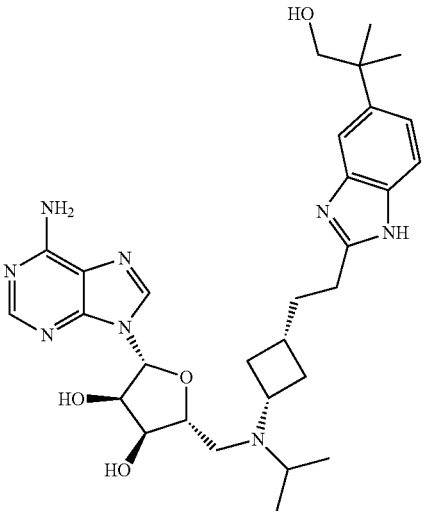 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)CO)ccc3[nH]2)C1] | (2R,3R,4S,5R)-2-(6-amino-9H-purin-9-yl)-5-((((1r,3S)-3-(2-(5-(1-hydroxy-2-methylpropan-2-yl)-1H-benzo[d]imidazol-2-yl)ethyl)cyclobutyl)(isopropyl)amino)methyl)tetrahydrofuran-3,4-diol | 579.4 (M + H)+ |

TABLE 1-continued

| Cmpd No. | Structure | Chemical Name | Data (MS or NMR) |
|---|---|---|---|
| 109 | 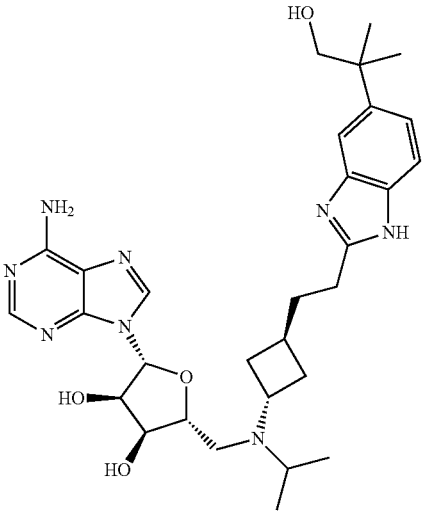 [SMILES: CC(C)N(C[C@H]1O[C@@H](n2cnc3c(N)ncnc32)[C@H](O)[C@@H]1O)[C@H]1C[C@H](CCc2nc3cc(C(C)(C)CO)ccc3[nH]2)C1] | (2R,3R,4S,5R)-2-(6-amino-9H-purin-9-yl)-5-((((1s,3R)-3-(2-(5-(1-hydroxy-2-methylpropan-2-yl)-1H-benzo[d]imidazol-2-yl)ethyl)cyclobutyl)(isopropyl)amino)methyl)tetrahydrofuran-3,4-diol | 579.4 (M + H)+ |
| 110 | 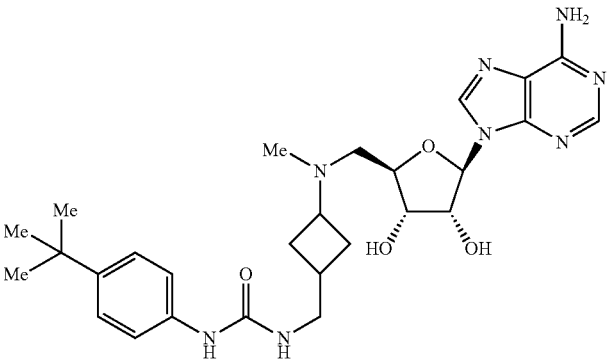 [SMILES: CN(C[C@H]1O[C@@H](n2cnc3c(N)ncnc32)[C@H](O)[C@@H]1O)C1CC(CNC(=O)Nc2ccc(C(C)(C)C)cc2)C1] | 1-((3-((((2R,3S,4R,5R)-5-(6-amino-9H-purin-9-yl)-3,4-dihydroxytetrahydrofuran-2-yl)methyl)(methyl)amino)cyclobutyl)methyl)-3-(4-(tert-butyl)phenyl)urea | 539.3 (M + H)+ |
| 111 | 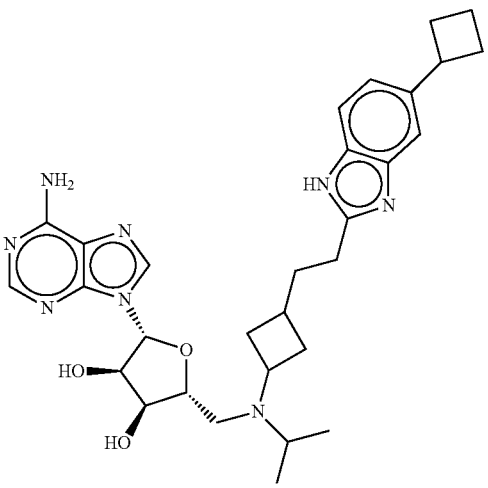 | (2R,3R,4S,5R)-2-(6-amino-9H-purin-9-yl)-5-(((3-(2-(5-cyclobutyl-1H-benzo[d]imidazol-2-yl)ethyl)cyclobutyl)(isopropyl)amino)methyl)tetrahydrofuran-3,4-diol | 561 (M + H)+ |

TABLE 1-continued

| Cmpd No. | Structure | Chemical Name | Data (MS or NMR) |
|---|---|---|---|
| 112 | 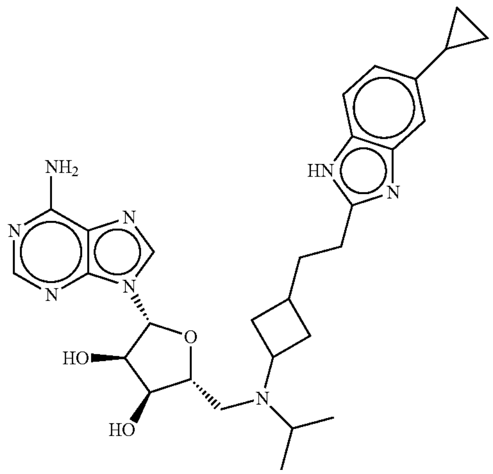 | (2R,3R,4S,5R)-2-(6-amino-9H-purin-9-yl)-5-(((3-(2-(5-cyclopropyl-1H-benzo[d]imidazol-2-yl)ethyl)cyclobutyl)(isopropyl)amino)methyl)tetrahydrofuran-3,4-diol | 547 (M + H)+ |
| 113 | 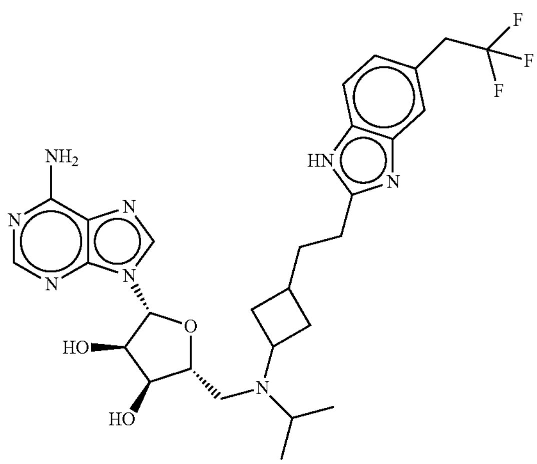 | (2R,3R,4S,5R)-2-(6-amino-9H-purin-9-yl)-5-((isopropyl(3-(2-(5-(2,2,2-trifluoroethyl)-1H-benzo[d]imidazol-2-yl)ethyl)cyclobutyl)amino)methyl)tetrahydrofuran-3,4-diol | 589 (M + H)+ |
| 114 | 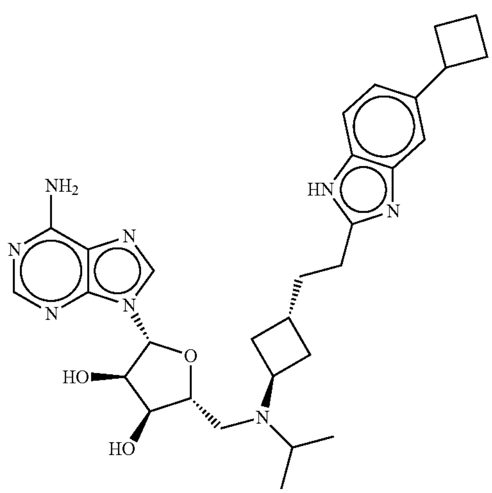 | (2R,3R,4S,5R)-2-(6-amino-9H-purin-9-yl)-5-(((((1s,3R)-3-(2-(5-cyclobutyl-1H-benzo[d]imidazol-2-yl)ethyl)cyclobutyl)(isopropyl)amino)methyl)tetrahydrofuran-3,4-diol | 561 (M + H)+ |

TABLE 1-continued

| Cmpd No. | Structure | Chemical Name | Data (MS or NMR) |
|---|---|---|---|
| 115 | 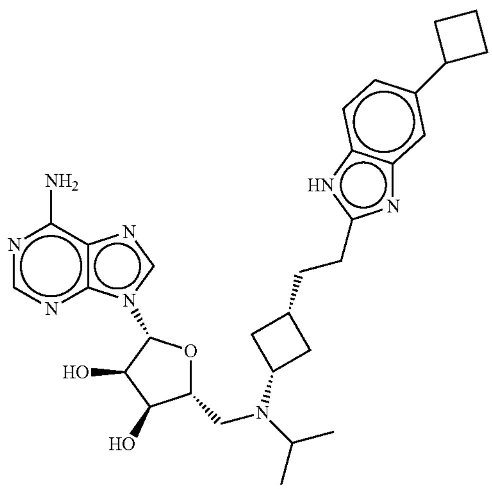 | (2R,3R,4S,5R)-2-(6-amino-9H-purin-9-yl)-5-((((1r,3S)-3-(2-(5-cyclobutyl-1H-benzo[d]imidazol-2-yl)ethyl)cyclobutyl)(isopropyl)amino)methyl)tetrahydrofuran-3,4-diol | 561 (M + H)+ |
| 116 | 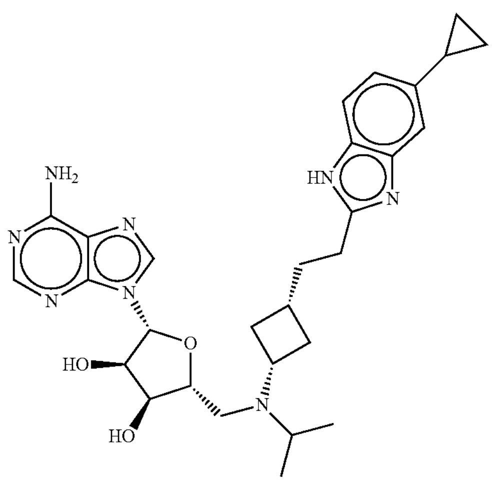 | (2R,3R,4S,5R)-2-(6-amino-9H-purin-9-yl)-5-((((1r,3S)-3-(2-(5-cyclopropyl-1H-benzo[d]imidazol-2-yl)ethyl)cyclobutyl)(isopropyl)amino)methyl)tetrahydrofuran-3,4-diol | 547 (M + H)+ |
| 117 | 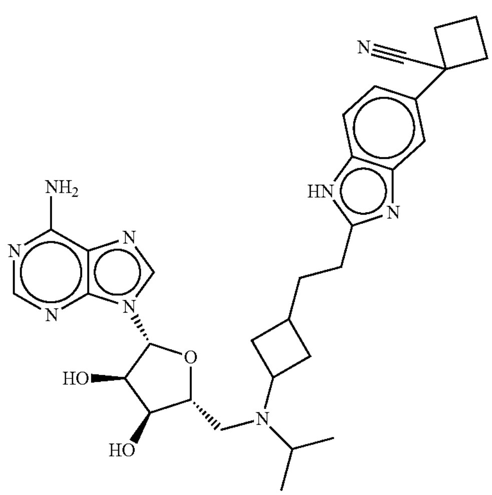 | 1-(2-(2-(3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)cyclobutanecarbonitrile | 586 (M + H)+ |

TABLE 1-continued

| Cmpd No. | Structure | Chemical Name | Data (MS or NMR) |
|---|---|---|---|
| 118 | 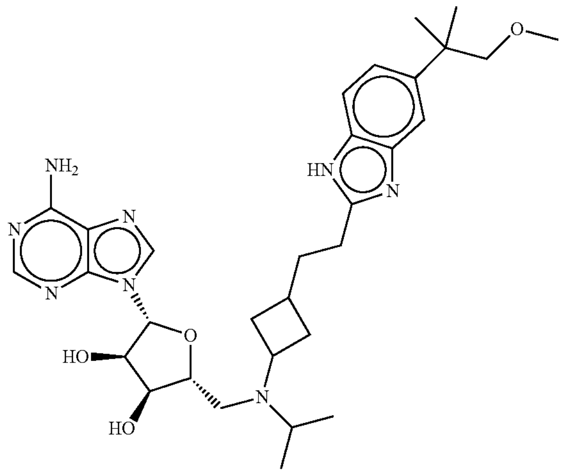 | (2R,3R,4S,5R)-2-(6-amino-9H-purin-9-yl)-5-((isopropyl(3-(2-(5-(1-methoxy-2-methylpropan-2-yl)-1H-benzo[d]imidazol-2-yl)ethyl)cyclobutyl)amino)methyl)tetrahydrofuran-3,4-diol | 593 (M + H)+ |
| 119 | 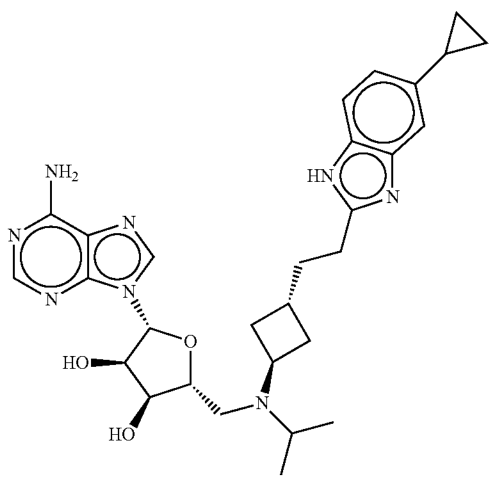 | (2R,3R,4S,5R)-2-(6-amino-9H-purin-9-yl)-5-(((((1s,3R)-3-(2-(5-cyclopropyl-1H-benzo[d]imidazol-2-yl)ethyl)cyclobutyl)(isopropyl)amino)methyl)tetrahydrofuran-3,4-diol | 547 (M + H)+ |
| 120 | 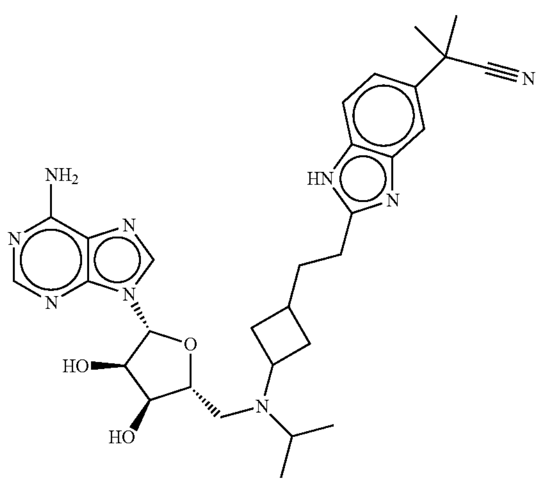 | 2-(2-(2-(3-(((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)-2-methylpropanenitrile | 574 (M + H)+ |

TABLE 1-continued

| Cmpd No. | Structure | Chemical Name | Data (MS or NMR) |
|---|---|---|---|
| 121 | 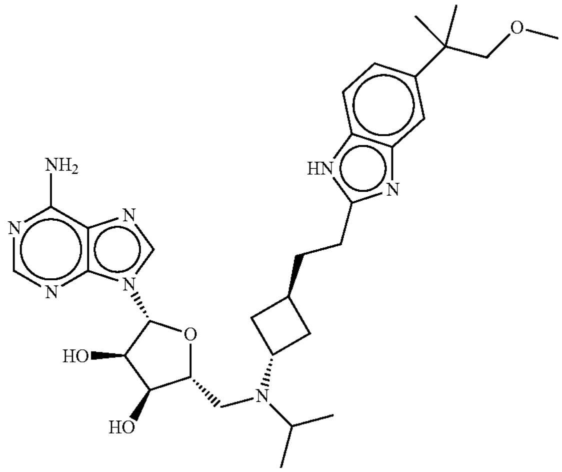 | (2R,3R,4S,5R)-2-(6-amino-9H-purin-9-yl)-5-((isopropyl((1s,3R)-3-(2-(5-(1-methoxy-2-methylpropan-2-yl)-1H-benzo[d]imidazol-2-yl)ethyl)cyclobutyl)amino)methyl)tetrahydrofuran-3,4-diol | 593 (M + H)+ |
| 122 | 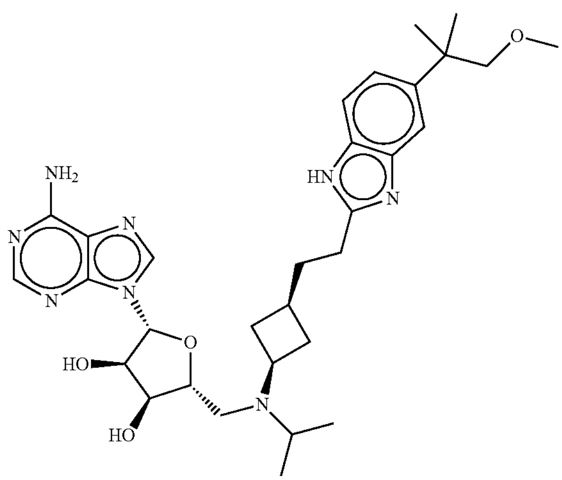 | (2R,3R,4S,5R)-2-(6-amino-9H-purin-9-yl)-5-((isopropyl((1r,3S)-3-(2-(5-(1-methoxy-2-methylpropan-2-yl)-1H-benzo[d]imidazol-2-yl)ethyl)cyclobutyl)amino)methyl)tetrahydrofuran-3,4-diol | 593 (M + H)+ |
| 123 | 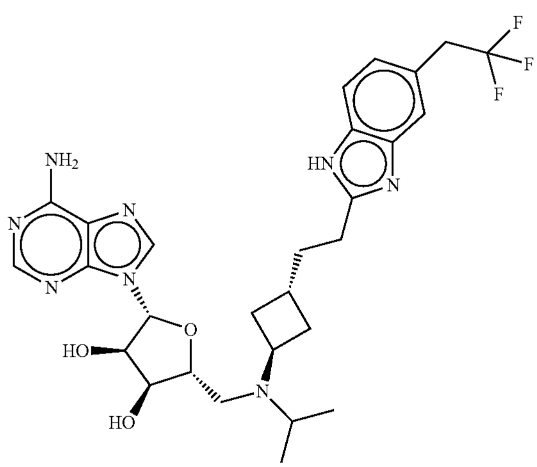 | (2R,3R,4S,5R)-2-(6-amino-9H-purin-9-yl)-5-((isopropyl((1s,3R)-3-(2-(5-(2,2,2-trifluoroethyl)-1H-benzo[d]imidazol-2-yl)ethyl)cyclobutyl)amino)methyl)tetrahydrofuran-3,4-diol | 589 (M + H)+ |

TABLE 1-continued

| Cmpd No. | Structure | Chemical Name | Data (MS or NMR) |
|---|---|---|---|
| 124 | 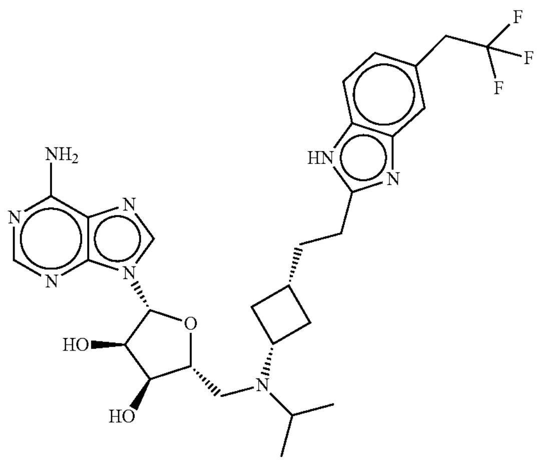 | (2R,3R,4S,5R)-2-(6-amino-9H-purin-9-yl)-5-((isopropyl((1r,3S)-3-(2-(5-(2,2,2-trifluoroethyl)-1H-benzo[d]imidazol-2-yl)ethyl)cyclobutyl)amino)methyl)tetrahydrofuran-3,4-diol | 589 (M + H)+ |
| 125 | 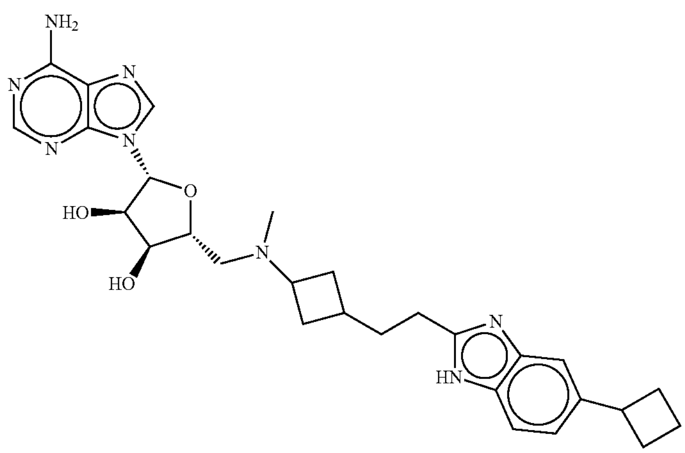 | (2R,3R,4S,5R)-2-(6-amino-9H-purin-9-yl)-5-(((3-(2-(5-cyclobutyl-1H-benzo[d]imidazol-2-yl)ethyl)cyclobutyl)(methyl)amino)methyl)tetrahydrofuran-3,4-diol | 533 (M + H)+ |
| 126 | 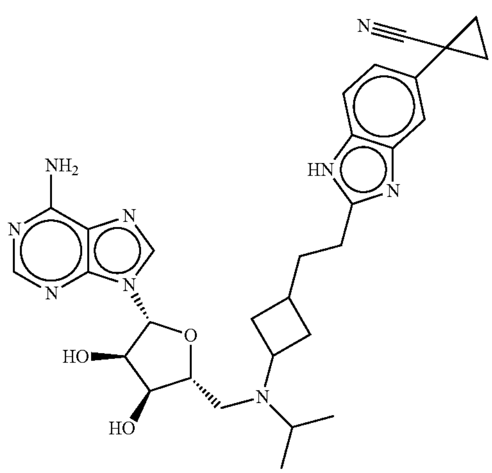 | 1-(2-(2-(3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)cyclopropanecarbonitrile | 572 (M + H)+ |

TABLE 1-continued

| Cmpd No. | Structure | Chemical Name | Data (MS or NMR) |
|---|---|---|---|
| 127 | 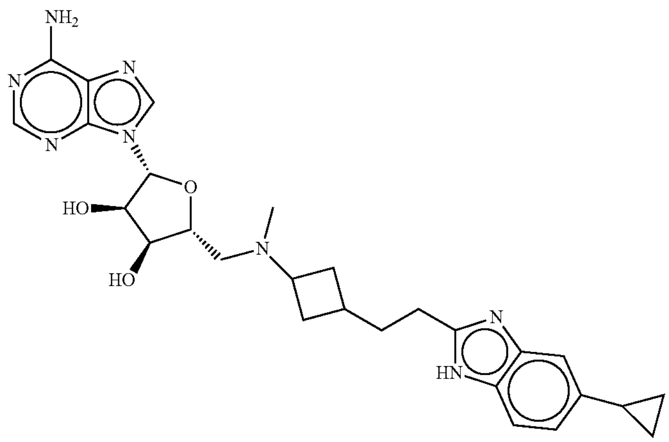 | (2R,3R,4S,5R)-2-(6-amino-9H-purin-9-yl)-5-(((3-(2-(5-cyclopropyl-1H-benzo[d]imidazol-2-yl)ethyl)cyclobutyl)(methyl)amino)methyl)tetrahydrofuran-3,4-diol | 519 (M + H)+ |
| 128 | 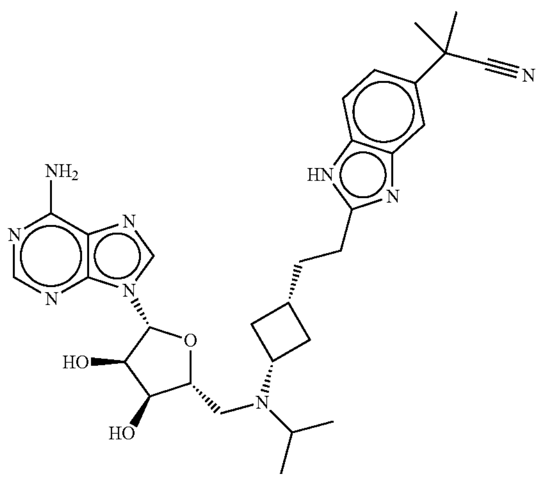 | 2-(2-(2-((1S,3r)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)-2-methylpropanenitrile | 574 (M + H)+ |
| 129 | 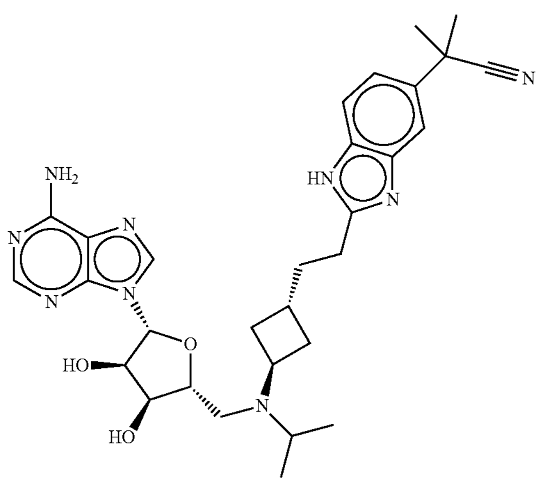 | 2-(2-(2-((1R,3s)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)-2-methylpropanenitrile | 574 (M + H)+ |

TABLE 1-continued

| Cmpd No. | Structure | Chemical Name | Data (MS or NMR) |
|---|---|---|---|
| 130 | 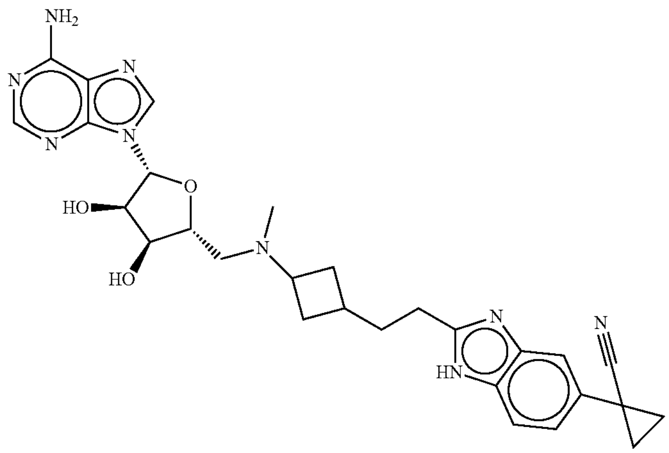 | 1-(2-(2-(3-((((2R,3S,4R,5R)-5-(6-amino-9H-purin-9-yl)-3,4-dihydroxytetrahydrofuran-2-yl)methyl)(methyl)amino)cyclobutyl)ethyl)-1H-benzo[d]imidazol-5-yl)cyclopropanecarbonitrile | 544 (M + H)+ |
| 131 | 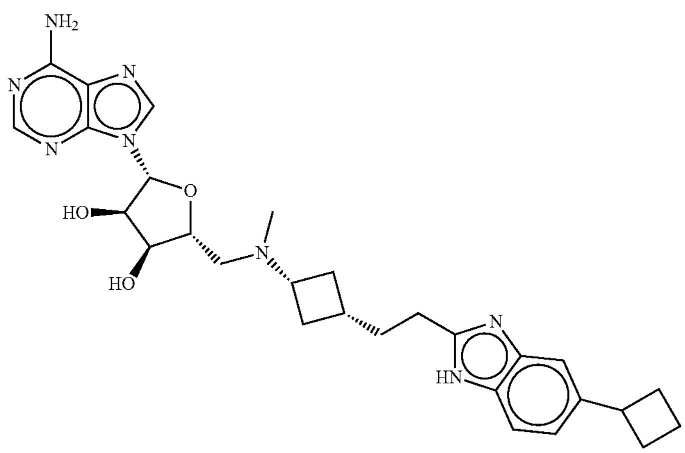 | (2R,3R,4S,5R)-2-(6-amino-9H-purin-9-yl)-5-((((1r,3S)-3-(2-(5-cyclobutyl-1H-benzo[d]imidazol-2-yl)ethyl)cyclobutyl)(methyl)amino)methyl)tetrahydrofuran-3,4-diol | 533 (M + H)+ |
| 132 | 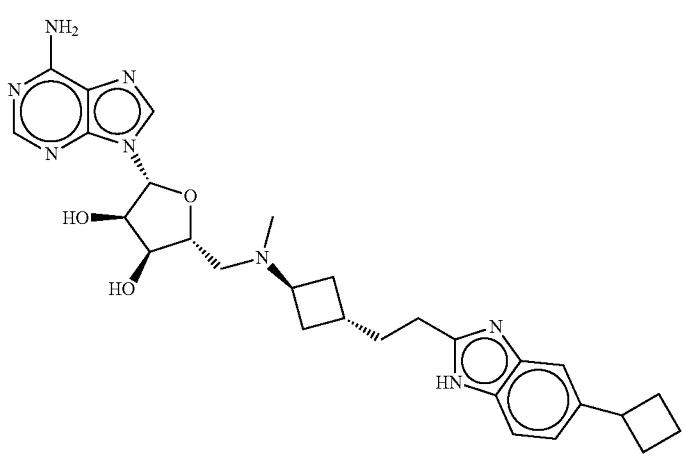 | (2R,3R,4S,5R)-2-(6-amino-9H-purin-9-yl)-5-((((1s,3R)-3-(2-(5-cyclobutyl-1H-benzo[d]imidazol-2-yl)ethyl)cyclobutyl)(methyl)amino)methyl)tetrahydrofuran-3,4-diol | 533 (M + H)+ |

TABLE 1-continued

| Cmpd No. | Structure | Chemical Name | Data (MS or NMR) |
|---|---|---|---|
| 133 | 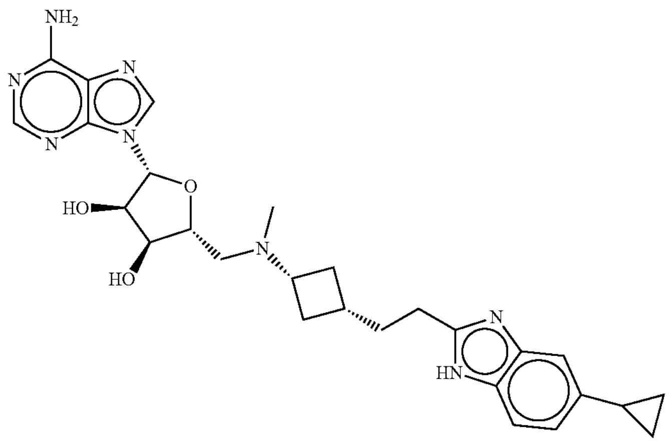 | (2R,3R,4S,5R)-2-(6-amino-9H-purin-9-yl)-5-((((1r,3S)-3-(2-(5-cyclopropyl-1H-benzo[d]imidazol-2-yl)ethyl)cyclobutyl)(methyl)amino)methyl)tetrahydrofuran-3,4-diol | 519 (M + H)+ |
| 134 | 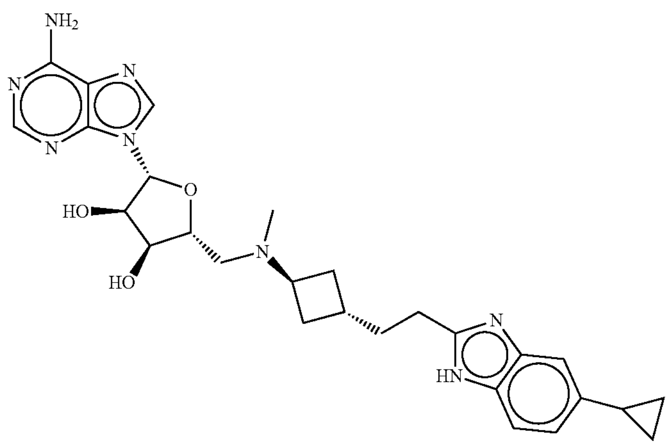 | (2R,3R,4S,5R)-2-(6-amino-9H-purin-9-yl)-5-((((1s,3R)-3-(2-(5-cyclopropyl-1H-benzo[d]imidazol-2-yl)ethyl)cyclobutyl)(methyl)amino)methyl)tetrahydrofuran-3,4-diol | 519 (M + H)+ |
| 135 | 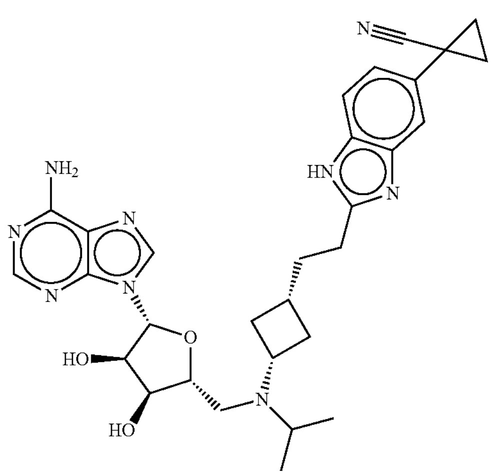 | 1-(2-(2-((1S,3r)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)cyclopropanecarbonitrile | 572 (M + H)+ |

TABLE 1-continued

| Cmpd No. | Structure | Chemical Name | Data (MS or NMR) |
|---|---|---|---|
| 136 | 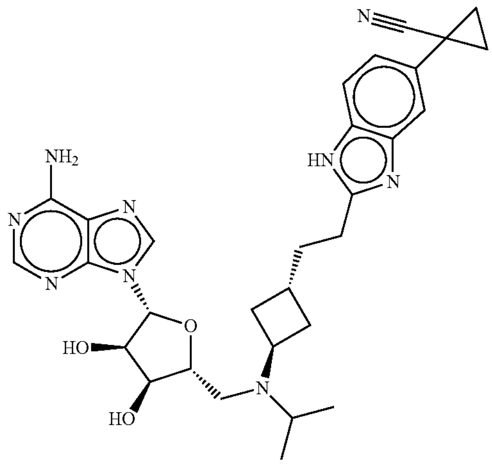 | 1-(2-(2-((1R,3s)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl(cyclopropanecarbonitrile | 572 (M + H)+ |
| 137 | 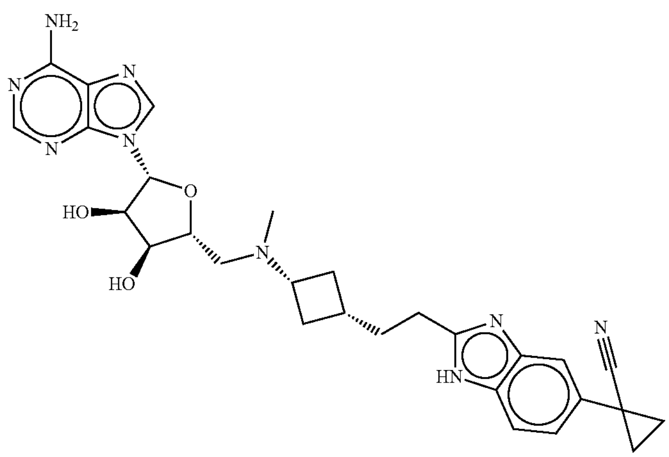 | 1-(2-(2-((1S,3r)-3-((((2R,3S,4R,5R)-5-(6-amino-9H-purin-9-yl)-3,4-dihydroxytetrahydrofuran-2-yl)methyl)(methyl)amino)cyclobutyl)ethyl)-1H-benzo[d]imidazol-5-yl)cyclopropanecarbonitrile | 544 (M + H)+ |
| 138 | 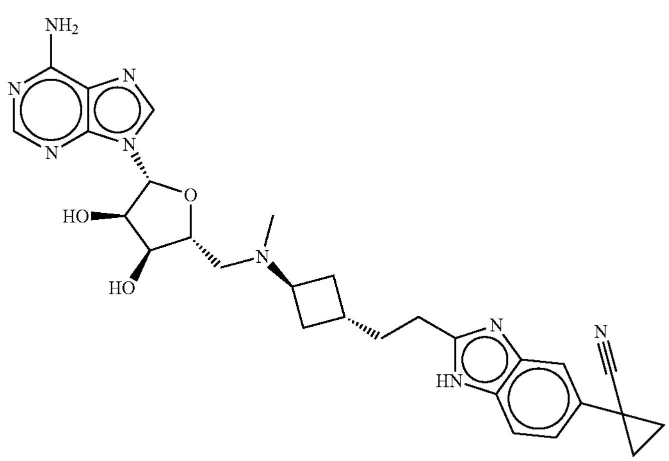 | 1-(2-(2-((1R,3s)-3-((((2R,3S,4R,5R)-5-(6-amino-9H-purin-9-yl)-3,4-dihydroxytetrahydrofuran-2-yl)methyl)(methyl)amino)cyclobutyl)ethyl)-1H-benzo[d]imidazol-5-yl)cyclopropanecarbonitrile | 544 (M + H)+ |

TABLE 1-continued

| Cmpd No. | Structure | Chemical Name | Data (MS or NMR) |
|---|---|---|---|
| 139 | 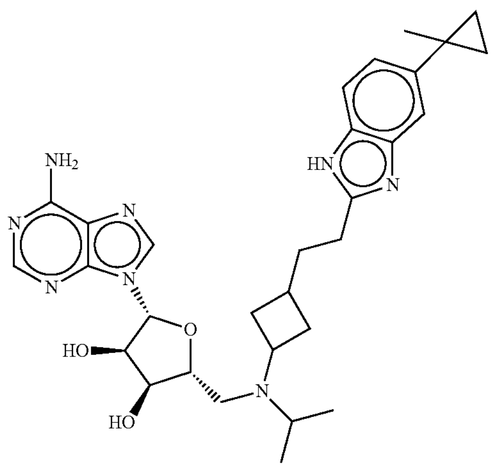 | (2R,3R,4S,5R)-2-(6-amino-9H-purin-9-yl)-5-((isopropyl(3-(2-(5-(1-methylcyclopropyl)-1H-benzo[d]imidazol-2-yl)ethyl)cyclobutyl)amino)methyl)tetrahydrofuran-3,4-diol | 561 (M + H)+ |
| 140 | 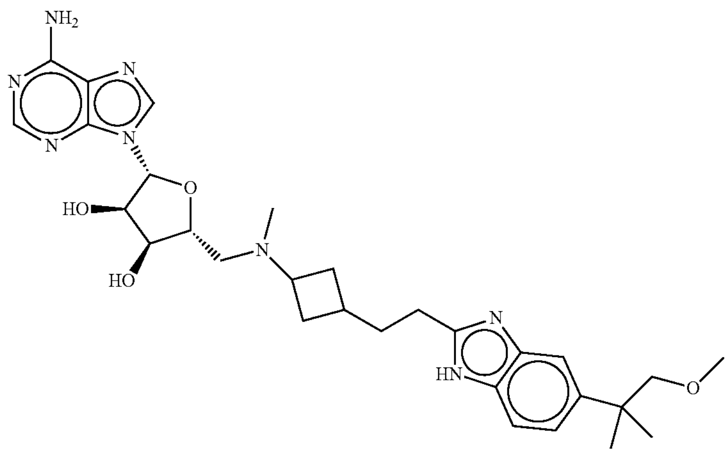 | (2R,3R,4S,5R)-2-(6-amino-9H-purin-9-yl)-5-(((3-(2-(5-(1-methoxy-2-methylpropan-2-yl)-1H-benzo[d]imidazol-2-yl)ethyl)cyclobutyl)(methyl)amino)methyl)tetrahydrofuran-3,4-diol | 565 (M + H)+ |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 5-8 membered monocyclic, 8-12 membered bicyclic, or 11-14 membered tricyclic ring system having one or more heteroatoms (such as O, N, S, or Se).

Examples of heterocycloalkyl groups include, but are not limited to, piperazinyl, pyrrolidinyl, dioxanyl, morpholinyl, and tetrahydrofuranyl.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5- or 6-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkyl aminocarbonyl, alkenyl aminocarbonyl, alkyl carbonyl, aryl carbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The twin "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Calm et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Calm, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

For example, compounds of Formula (I) includes those of the following chiral isomers and geometric isomers.

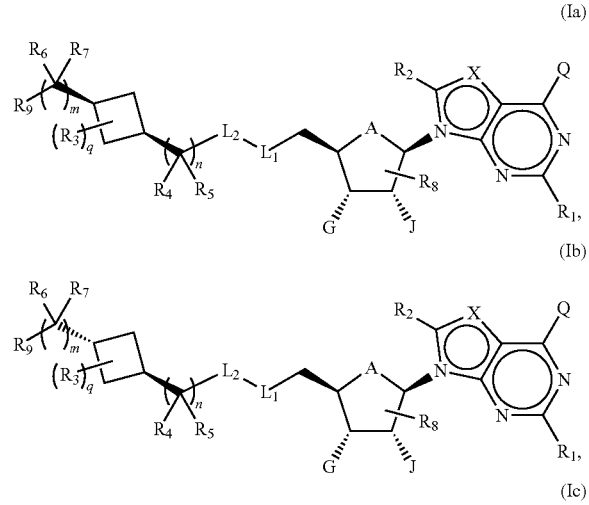

(Ia)

(Ib)

(Ic)

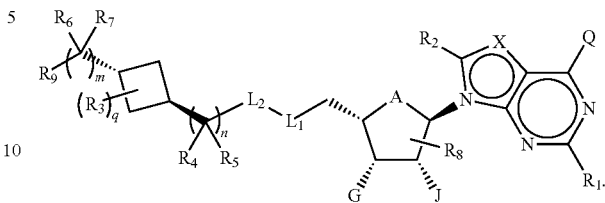

(Id)

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. Benzimidazoles also exhibit tautomerism, when the benzimidazole contains one or more substituents in the 4, 5, 6 or 7 positions, the possibility of different isomers arises. For example, 2,5-dimethyl-1H-benzo[d]imidazole can exist in equilibrium with its isomer 2,6-dimethyl-1H-benzo[d]imidazole via tautomerization.

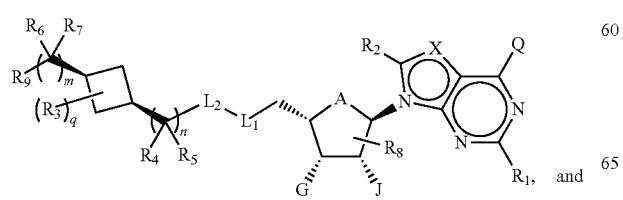 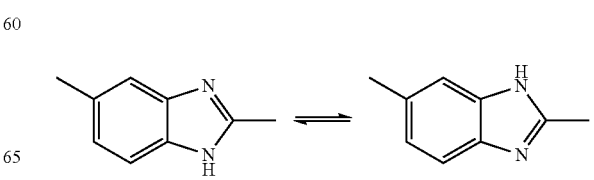

2,5-dimethyl-1H-benzo[d]imidazole
2,6-dimethyl-1H-benzo[d]imidazole

Another example of tautomerism is shown below.

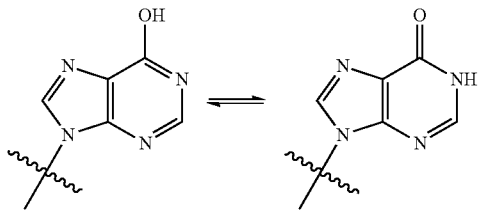

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compounds of the invention may be crystalline, semi-crystalline, non-crystalline, amorphous, mesomorphous, etc.

The compounds of Formula (I), (II), (IIIa), (IIIb), (IIIc) or (IV) include the compounds themselves, as well as their N-oxides, salts, their solvates, and their prodrugs, if applicable. A salt, for example, can be formed between an anion and a positively charged group (e.g., amino) on a substituted purine or 7-deazapurine compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a substituted purine or 7-deazapurine compound. Suitable cations include sodium ion, potassium ion, magnesium ion, calcium ion, and an ammonium cation such as tetramethylammonium ion. The substituted purine or 7-deazapurine compounds also include those salts containing quaternary nitrogen atoms. Examples of prodrugs include esters and other pharmaceutically acceptable derivatives, which, upon administration to a subject, are capable of providing active substituted purine or 7-deazapurine compounds.

Additionally, the compounds of the present invention, for example, the salts of the compounds, can exist in either hydrated or unhydrated (the anhydrous) form or as solvates with other solvent molecules. Nonlimiting examples of hydrates include hemihydrates, monohydrates, dihydrates, trihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are substituted purine compounds or substituted 7-deazapurine compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

2. SYNTHESIS OF SUBSTITUTED PURINE COMPOUNDS AND SUBSTITUTED 7-DEAZAPURINE COMPOUNDS

The present invention provides methods for the synthesis of the compounds of Formulae (I), (II), (IIIa), (IIIb), (IIIc) and (IV). The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; Greene, T. W., Wuts, P. G. M., *Protective Groups in Organic Synthesis*, $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with Formulae (I), (II), (IIIa), (IIIb), (IIIc) and (IV) may be prepared according to the procedures illustrated in Schemes A-W below, from commercially available starting materials or starting materials which can be prepared using literature procedures. The R groups (such as R, R', and Ra) in Schemes A-P may correspond to variables (i.e., $R_1$, $R_2$, $R_b$, and $R_c$) as defined in Formula (I), (II), (IIIa), (IIIb), (IIIc) or (IV), unless otherwise specified. "PG" in the schemes refers to a protecting group.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, $3^{rd}$ edition, John Wiley & Sons: New York, 1999.

Preferred protecting groups include, but are not limited to:
For the hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:
AA ammonium acetate
Ac acetyl
ACN acetonitrile
AcOH acetic acid
atm atmosphere
Bn benzyl
BOC tert-butoxy carbonyl
BOP (benzotriazol-1-yloxy)tris(dimethylamino)phosphonium hexafluorophosphate
Cbz benzyloxycarbonyl
COMU (1-cyano-2-ethoxy-2-oxoethylidenaminooxy)dimethylamino-morpholino-carbenium hexafluorophosphate
d days
DBU 1,8-diazabicyclo[5.4.0]undec-7-ene
DCE 1,2 dichloroethane
DCM dichloromethane
DEA diethylamine
DEAD diethyl azodicarboxylate
DIAD diisopropyl azodicarboxylate
DiBAL-H diisobutylalumininium hydride
DIPEA N,N-diisopropylethylamine (Hunig's base)
DMAP N,N-dimethyl-4-aminopyridine
DMB 2,4 dimethoxybenzyl
DMF dimethylfoiniamide
DMSO dimethylsulfoxide
DPPA diphenylphosphoryl azide
EA or EtOAc ethylacetate
EDC or EDCI N-(3-dimethylaminopropyl)-N'-ethylcarbodiimide
ELS Evaporative Light Scattering
ESI– Electrospray negative mode
ESI+ Electrospray positive mode
$Et_2O$ diethyl ether
$Et_3N$ or TEA triethylamine
EtOH ethanol
FA formic acid
FC flash chromatography
h hours
$H_2O$ water
HATU O-(7-azabenzotriazol-1-yl)-N,N,N',N'-tetramethyluronium hexafluorophosphate
HCl hydrochloric acid
HOAT 1-hydroxy-7-azabenzotriazole
HOBt 1-hydroxybenzotriazole
HOSu N-hydroxysuccinimide
HPLC high performance liquid chromatography
Inj. Vol. injection volume
I.V. or IV intravenous
KHMDs potassium hexamethyldisilazide
LC/MS or LC-MS liquid chromatography mass spectrum
LDA lithium diisopropylamide
LG leaving group
LiHMs lithium hexamethyldisilazide
M Molar
m/z mass/charge ratio
m-CPBA meta-chloroperbenzoic acid
MeCN acetonitrile
MeOD $d_4$-methanol
MeOH methanol MgSO₄ magnesium sulfate
min minutes
MS mass spectrometry or mass spectrum
Ms mesyl
MsCl methanesulfonyl chloride
MsO mesylate
MWI microwave irradiation
Na₂CO₃ sodium carbonate
NaHCO₃ sodium bicarbonate
NaHMDs sodium hexamethyldisilazide
NaOH sodium hydroxide
NIS N-iodosuccinimide
NMR Nuclear Magnetic Resonance
o/n or O/N overnight
PE petroleum ether
PG protecting group
PMB para-methoxybenzyl
PPAA 1-propanephosphonic acid cyclic anhydride
ppm parts per million
prep HPLC preparative high performance liquid chromatography
prep TLC preparative thin layer chromatography
p-TsOH para-toluenesulfonic acid
rt or RT room temperature
SEM 2-(trimethylsilyl)ethoxymethyl
SEMC1 (trimethylsilyl)ethoxymethyl chloride
SFC supercritical chromatography
SGC silica gel chromatography
STAB sodium triacetoxyborohydride
TBAF tetra-n-butylammonium fluoride
TFA trifluoroacetic acid
TfO triflate
THF tetrahydrofuran
THP tetrahydropyran
TLC thin layer chromatography
Ts tosyl
TsOH tosic acid
UV ultraviolet The invention provides methods for making the compounds of the invention. The following schemes depict exemplary chemistries available for synthesizing the compounds of the invention.

Scheme A: 5'- Amino Purine Ribose (A-V) Synthesis

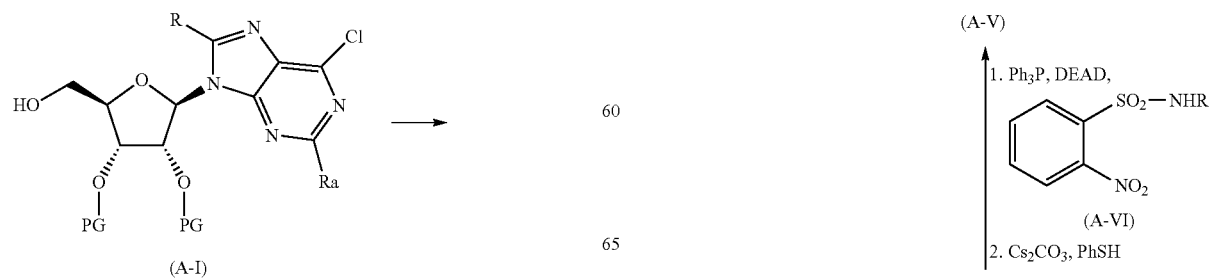

-continued

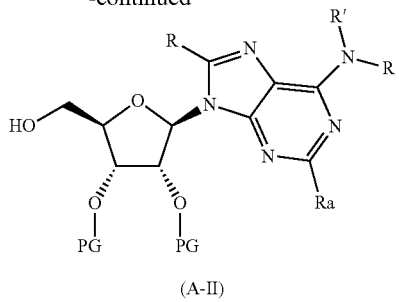

(A-II)

-continued

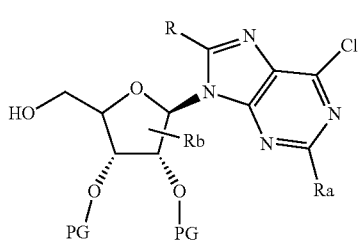

(A-VIII)

5'-Amino purine-ribose intermediates (A-V) can be synthesized as depicted in Scheme A above. A suitable protected 6-Cl adenosine derivative (A-I) is converted into a 6-amino derivative (A-II) by treatment with the appropriate amine (including ammonia) in the presence of a base such as $Et_3N$, $K_2CO_3$ or Hunig's base in solvent such as MeCN or DMF, THF, iPrOH or a mixture thereof. If required, the reaction may be heated to 100° C. (if the temperature required is greater than the boiling point of one or more of the components in the mixture, the reaction may be performed in a sealed tube). The R groups in the scheme may represent alkyl protecting groups (e.g., 2,4 dimethoxybenzyl). The 6-amino product (A-II) may be transformed into the 5'-azido intermediate (A-III) by converting the 5'-hydroxyl group into a leaving group such as MsO (i.e., $CH_3S(O)_2O$) by treatment with methanesulfonyl chloride (MsCl) in the presence of a base such as $Et_3N$, pyridine or $K_2CO_3$ in an inert solvent such as $CH_2Cl_2$, THF, MeCN, DMF or a mixture thereof. The 5'-leaving group is then displaced with azide anion from $NaN_3$ in an inert solvent such as DMF. Alternatively (A-II) may be directly transformed into (A-III) by treatment with DPPA, $Ph_3P$, and DIAD in a solvent such as THF. The azido group of (A-III) may be reduced to the primary amine (A-IV) by reduction with $H_2$ in the presence of a metal catalyst (e.g. Pd/C, $PtO_2$) or by a Staudinger reaction with a phosphine such as $Ph_3P$ or $PMe_3$. The primary amine (A-IV) may be converted into the secondary amine (A-V) by treatment with the appropriate ketone or aldehyde in the presence of a suitable reducing agent such as $NaBH(OAc)_3$ or $NaCNBH_3$. Additional reagents such as $Ti(OiPr)_4$ may be added.

Alternatively the 5'-hydroxy intermediate (A-II) may be treated with the sulfonamide (A-VI), DEAD and $Ph_3P$ in an inert solvent such as THF. The resultant sulfonamide product may then be treated with benzenethiol in the presence of a base such as $K_2CO_3$, $Cs_2CO_3$ to give the secondary amine (A-V).

These reaction sequences above may also be applied to lyxose derivatives starting from (A-VII) to give the diastereomer with opposite configuration at the 5' position.

A similar set of reaction sequences may be employed for 2'-deoxy, or 3'-deoxy, or substituted ribose or lyxose (A-VIM above to obtain 5'-amino purine-ribose/lyxose intermediates.

An alternative method for introduction of a 6-$NH_2$ group, as shown below, is via treating (A-IX) derivatives with $NaN_3$ to produce a 6-azido intermediate followed by reduction to the $NH_2$ moiety (A-X) with a trialkyl phosphine such as $PMe_3$ or $PPh_3$.

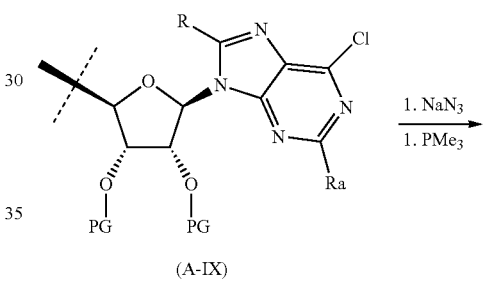

(A-IX)

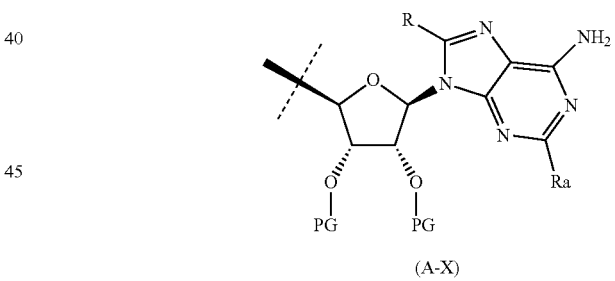

(A-X)

Scheme B: 5' Amino 7-Deazapurine Ribose Synthesis

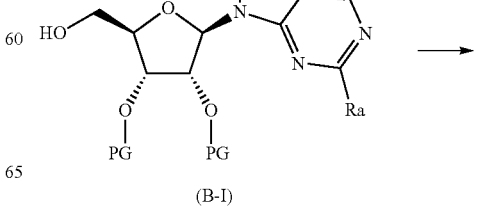

(A-VII)

(B-I)

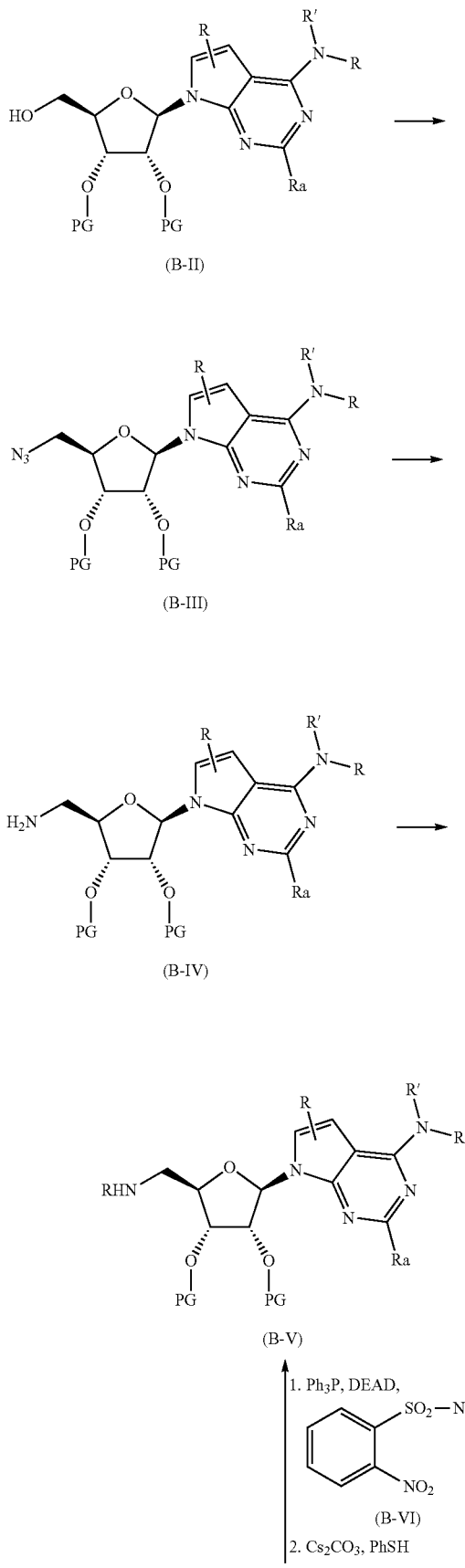

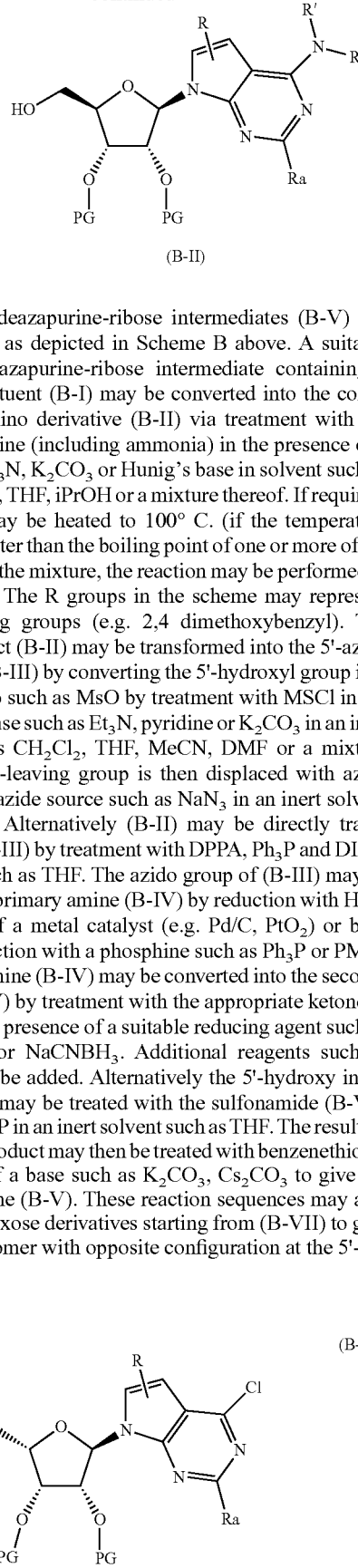

5'-Amino-7-deazapurine-ribose intermediates (B-V) can be synthesized as depicted in Scheme B above. A suitable protected 7-deazapurine-ribose intermediate containing a 6-chloro substituent (B-I) may be converted into the corresponding 6-amino derivative (B-II) via treatment with the appropriate amine (including ammonia) in the presence of a base such as $Et_3N$, $K_2CO_3$ or Hunig's base in solvent such as MeCN or DMF, THF, iPrOH or a mixture thereof. If required, the reaction may be heated to 100° C. (if the temperature required is greater than the boiling point of one or more of the components in the mixture, the reaction may be performed in a sealed tube). The R groups in the scheme may represent alkyl protecting groups (e.g. 2,4 dimethoxybenzyl). The 6-amino product (B-II) may be transformed into the 5'-azido intermediate (B-III) by converting the 5'-hydroxyl group into a leaving group such as MsO by treatment with MSCl in the presence of a base such as $Et_3N$, pyridine or $K_2CO_3$ in an inert solvent such as $CH_2Cl_2$, THF, MeCN, DMF or a mixture thereof. The 5'-leaving group is then displaced with azide anion from an azide source such as $NaN_3$ in an inert solvent such as DMF. Alternatively (B-II) may be directly transformed into (B-III) by treatment with DPPA, $Ph_3P$ and DIAD in a solvent such as THF. The azido group of (B-III) may be reduced to the primary amine (B-IV) by reduction with $H_2$ in the presence of a metal catalyst (e.g. Pd/C, $PtO_2$) or by a Staudinger reaction with a phosphine such as $Ph_3P$ or $PMe_3$. The primary amine (B-IV) may be converted into the secondary amine (B-V) by treatment with the appropriate ketone or aldehyde in the presence of a suitable reducing agent such as $NaBH(OAc)_3$ or $NaCNBH_3$. Additional reagents such as $Ti(OiPr)_4$ may be added. Alternatively the 5'-hydroxy intermediate (B-II) may be treated with the sulfonamide (B-VI), DEAD and $Ph_3P$ in an inert solvent such as THF. The resultant sulfonamide product may then be treated with benzenethiol in the presence of a base such as $K_2CO_3$, $Cs_2CO_3$ to give the secondary amine (B-V). These reaction sequences may also be applied to lyxose derivatives starting from (B-VII) to give the diastereoisomer with opposite configuration at the 5'-position -continued

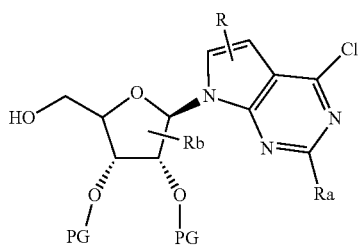

(B-VIII)

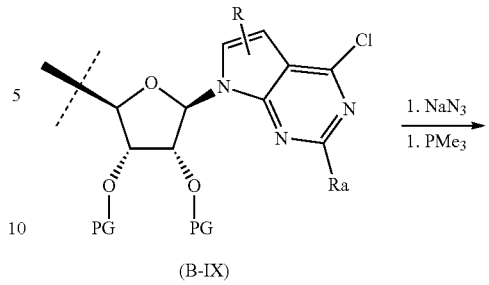

(B-IX)

A similar set of reaction sequences may be employed for 2'-deoxy, or 3'-deoxy, or substituted ribose or lyxose (B-VIII) above to obtain 5'-amino 7-deazapurine-ribose/lyxose intermediates.

An alternative method for introduction of a 6-$NH_2$ group, as shown below, is via treating (B-IX) derivatives with $NaN_3$ to produce a 6-azido intermediate followed by reduction to the $NH_2$ moiety (B-X) with a trialkyl phosphine such as $PMe_3$ or $PPh_3$.

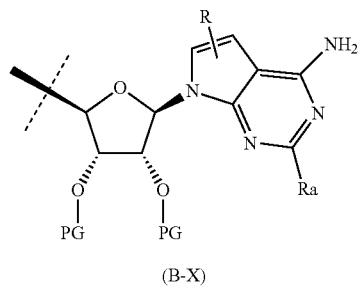

(B-X)

Scheme C: Purine-carbocyclic Intermediates Synthesis

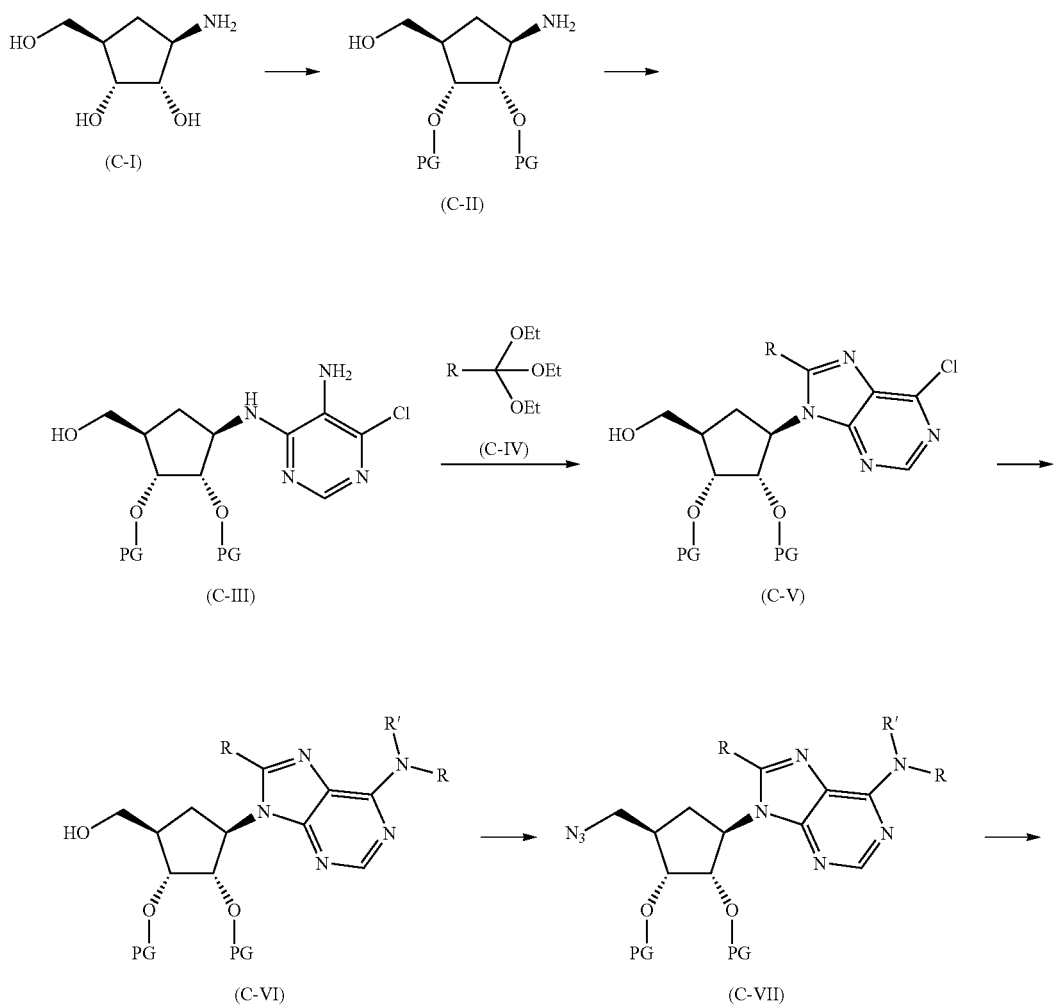

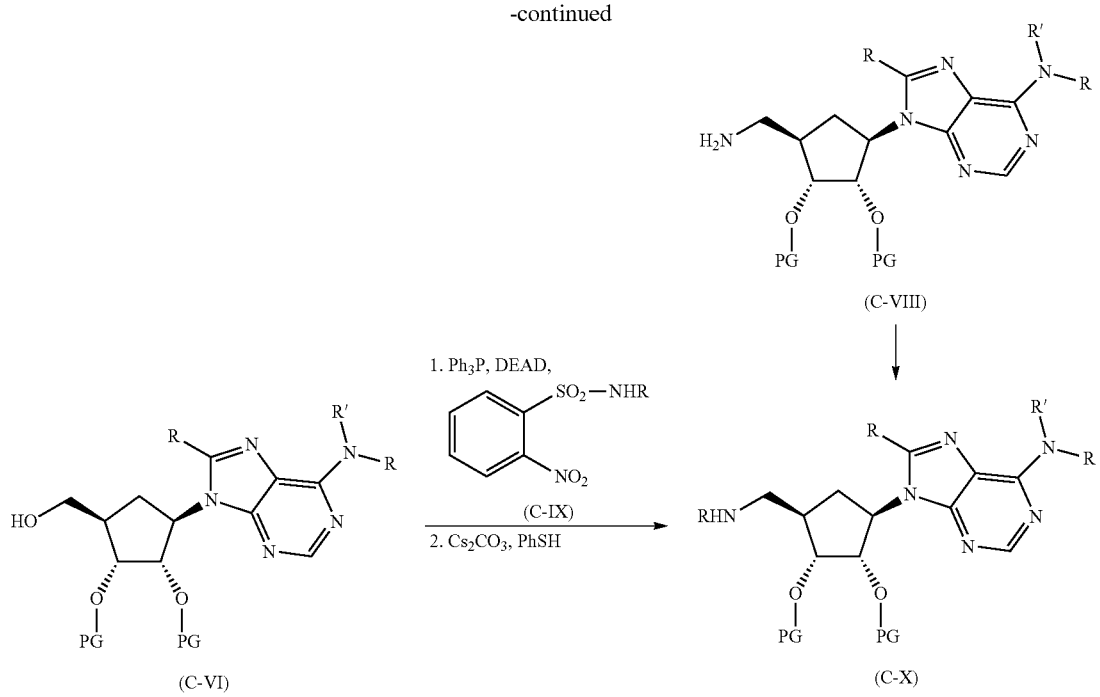

The 5'-amino purine carbocyclic intermediates (C-X) may be prepared as depicted in Scheme C. The cyclopentane (C-I) is optionally protected by methods known to those of ordinary skill in the art to give (C-II). (C-II) is treated with the appropriate 4,6-dichloropyrimidine-5-amine in the presence of a base such as $Et_3N$ in a protic solvent such as n-butanol. The reaction is heated or submitted to microwave conditions to give the intermediate (C-III). The purine intermediate (C-V) is produced by treating (C-III) with the orthoester (C-IV) in the presence of an acid, such as AcOH. The reaction is usually heated. The 6-amino substituent may be introduced by treatment with the appropriate amine (including ammonia) in the presence of a base such as $Et_3N$, $K_2CO_3$ or Hunig's base in solvent such as MeCN or DMF, THF, iPrOH, or a mixture thereof. If required, the reaction may be heated to 100° C. (if the temperature required is greater than the boiling point of one or more of the components in the mixture, the reaction may be performed in a sealed tube). The R groups in the scheme may represent alkyl protecting groups (e.g., 2,4 dimethoxybenzyl). The 6-amino product (C-VI) may be transformed into the 5'-azido intermediate (C-VII) by converting the 5'-hydroxyl group into a leaving group such as MsO by treatment with MsCl in the presence of a base such as $Et_3N$, pyridine or $K_2CO_3$ in an inert solvent such as $CH_2Cl_2$, THF, MeCN, DMF or a mixture thereof. The 5'-leaving group is then displaced with azide anion from $NaN_3$ in an inert solvent such as DMF. Alternatively (C-VI) may be directly transformed into (C-VII) by treatment with DPPA, $Ph_3P$ and DIAD in a solvent such as THF. The azido group of (C-VII) may be reduced to the primary amine (C-VIII) by reduction with $H_2$ in the presence of a metal catalyst (e.g. Pd/C, $PtO_2$) or by a Staudinger reaction with a phosphine such as $Ph_3P$ or $PMe_3$. The primary amine (C-VIII) may be converted into the secondary amine (C-X) by treatment with the appropriate ketone or aldehyde in the presence of a suitable reducing agent such as $NaBH(OAc)_3$ or $NaCNBH_3$. Additional reagents such as $Ti(OiPr)_4$ may be added. Alternatively the 5'-hydroxy intermediate (C-VI) may be treated with the sulfonamide (C-IX), DEAD and $Ph_3P$ in an inert solvent such as THF. The resultant sulfonamide product may then be treated with benzenethiol in the presence of a base such as $K_2CO_3$, $Cs_2CO_3$ to give the secondary amine (C-X).

Scheme D: 7-Deazapurine-carbocyclic Intermediates Synthesis

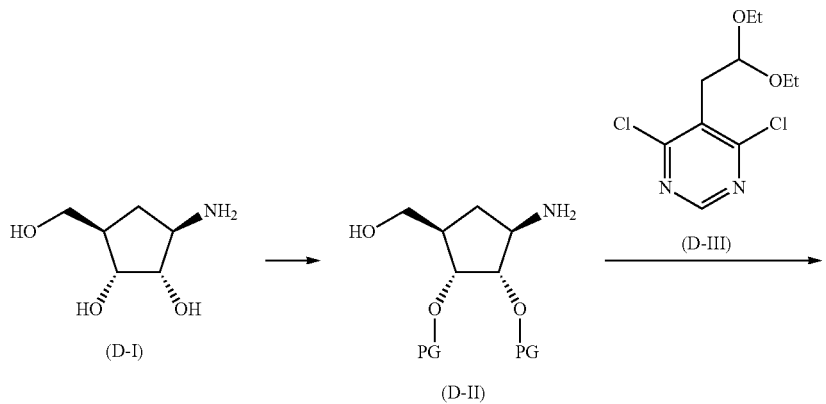

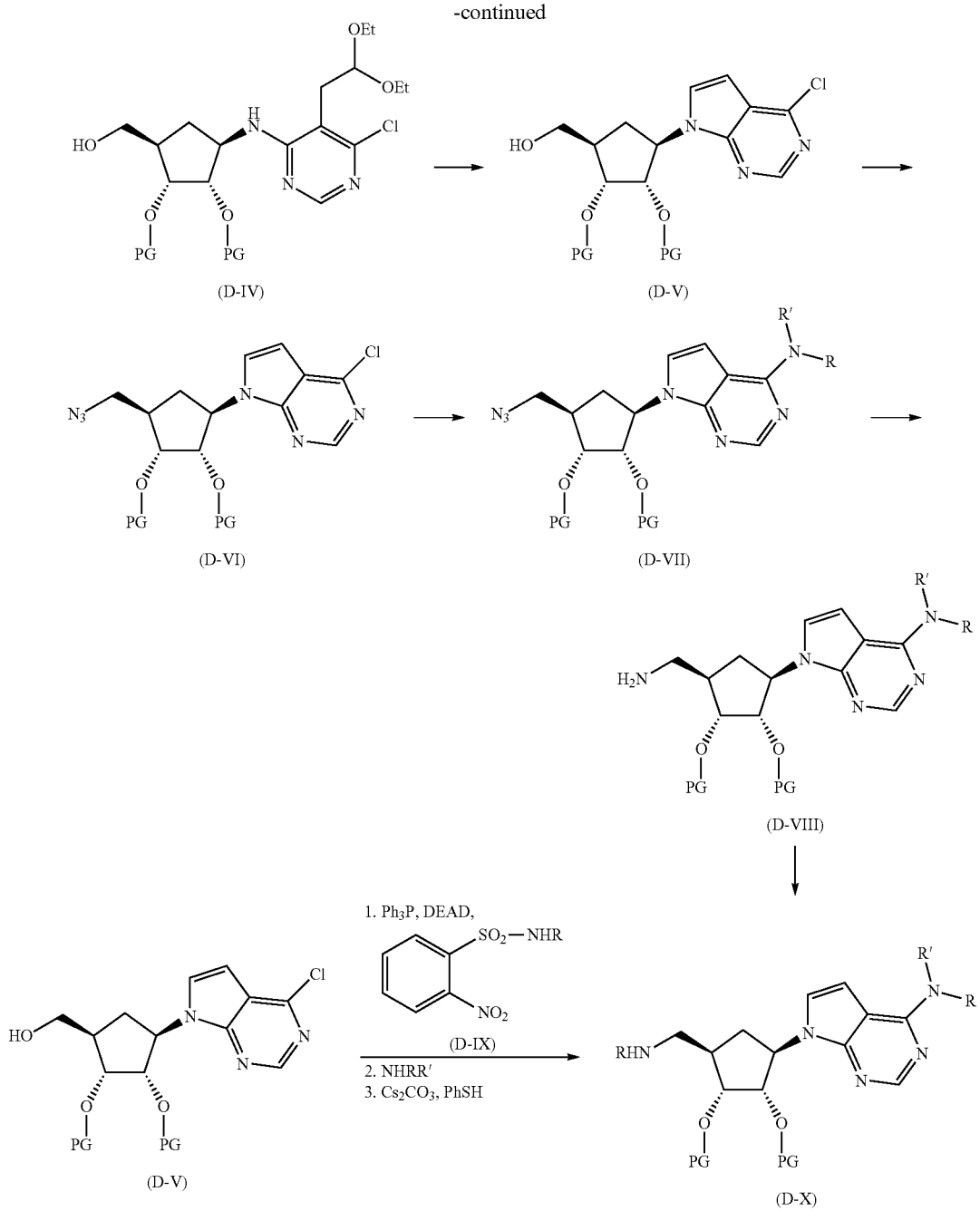

The 5'-amino 7-deazapurine carbocyclic intermediates (D-X) may be prepared as depicted in Scheme D. The cyclopentane (D-I) is optionally protected by methods known to those of ordinary skill in the art to give (D-II). (D-II) is treated with the appropriate 4,6-dichloropyrimidine (D-III) in the presence of a base such as $Et_3N$ in a protic solvent such as EtOH, n-butanol. The reaction is heated to give the intermediate (D-IV). The intermediate (D-V) is produced by treating (D-IV) with an acid, such as HCl or AcOH.

The 5'-hydroxyl of (D-V) may be transformed into the 5'-azido intermediate (D-VI) by initially converting the 5'-hydroxyl group into a leaving group such as MsO by treatment with MsCl in the presence of a base such as $Et_3N$, pyridine or $K_2CO_3$ in an inert solvent such as $CH_2Cl_2$, THF, MeCN, DMF or a mixture thereof and then displacing the leaving group with azide anion from $NaN_3$ in an inert solvent such as DMF. Alternatively (D-V) may be directly transformed into (D-VI) by treatment with DPPA, $Ph_3P$ and DIAD in a solvent such as THF.

The 6-amino substituent may be introduced by treatment of (D-VI) with the appropriate amine (including ammonia) in the presence of a base such as $Et_3N$, $K_2CO_3$ or Hunig's base in solvent such as MeCN or DMF, THF, iPrOH or a mixture thereof. If required, the reaction may be heated to 100° C. (if the temperature required is greater than the boiling point of one or more of the components in the mixture, the reaction may be performed in a sealed tube). The R groups in the scheme may represent alkyl protecting groups (e.g. 2,4 dimethoxybenzyl). The azido group of (D-VII) may be reduced to the primary amine (D-VIII) by reduction with $H_2$ in the presence of a metal catalyst (e.g. Pd/C, $PtO_2$) or by a Staudinger reaction with a phosphine such as $Ph_3P$ or $PMe_3$. The primary amine (D-VIII) may be converted into the secondary amine (D-X) by treatment with the appropriate ketone or aldehyde in the presence of a suitable reducing agent such as $NaBH(OAc)_3$ or $NaCNBH_3$. Additional reagents such as $Ti(OiPr)_4$ may be added. Alternatively the 5'-hydroxy intermediate (D-V) may be treated with the sulfonamide (D-IX), DEAD and $Ph_3P$ in an inert solvent such as THF. 6-Amino group may then be introduced using conditions similar to those used for converting (D-VI) into (D-VII). The resultant sulfonamide product may then be treated with benzenethiol in the presence of a base such as $K_2CO_3$, $Cs_2CO_3$ to give the secondary amine (D-X).

A person of ordinary skill will recognize that having an appropriately substituted dichloropyrimidine (D-III) will allow for substitution on the 7-deazapurine moiety.

To generate the appropriate intermediates of opposite stereochemistry at 5'-position, a reaction sequence as depicted in Scheme E above may be followed. The cyclopentane (E-I) is optionally protected, upon which the 5'-hydroxyl is converted into a leaving group via treatment with MsCl in the presence of $Et_3N$ in a solvent such a $CH_2Cl_2$. The 5'-leaving group is displaced with $Me_2NH$, by treatment with $Me_2NH$ as a 2.0M solution in THF in a sealed tube. The reaction is heated to 40-80° C. The resultant tertiary amine is oxidized with an oxidant such as mCPBA in a solvent such a $CH_2Cl_2$ to give the corresponding N-oxide. The N-oxide is then subjected to heat, 50-120° C. in an inert solvent such N,N-dimethylacetamide to give the alkene (E-III). The alkene is subjected to hydroboration/oxidative work up to produce the inverted 5' stereoisomer (E-IV). Suitable hydroboration reagents include $BH_3$-THF and suitable oxidative work-up conditions include $H_2O_2$/NaOH. The intermediate (E-IV) may then be subjected to the reaction sequences depicted in schemes C and D to furnish the intermediates (E-V) and (E-VI).

Scheme E: Inversion of stereochemistry at 5'-Position

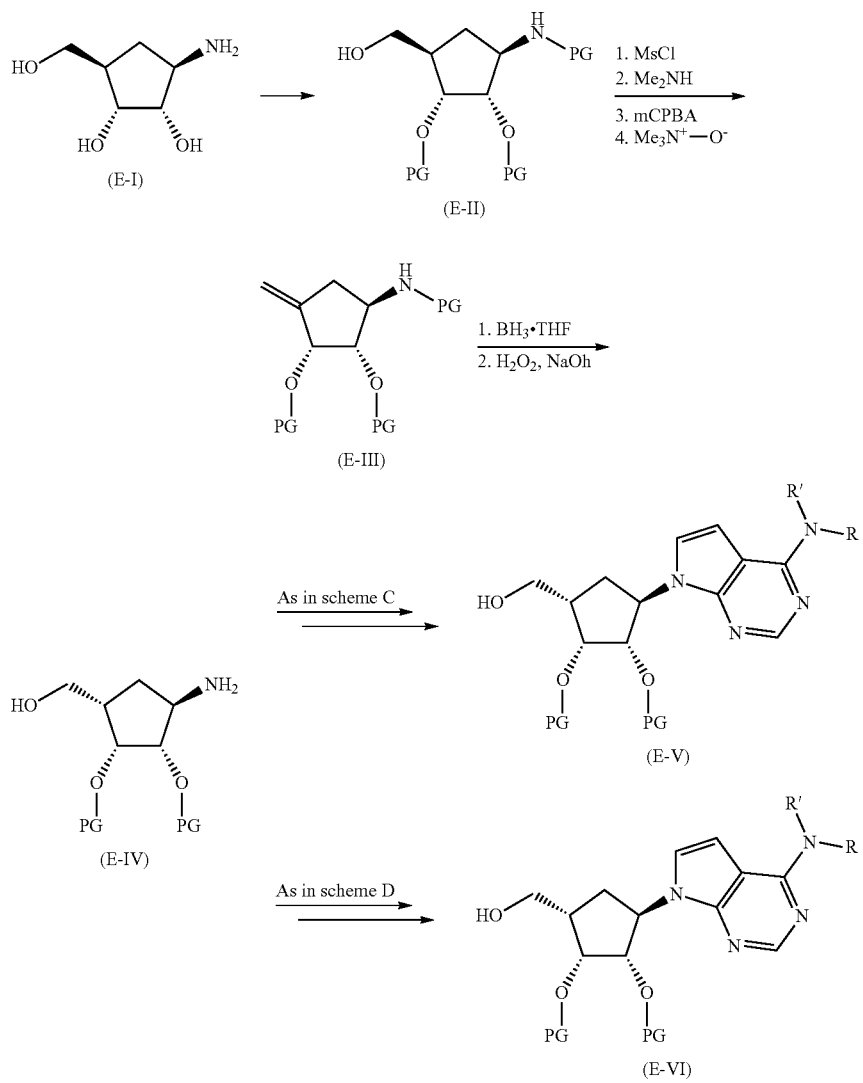

Scheme F: 2' and 3' Deoxycyclopentanes and Riboses

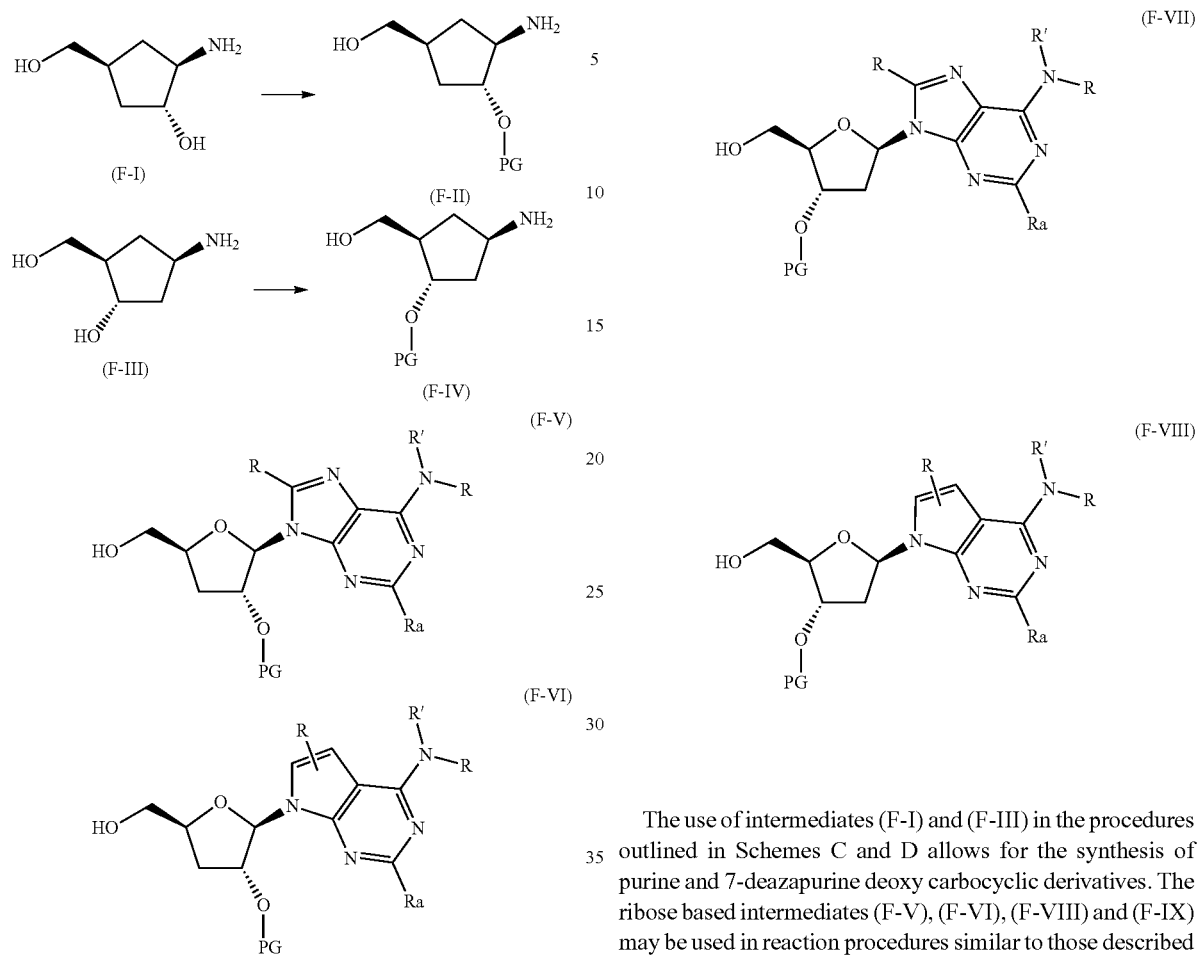

The use of intermediates (F-I) and (F-III) in the procedures outlined in Schemes C and D allows for the synthesis of purine and 7-deazapurine deoxy carbocyclic derivatives. The ribose based intermediates (F-V), (F-VI), (F-VIII) and (F-IX) may be used in reaction procedures similar to those described in Schemes A and B above.

Scheme G: Cyclobutane Synthesis

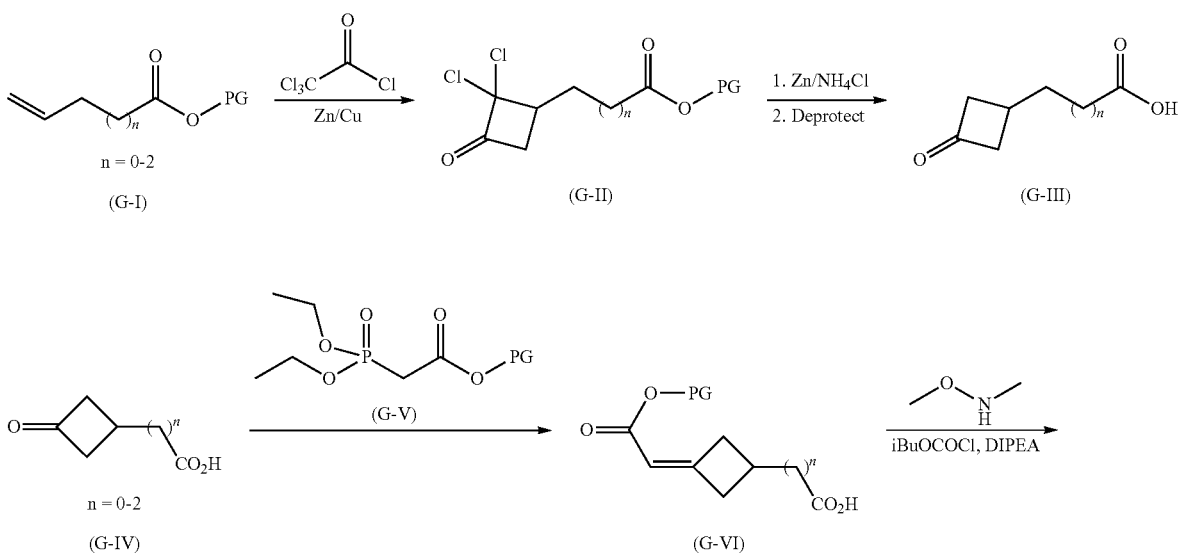

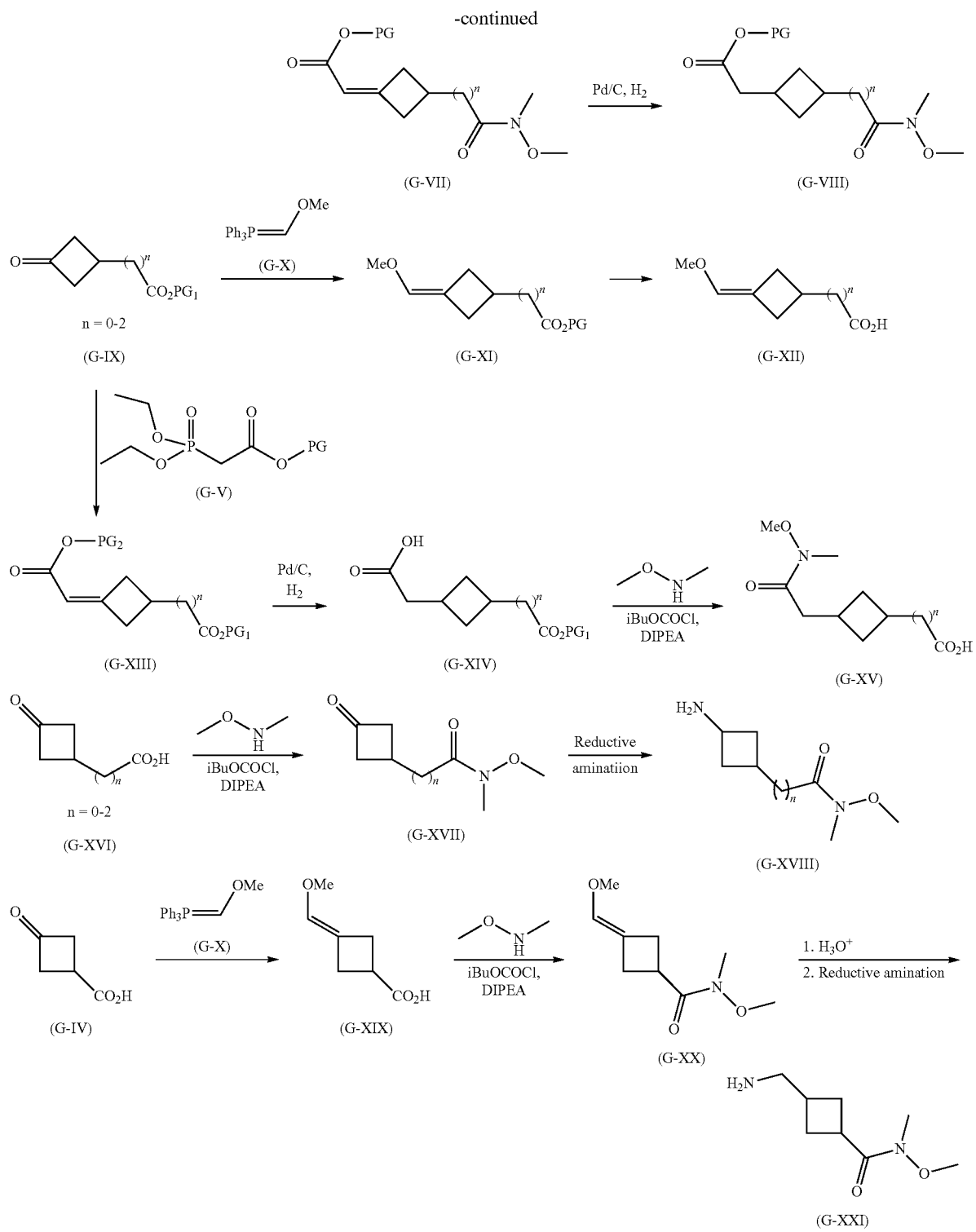

Cyclobutanes of formulae (G-VIII), (G-XV) and (G-XXI) may be synthesized as depicted in Scheme G. The alkenyl esters (G-I) may be subjected to a [2+2] cycloaddition with trichloroacetyl chloride in the presence of Zn/Cu couple in an inert solvent such as $Et_2O$, DME, THF or a mixture thereof. Alternatively the [2+2] cycloaddition reaction may be performed using Zn dust under sonication conditions. The dichlorides (G-II) are reduced via treatment with Zn powder in the presence of a proton donor such as $NH_4Cl$ in a solvent such as MeOH. The cyclobutanones (G-IV) (which include (G-III)) may be further elaborated by treatment with a phosphonate (G-V) to give the α, β unsaturated esters (G-VI). The acid (VI) is converted to the Weinreb amide (G-VII) under standard conditions (e.g. iso-butyl chloroformate, Hunig's base, N,O-dimethyl hydroxylamine). The double bond may then be reduced via hydrogenation using $H_2$ in the presence of a metal catalyst such as Pd/C, $PtO_2$ or $Pd(OH)_2$ to give the cyclobutane intermediates (G-VIII).

The cyclobutanones (G-IX) may be treated with the Wittig reagent (G-X) to give the cyclobutane enol ether (G-XI) which upon deprotection gives the corresponding acid (G-XII).

The cyclobutanones (G-IX) may also be treated with the stabilized phosphonate (G-V) in the presence of a base such as KOtBu, LDA, NaHMDS, KHMDS or LiHMDS or with $Et_3N$ in the presence of LiCl in an inert solvent to give the α, β unsaturated ester (G-XIII) which can be reduced to the (G-XIV) by treatment with $H_2$ in the presence of a metal catalyst such as Pd/C, $Pd(OH)_2$ or $PtO_2$ in an inert solvent. The acid functionality of (G-XIV) may be converted into the corresponding Weinreb amide by treatment with N,O-dimethylhydroxylamine in presence of a suitable coupling agent such as iso-butylchloroformate and a base such as Hunig's base to give (G-XV).

The cyclobutanones (G-XVI) may also be treated with N,O-dimethylhydroxylamine in presence of a suitable coupling agent such as iso-butylchloroformate and a base such as Hunig's base to give the corresponding Weinreb amide (G-XVII) which upon reductive amination with an ammonia equivalent followed by deprotection as needed gives the amine (G-XVIII). Suitable ammonia equivalents include benzhydryl amine, $NH_3$, $NH_4Cl$, $BnNH_2$, $PMB-NH_2$, 2,4 DMB-$NH_2$ which may be treated with the ketone (G-XVII) and a suitable reducing agent such as $NaCN(BH_3)$ or $Na(OAc)_3BH$ in the presence of an acid if required such as HCl or AcOH. Protecting groups on the reductive amination products may be removed by methods known to those of ordinary skill in the art. Alternatively the ketone (G-XVII) can be treated with hydroxyl amine to form the corresponding oxime which then can be reduced with $H_2$ in the presence of a metal catalyst such as Pd/C, $PtO_2$ or $Pd(OH)_2$ to give the intermediate (G-XVIII).

The cyclobutane (G-IV) may converted into the amine (G-XXI) via a multi-step sequence involving treating (G-IV) with the phosphorane (G-V) to produce the enol ether (G-XIX). Treatment of (G-XIX) with which is then N,O-dimethylhydroxylamine in presence of a suitable coupling agent such as iso-butyl chloroformate and a base such as Hunig's base to give the corresponding Weinreb amide (G-XX) which after aqueous hydrolysis of the enol ether (e.g. $TsOH/H_2O$, $HCl/H_2O$) and reductive amination with an ammonia equivalent followed by deprotection as needed gives the amine (G-XXI). Suitable ammonia equivalents include benzhydryl amine, $NH_3$, $NH_4Cl$, $BnNH_2$, $PMB-NH_2$, 2,4 DMB-$NH_2$. Suitable reducing agents for the reductive amination include $NaCN(BH_3)$ or $Na(OAc)_3BH$ used in the presence of an acid if required such as HCl or AcOH. Protecting groups on the reductive amination products may be removed by methods known to those of ordinary skill in the art.

Scheme H: Elaboration of Cyclobutanes

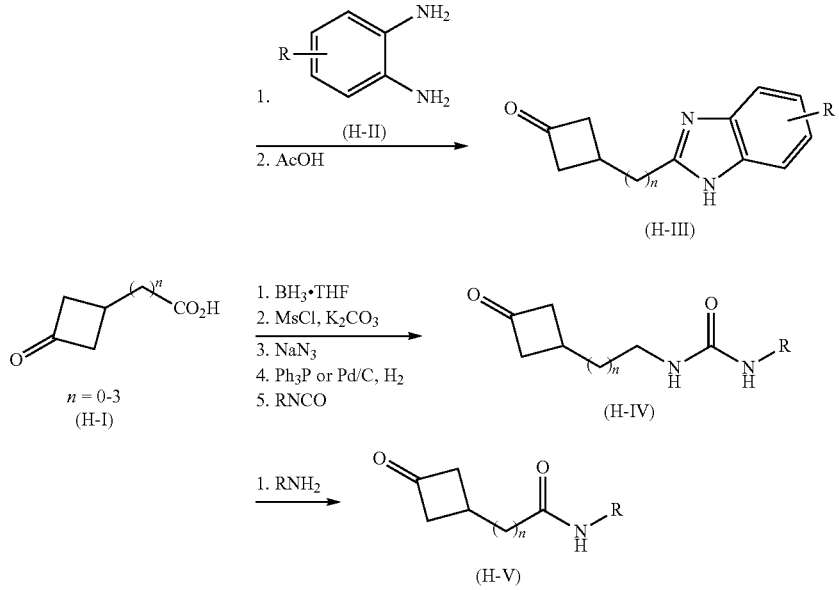

The cyclobutanones (H-I) can be converted into the benzimidazoles (H-III), ureas (H-IV) and amides (H-V) via the reaction sequences depicted in Scheme H. The benzimidazoles (H-III) may be formed by treating the acids (H-I) with the appropriate benzene diamine (H-II) in the presence of a suitable coupling agent (e.g., HATU, PPAA, COMU, EDC, EDCI), in the presence of a base (e.g., $Et_3N$, Hunig's base, $K_2CO_3$). Additional reagents such as HOAT, HOBt or HOSu may be added if necessary. The resultant amino-amides are then cyclized to the benzimidazoles in the presence of acid, e.g. AcOH which may also serve as the solvent. The reaction is normally carried at a temperatures ranging from RT to 80° C. The ureas (H-IV) may be prepared by converting the acids (H-I) as follows. The acid is reduced to the corresponding primary alcohol using a reagent such as $LiAlH_4$ or $BH_3.THF$. If needed the ketone functionality may first be protected (e.g., as a ketal) prior to reduction and subsequently deprotected. The primary alcohol is then converted into a leaving group such as a mesylate. The resultant leaving group is displaced with azide from a source such as $NaN_3$. The azido product compound is reduced to the corresponding amino compound using $H_2$ in the presence of a metal catalyst such as Pd/C or via a Staudinger reaction with a phosphine such as $PMe_3$ or $PPh_3$. The urea (H-IV) is then formed by treatment of the primary amine with the appropriate isocyanate, R—C=N=O in the presence of a base such as $Et_3N$ or $K_2CO_3$ in an inert solvent such as $CH_2Cl_2$. The amides (H-V) are formed by treating the acids (H-I) with the appropriate amine R—$NH_2$ is the presence of a suitable coupling agent (e.g. HATU, PPAA, COMU, EDC, EDCI), in the presence of a base (e.g. $Et_3N$, Hunig's base, $K_2CO_3$). Additional reagents such as HOAT, HOBt or HOSu may be added if necessary.

Scheme I: Elaboration of Cyclobutane Weinreb Amides

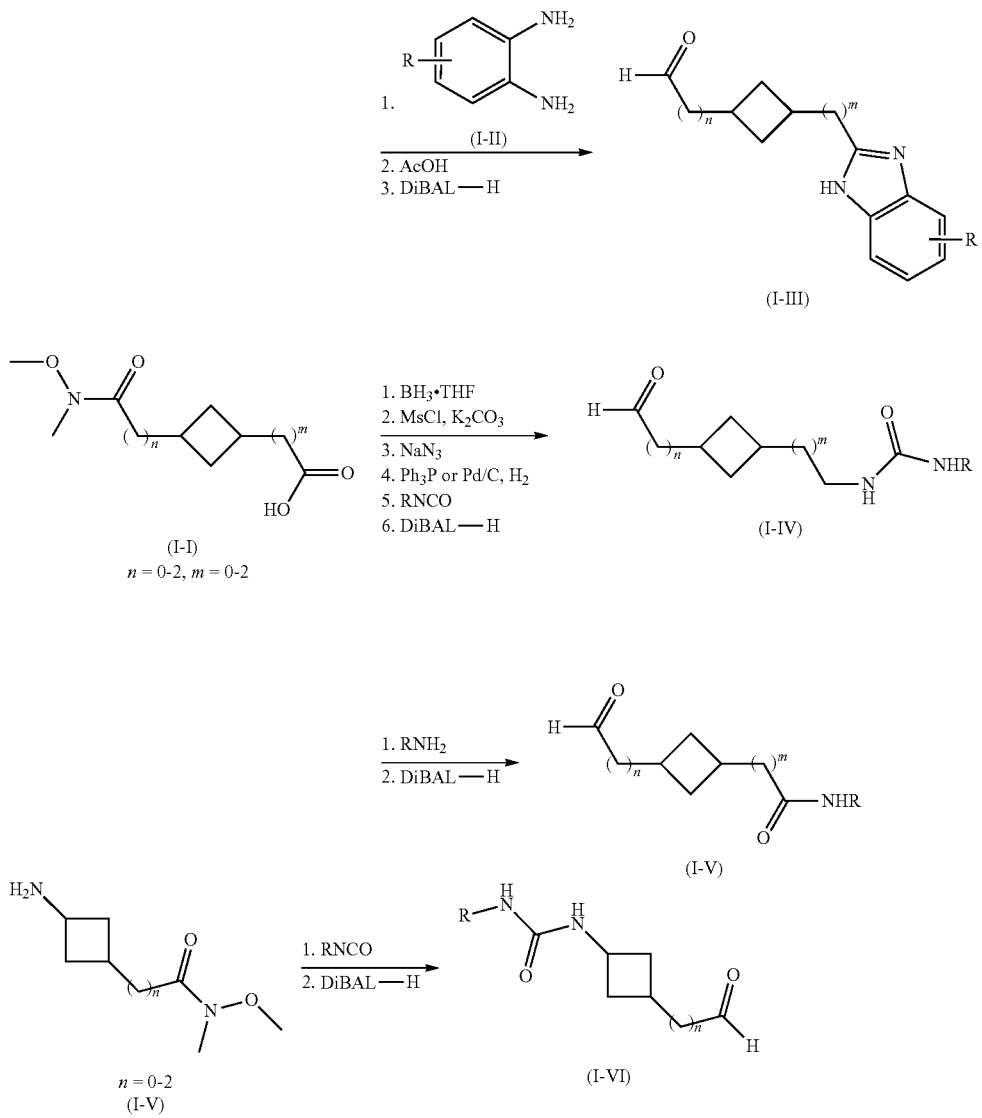

As shown in Scheme I above, the Weinreb amides (I-I) and (I-V) may be transformed into the benzimidazole aldehydes (I-III), urea aldehydes (I-IV) and (I-VI) and amide aldehydes (I-V) using similar procedures as described in Scheme H followed by Weinreb amide reduction. The reduction of the Weinreb amide can be performed using DiBAL-H in an inert solvent such as $CH_2Cl_2$, THF at a temperature of 10 to −78° C. The amino Weinreb amide (I-V) may also be converted into the urea (I-VI) via treatment with the appropriate isocyanate followed by reduction with DiBAL-H.

Scheme J: Elaboration of Cyclobutane

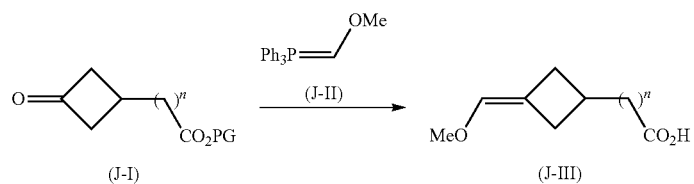

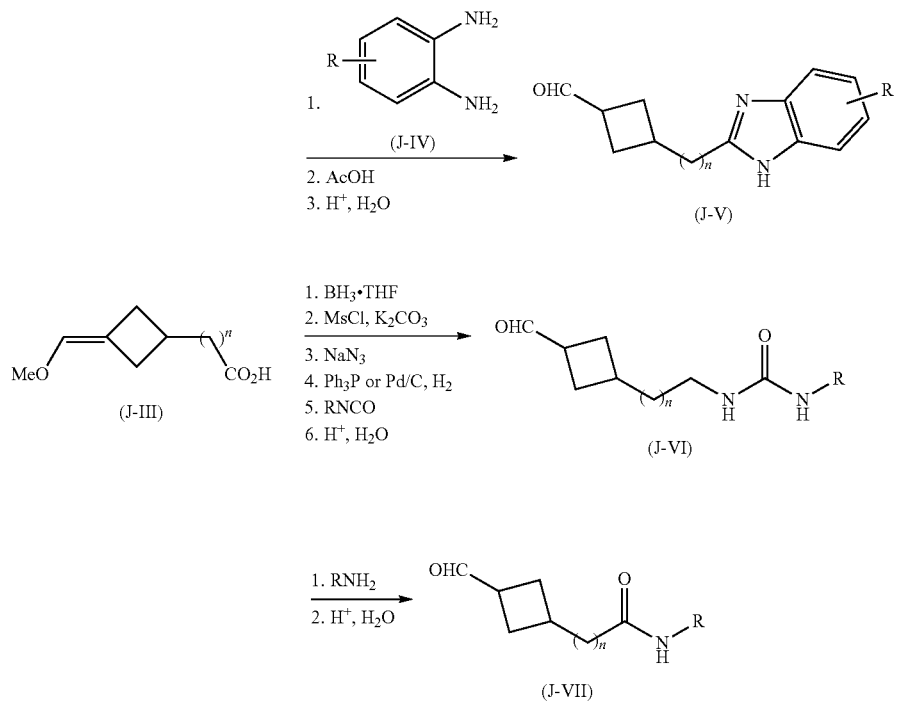

The benzimidazole (J-V), urea (J-VI) and amide (J-VII) intermediates may be synthesized as depicted in Scheme J. The cyclobutanones (J-I) may be subjected to a Wittig reaction with the phosphorane (J-II) to produce the enol ether (J-III). The enol ether acid is then subjected to reactions conditions similar to those as described in scheme H to produce the corresponding enol ether benzimidazoles, ureas and amides, which upon treatment with aqueous acid, such as TsOH/H$_2$O, HCl generates the corresponding aldehyde intermediates (J-V), (J-VI) and (J-VII) respectively.

Scheme K: Coupling of Cyclobutanes to Amines

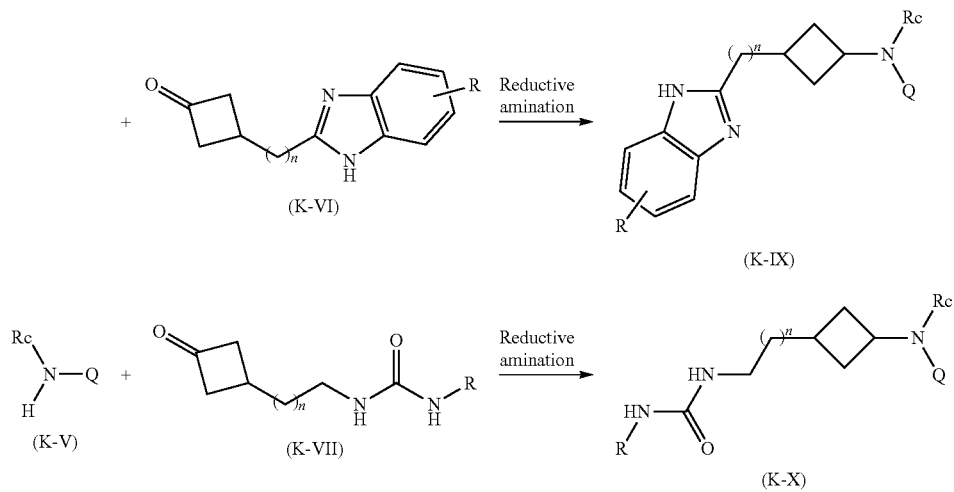

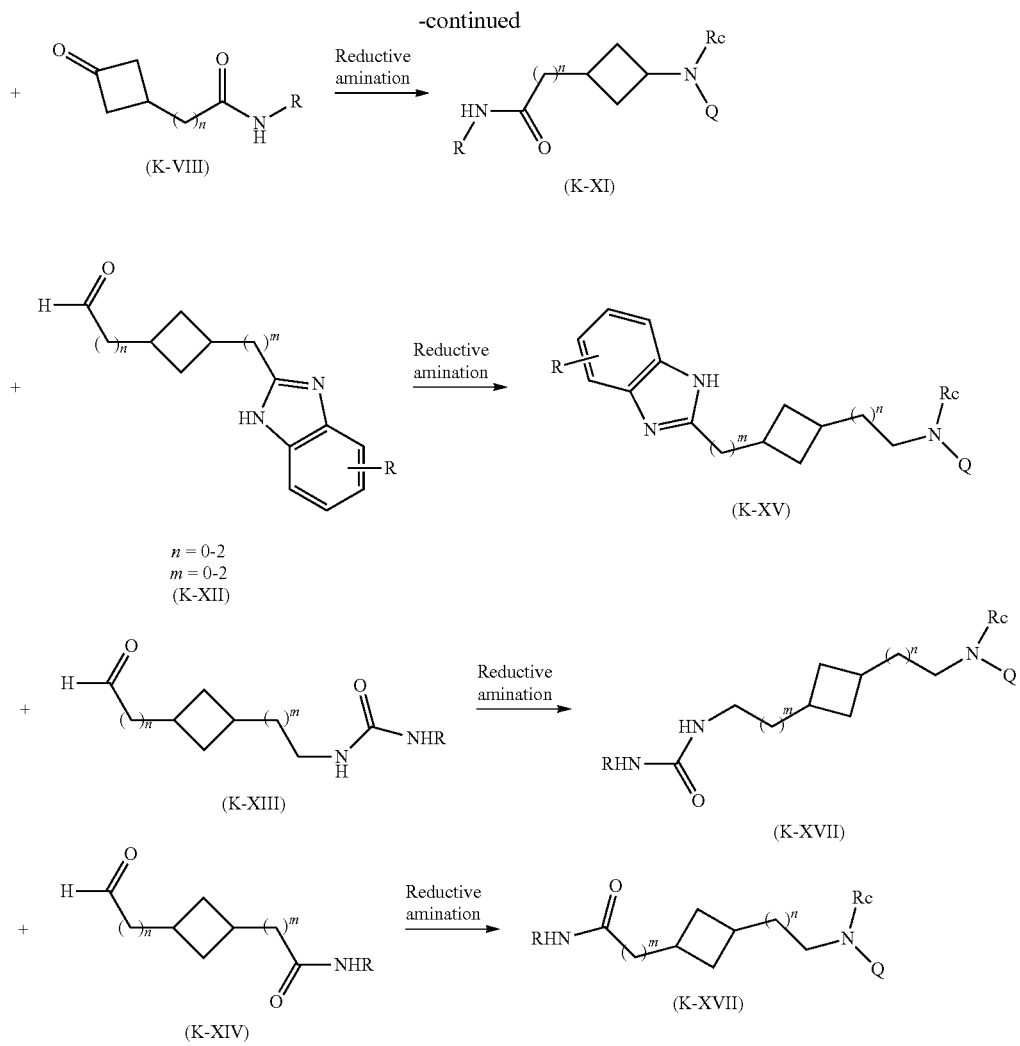
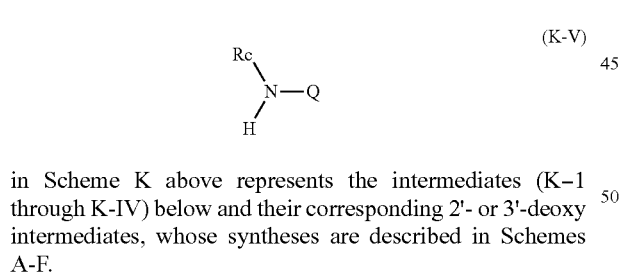
The formula (K-V)
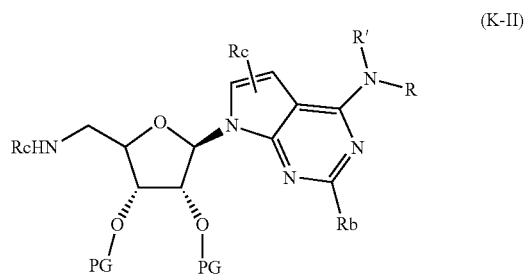
in Scheme K above represents the intermediates (K-1 through K-IV) below and their corresponding 2'- or 3'-deoxy intermediates, whose syntheses are described in Schemes A-F.
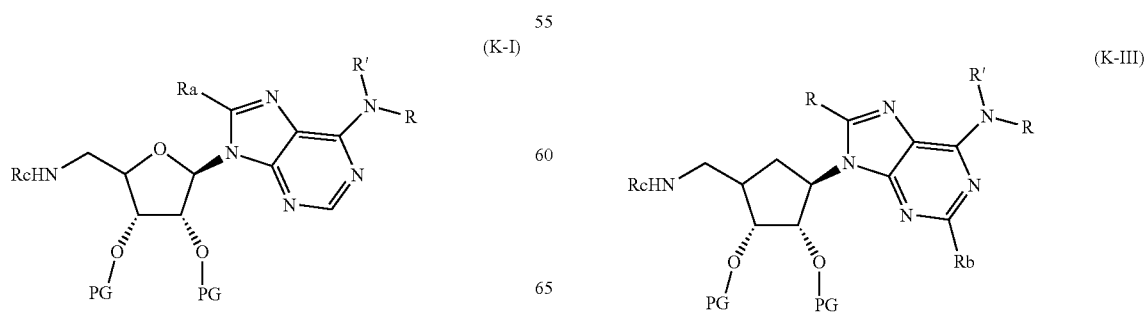

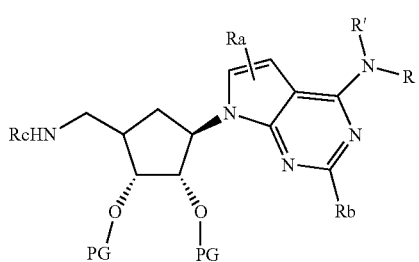

As shown in Scheme K, the ketones (K-VI), (K-VII) and (K-VIII) and the aldehydes (K-XII), (K-XIII) and (K-XIV) are converted into the corresponding benzimidazoles (K-IX) and (K-XV), ureas (K-X) and (K-XVI) and amides (K-XI) and (K-XVII) via reductive amination with (K-V). The reductive amination can be performed with a suitable reducing agent such as NaCN(BH$_3$) or Na(OAc)$_3$BH in the presence of an acid if required such as HCl or AcOH or a Lewis acid/dehydrating agent such as Ti(OiPr)$_4$ or MgSO$_4$.

In an alternative reaction sequence, the target benzimidazoles (L-V), ureas (L-VI) and amides (L-VII) may be prepared by the reaction sequence depicted in Scheme L. The amines (L-I), where Q and R$_c$ have the same definitions as in Scheme K, are treated with the cyclobutanes (L-II) under reductive amination conditions using a reducing agent such as NaCNBH$_3$ or Na(OAc)$_3$BH in the presence of an acid such as HCl or AcOH or a Lewis acid such as Ti(OiPr)$_4$, to give the acid (L-III). The acid may be converted into the corresponding target benzimidazoles (L-V), ureas (L-VI) and amides (L-VII) using reaction conditions similar to those in scheme H.

Scheme L: Alternative Coupling

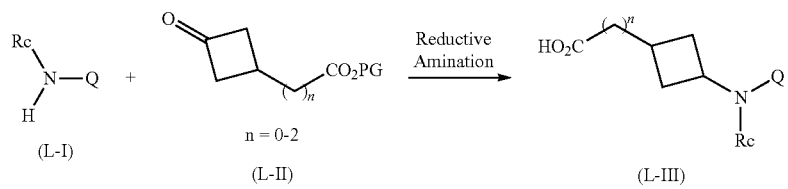

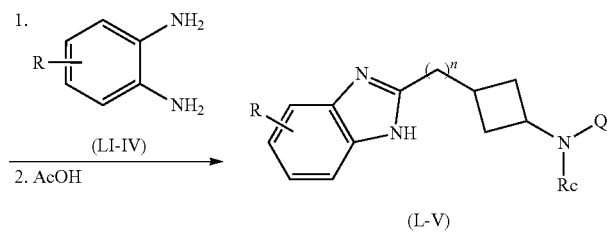

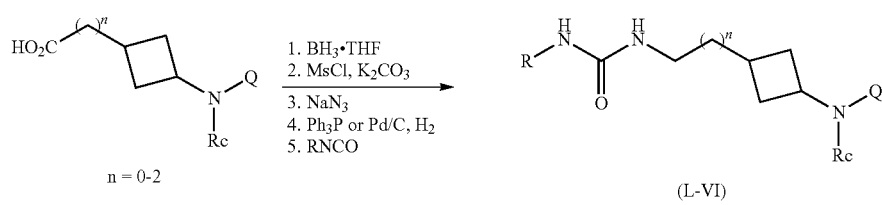

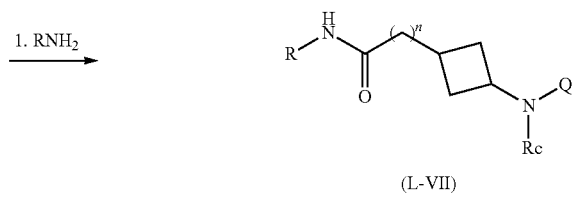

Scheme M: Alternative coupling

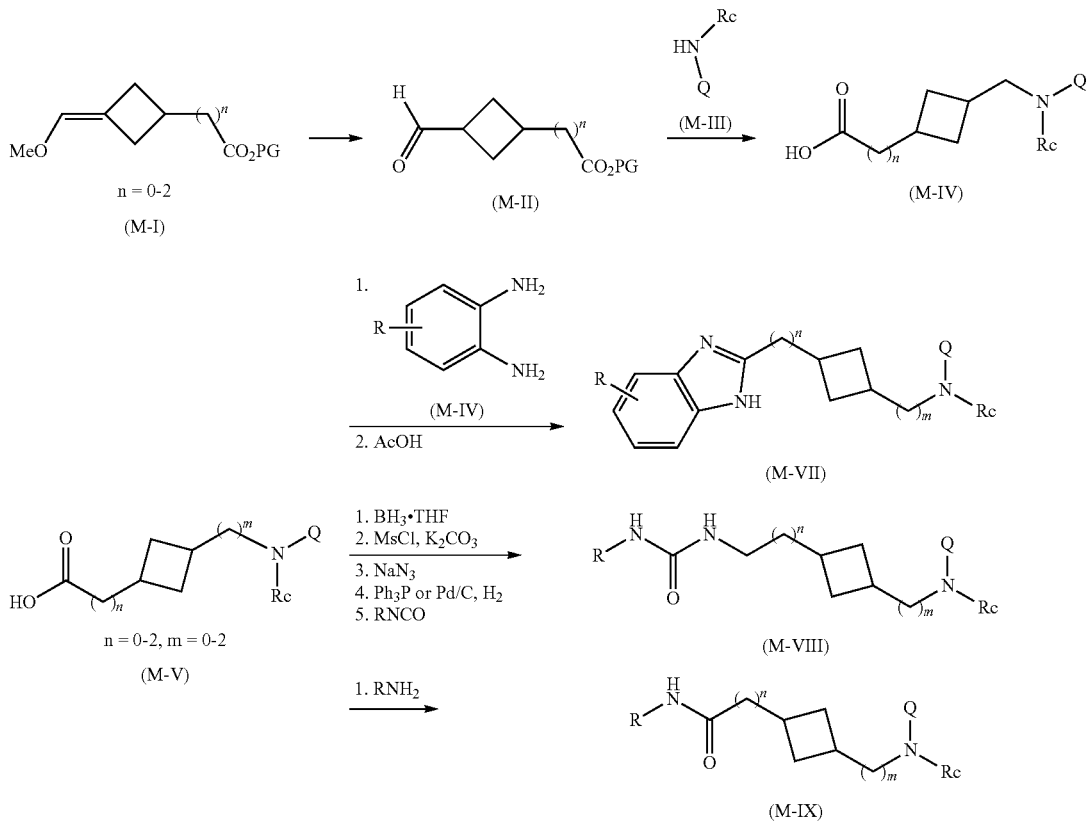

The enol ethers (M-1) may be hydrolyzed under acidic conditions (e.g. TsOH/$H_2O$, HCl/$H_2O$) to give the aldehydes (M-II). Reductive amination of (M-II) is conducted with amines (M-III) where Q and $R_c$ have the same meaning as in scheme K, using a reducing agent such as NaCNBH$_3$ or Na(OAc)$_3$BH in the presence of an acid such as HCl or AcOH or a Lewis acid/dehydrating agent such as Ti(OiPr)$_4$ or MgSO$_4$. Subsequent ester protecting group removal is then carried out to give the acid (M-IV). The acids (M-V) (which include the acids (M-IV)) may be transformed into the corresponding target benzimidazoles (M-VII), ureas (M-VIII) and amides (M-IX) using reaction conditions similar to those described in scheme H.

Scheme N: Synthesis of Amides

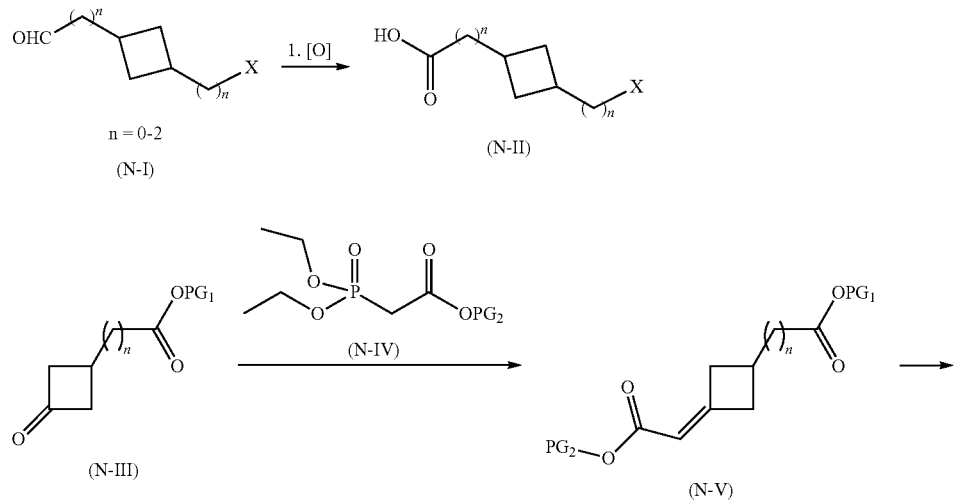

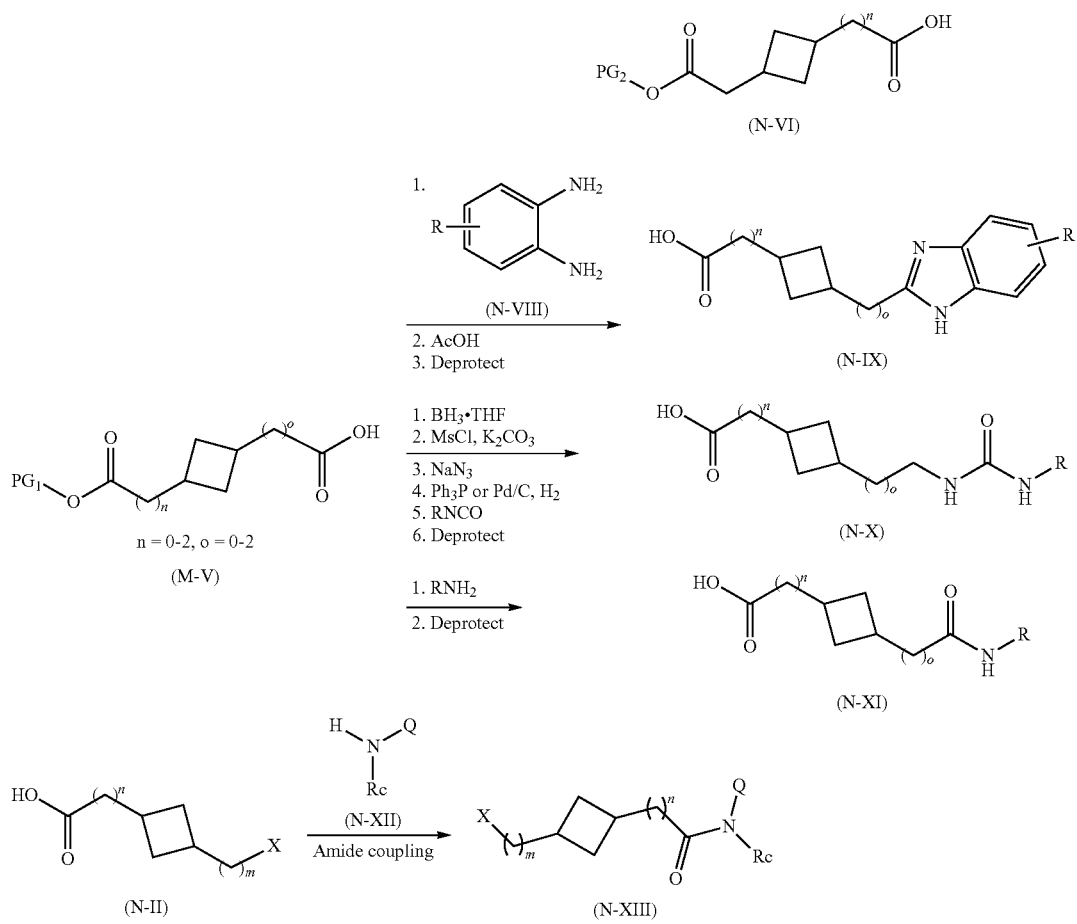

The benzimidazoles, ureas and amides of formula (N-XIII) may be synthesized as depicted in Scheme N. The aldehyde (N-I) where X represents a benzimidazole, urea or amide functionality, may be converted in the corresponding acid via oxidation with a reagent such as $NaClO_2$. The cyclobutanones of formula (N-III) may be treated with phosphonates of formula (N-IV) and a suitable base such as LiHMDS, NaHMDS, KHMDS, KOtBu, LDA or $Et_3N/LiCl$ in an inert solvent to give the cyclobutanes (N-V), which upon reduction via treatment with $H_2$ in the presence of suitable metal catalyst such as Pd/C, $PtO_2$ or $Pd(OH)_2$ gives the acid (N-VI).

The acids of formula (N-VII) which include the acids of formula (N-VI) may be converted into the corresponding benzimidazoles (N-IX), ureas (N-X) and amides (N-XI) via a series of reactions similar to those depicted in scheme H. The benzimidazoles, ureas and amides of formula (N-II) may then be converted to the benzimidazoles, ureas and amides of formula (N-XIII) via an amide coupling reaction with the amine (N-XIII) where Rc and Q have the same definitions as in Scheme K, using a suitable coupling agent (e.g. HATU, PPAA, COMU, EDC, EDCI), in the presence of a base (e.g. $Et_3N$, Hunig's base, $K_2CO_3$). Additional reagents such as HOAT, HOBt or HOSu may be added if necessary.

Scheme O: 5'-Sulfur Containing Analogs

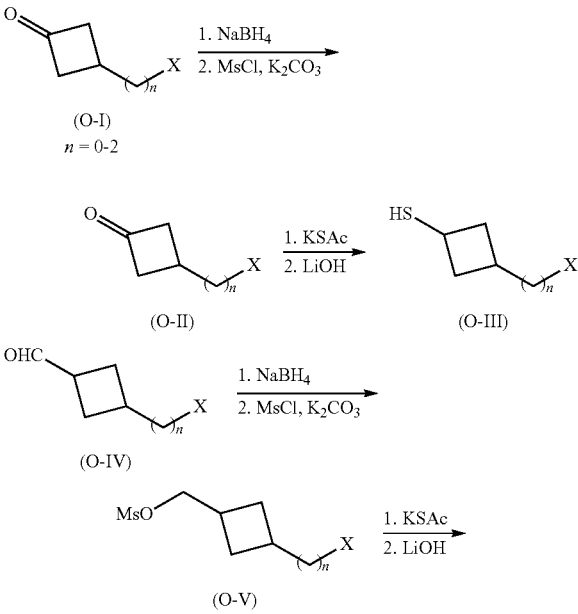

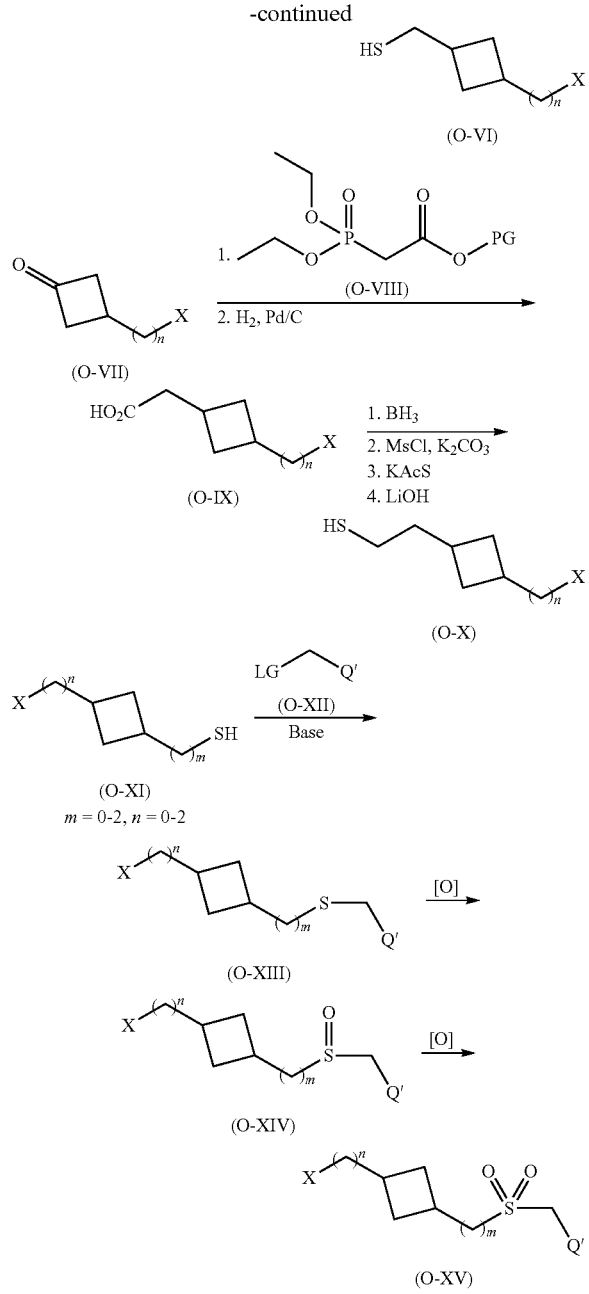

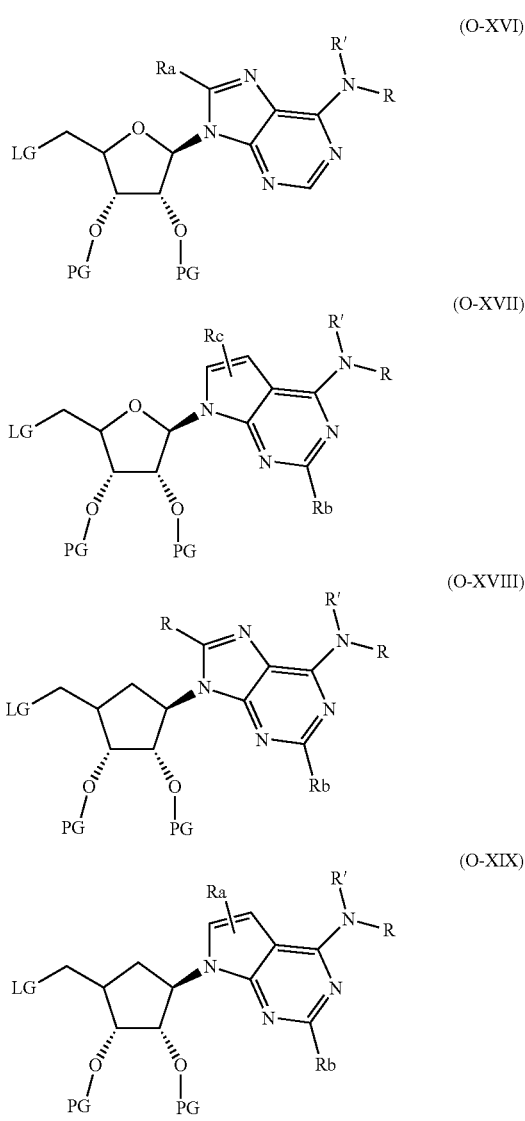

in the presence of a suitable base ($Cs_2CO_3$, $K_2CO_3$, LiHMDS, NaHMDS, KHMDS, KOtBu, LDA), followed by reduction using $H_2$ in the presence of a suitable metal catalyst such as Pd/C, $PtO_2$ or $Pd(OH)_2$. The acid is the selectively reduced to the primary alcohol using a reagent such as $BH_3$:THF or by reaction with carbonyldiimidazole, $Et_3N$ followed by $NaBH_4$. The primary alcohol is converted to the corresponding thiol using reactions similar to those used for the synthesis of (O-III) and (O-VI) from their secondary alcohol intermediates.

The thiols (O-XI) may then be treated with the intermediates (O-XII) where Q' represents the intermediates (O-XVI), (O-XVII), (O-XVIII) and (O-XIX) depicted below (and also the corresponding 2- or 3'-deoxy intermediates) and LG represents a leaving group such as Cl, TfO or MsO. The reaction may carried out in the presence of a suitable base such as $K_2CO_3$, $Cs_2CO_3$, $Et_3N$ or Hunig's base to give the thioethers (O-XIII) which may be converted into the corresponding sulfoxides (O-XIV) or sulfones (O-XV) via treatment with suitable oxidizing agents such as $H_2O_2$ or mCPBA.

The thioethers (O-XIII), sulfoxides (O-XIV) and sulfones (O-XV) may be synthesized as depicted in Scheme O. The cyclobutanones (O-I), where X represents benzimidazole, urea or amide functionality, may be reduced with a reducing reagent such as $NaBH_4$ to give the corresponding alcohol, which in turn may converted to a leaving group such a MsO, by treatment with MsCl with a base such as $K_2CO_3$ in an inert solvent. The cyclobutane (O-II) is then converted into the corresponding thiol (O-III) by first treating with a sulfur based nucleophile such as KSAc followed by hydrolysis of the thioester under basic conditions, e.g. $LiOH/H_2O/MeOH$.

The aldehydes (O-IV) may be converted into the corresponding thiols via a reaction sequence similar to that as described for converting (O-I) into (O-III).

The cyclobutanones (O-VII) may be converted into acids (O-IX) by treatment with a phosphonate of formula (O-VIII)

Scheme P: Amine, Amide and Sulfonamide Caps

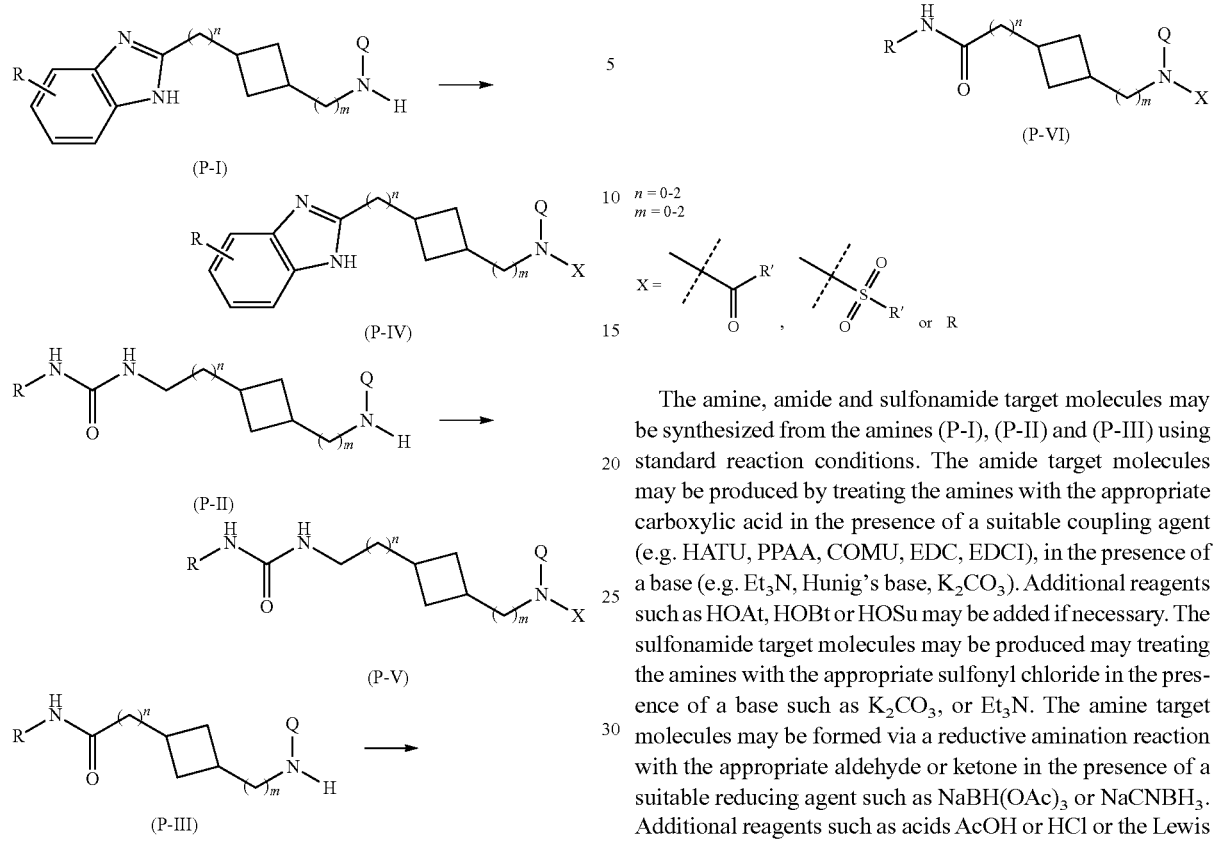

$n = 0\text{-}2$
$m = 0\text{-}2$

The amine, amide and sulfonamide target molecules may be synthesized from the amines (P-I), (P-II) and (P-III) using standard reaction conditions. The amide target molecules may be produced by treating the amines with the appropriate carboxylic acid in the presence of a suitable coupling agent (e.g. HATU, PPAA, COMU, EDC, EDCI), in the presence of a base (e.g. $Et_3N$, Hunig's base, $K_2CO_3$). Additional reagents such as HOAt, HOBt or HOSu may be added if necessary. The sulfonamide target molecules may be produced may treating the amines with the appropriate sulfonyl chloride in the presence of a base such as $K_2CO_3$, or $Et_3N$. The amine target molecules may be formed via a reductive amination reaction with the appropriate aldehyde or ketone in the presence of a suitable reducing agent such as $NaBH(OAc)_3$ or $NaCNBH_3$. Additional reagents such as acids AcOH or HCl or the Lewis acid/dehydrating agents $Ti(OiPr)_4$ or $MgSO_4$ may be added.

Scheme Q: Preparation of 4-(1-methoxy-2-methylpropan-2-yl)benzene-1,2-diamine

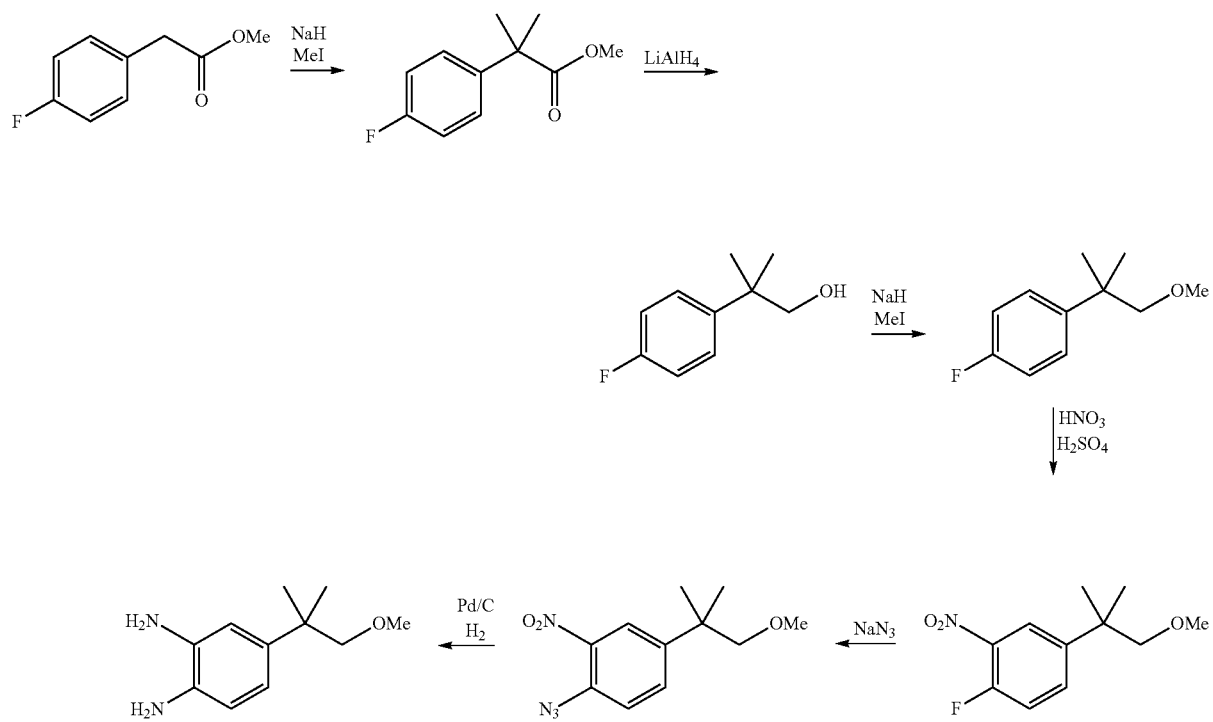

Scheme R: Preparation of 4-cyclobutylbenzene-1,2-diamine
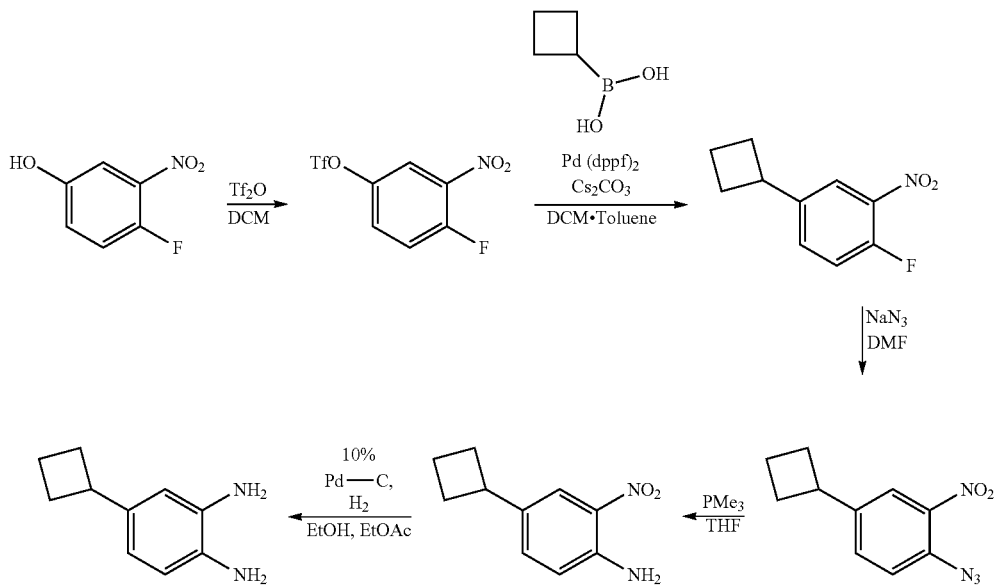
Scheme S: Preparation of 1-(3,4-diaminophenyl)cyclobutanecarbonitrile
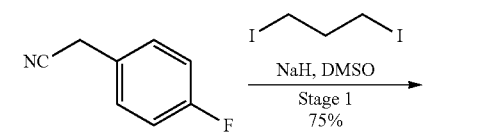
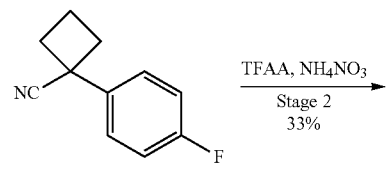
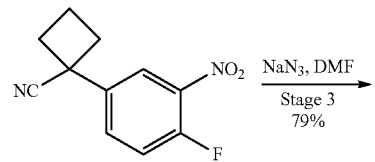
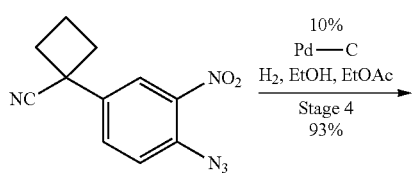
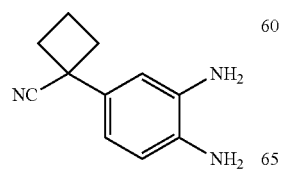
Scheme T: Preparation of 4-cyclopropylbenzene-1,2-diamine
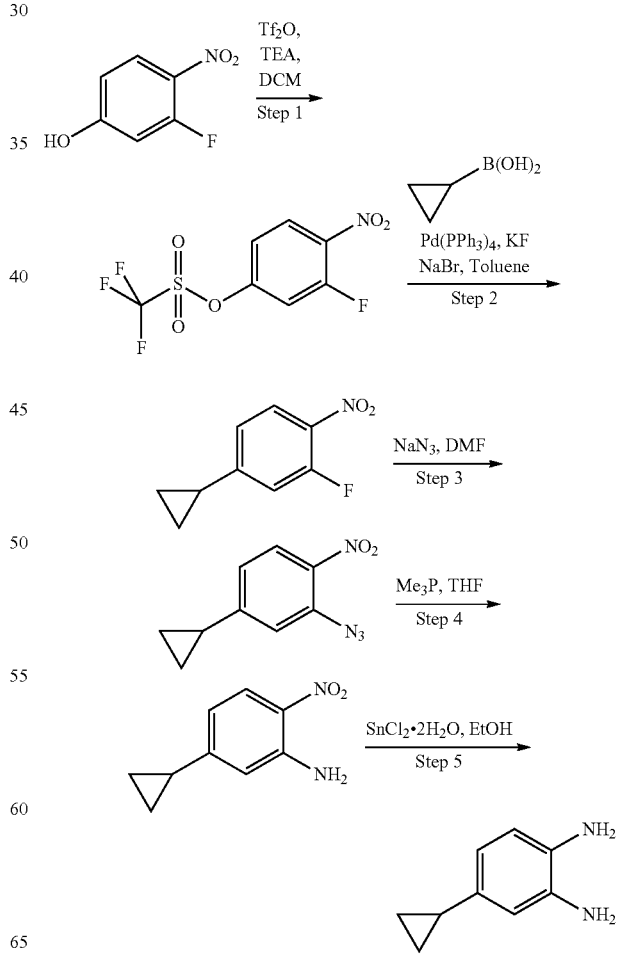

Scheme U: Preparation of 1-(3,4-diaminophenyl)cyclopropanecarbonitrile

Scheme W: Preparation of 2-(3,4-diaminophenyl)-2-methylpropanenitrile

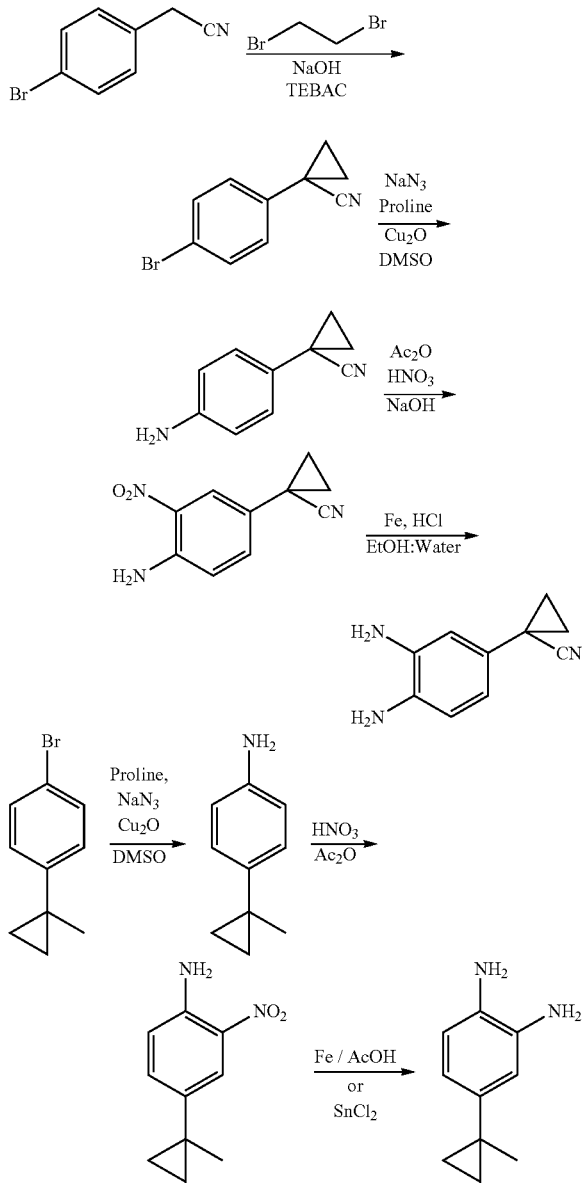

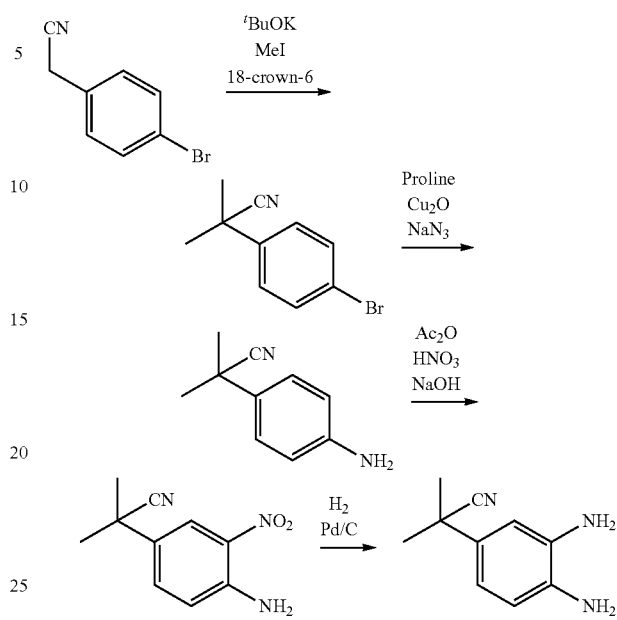

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions can be conducted simultaneously.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be Scheme V: Preparation of 4-(2,2,2-trifluoroethyl)benzene-1,2-diamine

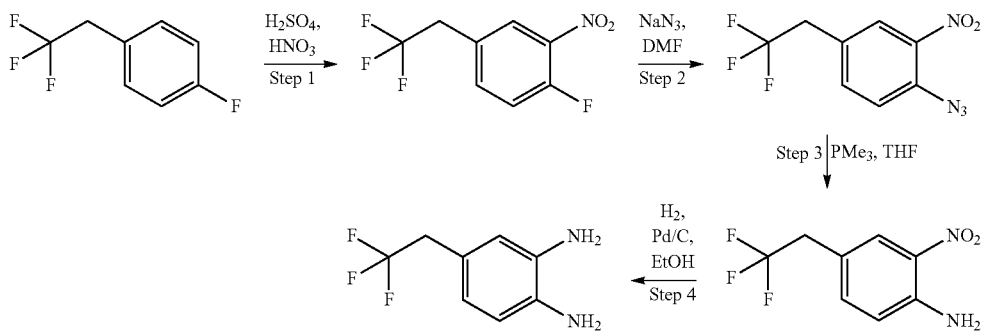

possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described herein.

To further assess a compound's drug-like properties, measurements of inhibition of cytochrome P450 enzymes and phase II metabolizing enzyme activity can also be measured either using recombinant human enzyme systems or more complex systems like human liver microsomes. Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

3. METHODS OF TREATMENT

Mixed lineage leukemia (MLL) is a genetically distinct form of acute leukemia that constitutes over 70% of infant leukemias and approximately 10% of adult acute myeloid leukemias (AML) (Hess, J. L. (2004), Trends Mol Med 10, 500-507; Krivtsov, A. V., and Armstrong, S. A. (2007), Nat Rev Cancer 7, 823-833). MLL represents a particularly aggressive form of leukemia and patients with this disease generally have poor prognoses; these patients often suffer from early relapse after treatment with current chemotherapies. There is thus a great and present need for new treatment modalities for patients suffering with MLL.

A universal hallmark of MLL disease is a chromosomal translocation affecting the MLL gene on chromosome 11q23 (Hess, 2004; Krivtsov and Armstrong, 2007). Normally, the MLL gene encodes for a SET-domain histone methyltransferase that catalyzes the methylation of lysine 4 of histone H3 (H3K4) at specific gene loci (Milne et al. (2002) Mol Cell 10, 1107-1117; Nakamura et al. (2002), Mol Cell 10, 1119-1128). Gene localization is conferred by specific interactions with recognition elements within MLL, external to the SET-domain (Ayton et al. (2004) Mol Cell Biol 24, 10470-10478; Slany et al., (1998) Mol Cell Biol 18, 122-129; Zeleznik-Le et al. (1994) Proc Natl Acad Sci USA 91, 10610-10614). In the disease-linked translocations, the catalytic SET-domain is lost and the remaining MLL protein is fused to a variety of partners, including members of the AF and ENL family of proteins such as AF4, AF9, AF10 and ENL (Hess, 2004; Krivtsov and Armstrong, 2007; Slany (2009) Haematologica 94, 984-993). These fusion partners are capable of interacting directly, or indirectly, with another histone methyltransferase, DOT1L (Bitoun et al. (2007) Hum Mol Genet 16, 92-106; Mohan et al. (2010) Genes Dev. 24, 574-589; Mueller et al. (2007) Blood 110, 4445-4454; Mueller et al. (2009) PLoS Biol 7, e1000249; Okada et al. (2005) Cell 121, 167-178; Park et al. (2010) Protein J 29, 213-223; Yokoyama et al. (2010) Cancer Cell 17, 198-212; Zhang et al. (2006) J Biol Chem 281, 18059-18068). As a result, translocation products retain gene-specific recognition elements within the remainder of the MLL protein, but also gain the ability to recruit DOT1L, to these locations (Monroe et al. (2010) Exp Hematol. 2010 Sep. 18. [Epub ahead of print] Pubmed PMID: 20854876; Mueller et al., 2007; Mueller et al., 2009; Okada et al., 2005). DOT1L catalyzes the methylation of H3K79, a chromatin modification associated with actively transcribed genes (Feng et al. (2002) Curr Biol 12, 1052-1058; Steger et al. (2008) Mol Cell Biol 28, 2825-2839). The ectopic H3K79 methylation that results from MLL fusion protein recruitment of DOT1L leads to enhanced expression of leukemogenic genes, including HOXA9 and MEIS1 (Guenther et al. (2008) Genes & Development 22, 3403-3408; Krivtsov et al. (2008) Nat Rev Cancer 7, 823-833; Milne et al. (2005) Cancer Res 65, 11367-11374; Monroe et al., 2010; Mueller et al., 2009; Okada et al., 2005; Thiel et al. (2010) Cancer Cell 17, 148-159). Hence, while DOT1L is not genetically altered in the disease per se, its mislocated enzymatic activity is a direct consequence of the chromosomal translocation affecting MLL patients; thus, DOT1L has been proposed to be a catalytic driver of leukemogenesis in this disease (Krivtsov et al., 2008; Monroe et al., 2010; Okada et al., 2005; Yokoyama et al. (2010) Cancer Cell 17, 198-212). Further support for a pathogenic role of DOT1L in MLL comes from studies in model systems that demonstrate a requirement for DOT1L in propagating the transforming activity of MLL fusion proteins (Mueller et al., 2007; Okada et al., 2005).

Evidence indicates that the enzymatic activity of DOT1L is critical to pathogenesis in MLL and inhibition of DOT1L may provide a pharmacologic basis for therapeutic intervention in this disease. Compound treatment results in selective, concentration-dependent killing of leukemia cells bearing the MLL-translocation without effect on non-MLL transformed cells. Gene expression analysis of inhibitor treated cells shows downregulation of genes aberrantly over expressed in MLL-rearranged leukemias and similarities with gene expression changes caused by genetic knockout of the Dot1L gene in a mouse model of MLL-AF9 leukemia.

The present invention provides methods for the treatment of a cell proliferative disorder in a subject in need thereof by administering to a subject in need of such treatment, a therapeutically effective amount of a compound of the present invention, or a pharmaceutically acceptable salt, prodrug, metabolite, polymorph or solvate thereof. The cell proliferative disorder can be cancer or a precancerous condition. The present invention further provides the use of a compound of the present invention, or a pharmaceutically acceptable salt, prodrug, metabolite, polymorph or solvate thereof, for the preparation of a medicament useful for the treatment of a cell proliferative disorder.

The present invention provides methods for the treatment of hematological cancer or hematologic tumors in a subject in need thereof by administering to a subject in need of such treatment, a therapeutically effective amount of a compound of the present invention, or a pharmaceutically acceptable salt, prodrug, metabolite, polymorph or solvate thereof. The present invention further provides the use of a compound of the present invention, or a pharmaceutically acceptable salt, prodrug, metabolite, polymorph or solvate thereof, for the preparation of a medicament useful for the treatment of hematological cancer or hematologic tumors.

The present invention provides methods for the treatment of leukemia in a subject in need thereof by administering to a subject in need of such treatment, a therapeutically effective amount of a compound of the present invention, or a pharmaceutically acceptable salt, prodrug, metabolite, polymorph or solvate thereof. The leukemia can be acute or chronic leukemia. Preferably, the leukemia is acute myeloid leukemia, acute lymphocytic leukemia or mixed lineage leukemia. The present invention further provides the use of a compound of the present invention, or a pharmaceutically acceptable salt, prodrug, metabolite, polymorph or solvate thereof, for the preparation of a medicament useful for the treatment of leukemia.

The present invention provides methods for the treatment of a disease or disorder mediated by translocation of a gene on chromosome 11q23 in a subject in need thereof by administering to a subject in need of such treatment, a therapeutically effective amount of a compound of the present invention, or a pharmaceutically acceptable salt, prodrug, metabolite, polymorph or solvate thereof. The gene can be the MLL gene. The present invention further provides the use of a compound of the present invention, or a pharmaceutically acceptable salt, prodrug, metabolite, polymorph or solvate thereof, for the preparation of a medicament useful for the treatment of a disease or disorder mediated by translocation of a gene on chromosome 11q23.

The present invention provides methods for the treatment of a disease or disorder mediated by DOT1 (e.g., DOT1L)-mediated protein methylation in a subject in need thereof by administering to a subject in need of such treatment, a therapeutically effective amount of a compound of the present invention, or a pharmaceutically acceptable salt, prodrug, metabolite, polymorph or solvate thereof. The present invention further provides the use of a compound of the present invention, or a pharmaceutically acceptable salt, prodrug, metabolite, polymorph or solvate thereof, for the preparation of a medicament useful for the treatment of a disease or disorder mediated by DOT1L-mediated protein methylation.

The present invention provides methods for the treatment of a disorder the course of which is influenced by modulating the methylation status of histones or other proteins, wherein said methylation status is mediated at least in part by the activity of DOT1L. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, prodrug, metabolite, polymorph, solvate, or stereoisomer or thereof.

The disorder in which DOT1L-mediated protein methylation plays a part can be cancer or a precancerous condition or a neurological disease. The present invention further provides the use of a compound of the present invention, or a pharmaceutically acceptable salt, prodrug, metabolite, polymorph or solvate thereof, for the preparation of a medicament useful for the treatment of cancer or a neurological disease.

The present invention also provides methods of protecting against a disorder in which DOT1L-mediated protein methylation plays a part in a subject in need thereof by administering a therapeutically effective amount of compound of the present invention, or a pharmaceutically acceptable salt, prodrug, metabolite, polymorph or solvate thereof, to a subject in need of such treatment. The disorder can be cancer or a neurological disease. The present invention also provides the use of compound of the present invention, or a pharmaceutically acceptable salt, prodrug, metabolite, polymorph, solvate, or stereoisomer or thereof, for the preparation of a medicament useful for the prevention of a cell proliferative disorder.

The compounds of this invention can be used to modulate protein (e.g., histone) methylation, e.g., to modulate histone methyltransferase or histone demethylase enzyme activity. Histone methylation has been reported to be involved in aberrant expression of certain genes in cancers, and in silencing of neuronal genes in non-neuronal cells. The compounds described herein can be used to treat these diseases, i.e., to decreases methylation or restores methylation to roughly its level in counterpart normal cells.

In general, compounds that are methylation modulators can be used for modulating cell proliferation, generally. For example, in some cases excessive proliferation may be reduced with agents that decrease methylation, whereas insufficient proliferation may be stimulated with agents that increase methylation. Accordingly, diseases that may be treated by the compounds of the invention include hyperproliferative diseases, such as benign cell growth and malignant cell growth.

As used herein, a "subject in need thereof" is a subject having a cell proliferative disorder, or a subject having an increased risk of developing a cell proliferative disorder relative to the population at large. The subject can have cancer or pre-cancer. Preferably, a subject in need thereof has cancer. More preferably, a hematologic cancer or leukemia. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute lymphocytic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodellnal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodelinal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung.

Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, polymorph, or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an single active compound. For example, cancer monotherapy with one of the compound of the present invention, or a pharmaceutically acceptable salt, prodrug, metabolite, analog or derivative thereof, to a subject in need of treatment of cancer. In one aspect, the single active compound is a compound of the present invention, or a pharmaceutically acceptable salt, prodrug, metabolite, polymorph or solvate thereof.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www-.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, prodrug, metabolite, polymorph or solvate thereof, can modulate the activity of a molecular target (e.g., a target protein methyltransferase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, prodrug, metabolite, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a protein methyltransferase of interest.

The present invention provides methods to assess biological activity of a compound of the present invention, or a pharmaceutically acceptable salt, prodrug, metabolite, polymorph or solvate thereof or methods of identifying a test compound as a modulator (e.g., an inhibitor) of DOT1L. DOT1L polypeptides and nucleic acids can be used to screen for compounds that bind to and/or modulate (e.g., increase or decrease) one or more biological activities of DOT1L, including but not limited to H3K79 HMTase activity, SAM binding activity, histone and/or nucleosome binding activity, AF10 binding activity, AF10-MLL or other MLL fusion protein binding activity, and/or any other biological activity of interest. A DOT1L polypeptide can be a functional fragment of a full-length DOT1L polypeptide or functional equivalent thereof, and may comprise any DOT1 domain of interest, including but not limited to the catalytic domain, the SAM binding domain and/or the positively charged domain, the AF10 interaction domain and/or a nuclear export signal.

Methods of assessing DOT1L binding to histones, nucleosomes, nucleic acids or polypeptides can be carried out using standard techniques that will be apparent to those skilled in the art (see the Exemplification for exemplary methods). Such methods include yeast and mammalian two-hybrid assays and co-immunoprecipitation techniques.

For example, a compound that modulates DOT1L H3K79 HMTase activity can be verified by: contacting a DOT1L polypeptide with a histone or peptide substrate comprising H3 in the presence of a test compound; detecting the level of H3K79 methylation of the histone or peptide substrate under conditions sufficient to provide H3K79 methylation, wherein an elevation or reduction in H3K79 methylation in the presence of the test compound as compared with the level of histone H3K79 methylation in the absence of the test compound indicates that the test compound modulates DOT1L H3K79 HMTase activity.

The screening methods of the invention can be carried out in a cell-based or cell-free system. As a further alternative, the assay can be performed in a whole animal (including transgenic non-human animals). Further, with respect to cell-based systems, the DOT1L polypeptide (or any other polypeptide used in the assay) can be added directly to the cell or can be produced from a nucleic acid in the cell. The nucleic acid can be endogenous to the cell or can be foreign (e.g., a genetically modified cell).

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention The compounds of the instant invention can also be utilized to treat or prevent neurologic diseases or disorders. Neurologic diseases or disorders that may be treated with the compounds of this invention include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of polyglutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCAT), and Spinocerebellar Ataxia 12 (SCA12).

Any other disease in which epigenetic methylation, which is mediated by DOT1, plays a role may be treatable or preventable using compounds and methods described herein.

4. PHARMACEUTICAL COMPOSITIONS

The present invention also provides pharmaceutical compositions comprising a compound of Formulae (I), (II), (IIIa), (IIIb), (IIIc) and (IV) in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug interaction(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in m$^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Compounds described herein are assayed for modulation of activity, for example, histone methylation, modulation of cell growth and/or $IC_{50}$, described in the examples below. $IC_{50}$ values are presented as A=<0.1 μM; B=>0.1 μM and <1 μM; C=>1 μM and <10 μM; and D=>10 μM and <50 μM.

| Compound | DOT1L $IC_{50}$ (μM) |
|---|---|
| 2 | 0.00074 |
| 3 | 0.00073 |
| 5 | 0.00059 |
| 69 | 0.00251 |
| 75 | 0.00059 |
| 86 | 0.00062 |
| 87 | 0.0008 |
| 91 | 0.00218 |
| 93 | 0.00292 |

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

5. EXAMPLES

Nuclear magnetic resonance (NMR) spectra were obtained on a Bruker Avance 400 operating at a field strength of 400.130 MHz or a Bruker DRX 500 MHz NMR or HNMR spectra were obtained on a 500 MHz Bruker AVANCE III spectrometer. Common reaction solvents were either high performance liquid chromatography (HPLC) grade or American Chemical Society (ACS) grade, and anhydrous as obtained from the manufacturer unless otherwise noted. LCMS was performed on a Waters Micromass ZMD with a Waters 2795 Separations Module and Waters 996 photodiode array detector and a Waters Micromass ZQ with a Waters 2695 Separations Module and Waters 996 photodiode array detector or a Waters Micromass Platform LCZ single quadrupole mass spectrometer with a Waters 600 solvent delivery module, Waters 515 ancillary pumps, Waters 2487 UV detector and a Gilson 215 autosampler and fraction collector. Or, LCMS analysis was performed using SQ mass spectrometer coupled to AGILENT 1200 Series HPLC. LCMS data, where available, are provided in the examples below as well as in Table 1. The MS data are provided using the convention for m/z in the format, $[M+H]^+$.

The compounds of the present invention can be prepared using known chemical transformations adapted to the particular situation at hand.

Preparative Example 1

Starting Materials or Intermediates

Step 1: (1R,2S,3R,5R)-3-((5-amino-6-chloropyrimidin-4-yl)amino)-5-(hydroxymethyl)cyclopentane-1,2-diol

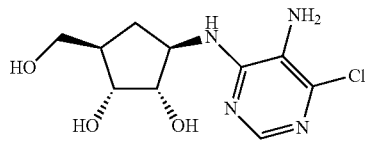 [SMILES: Nc1c(Cl)ncnc1N[C@@H]1C[C@H](CO)[C@@H](O)[C@H]1O]

A mixture of (1R,2S,3R,5R)-3-amino-5-(hydroxymethyl)cyclopentane-1,2-diol hydrochloride (16.9 g, 45.1 mmol) and 4,6-dichloropyrimidin-5-amine (5.7 g, 35 mmol) in ethanol (45 mL) was evenly distributed amongst three tubes and subjected to microwave conditions (CEM apparatus, 300 W max, 150° C. max, 250 psi max, 3 min ramp, 30 min hold) to afford brown solutions; HPLC/LC MS indicated conversion to the desired product. The three reaction mixtures were combined and concentrated in vacuo to afford the crude title compound as a dark brown oil, which was concentrated from toluene (2×30 mL) and carried on without purification: MS (ESI+) for $C_{10}H_{15}ClN_4O_3$ m/z 275.0 (M+H)$^+$; MS (ESI−) for $C_{10}H_{15}ClN_4O_3$ m/z 273.0 (M−H)$^-$.

Step 2: ((3aR,4R,6R,6aS)-6-(6-chloro-9H-purin-9-yl)-2-ethoxytetrahydro-3aH-cyclopenta[d][1,3]dioxol-4-yl)methanol

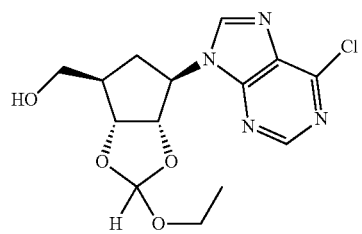

The above crude (1R,2S,3R,5R)-3-((5-amino-6-chloropyrimidin-4-yl)amino)-5-(hydroxymethyl)cyclopentane-1,2-diol was treated with ethyl orthoformate (120 mL, 720 mmol) and 10-camphorsulfonic acid (8.11 g, 34.9 mmol). The heterogeneous brown mixture was stirred vigorously to afford a nearly homogeneous brown solution after 10 min. At 5 h, LC MS indicated the desired product as the major product and the reaction was quenched with saturated aqueous NaHCO$_3$ (120 mL). The mixture was diluted with water (75 mL), extracted with CH$_2$Cl$_2$ (3×200 mL), and the combined organics were dried (Na$_2$SO$_4$) and concentrated in vacuo to afford the crude title compound as a dark brown liquid, which was carried on without further manipulation: MS (ESI+) for $C_{14}H_{17}ClN_4O_4$ m/z 341.0 (M+H)$^+$.

Step 3: ((3aR,4R,6R,6aS)-6-(6-chloro-9H-purin-9-yl)-2,2-dimethyltetrahydro-3aH-cyclopenta[d][1,3]dioxol-4-yl)methanol

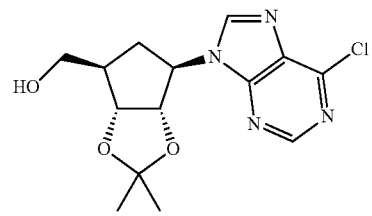 [SMILES: CC1(C)O[C@@H]2[C@@H](CO)C[C@@H](n3cnc4c(Cl)ncnc43)[C@@H]2O1]

The above crude ((3aR,4R,6R,6aS)-6-(6-chloro-9H-purin-9-yl)-2-ethoxytetrahydro-3aH-cyclopenta[d][1,3]dioxol-4-yl)methanol was taken up in 2,2-dimethoxypropane (214 mL, 1740 mmol) and treated with p-toluenesulfonic acid monohydrate (13.2 g, 69.5 mmol) to afford a brown oil partially suspended in a cloudy solution, which was stirred at rt for 1 h 20 min; HPLC/LC MS indicated complete conversion to the desired product. The reaction was quenched by the careful addition of sodium bicarbonate (8.76 g, 104 mmol) and a minimal amount of water. The volatiles were removed in vacuo and the remaining aqueous layer was diluted with water (100 mL) and extracted with CH$_2$Cl$_2$ (3×400 mL). The combined organics were dried (Na$_2$SO$_4$) and concentrated in vacuo to afford a brown oil. Purification by column chromatography (7×16 cm silica; 0-5% MeOH/CH$_2$Cl$_2$) afforded the title compound (8.30 g, 74% over 3 steps) as a yellow foam: MS (ESI+) for $C_{14}H_{17}ClN_4O_3$ m/z 325.1 (M+H)$^+$; MS (ESI−) for $C_{14}H_{17}ClN_4O_3$ m/z 369.0 (M+HCO$_2$)$^-$; HPLC purity >95 area %.

Step 4: 9-((3aS,4R,6R,6aR)-6-(azidomethyl)-2,2-dimethyltetrahydro-3aH-cyclopenta[d][1,3]dioxol-4-yl)-6-chloro-9H-purine

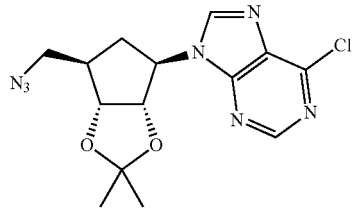 [SMILES: CC1(C)O[C@@H]2[C@@H](CN=[N+]=[N-])C[C@@H](n3cnc4c(Cl)ncnc43)[C@@H]2O1]

A mixture of ((3aR,4R,6R,6aS)-6-(6-chloro-9H-purin-9-yl)-2,2-dimethyltetrahydro-3aH-cyclopenta[d][1,3]dioxol-4-yl)methanol (7.9 g, 24 mmol) and polymer-supported triphenylphosphine (3 mmol/g loading; 11 g, 34 mmol) in THF (100 mL) was cooled to 0° C. (ice/brine bath) and treated dropwise with diisopropyl azodicarboxylate (6.7 mL, 34 mmol). The tan slurry was stirred for 15 min, and treated dropwise with a solution of diphenylphosphonic azide (7.3 mL, 34 mmol) in THF (24 mL). The brown reaction mixture was stirred for 18.5 h as the ice bath expired; HPLC indicated conversion to the desired product. At 21.5 h the reaction mixture was filtered, the solids were washed with CH$_2$Cl$_2$, and the filtrate was concentrated in vacuo. The red-brown residue was taken up in $CH_2Cl_2$ (300 mL) and washed with saturated aqueous $NaHCO_3$ (1×100 mL), water (1×100 mL), and brine (1×150 mL). The separated organic layer was dried ($Na_2SO_4$) and concentrated in vacuo to afford a red-orange oil. Purification by column chromatography (7×16 cm silica; 0-10% acetone/$CH_2Cl_2$) afforded the title compound (4.82 g, 57%) as a yellow oil/foam: MS (ESI+) for $C_{14}H_{16}ClN_7O_2$ m/z 350.1 (M+H)$^+$; MS (ESI−) for $C_{14}H_{16}ClN_7O_2$ m/z 394.1 (M+HCO$_2$)$^-$; HPLC purity >95 area %.

Step 5: 9-((3aS,4R,6R,6aR)-6-(azidomethyl)-2,2-dimethyltetrahydro-3aH-cyclopenta[d][1,3]dioxol-4-yl)-N-(2,4-dimethoxybenzyl)-9H-purin-6-amine

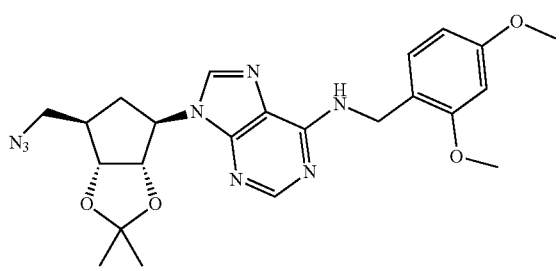 [SMILES: COc1ccc(CNc2ncnc3c2ncn3[C@@H]2C[C@H](CN=[N+]=[N-])[C@H]3OC(C)(C)O[C@H]32)c(OC)c1]

A solution of 9-((3aS,4R,6R,6aR)-6-(azidomethyl)-2,2-dimethyltetrahydro-3aH-cyclopenta[d][1,3]dioxol-4-yl)-6-chloro-9H-purine (1.29 g, 3.69 mmol) and (2,4-dimethoxyphenyl)methanamine (0.71 mL, 4.7 mmol) in 1-butanol (10 mL) was treated with N,N-diisopropylethylamine (0.93 mL, 5.3 mmol) and heated at 80° C. for 16.5 h; HPLC/LC MS indicated conversion to the desired product. The reaction mixture was allowed to cool to rt and the volatiles were removed under the flow of air to afford a brown-orange paste. Purification by column chromatography (2×8 cm silica; 0-10% acetone/$CH_2Cl_2$) afforded the title compound (1.72 g, 97%) as a yellow-orange foam/oil: MS (ESI+) for $C_{23}H_{28}N_8O_4$ m/z 481.2 (M+H)$^+$; HPLC purity >95 area %.

Step 6: 9-((3aS,4R,6R,6aR)-6-(aminomethyl)-2,2-dimethyltetrahydro-3aH-cyclopenta[d][1,3]dioxol-4-yl)-N-(2,4-dimethoxybenzyl)-9H-purin-6-amine

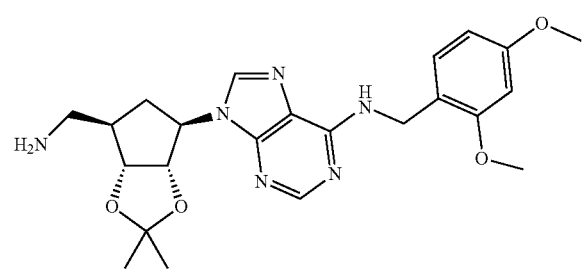 [SMILES: COc1ccc(CNc2ncnc3c2ncn3[C@@H]2C[C@H](CN)[C@H]3OC(C)(C)O[C@H]32)c(OC)c1]

A solution of 9-((3aS,4R,6R,6aR)-6-(azidomethyl)-2,2-dimethyltetrahydro-3aH-cyclopenta[d][1,3]dioxol-4-yl)-N-(2,4-dimethoxybenzyl)-9H-purin-6-amine (1.72 g, 3.58 mmol) in THF (16 mL) was cooled to 0° C. (ice/brine bath) and treated dropwise with a 1.0 M solution of trimethylphosphine in THF (6.30 mL, 6.30 mmol). The cold bath was removed after 30 min and the reaction mixture was stirred for 1.5 h; HPLC/LC MS indicated complete consumption of the starting azide. Water (2.84 mL, 157 mmol) was added to the orange solution (gas evolution noted) and the reaction mixture was stirred for 2.75 h at rt; HPLC indicated complete conversion to the desired amine. The reaction mixture was concentrated in vacuo to afford an orange oil. The residue was taken up in $CH_2Cl_2$ (150 mL) and washed with water (2×50 mL) and brine (1×75 mL). The separated organic layer was dried ($Na_2SO_4$) and concentrated in vacuo to afford the title compound (1.6 g, 98%) as a pale yellow foam: MS (ESI+) for $C_{23}H_{30}N_6O_4$ m/z 455.2 (M+H)$^+$; HPLC purity >95 area %.

Step 1: ethyl 3-(3-(((((3aR,4R,6R,6aS)-6-(6-((2,4-dimethoxybenzyl)amino)-9H-purin-9-yl)-2,2-dimethyltetrahydro-3aH-cyclopenta[d][1,3]dioxol-4-yl)methyl)amino)cyclobutyl)propanoate

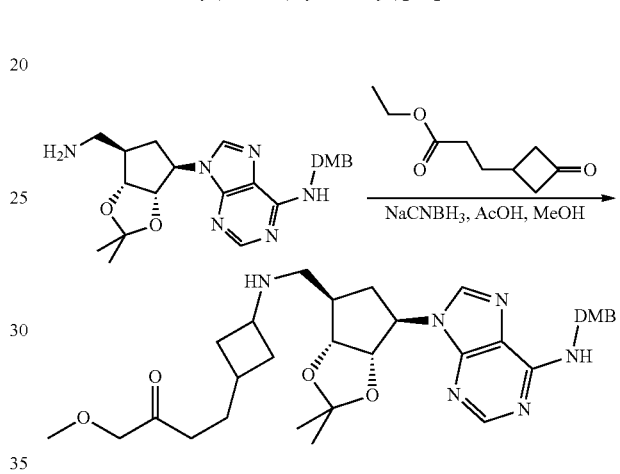

Sodium triacetoxyborohydride (0.839 g, 3.96 mmol) was added to a solution of 9-43aS,4R,6R,6aR)-6-(aminomethyl)-2,2-dimethyltetrahydro-3aH-cyclopenta[d][1,3]dioxol-4-yl)-N-(2,4-dimethoxybenzyl)-9H-purin-6-amine (1.5 g, 3.3 mmol), ethyl 3-(3-oxocyclobutyl)propanoate (0.562 g, 3.30 mmol) and acetic acid (0.188 mL, 3.30 mmol) in 1,2-dichloroethane (26.0 mL, 3.30E2 mmol) and the reaction was stirred at RT overnight. The following morning the starting material was consumed by HPLC so $NaHCO_3$ was added and the aqueous extracted 3× with DCM. Combined organics were dried with $MgSO_4$ and purified by FC (DCM/7N $NH_3$ in MeOH 95:5) to yield ethyl 3-3-(((((3aR,4R,6R,6aS)-6-(6-((2,4-dimethoxybenzyeamino)-9H-purin-9-yl)-2,2-dimethyltetrahydro-3aH-cyclopenta[d][1,3]dioxol-4-yl)methyl)amino)cyclobutyl)propanoate (1.5 g; 75%) as a thick yellow resin/foam. MS (ESI$^+$) for $C_{32}H_{44}N_6O_6$ m/z 609.3 [M+H]$^+$.

Step 2: ethyl 3-(3-(((((3aR,4R,6R,6aS)-6-(6-((2,4-dimethoxybenzyl)amino)-9H-purin-9-yl)-2,2-dimethyltetrahydro-3aH-cyclopenta[d][1,3]dioxol-4-yl)methyl)(isopropyl)amino)cyclobutyl)propanoate

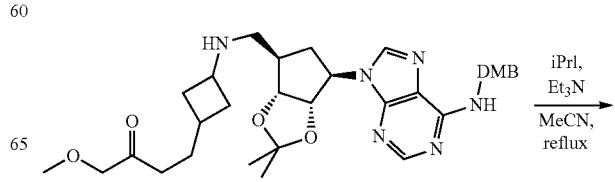

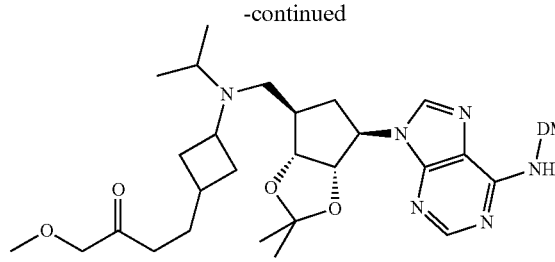

Ethyl 3-(3-(((((3aR,4R,6R,6aS)-6-(6-((2,4-dimethoxybenzyl)amino)-9H-purin-9-yl)-2,2-dimethyltetrahydro-3aH-cyclopenta[d][1,3]dioxol-4-yl)methyl)amino)cyclobutyl)propanoate (0.06 g, 0.1 mmol) was taken up in acetonitrile (2.6 mL, 50 mmol) and isopropyl iodide (0.098 mL, 0.98 mmol) and triethylamine (0.21 mL, 1.5 mmol) were added. The reaction was heated to 80° C. for 12 hours at which point the reaction appeared to stall. Another 15 equivalents triethylamine and another 15 equivalents isopropyl iodide were added and the reaction continued 8 hours more. Reaction appeared to have stalled again so another 15 equivalents each of isopropyl iodide and triethylamine were added. Upon consumption of the starting material the reaction was concentrated and saturated $Na_2CO_3$ (20 mls) and DCM (20 mls) was added. The residue was partitioned between the organic layer and the aqueous layer. The aqueous layer was extracted 3 times with DCM, then the combined organics were dried and purified by FC (DCM/7N $NH_3$ in MeOH 97:3). Product was still contaminated with TEA-H+I—, so to a 30 ml solution of the product in DCM was added 20 mls saturated $NaHCO_3$ and 10 mls 1N NaOH. The mixture was stirred for 15 minutes then the aqueous was extracted with DCM 3 times. The combined organics were dried with $MgSO_4$ and solvent removed to yield pure ethyl 3-(3-(((((3aR,4R,6R,6aS)-6-(6-((2,4-dimethoxybenzyl)amino)-9H-purin-9-yl)-2,2-dimethyltetrahydro-3aH-cyclopenta[d][1,3]dioxol-4-yl)methyl)(isopropyl)amino)cyclobutyl)propanoate (0.045 g; 70%) as a brown foam/solid with no more amine salts present by NMR. MS (ESI$^+$) for $C_{35}H_{50}N_6O_6$ m/z 651.3 [M+H]$^+$.

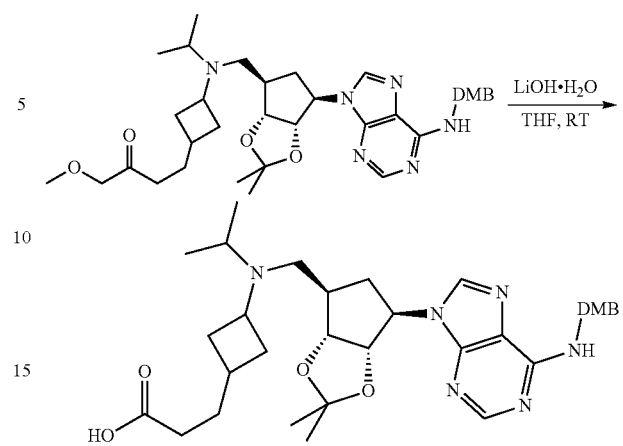

Lithium hydroxide monohydrate (0.838 g, 20.0 mmol) was added to a solution of ethyl 3-(3-(((((3aR,4R,6R,6aS)-6-(6-((2,4-dimethoxybenzyl)amino)-9H-purin-9-yl)-2,2-dimethyltetrahydro-3aH-cyclopenta[d][1,3]dioxol-4-yl)methyl)(isopropyl)amino)cyclobutyl)propanoate (1.3 g, 2.0 mmol) in tetrahydrofuran (30 mL, 300 mmol) and methanol (6.5 mL, 160 mmol). The reaction was stirred overnight at RT and by next morning the starting material was consumed and had been transformed into the acid. The reaction was acidified with 1N HCl to pH=6. Volatiles were removed in vacuo and remaining water removed by azeotropic distillation with ethanol followed by 24 hours of lyophilization. The resulting brown solid was used without further purification.

Ethyl 3-(3-(((((3 aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl) propanoate

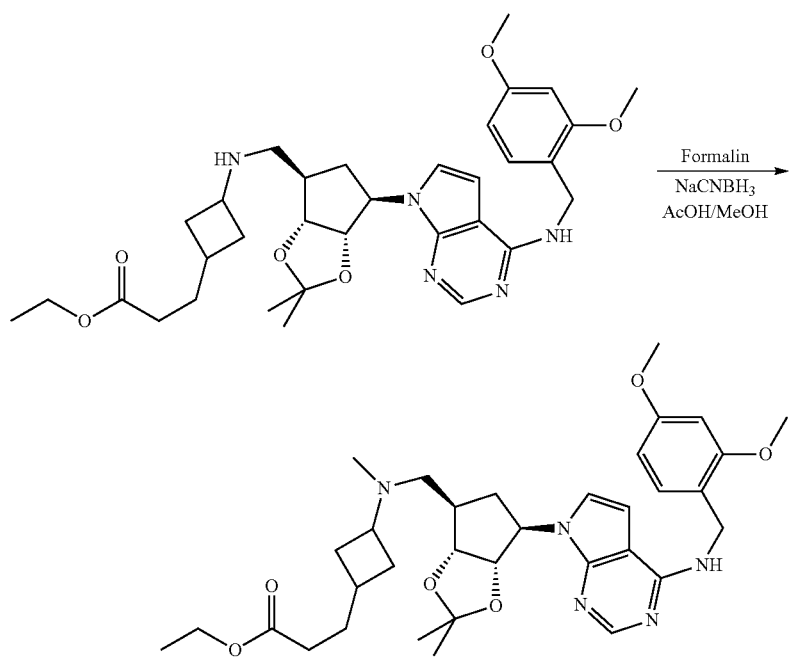

The amine ethyl 3-[3-({[(3aR,4R,6R,6aS)-6-{4-[(2,4-dimethoxybenzyl)amino]-7H-pyrrolo[2,3-d]pyrimidin-7-yl}-2,2-dimethyltetrahydro-3aH-cyclopenta[d][1,3]dioxol-4-yl]methyl}amino)cyclobutyl]propanoate (1.8 g, 3.0 mmol) was taken up in methanol (20 mL, 600 mmol) and sodium cyanoborohydride (0.19 g, 3.0 mmol) was added. The pH was adjusted to ca. 6 using a 10% solution of AcOH in MeOH, then formalin (0.29 mL, 3.9 mmol) was added in one portion. The reaction was allowed to proceed for 3 hours at which time MS indicated complete consumption of the starting material. NaHCO$_3$ (saturated) added to the reaction mixture which was then extracted 3 times with DCM. The combined organics were dried with MgSO$_4$ and concentrated to a yellow resin. This residue was purified by FC (DCM/7N NH$_3$ in MeOH 93:7) to yield ethyl 3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanoate (1.6 g; 87%) as a colorless foam. MS (ESI$^+$) for C$_{34}$H$_{47}$N$_5$O$_6$ m/z 622.3 [M+H].

$^1$H NMR (400 MHz, d$_3$-chloroform) δ$_H$ 8.282 (s, 1H), 7.203-7.168 (m, 1H), 6.877-6.865 (m, 1H), 6.399-6.334 (m, 2H), 6.242-6.236 (m, 1H), 5.330 (s, 1H), 4.890-4.835 (m, 2H), 4.664-4.650 (d, J=5.6 Hz, 2H), 4.391-4.354 (m, 1H), 4.067-4.000 (m, 2H), 3.757 (s, 3H), 3.710 (s, 3H), 2.864-2.784 (m, 0.5H (methine of trans isomer)), 2.553-2.474 (m, 0.5H (methine of cis isomer), 2.432-2.370 (m, 1H), 2.322-2.278 (m, 2H), 2.212-2.089 (m, 4H), 2.022 & 2.018 (s, 3H (overlapping singlets due to N-methyl of cis and trans isomers), 1.964-1.908 (m, 3H), 1.778-1.584 (m, 4H), 1.486 (s, 3H), 1.363-1.296 (m, 1H), 1.219 (s, 3H), 1.182-1.146 (m, 3H).

((3aR,4R,6R,6aS)-6-(6-chloro-9H-purin-9-yl)-2-ethoxytetrahydro-3aH-cyclopenta[d][1,3]dioxol-4-yl)methanol

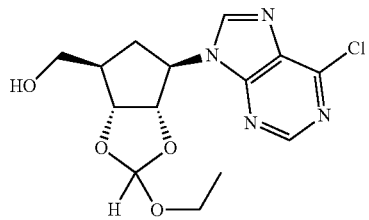

The above crude (1R,2S,3R,5R)-3-((5-amino-6-chloropyrimidin-4-yl)amino)-5-(hydroxymethyl)cyclopentane-1,2-diol was treated with ethyl orthoformate (120 mL, 720 mmol) and 10-camphorsulfonic acid (8.11 g, 34.9 mmol). The heterogeneous brown mixture was stirred vigorously to afford a nearly homogeneous brown solution after 10 min. At 5 h, LC MS indicated the desired product as the major product and the reaction was quenched with saturated aqueous NaHCO$_3$ (120 mL). The mixture was diluted with water (75 mL), extracted with CH$_2$Cl$_2$ (3×200 mL), and the combined organics were dried (Na$_2$SO$_4$) and concentrated in vacuo to afford the crude title compound as a dark brown liquid, which was carried on without further manipulation: MS (ESI+) for C$_{14}$H$_{17}$ClN$_4$O$_4$ m/z 341.0 (M+H)$^+$.

Step 3: ((3aR,4R,6R,6aS)-6-(6-chloro-9H-purin-9-yl)-2,2-dimethyltetrahydro-3aH-cyclopenta[d][1,3]dioxol-4-yl)methanol

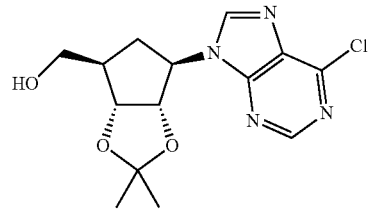 [SMILES: CC1(C)O[C@@H]2[C@@H](CO)C[C@@H](n3cnc4c(Cl)ncnc43)[C@@H]2O1]

The above crude ((3aR,4R,6R,6aS)-6-(6-chloro-9H-purin-9-yl)-2-ethoxytetrahydro-3aH-cyclopenta[d][1,3]dioxol-4-yl)methanol was taken up in 2,2-dimethoxypropane (214 mL, 1740 mmol) and treated with p-toluenesulfonic acid monohydrate (13.2 g, 69.5 mmol) to afford a brown oil partially suspended in a cloudy solution, which was stirred at rt for 1 h 20 min; HPLC/LC MS indicated complete conversion to the desired product. The reaction was quenched by the careful addition of sodium bicarbonate (8.76 g, 104 mmol) and a minimal amount of water. The volatiles were removed in vacuo and the remaining aqueous layer was diluted with water (100 mL) and extracted with CH$_2$Cl$_2$ (3×400 mL). The combined organics were dried (Na$_2$SO$_4$) and concentrated in vacuo to afford a brown oil. Purification by column chromatography (7×16 cm silica; 0-5% MeOH/CH$_2$Cl$_2$) afforded the title compound (8.30 g, 74% over 3 steps) as a yellow foam: MS (ESI+) for C$_{14}$H$_{17}$ClN$_4$O$_3$ m/z 325.1 (M+H)$^+$; MS (ESI−) for C$_{14}$H$_{17}$ClN$_4$O$_3$ m/z 369.0 (M+HCO$_2$)$^-$.

Step 4: 9-((3aS,4R,6R,6aR)-6-(azidomethyl)-2,2-dimethyltetrahydro-3aH-cyclopenta[d][1,3]dioxol-4-yl)-6-chloro-9H-purine

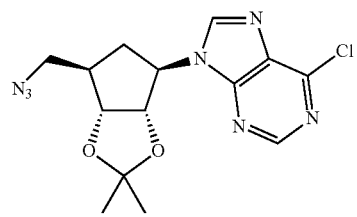 [SMILES: CC1(C)O[C@@H]2[C@@H](CN=[N+]=[N-])C[C@@H](n3cnc4c(Cl)ncnc43)[C@@H]2O1]

A mixture of ((3aR,4R,6R,6aS)-6-(6-chloro-9H-purin-9-yl)-2,2-dimethyltetrahydro-3aH-cyclopenta[d][1,3]dioxol-4-yl)methanol (7.9 g, 24 mmol) and polymer-supported triphenylphosphine (3 mmol/g loading; 11 g, 34 mmol) in THF (100 mL) was cooled to 0° C. (ice/brine bath) and treated dropwise with diisopropyl azodicarboxylate (6.7 mL, 34 mmol). The tan slurry was stirred for 15 min, and treated dropwise with a solution of diphenylphosphonic azide (7.3 mL, 34 mmol) in THF (24 mL). The brown reaction mixture was stirred for 18.5 h as the ice bath expired; HPLC indicated conversion to the desired product. At 21.5 h the reaction mixture was filtered, the solids were washed with CH$_2$Cl$_2$, and the filtrate was concentrated in vacuo. The red-brown residue was taken up in CH$_2$Cl$_2$ (300 mL) and washed with saturated aqueous NaHCO$_3$ (1×100 mL), water (1×100 mL), and brine (1×150 mL). The separated organic layer was dried (Na$_2$SO$_4$) and concentrated in vacuo to afford a red-orange oil. Purification by column chromatography (7×16 cm silica; 0-10% acetone/CH$_2$Cl$_2$) afforded the title compound (4.82 g, 57%) as a yellow oil/foam: MS (ESI+) for C$_{14}$H$_{16}$ClN$_7$O$_2$ m/z 350.1 (M+H)$^+$; MS (ESI−) for C$_{14}$H$_{16}$ClN$_7$O$_2$ m/z 394.1 (M+HCO$_2$)$^-$.

Step 5: 9-((3aS,4R,6R,6aR)-6-(azidomethyl)-2,2-dimethyltetrahydro-3aH-cyclopenta[d][1,3]dioxol-4-yl)-N-(2,4-dimethoxybenzyl)-9H-purin-6-amine

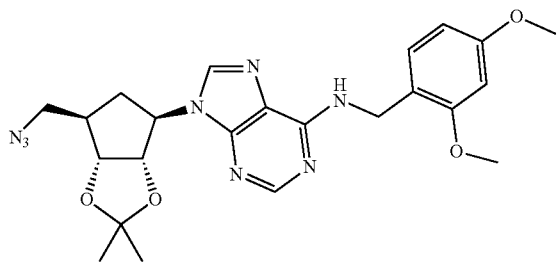 [SMILES: COc1ccc(CNc2ncnc3c2ncn3[C@@H]2C[C@H](CN=[N+]=[N-])[C@H]3OC(C)(C)O[C@H]32)c(OC)c1]

A solution of 9-((3aS,4R,6R,6aR)-6-(azidomethyl)-2,2-dimethyltetrahydro-3aH-cyclopenta[d][1,3]dioxol-4-yl)-6-chloro-9H-purine (1.29 g, 3.69 mmol) and (2,4-dimethoxyphenyl)methanamine (0.71 mL, 4.7 mmol) in 1-butanol (10 mL) was treated with N,N-diisopropylethylamine (0.93 mL, 5.3 mmol) and heated at 80° C. for 16.5 h; HPLC/LC MS indicated conversion to the desired product. The reaction mixture was allowed to cool to rt and the volatiles were removed under the flow of air to afford a brown-orange paste. Purification by column chromatography (2×8 cm silica; 0-10% acetone/CH$_2$Cl$_2$) afforded the title compound (1.72 g, 97%) as a yellow-orange foam/oil: MS (ESI+) for C$_{23}$H$_{28}$N$_8$O$_4$ m/z 481.2 (M+H)$^+$.

Step 6: 9-((3aS,4R,6R,6aR)-6-(aminomethyl)-2,2-dimethyltetrahydro-3aH-cyclopenta[d][1,3]dioxol-4-yl)-N-(2,4-dimethoxybenzyl)-9H-purin-6-amine

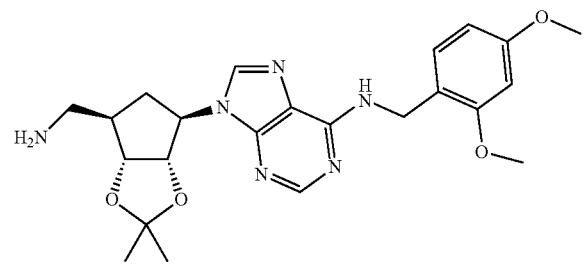 [SMILES: COc1ccc(CNc2ncnc3c2ncn3[C@@H]2C[C@H](CN)[C@H]3OC(C)(C)O[C@H]32)c(OC)c1]

A solution of 9-((3aS,4R,6R,6aR)-6-(azidomethyl)-2,2-dimethyltetrahydro-3aH-cyclopenta[d][1,3]dioxol-4-yl)-N-(2,4-dimethoxybenzyl)-9H-purin-6-amine (1.72 g, 3.58 mmol) in THF (16 mL) was cooled to 0° C. (ice/brine bath) and treated dropwise with a 1.0 M solution of trimethylphosphine in THF (6.30 mL, 6.30 mmol). The cold bath was removed after 30 min and the reaction mixture was stirred for 1.5 h; HPLC/LC MS indicated complete consumption of the starting azide. Water (2.84 mL, 157 mmol) was added to the orange solution (gas evolution noted) and the reaction mixture was stirred for 2.75 h at rt; HPLC indicated complete conversion to the desired amine. The reaction mixture was concentrated in vacuo to afford an orange oil. The residue was taken up in CH$_2$Cl$_2$ (150 mL) and washed with water (2×50 mL) and brine (1×75 mL). The separated organic layer was dried (Na$_2$SO$_4$) and concentrated in vacuo to afford the title compound (1.6 g, 98%) as a pale yellow foam: MS (ESI+) for C$_{23}$H$_{30}$N$_6$O$_4$ m/z 455.2 (M+H)$^+$.

Step 1: ethyl 3-(3-((((3aR,4R,6R,6aR)-6-(6-amino-9H-purin-9-yl)-2,2-dimethyltetrahydrofuro[3,4-d][1,3]dioxol-4-yl)methyl)amino)cyclobutyl)propanoate

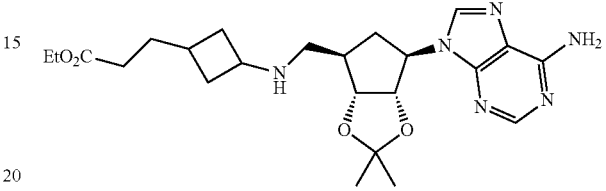

A mixture of 9-((3aR,4R,6R,6aR)-6-(aminomethyl)-2,2-dimethyltetrahydrofuro[3,4-d][1,3]dioxol-4-yl)-9H-purin-6-amine (0.50 g, 1.6 mmol) and ethyl 3-(3-oxocyclobutyl)propanoate (0.27 g, 1.6 mmol) in methanol (10 mL) was treated with acetic acid (0.09 mL, 2 mmol) at rt and the flask was evacuated and flushed with nitrogen (×3). The reaction mixture was treated at rt with sodium cyanoborohydride (0.26 g, 4.1 mmol), which afforded instant gas evolution and a nearly colorless, clear solution in a few minutes. The reaction mixture was stirred for 1 h at rt; HPLC/LC MS indicated a ~2:1 mixture of product to starting amine. At 1.5 h additional ethyl 3-(3-oxocyclobutyl)propanoate (66 mg, 0.39 mmol) in MeOH (1.0 mL) was added and the reaction mixture was stirred at rt for 30 min; HPLC/LC MS indicated ~70% conversion and some dialkylation. At 2 h 15 min water (4.0 mL) was added and the mixture was concentrated in vacuo. The residual aqueous layer was diluted with saturated aqueous sodium bicarbonate (10 mL, to pH 9) and extracted with CH$_2$Cl$_2$ (3×15 mL). The combined organics were dried (Na$_2$SO$_4$) and concentrated in vacuo to afford the reductive amination product as a white foam, which was carried on without further purification: MS (ESI+) for C$_{22}$H$_{32}$N$_6$O$_5$ m/z 461.1 (M+H)$^+$, 483.1 (M+Na)$^+$.

Step 2: ethyl 3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl) propanoate

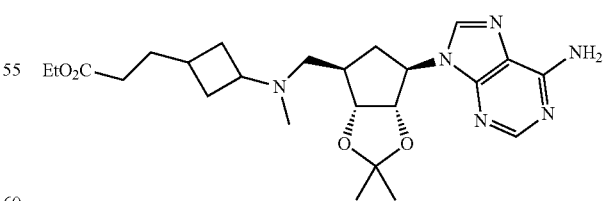

The above crude secondary amine was taken up in methanol (10 mL) and treated with sodium cyanoborohydride (0.30 g, 4.8 mmol). A solution of 10% v/v acetic acid in methanol was added to adjust the pH to ~6, followed by the dropwise addition of 37% aqueous formaldehyde (0.65 mL, 6.3 mmol), which afforded gas evolution. The reaction mixture was stirred at rt for 1 h; HPLC/LC MS indicated complete conversion to the desired product. At 1.5 h, water (5.0 in L) was added and the reaction mixture was concentrated in vacuo. The residue was diluted with saturated aqueous NaHCO$_3$ (10 mL, to pH ~9) and extracted with CH$_2$Cl$_2$ (3×15 mL). The combined organics were diluted with a small amount of EtOH to afford a clear solution, dried (Na$_2$SO$_4$), and concentrated in vacuo to afford a nearly colorless oil. Purification by column chromatography (4×17 cm silica; 0-5% 7 N methanolic NH$_3$/CH$_2$Cl$_2$) afforded the title compound (0.50 g, 60%) as a white foam/colorless oil: MS (ESI+) for C$_{23}$H$_{34}$N$_6$O$_5$ m/z 475.1 (M+H)$^+$, 497.1 (M+Na)$^+$.

Step 1: ethyl 3-(3-(((((3aR,4R,6R,6aR)-6-(6-amino-9H-purin-9-yl)-2,2-dimethyltetrahydrofuro[3,4-d][1,3]dioxol-4-yl)methyl)amino)cyclobutyl)propanoate

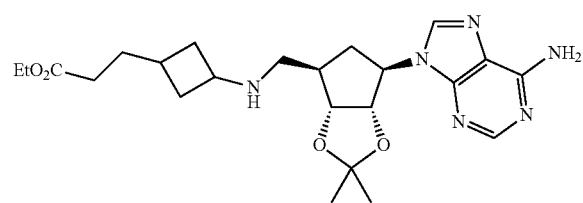 [SMILES: CCOC(=O)CCC1CC(NC[C@H]2C[C@@H](n3cnc4c(N)ncnc43)[C@@H]3OC(C)(C)O[C@H]23)C1]

A mixture of 9-((3aR,4R,6R,6aR)-6-(aminomethyl)-2,2-dimethyltetrahydrofuro[3,4-d][1,3]dioxol-4-yl)-9H-purin-6-amine (2.04 g, 6.66 mmol) and ethyl 3-(3-oxocyclobutyl)propanoate (1.2 g, 7.0 mmol) in methanol (41 mL) was treated with acetic acid (0.37 mL, 6.5 mmol) at rt and the flask was evacuated and flushed with nitrogen (×3). The reaction mixture was treated at rt with sodium cyanoborohydride (1.0 g, 16 mmol), which afforded instant gas evolution and a nearly colorless, clear solution in a few minutes. The reaction mixture was stirred for 1 h at rt; HPLC/LC MS indicated starting material remained. At 1 h 20 min additional ethyl 3-(3-oxocyclobutyl)propanoate (0.50 g, 2.93 mmol) in MeOH (3 mL) was added. The reaction mixture was stirred for 30 min and treated with water (12 mL). The mixture was concentrated in vacuo and the residual aqueous layer was diluted with saturated aqueous sodium bicarbonate (40 mL, to pH 9) and extracted with CH$_2$Cl$_2$ (3×60 mL). The combined organics were dried (Na$_2$SO$_4$) and concentrated in vacuo to afford the crude title compound as a white foam/very pale yellow oil, which was carried on without further purification: MS (ESI+) for C$_{22}$H$_{32}$N$_6$O$_5$ m/z 461.2 (M+H)$^+$ and 483.1 (M+Na)$^+$.

Step 2: ethyl 3-(3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoate

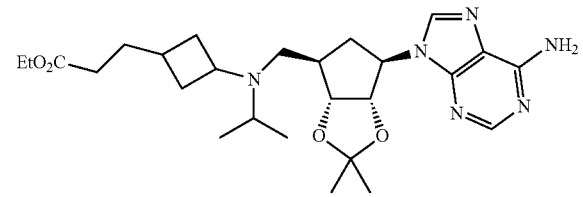 [SMILES: CCOC(=O)CCC1CC(N(C[C@H]2C[C@@H](n3cnc4c(N)ncnc43)[C@@H]3OC(C)(C)O[C@H]23)C(C)C)C1]

A solution of the above crude ethyl 3-(3-(((((3aR,4R,6R,6aR)-6-(6-amino-9H-purin-9-yl)-2,2-dimethyltetrahydrofuro[3,4-d][1,3]dioxol-4-yl)methyl)amino)cyclobutyl)propanoate in acetonitrile (30 mL) was treated with potassium carbonate (6.3 g, 46 mmol) and isopropyl iodide (3.9 mL, 39 mmol). The reaction mixture in a sealed tube was heated at 90° C. for 6.5 h; HPLC indicated a 4:1 mixture of product to starting material. The reaction mixture was stirred overnight (17.5 h) at rt, treated with additional isopropyl iodide (2.0 mL, 20 mmol), and heated at 90° C. for 3 h; HPLC/LC MS indicated nearly complete conversion. The reaction mixture was cooled to rt and the solids were removed by vacuum filtration, rinsing with CH$_3$CN, and the filtrate was concentrated in vacuo to afford a dull orange oil with precipitate. Purification by column chromatography (5×14.5 cm silica; 0-10% 7 N methanolic NH$_3$/CH$_2$Cl$_2$) afforded the title compound (0.49 g, 15%) as a white foam/colorless oil. The mixed fractions containing product were repurified by column chromatography (4×10.5 cm silica; 0-5% 7 N methanolic NH$_3$/CH$_2$Cl$_2$) to afford the title compound (1.66 g, 40%) as a white foam/colorless oil contaminated with the bisreductive amination byproduct from Step 1: MS (ESI+) for C$_{25}$H$_{38}$N$_6$O$_5$ m/z 503.2 (M+H)$^+$.

ethyl 3-(3-(((((1R,2R,3S,4R)-4-(4-((2,4-dimethoxybenzyl)amino)-7H-pyrrolo[2,3-d]pyrimidin-7-yl)-2,3-dihydroxycyclopentyl)methyl)amino)cyclobutyl) propanoate

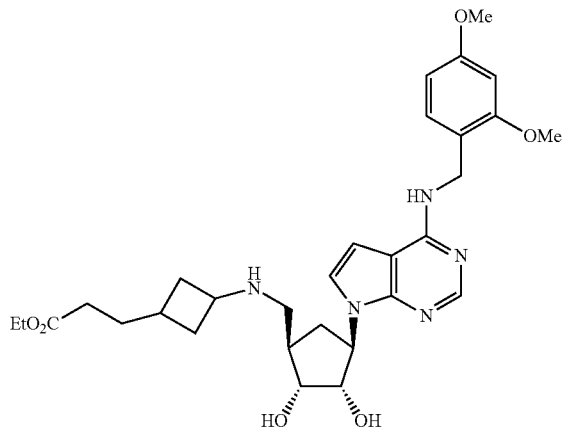 [SMILES: CCOC(=O)CCC1CC(NC[C@H]2C[C@@H](n3ccc4c(NCc5ccc(OC)cc5OC)ncnc43)[C@H](O)[C@@H]2O)C1]

Sodium triacetoxyborohydride (2.43 g, 11.5 mmol) was added to a solution of (1S,2R,3R,5R)-3-(aminomethyl)-5-(4-((2,4-dimethoxybenzyl)amino)-7H-pyrrolo[2,3-d]pyrimidin-7-yl)cyclopentane-1,2-diol (2.6 g, 5.7 mmol) and ethyl 3-(3-oxocyclobutyl)propanoate (0.976 g, 5.73 mmol) and Acetic acid (0.326 ml, 5.73 mmol) in 1,2-Dichloroethane (20 ml) and reaction was stirred at RT overnight. NaHCO$_3$ was added and the aqueous layer was extracted 3× with DCM. The combined organics were dried with MgSO$_4$, filtered, concentrated and purified by flash chromatogrpahy (DCM/7N NH$_3$ in MeOH 90:10) to give the desired compound (1.8 g) as a thick yellow resin.

N-(2,4-dimethoxybenzyl)-7-((3aS,4R,6R,6aR)-6-((isopropylamino)methyl)-2,2-dimethyltetrahydro-3aH-cyclopenta[d][1,3]dioxol-4-yl)-7H-pyrrolo[2,3-d]pyrimidin-4-amine

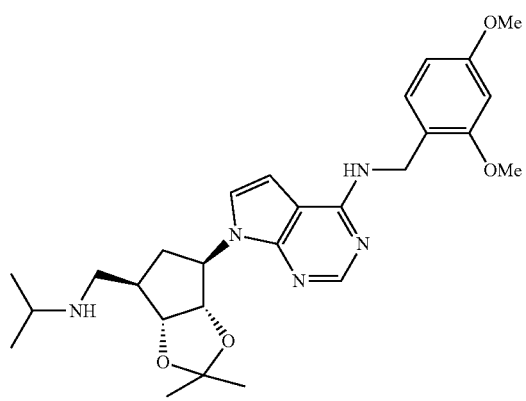 [SMILES: COc1ccc(CNc2ncnc3c2ccn3[C@@H]2C[C@H](CNC(C)C)[C@H]3OC(C)(C)O[C@H]32)c(OC)c1]

A solution of 7-((3aS,4R,6R,6aR)-6-(aminomethyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (7.50 g, 16.5 mmol) in 1,2-Dichloroethane (140 mL, 1800 mmol) was treated with Acetone (1.34 mL, 18.2 mmol) and Acetic acid (0.94 mL, 16 mmol) dropwise followed by Sodium triacetoxyborohydride (4.20 g, 19.8 mmol) and the mixture was stirred at RT for 4 h. HPLC analysis indicated the reaction was complete. The reaction mixture was diluted with 200 mL CH$_2$Cl$_2$ and washed with 150 mL sat NaHCO$_3$. The aqueous phase was washed with 100 mL CH$_2$Cl$_2$ and the combined organic phase was dried over Na$_2$SO$_4$, filtered and concentrated to yield a an oil that produced a stiff foam when placed under high vac. The crude material (9.3 g) was carried on directly to the next step.

ethyl 3-(3-(((((3 aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isopropyl)amino)cyclobutyl)propanoate

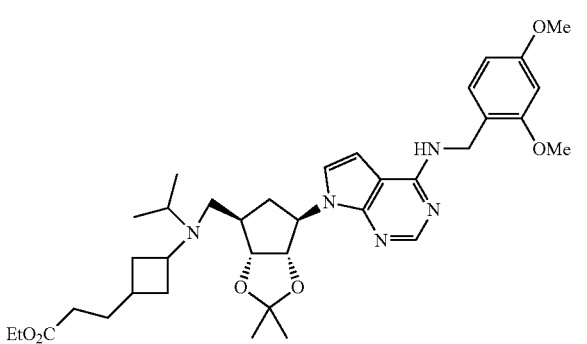 [SMILES: CCOC(=O)CCC1CC(N(C[C@H]2C[C@@H](n3ccc4c(NCc5ccc(OC)cc5OC)ncnc43)[C@@H]3OC(C)(C)O[C@H]23)C(C)C)C1]

A solution of N-(2,4-dimethoxybenzyl)-7-((3aS,4R,6R,6aR)-6-((isopropylamino)methyl)-2,2-dimethyltetrahydro-3aH-cyclopenta[d][1,3]dioxol-4-yl)-7H-pyrrolo[2,3-d]pyrimidin-4-amine (9.50 g, 15.3 mmol) in 1,2-Dichloroethane (75 mL, 950 mmol) was treated with ethyl 3-(3-oxocyclobutyl)propanoate (3.92 g, 23.0 mmol) and Acetic acid (1.0 mL, 18 mmol) dropwise followed by Sodium triacetoxyborohydride (4.58 g, 21.6 mmol) and the mixture was stirred at RT for 6 days. The reaction mixture was diluted with 150 mL CH$_2$Cl$_2$ and washed with 100 mL sat NaHCO$_3$. The aqueous phase was washed with 100 mL CH$_2$Cl$_2$ and the combined organic phase was dried over Na$_2$SO$_4$, filtered and concentrated to yield a light brown viscous glass.

The crude material was purified by flash chromatography (SiO$_2$ eluting with 2-3% 7N NH$_3$ in CH$_3$OH/CH$_2$Cl$_2$) to yield a slightly glass/stiff foam (7.10 g).

ethyl 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoate

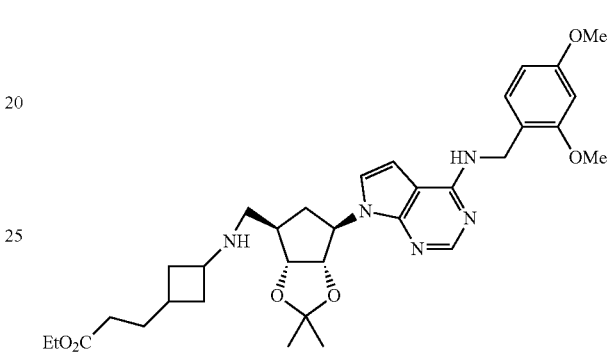

A solution of 7-((3aS,4R,6R,6aR)-6-(aminomethyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (8.00 g, 15.2 mmol) in 1,2-Dichloroethane (119.5 mL, 1517 mmol) was treated with ethyl 3-(3-oxocyclobutyl)propanoate (2.58 g, 15.2 mmol) and Acetic acid (0.86 mL, 15 mmol) dropwise followed by Sodium triacetoxyborohydride (3.86 g, 18.2 mmol) and the mixture was stirred at RT for 19 h. The reaction mixture was diluted with 150 mL CH$_2$Cl$_2$ and washed with 150 mL sat NaHCO$_3$. The aqueous phase was washed with 70 mL CH$_2$Cl$_2$ and the combined organic phase was dried over Na$_2$SO$_4$, filtered and concentrated to yield a tan glass that produced a sticky foam when placed under high vac. The crude material was purified by flash chromatography (SiO$_2$ eluting with 3-4% 7N NH$_3$ in CH$_3$OH/CH$_2$Cl$_2$) to yield a light yellow viscous oil that producted a sticky foam under high vacuum (5.03 g). MS 608.3 (M+H).

Example 1

Synthesis of 1-((3-(((((2R,3S,4R,5R)-5-(6-amino-9H-purin-9-yl)-3,4-dihydroxytetrahydrofuran-2-yl)methyl)(methyl)amino)cyclobutyl)methyl)-3-(4-(tert-butyl)phenyl)urea (Compound 110)

Step 1: Synthesis of methyl 3-oxocyclobutanecarboxylate

To a solution of DCC (5.96 g, 28.95 mmol) in DCM (20 ml) was added dropwise a mixture of 3-oxocyclobutanecarboxylic acid (3.0 g, 26.31 mmol), MeOH (1.68 g, 52.62 mmol) and DMAP (2.57 g, 21.05 mmol) in DCM (30 ml). The reaction mixture was stirred at RT overnight. The mixture was filtrated. The filtrate was washed with 0.5 M HCl solution (50 ml). The organic layer was dried over $Na_2SO_4$ and concentrated. The residue was purified by SGC (PE:EA=5:1) to obtain the title compound (4.0 g). $^1$H N.R (500 MHz, $CDCl_3$): δ 3.77 (s, 3H), 3.42-3.26 (m, 5H) ppm.

Step 2: Synthesis of methyl3-(((((3aR,4R,6R,6aR)-6-(6-amino-9H-purin-9-yl)-2,2-dimethyl tetrahydro furo[3,4-d][1,3]dioxol-4-yl)methyl)(methyl)amino)cyclobutanecarboxylate

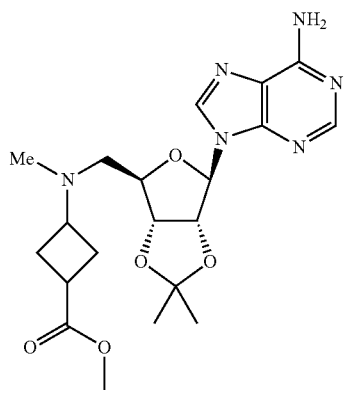 [SMILES: COC(=O)C1CC(N(C)C[C@H]2O[C@@H](n3cnc4c(N)ncnc43)[C@@H]3OC(C)(C)O[C@@H]32)C1]

A solution of methyl 3-oxocyclobutanecarboxylate (1.28 g crude), 9-((3aR,4R,6R,6aR)-2,2-dimethyl-6-((methylamino)methyl)tetrahydrofuro[3,4-d][1,3]dioxol-4-yl)-9H-purin-6-amine (2.0 g, 6.25 mmol) (Townsend et al Org Lett 2009, 11, 2976-2679) and $Ti(iPrO)_4$ (1.78 g, 6.25 mmol) in MeOH (50 mL) was stirred at 45° C. for 2 h, then $NaCNBH_3$ (0.79 g, 12.50 mmol) was added. The reaction was stirred at RT overnight. The reaction was quenched with aq. sat. $NaHCO_3$ (40 mL), filtered, extracted with DCM (40 mL×3), dried over $Na_2SO_4$ and concentrated. The residue was purified by SGC (DCM:MeOH=12:1) to obtain title compound (1.7 g, Yield 63%). $^1$H NMR (500 MHz, MeOD): $δ_H$ 8.28-8.27 (m, 1H), 8.21 (s, 1H), 6.20-6.18 (m, 1H), 5.52 (dd, J=1.5, 6.0 Hz, 1H), 5.00 (dd, J=3.0, 6.0 Hz, 1H), 5.33 (brs, 1H), 3.65-3.63 (m, 3H), 2.77-2.55 (m, 4H), 2.19-2.11 (m, 5H), 2.00-1.82 (m, 2H), 1.59 (s, 3H), 1.38 (s, 3H) ppm; ESI-MS (m/z): 433.2 [M+1]$^+$.

Step 3: Synthesis of (3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)methanol

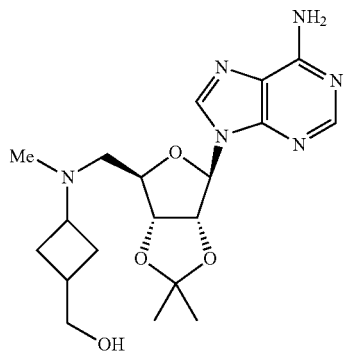 [SMILES: CN(C[C@H]1O[C@@H](n2cnc3c(N)ncnc32)[C@@H]2OC(C)(C)O[C@@H]21)C1CC(CO)C1]

To a solution of methyl 3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutanecarboxylate (1.0 g, 2.31 mmol) in THF (40 ml) was added $LiAlH_4$ (0.53 g, 13.89 mmol) at 0° C. and the mixture was stirred overnight. Water (1.0 g) and 15% NaOH solution (3.0 g) were added slowly to the mixture and upon stirring for 15 min, the mixture was filtered. The filtrate was concentrated to obtain the crude title compound which was used directly in the next step.

Step 4: Synthesis of (3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)methyl methanesulfonate

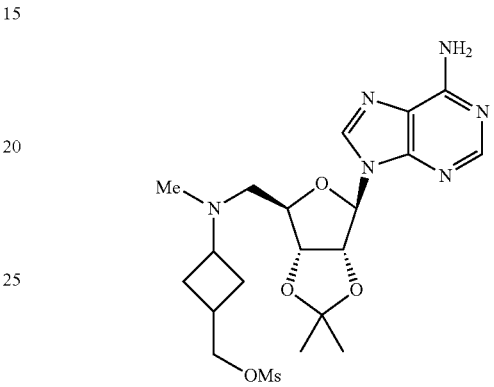

To a solution of (3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)methanol taken directly from the previous step in DCM (25 ml) was added $Et_3N$ (467 mg, 4.62 mmol) and MsCl (264 mg, 2.31 mmol) as a solution in DCM (5 ml). The mixture was stirred for 2 h. Water (20 ml) and DCM (30 ml×2) was added. The organic layer was dried over $Na_2SO_4$ and concentrated, purified with Prep-TLC (DCM:MeOH=10:1) to give the title compound (390 mg, Yield 35% for two steps). $^1$H NMR (500 MHz, MeOD): $δ_H$ 8.27 (s, 1H), 8.21 (s, 1H), 6.203-6.200 (m, 1H), 5.529 (dd, J=2.0, 7.0 Hz, 1H), 5.010 (dd, J=3.0, 6.0 Hz, 1H), 4.354 (dd, J=3.5, 8.0 Hz, 1H), 4.197-4.182 (m, 2H), 3.585 (brs, 1H), 3.073-2.948 (m, 5H), 2.595-2.513 (m, 2H), 2.394 (brs, 1H), 2.207 (brs, 1H), 2.107 (s, 3H), 2.030-1.989 (m, 1H), 1.840-1.811 (m, 2H), 1.586 (s, 3H), 1.390 (brs, 1H), 1.329-1.280 (m, 6H), 0.905-0.878 (m, 1H) ppm; ESI-MS (m/z): 483.3[M+1]$^+$.

Step 5: Synthesis of 9-((3aR,4R,6R,6aR)-6-(((3-(azidomethyl)cyclobutyl)(methyl)amino)methyl)-2,2-dim ethyltetrahydro furo[3,4-d][1,3]dioxol-4-yl)-9H-purin-6-amine

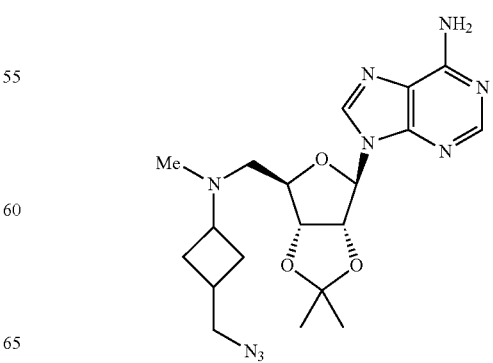

To a solution of (3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)methyl methane sulfonate (150 mg, 0.31 mmol) in DMF (3 ml) was added NaN₃ (81 mg, 1.24 mmol). The mixture was heated at 70° C. for 3 h. Water (30 ml) was added and the mixture was extracted with ethyl acetate (20 ml×3). The combined organic layers were dried over Na₂SO₄ and concentrated. The residue was purified by Prep-TLC (DCM:MeOH=30:1) to obtain the title compound (90 mg, Yield 67%). ESI-MS (m/z): 430.2[M+1]⁺.

Step 6: Synthesis of 9-((3aR,4R,6R,6aR)-6-(((3-(aminomethyl)cyclobutyl)(methyl)amino)methyl)-2,2-dimethyltetrahydro furo[3,4-d][1,3]dioxol-4-yl)-9H-purin-6-amine

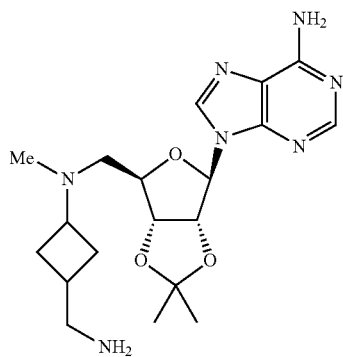 [SMILES: CN(C[C@H]1O[C@@H](n2cnc3c(N)ncnc32)[C@@H]2OC(C)(C)O[C@@H]21)C1CC(CN)C1]

Pd/C (10 mg) was added to a solution of 9-((3aR,4R,6R,6aR)-6-(((3-(azidomethyl)cyclobutyl)(methyl)amino)methyl)-2,2-dimethyltetrahydrofuro[3,4-d][1,3]dioxol-4-yl)-9H-purin-6-amine (90 mg, 0.21 mmol) in MeOH (6 ml). The mixture was stirred at RT overnight under an atmosphere of H₂. The mixture was filtered and the filtrate was concentrated to obtain the title compound which was used directly in the next step.

Step 7: Synthesis of 1-((3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)methyl)-3-(4-(tert-butyl)phenyl)urea

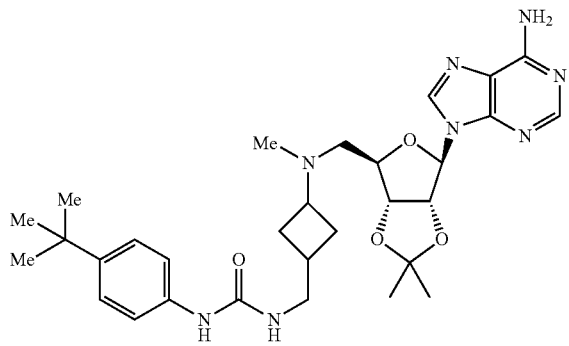 [SMILES: CN(C[C@H]1O[C@@H](n2cnc3c(N)ncnc32)[C@@H]2OC(C)(C)O[C@@H]21)C1CC(CNC(=O)Nc2ccc(C(C)(C)C)cc2)C1]

To a solution of 9-((3aR,4R,6R,6aR)-6-(((3-(aminomethyl)cyclobutyl)(methyl)amino)methyl)-2,2-dimethyltetrahydrofuro[3,4-d][1,3]dioxol-4-yl)-9H-purin-6-amine in DCM (4 ml) was added 1-tert-butyl-4-isocyanatobenzene (37 mg). The mixture was stirred at RT for 1 h. The mixture was concentrated and purified via preparative-TLC (DCM: MeOH=10:1) to give the title compound (55 mg, Yield 45% for two steps). ESI-MS (m/z): 578.3[M+1]⁺.

Step 8: Synthesis of Compound 110

A solution of 1-((3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)methyl)-3-(4-(tert-butyl)phenyl)urea (55 mg) in HCl/MeOH (2.5 mol/L) (2 mL) was stirred at RT for 2 h and then concentrated to dryness. K₂CO₃ (52 mg) in water (0.5 mL) and MeOH (5 mL) was added. The resulting mixture was stirred for another 10 min at RT, filtered and the filtrate was concentrated. The residue was purified by preparative-HPLC to give Compound 110 (10 mg, yield: 25%) as a white solid. ¹HNMR (500 MHz, MeOD): $\delta_H$ 8.26 (s, 1H), 8.18 (s, 1H), 7.26-7.19 (m, 4H), 5.96 (d, J=4.5 Hz, 1H), 4.674-4.655 (m, 1H), 4.24-4.16 (m, 2H), 3.15 (d, J=5.0 Hz, 2H), 2.83-2.73 (m, 3H), 2.20-1.59 (m, 8H), 1.26 (s, 9H) ppm; ESI-MS (m/z): 539.3 [M+1]⁺.

Example 2

Synthesis of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino) methyl)tetrahydrofuran-3,4-diol (Compound 2)

Step 1: Synthesis of cis and trans methyl 3-((((3aR,4R,6R,6aR)-6-(6-amino-9H-purin-9-yl)-2,2-dimethyltetrahydrofuro[3,4-d][1,3]dioxol-4-yl)methyl)amino)cyclobutanecarboxylate

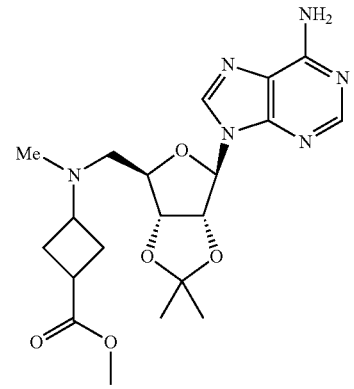 [SMILES: COC(=O)C1CC(N(C)C[C@H]2O[C@@H](n3cnc4c(N)ncnc43)[C@@H]3OC(C)(C)O[C@@H]32)C1]

A solution of methyl 3-oxocyclobutanecarboxylate (4.60 g, 35.94 mmol), 9-((3aR,4R,6R,6aR)-6-(aminomethyl)-2,2-dimethyltetrahydrofuro[3,4-d][1,3]dioxol-4-yl)-9H-purin-6-amine (11.0 g, 35.94 mmol) and Ti(iPrO)₄ (4.0 g, 14.08 mmol) in MeOH (80 mL) was stirred at 45° C. for 2 h, then NaCNBH₃ (4.5 g, 71.87 mmol) was added. The reaction was stirred at RT overnight. The reaction was quenched with aq. sat. NaHCO₃ (40 mL) and filtered, extracted with DCM (80 mL×3), dried over Na₂SO₄ and concentrated. The residue was purified by preparative-HPLC to obtain the title compound (6.2 g, Yield 41%). ¹H NMR (500 MHz, CDCl₃): $\delta_H$ 8.38-8.34 (m, 1H), 7.90 (s, 1H), 5.98 (d, J=3.0 Hz, 1H), 5.75 (br s, 2H), 5.48-5.46 (m, 1H), 5.03-5.01 (m, 1H), 4.35-4.33 (m, 1H), 3.69-3.66 (m, 3H), 3.50-3.17 (m, 1H), 3.05-2.73 (m, 3H), 2.48-2.44 (m, 2H), 1.95-1.91 (m, 2H), 1.62 (s, 3H), 1.39 (s, 3H) ppm; ESI-MS (m/z): 419.2[M+1]⁺.

The cis/trans mixture of methyl 3-((((3aR,4R,6R,6aR)-6-(6-amino-9H-purin-9-yl)-2,2-dimethyltetrahydrofuro[3,4-d]

[1,3]dioxol-4-yl)methyl)amino)cyclobutanecarboxylate (6.2 g) was separated via chiral HPLC (CHIRALCEL AD-H 20*250 mm, 5um (Daicel), Column temperature: 35° C., Mobile phase: CO2/Methanol (0.1% DEA)=70/30, Flow rate: 50 g/min) to give the pure cis product (3.5 g) and pure trans product (1.7 g).

Step 2: Synthesis of (1S,3s)-methyl 3-((((3aR,4R,6R, 6aR)-6-(6-amino-9H-purin-9-yl)-2,2-dimethyltetrahydrofuro[3,4-d][1,3]dioxol-4-yl)methyl)(isopropyl)amino)cyclobutanecarboxylate

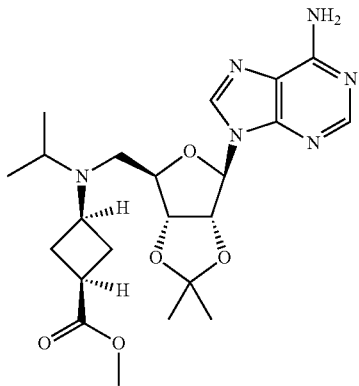 [SMILES: COC(=O)[C@H]1C[C@@H](N(C[C@H]2O[C@@H](n3cnc4c(N)ncnc43)[C@@H]3OC(C)(C)O[C@@H]32)C(C)C)C1]

To a solution of cis methyl 3-((((3aR,4R,6R,6aR)-6-(6-amino-9H-purin-9-yl)-2,2-dimethyltetrahydrofuro[3,4-d][1,3]dioxol-4-yl)methyl)amino)cyclobutanecarboxylate (2.0 g, 4.78 mmol) in CH$_3$CN (15 ml) was added 2-iodopropane (4.0 g, 23.92 mmol) and K$_2$CO$_3$ (1.0 g, 7.18 mmol). The reaction was heated to 95° C. overnight in a sealed tube. The mixture was filtered, the filtrate was concentrated and purified by SGC (DCM:MeOH=12:1) to obtain the title compound (1.9 g, Yield 86%). $^1$H NMR (500 MHz, CDCl$_3$): $\delta_H$ 8.37 (s, 1H), 7.89 (s, 1H), 6.03 (d, J=1.5 Hz, 1H), 5.53-5.48 (m, 3H), 5.00 (br s, 1H), 4.25 (bis, 1H), 3.66 (s, 3H), 3.19-3.18 (m, 1H), 2.96 (br s, 1H), 2.80-2.78 (m, 1H), 2.67-2.58 (m, 2H), 2.20-2.12 (m, 4H), 1.62 (s, 3H), 1.39 (s, 3H), 1.00 (d, J=6.0 Hz, 3H), 0.84 (d, J=6.0 Hz, 3H) ppm; ESI-MS (m/z): 461.4[M+1]$^+$.

Step 3: Synthesis of (1S,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutanecarbaldehyde

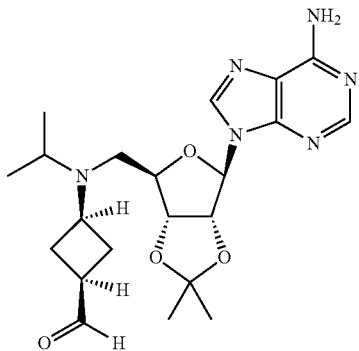 [SMILES: CC(C)N(C[C@H]1O[C@@H](n2cnc3c(N)ncnc32)[C@@H]2OC(C)(C)O[C@@H]21)[C@H]1C[C@@H](C=O)C1]

To a solution of (1S,3s)-methyl 3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutanecarboxylate (1.2 g, 2.60 mmol) in DCM (50 ml) was added DIBAL-H dropwise at −78° C. until all the starting material was consumed as determined by TLC. MeOH (2 ml) was added and the mixture was stirred to RT for 30 min. upon which water (50 ml) was added and the mixture was extracted with DCM (50 ml×2). The organic layer was dried over Na$_2$SO$_4$ and concentrated to obtain crude title compound (1.0 g which was used) directly in the next step. $^1$H NMR (500 MHz, CDCl$_3$): $\delta_H$ 9.56 (d, J=2.5 Hz, 1H), 8.36 (s, 1H), 7.88 (s, 1H), 6.03 (d, J=2.5 Hz, 1H), 5.66 (br s, 2H), 5.50 (dd, J=2.0, 6.5 Hz, 1H), 5.01 (dd, J=3.5, 6.5 Hz, 1H), 3.331-3.337 (m, 1H), 2.96-2.97 (m, 1H), 2.77-2.59 (m, 3H), 2.14-2.05 (m, 4H), 1.60 (s, 3H), 1.39 (s, 3H), 1.01 (d, J=6.5 Hz, 3H), 0.85 (d, J=6.0 Hz, 3H) ppm.

Step 4: Synthesis of (E)-ethyl 3-((1S,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)acrylate

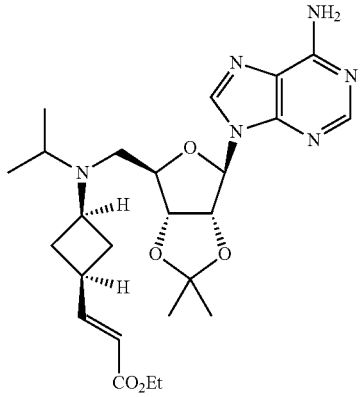 [SMILES: CCOC(=O)/C=C/[C@H]1C[C@@H](N(C[C@H]2O[C@@H](n3cnc4c(N)ncnc43)[C@@H]3OC(C)(C)O[C@@H]32)C(C)C)C1]

To a solution of (1S,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutane carbaldehyde (930 mg, 2.16 mmol) in CH$_3$CN:DCM=5:1 (50 ml) was added ethyl 2-(diethoxyphosphoryl)acetate (484 mg, 2.16 mmol), DBU (328 mg, 2.16 mmol) and LiCl (91 mg, 2.16 mmol). The mixture was stirred at RT for 1 h and then concentrated. Water (20 ml) was added and the mixture extracted with DCM (25 ml×3). The combined organic layers were dried over Na$_2$SO$_4$, concentrated and the residue was purified by SGC (DCM:MeOH=30:1) to obtain title compound (900 mg, Yield 83%). $^1$H NMR (500 MHz, CDCl$_3$): $\delta_H$ 8.36 (s, 1H), 7.89 (s, 1H), 6.94-6.90 (m, 1H), 6.03 (s, 1H), 5.72-5.89 (m, 1H), 5.57 (s, 2H), 5.52 (d, J=4.5 Hz, 1H), 5.00 (dd, J=3.5, 6.0 Hz, 1H), 4.25 (d, J=3.0 Hz, 1H), 4.21-4.17 (m, 2H), 3.14 (brs, 1H), 2.961-2.936 (m, 1H), 2.74-2.52 (m, 3H), 2.22-2.14 (m, 2H), 1.79-1.76 (m, 2H), 1.60 (s, 3H), 1.40 (s, 3H), 1.30-1.27 (m, 3H), 1.00 (d, J=7.0 Hz, 3H), 0.82 (d, J=6.5 Hz, 3H) ppm; ESI-MS (m/z): 501.4[M+1]$^+$.

Step 5: Synthesis of ethyl 3-((1S,3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoate

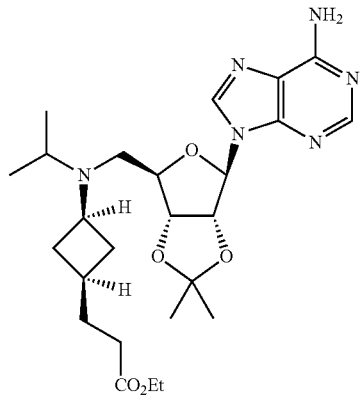 [SMILES: CC(C)N(C[C@H]1O[C@@H](n2cnc3c(N)ncnc32)[C@@H]2OC(C)(C)O[C@@H]21)[C@H]1C[C@@H](CCC(=O)O)C1]

To a solution of (E)-ethyl 3-((1S,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)acrylate (900 mg, 1.8 mmol) in MeOH (50 ml) was added Pd/C (20 mg). The mixture was stirred at RT overnight under an atmosphere of hydrogen. The mixture was filtered and the filtrate was concentrated to obtain title compound (700 mg, Yield 78%). $^1$H NMR (500 MHz, CDCl$_3$): $\delta_H$ 8.36 (s, 1H), 7.89 (s, 1H), 6.03 (d, J=2.5 Hz, 1H), 5.69 (s, 2H), 5.51 (dd, J=2.5, 8.0 Hz, 1H), 4.99 (dd, J=4.0, 7.5 Hz, 1H), 4.26 (brs, 1H), 4.13-4.08 (m, 2H), 2.99-2.92 (m, 2H), 2.706-2.655 (m, 1H), 2.539-2.486 (m, 1H), 2.18-2.02 (m, 4H), 1.76 (brs, 1H), 1.65-1.60 (m, 5H), 1.43-1.37 (m, 5H), 1.26-1.23 (m, 2H), 0.97 (d, J=9.0 Hz, 3H), 0.79 (d, J=8.5 Hz, 3H) ppm; ESI-MS (m/z): 503.4[M+1]$^+$.

Step 6: Synthesis of 3-((1S,3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoic acid

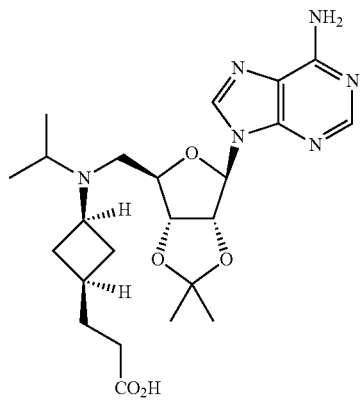

To a solution of ethyl 3-((1S,3r)-3-((((3aR,4R,6R,6aR)-6-(6-amino-9H-purin-9-yl)-2,2-dimethyltetrahydrofuro[3,4-d][1,3]dioxol-4-yl)methyl) (isopropyl)amino)cyclobutyl)propanoate (650 mg, 1.29 mmol) in THF:MeOH=5:1 (30 ml) was added LiOH.H$_2$O (543 mg, 1.29 mmol). The mixture was stirred at RT overnight, concentrated and then taken up in MeOH (10 ml). 1M HCl solution was added dropwise at 0° C. until pH=7. The mixture was concentrated and purified with preparative-HPLC to give title compound (170 mg).

Step 7: Synthesis of N-(2-amino-4-(tert-butyl)phenyl)-3-((1S,3r)-3-((((3 aR,4R,6R,6aR)-6-(6-amino-9H-purin-9-yl)-2,2-dimethyltetrahydro furo[3,4-d][1,3]dioxol-4-yl)methyl)(isopropyl)amino)cyclobutyl) propanamide

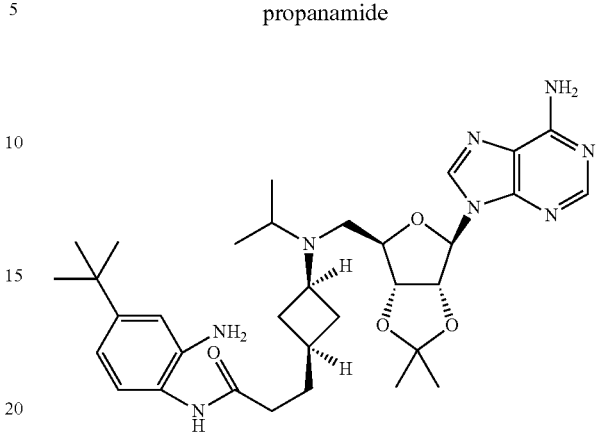

To a solution of 3-((1S,3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoic acid (170 mg, 0.36 mmol) in DCM (15 ml) was added 4-tert-butylbenzene-1,2-diamine (117 mg, 0.72 mmol), EDCI (137 mg, 0.72 mmol), HOBT (97 mg, 0.72 mmol) and TEA (217 mg, 2.15 mmol). The mixture was stirred at RT overnight and concentrated. Saturated NaHCO$_3$ solution (20 ml) was added and the mixture extracted with DCM (20 ml×3). The organic layers were dried over Na$_2$SO$_4$ and concentrated. The crude was purified with preparative-TLC (DCM:MeOH=12:1) to afford the title compound (110 mg crude).

Step 8: Synthesis of 9-((3aR,4R,6R,6aR)-6-((((1r,3S)-3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine

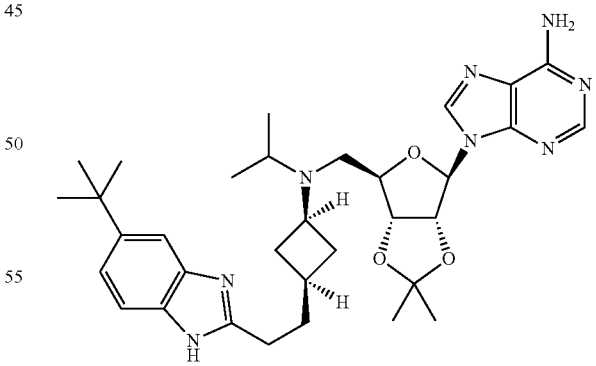

A solution of N-(2-amino-4-(tert-butyl)phenyl)-3-((1S, 3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanamide (110 mg) in AcOH (10 ml) was heated to 65° C. overnight. The mixture was concentrated, saturated NaHCO$_3$ solution (20 ml) was added and the mixture extracted with DCM (20 ml×3). The combined organic layers were dried over Na$_2$SO$_4$ and concentrated to give the title compound (105 mg crude). $^1$H NMR (500 MHz, CDCl$_3$): δ$_H$ 8.36 (s, 1H), 7.89 (s, 1H), 7.48-7.24 (m, 3H), 6.01 (d, J=1.5 Hz, 1H), 5.60-5.53 (m, 3H), 4.98 (dd, J=3.0, 6.5 Hz, 1H), 4.22 (brs, 1H), 2.97 (brs, 1H), 2.874-2.847 (m, 1H), 2.56-2.50 (m, 3H), 1.87-1.78 (m, 2H), 1.70-1.54 (m, 7H), 1.35-1.17 (m, 14H), 0.90 (d, J=6.5 Hz, 3H), 0.80 (d, J=6.5 Hz, 3H) ppm; ESI-MS (m/z): 603.5[M+1]$^+$.

Step 9: Synthesis of Compound 2

A solution of 9-((3aR,4R,6R,6aR)-6-(((((1r,3S)-3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine (105 mg) in HCl/MeOH (2.5 mol/L) (10 mL) was stirred at RT for 2 h, then concentrated to dryness. K$_2$CO$_3$ (96 mg) in water (0.5 mL) and MeOH (5 mL) were added and the resulting mixture was stirred for another 10 min at RT and then filtered. The filtrate was concentrated and the residue was purified by preparative-HPLC (xbridge 30 mm*150 mm, Mobile phase: A: water (10 mM NH4HCO3) B: CAN, Gradient: 35-45% B in 10 min, 45-45% B in 6 min, stop at 20 min, Flow rate: 50 ml/min) to give Compound 2 (50 mg, yield: 51%) as a white solid. $^1$HNMR (500 MHz, MeOD): δ$_H$ 8.29 (s, 1H), 8.20 (s, 1H), 7.47-7.39 (m, 3H), 5.96 (d, J=4.0 Hz, 1H), 4.70-4.75 (m, 1H), 4.26-4.27 (m, 1H), 4.05-4.06 (m, 1H), 3.140-3.155 (m, 1H), 3.00-2.76 (m, 5H), 2.18-2.16 (m, 2H), 1.87-1.85 (m, 2H), 1.57-1.55 (m, 2H), 1.36 (s, 9H), 1.01 (d, J=6.5 Hz, 3H), 0.94 (d, J=6.5 Hz, 3H) ppm; ESI-MS (m/z): 563.4 [M+1]$^+$.

Example 3

Synthesis of (2R,3R,4S,5R)-2-(6-amino-9H-purin-9-yl)-5-(((((1s,3R)-3-(2-(5-(tert-butyl)-1H-benzo[d]imidazol-2-yl)ethyl)cyclobutyl)(isopropyl)amino)methyl)tetrahydrofuran-3,4-diol (Compound 3)

Step 1: Synthesis of (1R,30-methyl 3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutanecarboxylate

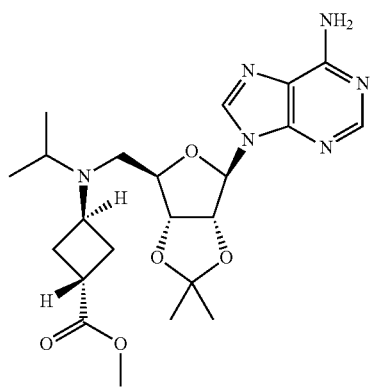 [SMILES: COC(=O)[C@H]1C[C@H](N(C[C@H]2O[C@@H](n3cnc4c(N)ncnc43)[C@@H]3OC(C)(C)O[C@@H]32)C(C)C)C1]

To a solution of (1R,30-methyl 3-(((((3aR,4R,6R,6aR)-6-(6-amino-9H-purin-9-yl)-2,2-dimethyltetrahydrofuro[3,4-d][1,3]dioxol-4-yl)methyl)amino)cyclobutanecarboxylate (1.7 g, 4.07 mmol) in CH$_3$CN (15 ml) was added 2-iodopropane (3.5 g, 20.3 mmol) and K$_2$CO$_3$ (0.84 g, 6.10 mmol). The reaction was heated to 95° C. overnight in a sealed tube. The mixture was filtered and the filtrate was and concentrated and purified by SGC (DCM:MeOH=12:1) to obtain title compound (1.35 g, Yield 72%). $^1$H NMR (500 MHz, CDCl$_3$): δ$_H$ 8.36 (s, 1H), 7.88 (s, 1H), 6.03 (d, J=2.0 Hz, 1H), 5.55 (m, 2H), 5.49 (dd, J=1.5, 6.0 Hz, 1H), 5.01 (dd, J=3.5, 6.0 Hz, 1H), 4.254-4.247 (m, 1H), 3.68 (s, 3H), 3.60-3.50 (m, 1H), 2.930-2.917 (m, 1H), 2.79-2.74 (m, 2H), 2.59-2.57 (m, 1H), 2.25-2.12 (m, 4H), 1.60 (s, 3H), 1.39 (s, 3H), 1.00 (d, J=6.5 Hz, 3H), 0.83 (d, J=7.0 Hz, 3H) ppm; ESI-MS (m/z): 461.3 [M+1]$^+$.

Step 2: Synthesis of (1R,3r)-3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutanecarbaldehyde

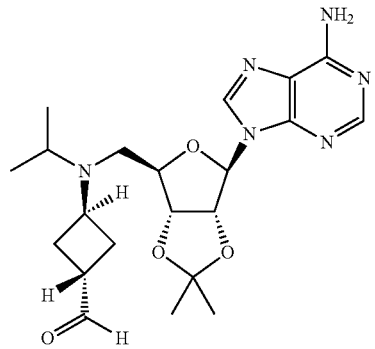 [SMILES: CC(C)N(C[C@H]1O[C@@H](n2cnc3c(N)ncnc32)[C@@H]2OC(C)(C)O[C@@H]21)[C@H]1C[C@H](C=O)C1]

To a solution of (1R,3r)-methyl 3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutanecarboxylate (1.35 g, 2.93 mmol) in DCM (50 ml) at −78° C. was added DiBAL-H dropwise until the starting material was completely consumed as determined by TLC. MeOH (2 ml) was added and the mixture was stirred at room temperature (RT) for 30 min. Water (50 ml) was added and the mixture was extracted with DCM (50 ml×2). The combined organic layers were dried over Na$_2$SO$_4$ and concentrated to obtain crude title compound (1.1 g) which was used directly in the next step. $^1$H NMR (500 MHz, CDCl$_3$): δ$_H$ 9.80 (s, 1H), 8.35 (s, 1H), 7.88 (s, 1H), 6.04 (s, 1H), 5.56 (s, 2H), 5.50 (d, J=6.5 Hz, 1H), 5.028-5.026 (m, 1H), 4.26 (brs, 1H), 3.33-3.30 (m, 1H), 2.956-2.930 (m, 1H), 2.80-2.55 (m, 3H), 2.27-2.07 (m, 4H), 1.60 (s, 3H), 1.39 (s, 3H), 1.00 (d, J=7.0 Hz, 3H), 0.82 (d, J=6.5 Hz, 3H) ppm.

Step 3: Synthesis of (E)-ethyl 3-((1R,3r)-3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)acrylate

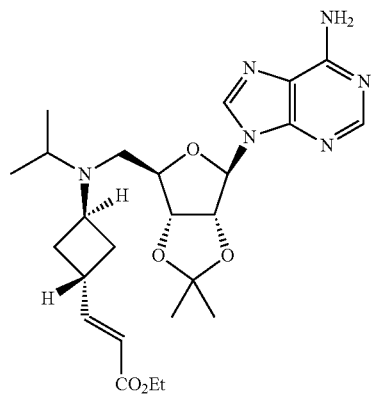 [SMILES: CCOC(=O)/C=C/[C@H]1C[C@H](N(C[C@H]2O[C@@H](n3cnc4c(N)ncnc43)[C@@H]3OC(C)(C)O[C@@H]32)C(C)C)C1]

To a solution of (1R,3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutanecarbaldehyde (1.1 g, 2.56 mmol) in CH₃CN:DCM=5:1 (50 ml) was added ethyl 2-(diethoxyphosphoryl)acetate (573 mg, 2.56 mmol), DBU (389 mg, 2.56 mmol) and LiCl (107 mg, 2.56 mmol). The mixture was stirred at RT for 1 h and concentrated, upon which water (20 ml) was added and the mixture was extracted with DCM (25 ml×3). The combined organic layers were dried over Na₂SO₄ and concentrated. The residue was purified by SGC (DCM:MeOH=30:1) to obtain the title compound (1.0 g, Yield 78%). ¹H NMR (500 MHz, CDCl₃): $\delta_H$ 8.35 (s, 1H), 7.89 (s, 1H), 7.16-7.11 (m, 1H), 6.03 (d, J=2.0 Hz, 1H), 5.79-5.76 (m, 1H), 5.56 (s, 2H), 5.51 (dd, J=1.5, 6.0 Hz, 1H), 5.02 (dd, J=3.0, 6.0 Hz, 1H), 4.25 (d, J=8.0 Hz, 1H), 4.22-4.17 (m, 2H), 3.44 (brs, 1H), 2.93 (brs, 1H), 2.78-2.56 (m, 3H), 2.27-2.16 (m, 2H), 1.93-1.91 (m, 2H), 1.60 (s, 3H), 1.40 (s, 3H), 1.31-1.27 (m, 3H), 0.98 (d, J=6.5 Hz, 3H), 0.82 (d, J=6.5 Hz, 3H) ppm; ESI-MS (m/z): 501.4[M+1]⁺.

Step 4: Synthesis of ethyl 3-((1R,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoate

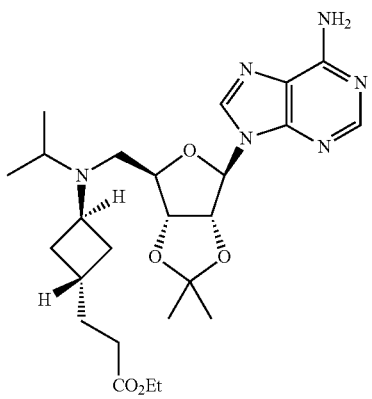 [SMILES: CCOC(=O)CC[C@H]1C[C@H](N(C[C@H]2O[C@@H](n3cnc4c(N)ncnc43)[C@@H]3OC(C)(C)O[C@@H]32)C(C)C)C1]

To a mixture of (E)-ethyl 3-((1R,3r)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)acrylate (1.0 g, 2.0 mmol) and 10% Pd/C (30 mg) in MeOH (50 ml) was added Pd/C (30 mg). The mixture was stirred at RT overnight under a hydrogen atmosphere. The resulting mixture was filtered and the filtrate was concentrated to obtain the title compound (1.0 g, Yield 100%). ¹H NMR (500 MHz, CDCl₃): $\delta_H$ 8.36 (s, 1H), 7.89 (s, 1H), 6.03 (d, J=2.5 Hz, 1H), 5.58 (s, 2H), 5.51 (dd, J=2.0, 6.5 Hz, 1H), 5.00 (dd, J=3.5, 6.0 Hz, 1H), 4.276-4.269 (m, 1H), 4.13-4.09 (m, 2H), 3.38-3.37 (m, 1H), 2.94-2.54 (m, 3H), 2.22-1.97 (m, 5H), 1.79-1.62 (m, 4H), 1.60 (s, 3H), 1.40 (s, 3H), 1.28-1.23 (m, 2H), 0.97 (d, J=7.0 Hz, 3H), 0.79 (d, J=7.0 Hz, 3H) ppm; ESI-MS (m/z): 503.4[M+1]⁺.

Step 5: Synthesis of 3-((1R,3 s)-3-((((3 aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoic acid

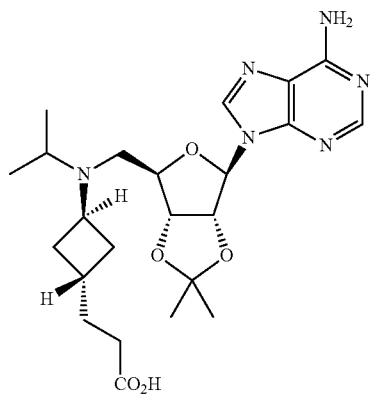 [SMILES: CC(C)N(C[C@H]1O[C@@H](n2cnc3c(N)ncnc32)[C@@H]2OC(C)(C)O[C@@H]21)[C@H]1C[C@H](CCC(=O)O)C1]

To a solution of ethyl 3-((1R,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoate (360 mg, 0.72 mmol) in THF:MeOH=5:1 (30 ml) was added LiOH.H₂O (301 mg, 7.20 mmol). The mixture was stirred at RT overnight, concentrated then dissolved in MeOH (10 ml). 1 M HCl solution was added dropwise at 0° C. until pH=7. The mixture was concentrated to give the title compound crude and was used directly in the next step.

Step 6: Synthesis of N-(2-amino-4-(tert-butyl)phenyl)-3-((1R,3s)-3-((((3 aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanamide

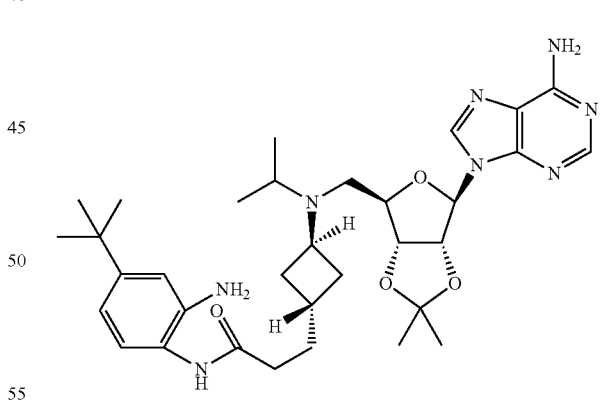

To a solution of 3-((1R,3s)-3-((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoic acid in DMF (5 ml) was added 4-(tert-butyl)benzene-1,2-diamine (235 mg, 1.43 mmol), EDCI (274 mg, 1.43 mmol), HOBT (193 mg, 1.43 mmol) and TEA (435 mg, 4.30 mmol). The mixture was heated to 45° C. overnight and concentrated. Saturated NaHCO₃ solution (20 ml) was added and the mixture was extracted with DCM (20 ml×3). The organic layers were dried over Na₂SO₄ and concentrated. The crude was purified with preparative-TLC (DCM:MeOH=12:

241

1) to afford the title compound (110 mg), which was carried forward into the next step without further purification.

Step 7: Synthesis of 9-((3 aR,4R,6R,6aR)-6-(((((1s,3R)-3-(2-(5-(tert-butyl)-1H-benzo[d]imidazol-2-yl)ethyl)cyclobutyl)(isopropyl)amino)methyl)-2,2-dimethyltetrahydro furo[3,4-d][1,3]dioxol-4-yl)-9H-purin-6-amine

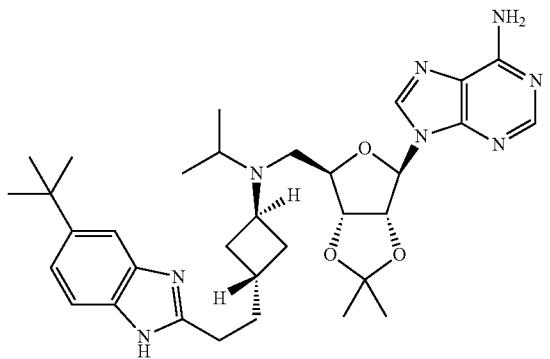 [SMILES: CC(C)N(C[C@H]1O[C@@H](n2cnc3c(N)ncnc32)[C@@H]2OC(C)(C)O[C@@H]21)[C@H]1C[C@H](CCc2nc3cc(C(C)(C)C)ccc3[nH]2)C1]

A solution of N-(2-amino-4-(tert-butyl)phenyl)-3-((1R,3s)-3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanamide (110 mg) in AcOH (15 ml) was heated at 65° C. overnight. The mixture was concentrated, saturated NaHCO₃ solution (20 ml) was added and the mixture was extracted with DCM (20 ml×3). The combined organic layers were dried over Na₂SO₄ and concentrated to give the title compound (100 mg crude). $^1$H NMR (500 MHz, CDCl₃): $\delta_H$ 8.36 (s, 1H), 7.94 (s, 1H), 7.48-7.27 (m, 3H), 6.07 (d, J=1.5 Hz, 1H), 5.64-5.58 (m, 3H), 5.02 (dd, J=3.0, 6.0 Hz, 1H), 4.30 (brs, 1H), 3.38-3.37 (m, 1H), 2.97-2.95 (m, 1H), 2.76-2.55 (m, 3H), 1.97-1.74 (m, 5H), 1.67-1.57 (m, 5H), 1.45-1.40 (m, 12H), 0.99 (d, J=6.5 Hz, 3H), 0.83 (d, J=6.5 Hz, 3H) ppm; ESI-MS (m/z): 603.5[M+1]⁺.

Step 8: Synthesis of Compound 3

A solution of 9-((3 aR,4R,6R,6aR)-6-(((((1s,3R)-3-(2-(5-(tert-butyl)-1H-benzo[d]imidazol-2-yl)ethyl)cyclobutyl)(isopropyl)amino)methyl)-2,2-dimethyltetrahydro furo[3,4-d][1,3]dioxol-4-yl)-9H-purin-6-amine (190 mg) in HCl/MeOH (2.5 mol/L) (15 mL) was stirred at RT for 2 h and concentrated to dryness. K₂CO₃ (161 mg) in water (0.5 mL) and MeOH (5 mL) were added. The resulting mixture was stirred for another 10 min at RT then filtered. The filtrate was concentrated and the residue was purified by preparative HPLC (xbridge 30 mm*150 mm, Mobile phase: A: water (10 mM NH4HCO3) B: CAN, Gradient: 35-45% B in 10 min, 45-45% B in 6 min, stop at 20 min, Flow rate: 50 ml/min) to give Compound 3 (65 mg, yield: 70%) as a white solid. $^1$HNMR (500 MHz, MeOD): $\delta_H$ 8.29 (s, 1H), 8.19 (s, 1H), 7.47-7.28 (m, 3H), 5.95 (d, J=4.5 Hz, 1H), 4.744-4.724 (m, 1H), 4.27-4.26 (m, 1H), 4.07-4.06 (m, 1H), 3.56 (brs, 1H), 3.01-2.78 (m, 5H), 2.17 (brs, 2H), 2.00-1.93 (m, 2H), 1.80-1.79 (m, 2H), 1.36 (s, 9H), 1.02 (d, J=5.5 Hz, 3H), 0.95 (d, J=6.0 Hz, 3H) ppm; ESI-MS (m/z): 563.5 [M+1]⁺.

Example 4

Synthesis of (2R,3R,4S,5R)-2-(6-amino-9H-purin-9-yl)-5-(((((1s,3R)-3-(2-(5-chloro-6-(trifluoromethyl)-1H-benzo[d]imidazol-2-yl)ethyl)cyclobutyl)(isopropyl)amino)methyl)tetrahydrofuran-3,4-diol (Compound 4)

Step 1: Synthesis of N-(2-amino-4-chloro-5-(trifluoromethyl)phenyl)-3-((1R,3s)-3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanamide

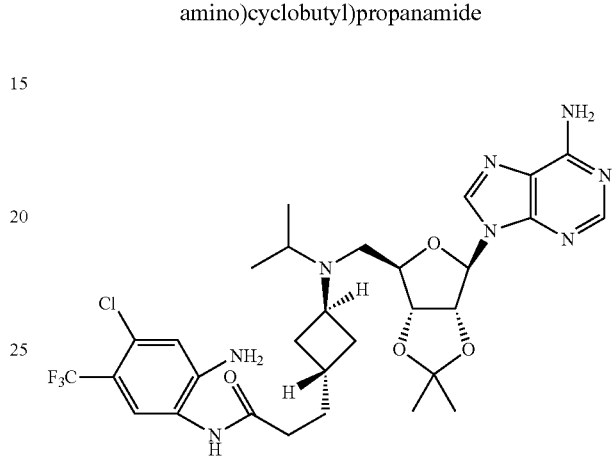

To a solution of 3-((1R,3s)-3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoic acid (250 mg, 0.53 mmol) in DCM (30 ml) was added 4-chloro-5-(trifluoromethyl)benzene-1,2-diamine (221 mg, 1.05 mmol), EDCI (201 mg, 1.05 mmol), HOBT (142 mg, 1.05 mmol) and TEA (320 mg, 3.15 mmol). The mixture was stirred at RT overnight, upon which saturated NaHCO₃ solution (20 ml) was added and the mixture was extracted with DCM (20 ml×3). The combined organic layers were dried over Na₂SO₄, filtered and concentrated. The crude was purified via preparative-TLC (DCM:MeOH=12:1) to afford the title compound (250 mg crude).

Step 2: Synthesis of 9-((3aR,4R,6R,6aR)-6-(((((1s,3R)-3-(2-(5-chloro-6-(trifluoromethyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine

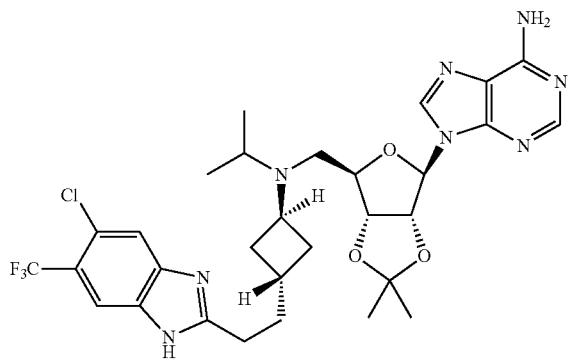 [SMILES: CC(C)N(C[C@H]1O[C@@H](n2cnc3c(N)ncnc32)[C@@H]2OC(C)(C)O[C@@H]21)[C@H]1C[C@H](CCc2nc3cc(Cl)c(C(F)(F)F)cc3[nH]2)C1]

A solution of N-(2-amino-4-chloro-5-(trifluoromethyl)phenyl)-3-((1R,3s)-3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanamide (250 mg) in AcOH (15 ml) was heated to 65° C. overnight. The mixture was concentrated, saturated NaHCO₃ solution (20 ml) was added and the mixture was extracted with DCM (20 ml×3). The combined organic layers were dried over Na₂SO₄ and concentrated to give the title compound (200 mg crude).

Step 3: Synthesis of Compound 4

A solution of 9-((3aR,4R,6R,6aR)-6-(((((1s,3R)-3-(2-(5-chloro-6-(trifluoromethyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine (200 mg) in HCl/MeOH (2.5 mol/L) (15 mL) was stirred at RT for 2 h upon which it was concentrated to dryness. K₂CO₃ (166 mg) in water (0.5 mL) and MeOH (5 mL) were added and the resulting mixture was stirred for another 10 min at RT. The mixture was filtered and the filtrate was concentrated. The residue was purified by preparative-HPLC to give Compound 4 (80 mg, yield: 43%) as a white solid. ¹HNMR (500 MHz, MeOD): δ$_H$ 8.29 (s, 1H), 8.19 (s, 1H), 7.88 (s, 1H), 7.68 (s, 1H), 5.96 (d, J=4.0 Hz, 1H), 4.748-4.730 (m, 1H), 4.284-4.263 (m, 1H), 4.09 (br s, 1H), 3.65-3.50 (m, 1H), 3.03-2.85 (m, 5H), 2.191-2.176 (m, 2H), 2.03-2.00 (m, 2H), 1.80 (brs, 2H), 1.02 (d, J=6.0 Hz, 3H), 0.96 (d, J=6.6 Hz, 3H) ppm; ESI-MS (m/z): 609.2 [M+1]⁺.

Example 5

Synthesis of (2R,3R,4S,5R)-2-(6-amino-9H-purin-9-yl)-5-(((((1r,3S)-3-(2-(5-chloro-6-(trifluoromethyl)-1H-benzo[d]imidazol-2-yl)ethyl)cyclobutyl)(isopropyl)amino)methyl)tetrahydrofuran-3,4-diol (Compound 5)

Step 1: Synthesis of N-(2-amino-4-chloro-5-(trifluoromethyl)phenyl)-3-((1S,3r)-3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanamide

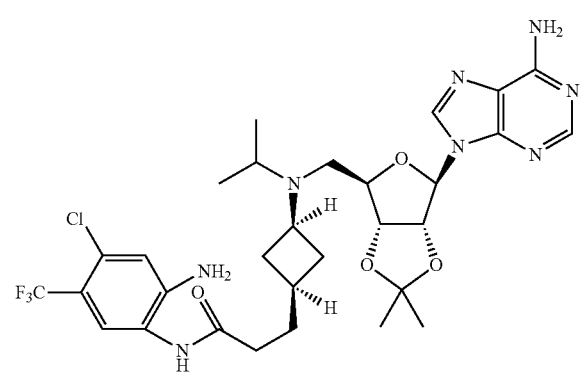 [SMILES: CC(C)N(C[C@H]1O[C@@H](n2cnc3c(N)ncnc32)[C@@H]2OC(C)(C)O[C@@H]21)[C@H]1C[C@@H](CCC(=O)Nc2cc(C(F)(F)F)c(Cl)cc2N)C1]

To a solution of 3-((1S,3r)-3-(((((3aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanoic acid in DCM:DMF=15:1 (30 ml) was added 4-chloro-5-(trifluoromethyl)benzene-1,2-diamine (334 mg, 1.60 mmol), EDCI (304 mg, 1.60 mmol), HOBT (215 mg, 1.60 mmol) and TEA (483 mg, 4.80 mmol). The mixture was stirred overnight at RT. The mixture was concentrated, saturated NaHCO₃ solution (20 ml) was added and the resultant mixture was extracted with DCM (20 ml×3). The combined organic layers were dried over Na₂SO₄ and concentrated. The crude residue was purified via preparative TLC (DCM:MeOH=12:1) to afford the title compound (220 mg).

Step 2: Synthesis of 9-((3aR,4R,6R,6aR)-6-(((((1r,3S)-3-(2-(5-chloro-6-(trifluoromethyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine

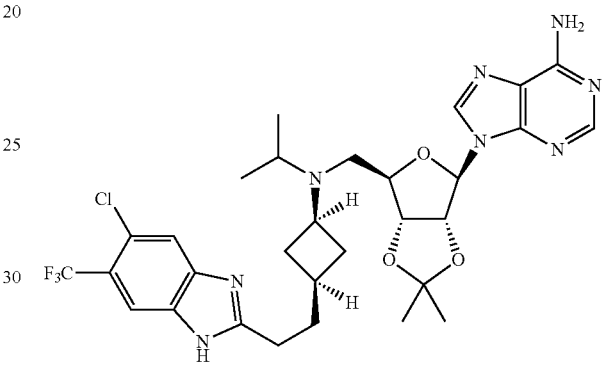

A solution of N-(2-amino-4-chloro-5-(trifluoromethyl)phenyl)-3-((1S,3r)-3-(((((3 aR,4R,6R,6aR)-6-(6-amino-9H-purin-9-yl)-2,2-dimethyltetrahydrofuro[3,4-d][1,3]dioxol-4-yl)methyl)(isopropyl)amino)cyclobutyl)propanamide (220 mg) in AcOH (15 ml) was heated at 65° C. overnight. The mixture was concentrated, saturated NaHCO₃ solution (20 ml) was added, and the mixture was extracted with DCM (20 ml×3). The combined organic layers were dried over Na₂SO₄ and concentrated to give the title compound (190 mg).

Step 3: Synthesis of Compound 5

A solution of 9-((3aR,4R,6R,6aR)-6-(((((1r,3S)-3-(2-(5-chloro-6-(trifluoromethyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine (190 mg) in HCl/MeOH (2.5 mol/L) (15 mL) was stirred at RT for 2 h then it was concentrated to dryness. K₂CO₃ (161 mg) in water (0.5 mL) and MeOH (5 mL) were added and the resulting mixture was stirred for another 10 min at RT. The mixture was filtered and the filtrate was concentrated. The residue was purified by preparative-HPLC to give Compound 5 (90 mg, yield: 51%) as a white solid. ¹HNMR (500 MHz, MeOD): δ$_H$ 8.29 (s, 1H), 8.19 (s, 1H), 7.88 (s, 1H), 7.67 (s, 1H), 5.95 (d, J=5.0 Hz, 1H), 4.736-4.716 (m, 1H), 4.268-4.246 (m, 1H), 4.070-4.051 (m, 1H), 3.15 (brs, 1H), 3.00-2.71 (m, 5H), 2.17 (brs, 2H), 1.93-1.88 (m, 2H), 1.58-1.56 (m, 2H), 1.01 (d, J=5.5 Hz, 3H), 0.95 (d, J=6.0 Hz, 3H) ppm; ESI-MS (m/z): 609.2 [M+1]$^+$.

Example 6

Synthesis of (2R,3R,4S,5R)-2-(4-amino-7H-pyrrolo[2,3-d]pyrimidin-7-yl)-5-(((3-((5-(tert-butyl)-1H-benzo[d]imidazol-2-yl)methyl)cyclobutyl)(methyl)amino)methyl)tetrahydrofuran-3,4-diol (Compound 6)

Step 1: Synthesis of 7-((3aR,4R,6R,6aR)-6-(azidomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine

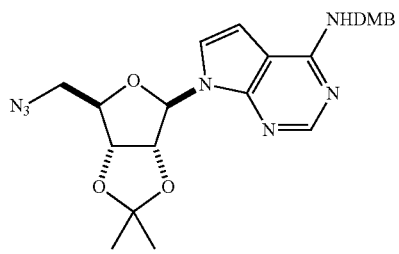

A solution of ((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methanol (2.83 g, 6.20 mmol) and triphenylphosphine (2.28 g, 8.68 mmol) in dry tetrahydrofuran (32 mL) was cooled at 0° C. in an ice/water bath. Diisopropyl azodicarboxylate (1.71 mL, 8.68 mmol) was added dropwise, followed by a solution of diphenylphosphonic azide (1.87 mL, 8.68 mmol) in tetrahydrofuran (5.3 mL, 66 mmol). Upon addition of the DPPA solution, a white milky precipitate formed. After about 30 minutes, the reaction mixture was allowed to warm to room temperature and stir overnight. After 24 h, HPLC indicated that all the starting material had been consumed. The reaction mixture was concentrated to about ½ the original volume and purified by flash chromatography (175 g silica gel, 10-55% EA/hept) to yield the title compound (2.49 g, 83%) as a slightly yellow stiff foam: MS (ESI+) for $C_{23}H_{27}N_7O_5$ m/z 482.2 (M+H)$^+$; (ESI−) for $C_{23}H_{27}N_7O_5$ m/z 480.1 (M+H)$^-$, m/z 526.1 (M+CO$_2$H)$^-$; HPLC purity 97%.

Step 2: Synthesis of 7-((3aR,4R,6R,6aR)-6-(aminomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine

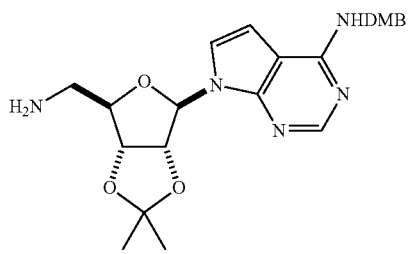

A solution of ((3aR,4R,6R,6aR)-6-(azidomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (2.49 g, 5.17 mmol) in tetrahydrofuran (50 mL, 600 mmol) was treated dropwise with a solution of 1.0 M of trimethylphosphine in tetrahydrofuran (7.24 mL, 7.24 mmol) and the mixture was stirred for 20 h. The reaction mixture was treated with water (1.80 mL, 99.9 mmol) and stirred at RT for 2 h. The reaction mixture was concentrated, the crude product was taken up in 90 mL CH$_2$Cl$_2$ and washed with four 30 mL portions of H$_2$O and 15 mL brine. The solution was dried over Na$_2$SO$_4$, filtered and concentrated. The crude material was purified by flash chromatography (120 g silica gel, 3-10% 7N NH$_3$ in CH$_3$OH/CH$_2$Cl$_2$) to yield the title compound (1.76 g, 75%) as a foam: MS (ESI+) for $C_{23}H_{29}N_5O_5$ m/z 456.2 (M+H)$^+$; (ESI−) for $C_{26}H_{35}N_5O_5$ m/z 454.1 (M−H)$^-$; HPLC purity 92% (ret. time, 2.65 min).

Step 3: Synthesis of methyl 2-(3-(((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)amino)cyclobutyl)acetate

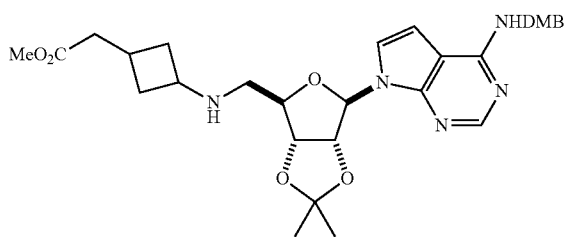

A solution 7-((3aR,4R,6R,6aR)-6-(aminomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (400 mg, 0.88 mmol) and methyl 2-(3-oxocyclobutyl)acetate (100 mg, 0.70 mmol) [prepared using the procedure found in US Patent Application Publication 2009/0118287] in 1,2-dichloroethane (12 mL) was treated dropwise with acetic acid (50 uL, 0.88 mmol). The solution was treated with sodium triacetoxyborohydride (260 mg, 1.2 mmol) in one portion and allowed to stir at room temperature until complete by HPLC. After 4 h, HPLC indicated the reaction was about 80% complete. An additional 20 mg of ketone was added and stirring was continued for 2.5 h. The reaction mixture was diluted with 30 mL CH$_2$Cl$_2$ and washed with 15 mL sat NaHCO$_3$. The aqueous phase was washed with 15 mL CH$_2$Cl$_2$ and the combined organic phase was dried over Na$_2$SO$_4$. The organic phase was filtered and concentrated to yield a light yellow glass that was purified by flash chromatography (70 g silica gel; 2% 7N NH$_3$ in CH$_3$OH/CH$_2$Cl$_2$) to yield the title compound (270 mg, 66%) as a colorless glass: MS (ESI+) for $C_{30}H_{39}N_5O_7$ m/z 582.2 (M+H)$^+$; HPLC purity >95% (ret. time, 2.88 min).

Step 4: Synthesis of methyl 2-(3-((((3aR,4R,6R, 6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(methyl)amino) cyclobutyl)acetate

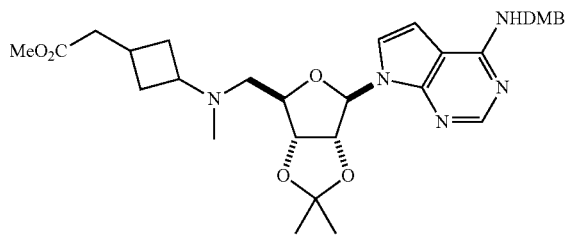

A solution of methyl 2-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)amino)cyclobutyl)acetate (267 mg, 0.459 mmol) in methanol (12 mL) was treated with sodium cyanoborohydride (380 mg, 6.1 mmol). The pH of the solution was adjusted to ~6 by the dropwise addition of a 10% (v/v) solution of glacial acetic acid in methanol. The mixture was treated with 37% formaldehyde (0.57 mL, 7.6 mmol) dropwise and the mixture was stirred at room temperature for 1 h at which time, HPLC indicated the starting material was consumed. The reaction mixture was concentrated to remove the methanol. The aqueous solution that remained was diluted with 25 mL NaHCO$_3$ and the aqueous phase was extracted with three 20 mL portions of CH$_2$Cl$_2$. The organic phase was washed with 20 mL sat NaHCO$_3$, dried over Na$_2$SO$_4$, filtered and concentrated to yield the title compound (272 mg, 100%) as a colorless stiff foam which was found to be of sufficient purity for use in the next step: MS (ESI+) for C$_{31}$H$_{41}$N$_5$O$_7$ m/z 596.5 (M+H)$^+$; HPLC purity >95% (ret. time, 2.89 min).

Step 5: Synthesis of 2-(3-(((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(methyl)amino)cyclobutyl) acetic acid

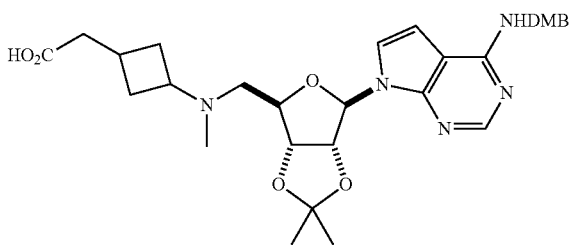

A solution of methyl 2-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(methyl)amino)cyclobutyl)acetate (270 mg, 0.453 mmol) in methanol (8.6 mL) was treated dropwise with a solution of sodium hydroxide (36 mg, 0.91 mmol) in water (0.9 mL, 50 mmol) and the mixture was heated at 50° C. After 17 h, HPLC indicated the reaction was complete. The reaction mixture was cooled to room temperature and treated with 0.91 mL 1.0N HCl to adjust the pH to ~7. The solution was concentrated to remove the methanol and the resulting aqueous suspension was lyophilized to yield a white solid. The material was used as is in the next step, assuming a quantitative recovery: MS (ESI+) for C$_{30}$H$_{39}$N$_5$O$_7$ m/z 582.4 (M+H)$^+$; MS (ESI−) for C$_{30}$H$_{39}$N$_5$O$_7$ m/z 580.4 (M−H)$^-$; HPLC purity >95% (ret. time, 2.72 min).

Step 6: Synthesis of N-(2-amino-4-(tert-butyl)phenyl)-2-(3-((((3aR,4R,6R,6aR)-6-(4-((2,4-dimethoxybenzyl)amino)-7H-pyrrolo[2,3-d]pyrimidin-7-yl)-2, 2-dimethyltetrahydrofuro[3,4-d][1,3]dioxol-4-yl) methyl)(methyl)amino)cyclobutyl)acetamide

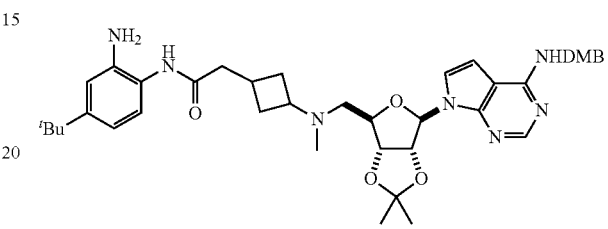

A solution of 2-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(methyl)amino)cyclobutyl)acetic acid and 4-tert-butylbenzene-1,2-diamine (89.4 mg, 0.545 mmol) in N,N-dimethylformamide (4.5 mL) was treated with N,N-diisopropylethylamine (0.261 mL, 1.50 mmol) dropwise followed by N,N,N',N'-tetramethyl-O-(7-azabenzotriazol-1-yl)uronium hexafluorophosphate (259 mg, 0.681 mmol). The solution was allowed to stir at room temperature for 18 h during which time LCMS indicated the starting material had been consumed. The reaction mixture was concentrated under high vac. The residue was taken up in 30 mL ethyl acetate and 20 mL 1/1 H$_2$O/sat NaHCO$_3$ solution. The mixture was extracted and the aqueous phase was washed with 35 mL ethyl acetate. The combined organic phase was washed with two 20 mL portions of H$_2$O, and 20 mL brine. The organic phase was dried over Na$_2$SO$_4$, filtered and concentrated to yield a tannish brown glass/stiff foam. The crude material was purified by flash chromatography (35 g silica gel; 4% 7N NH$_3$ in CH$_3$OH/CH$_2$Cl$_2$) to yield the title compound (272 mg, 82%) as a light tan glass/stiff foam which was a mixture of regioisomeric amides: MS (ESI+) for C$_{41}$H$_{53}$N$_7$O$_6$ m/z 728.8 (M+H)$^+$; MS (ESI−) for C$_{41}$H$_{53}$N$_7$O$_6$ m/z 726.9 (M−H)$^-$; HPLC purity >95%, (ret. time, 3.14, 3.17 min) two peaks observed due to amide regioisomers.

Step 7: Synthesis of 7-((3aR,4R,6R,6aR)-6-(((3-((5-(tert-butyl)-1H-benzo[d]imidazol-2-yl)methyl)cyclobutyl)(methyl)amino)methyl)-2,2-dimethyltetrahydrofuro[3,4-d][1,3]dioxol-4-yl)-N-(2,4-dimethoxybenzyl)-7H-pyrrolo[2,3-d]pyrimidin-4-amine

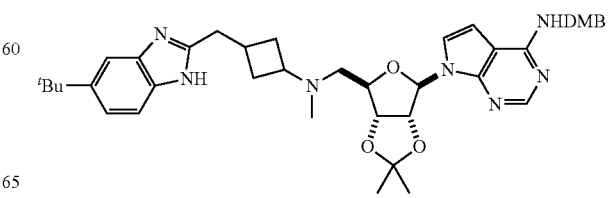

N-(2-amino-4-(tert-butyl)phenyl)-2-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(methyl)amino)cyclobutyl)acetamide (272 mg, 0.374 mmol) was taken up in acetic acid (7.2 mL) and the solution was heated at 65° C. After 1.5 h, HPLC indicated the reaction was complete. The reaction was cooled to room temperature and the solvent removed under high vac. The residue was taken up in 35 mL CH$_2$Cl$_2$ and the organic phase was washed with 25 mL sat NaHCO$_3$ solution and 20 mL 2% Na$_2$CO$_3$ solution. The organic phase was dried over Na$_2$SO$_4$, filtered and concentrated to yield a light tan glass/stiff foam. The crude material was purified by flash chromatography (30 g silica gel; 4% 7N NH$_3$ in CH$_3$OH/CH$_2$Cl$_2$) to yield the title compound (224 mg, 84%) as a light tan glass which was a mixture of cis and trans diastereomers about the cyclobutyl ring: MS (ESI+) for C$_{40}$H$_{51}$N$_7$O$_5$ m/z 710.6 (M+H)$^+$; MS (ESI−) for C$_{41}$H$_{51}$N$_7$O$_5$ m/z 708.7 (M−H)$^-$; HPLC purity >95% (ret. time, 3.29, 3.33 min), two peaks observed due to diastereomers about the cyclobutyl ring.

Step 8: Synthesis of Compound 6

7-((3aR,4R,6R,6aR)-6-(((3-((5-(tert-butyl)-1H-benzo[d]imidazol-2-yl)methyl)cyclobutyl)(methyl)amino)methyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (170 mg, 0.24 mmol) was dissolved in a mixture of trifluoroacetic acid (5.0 mL) and water (0.5 mL) which had been precooled at 0° C. in an ice bath. The solution was stirred at 0° C. for 30 minutes, and warmed to room temperature. After 5 h at room temperature, the now very pink reaction mixture was concentrated. The residue was taken up in 10 mL MeOH and concentrated. This procedure was repeated twice and the residue placed on high vac for 1 h. The material was taken up in 7 mL MeOH and was treated with 130 mg K$_2$CO$_3$ and five drops of water. The mixture was allowed to stir for 1 hr, during which time the solution was found to be basic. The mixture was filtered through a fine frit, the solids were washed with 10 mL MeOH and the filtrate was concentrated to yield a nearly colorless solid. The crude material was purified by flash chromatography (30 g silica gel; 12% 7N NH$_3$ in CH$_3$OH/CH$_2$Cl$_2$) to yield Compound 6 (81 mg, 65%) as a colorless glass/stiff foam: MS (ESI+) for C$_{28}$H$_{37}$N$_7$O$_3$ m/z 520.4 (M+H)$^+$; MS (ESI−) for C$_{28}$H$_{37}$N$_7$O$_3$ m/z 518.5 (M−H)$^-$; HPLC purity >95% (ret. time, 2.51 min); $^1$H NMR (400 MHz, d4-MeOH) $\delta_H$ ppm 8.08 (s, 1H), 7.48 (br. s., 1H), 7.39 (d, J=8.50 Hz, 1H), 7.29 (dd, J=8.40, 4.87 Hz, 1H), 6.63 (m, 1H), 6.12 (d, J=4.15 Hz, 1H), 4.40 (m, 1H), 4.09 (m, 2H), 3.15 (m, 0.5H), 3.02 (d, J=8.09 Hz, 1H), 2.92 (d, J=7.26 Hz, 1H), 2.84 (m, 0.5H), 2.65 (m, 2H), 2.43 (m, 1H), 2.29 (m, 1H), 2.20 (d, J=5.80 Hz, 3H), 2.13 (m, 1H), 1.99 (br. s., 1H), 1.67 (m, 1H), 1.37 (d, J=3.94 Hz, 9H), 1.30 (dd, J=13.99, 4.66 Hz, 1H).

Example 7

Synthesis of (1R,2S,3R,5R)-3-(4-amino-7H-pyrrolo[2,3-d]pyrimidin-7-yl)-5-(((3-(2-(6-chloro-5-(trifluoromethyl)-1H-benzo[d]imidazol-2-yl)ethyl)cyclobutyl)(methyl)amino)methyl)cyclopentane-1,2-diol (Compound 7)

Step 1: Synthesis of 4,6-dichloro-5-(2,2-diethoxyethyl)pyrimidine

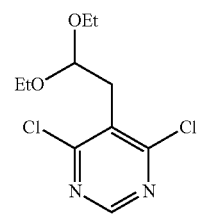 [SMILES: CCOC(Cc1c(Cl)ncnc1Cl)OCC]

Title compound was prepared by the method of Montgomery, see: Montgomery, J. A.; Hewson, K. *J. Med. Chem.* 10, 665 (1967).

Step 2: Synthesis of (1R,2S,3R,5R)-3-((6-chloro-5-(2,2-diethoxyethyl)pyrimidin-4-yl)amino)-5-(hydroxymethyl)cyclopentane-1,2-diol

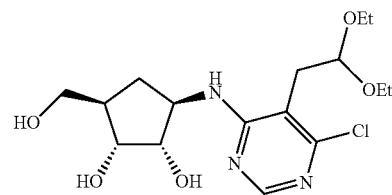 [SMILES: CCOC(Cc1c(Cl)ncnc1N[C@@H]1C[C@H](CO)[C@@H](O)[C@H]1O)OCC]

A mixture of 4,6-dichloro-5-(2,2-diethoxyethyl)pyrimidine (5.35 g, 20.2 mmol) and (1R,2S,3R,4R)-2,3-dihydroxy-4-(hydroxymethyl)cyclopentanaminium chloride (9.29 g, 24.3 mmol) was taken up in ethanol (236 mL), treated with Et$_3$N (11.2 mL, 80.8 mmol) and heated at reflux for 23 h; HPLC/LC MS indicated consumption of starting materials and presence of product. The reaction mixture was concentrated to afford a tan slurry, which was carried on crude: MS (ESI+) for C$_{16}$H$_{26}$ClN$_3$O$_5$ m/z 376.2 (M+H)$^+$; MS (ESI−) for C$_{16}$H$_{26}$ClN$_3$O$_5$ m/z 374.2 (M−H)$^-$; HPLC purity >95% (ret. time, 2.436 min). Variation on route from J. Med. Chem. 10, 665 (1967).

Step 3: Synthesis of (1R,2S,3R,5R)-3-(4-chloro-7H-pyrrolo[2,3-d]pyrimidin-7-yl)-5-(hydroxymethyl)cyclopentane-1,2-diol

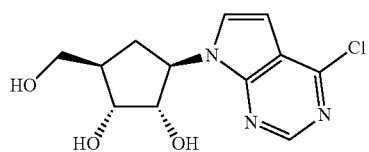 [SMILES: OC[C@H]1C[C@@H](n2ccc3c(Cl)ncnc32)[C@H](O)[C@@H]1O]

A suspension of crude (1R,2S,3R,5R)-3-((6-chloro-5-(2,2-diethoxyethyl)pyrimidin-4-yl)amino)-5-(hydroxymethyl)cyclopentane-1,2-diol in 1,4-dioxane (160 mL) was treated with a 1 M aqueous solution of HCl (30 in L, 30 mmol) and stirred at RT for 69.5 h; HPLC indicated clean conversion to one product, LC MS showed mass for desired product. The reaction mixture was neutralized with concentrated aqueous NH₄OH (to pH 7) and the volatiles were removed in vacuo to afford a brown slurry, which was carried on without further purification: MS (ESI+) for $C_{12}H_{14}ClN_3O_3$ m/z 284.1 $(M+H)^+$; MS (ESI−) for $C_{12}H_{14}ClN_3O_3$ m/z 282.2 $(M-H)^−$, 328.2 $(M+HCO_2)^−$; HPLC purity >95% (ret. time, 1.947 min). Variation on route from J. Med. Chem. 10, 665 (1967).

Step 4: Synthesis of ((3aR,4R,6R,6aS)-6-(4-chloro-7H-pyrrolo[2,3-c]pyrimidin-7-yl)-2,2-dimethyltetrahydro-3aH-cyclopenta[d][1,3]dioxol-4-yl)methanol

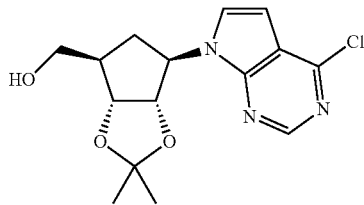 [SMILES: CC1(C)O[C@@H]2[C@@H](CO)C[C@@H](n3ccc4c(Cl)ncnc43)[C@@H]2O1]

A mixture of crude (1R,2S,3R,5R)-3-(4-chloro-7H-pyrrolo[2,3-c]pyrimidin-7-yl)-5-(hydroxymethyl)cyclopentane-1,2-diol (10 g, ~20 mmol, 54% pure by NMR) and 2,2-dimethoxypropane (100 mL, 800 mmol) was treated with p-toluenesulfonic acid monohydrate (7.28 g, 38.3 mmol) and the yellow-brown reaction mixture was stirred vigorously for 1.25 h, at which time the only solids were a fine tan precipitate. HPLC indicated nearly complete consumption of the starting material. The reaction mixture was diluted with water (30 mL) and neutralized with solid NaHCO₃ (4.80 g, 57.1 mmol). The volatiles were carefully removed in vacuo and the resulting brown aqueous solution was extracted with EtOAc (3×100 mL). The combined organics were dried (Na₂SO₄) and concentrated in vacuo to afford a tan paste. Purification by column chromatography (4×22 cm silica; 0-66% EtOAc/Hex) afforded the title compound (4.38 g, 70%, one step) as a colorless foam/glass: MS (ESI+) for $C_{15}H_{18}ClN_3O_3$ m/z 324.2 $(M+H)^+$; MS (ESI−) for $C_{15}H_{18}ClN_3O_3$ m/z 368.2 $(M+HCO_2)^−$; HPLC purity >95% (ret. time, 3.034 min).

Step 5: Synthesis of 7-((3aS,4R,6R,6aR)-6-(azidomethyl)-2,2-dimethyltetrahydro-3aH-cyclopenta[d][1,3]dioxol-4-yl)-4-chloro-7H-pyrrolo[2,3-d]pyrimidine

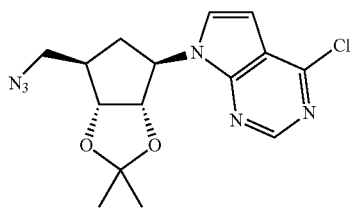 [SMILES: CC1(C)O[C@@H]2[C@@H](CN=[N+]=[N-])C[C@@H](n3ccc4c(Cl)ncnc43)[C@@H]2O1]

((3aR,4R,6R,6aS)-6-(4-chloro-7H-pyrrolo[2,3-d]pyrimidin-7-yl)-2,2-dimethyltetrahydro-3aH-cyclopenta[d][1,3]di-oxol-4-yl)methanol (2.68 g, 8.28 mmol) was dissolved in THF (32 mL), treated with PPh₃ (3.05 g, 11.6 mmol), and the reaction vessel was cooled in an ice-brine bath. Diisopropyl azodicarboxylate [DIAD] (2.3 mL, 12 mmol) was added dropwise via syringe and the mixture was stirred for 10 min. A solution of diphenylphosphonic azide [DPPA] (2.50 mL, 11.6 mmol) in THF (7.8 mL) was added dropwise via syringe to afford a off-white mixture, which was stirred for 21 h, allowing the ice bath to warm to RT; HPLC/LC MS indicated complete consumption of starting material and formation of product. At 22.5 h the reaction mixture was concentrated in vacuo and purified by column chromatography (4×22 cm silica; 0-25% EtOAc/Hex) to afford the title compound (2.27 g, 78%) as a clear, colorless oil: MS (ESI+) for $C_{15}H_{17}ClN_6O_2$ m/z 349.2 $(M+H)^+$; MS (ESI−) for $C_{15}H_{17}ClN_6O_2$ m/z 393.2 $(M+HCO_2)^−$; HPLC purity >95% (ret. time, 4.169 min).

Step 6: Synthesis of 7-((3aS,4R,6R,6aR)-6-(azidomethyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

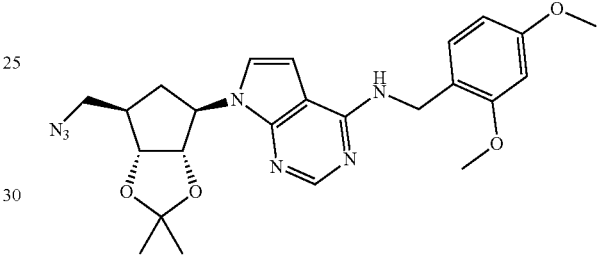

A solution of 7-((3aS,4R,6R,6aR)-6-(azidomethyl)-2,2-dimethyltetrahydro-3aH-cyclopenta[d][1,3]dioxol-4-yl)-4-chloro-7H-pyrrolo[2,3-d]pyrimidine and 2,4-dimethoxybenzylamine (1.2 mL, 7.8 mmol) in 1-butanol (18.6 mL) was treated with N,N-diisopropylethylamine (1.4 mL, 7.8 mmol) and heated at 80° C. for 22 h; HPLC/LC MS indicated ~90% conversion to the desired product. The volatiles were removed and the yellow-brown paste was taken up in CH₂Cl₂ (90 mL) and washed with water (2×30 mL) and brine (1×45 mL). The separated organic layer was dried (Na₂SO₄) and concentrated in vacuo to afford an orange oil. Purification by column chromatography (2×22 cm silica; 0-50% EtOAc/Hex) afforded the title compound (2.23 g, 72%) as a pale yellow glass/foam: MS (ESI+) for $C_{24}H_{29}N_7O_4$ m/z 480.5 $(M+H)^+$; MS (ESI−) for $C_{24}H_{29}N_7O_4$ m/z 524.3 $(M+HCO_2)^−$; HPLC purity >95% (ret. time, 3.551 min).

Step 7: Synthesis of 7-((3aS,4R,6R,6aR)-6-(aminomethyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

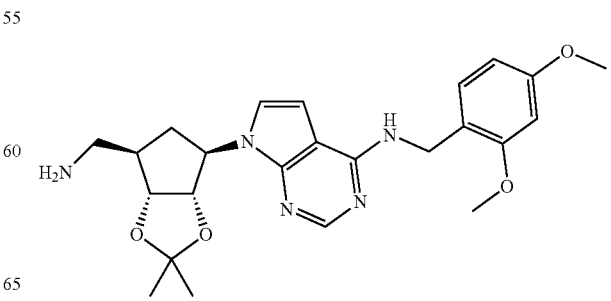

A solution of 7-((3aS,4R,6R,6aR)-6-(azidomethyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (2.23 g, 4.65 mmol) in THF (33 mL, 410 mmol) was cooled to 0° C. and treated dropwise with a 1.0 M solution of trimethylphosphine in THF (9.3 mL, 9.3 mmol). The cold bath was removed and the reaction mixture was allowed to warn to RT with stirring for 1 h; no starting material remained by HPLC. At 1.5 h, water (4.3 mL, 240 mmol) was added and the reaction mixture was stirred for 1 h 15 min; TLC indicated one product. The reaction mixture was concentrated in vacuo to afford a light orange paste. The residue was diluted with $CH_2Cl_2$ (120 mL) and washed with water (2×40 mL) and brine (1×40 mL). The organic layer was dried ($Na_2SO_4$) and concentrated in vacuo to afford an orange oil. Purification by column chromatography (2×22 cm silica; 0-5% 7 N $NH_3$ in $CH_3OH/CH_2Cl_2$) afforded the title compound (1.97 g, 53% over 3 steps) as a colorless foam: MS (ESI+) for $C_{24}H_{31}N_5O_4$ m/z 454.3 (M+H)$^+$; HPLC purity >95% (ret. time, 2.541 min).

Step 8: Synthesis of ethyl
3-(2,2-dichloro-3-oxocyclobutyl)propanoate

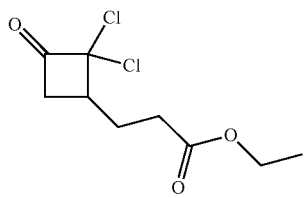

A mixture of 4-pentenoic acid ethyl ester (7.07 g, 55.2 mmol) and zinc-copper couple (10.2 g, 140 mmol) in diethyl ether (170 mL) and 1,2-dimethoxyethane (25 mL) was treated dropwise with trichloroacetyl chloride (25 g, 140 mmol). The mixture was stirred at room temperature for 3 days. The reddish heterogeneous reaction mixture was filtered through a pad of celite and the pad was washed with 300 mL $Et_2O$. The filtrate was concentrated to about one half the original volume and the organic phase was washed with two 150 mL portions of $H_2O$ and one 150 mL portion of sat $NaHCO_3$. The organic phase was dried over $MgSO_4$, filtered and concentrated to yield a brown liquid. The material was purified by vacuum distillation (90-100° C. @0.044 torr) to yield the title compound (10.49 g, 80%) as a light yellow liquid: GC purity 95.8% (ret. time, 4.92 min).

Step 9: Synthesis of ethyl
3-(3-oxocyclobutyl)propanoate

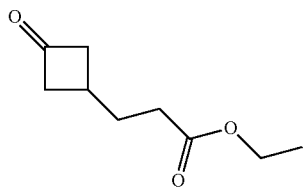

A solution of ethyl 3-(2,2-dichloro-3-oxocyclobutyl)propanoate (10.49 g, 43.87 mmol) and ammonium chloride (12 g, 220 mmol) in methanol (310 mL, 7600 mmol) was treated in small portions with zinc powder (14 g, 220 mmol). The reaction mixture was heated at reflux for 3 h after which time GC indicated the reaction was complete. The reaction mixture was cooled to room temperature and was filtered through Celite, washing the pad with $Et_2O$. The filtrate was concentrated in vacuo to afford pale yellow solution. The solution was diluted with 200 mL $Et_2O$ and washed with 100 mL water. The separated aqueous layer was back extracted with 100 mL $Et_2O$ and the combined organic phase was washed with 100 mL 1:1 water/brine, 50 mL water, and 150 mL saturated aqueous $NaHCO_3$. The organic layer was dried over $MgSO_4$, filtered and concentrated in vacuo to afford the title compound (4.49 g, 60%) as a pale yellow oil which was of sufficient purity for use in the next step: GC purity >95% (ret. time, 4.24 min).

Step 10: Synthesis of 3-(3-oxocyclobutyl)propanoic acid

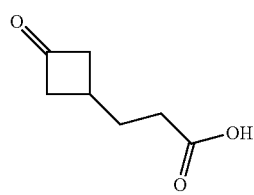

A solution of ethyl 3-(3-oxocyclobutyl)propanoate (200 mg, 1.18 mmol) in methanol (4 mL) was treated with water (0.75 mL) and a 2N solution of sodium hydroxide (0.75 mL, 1.41 mmol) and the solution was heated at 55° C. till the starting material was consumed by TLC (25% EA/hept). After 1 h the starting material was found to be consumed. The reaction mixture was cooled to room temperature and concentrated to remove the MeOH. The aqueous phase was diluted with 2 mL $H_2O$ and made acidic to pH~2 with 1N HCl. The solution was saturated with NaCl and extracted with three 10 mL portions of ethyl acetate. The organic phase was dried over $Na_2SO_4$, filtered and concentrated to yield the title compound (157 mg, 94%) as a light orange viscous oil that was used as is in the next step: GC purity 63.2% (ret. time, 4.27 min).

Step 11: Synthesis of N-(2-amino-4-chloro-5-(trifluoromethyl)phenyl)-3-(3-oxocyclobutyl)propanamide

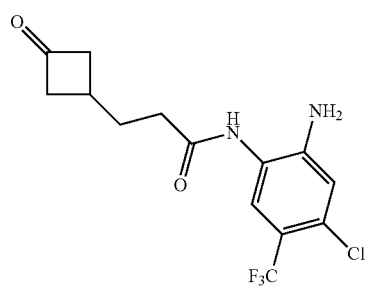 [SMILES: Nc1cc(Cl)c(C(F)(F)F)cc1NC(=O)CCC1CC(=O)C1]

A solution of 3-(3-oxocyclobutyl)propanoic acid (157 mg, 0.696 mmol) and 4-chloro-5-(trifluoromethyl)benzene-1,2-diamine (146 mg, 0.696 mmol) in N,N-dimethylformamide (2.5 mL) was cooled at 0° C. The solution was treated with N,N-diisopropylethylamine (0.364 mL, 2.09 mmol) dropwise followed by N,N,N',N'-tetramethyl-O-(7-azabenzotriazol-1-yl)uronium hexafluorophosphate (291 mg, 0.765 mmol) in one portion. The solution was allowed to stir and slowly wane to room temperature. After 40 h, the reaction mixture was concentrated partially under high vac. The remaining brown liquid was taken up in 25 mL EA and 15 mL 1/1 sat NaHCO$_3$/H$_2$O and extracted. The aqueous phase was washed with two 15 mL portions of ethyl acetate and the combined organic phase was washed with 30 mL portions of H$_2$O and brine. The organic phase was dried over MgSO$_4$, filtered and concentrated to yield a tannish brown viscous oil/glass. The crude material was purified by flash chromatography (40 g silica gel, 50-80% EA/hept) to yield the title compound (72 mg, 31%) as a slightly tan glass/stiff foam: MS (ESI+) for C$_{14}$H$_{14}$ClF$_3$N$_2$O$_2$ m/z 335.2 (M+H)$^+$; MS (ESI−) for C$_{14}$H$_{14}$ClF$_3$N$_2$O$_2$ m/z 333.3 (M−H)$^-$; HPLC purity 78.2% (ret. time, 3.56 min).

Step 12: Synthesis of 3-(2-(6-chloro-5-(trifluoromethyl)-1H-benzo[d]imidazol-2-yl)ethyl)cyclobutanone

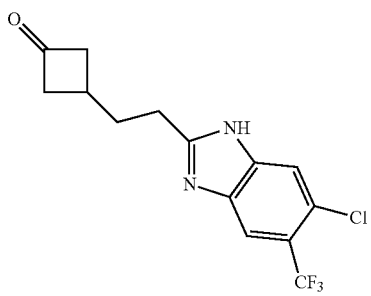 [SMILES: O=C1CC(CCc2nc3cc(C(F)(F)F)c(Cl)cc3[nH]2)C1]

N-(2-amino-4-chloro-5-(trifluoromethyl)phenyl)-3-(3-oxocyclobutyl)propanamide (72 mg, mmol) was taken up in acetic acid (3.2 mL) and the solution was heated at 65° C. for 26 h, upon which HPLC indicated the starting material was consumed and a new product had formed. The reaction mixture was cooled and the solvent was removed under high vac. The light brown residue was taken up in 20 mL ethyl acetate and the organic phase was washed with 10 mL portions of sat NaHCO$_3$ and H$_2$O. The organic phase was dried over Na$_2$SO$_4$, filtered and concentrated to yield a light brown glass. The crude material was purified by prep TLC (20 cm×20 cm×1.0 mm prep TLC plate, 3% MeOH/EA) to yield the title compound (45 mg, 66%) as a tan glass: MS (ESI+) for C$_{14}$H$_{12}$ClF$_3$N$_2$O m/z 317.2 (M+H)$^+$; MS (ESI−) for C$_{14}$H$_{12}$ClF$_3$N$_2$O m/z 315.2 (M−H)$^-$; HPLC purity 84.1% (ret. time, 2.98 min).

Step 13: Synthesis of 7-((3aS,4R,6R,6aR)-6-(((3-(2-(6-chloro-5-(trifluoromethyl)-1H-benzo[d]imidazol-2-yl)ethyl)cyclobutyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

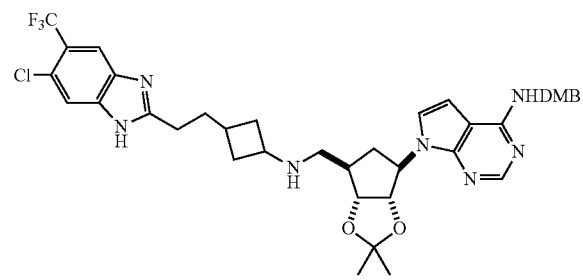

A solution of 7-((3aS,4R,6R,6aR)-6-(aminomethyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (80 mg, 0.18 mmol) and 3-(2-(6-chloro-5-(trifluoromethyl)-1H-benzo[d]imidazol-2-yl)ethyl)cyclobutanone (45 rug, 0.14 mmol) in 1,2-dichloroethane (2.4 mL) was treated dropwise with acetic acid (10 uL, 0.18 mmol). The solution was treated with sodium triacetoxyborohydride (53 mg, 0.25 mmol) in one portion and allowed to stir at room temperature till complete by HPLC. After 4 h, the reaction mixture was diluted with 10 mL CH$_2$Cl$_2$ and washed with 10 mL sat NaHCO$_3$. The aqueous phase was washed with 10 mL CH$_2$Cl$_2$ and the combined organic phase was dried over Na$_2$SO$_4$. The solution was filtered and concentrated to yield a light tan glass/stiff foam. The crude material was purified by flash chromatography (25 g silica gel; 5% 7N NH$_3$ in CH$_3$OH/CHCl$_3$) to yield the title compound (76 mg, 71%) as a colorless glass/stiff foam: MS (ESI+) for C$_{38}$H$_{43}$ClF$_3$N$_7$O$_4$ m/z 754.3 (M+H)$^+$; MS (ESI−) for C$_{38}$H$_{43}$ClF$_3$N$_7$O$_4$ m/z 752.3 (M−H)$^-$; HPLC purity 90.5% (ret. time, 3.24 min).

Step 14: Synthesis of 7-((3aS,4R,6R,6aR)-6-(((3-(2-(6-chloro-5-(trifluoromethyl)-1H-benzo[d]imidazol-2-yl)ethyl)cyclobutyl)(methyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

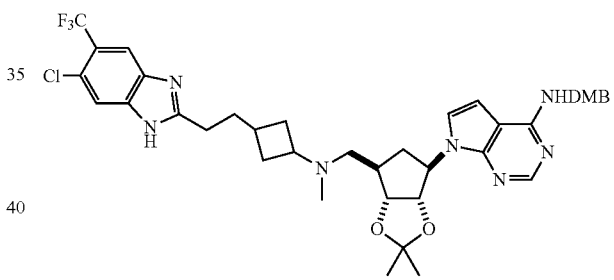

A solution of 7-((3aS,4R,6R,6aR)-6-(((3-(2-(6-chloro-5-(trifluoromethyl)-1H-benzo[d]imidazol-2-yl)ethyl)cyclobutyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (76 mg, 0.10 mmol) in methanol (2.5 mL) was treated with sodium cyanoborohydride (84 mg, 1.3 mmol). The pH of the solution was adjusted to ~6 by the dropwise addition of a 10% (v/v) solution of glacial acetic acid in methanol. The mixture was treated with 37% aqueous formaldehyde (0.12 mL, 1.7 mmol) dropwise and the mixture was stirred at room temperature till complete by LCMS. After 2 h, the reaction was complete and the reaction mixture was concentrated to remove the methanol. The aqueous solution that remained was diluted with 7 mL NaHCO$_3$ and the aqueous phase was extracted with three 10 mL portions of CH$_2$Cl$_2$. The organic phase was dried over Na$_2$SO$_4$, filtered, and concentrated to yield a colorless stiff foam/glass. The crude material was purified by flash chromatography (20 g silica gel; 4% 7N NH$_3$ in CH$_3$OH/CH$_2$Cl$_2$) to yield the title compound (62 mg, 80%) as a colorless glass: MS (ESI+) for C$_{39}$H$_{45}$ClF$_3$N$_7$O$_4$ m/z 768.0 (M+H)$^+$; MS (ESI−) for C$_{39}$H$_{45}$ClF$_3$N$_7$O$_4$ m/z 766.3 (M−H)$^-$; HPLC purity 92.1% (ret. time, 3.29 min).

Step 15: Synthesis of Compound 7

7-((3aS,4R,6R,6aR)-6-(((3 chloro-5-(trifluoromethyl)-1H-benzo[d]imidazol-2-yl)ethyl)cyclobutyl)(methyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (60 mg, 0.078 mmol) was dissolved in a mixture of trifluoroacetic acid (3.6 mL) and water (0.4 mL) which had been precooled at 0° C. in an ice bath. The solution was stirred at 0° C. for 30 minutes, and then warmed to room temperature. After 3 h at room temperature, HPLC indicated the reaction was complete. The now very pink reaction mixture was concentrated. The residue was taken up in 10 mL MeOH and concentrated. This procedure was repeated twice and the residue placed on high vac for 1 h. The material was taken up in 7 mL MeOH and was treated with 120 mg $K_2CO_3$ and ten drops of water. The mixture was allowed to stir for 1 hr. The mixture was filtered through a fine frit, the solids were washed with 10 mL MeOH and the filtrate was concentrated to yield a nearly colorless solid. The crude material was purified by flash chromatography (30 g silica gel; 10-15% 7N $NH_3$ in $CH_3OH/CH_2Cl_2$) to yield Compound 7 (31 mg, 69%) as a colorless glass/stiff foam: MS (ESI+) for $C_{27}H_{31}ClF_3N_7O_2$ m/z 578.3 (M+H)$^+$; MS (ESI−) for $C_{27}H_{31}ClF_3N_7O_2$ m/z 576.4 (M−H)$^-$; HPLC purity >95% (ret. time, 2.57 min); 1H NMR (400 MHz, d4-MeOD) $\delta_H$ 8.06 (s, 1H), 7.89 (d, J=2.07 Hz, 1H), 7.69 (d, J=2.28 Hz, 1H), 7.21 (dd, J=3.42, 1.76 Hz, 1H), 6.59 (d, J=3.52 Hz, 1H), 4.33 (t, J=6.84 Hz, 1H), 3.89 (q, J=5.25 Hz, 1H), 3.03 (m, 0.5H), 2.89 (m, 2H), 2.70 (0.5H), 2.49 (m, 1H), 2.40 (m, 2H), 2.27 (br. s., 2H), 2.16 (d, J=7.26 Hz, 4H), 2.06 (m, 2H), 1.91 (m, 2H), 1.62 (m, 1H), 1.52 (m, 1H).

Example 8

Synthesis of Compounds 8-140

Compounds 8-140 were synthesized by methods similar to those described for Examples 1-7 or by reaction schemes depicted in the general schemes. Detailed descriptions of how some of them were prepared are provided below. The MS and NMR data of Compounds 2-140 are provided in Table 1 or Examples provided herein.

Compound 8: 1-(3-((((2R,3S,4R,5R)-5-(6-amino-9H-purin-9-yl)-3,4-dihydroxytetrahydrofuran-2-yl)methyl)(methyl)amino)cyclobutyl)-3-(4-(tert-butyl)phenyl)urea

Benzyl (3-oxocyclobutyl)carbamate

To a solution of 3-oxocyclobutanecarboxylic acid (1.0 g, 8.77 mmol) and DIEA (1.92 g, 14.92 mmol) in toluene (8 mL) was added DPPA (2.89 g, 10.52 mmol) at rt. The mixture was heated to 60° C. under Argon for 3 h, then benzyl alcohol (1.14 g, 10.52 mmol) was added. The mixture was stirred at 60° C. overnight. The reaction was concentrated, the residue was purified by SGC (PE:EA=8:1) to afford the desired compound (240 mg, yield 50%). $^1$H NMR (500 MHz, CDCl$_3$): $\delta_H$ 7.38-7.33 (m, 5H), 5.12 (d, J=7.5 Hz, 2H), 4.34-4.33 (brs, 1H), 3.44-3.39 (m, 2H), 3.10-3.07 (brs, 2H) ppm; ESI-MS (m/z): 220.2 [M+1]$^+$.

benzyl(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)carbamate To a solution of 9-((3aR,4R,6R,6aR)-2,2-dimethyl-6-((methylamino)methyl)tetrahydrofuro[3,4-d][1,3]dioxol-4-yl)-9H-purin-6-amine (190 mg, 0.59 mmol) and benzyl (3-oxocyclobutyl)carbamate (240 mg, 1.37 mmol) in MeOH (5 mL) was added Ti[OCH(CH$_3$)$_2$]$_4$ (216 mg, 0.59 mmol). The mixture was stirred at rt for 1 h. Then NaCNBH$_3$ (95 mg, 1.52 mmol) was added, the reaction was stirred at rt overnight. The reaction was filtered and evaporated, the residue was purified by prep-TLC (DCM:MeOH=20:1) to obtain the desired compound (90 mg, yield 29%).
$^1$H NMR (500 MHz, MeOD): $\delta_H$ 8.28 (s, 1H), 8.21 (s, 1H), 7.33-7.28 (m, 5H), 6.19 (d, J=2.0 Hz, 1H), 5.52-5.51 (m, 1H), 5.03 (s, 1H), 5.00-4.98 (m, 1H), 4.34 (t, J=3.5 Hz, 1H), 3.70 (m, 1H), 2.58-2.47 (m, 4H), 2.38-2.26 (m, 2H), 2.09 (s, 3H), 1.69-1.67 (m, 1H), 1.58 (s, 3H), 1.37 (s, 3H) ppm; ESI-MS (m/z): 524.3 [M+1]$^+$.

N1-(((3aR,4R,6R,6aR)-6-(6-amino-9H-purin-9-yl)-2,2-dimethyltetrahydrofuro[3,4-d][1,3]dioxol-4-yl)methyl)-N1-methylcyclobutane-1,3-diamine To a solution of benzyl (3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)carbamate (190 mg, 0.17 mmol) and Pd(OH)$_2$ (14 mg, 0.1 mmol) in MeOH (5 mL) was charged with H$_2$. The reaction was stirred at 35° C. for 5 h. The reaction was filtered with Celite and concentrated to dryness. The residue was purified by prep-TLC (DCM:MeOH=10:1) to the desired compound (28 mg, yield 42%). $^1$HNMR (500 MHz, MeOD): $\delta_H$ 8.29 (s, 1H), 8.21 (s, 1H), 6.19 (d, J=2.0 Hz, 1H), 5.51 (dd, J=6.5 and 2.0 Hz, 1H), 5.00 (dd, J=6.0 and 3.5 Hz, 1H), 4.34 (d, J=8.5 Hz, 1H), 3.14-3.11 (m, 1H), 2.60-2.57 (m, 1H), 2.52-2.48 (m, 2H), 2.34-2.31 (m, 2H), 2.10 (s, 3H), 1.66 (q, J=10.0 Hz, 1H), 1.58 (s, 3H), 1.48 (q, J=10.0 Hz, 1H), 1.37 (s, 3H) ppm; ESI-MS (m/z): 390.2[M+1]$^+$.

1-(3-((((3 aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)-3-(4-(tert-butyl)phenyl)urea A solution of N1-(((3aR,4R,6R,6aR)-6-(6-amino-9H-purin-9-yl)-2,2-dimethyltetrahydrofuro[3,4-d][1,3]dioxol-4-yl)methyl)-N1-methylcyclobutane-1,3-diamine (28 mg, 0.072 mmol) and TEA (22 mg, 0.22 mmol) in THF (3 mL) was added dropwise 1-tert-butyl-4-isocyanatobenzene (18 mg, 0.11 mmol) in DCM (0.5 mL). The reaction was stirred for 1 hour at room temperature. The reaction was concentrated and purified by Prep-TLC (twice, DCM:MeOH:NH$_4$OH=300:30:8, V/V) to obtain the desired compound (28 mg, Yield: 88%) as pale white solid. $^1$H NMR (500 MHz, MeOD): $\delta_H$ 8.29 (s, 1H), 8.24 (s, 1H), 7.28-7.22 (m, 4H), 6.25 (d, J=2.5 Hz, 1H), 5.52-5.50 (m, 1H), 5.07-5.05 (m, 1H), 4.46-4.44 (m, 1H), 3.88-3.85 (m, 1H), 2.97 (brs, 1H), 2.80-2.78 (m, 2H), 2.48-2.42 (m, 2H), 2.30 (s, 3H), 1.84-1.82 (m, 1H), 1.60 (s, 3H), 1.58-1.56 (m, 1H), 1.39 (s, 3H), 1.28 (s, 9H) ppm; ESI-MS (m/z): 565.3 [M+1]$^+$.

1-(3-(((((2R,3S,4R,5R)-5-(6-amino-9H-purin-9-yl)-3,4-dihydroxytetrahydrofuran-2-yl)methyl)(methyl)amino)cyclobutyl)-3-(4-(tert-butyl)phenyl)urea

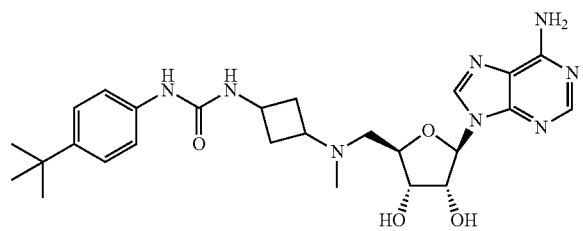 [SMILES: CN(C[C@H]1O[C@@H](n2cnc3c(N)ncnc32)[C@H](O)[C@@H]1O)C1CC(NC(=O)Nc2ccc(C(C)(C)C)cc2)C1]

A solution of 1-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)-3-(4-(tert-butyl)phenyl)urea (125 mg, 0.23 mmol) in TFA (0.90 mL) and 0.10 mL of water were stirred for 1 hour at room temperature. The reaction was concentrated to dryness, dissolved in MeOH (5 mL) and K$_2$CO$_3$ (60 mg) in 0.5 mL of water was added dropwise. The reaction was stirred at rt for 0.5 h and concentrated to obtain the residue which was purified by prep-TLC (DCM:MeOH:NH$_4$OH=300:30:8, V/V) to obtain the desired compound (75 mg, Yield: 65%) as pale white solid. $^1$H NMR (500 MHz, MeOD): $\delta_H$ 8.27 (s, 1H), 8.21 (s, 1H), 7.28-7.20 (m, 4H), 6.00-5.99 (m, 1H), 4.77-4.75 (m, 1H), 4.28-4.23 (m, 2H), 3.92-3.88 (m, 1H), 2.92 (brs, 1H), 2.83-2.81 (m, 2H), 2.59-2.56 (m, 2H), 2.32 (s, 3H), 1.74-1.64 (m, 2H), 1.27 (s, 9H) ppm; ESI-MS (m/z): 525.3 [M+1]$^+$.

Compounds 9 and 12

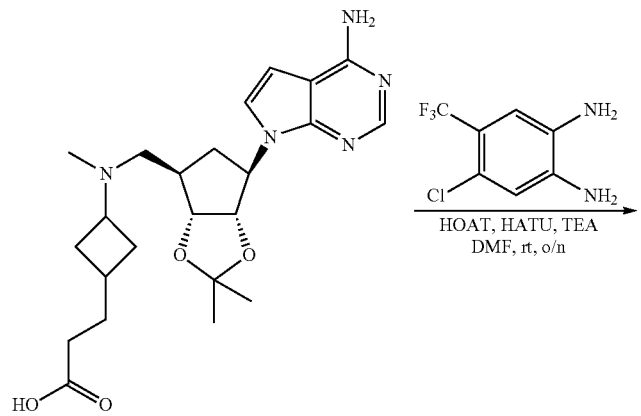

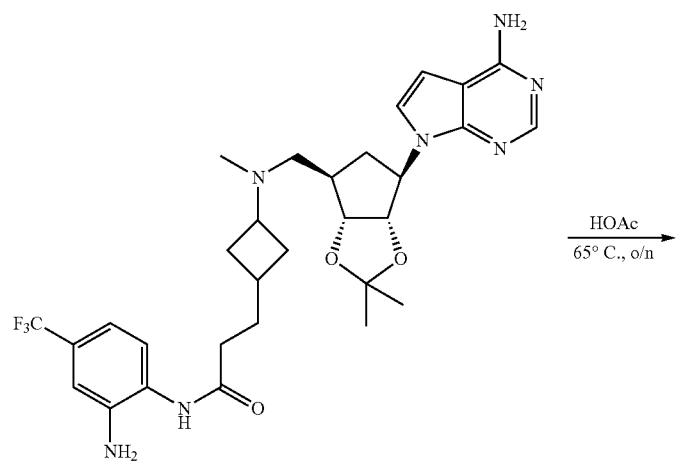

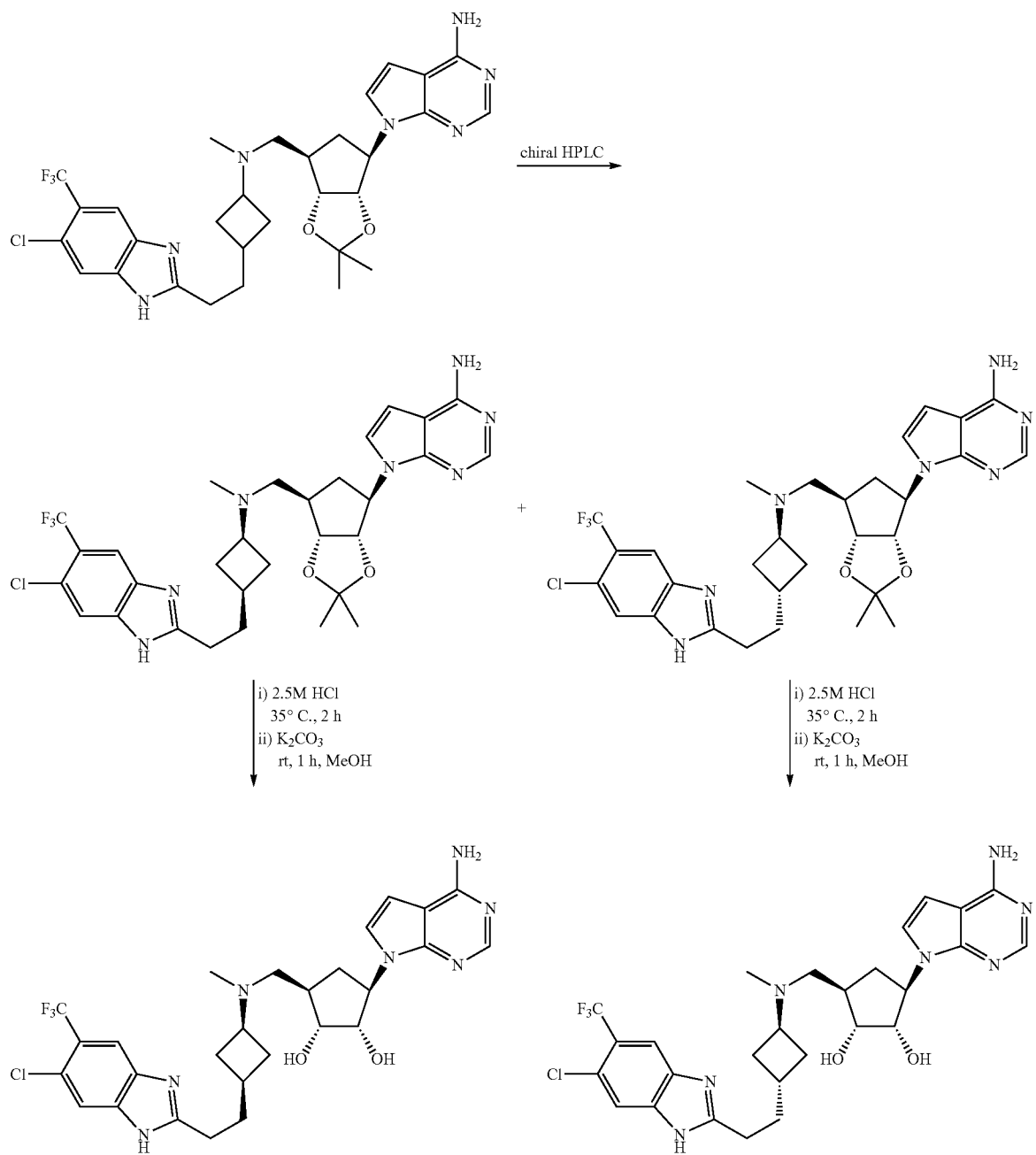

Compound 9: (1R,2S,3R,5R)-3-(4-amino-7H-pyrrolo[2,3-d]pyrimidin-7-yl)-5-(((((1r,3S)-3-(2-(6-chloro-5-(trifluoromethyl)-1H-benzo[d]imidazol-2-yl)ethyl)cyclobutyl)(methyl)amino)methyl)cyclopentane-1,2-diol $^1$H NMR (500 MHz, MeOD): $\delta_H$ 8.07 (s, 1H), 7.90 (s, 1H), 7.69 (s, 1H), 7.22 (d, J=3.5 Hz, 1H), 6.61 (d, J=3.5 Hz, 1H), 4.34 (t, J=6.5 Hz, 1H), 3.89 (t, J=5.0 Hz, 1H), 2.88 (t, J=7.0 Hz, 2H), 2.74-2.68 (m, 1H), 2.55-2.49 (m, 1H), 2.46-2.35 (m, 2H), 2.32-2.22 (m, 3H), 2.17 (s, 3H), 2.00-1.90 (m, 3H), 1.68-1.60 (m, 1H), 1.58-1.48 (m, 2H) ppm; LC-MS (m/z): 578.3 [M+1]$^+$.

Compound 12: (1R,2S,3R,5R)-3-(4-amino-7H-pyrrolo[2,3-d]pyrimidin-7-yl)-5-(((((1s,3R)-3-(2-(6-chloro-5-(trifluoromethyl)-1H-benzo[d]imidazol-2-yl)ethyl)cyclobutyl)(methyl)amino)methyl)cyclopentane-1,2-diol $^1$H NMR (500 MHz, MeOD): $\delta_H$ 8.07 (s, 1H), 7.91 (s, 1H), 7.70 (s, 1H), 7.22 (d, J=3.5 Hz, 1H), 6.61 (d, J=4.0 Hz, 1H), 4.34 (dd, J=7.0 and 6.0 Hz, 1H), 3.90 (t, J=5.0 Hz, 1H), 3.05-3.00 (m, 1H), 2.92 (t, J=7.5 Hz, 2H), 2.55-2.49 (m, 1H), 2.47-2.35 (m, 2H), 2.32-2.22 (m, 1H), 2.20-2.02 (m, 8H), 1.93-1.86 (m, 2H), 1.70-1.60 (m, 1H) ppm; LC-MS (m/z): 578.3 [M+1]$^+$.

Compounds 10 and 11
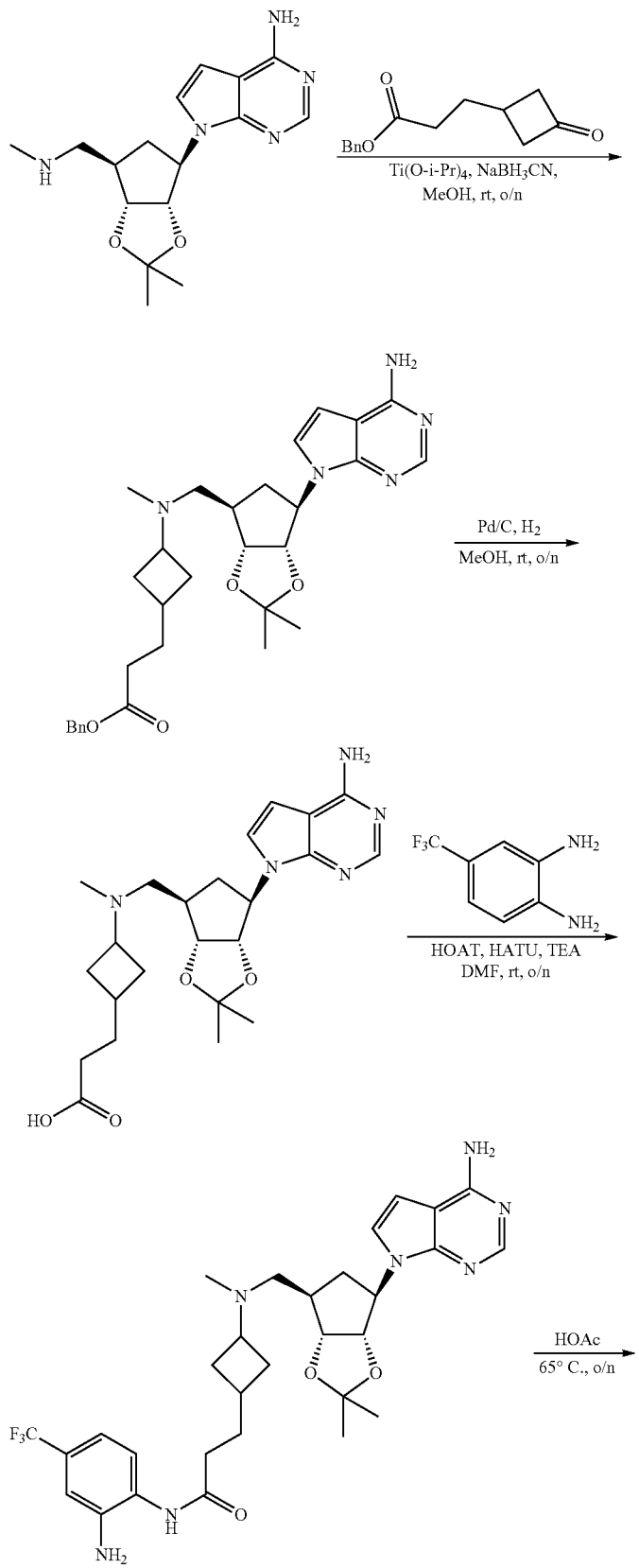

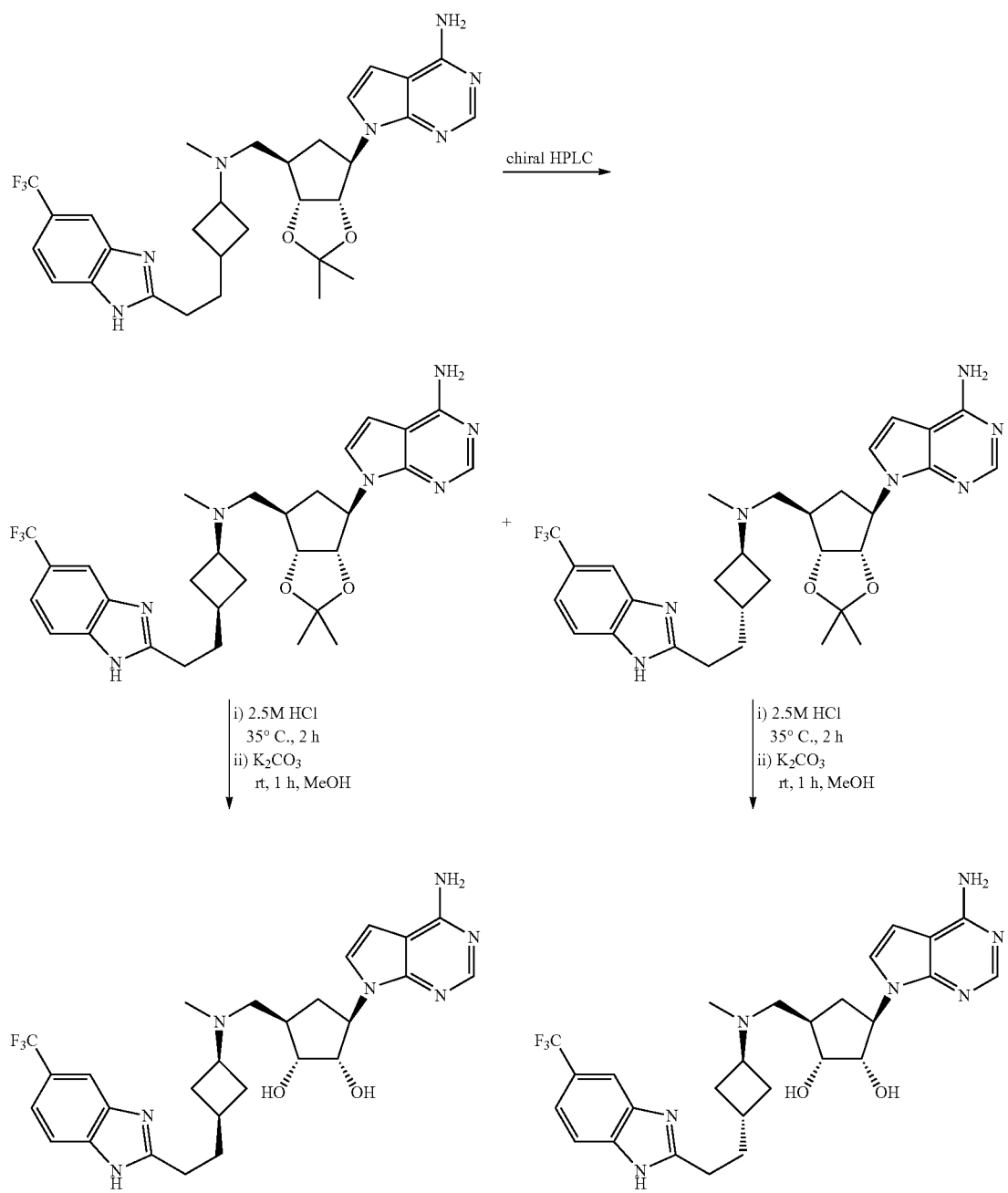

Compound 10: (1R,2S,3R,5R)-3-(4-amino-7H-pyrrolo[2,3-d]pyrimidin-7-yl)-5-((methyl((1r,3S)-3-(2-(5-(trifluoromethyl)-1H-benzo[d]imidazol-2-yl)ethyl)cyclobutyl)amino)methyl)cyclopentane-1,2-diol $^1$H NMR (500 MHz, MeOD): $\delta_H$ 8.06 (s, 1H), 7.79 (s, 1H), 7.62 (d, J=9.0 Hz, 1H), 7.47 (d, J=8.5 Hz, 1H), 7.20 (d, J=3.5 Hz, 1H), 6.59 (d, J=3.0 Hz, 1H), 4.33-4.30 (m, 1H), 3.88-3.86 (m, 1H), 3.32-3.31 (m, 1H), 2.89-2.86 (m, 2H), 2.67-2.66 (m, 1H), 2.48-2.26 (m, 6H), 2.14 (s, 3H), 1.95-1.93 (m, 3H), 1.62-1.48 (m, 3H) ppm; LC-MS (m/z): 544.3 [M+1]$^+$.

Compound 11: (1R,2S,3R,5R)-3-(4-amino-7H-pyrrolo[2,3-d]pyrimidin-7-yl)-5-((methyl((1s,3R)-3-(2-(5-(trifluoromethyl)-1H-benzo[d]imidazol-2-yl)ethyl)cyclobutyl)amino)methyl)cyclopentane-1,2-diol $^1$H NMR (500 MHz, MeOD): $\delta_H$ 8.06 (s, 1H), 7.79 (s, 1H), 7.62 (d, J=8.5 Hz, 1H), 7.47 (d, J=8.5 Hz, 1H), 7.20 (d, J=3.0 Hz, 1H), 6.59 (d, J=3.5 Hz, 1H), 4.33-4.31 (m, 1H), 3.90-3.87 (m, 1H), 3.01-3.0 (m, 1H), 2.92-2.89 (m, 2H), 2.48-2.03 (m, 13H), 1.93-1.89 (m, 2H), 1.63-1.61 (m, 1H) ppm; LC-MS (m/z): 544.3 [M+1]$^+$.

267

Compound 13: (1R,2S,3R,5R)-3-(4-amino-7H-pyr-rolo[2,3-d]pyrimidin-7-yl)-5-((methyl(3-(2-(5-(trif-luoromethyl)-1H-benzo[d]imidazol-2-yl)ethyl)cy-clobutyl)amino)methyl)cyclopentane-1,2-diol N-(2-amino-4-(trifluoromethyl)phenyl)-3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanamide

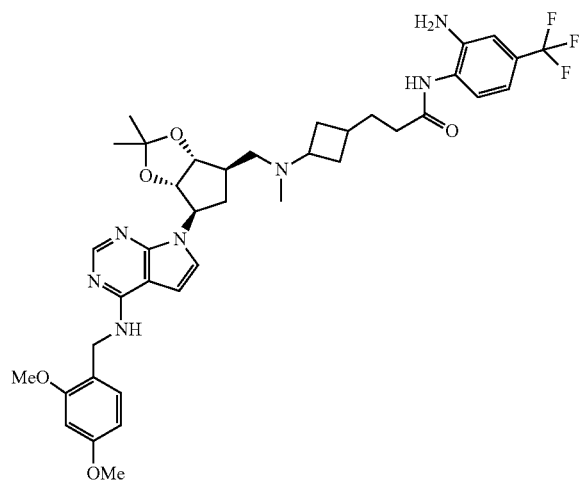 [SMILES: COc1ccc(CNc2ncnc3c2ccn3[C@@H]2C[C@H](CN(C)C3CC(CCC(=O)Nc4ccc(C(F)(F)F)cc4N)C3)[C@H]3OC(C)(C)O[C@H]32)c(OC)c1]

N,N,N',N'-Tetramethyl-O-(7-azabenzotriazol-1-yl)uronium Hexafluorophosphate (0.44 g, 1.2 mmol) was added to a solution of 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanoic acid (460 mg, 0.77 mmol), N,N Diisopropylethylamine (0.44 mL, 2.6 mmol) in N,N-Dimethylformamide (5 mL). The reaction was stirred overnight at RT, partially concentrated then NaHCO₃ (saturated) was added. The aqueous layer was extracted 3× with EtOAc and the combined organics were dried with MgSO₄, filtered, concentrated and purified by flash chromatography (DCM/7N NH₃ in MeOH 95:5) to give the desired compound (0.34 g) as a solid.

N-(2,4-dimethoxybenzyl)-7-((3aS,4R,6R,6aR)-2,2-dimethyl-6-((methyl(3-(2-(5-(trifluoromethyl)-1H-benzo[d]imidazol-2-yl)ethyl)cyclobutyl)amino)methyl)tetrahydro-3aH-cyclopenta[d][1,3]dioxol-4-yl)-7H-pyrrolo[2,3-d]pyrimidin-4-amine

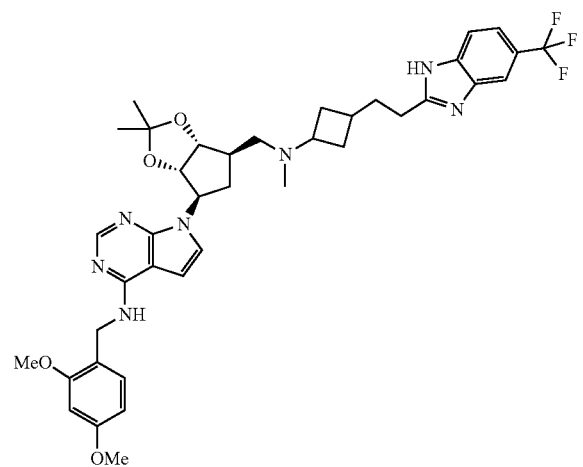 [SMILES: COc1ccc(CNc2ncnc3c2ccn3[C@@H]2C[C@H](CN(C)C3CC(CCc4nc5cc(C(F)(F)F)ccc5[nH]4)C3)[C@H]3OC(C)(C)O[C@H]32)c(OC)c1]

268

N-(2-amino-4-(trifluoromethyl)phenyl)-3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanamide (0.38 g, 0.50 mmol) and Acetic acid (5 ml) were stirred overnight at 65° C. The volatiles were removed in vacuo and remaining water was removed by azeotropic distillation with ethanol followed by 1 hour on high vacuum. The resulting residue was partitioned between NaHCO₃ (saturated) and DCM. The aqueous layer was extracted (3×) and combined organics were dried with MgSO₄, filtered, concentrated and then purified by flash chromatography (DCM/7N NH₃ in MeOH 93:7) to yield an off white foam.

(1R,2S,3R,5R)-3-(4-amino-7H-pyrrolo[2,3-d]pyrimidin-7-yl)-5-((methyl(3-(2-(5-(trifluoromethyl)-1H-benzo[d]imidazol-2-yl)ethyl)cyclobutyl)amino)methyl)cyclopentane-1,2-diol

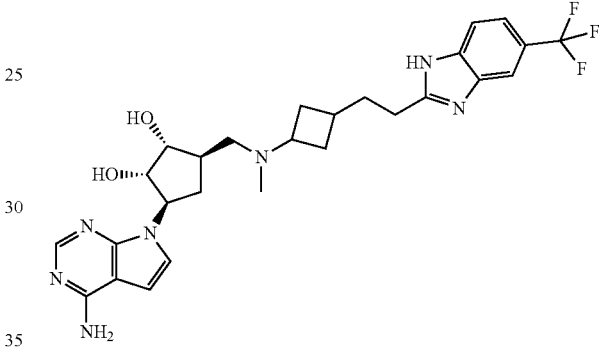

Trifluoroacetic Acid (5 ml) added to a mixture of Water (0.5 ml) N-(2,4-dimethoxybenzyl)-7-((3aS,4R,6R,6aR)-2,2-dimethyl-6-((methyl(3-(2-(5-(trifluoromethyl)-1H-benzo[d]imidazol-2-yl)ethyl)cyclobutyl)amino)methyl)tetrahydro-3aH-cyclopenta[d][1,3]dioxol-4-yl)-7H-pyrrolo[2,3-d]pyrimidin-4-amine (0.31 g, 0.42 mmol) at RT. The reaction was allowed to proceed overnight when it was quenched with Triethylsilane (0.13 ml, 0.84 mmol). The volatiles were removed in vacuo and resulting residue was partitioned between saturated NaHCO₃ and DCM/MeOH (10:1). The aqueous layer was extracted (3×) more with DCM/MeOH (10:1) and the combined organics were dried over MgSO₄, filtered and concentrated. The residue was purified by flash chromatography (DCM/7N NH₃ in MeOH 87:13) to give the desired compound (0.12 g) as an off-white foam/gum. MS (ESI⁺) for $C_{27}H_{32}F_3N_7O_2$ m/z 544.5 [M+H]⁺; MS (ESI⁻) for $C_{27}H_{32}F_3N_7O_2$ m/z 542.3 [M−H]⁻; HPLC purity >85% (ret. time, 2.418 min.) ¹H NMR (400 MHz, d₄-MeOH) δ_H 8.078 (s, 1H), 7.812 (s, 1H), 7.654-7.634 (m, 1H), 7.507-7.487 (m, 1H), 7.229-7.214 (m, 1H), 6.617-6.608 (d, J=3.6 Hz, 1H), 4.361-4.322 (m, 1H), 3.927-3.887 (m, 1H), 3.062-3.024 (m, 0.5H (methine of trans isomer)), 2.944-2.873 (m, 2H), 2.758-2.554 (m, 0.5H (methine of cis isomer)), 2.554-2.507 (m, 1H), 2.447-2.351 (m, 2H), 2.291-2.263 (m, 2H), 2.194-2.054 (m, 6H), 1.960-1.887 (m, 3H), 1.686-1.480 (m, 2H). Retention time: 2.418 HPLC Conditions: Agilent Zorbax Exlipse XDB-C18 column, 4.6×50 mm (1.8 um packing), Solvent A—Water (0.1% TFA), Solvent B—Acetonitrile (0.07% TFA). 6 min gradient from 5 to 95% B; 1 min hold; then recycle.

269

Compound 14: (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(methyl)amino)methyl)cyclopentane-1,2-diol N-(2-amino-4-(tert-butyl)phen yl)-3-(3-(((((3 aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanamide

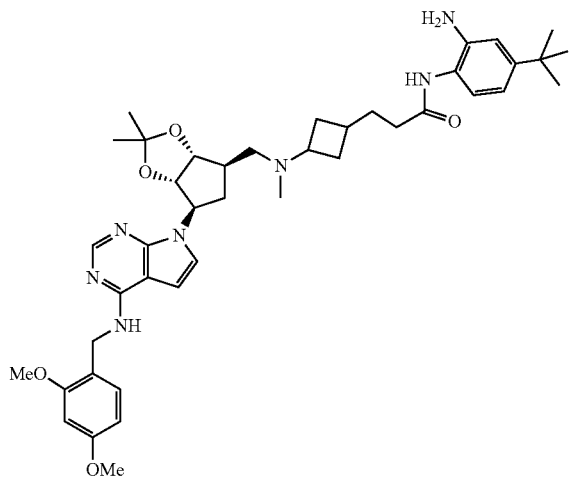 [SMILES: COc1ccc(CNc2ncnc3c2ccn3[C@@H]2C[C@H](CN(C)C3CC(CCC(=O)Nc4ccc(C(C)(C)C)cc4N)C3)[C@H]3OC(C)(C)O[C@H]32)c(OC)c1]

N,N,N',N'-Tetramethyl-0-(7-azabenzotriazol-1-yl}uronium Hexafluorophosphate (0.44 g, 1.2 mmol) added to a solution of 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanoic acid (460 mg, 0.77 mmol) and N,N-Diisopropylethylamine (0.44 mL, 2.6 mmol) and 4-tert-butylbenzene-1,2-diamine (0.15 g, 0.93 mmol) in N,N-Dimethylformamide (5 mL, 60 mmol). The reaction was stirred overnight at RT, partially concentrated to ca. 2 mls and then NaHCO$_3$ (saturated) was added. The mixture was extracted with EtOAc (3×) and the combined organics were dried with MgSO$_4$ and concentrated. Purified by flash chromatography (DCM/7N NH$_3$ in MeOH 95:5) to yield a solid (0.24 g).

7-((3aS,4R,6R,6aR)-6-(((3-(2-(5-(tert-butyl)-1H-benzo[d]imidazol-2-yl)ethyl)cyclobutyl)(methyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

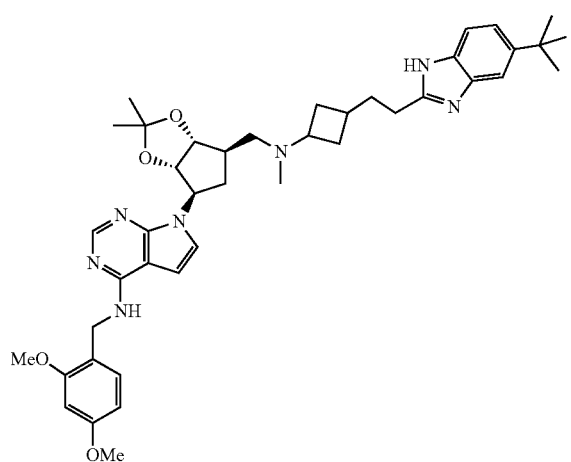 [SMILES: COc1ccc(CNc2ncnc3c2ccn3[C@@H]2C[C@H](CN(C)C3CC(CCc4nc5cc(C(C)(C)C)ccc5[nH]4)C3)[C@H]3OC(C)(C)O[C@H]32)c(OC)c1]

270

A solution of N-(2-amino-4-(tert-butyl)phenyl)-3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanamide (0.24 g, 0.32 mmol) in Acetic acid (5 ml, 90 mmol) was stirred overnight at 60° C. The volatiles were removed in vacuo and remaining residue partitioned between Na2CO3 (2N) and DCM. The aqueous layer was extracted 3× with DCM and the combined organics dried with MgSO$_4$, filtered and concentrated. The residue was purified by flash chromatography (DCM/7N NH$_3$ in MeOH 94:6) to yield the desired compound (0.20 g) as a solid.

(1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(methyl)amino)methyl)cyclopentane-1,2-diol

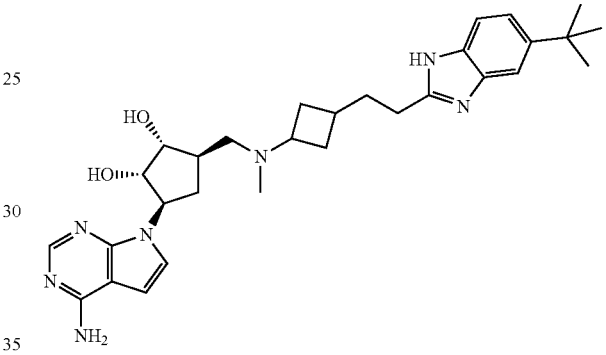

Trifluoroacetic Acid (5 ml) added to a mix lure of Water (0.5 ml) and 7-((3aS,4R,6R,6aR)-6-(((3-(2-(5-(tert-butyl)-1H-benzo[d]imidazol-2-yl)ethyl)cyclobutyl)(methyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (0.20 g, 0.28 mmol) at RT. The reaction was allowed to proceed overnight upon which it was quenched with Triethylsilane (0.088 ml, 0.55 mmol). The volatiles were removed in vacuo and resulting residue was partitioned between saturated NaHCO$_3$ and DCM/MeOH (10:1). Aqueous extracted 3× more with DCM/MeOH (10:1) and combined organics were dried over MgSO$_4$, filtered, concentrated and purified by flash chromatography (DCM/7N NH$_3$ in MeOH 87:13) to give the desired product as an off-white foam (0.060 g). MS (ESI$^+$) for $C_{30}H_{41}N_7O_2$ m/z 532.3 [M+H]$^+$; MS (ESI$^-$) for $C_{30}H_{41}N_7O_2$ m/z 530.4 [M−H]$^-$; HPLC purity >94% (ret. time, 2.723 min.) $^1$H NMR (400 MHz, d$_4$-MeOH) δ$_H$ 8.079 (s, 1H), 7.500 (s, 1H), 7.418-7.398 (m, 1H), 7.310-7.307 (m, 1H), 7.230-7.216 (m, 1H), 6.619-6.610 (m, 1H), 4.355-4.316 (m, 1H), 3.926-3.887 (m, 1H), 3.088-3.017 (m, 0.5H (methine of trans isomer)), 2.879-2.809 (m, 2H), 2.745-2.685 (m, 0.5H (methine of cis isomer), 2.532-2.512 (m, 1H), 2.446-2.373 (m, 2H), 2.294-2.276 (m, 2H), 2.202-2.012 (m, 5H), 1.685-1.603 (m, 1H), 1.545-1.504 (m, 1H), 1.383 (s, 1H). Retention time: 2.723 mins HPLC Conditions: Agilent Zorbax Exlipse XDB-C18 column, 4.6× 50 mm (1.8 um packing), Solvent A—Water (0.1% TFA), Solvent B—Acetonitrile (0.07% TFA) 6 min gradient from 5 to 95% B; 1 min hold; then recycle.

Compound 15: (1R,2S,3R,5R)-3-{4-amino-7H-pyr-rolo[2,3-d]pyrimidin-7-yl}-5-{[propan-2-yl({4-[5-(trifluoromethyl)-1H-1,3-benzodiazol-2-yl]butyl})amino]methyl}cyclopentane-1,2-diol Step 1: 7-[(3aS,4R,6R,6aR)-2,2-dimethyl-6-{[propan-2-yl({4-[5-(trifluoromethyl)-1-{[2-(trimethylsilyl)ethoxy]methyl}-1H-1,3-benzodiazol-2-yl]butyl})amino]methyl}-hexahydrocyclopenta[d][1,3]dioxol-4-yl]-7H-pyrrolo[2,3-d]pyrimidin-4-amine

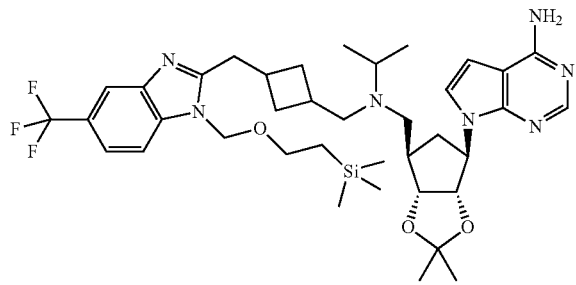 [SMILES: CC(C)N(CC1CC(Cc2nc3cc(C(F)(F)F)ccc3n2COCC[Si](C)(C)C)C1)C[C@H]1C[C@@H](n2ccc3c(N)ncnc32)[C@@H]2OC(C)(C)O[C@H]12]

A solution of 3-{[5-(trifluoromethyl)-1-{[2-(trimethylsilyl)ethoxy]methyl}-1H-1,3-benzodiazol-2-yl]methyl}cyclobutane-1-carbaldehyde (243 mg, 0.59 mmol), 7-[(3aS,4R,6R,6aR)-2,2-dimethyl-6-[(propan-2-ylamino)methyl]-hexahydrocyclopenta[d][1,3]dioxol-4-yl]-7H-pyrrolo[2,3-d]pyrimidin-4-amine (170 mg, 0.49 mmol) and MgSO$_4$ (710 mg, 5.90 mmol) in DCE (10 ml) was stirred for 15 min. STAB (175 mg, 0.83 mmol) was then added to the reaction mixture and stirred for 1 h at RT. The reaction was monitored by LCMS, no amine was seen after 1 h. Sat. NaHCO$_3$ (20 ml) was added to the reaction mixture and stirred for 5 mins. Brine (10 ml) was then added to the reaction mixture. The product was extracted with DCM (2×30 ml), dried over Na$_2$SO$_4$, filtered and evaporated. Purification by silica gel column chromatography, eluting with 7N NH$_3$ in MeOH:DCM (1:99-4:96) gave the desired product (170 mg, 47%) as an oil; MS (ESI$^+$) for C$_{38}$H$_{54}$F$_3$N$_7$O$_3$Si m/z 742.40 [M+H]$^+$; HPLC purity 100% (ret. time, 1.78 min); $^1$H NMR (500 MHz, CHLOROFORM-d) δ$_H$ ppm −0.25-0.11 (9H, m), 0.66-1.04 (8H, m), 1.17-1.48 (5H, m), 1.49-1.61 (3H, m), 1.77-2.04 (2H, m), 2.19-2.37 (5H, m), 2.37-2.51 (2H, m), 2.52-2.80 (2H, m), 2.81-2.91 (1H, m), 2.91-3.22 (2H, m), 3.34-3.79 (2H, m), 4.29-4.52 (1H, m), 4.78-5.12 (2H, m), 5.28-5.70 (4H, m), 6.34 (1H, d, J=3.63 Hz), 6.80-7.16 (1H, m), 7.29-7.71 (2H, m), 7.71-8.11 (1H, m), 8.11-8.46 (1H, m)

Step 2. (1R,2S,3R,5R)-3-{4-amino-7H-pyrrolo[2,3-d]pyrimidin-7-yl}-5-{[propan-2-yl({4-[5-(trifluoromethyl)-1H-1,3-benzodiazol-2-yl]butyl})amino]methyl}cyclopentane-1,2-diol

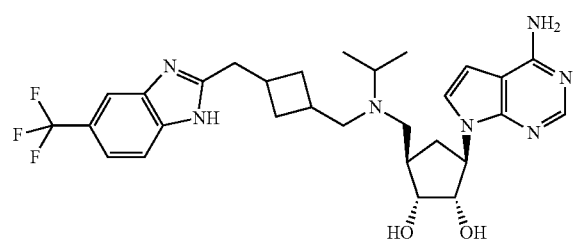 [SMILES: CC(C)N(CC1CC(Cc2nc3cc(C(F)(F)F)ccc3[nH]2)C1)C[C@H]1C[C@@H](n2ccc3c(N)ncnc32)[C@H](O)[C@@H]1O]

12N HCl (3 ml) was added slowly to a solution of 7-[(3aS,4R,6R,6aR)-2,2-dimethyl-6-({propan-2-yl[(3-{[5-(trifluoromethyl)-1-{[2-(trimethylsilyl)ethoxy]methyl}-1H-1,3-benzodiazol-2-yl]methyl}cyclobutyl)methyl]amino}methyl)-hexahydro cyclopenta[d][1,3]dioxol-4-yl]-7H-pyrrolo[2,3-d]pyrimidin-4-amine (170 mg, 0.23 mmol) in MeOH (3 ml) and stirred at 40° C. for 2.5 h. The reaction was monitored by LCMS, no starting material seen after 2.5 h. The reaction mixture was concentrated in vacuo, then basified with 7N NH$_3$ in MeOH. This was then evaporated to dryness. Purification by silica gel column chromatography, eluting with 7N NH$_3$ in MeOH:DCM (1:9) gave the desired product (100 mg, 76%) as a white solid; MS (ESI$^+$) for C$_{29}$H$_{36}$F$_3$N$_7$O$_3$ m/z 572.40 [M+H]$^+$; HPLC purity 99% (ret. time, 2.17 min); $^1$H NMR (500 MHz, CHLOROFORM-d) δ$_H$ ppm 0.78-1.19 (6H, m), 1.35-1.69 (2H, m), 1.80-2.04 (1H, m), 2.11-2.87 (10H, m), 2.88-3.18 (3H, m), 3.79-4.06 (1H, m), 4.15-4.47 (1H, m), 4.82-5.12 (1H, m), 6.43-6.77 (1H, m), 7.19 (1H, d, J=3.47 Hz), 7.47 (1H, d, J=8.35 Hz), 7.63 (1H, d, J=8.51 Hz), 7.79 (1H, s), 7.95-8.24 (1H, m).

Compound 18: (1R,2S,3R,5R)-3-{4-amino-7H-pyrrolo[2,3-d]pyrimidin-7-yl}-5-({methyl[(3-{[5-(trifluoromethyl)-1H-1,3-benzodiazol-2-yl]methyl}cyclobutyl)methyl]amino}methyl)cyclopentane-1,2-diol Step 1: 3-[2-(benzyloxy)-2-oxoethylidene]cyclobutane-1-carboxylic acid

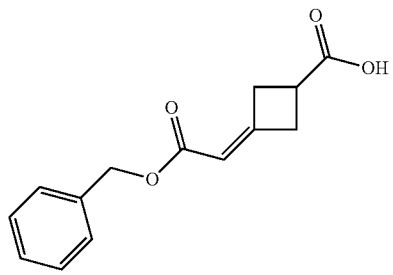 [SMILES: O=C(C=C1CC(C(=O)O)C1)OCc1ccccc1]

A mixture of cyclobutaneone-3-carboxylic acid (5 g, 43.82 mmol), benzyl-2-(dimethoxyphosphorypacetate (13.58 g, 52.59 mmol), LiOH (4.20 g, 23.95 mmol) and 3 Å activated molecular sieves (25 g, powder form) in THF (250 ml) was heated to reflux under nitrogen for 4 h. The reaction was allowed to cool to RT and EtOAc (100 ml) followed by HCl (1N, 100 ml) were added. This mixture was filtered through celite. The phases were separated and the aqueous layer was extracted with EtOAc (4×50 ml). The combined organic layers were dried over Na$_2$SO$_4$, filtered and concentrated to yield a colorless oil. Dry flash chromatography over SiO$_2$, eluting with Hept:EtOAc from 7:3 to 1:1 gave the desired product as a colorless oil (5.2 g, 39%); MS (ESI$^+$) for C$_{14}$H$_{14}$O$_4$ m/z 269.05 [M+Na]$^+$; MS (ESI$^-$) for C$_{14}$H$_{14}$O$_4$ m/z 245.15 [M−H]$^-$; HPLC purity 81% (ret. time, 1.85 min); $^1$H NMR (250 MHz, CHLOROFORM-d) δ$_H$ ppm 2.95-3.62 (5H, m), 4.96-5.31 (2H, m), 5.75 (1H, t, J=2.21 Hz), 7.27-7.45 (5H, m).

Step 2. benzyl 2-{3-[methoxy(methyl)carbamoyl] cyclobutylidene}acetate

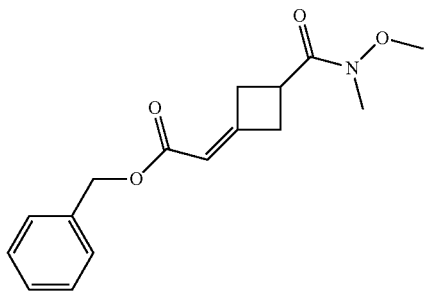 [SMILES: CON(C)C(=O)C1CC(=CC(=O)OCc2ccccc2)C1]

To an ice cold solution of 3-[2-(benzyloxy)-2-oxoethylidene]cyclobutane-1-carboxylic acid (2.0 g, 8.12 mmol), N-Methyl-morpholine (2.70 ml, 24.36 mmol) in DCM (50 ml) was added isobutyl chloroformate (1.70 ml, 12.99 mmol) drop-wise over 5 min. After an additional 5 min, methoxy (methyl)amine hydrochloride (1.58 g, 16.24 mmol) was added and the mixture was stirred overnight whislt allowing to warm to RT. The reaction mixture was then diluted with DCM (30 ml), washed with 0.1N HCl (50 ml) then sat. NaHCO$_3$ (50 ml), dried over Na$_2$SO$_4$, filtered and evaporated. Purification by silica gel column chromatography, eluting with EtOAc:heptanes from 1:9 to 3:7 gave the desired product (1.54 g, 65%); MS (ESI$^+$) for C$_{16}$H$_{19}$NO$_4$ m/z 290.10 [M+H]$^+$; HPLC purity 100% (ret. time, 1.86 min); $^1$H NMR (500 MHz, CHLOROFORM-d) $\delta_H$ ppm 2.96 (1H, ddd, J=16.98, 8.79, 1.81 Hz), 3.17-3.30 (4H, m), 3.30-3.48 (2H, m), 3.51-3.63 (1H, m), 3.64-3.75 (3H, m), 5.15 (2H, s), 5.73 (1H, quin, J=2.25 Hz), 7.29-7.42 (5H, m).

Step 3. 2-{3-[methoxy(methyl)carbamoyl] cyclobutyl}acetic acid

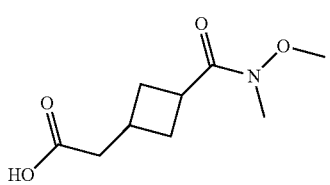

Palladium on charcoal (10%, 0.1 g) was added to a solution of benzyl 2-{3-[methoxy(methyl)carbamoyl] cyclobutyldene}acetate (1.54 g, 5.32 mmol) in EtOH (20 ml) and stirred under an atmosphere of hydrogen at RT for 6 h. The reaction mixture was filtered through celite and evaporated to dryness to give a colorless oil (1.04 g, 89%); MS (ESI$^+$) for C$_9$H$_{15}$NO$_4$ m/z 202.00 [M+H]$^+$; MS (ESI)$^-$ for C$_9$H$_{15}$NO$_4$ m/z 200.05 [M–H]$^-$; HPLC purirty 92% (ret. time, 1.10 min); $^1$H NMR (500 MHz, MeOD) $\delta_H$ ppm 1.84-2.08 (2H, m), 2.28-2.53 (4H, m), 2.56-2.72 (1H, m), 3.06-3.22 (3H, m), 3.38-3.56 (1H, m), 3.68 (3H, d, J=8.04 Hz).

Step 4i. 3-({[2-amino-5-(trifluoromethyl)phenyl] carbamoyl}methyl)-N-methoxy-N-methylcyclobutane-1-carboxamide

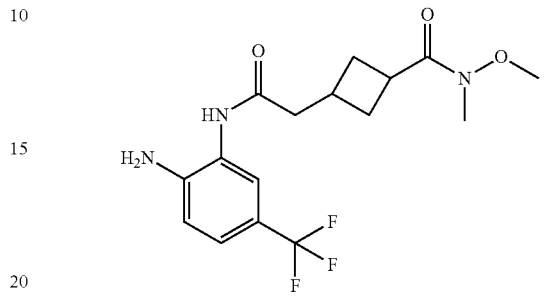

TEA (1.49 ml, 10.70 mmol) was added to a suspension of 2-{3-[methoxy(methyl)carbamoyl]cyclobutyl}acetic acid, EDC.HCl 1.18 g, 6.20 mmol), HOBt.xH$_2$O (0.77 g, 5.69 mmol) in DCM (20 ml) at 0° C. and stirred for 5 min before the addition of 4-(trifluoromethyl)benzene-1,2-diamine (1.04 g, 10.34 mmol). This was stirred for a further 20 min at 0° C. then allowed to warm to RT. The reaction was monitored by LC MS, after 2 hours the reaction mixture was washed with 1N HCl (50 ml) then sat. NaHCO$_3$ (50 ml). This was dried over Na$_2$SO$_4$, filtered and evaporated to dryness. Purification by silica gel column chromatography, eluting with EtOAc gave the desired product (0.83 g, 44%) as a beige solid; MS (ESI$^+$) for C$_{16}$H$_{20}$N$_3$O$_3$ m/z 360.00 [M+H]$^+$; HPLC purirty 90% (ret. time, 1.64 min); $^1$H NMR (500 MHz, MeOD) $\delta_H$ ppm 2.02-2.16 (2H, m), 2.31-2.68 (4H, m), 2.69-2.88 (1H, m), 3.18 (3H, d, J=4.41 Hz), 3.36-3.59 (1H, m), 3.65-3.76 (3H, m), 6.81-6.97 (1H, m), 7.02-7.27 (1H, m), 7.28-7.48 (1H, m).

Step 4ii. N-methoxy-N-methyl-3-{[5-(trifluoromethyl)-1H-1,3-benzediazol-2-yl]methyl}-cyclobutane-1-carboxamide

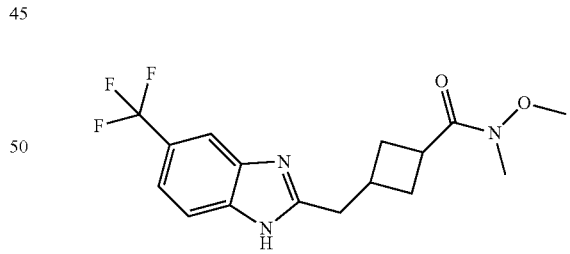

A solution of the 3-({[2-amino-5-(trifluoromethyl)phenyl] carbamoyl}methyl)-N-methoxy-N-methylcyclobutane-1-carboxamide (0.82 g, 2.29 mmol) in AcOH (10 ml) was heated to reflux (~125° C.) whilst stirring for 2.5 h. The reaction was monitored by LC MS. The reaction mixture was allowed to cool to RT and then evaporated in vacuo. The residue was dissolved in DCM (30 ml) and washed with sat. NaHCO$_3$ (50 ml), dried over Na$_2$SO$_4$, filtered and evaporated. The crude was purified by silica gel column chromatography, eluting with MeOH:DCM (2:98-5:95) to give a yellow-brown oil (0.75 g, 94%); MS (ESI$^+$) for C$_{16}$H$_{18}$F$_3$N$_3$O$_2$ m/z 342.10 [M+H]$^+$; HPLC purirty 97% (ret. time, 1.40 min); NMR (500

MHz, MeOD) $\delta_H$ ppm 1.96-2.17 (2H, m), 2.27-2.55 (2H, m), 2.66-2.92 (1H, m), 2.97-3.15 (2H, m), 3.15-3.22 (3H, m), 3.32-3.62 (1H, m), 3.63-3.73 (3H, m), 7.37-7.53 (1H, m), 7.53-8.00 (2H, m).

Step 5. N-methoxy-N-methyl-3-{[5-(trifluoromethyl)-1-{[2-(trimethylsilyl)ethoxy]methyl}-1H-1,3-benzodiazol-2-yl]methyl}cyclobutane-1-carboxamide

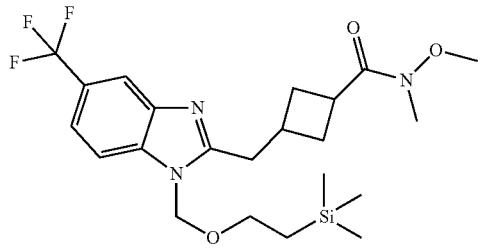 [SMILES: CON(C)C(=O)C1CC(Cc2nc3cc(C(F)(F)F)ccc3n2COCC[Si](C)(C)C)C1]

K$_2$CO$_3$ (381 mg, 2.76 mmol), followed by SEM-0 (430 µl, 2.43 mmol) was added to a solution of the N-methoxy-N-methyl-3-{[5-(trifluoromethyl)-1H-1,3-benzodiazol-2-yl]methyl}cyclobutane-1-carboxamide (754 mg, 2.21 mmol) in DMF (10 ml) at RT and stirred overnight. The reaction was monitored by LCMS. The reaction mixture was diluted with water (3 ml), brine (30 ml) and then extracted with EtOAc (2×50 ml). This was dried over Na$_2$SO$_4$, filtered and evaporated to give a clear orange oil. Purification by silica gel column chromatography, eluting with EtOAc:heptanes (1:1-1) gave the desired products as a beige oils as a single regioisomer (217 mg, 21%); MS (ESI$^+$) for C$_{22}$H$_{32}$F$_3$N$_3$O$_3$Si m/z 472.55 [M+H]$^+$; HPLC purirty 99% (ret. time, 2.37 min); $^1$H NMR (250 MHz, CHLOROFORM-d) $\delta_H$ ppm −0.31-0.22 (9H, m), 0.83-1.00 (2H, m), 2.03-2.25 (2H, m), 2.30-2.74 (2H, m), 2.85-3.14 (3H, m), 3.18 (3H, s), 3.32-3.60 (3H, m), 3.61-3.72 (3H, m), 5.52 (2H, s), 7.51 (1H, dd, J=8.38, 1.22 Hz), 7.70 (1H, s), 7.79 (1H, d, J=8.53 Hz) and as a mixture of regioisomers (280 mg, 27%); C$_{22}$H$_{32}$F$_3$N$_3$O$_3$Si m/z 472.55 [M+H]$^+$; HPLC purirty 72% & 21% (ret. time, 2.39 & 2.36 min); $^1$H NMR (250 MHz, CHLOROFORM-d) $\delta$ ppm −0.08--0.01 (9H, m), 0.81-0.99 (2H, m), 1.94-2.24 (2 m), 2.38-2.74 (2H, m), 2.90-3.14 (3H, m), 3.14-3.22 (3H, m), 3.33-3.63 (3H, m), 3.63-3.70 (3H, m), 5.40-5.64 (2H, m), 7.40-7.74 (2H, m), 7.75-8.14 (1H, m).

Step 6. 3-{[5-(trifluoromethyl)-1-{[2-(trimethylsilyl)ethoxy]methyl}-1H-1,3-benzodiazol-2-yl]methyl}cyclobutane-1-carbaldehyde

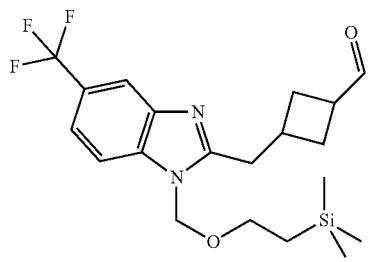 [SMILES: C[Si](C)(C)CCOCn1c(CC2CC(C=O)C2)nc2cc(C(F)(F)F)ccc21]

DIBAL (0.69 ml, 0.69 mmol, 1M in THF) was added dropwise to a solution of N-methoxy-N-methyl-3-{[5-(trifluoromethyl)-1-{[2-(trimethylsilyl)ethoxy]methyl}-1H-1,3-benzodiazol-2-yl]methyl}cyclobutane-1-carboxamide in THF at −10° C. whilst stirring. The reaction was continued for 3 hours at −10° C. The reaction mixture was poured onto sat. aq. Rochelle's salt (20 ml), diluted with Et$_2$O (50 ml) and stirred for 30 min. This was then separated and the organic layer was washed with Rochelle's salt (30 ml), sat. NaHCO$_3$, (30 ml) and brine (30 ml). This was dried over Na$_2$SO$_4$, filtered and evaporated to give a colorless gum (190 mg, 87%); MS (ESI$^+$) for C$_{20}$H$_{27}$F$_3$N$_2$O$_2$Si m/z 413.6 [M+H]$^+$; HPLC purirty 87% (ret. time, 2.25 min); $^1$H NMR (500 MHz, CHLOROFORM-d) $\delta_H$ ppm −0.10-0.09 (9H, m), 0.88-1.00 (4H, m), 1.63-1.97 (2H, m), 2.07-2.23 (2H, m), 2.24-2.37 (0H, m), 2.37-2.42 (1H, m), 2.43-2.66 (2H, m), 2.93-3.34 (4H, m), 5.49-5.61 (2H, m), 7.16-7.31 (2H, m), 7.32-7.32 (2H, m), 7.49-7.61 (1H, m), 7.73 (1H, s), 7.83 (1H, d, J=8.35 Hz).

Step 7. 7-[(3aS,4R,6R,6aR)-2,2-dimethyl-6-({[(3-{5-(trifluoromethyl)-1-{[2-(trimethylsilyl)ethoxy]methyl}-1H-1,3-benzodiazol-2-yl]methyl}cyclobutyl)methyl]amino}methyl)-hexahydrocyclopenta[d][1,3]dioxol-4-yl]-7H-pyrrolo[2,3-d]pyrimidin-4-amine

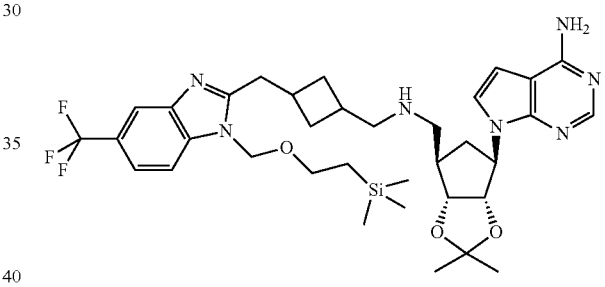

A solution of 3-{[5-(trifluoromethyl)-1-{[2-(trimethylsilyl)ethoxy]methyl}-1H-1,3-benzodiazol-2-yl]methyl}cyclobutane-1-carbaldehyde (190 mg, 0.46 mmol), (1R,2S,3R,5R)-3-{4-amino-7H-pyrrolo[2,3-d]pyrimidin-7-yl}-5-(aminomethyl)cyclopentane-1,2-diol (140 mg, 0.46 mmol) and MgSO$_4$ (554 mg, 4.61 mmol) in DCE (10 ml) was stirred for 15 min. STAB (137 mg, 0.645 mmol) was then added to the reaction mixture and stirred. The reaction was monitored by LCMS, after which no amine was seen. Sat. NaHCO$_3$ (20 ml) was added to the reaction mixture and stirred for 5 mins. Brine (10 ml) was added to the reaction mixture and the product was extracted with DCM (2×30 ml), dried over Na$_2$SO$_4$, filtered and evaporated. Purification by silica gel column chromatography, eluting with 7N NH$_3$ in MeOH:DCM (1:99-5:95) gave the desired product as a pink foamy solid. The mixed fractions were combined and purified on a prep. TLC plate eluting with 7N NH$_3$ in MeOH:DCM (2×4:96) to give a total of 170 mg, 53%. MS (ESI$^+$) for C$_{35}$H$_{48}$F$_3$N$_7$O$_3$Si m/z 700 [M+H]$^+$; HPLC purirty 100% (ret. time, 1.79 min); $^1$H NMR (250 MHz, CHLOROFORM-d) $\delta_H$ ppm −0.26-0.16 (9H, m), 0.72-0.97 (2H, m), 1.30 (3H, s), 1.38-1.60 (5H, m), 1.91-2.59 (8H, 2.60-3.27 (6H, m), 3.35-3.70 (4H, m), 4.52 (1H, t, J=5.94 Hz), 4.78-5.20 (4H, m), 5.39-5.66 (2H, m), 6.36 (1H, d, J=3.65 Hz), 7.03 (1H, d, J=3.65 Hz), 7.42-7.59 (1H, m), 7.69 (1H, s), 7.79 (1H, d, J=8.53 Hz), 8.32 (1H, s).

Step 8. 7-[(3 aS,4R,6R,6 aR)-2,2-dimethyl-6-({methyl[(3-{[5-(trifluoromethyl)-1-{[2-(trimethylsilyl)ethoxy]methyl}-1H-1,3-benzodiazol-2-yl]methyl}cyclobutyl)methyl]amino}methyl)-hexahydrocyclopenta[d][1,3]dioxol-4-yl]-7H-pyrrolo[2,3-d]pyrimidin-4-amine

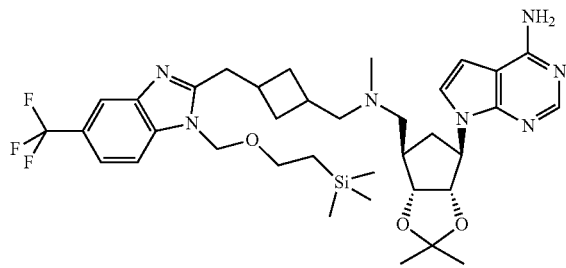 [SMILES: CN(CC1CC(Cc2nc3cc(C(F)(F)F)ccc3n2COCC[Si](C)(C)C)C1)C[C@H]1C[C@@H](n2ccc3c(N)ncnc32)[C@@H]2OC(C)(C)O[C@H]12]

Formaldehyde (36 μl, 0.49 mmol, 37%$_{(aq)}$) was added to a solution of 7-[(3aS,4R,6R,6aR)-2,2-dimethyl-6-({[(3-{[5-(trifluoromethyl)-1-{[2-(trimethylsilyl)ethoxy]methyl}-1H-1,3-benzodiazol-2-yl]methyl}cyclobutyl)methyl]amino}methyl)-hexahydro cyclopenta[d][1,3]dioxol-4-yl]-7H-pyrrolo[2,3-d]pyrimidin-4-amine in MeOH (5 ml) and THF (5 ml), and the reaction was stirred at RT for 30 mins. NaCNBH$_3$ (18 mg, 0.29 mmol) was added portionwise, and the reaction stirred for a further 2 hours at RT after which LC MS showed the reaction to be complete. The reaction mixture was concentrated under in vacuo, and the residue partitioned between water (20 ml) and DCM (20 ml) and the layers were separated. The aqueous layer was extracted with DCM (2×20 ml), the combined organics were then dried over Na$_2$SO$_4$, and concentrated. Purification by prep. TLC, eluting with 7N NH$_3$ in MeOH:DCM (5:95) gave the desired product (114 mg, 66%) as a colourless oil; MS (EST$^+$) for C$_{36}$H$_{50}$F$_3$N$_7$O$_3$Si m/z 714.45 [M+H]$^+$; HPLC purity 100% (ret. time, 1.77 min); $^1$H NMR (500 MHz, CHLOROFORM-d) δ$_H$ ppm −0.14-0.05 (9H, m), 0.85-0.99 (2H, m), 1.18-1.35 (3H, m), 1.37-1.53 (2H, m), 1.52-1.64 (3H, m), 1.89-2.15 (3H, m), 2.18-2.28 (2H, m), 2.29-2.70 (6H, m), 2.72-2.96 (1H, m), 2.97-3.20 (2H, m), 3.48 (3H, s), 3.50-3.58 (2H, m), 4.37-4.58 (1H, m), 4.85-5.05 (2H, m), 5.11-5.38 (2H, m), 5.41-5.57 (2H, m), 6.35 (1H, d, J=3.63 Hz), 6.84-7.19 (1H, m), 7.50 (1H, d, J=8.35 Hz), 7.68 (1H, s), 7.78 (1H, d, J=8.35 Hz), 8.13-8.52 (1H, m)

Step 9. (1R,2S,3R,5R)-3-{4-amino-7H-pyrrolo[2,3-d]pyrimidin-7-yl}-5-({methyl[(3-{[5-(trifluoromethyl)-1H-1,3-benzodiazol-2-yl]methyl}cyclo butyl)methyl]amino}methyl)cyclopentane-1,2-diol

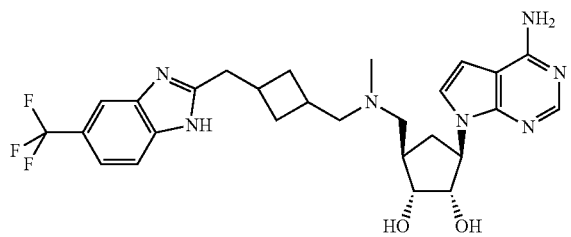 [SMILES: CN(CC1CC(Cc2nc3cc(C(F)(F)F)ccc3[nH]2)C1)C[C@H]1C[C@@H](n2ccc3c(N)ncnc32)[C@H](O)[C@@H]1O]

A solution of HCl in MeOH (1:1, 3 ml) was added to 7-[(3aS,4R,6R,6aR)-2,2-dimethyl-6-({methyl[(3-{[5-(trifluoromethyl)-1-{[2-(trimethylsilyl)ethoxy]methyl}-1H-1,3-benzodiazol-2-yl]methyl}cyclobutyl)methyl]amino}methyl)-hexahydro cyclopenta[d][1,3]dioxol-4-yl]-7H-pyrrolo[2,3-d]pyrimidin-4-amine at 0° C. and stirred. This was then immediately stirred at 40° C. for 4 h (reaction monitored by LCMS) The reaction was continued for a further 1 h. LCMS still showed 30% acetal deprotected SM. A further 1 ml of HCl (36% aq) was added to the reaction mixture and continued at 40° C. for a further 1 h. The reaction mixture was then evaporated in vacuo. The residue was dissolve in DCM (100 ml)+MeOH (1 ml) and washed with sat. NaHCO$_3$ (2×50 ml), dried over Na$_2$SO$_4$, filtered and evaporated. Purification by prep. TLC, eluting with 7N NH$_3$ in MeOH:DCM (1:9); MS (ESI$^+$) for C$_{27}$H$_{32}$F$_3$N$_7$O$_2$ m/z 544 [M+H]$^+$; HPLC purirty 96% (ret. time, 2.03 min); $^1$H NMR (500 MHz, MeOD) δ$_H$ ppm 1.47-1.58 (1H, m), 1.58-1.69 (1H, m), 1.87-2.12 (1H, m), 2.12-2.54 (10H, m), 2.53-2.91 (3H, m), 2.93-3.15 (2H, m), 3.88-4.08 (1H, m), 4.32 (1H, dd, J=7.57, 6.15 Hz), 4.88-5.01 (1H, m), 6.59 (1H, d, J=3.63 Hz), 7.20 (1H, d, J=3.63 Hz), 7.42-7.53 (1H, m), 7.63 (1H, d, J=8.20 Hz), 7.79 (1H, s), 7.95-8.22 (1H, m).

Compound 19: 7-((3aS,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine A solution of 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isopropyl)amino)cyclobutyl)propanoic acid (490 mg, 0.79 mmol) and 4-tert-butylbenzene-1,2-diamine (155 mg, 0.946 mmol) in N,N-Dimethylformamide (8.1 ml) was treated with N,N-Diisopropylethylamine (0.453 ml, 2.60 mmol) dropwise followed by N,N,N',N'-Tetramethyl-0-(7-azabenzotriazol-1-yl)uronium Hexafluorophosphate (449 mg, 1.18 mmol) in one portion. The reaction mixture was stirred at RT overnight. The reaction mixture was concentrated under high vacuum and the residue was partitioned between 50 ml EtOAc and 50 ml 1/1 H$_2$O/sat NaHCO$_3$. The aqueous phase was extracted with 30 ml EtOAc and the combined organic phase was washed with 30 ml portions of H$_2$O and brine. The organic phase was dried over Na$_2$SO$_4$, filtered and concentrated to give a glass/stiff foam. The crude material was purified by flash chromatography (SiO$_2$, eluting with 4% 7N N NH$_3$ in CH$_3$OH/CH$_2$Cl$_2$) to give the desired intermediate as a mixture of amide regioisomers (400 mg). A solution of intermediate (0.40 g) in Acetic acid (15 ml) was heated at 65° C. for 2.5 h, the reaction mixture was cooled and placed under high vacuum to remove the acetic acid. The residue was taken up in 60 ml CH$_2$Cl$_2$ and washed with 40 ml portions of sat NaHCO$_3$ and 2% Na$_2$CO$_3$ solution. The organic phase was dried over Na$_2$SO$_4$, filtered and concentrated to yield a glass/stiff foam. The material was placed on high vacuum and used directly in the next step (380 mg)

(1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(isopropyl)amino)methyl)cyclopentane-1,2-diol

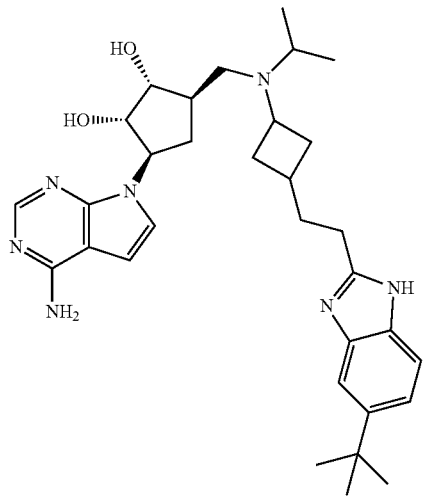 [SMILES: CC(C)N(C[C@H]1C[C@@H](n2ccc3c(N)ncnc32)[C@H](O)[C@@H]1O)C1CC(CCc2nc3cc(C(C)(C)C)ccc3[nH]2)C1]

7-((3aS,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (390 mg, 0.52 mmol) was dissolved in a mixture of Trifluoroacetic Acid (7.2 ml) and Water (0.8 ml) which had been pre-cooled at 0° C. in an ice bath. The solution was stirred at 0° C. for 30 minutes, then warmed to RT After 2.5 at RT the residue was taken up in 15 ml MeOH and concentrated. This procedure was repeated twice and the residue placed on high vacuum. The material was taken up in 15 ml MeOH (gave a slurry) and was treated with 500 mg $K_2CO_3$ and 8 drops of water. The mixture was allowed to stir for 1 hr, during which time the solution was found to be basic. The mixture was filtered through a finefrit, the solids were washed with 10 ml MeOH and the filtrate was concentrated to yield an offwhite solid. The material was left on high vacuum overnight. The crude material was purified by flash chromatography (SiO₂, eluting with 8-10% 7N NH₃ in CH₃OH/CH₂Cl₂) to give a glass/stiff foam (0.22 g). ¹H NMR (400 MHz, MeOD) $\delta_H$ ppm 8.06 (s, 1H), 7.48 (br. s., 1H), 7.39 (m, 1H), 7.27 (m, 1H), 7.20 (d, J=3.52 Hz, 1H), 6.60 (m, 1H), 4.32 (t, J=6.43 Hz, 1H), 3.93 (t, J=5.29 Hz, 1H), 3.54 (m, 0.2H), 3.11 (t, J=9.33 Hz, 1H), 3.02 (m, 1H), 2.82 (m, 2H), 2.66 (dd, J=13.68, 8.09 Hz, 1H), 2.46 (m, 1H), 2.36 (m, 1H), 2.23 (m, 3H), 2.05 (m, 1H), 1.91 (m, 3H), 1.59 (m, 3H), 1.36 (s, 9H), 1.02 (m, 6H).

Compound 20: (1R,2S,3R,5R)-3-(4-amino-7H-pyrrolo[2,3-d]pyrimidin-7-yl)-5-(((3-(2-(6-chloro-5-(trifluoromethyl)-1H-benzo[d]imidazol-2-yl)ethyl)cyclobutyl)(isopropyl)amino)methyl)cyclopentane-1,2-diol 7-((3aS,4R,6R,6aR)-6-(((3-(2-(6-chloro-5-(trifluoromethyl)-1H-benzo[d]imidazol-2-yl)ethyl)cyclobutyl)(isopropyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

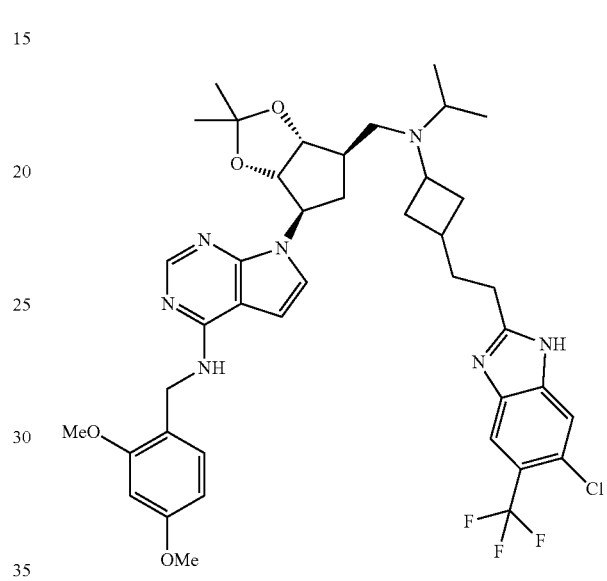

A solution of 3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isopropyl)amino)cyclobutyl)propanoic acid (78.5 mg, 0.126 mmol) and 4-chloro-5-(trifluoromethyl)benzene-1,2-diamine (31.9 mg, 0.151 mmol) in N,N-Dimethylformamide (1.3 ml) was treated with N,N-Diisopropylethylamine (72.5 ul, 0.416 mmol dropwise followed by N,N,N',N'-Tetramethyl-0-(7-azabenzotriazol-1-yl)uronium Hexafluorophosphate (72.0 mg, 0.189 mmol) in one portion. The reaction mixture was stirred at RT for 7.5 h. The reaction mixture was placed in the fridge overnight. The reaction mixture was concentrated under high vacuum and the residue was partitioned between 20 ml EtOAc and 20 ml 1/1 H₂O/sat NaHCO₃. The aqueous phase was extracted with 10 ml EtOAc and the combined organic phase was washed with 10 ml portions of H₂O and brine. The organic phase was dried over Na₂SO₄, filtered and concentrated. The crude material was purified by flash chromatography (SiO₂, eluting with 3% 7N NH₃ in CH₃OH/CH₂Cl₂) to give the desired intermediate as a glass/stiff foam (regiosomeric amides and the cis/trans diastereomers, 87 mg). The intermediate (0.087 g) was taken up in in Acetic acid (4.5 ml) was heated at 65° C. for 6 h, it was cooled to RT and stirred at RT for 48 hr. The reaction was heated at 65° C. for 8 hr, then at RT o/n then at 65° C. for a further 6.5 h. The mixture was cooled and placed under high vacuum to remove the acetic acid. The residue was taken up in 15 ml CH₂Cl₂ and washed with 10 ml portions of sat. NaHCO₃ and 2% Na₂CO₃ solution. The organic phase was dried over Na₂SO₄, filtered and concentrated to yield a glass/stiff foam. The material was placed on high vacuum overnight. The crude material was purified by prep TLC on a 20 cm×20 cm×1.0 mm prep TLC plate eluting twice with 4% 7N NH₃ in CH₃OH/CH₂Cl₂. The product band was isolated to yield the product as a white solid (48 mg).

(1R,2S,3R,5R)-3-(4-amino-7H-pyrrolo[2,3-d]pyrimidin-7-yl)-5-(((3-(2-(6-chloro-5-(trifluoromethyl)-1H-benzo[d]imidazol-2-yl)ethyl)cyclobutyl)(isopropyl)amino)methyl)cyclopentane-1,2-diol

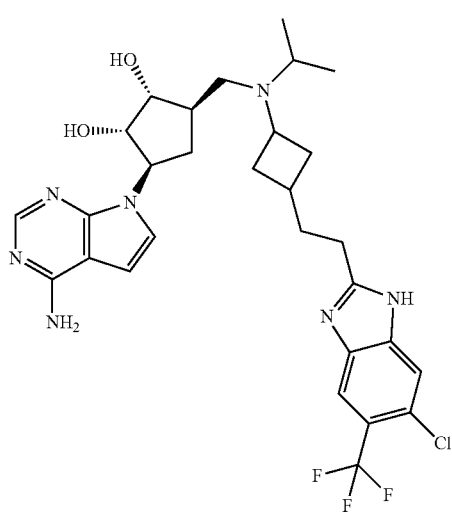 [SMILES: CC(C)N(C[C@H]1C[C@@H](n2ccc3c(N)ncnc32)[C@H](O)[C@@H]1O)C1CC(CCc2nc3cc(C(F)(F)F)c(Cl)cc3[nH]2)C1]

7-((3aS,4R,6R,6aR)-6-(((3-(2-(6-chloro-5-(trifluoromethyl)-1H-benzo[d]imidazol-2-yl)ethyl)cyclobutyl)(isopropyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (525 mg, 0.683 mmol) was dissolved in a mixture of Trifluoroacetic Acid (9 ml) and Water (1 ml) which had been pre-cooled at 0° C. in an ice bath. The solution was stirred at 0° C. for 30 minutes, then warmed to RT. After 4 h at RT, the mixture was concentrated. The residue was taken up in 20 ml MeOH and concentrated. This procedure was repeated twice and the residue placed on high vacuum. The material was taken up in 15 ml MeOH (gave a slurry) and was treated with 500 mg K₂CO₃ and 15 drops of water. The mixture was allowed to stir for 1 hr, during which time the solution was found to be basic. The mixture was filtered through a fine frit, the solids were washed with 10 ml MeOH and the filtrate was concentrated to yield an off white solid. The material was left on high vacuum overnight. The crude material was purified by flash chromatography (SiO₂, eluting with 12% 7N NH₃ in CH₃OH/CH₂Cl₂) to give a colorless glass/stiff foam. ¹H NMR (400 MHz, MeOD) $\delta_H$ ppm 8.06 (s, 1H), 7.89 (d, J=2.07 Hz, 1H), 7.69 (d, J=2.28 Hz, 1H), 7.21 (dd, J=3.42, 1.76 Hz, 1H), 6.59 (d, J=3.52 Hz, 1H), 4.33 (t, J=6.84 Hz, 1H), 3.89 (q, J=5.25 Hz, 1H), 3.03 (m, 0.5H), 2.89 (m, 2H), 2.70 (m, 0.5H), 2.49 (m, 1H), 2.40 (m, 2H), 2.27 (br. s., 2H), 2.16 (d, J=7.26 Hz, 4H), 2.06 (m, 2H), 1.91 (m, 2H), 1.62 (m, 1H), 1.52 (m, 1H).

Compound 21: (1R,2S,3R,5R)-3-{4-amino-7H-pyrrolo[2,3-d]pyrimidin-7-yl}-5-({[(3-{[6-chloro-5-(trifluoromethyl)-1H-1,3-benzodiazol-2-yl]methyl}cyclobutyl)methyl](propan-2-yl)amino}methyl)cyclopentane-1,2-diol Step 1: 7-[(3aS,4R,6R,6aR)-6-({[(3-{[6-chloro-5-(trifluoromethyl)-1-{[2-(trimethylsilyl)ethoxy]methyl}-1H-1,3-benzodiazol-2-yl]methyl}cyclobutyl)methyl](propan-2-yl)amino}methyl)-2,2-dimethyl-hexahydrocyclopenta[d][1,3]dioxol-4-yl]-7H-pyrrolo[2,3-d]pyrimidin-4-amine

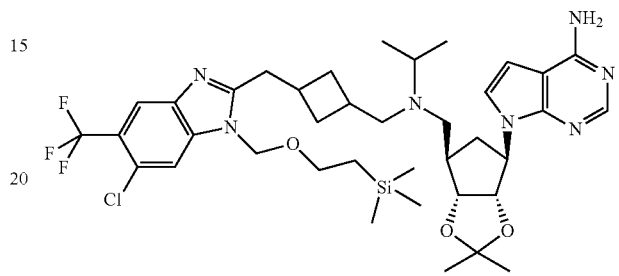

A solution of 3-{[6-chloro-5-(trifluoromethyl)-1-{[2-(trimethylsilyl)ethoxy]methyl}-1H-1,3-benzodiazol-2-yl]methyl}cyclobutane-1-carbaldehyde (223 mg, 0.50 mmol), 7-[(3aS,4R,6R,6aR)-2,2-dimethyl-6-[(propan-2-ylamino)methyl]-hexahydrocyclopenta[d][1,3]dioxol-4-yl]-7H-pyrrolo[2,3-d]pyrimidin-4-amine (172 mg, 0.50 mmol) and MgSO₄ (600 mg, 5.00 mmol) in DCE (10 ml) was stirred for 15 min. STAB (148 mg, 0.70 mmol) was then added to the reaction mixture and stirred for 1 h at RT. The reaction was monitored by LCMS, no amine was seen after 2.5 h. Sat. NaHCO₃ (20 ml) was added to the reaction mixture and stirred for 5 mins. Brine (20 ml) was then added to the reaction mixture. The product was extracted with DCM (2×30 ml), dried over Na₂SO₄, filtered and evaporated. Purification by prep. HPLC gave the desired product (174 mg, 45%) as a white solid; MS (ESI⁺) for C₃₈H₅₃ClF₃N₇O₃Si m/z 776.30 [M+H]⁺; HPLC purity 100% (ret. time, 1.68 min); ¹H NMR (500 MHz, MeOD) $\delta_H$ ppm −0.25-0.11 (9H, m), 0.90 (2H, td, J=7.88, 3.47 Hz), 1.30 (3H, s), 1.37 (6H, t, J=7.49 Hz), 1.55 (3H, s), 1.63-1.84 (1H, m), 1.99-2.37 (2H, m), 2.37-3.03 (6H, m), 3.04-3.28 (3H, m), 3.34-3.50 (1H, m), 3.61 (2H, td, J=7.92, 2.29 Hz), 3.79 (1H, br. s.), 4.68 (1H, t, J=6.70 Hz), 4.95-5.27 (2H, m), 5.55-5.81 (1H, m), 6.88 (1H, d, J=3.63 Hz), 7.06-7.62 (2H, m), 7.61-7.94 (1H, m), 7.94-8.16 (1H, m), 8.22 (1H, s)

Step 2. (1R,2S,3R,5R)-3-{4-amino-7H-pyrrolo[2,3-d]pyrimidin-7-yl}-5-({[(3-{[6-chloro-5-(trifluoromethyl)-1H-1,3-benzodiazol-2-yl]methyl}cyclobutyl)methyl](propan-2-yl)amino}methyl)cyclopentane-1,2-diol

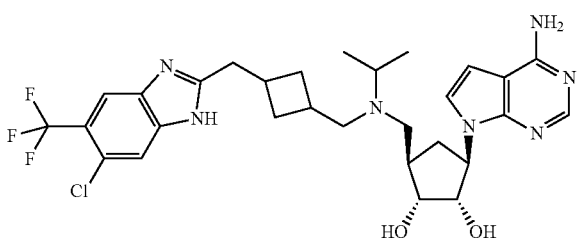 [SMILES: CC(C)N(CC1CC(Cc2nc3cc(C(F)(F)F)c(Cl)cc3[nH]2)C1)C[C@H]1C[C@@H](n2ccc3c(N)ncnc32)[C@H](O)[C@@H]1O]

12N HCl (1.5 ml) was added slowly to a solution of 7-[(3aS,4R,6R,6aR)-6-({[(3-{[6-chloro-5-(trifluoromethyl)-1-{[2-(trimethylsilyl)ethoxy]methyl}-1H-1,3-benzodiazol-2-yl]methyl}cyclobutyl)methyl](propan-2-yl)amino]methyl)-2,2-dimethyl-hexahydrocyclopenta[d][1,3]dioxol-4-yl]-7H-pyrrolo[2,3-d]pyrimidin-4-amine (174 mg, 0.22 mmol) in MeOH (1.5 ml) and stirred at 40° C. for 6 h. The reaction was monitored by LCMS, no starting material seen after 2.5 h. The reaction mixture was concentrated in vacuo, then basified with 7N NH$_3$ in MeOH (5 ml). This was then evaporated to dryness. Purification by silica gel column chromatography, eluting with 7N NH$_3$ in MeOH:DCM (1:9) gave the desired product (36 mg, 27%) as a white solid; MS (ESI$^+$) for C$_{29}$H$_{35}$ClF$_3$N$_7$O$_2$ m/z 606.30 [M+H]$^+$; HPLC purity 100% (ret. time, 2.59 min); $^1$H NMR (500 MHz, MeOD) δ$_H$ ppm 0.93-1.09 (6H, m), 1.41-1.64 (2H, m), 1.76-2.06 (1H, m), 2.15-2.65 (9H, m), 2.65-2.88 (1H, m), 2.91-3.13 (3H, m), 3.80-4.09 (1H, m), 4.19-4.46 (1H, m), 4.88-4.94 (1H, m), 6.46-6.77 (1H, m), 7.19 (1H, d, J=3.63 Hz), 7.69 (1H, s), 7.89 (1H, s), 8.06 (1H, s)

Compound 22: (1R,2S,3R,5R)-3-{4-amino-7H-pyrrolo[2,3-d]pyrimidin-7-yl}-5-{[({3-[(5-tert-butyl-1H-1,3-benzodiazol-2-yl)methyl]cyclobutyl}methyl)(propan-2-yl)amino]methyl}cyclopentane-1,2-diol Stage 1: 3-{[(2-amino-4-tert-butylphenyl)carbamoyl]methyl}-N-methoxy-N-methylcyclobutane-1-carboxamide

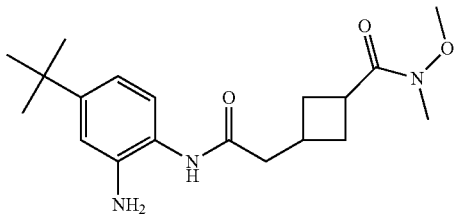 [SMILES: CON(C)C(=O)C1CC(CC(=O)Nc2ccc(C(C)(C)C)cc2N)C1]

N,N-Diisopropylethylamine (5.19 ml, 29.82 mmol) was added to a suspension of 2-{3-[methoxy(methyl)carbamoyl]cyclobutyl}acetic acid (3 g, 14.91 mmol), 4-tBu phenylene diamine (2.69 g, 16.4 mmol) and (1-cyano-2-ethoxy-2-oxo-ethylidenaminooxy)dimethylamino-morpholino-carbenium hexafluorophosphate (7.02 g, 16.4 mmol) in dichloromethane (60 ml) at 0° C. and stirred for 20 mins before being allowed to warm to RT. The reaction was left at RT for 4 h. The reaction mixture was concentrated, and the residue redissolved in EtOAc (60 ml). The solution was washed with water (3×60 ml), then brine (60 ml), dried (MgSO$_4$) and concentrated under reduced pressure. The crude material was purified by dry flash chromatography, eluting with 100% EtOAc to afford the title compound (3.74 g, 46%) as a brown oil: MS (ESI$^+$) for C$_{19}$H$_{29}$N$_3$O$_3$ m/z 348.5 [M+H]$^+$; LC purity 26% and 44% (UV), 18% and 68% (ELS), (ret. time, 1.65 and 1.71 min).

Stage 2: 3-[(5-tert-butyl-1H-1,3-benzodiazol-2-yl)methyl]-N-methoxy-N-methylcyclobutane-1-carboxamide

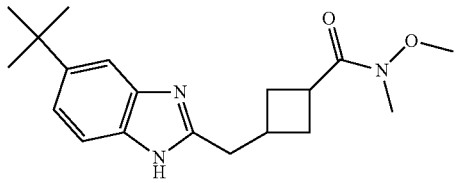 [SMILES: CON(C)C(=O)C1CC(Cc2nc3cc(C(C)(C)C)ccc3[nH]2)C1]

A stirred solution of 3-{[(2-amino-4-tert-butylphenyl)carbamoyl]methyl}-N-methoxy-N-methylcyclobutane-1-carboxamide (70%, 2.62 g, 5.28 mmol) in acetic acid (25 ml) was heated to reflux for 1 h. The reaction mixture was concentrated under reduced pressure, and the residue partitioned between sat. NaHCO$_3$ (aq) (25 ml) and EtOAc (25 ml), and the layers separated. The aqueous layer was extracted with EtOAc (2×25 ml), the combined organics were washed with brine (50 ml), dried (MgSO$_4$) and concentrated. The crude material was purified by silica flash column chromatography, eluting with 1-10% 2M NH$_3$ in MeOH in DCM to afford the title compound (2.02 g, 93%) as a yellow gum: MS (ESI$^+$) for C$_{19}$H$_{27}$N$_3$O$_2$ m/z 330.5 [M+H]$^+$; LC purity 80% (UV), 100% (ELS), (ret. time, 1.51 min); 1H NMR (500 MHz, CHLOROFORM-d) δ$_H$ ppm 7.56 (br. s., 1H), 7.48 (d, J=8.5 Hz, 1H), 7.30 (dd, J=8.5, 1.7 Hz, 1H), 3.80-3.90 (m, 1H), 3.65 (s, 3H), 3.47-3.57 (m, 1H), 3.20 (s, 3H), 2.94-3.13 (m, 2H), 2.88 (dt, J=16.1, 8.1 Hz, 1H), 2.32-2.60 (m, 2H), 2.01-2.17 (m, 2H), 1.38 (s, 9H).

Stage 3: 3-[(5-tert-butyl-1-{[2-(trimethylsilyl)ethoxy]methyl}-1H-1,3-benzodiazol-2-yl)methyl]-N-methoxy-N-methylcyclobutane-1-carboxamide

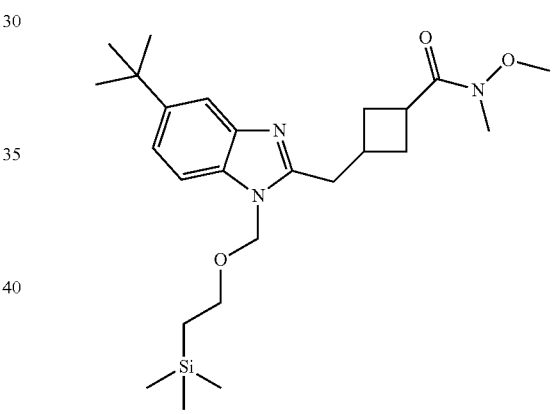

To a solution of 3-[(5-tert-butyl-1H-1,3-benzodiazol-2-yl)methyl]-N-methoxy-N-methylcyclobutane-1-carboxamide (80%, 2.02 g, 4.91 mmol) in N,N-dimethylformamide (40 ml) under N$_2$ was added potassium carbonate (1.36 g, 9.81 mmol) and the reaction was stirred for 1 h. 2-(Trimethylsilyl)ethoxymethyl chloride (1.31 ml, 7.36 mmol) was added slowly, and stirring maintained for 20 h. The reaction mixture was filtered and concentrated under reduced pressure. The residue was taken up in EtOAc (50 ml) and washed with water (3×50 ml), then brine (50 ml) before being dried (MgSO$_4$) and concentrated. The crude material was purified by silica flash column chromatography, eluting with 50-100% EtOAc in heptane to afford the title compound (1.21 g, 54%) as a colourless gum: MS (ESI$^+$) for C$_{25}$H$_{41}$N$_3$O$_3$Si m/z 461.0 [M+H]$^+$; LC purity 97% (UV), 100% (ELS), (ret. time, 1.98 min); $^1$H NMR (500 MHz, CHLOROFORM-d) δ ppm 7.58-7.89 (m, 1H), 7.33 (s, 2H), 5.39-5.53 (m, 2H), 3.65 (s, 3H), 3.49-3.58 (m, 2H), 3.41 (br. s., 1H), 3.10-3.23 (m, 3H), 3.03 (s, 3H), 2.32-2.63 (m, 2H), 2.00-2.18 (m, 2H), 1.32-1.45 (m, 9H), 0.91 (td, J=8.1, 4.9 Hz, 2H), −0.13-0.07 (m, 9H).

Stage 4: 3-[(5-tert butyl-1-{[2-(trimethylsilyl)ethoxy]methyl}-1H-1,3-benzodiazol-2-yl)methyl]cyclobutane-1-carbaldehyde

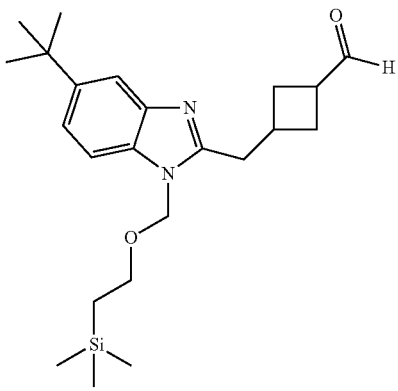 [SMILES: CC(C)(C)c1ccc2c(c1)nc(CC1CC(C=O)C1)n2COCC[Si](C)(C)C]

To a solution of 3-[(5-tert-butyl-1-{[2-(trimethylsilyl)ethoxy]methyl}-1H-1,3-benzodiazol-2-yl)methyl]-N-methoxy-N-methylcyclobutane-1-carboxamide (0.61 g, 1.32 mmol) in tetrahydrofuran (15 ml) was added dropwise 1M diisobutylaluminum hydride solution in toluene (3.29 ml) under $N_2$ at −10° C. The reaction was stirred at this temperature for 2.5 h before being quenched by the addition of methanol (2 ml) and stirred for 5 mins. The solution was poured onto saturated aq. Rochelle's salt (20 ml), diluted with $Et_2O$ (30 ml) and stirred for 30 min. This was then separated and the organic layer was washed with Rochelle's salt (30 ml), sat. $NaHCO_3$ (30 ml), and brine (30 ml). This was dried ($MgSO_4$) and concentrated to afford the title compound (0.69 g, 130%) as a colourless gum which was used crude in the next reaction.

Stage 5: 7-[(3 aS,4R,6R,6 aR)-6-{[({3-[(5-tert-butyl-1-{[2-(trimethylsilyl)ethoxy]methyl}-1H-1,3-benzodiazol-2-yl)methyl]cyclobutyl}methyl)(propan-2-yl)amino]methyl}-2,2-dimethyl-hexahydrocyclopenta[d][1,3]dioxol-4-yl]-7H-pyrrolo[2,3-d]pyrimidin-4-amine

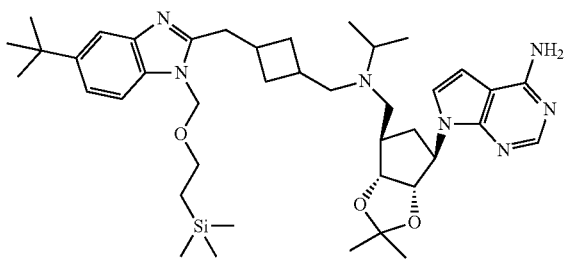 [SMILES: CC(C)N(CC1CC(Cc2nc3cc(C(C)(C)C)ccc3n2COCC[Si](C)(C)C)C1)C[C@H]1C[C@@H](n2ccc3c(N)ncnc32)[C@@H]2OC(C)(C)O[C@H]12]

3-[(5-Tert-butyl-1-{[2-(trimethylsilyl)ethoxy]methyl}-1H-1,3-benzodiazol-2-yl)methyl]cyclobutane-1-carbaldehyde (282.3 mg, 0.7 mmol), 7-[(3aS,4R,6R,6aR)-2,2-dimethyl-6-[(propan-2-ylamino)methyl]-hexahydrocyclopenta[d][1,3]dioxol-4-yl]-7H-pyrrolo[2,3-d]pyrimidin-4-amine (243.41 mg, 0.7 mmol) and magnesium sulfate (127.22 mg, 1.06 mmol) were stirred in 1,2-dichloroethane (10 ml) for 15 mins. Sodium triacetoxyborohydride (179.21 mg, 0.85 mmol) was added, and the reaction stirred overnight. The reaction was quenched by the addition of sat. $Na_2CO_3$ (10 ml), and the solution was extracted with DCM (3×10 ml). The combined organics were dried ($MgSO_4$) and concentrated. The crude material was purified by mass directed prep-HPLC (acidic method). After combining the fractions, a small amount of 7M $NH_3$ in MeOH was added to basify the solution. After concentration, the residue was partitioned between water (5 ml) and DCM (5 ml), and the layers separated. The aqueous layer was extracted with DCM (2×3 ml) and the combined organics were dried ($MgSO_4$) and concentrated to afford the title compound (58.7 mg, 11%) as a colourless gum: MS (ESI) for $C_{41}H_{63}N_7O_3Si$ m/z 730.2 $[M+H]^+$; LC purity 95% (UV), 100% (ELS), (ret. time, 1.65 min); $^1H$ NMR (500 MHz, CHLOROFORM-d) $\delta_H$ 8.30 (s, 1H), 7.75 (s, 1H), 7.32 (s, 2H), 7.04 (d, J=3.6 Hz, 1H), 6.37 (d, J=3.6 Hz, 1H), 5.40-5.50 (m, 2H), 5.24 (br. s., 2H), 4.89-5.04 (m, 2H), 4.45 (d, J=5.2 Hz, 1H), 3.50 (s, 3H), 2.11-3.09 (m, 13H), 2.01 (s, 6H), 1.34-1.49 (m, 6H), 1.29 (s, 3H), 0.85-1.02 (m, 8H), −0.11-0.05 (m, 9H).

Stage 6: (1R,2S,3R,5R)-3-{4-amino-7H-pyrrolo[2,3-d]pyrimidin-7-yl}-5-{[({3-[(5-tert-butyl-1H-1,3-benzodiazol-2-yl)methyl]cyclobutyl}methyl)(propan-2-yl)amino]methyl}cyclopentane-1,2-diol

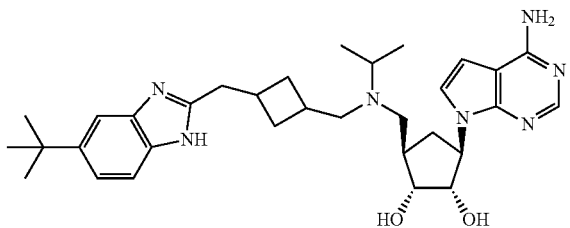 [SMILES: CC(C)N(CC1CC(Cc2nc3cc(C(C)(C)C)ccc3[nH]2)C1)C[C@H]1C[C@@H](n2ccc3c(N)ncnc32)[C@H](O)[C@@H]1O]

7-[(3aS,4R,6R,6aR)-6-{[({3-[(5-tert-butyl-1-{[2-(trimethylsilyl)ethoxy]methyl}-1H-1,3-benzodiazol-2-yl)methyl]cyclobutyl}methyl)(propan-2-yl)amino]methyl}-2,2-dimethyl-hexahydrocyclopenta[d][1,3]dioxol-4-yl]-7H-pyrrolo[2,3-d]pyrimidin-4-amine (58.7 mg, 0.08 mmol) was dissolved in conc. HCl solution (5 ml) and methanol (5 ml) and heated to 40° C. for 2 h. The reaction mixture was concentrated under reduced pressure, and the residue partitioned between sat. $NaHCO_3$(aq) (10 ml) and EtOAc (10 ml). The layers were separated and the aqueous layer was extracted with EtOAc (2×10 ml), the combined organics were then dried ($MgSO_4$) and concentrated. The crude material was purified by prep TLC, eluting with 10% 2M $NH_3$ in MeOH in DCM to afford the title compound (24.7 mg, 55%) as a colourless gum: MS ($ESI^+$) for $C_{32}H_{45}N_7O_2$ m/z 560.4 $[M+H]^+$; LC purity 100% (UV), (ret. time, 5.10 min); $^1H$ NMR (500 MHz, Acetone) $\delta_H$ 8.12 (s, 1H), 7.30-7.60 (m, 2H), 7.13-7.28 (m, 2H), 6.54 (d, J=3.5 Hz, 1H), 6.33 (br. s., 1H), 4.85-5.07 (m, 1H), 4.36 (t, J=6.2 Hz, 1H), 4.08 (t, J=5.2 Hz, 1H), 3.01 (d, J=7.7 Hz, 1H), 2.93 (d, J=7.4 Hz, 2H), 2.78 (br. s., 2H), 2.59-2.73 (m, 2H), 2.15-2.56 (m, 7H), 1.68 (dt, J=12.4, 9.7 Hz, 1H), 1.44-1.62 (m, 2H), 1.35 (s, 9H), 0.90-1.07 (m, 6 II).

Compound 23: (1R,2S,3R,5R)-3-(4-amino-7H-pyrrolo[2,3-d]pyrimidin-7-yl)-5-(((3-(2-(5,6-dichloro-1H-benzo[d]imidazol-2-yl)ethyl)cyclobutyl)(methyl)amino)methyl)cyclopentane-1,2-diol 7-((3aS,4R,6R,6aR)-6-(((3-(2-(5,6-dichloro-1H-benzo[d]imidazol-2-yl)ethyl)cyclobutyl)(methyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

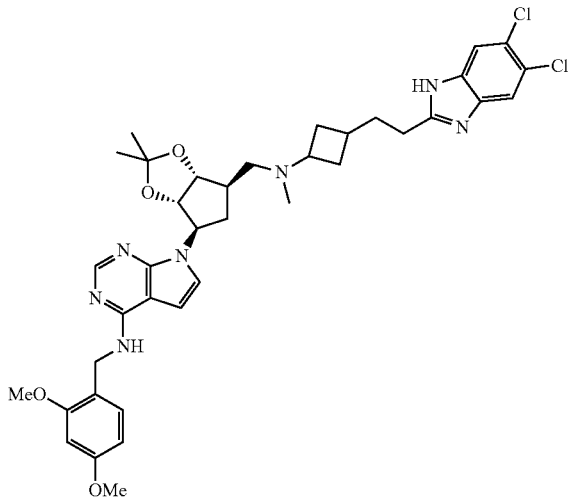 [SMILES: COc1ccc(CNc2ncnc3c2ccn3[C@@H]2C[C@H](CN(C)C3CC(CCc4nc5cc(Cl)c(Cl)cc5[nH]4)C3)[C@H]3OC(C)(C)O[C@H]32)c(OC)c1]

A solution of 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanoic acid (450 mg, 0.76 mmol) and 4,5-Dichloro-1,2-phenylenediamine (161 mg, 0.910 mmol) in N,N-Dimethylformamide (7.8 ml) was treated with N,N-Diisopropylethylamine (0.44 ml, 2.5 mmol) dropwise followed by N,N,N',N'-Tetramethyl-0-(7-azabenzotriazol-1-yl}uronium Hexafluorophosphate (432 mg, 1.14 mmol) in one portion. The reaction mixture was stirred at RT 5.5 h. The reaction mixture was concentrated under high vac and the residue was partitioned between 50 ml EtOAC and 50 ml 1/1 $H_2O$/sat $NaHCO_3$. The aqueous phase was extracted with 30 ml EtOAc and the combined organic phase was washed with 30 ml portions of $H_2O$ and brine. The organic phase was dried over $Na_2SO_4$, filtered and concentrated to a foam. The crude material was purified by flash chromatography ($SiO_2$ eluting with 5% 7N $NH_3$ in $CH_3OH$/$CH_2Cl_2$) to give the intermediate amide (as a mixture of amide regioisomers, 520 mg).

The intermediate amide (0.52 g) in Acetic acid (16 ml) was heated at 65° C. for 5.5 h, the reaction mixture was cooled and placed under high vac to remove the acetic acid. The residue was taken up in 70 ml $CH_2Cl_2$ and washed with 50 ml portions of sat $NaHCO_3$ and 2% $Na_2CO_3$ solution. The organic phase was dried over $Na_2SO_4$, filtered and concentrated to yield a foam. The material was placed on high vacuum overnight and the residue was purified twice by flash chromatography ($SiO_2$, eluting with 4% 7NH $NH_3$ in $CH_3OH$/$CH_2Cl_2$, $2^{nd}$ column eluting with 2-6% EtOH sat w/$NH_3$/$CH_2Cl_2$) to give the desired compound (377 mg) $^1$H NMR (400 MHz, MeOD) $\delta_H$ ppm 8.10 (s, 1H), 7.63 (d, J=1.66 Hz, 2H), 7.21 (m, 1H), 7.13 (d, J=8.29 Hz, 1H), 6.62 (d, J=3.32 Hz, 1H), 6.54 (d, J=2.07 Hz, 1H), 6.43 (dd, J=8.40, 2.38 Hz, 1H), 4.96 (m, 2H), 4.65 (s, 2H), 4.51 (m, 1H), 3.84 (d, J=1.04 Hz, 3H), 3.76 (s, 3H), 2.99 (m, 0.5H), 2.83 (m, 2H), 2.66 (m, 0.5H), 2.38 (m, 4H), 2.22 (m, 1H), 2.15 (d, J=7.67 Hz, 3H), 2.08 (m, 2H), 2.00 (m, 2H), 1.90 (m, 1H), 1.84 (m, 1H), 1.53 (s, 3H), 1.46 (m, 1H), 1.29 (s, 3H)

(1R,2S,3R,5R)-3-(4-amino-7H-pyrrolo[2,3-d]pyrimidin-7-yl)-5-(((3-(2-(5,6-dichloro-1H-benzo[d]imidazol-2-yl)ethyl)cyclobutyl)(methyl)amino)methyl)cyclopentane-1,2-diol

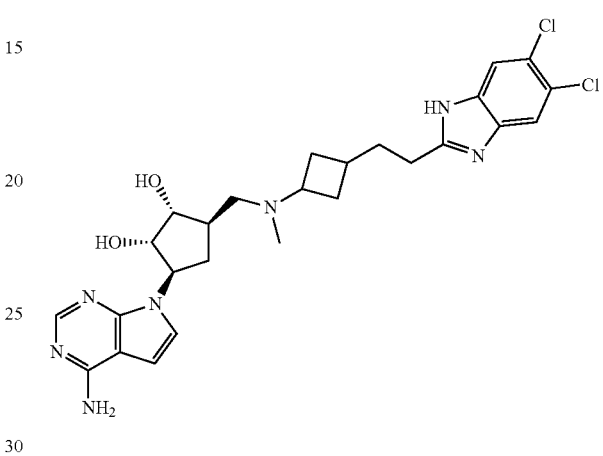

7-((3aS,4R,6R,6aR)-6-(((3-(2-(5,6-Dichloro-1H-benzo[d]imidazol-2-yl)ethyl)cyclobutyl)(methyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (377 mg, 0.513 mmol) was dissolved in a mixture of Trifluoroacetic Acid (7.1 ml) and Water (0.8 ml) which had been pre-cooled at 0° C. in an ice bath. The solution was stirred at 0° C. for 30 minutes, then warmed to and stirring was continued for 3 h at RT. The suspension was concentrated and the residue was taken up in 15 ml MeOH and concentrated. This procedure was repeated twice and the residue placed on high vacuum. The material was taken up in 10 ml MeOH (gave a slurry) and was treated with 500 mg $K_2CO_3$ and 0.2 ml of water. The mixture was allowed to stir for 1.5 hr, during which time the pH of the solution was –9. The mixture was filtered through a fine frit, the solids were washed with 20 ml MeOH and the filtrate was concentrated to yield an off white solid. The material was left on high vacuum overnight and purified by flash chromatography ($SiO_2$, eluting with 10-12% 7N $NH_3$ in $CH_3OH$/$CH_2Cl_2$) to give the desired product (227 mg). $^1$H NMR (400 MHz, MeOD) $\delta_H$ ppm 8.06 (s, 1H), 7.63 (m, 2H), 7.21 (dd, J=3.63, 2.38 Hz, 1H), 6.59 (d, J=3.52 Hz, 1H), 4.32 (m, 1H), 3.88 (m, 1H), 3.01 (m, 0.5H), 2.84 (m, 2H), 2.70 (m, 0.5H), 2.51 (m, 1H), 2.40 (m, 2H), 2.26 (m, 2H), 2.17 (d, J=7.05 Hz, 3H), 2.11 (m, 2H), 2.02 (m, 1H), 1.90 (m, 3H), 1.62 (m, 1H), 1.49 (m, 1H).

Compound 24: (1R,2S,3R,5R)-3-(4-amino-7H-pyrrolo[2,3-d]pyrimidin-7-yl)-5-((methyl(3-(2-(5-(trifluoromethoxy)-1H-benzo[d]imidazol-2-yl)ethyl)cyclobutyl)amino)methyl)cyclopentane-1,2-diol N-(2-amino-4-(trifluoromethoxy)phenyl)-3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanamide

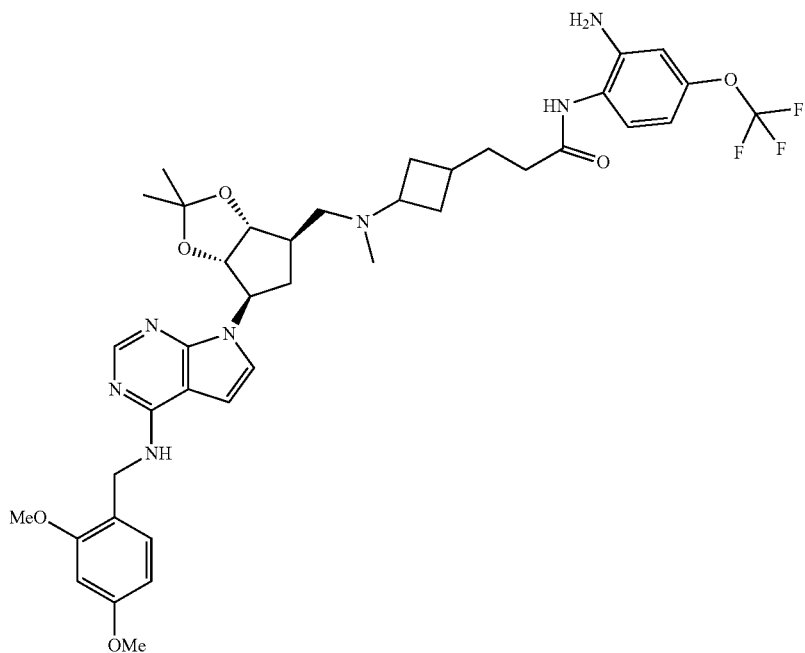 [SMILES: COc1ccc(CNc2ncnc3c2ccn3[C@@H]2C[C@H](CN(C)C3CC(CCC(=O)Nc4ccc(OC(F)(F)F)cc4N)C3)[C@H]3OC(C)(C)O[C@H]32)c(OC)c1]

N,N,N',N'-Tetramethyl-O-(7-azabenzotriazol-1-yl)uronium Hexafluorophosphate (1.2 g, 3.2 mmol) added to a solution 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanoic acid (1.25 g, 2.10 mmol) and N,N-Diisopropylethylamine (1.2 mL, 6.9 mmol) and 4-(trifluoromethoxy)benzene-1,2-diamine (0.48 g, 2.5 mmol) in N,N-Dimethylformamide (10 mL). The mixture was stirred overnight at RT, partially concentrated to ca. 2 mls and then NaHCO$_3$ (saturated) was added. The mixture was extracted with EtOAc (3×) and the combined organics were dried with MgSO$_4$, filtered and concentrated. The residue was purified by flash chromatography (DCM/7N NH$_3$ in MeOH 95:5) to give the desired compound (2 g) as an oil.

N-(2,4-dimethoxybenzyl)-7-((3aS,4R,6R,6aR)-2,2-dimethyl-6-((methyl(3-(2-(5-(trifluoromethoxy)-1H-benzo[d]imidazol-2-yl)ethyl)cyclobutyl)amino)methyl)tetrahydro-3aH-cyclopenta[d][1,3]dioxol-4-yl)-7H-pyrrolo[2,3-d]pyrimidin-4-amine

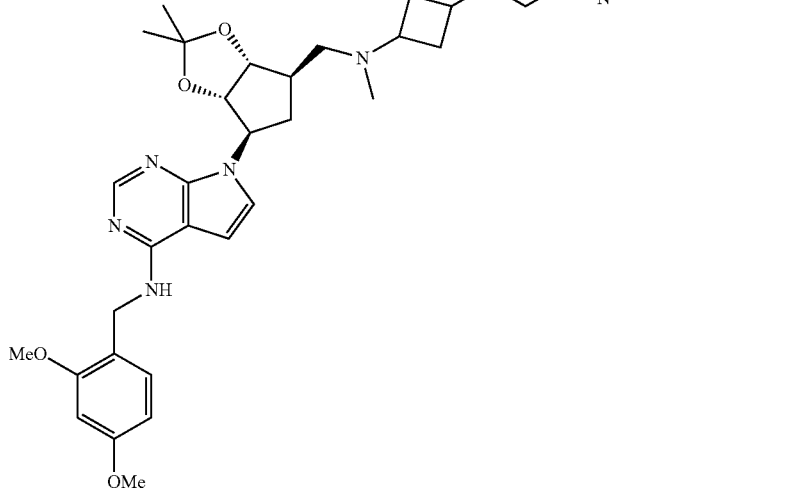

A solution of N-(2-amino-4-(trifluoromethoxy)phenyl)-3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanamide (2 g, 2 mmol) in Acetic acid (4 ml) was stirred overnight at 60° C. The volatiles removed in vacuo and remaining residue purified by flash chromatography (DCM/7N $NH_3$ in MeOH 92:8) to give the desired compound (1 g) as a solid.

(1R,2 S,3R,5R)-3-(4-amino-7H-pyrrolo[2,3-d]pyrimidin-7-yl)-5-((methyl(3-(2-(5-(trifluoromethoxy)-1H-benzo[d]imidazol-2-yl)ethyl)cyclobutyl)amino)methyl)cyclopentane-1,2-diol

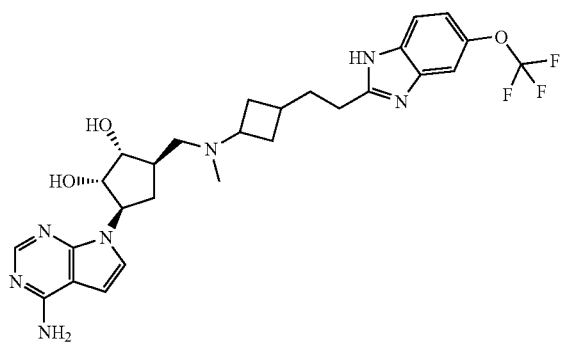 [SMILES: CN(C[C@H]1C[C@@H](n2ccc3c(N)ncnc32)[C@H](O)[C@@H]1O)C1CC(CCc2nc3cc(OC(F)(F)F)ccc3[nH]2)C1]

Trifluoroacetic Acid (20 ml) added to a mixture of Water (2 ml) and N-(2,4-dimethoxybenzyl)-7-((3 aS,4R,6R,6aR)-2,2-dim ethyl-6-((methyl(3-(2-(5-(trifluoromethoxy)-1H-benzo[d]imidazol-2-yl)ethyl)cyclobutyl)amino)methyl)tetrahydro-3aH-cyclopenta[d][1,3]dioxol-4-yl)-7H-pyrrolo[2,3-d]pyrimidin-4-amine (1 g, 1 mmol) at RT.

The reaction was stirred for 1.5 hours then quenched with Triethylsilane (0.43 ml, 2.7 mmol). The volatiles were removed in vacuo and resulting residue was purified twice by flash chromatography (DCM/7N $NH_3$ in MeOH 87:13) to give the desired product (0.28 g) as a foam. MS (ESI$^+$) for $C_{27}H_{32}F_3N_7O_3$ m/z 560.2 [M+H]$^+$; MS (ESI$^-$) for $C_{27}H_{32}F_3N_7O_3$ m/z 558.2 [M−H]$^-$; HPLC purity >93% (ret. time, 2.504 min.) $^1$H NMR (400 MHz, $d_4$-MeOH) $\delta_H$ 8.081 (s, 1H), 7.551-7.530 (m, 1H), 7.414 (s, 1H), 7.230-7.216 (m, 1H), 7.156-7.134 m, 1H), 6.621-6.613 (d, J=3.2 Hz, 1H), 4.362-4.326 (m, 1H), 3.952-3.915 (m, 1H), 3.237-3.182 (m, 0.5H (methine of trans isomer), 2.927-2.857 (m, 2.5H (contains methine of cis isomer)), 2.697-2.646 (m, 1H), 2.590-2.515 (m, 1H), 2.479-2.408 (m, 1H), 2.343-2.305 (m, 5H), 2.210-2.174 (m, 2H), 2.086-1.949 (m, 4H), 1.721-1.545 (m, 2H). Retention time: 2.52 min 1HPLC Conditions: Agilent Zorbax Exlipse XDB-C18 column, 4.6×50 mm (1.8 um packing), Solvent A—Water (0.1% TFA), Solvent B—Acetonitrile (0.07% TFA) 6 min gradient from 5 to 95% B; 1 min hold; then recycle.

Compound 25: (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(ethyl)amino)methyl)cyclopentane-1,2-diol N-(2-amino-4-(tert-butyl)phenyl)-3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(ethyl)amino)cyclobutyl)propanamide

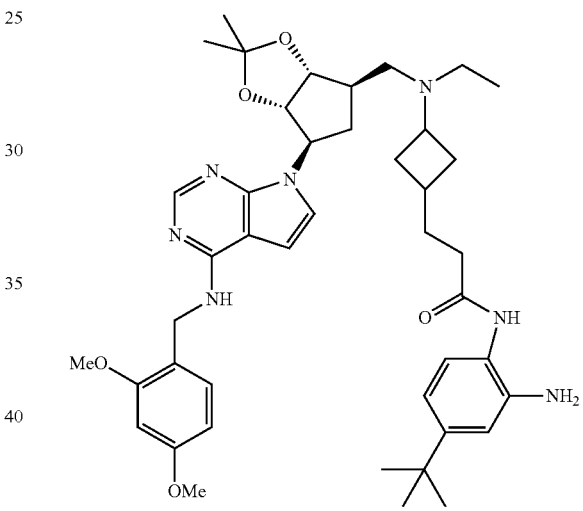

N,N,N',N'-Tetramethyl-0-(7-azabenzotriazol-1-yl)uronium Hexafluorophosphate (0.84 g, 2.2 mmol) added to a solution 3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(ethyl)amino)cyclobutyl)propanoic acid (0.89 g, 1.5 mmol) and N,N-Diisopropylethylamine (0.84 ml, 4.8 mmol) and 4-tert-butylbenzene-1,2-diamine (0.29 g, 1.8 mmol) in N,N-Dimethylformamide (9 ml). The reaction was stirred overnight at RT, partially concentrated to ca. 2 ml and then $NaHCO_3$ (saturated) was added. The mixture was extracted with EtOAc (3×) and the combined organics were dried with $MgSO_4$, filtered and concentrated. The residue was purified by flash chromatography (DCM I 7N $NH_3$ in MeOH 94:6) to give the desired compound (0.88 g) as a colorless solid. Retention time C, 3.363 minutes.

7-((3aS,4R,6R,6aR)-6-(((3-(2-(5-(tert-butyl)-1H-benzo[d]imidazol-2-yl)ethyl)cyclobutyl)(ethyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

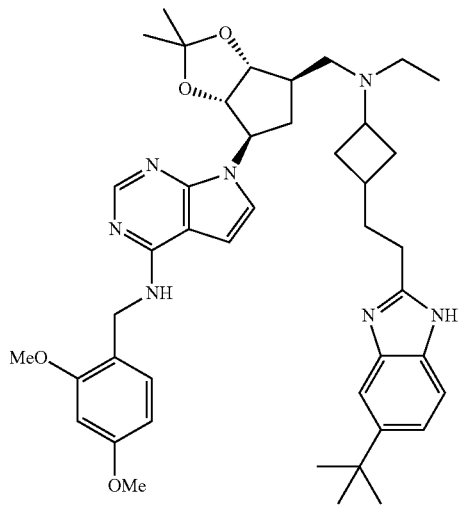 [SMILES: CCN(C[C@H]1C[C@@H](n2ccc3c(NCc4ccc(OC)cc4OC)ncnc32)[C@@H]2OC(C)(C)O[C@H]12)C1CC(CCc2nc3cc(C(C)(C)C)ccc3[nH]2)C1]

A solution of N-(2-amino-4-(tert-butyl)phenyl)-3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(ethyl)amino)cyclobutyl)propanamide (0.88 g, 1.2 mmol) in Acetic acid (3 mL) was stirred overnight at 60° C., the volatiles removed in vacuo and remaining residue purified by flash chromatography (DCM/7N NH₃ in MeOH 93:7) to give the desired compound (0.85 g) as a foam.

(1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(ethyl)amino)methyl)cyclopentane-1,2-diol

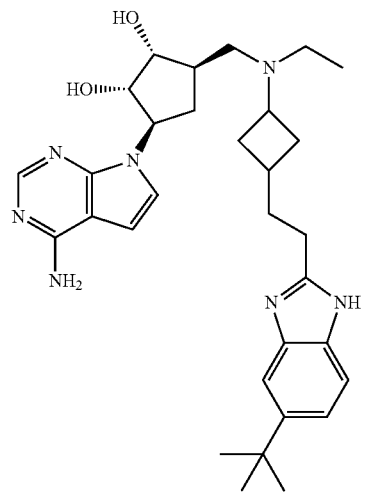 [SMILES: CCN(C[C@H]1C[C@@H](n2ccc3c(N)ncnc32)[C@H](O)[C@@H]1O)C1CC(CCc2nc3cc(C(C)(C)C)ccc3[nH]2)C1]

Trifluoroacetic Acid (20 mL) was added to a mixture of Water (2 mL) and 7-((3aS,4R,6R,6aR)-6-(((3-(2-(5-(tert-butyl)-1H-benzo[d]imidazol-2-yl)ethyl)cyclobutyl)(ethyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (0.85 g, 1.2 mmol) at RT. The reaction was allowed to proceed for one hour at which time Triethylsilane (0.37 mL, 2.3 mmol) was added. The volatiles were removed in vacuo and resulting residue was taken up in MeOH (3 mls), 1 ml of K₂CO₃ (saturated) was added and reaction stirred at RT for 1 hour. The mixture was partitioned between H₂O and DCM/MeOH (9:1). The aqueous layer was extracted (3×) and the combined organics dried with MgSO₄, filtered and concentrated. The resulting residue was purified by flash chromatography (DCM/7N NH₃ in MeOH 90:10) to yield the desired product (0.150 g) as an off white foam. MS (ESL⁺) for $C_{31}H_{43}N_7O_2$ m/z 546.3 [M+H]⁺; MS (ESI⁻) for $C_{31}H_{43}N_7O_2$ m/z 544.3 [M−H]⁻; HPLC purity >91% (ret. time, 2.734 min.) ¹H NMR (400 MHz, d₄-MeOH) δ_H 8.081 (s, 1H), 7.493 (s, 1H), 7.414-7.393 (m, 1H), 7.291-7.266 (m, 1H), 7.215-7.202 (m, 1H), 6.619-6.609 (d, J=4.0 Hz, 1H), 4.345-4.312 (m, 1H), 3.923-3.885 (m, 1H), 2.994-2.915 (m, 0.5; H (methine of trans isomer)), 2.860-2.793 (m, 2H), 2.701-2.578 (m, 3H), 2.501-2.380 (m, 2H), 2.259-2.234 (m, 2H), 2.109-2.008 (m, 3H), 1.920-1.880 (m, 3H), 1.658-1.499 (m, 2H), 1.364 (s, 9H), 1.036-0.991 (m, 3H). Retention time: 2.734 minutes. HPLC Conditions: Agilent Zorbax Exlipse XDB-C18 column, 4.6×50 mm (1.8 um packing), Solvent A—Water (0.1% TFA), Solvent B—Acetonitrile (0.07% TFA). 6 min gradient from 5 to 95% B; 1 min hold; then recycle Compound 26: (1R,2S,3R,5R)-3-(4-amino-7H-pyrrolo[2,3-d]pyrimidin-7-yl)-5-(((3-(2-(5-bromo-1H-benzo[d]imidazol-2-yl)ethyl)cyclobutyl)(methyl)amino)methyl)cyclopentane-1,2-diol N-(2-amino-4-bromophenyl)-3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanamide

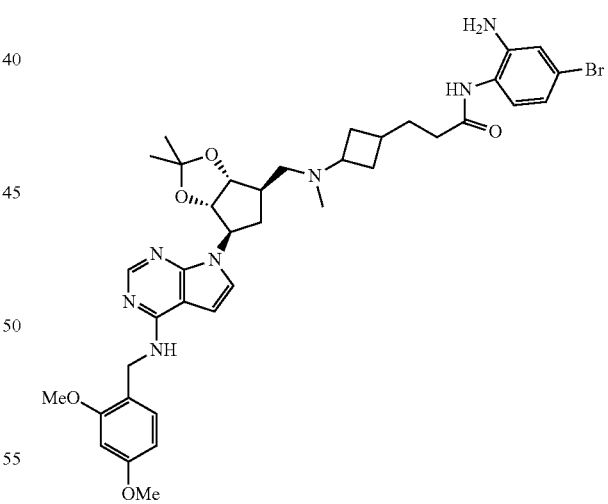

N,N,N',N'-Tetramethyl-0-(7-azabenzotriazol-1-yl)uronium Hexafluorophosphate (1.20 g, 3.16 mmol) was added to a solution 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanoic acid (1.25 g, 2.10 mmol) and N,N-Diisopropylethylamine (1.21 ml, 6.95 mmol) and 4-bromobenzene-1,2-diamine (0.472 g, 2.53 mmol) in N,N-Dimethylformamide (13.0 ml). The reaction was stirred overnight at RT, partially concentrated to ca. 2 mls and then NaHCO₃ (saturated) was added. The mixture was extracted with EtOAc (3×) and the combined organics were dried with MgSO₄, filtered and concentrated. The residue was purified by flash chromatography (DCM/7N NH₃ in MeOH 95:5) to give the desired compound (1.2 g) as a solid.

7-((3aS,4R,6R,6aR)-6-(((3-(2-(5-bromo-1H-benzo[d]imidazol-2-yl)ethyl)cyclobutyl)(methyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

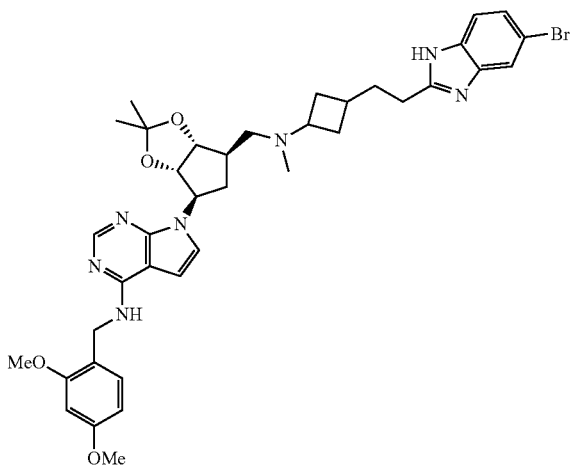 [SMILES: COc1ccc(CNc2ncnc3c2ccn3[C@@H]2C[C@H](CN(C)C3CC(CCc4nc5cc(Br)ccc5[nH]4)C3)[C@H]3OC(C)(C)O[C@H]32)c(OC)c1]

A solution of N-(2-amino-4-bromophenyl)-3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanamide (1.2 g, 1.6 mmol) in Acetic acid (4 ml, 70 mmol) was stirred overnight at 60° C., the volatiles were removed in vacuo and remaining residue purified directly by flash chromatography (DCM/7N NH₃ in MeOH 91:9) to give (0.9 g) as a foam.

(1R,2S,3R,5R)-3-(4-amino-7H-pyrrolo[2,3-d]pyrimidin-7-yl)-5-(((3-(2-(5-bromo-1H-benzo[d]imidazol-2-yl)ethyl)cyclobutyl)(methyl)amino)methyl)cyclopentane-1,2-diol

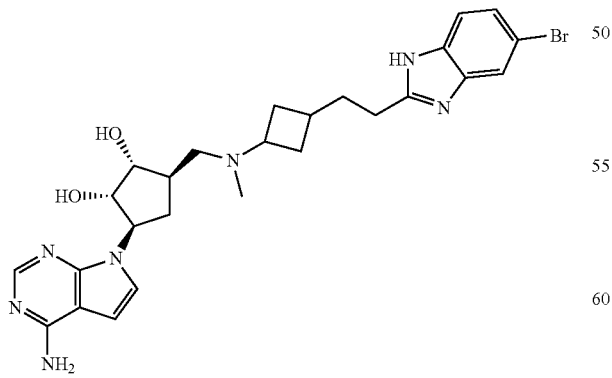

Trifluoroacetic Acid (20 ml) added to a mixture of Water (2 ml) and 7-((3aS,4R,6R,6aR)-6-(((3-(2-(5-bromo-1H-benzo[d]imidazol-2-yl)ethyl)cyclobutyl)(methyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (0.9 g, 1 mmol) at RT. The reaction mixture was stirred for one hour, Triethylsilane (0.39 ml, 2.4 mmol) was added. The volatiles were removed in vacuo and resulting residue was purified twice by flash chromatography (DCM/7N NH₃ in MeOH 87:13). The residue was taken up in MeOH/H₂O (5:0.5 ml) and K₂CO₃ (100 mg) added. The mixture was stirred for 1 hour, then concentrated and purified by flash chromatography (DCM/7N NH₃ in MeOH 87:13) to give the desired product (0.15 g) as an off-white foam/gum. cyclobutyl)(methyl)amino)methyl)cyclopentane-1,2-diol (0.15 g; 20%) as an off-white foam/gum. MS (ESI⁺) for C₂₆H₃₂BrN₇O₂ m/z 554.1 [M+H]⁻; MS (ESI⁻) C₂₆H₃₂BrN₇O₂ m/z 552.1 [M−H]⁻; HPLC purity >90% (ret. time, 2.298 min.) ¹H NMR (400 MHz, d₄-MeOH) δ_H 8.080 (s, 1H), 7.652 (s, 1H), 7.425-7.403 (m, 1H), 7.342-7.7.312 (m, 1H), 7.232-7.217 (m, 1H), 6.620-6.611 (d, J=3.6 Hz, 1H), 4.358-4.318 (m, 1H), 3.928-3.888 (m, 1H), 3.099-3.039 (m, 0.5H (methine of trans isomer)), 2.898-2.829 (m, 2H), 2.777-2.726 (m, 0.5H (methine of cis isomer)), 2.580-2.529 (m, 1H), 2.453-2.397 (m, 2H), 2.307-2.141 (7H), 2.068-2.017 (m, 1H), 1.955-1.891 (m, 3H), 1.695-1.506 (m, 2H).

Compound 27: (2R,3R,4S,5R)-2-(6-amino-9H-purin-9-yl)-5-((isopropyl(3-(2-(5-(1-methylcyclobutyl)-1H-benzo[d]imidazol-2-yl)ethyl)cyclobutyl)amino)methyl)tetrahydrofuran-3,4-diol 9-((3 aR,4R,6R,6aR)-6-((isopropyl(3-(2-(5-(1-methylcyclobutyl)-1H-benzo[d]imidazol-2-yl)ethyl)cyclobutyl)amino)methyl)-2,2-dimethyltetrahydrofuro[3,4-d][1,3]dioxol-4-yl)-9H-purin-6-amine

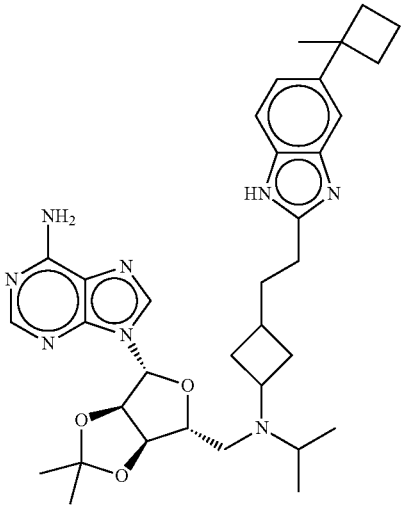

A solution of 5'-{[3-(2-carboxyethyl)cyclobutyl](isopropyl)amino}-5'-deoxy-2',3'-0-isopropylideneadenosine (0.463 g, 0.976 mmol) and 4-(1-methylcyclobutyl)benzene-1,2-diamine (0.184 g, 1.04 mmol) in N,N-Dimethylformamide (10 ml) was cooled at 0° C. The solution was treated with N,N-Diisopropylethylamine (0.462 ml, 2.65 mmol) dropwise followed by N,N,N',N'-Tetramethyl-0-(7-azabenzotriazol-1-yl)uronium Hexafluorophosphate (0.367 g, 0.965 mmol) in one portion. The mixture was stirred at 0° C. for 1 h then slowly warmed to RT. After 5 h at RT the reaction mixture was stored in the fridge overnight, the reaction mixture was placed under high vacuum. The resultant glass was taken up in 30 ml H$_2$O and extracted with 30 ml portion of 10% MeOH/EtOAc. The aqueous phase was further extracted with 30 ml portion of EtOAc. The combined organic phases were washed with 25 ml portions of sat NaHCO$_3$ and brine and dried over Na$_2$SO$_4$. The mixture was filtered and concentrated to yield a glass/foam (700 mg). The crude material was purified by flash chromatography (SiO$_2$, 4-5% 7N NH$_3$ in MeOH/CH$_2$Cl$_2$) to give the intermediate amide (~80% purity, 390 mg).

The intermediate amide (110 mg, 0.174 mmol) was taken up in 4 ml acetic acid and the solution was heated at 65° C. The reaction mixture was cooled and the volatiles were removed under high vacuum to yield a glass. The crude product was taken up in 25 ml CH$_2$Cl$_2$ and washed with 20 ml sat NaHCO$_3$ and 2% Na$_2$CO$_3$ solution, dried over Na$_2$SO$_4$, filtered and concentrated to yield a glass/stiff foam. The crude material was purified by prep TLC (SiO$_2$, eluting with 7% 7N NH$_3$ in CH$_3$OH/CH$_2$Cl$_2$) to give the desired product as a stiff foam (54 mg). This above procedure was repeated (except purification was by flash chromatography, SiO$_2$ eluting with 4-5% 7N NH$_3$ in CH$_3$OH/CH$_2$Cl$_2$) on a further batch of the intermediate amide (389 mg) to yield a further 368 mg of the desired compound which was combined with the above benzimidazole.

(2R,3R,4S,5R)-2-(6-amino-9H-purin-9-yl)-5-((isopropyl(3-(2-(5-(1-methylcyclobutyl)-1H-benzo[d]imidazol-2-yl)ethyl)cyclobutyl)amino)methyl)tetrahydrofuran-3,4-diol

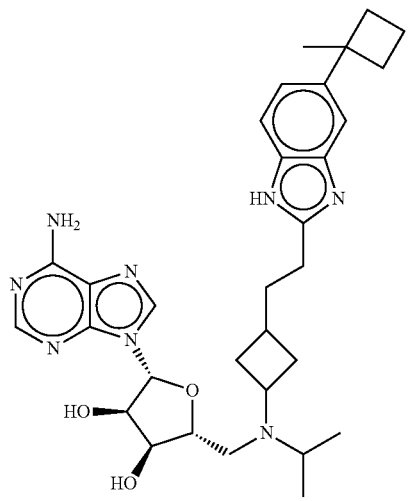

9-((3aR,4R,6R,6aR)-6-((isopropyl(3-(2-(5-(1-methylcyclobutyl)-1H-benzo[d]imidazol-2-yl)ethyl)cyclobutyl)amino)methyl)-2,2-dimethyltetrahydrofuro[3,4-d][1,3]dioxol-4-yl)-9H-purin-6-amine 422 mg, 0.686 mmol) was dissolved in a mixture of Trifluoroacetic Acid (6.3 ml, 82 mmol) and water (0.7 ml, 40 mmol) which had been pre-cooled at 0° C. in an ice bath. The solution was stirred at 0° C. for 30 minutes, upon which the ice bath was removed and the mixture was warmed to RT. The mixture was stirred at RT for 2.5 h upon which the residue was taken up in 12 ml MeOH, concentrated to dryness. This was repeated twice, the resultant glass was placed under high vacuum. The crude residue was diluted with 11 ml MeOH, treated with 600 mg K$_2$CO$_3$ and 0.5 ml H$_2$O and allowed to stir at RT till the solution was basic as determined by pH paper. The mixture was filtered and the solids were washed with 20 ml MeOH. The solution was concentrated to a residue that was placed under high vacuum. The crude material was purified by flash chromatography (SiO$_2$, eluting with 10-12% 7N NH$_3$ in CH$_3$OH/CH$_2$Cl$_2$) to give the desired compound as a stiff foam/glass (256 mg). $^1$H NMR (400 MHz, MeOD) δ$_H$ ppm 8.30 (m, 1H), 8.20 (d, J=1.04 Hz, 1H), 7.38 (d, J=8.09 Hz, 1H), 7.22 (br. s., 1H), 6.98 (dd, J=8.50, 1.66 Hz, 1H), 5.96 (m, 1H), 4.74 (t, J=4.87 Hz, 1H), 4.27 (d. J=3.11 Hz, 1H), 4.08 (m, 1H), 3.56 (m, 1H), 3.13 (m, 1H), 3.00 (m, 1H), 2.90 (dd, J=14.51, 4.35 Hz, 1H), 2.75 (m, 3H), 2.41 (m, 2H), 2.12 (m, 5H), 2.00 (m, 1H), 1.84 (m, 3H), 1.58 (m, 1H), 1.46 (s, 3H), 1.02 (m, 3H), 0.95 (d, J=6.63 Hz, 3H).

Compound 28 (2R,3R,4S,5R)-2-(6-amino-9H-purin-9-yl)-5-((isopropyl((1r,3S)-3-(2-(5-(1-methylcyclobutyl)-1H-benzo[d]imidazol-2-yl)ethyl)cyclobutyl)amino)methyl)tetrahydrofuran-3,4-diol The diastereomers were separated by SFC. The material was taken up in MeOH/H$_2$O and lyophilized to a white powder (132 mg). $^1$H NMR (400 MHz, MeOD) d ppm 8.30 (s, 1H), 8.20 (s, 1H), 7.38 (d, J=8.09 Hz, 1H), 7.22 (s, 1H), 6.99 (dd, J=8.40, 1.55 Hz, 1H), 5.96 (d, J=4.56 Hz, 1H), 4.73 (m, 1H), 4.26 (t, J=5.29 Hz, 1H), 4.07 (m, 1H), 3.13 (m, 1H), 3.00 (m, 1H), 2.90 (dd, J=14.41, 4.46 Hz, 1H), 2.76 (t, J=7.15 Hz, 2H), 2.70 (m, 1H), 2.42 (m, 2H), 2.18 (m, 2H), 2.11 (m, 3H), 1.85 (m, 4H), 1.57 (q, J=8.85 Hz, 2H), 1.47 (s, 3H), 1.02 (d, J=6.84 Hz, 3H), 0.95 (d, J=6.63 Hz, 3H).

Compound 29: (1R,2S,3R,5R)-3-(4-amino-7H-pyrrolo[2,3-d]pyrimidin-7-yl)-5-((methyl(3-(2-(5-(1-methylcyclobutyl)-1H-benzo[d]imidazol-2-yl)ethyl)cyclobutyl)amino)methyl)cyclopentane-1,2-diol (1-methylcyclobutyl)benzene

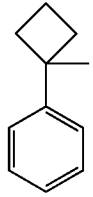

A stirred mixture of benzene (5.0 ml, 56 mmol) and Sulfuric acid (1.17 ml, 21.9 mmol) was cooled to 0° C. and treated dropwise with a solution of Methylenecyclobutane (1.00 ml, 10.8 mmol) in Benzene (3.0 ml, 34 mmol) over-1 h. Upon completion of the addition, the reaction mixture was stirred an additional 1 h while being warmed to RT. The mixture extracted with 15 ml of hexane. The organic phase was washed with 10 ml H$_2$O and 10 ml sat NaHCO$_3$, dried over Na$_2$SO$_4$, filtered and concentrated to yield a colorless liquid. The liquid was purified by kugelrohr distillation (5-10 torr) to yield the desired compound as a colourless liquid.

First fraction was collected at 75-85° C. as a colorless liquid (330 mg) of product as a colorless liquid.

1-(1-methylcyclobutyl)-4-nitrobenzene

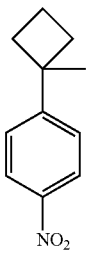

70% Nitric acid (7:3, Nitric acid:Water, 0.375 ml, 5.92 mmol) was added dropwise over 60 minutes to a solution of (1-methylcyclobutyl)benzene (346 mg. 2.37 mmol) in Acetic anhydride (1.4 mL, 15 mmol) cooled at 0° C. The temperature of the solution was maintained below 5° C. during the addition. Upon completion of the addition, the reaction was stirred for 60 minutes with cooling. The reaction mixture was poured into 40 ml ice water and the ice was allowed to melt. The aqueous phase was extracted with three×20 ml portions of Et$_2$O and the combined organic phase was washed with 25 ml H$_2$O followed by two 20 ml portions of sat NaHCO$_3$ solution. The organic phase was dried over Na$_2$SO$_4$, filtered and concentrated to yield a light the product as an oil (418 mg) which was used as is in the next step. $^1$H NMR (400 MHz, CDCl$_3$) d ppm 8.16 (d. J=8.71 Hz, 2H), 7.29 (d, J=8.71 Hz, 2H), 2.41 {m, 2H), 2.15 (m, 3H), 1.88 (m, 1H). 1.48 (s, 3H)

4-(1-methylcyclobutyl)aniline

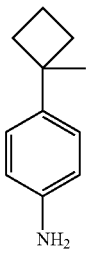

A solution of 1-(1-methylcyclobutyl)-4-nitrobenzene (708 mg, 3.70 mmol) in Ethanol (24 mL, 410 mmol) was treated carefully with 5% Pd on Carbon (87 mg. 0.041 mmol). The reaction flask was evacuated and filled with hydrogen gas three times and the reaction mixture was stirred under an atmosphere of Hydrogen for 19 h. The reaction mixture was filtered through a pad of solka Floc® and the pad was washed with 25 mL EtOH. The solvent was removed to yield an oil that was placed under high vacuum briefly to yield the desired compound (609 mg) which was used directly in the next step.

$^1$H NMR (400 MHZ, CDCl3) o ppm 6.99 (m, 2H), 6.66 (m, 2H), 3.39 (br. s., 2H), 2.35 (m, 2H), 2.05 (m, 3H), 1.82 (m, 1H), 1.42 (s, 3H).

2,2,2-trifluoro-N-(4-(1-methylcyclobutyl)-2-nitrophenyl)acetamide

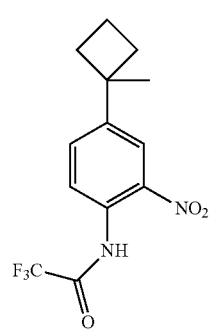 [SMILES: CC1(c2ccc(NC(=O)C(F)(F)F)c([N+](=O)[O-])c2)CCC1]

4-(1-Methylcyclobutyl)aniline (500 mg, 2.79 mmol) and Ammonium Nitrate (220 mg, 2.8 mmol) were treated with Trifluoroacetic anhydride (1.97 mL, 14.0 mmol) followed by Chloroform (10 mL, 120 mmol). The reaction mixture was allowed to stir at RT till for 5 h upon which all the solids had dissolved. The reaction mixture was poured into 50 ml H$_2$O and extracted with three 25 ml portions of CH$_2$Cl$_2$. The combined organic phase was washed with 10 mL sat. NaHCO$_3$, dried over Na$_2$SO$_4$, filtered and concentrated to an oil. The crude material was purified by flash chromatography (SiO$_2$, eluting with 2.5-3.5% ethyl ether/hex.) to give the desired compound (800 mg).

4-(1-methylcyclobutyl)-2-nitroaniline

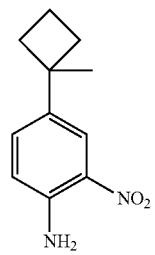

A solution of 2,2,2-trifluoro-N-[4-(1-methylcyclobutyl)-2-nitrophenyl]acetamide (580 mg. 1.9 mmol) in Methanol (18 ml, 440 mmol) was treated with a solution of Potassium carbonate (788 mg, 5.70 mmol) in Water (4.5 ml, 250 mmol) and the mixture was heated at 45° C. for 50 minutes The reaction mixture was cooled to RT and the methanol was removed in vacuo. The remaining aqueous phase was diluted with 10 ml H$_2$O and extracted with three 20 ml portions of EtOAc. The combined organic phase was dried over Na$_2$SO$_4$, filtered and concentrated to yield an oil. The material was placed on high vacuum where upon it solidified giving the desired compound (400 mg). The material was used directly in the next step $^1$H NMR (400 MHz. CDCl3) d ppm 7.90 (d, J=2.07 Hz, 1H), 7.23 (dd, J=8.50, 2.28 Hz, 1H), 6.77 (d, J=8.71 Hz, 1H), 5.96 (br. s., 2H), 2.33 (m, 2H), 2.13 (m, 1H), 2.04 (m, 2H), 1.84 (m, 1H), 1.43 (s, 3H).

4-(1-methylcyclobutyl)benzene-1,2-diamine

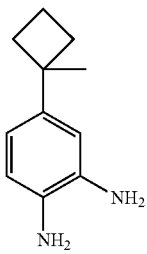

A solution of 4-(1-methylcyclobutyl)-2-nitroaniline (138 mg. 0.668 mmol) in ethanol (8.5 mL, 140 mmol) was carefully treated with 10% Palladium on Carbon (14.2 mg, 0.0134 mmol) as a slurry in ethanol. The reaction flask was evacuated and filled with hydrogen gas three times and the reaction mixture was stirred under an atmosphere of Hydrogen for 4 h. The reaction mixture was filtered through a pad of solka Floc® and the pad was washed with 20 ml MeOH. The filtrate was concentrated to yield an oil which was placed under high vacuum yielding the desired compound as a solid (119 mg) which was used directly in the next step. $^1$H NMR (400 MHZ. CDCl$_3$) $\delta_H$ ppm 6.66 (m, 1H), 6.53 (m, 2H), 3.34 (br. s., 4H), 2.33 (m, 2H), 2.08 (m, 1H), 1.99 (m. 2H). 1.80 (m, 1H), 1.42 (s, 3H).

N-(2,4-dimethoxybenzyl)-7-((3aS,4R,6R,6aR)-2,2-dimethyl-6-((methyl(3-(2-(5-(1-methylcyclobutyl)-1H-benzo[d]imidazol-2-yl)ethyl)cyclobutyl)amino)methyl)tetrahydro-3aH-cyclopenta[d][1,3]dioxol-4-yl)-7H-pyrrolo[2,3-d]pyrimidin-4-amine A solution of 3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanoic acid (387 mg, 0.652 mmol) and [8]4-(1-methylcyclobutyl)benzene-1,2-diamine (120 mg, 0.68 mmol) in N,N-Dimethylformamide (6.7 ml, 87 mmol) was treated with N,N-Diisopropylethylamine (0.38 ml, 2.2 mmol) dropwise followed by N,N,N',N'-Tetramethyl-0-(7-azabenzotriazol-1-yl)uronium Hexafluorophosphate (372 mg, 0.978 mmol) in one portion. The reaction mixture was stirred at RT for 2.5 hr, the reaction mixture was then concentrated under high vacuum. The residue was partitioned between 40 ml EtOAc (some CH$_2$Cl$_2$ was added to aid in solublizing the product) and 40 ml 1/1 H$_2$O/sat NaHCO$_3$. The aqueous phase was extracted with 30 ml 1/1 EA/CH$_2$Cl$_2$ and the combined organic phase was dried over Na$_2$SO$_4$, filtered and concentrated. The crude material was purified by flash chromatography (SiO$_2$, eluting with 5-6% 7N NH$_3$ in CH$_3$OH/CH$_2$Cl$_2$) to give the desired intermediate as a mixture of amide regioisomers.

The intermediate was taken up in Acetic acid (5.4 ml, 95 mmol) and the solution was heated at 65° C. for 3 hours. The acetic acid was removed under high vacuum with the aid of a warm water bath. The crude product was taken up in 30 ml CH$_2$Cl$_2$ and the organic phase was washed with 10 ml portions of sat NaHCO$_3$ and 2% K$_2$CO$_3$ solutions, dried over Na$_2$SO$_4$, filtered and concentrated to a glass that produced a foam under high vacuum. The crude material was purified by flash chromatography (SiO$_2$ eluting with 5% 7N NH$_3$ in CH$_3$OH/CH$_2$Cl$_2$ to yield the desired product (140 mg).

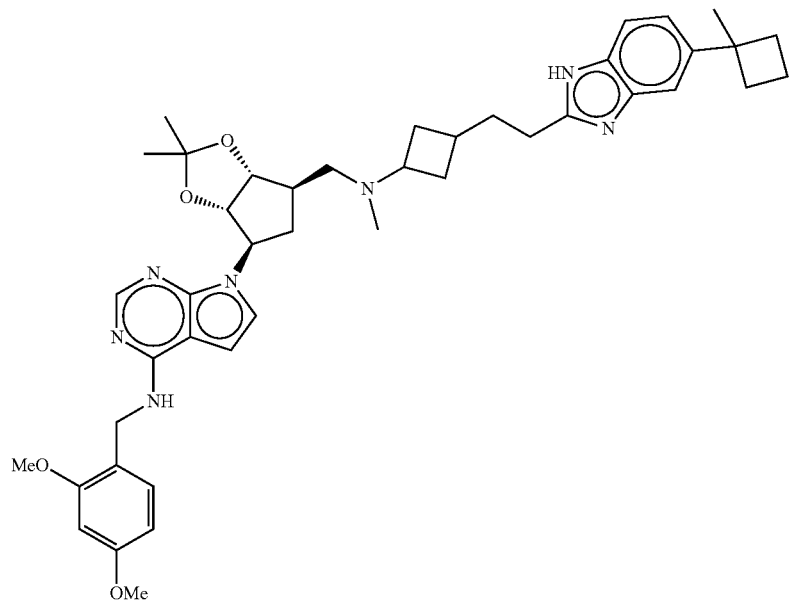

(1R,2S,3R,5R)-3-(4-amino-7H-pyrrolo[2,3-d]pyrimidin-7-yl)-5-((methyl(3-(2-(5-(1-methylcyclobutyl)-1H-benzo[d]imidazol-2-yl)ethyl)cyclobutyl)amino)methyl)cyclopentane-1,2-diol

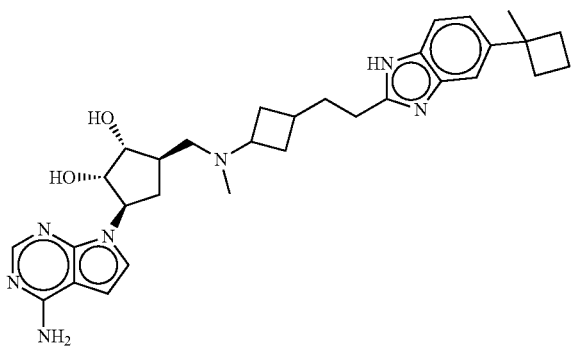

N-(2,4-dimethoxybenzyl)-7-((3aS,4R,6R,6aR)-2,2-dimethyl-6-((methyl(3-(2-(5-(1-methylcyclobutyl)-1H-benzo[d]imidazol-2-yl)ethyl)cyclobutyl)amino)methyl)tetrahydro-3aH-cyclopenta[d][1,3]dioxol-4-yl)-7H-pyrrolo[2,3-d]pyrimidin-4-amine (128 mg, 0.174 mmol) was dissolved in a mixture of Trifluoroacetic Acid (3.60 ml, 46.7 mmol) and Water (0.4 ml, 20 mmol) which had been pre-cooled at 0° C. in an ice bath. The solution was stirred at 0° C. for 30 minutes, then the ice bath was removed and the mixture was warmed to RT at which this temperature was maintained for a further 2.5 hours. The reaction mixture was concentrated in vacuo. The residue was taken up in 3 ml MeOH and concentrated and the process was repeated twice. The resultant white residue was placed on high vacuum. The crude residue was combined with another batch of crude material (prepared identically, ~⅓ of the amount used in this reaction), diluted with 5 mL MeOH, treated with 140 mg $K_2CO_3$, 10 drops of $H_2O$ and allowed to stir at RT till the solution was basic by pH paper. The mixture was filtered and the solids were washed with 15 ml MeOH. The solution was concentrated to an oil that was placed on high vacuum. The crude material was purified by flash chromatography ($SiO_2$, eluting with 10-15% 7N $NH_3$ in $CH_3OH/CH_2Cl_2$ to yield the desired product as glass/stiff foam (68 mg). $^1H$ NMR (400 MHz, MeOD) $\delta_H$ ppm 8 06 (s, 1H), 7.39 (d, J=7.88 Hz, 1H), 7.23 (s, 1H), 7.21 (dd, J=3.63, 1.76 Hz, 1H), 6.99 (m, 1H), 6.60 (d, J=3.52 Hz, 1H), 4.93 (m, 1H), 4.32 (m, 1H), 3.89 (m, 1H), 3.03 (m, 1H), 2.83 (m, 2H), 2.70 (q, J=8.15 Hz, 1H), 2.52 (m, 1H), 2.40 (m, 4H), 2.27 (m, 2H), 2.18 (d, J=6.22 Hz, 3H), 2.11 (m, 4H), 2.03 (m, 1H), 1.86 (m, 4H), 1.62 (m, 1H), 1.51 (m, 1H), 1.47 (s, 3H).

Compound 30: (2R,3R,4S,5R)-2-(6-amino-9H-purin-9-yl)-5-((methyl(1r,3S)-3-(2-(5-(1-methylcyclobutyl)-1H-benzo[d]imidazol-2-yl)ethyl)cyclobutyl)amino)methyl)tetrahydrofuran-3,4-diol

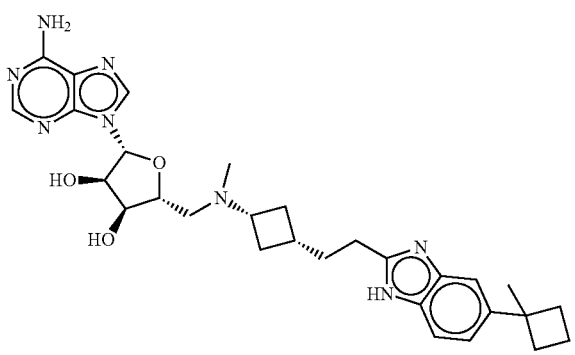

The diastereomers were separated by SFC. The material was taken up in MeOH/$H_2O$ and lyophilized to a white powder (67 mg). $^1H$ NMR (400 MHz, MeOD) $\delta_H$ ppm 8.27 (s, 1H), 8.20 (s, 1H), 7.38 (d, J=8.29 Hz, 1H), 7.22 (br. s., 1H), 6.99 (dd, J=8.40, 1.55 Hz, 1H), 5.97 (d, J=4.15 Hz, 1H), 4.69 (dd, J=5.18, 4.15 Hz, 1H), 4.22 (t, J=5.60 Hz, 1H), 4.16 (m, 1H), 2.77 (m, 2H), 2.72 (d, J=8.09 Hz, 1H), 2.67 (m, 2H), 2.42 (m, 2H), 2.21 (m, 2H), 2.15 (s, 3H), 2.10 (m, 3H), 1.85 (m, 4H), 1.47 (s, 3H), 1.46 (m, 2H).

Compound 31: (2R,3R,4S,5R)-2-(6-amino-9H-purin-9-yl)-5-((isopropyl((1s,3R)-3-(2-(5-(1-methylcyclobutyl)-1H-benzo[d]imidazol-2-yl)ethyl)cyclobutyl)amino)methyl)tetrahydrofuran-3,4-diol

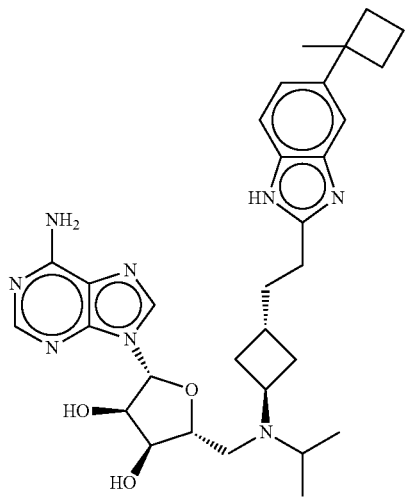

The diastereomers were separated by SFC. The material was found to be the trans diastereomer by NMR. The material was taken up in MeOH/$H_2O$ and lyophilized to a white powder. (63 mg). $^1H$ NMR (400 MHz, MeOD) $\delta_H$ ppm 8.31 (s, 1H), 8.20 (s, 1H), 7.38 (d, J=8.29 Hz, 1H), 7.22 (s, 1H), 6.99 (dd, J=8.29, 1.66 Hz, 1H), 5.97 (d, J=4.56 Hz, 1H), 4.74 (m, 1H), 4.27 (t, J=5.39 Hz, 1H), 4.09 (m, 1H), 3.53 (m, 1H), 3.01 (m, 1H), 2.93 (dd, J=14.72, 4.35 Hz, 1H), 2.80 (t, J=7.46 Hz, 2H), 2.73 (dd, J=14.51, 7.46 Hz, 1H), 2.42 (m, 2H), 2.13 (m, 5H), 2.01 (m, 3H), 1.82 (m, 3H), 1.47 (s, 3H), 1.02 (d, J=6.63 Hz, 3H), 0.95 (d, J=6.63 Hz, 3H).

Compound 32: (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(methyl)amino)methyl)cyclopentane-1,2-diol

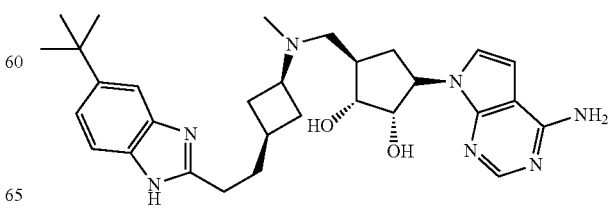

The disatereosisomers were separated by SFC. (conditions listed below) yielded 120 mg. Preparative Method: IC (2×15 cm), 35% isopropanol (0.2% DEA))/CO$_2$, 100 bar, 60 mL/min, 220 nm., inj vol.: 0.75 mL, 4 mg/mL methanol Peak 1: 5.27 minutes. $^1$H NMR (400 MHz, d$_4$-MeOH) δ$_H$ 8.080 (s, 1H), 7.495 (s, 1H), 7.417-7.395 (m, 1H), 7.303-7.281 (m, 1H), 7.220-7.212 (m, 1H), 6.619-6.610 (m, 1H), 4.349-4.315 (m, 1H), 2.837-2.802 (m, 2H), 2.718-2.641 (m, 1H), 2.508-2.365 (m, 3H), 2.284-2.258 (m, 3H), 2.156 (s, 3H), 1.954-1.906 (m, 1H), 1.549-1.460 (m, 2H), 1.375 (s, 9H).

Compound 33: (2R,3R,4S,5R)-2-(6-amino-9H-purin-9-yl)-5-((methyl(3-(2-(5-(1-methylcyclobutyl)-1H-benzo[d]imidazol-2-yl)ethyl)cyclobutyl)amino) methyl)tetrahydrofuran-3,4-diol

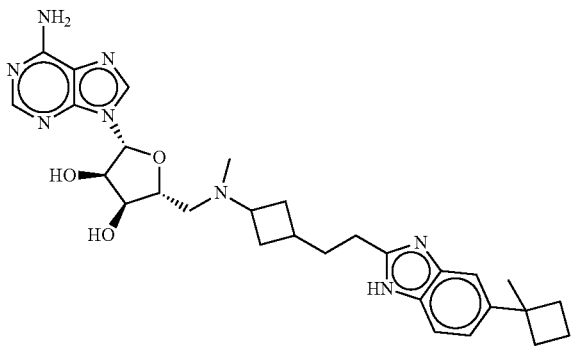

9-((3 aR,4R,6R,6 aR)-2,2-dimethyl-6-((methyl(3-(2-(5-(1-methylcyclobutyl)-1H-benzo[d]imidazol-2-yl) ethyl)cyclobutyl)amino)methyl)tetrahydrofuro[3,4-d] [1,3]dioxol-4-yl)-9H-purin-6-amine

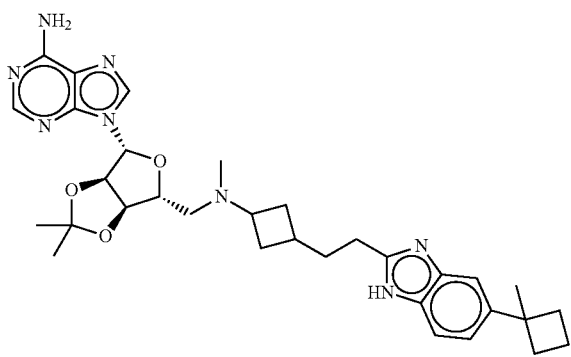

A solution of 3-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanoic acid (0.461 g, 1.03 mmol) and 4-(1-methylcyclobutyl)benzene-1,2-diamine (0.150 g, 0.851 mmol) in N,N-Dimethylformamide (11 ml, 140 mmol) was cooled at 0° C. The solution was treated with N,N-Diisopropylethylamine (0.489 ml, 2.81 mmol) dropwise followed by N,N,N',N'-Tetramethyl-0-(7-azabenzotriazol-1-yl)uronium Hexafluorophosphate (0.388 g, 1.02 mmol) in one portion. The mixture was stirred at 0° C. for 30 minutes then slowly warmed to RT, stirring was continued at RT for 6 h. The reaction mixture was diluted with 30 ml H$_2$O and extracted with 25 ml portions of 10% MeOH/EtOAc. The aqueous phase was further extracted with two 20 ml portions of EtOAc. The combined organic phases were washed with 25 ml portions of sat. NaHCO$_3$, brine and dried over Na$_2$SO$_4$. The solution was filtered and concentrated to yield a glass. The crude material was purified by flash chromatography (SiO$_2$, eluting with 5% 7N NH$_3$ in MeOH/CH$_2$Cl$_2$.

The intermediate amide was taken up in Acetic acid (7.0 ml, 120 mmol) and the solution was heated at 65° C. for 2.5 h, the reaction mixture was cooled and the acetic acid was removed under high vacuum to yield a glass. The crude product was taken up in 25 ml CH$_2$Cl$_2$ and washed with 20 ml sat NaHCO$_3$, 2% Na$_2$CO$_3$ solution, dried over Na$_2$SO$_4$, filtered and concentrated in vacuo to yield a glass/stiff foam. The crude material was purified by flash chromatography (SiO$_2$, eluting with 5-7% 7N NH$_3$ in CH$_3$OH/CH$_2$Cl$_2$) to give the desired compound (214 mg). (2R,3R,4S,5R)-2-(6-amino-9H-purin-9-yl)-5-((methyl(3-(2-(5-(1-methylcyclobutyl)-1H-benzo[d]imidazol-2-yl)ethyl)cyclobutyl)amino)methyl) tetrahydrofuran-3,4-diol

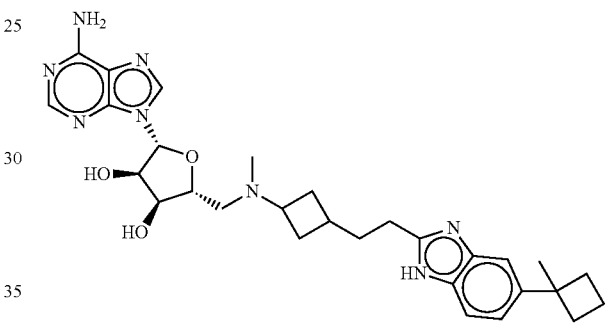

9-((3aR,4R,6R,6aR)-2,2-dimethyl-6-((methyl(3-(2-(5-(1-methylcyclobutyl)-1H-benzo[d]imidazol-2-yl)ethyl)cyclobutyl)amino)methyl)tetrahydrofuro[3,4-d][1,3]dioxol-4-yl)-9H-purin-6-amine (188 mg, 0.320 mmol) was dissolved in a mixture of Trifluoroacetic Acid (4.00 ml, 51.9 mmol) and Water (0.4 ml, 20 mmol) which had been pre-cooled at 0° C. in an ice bath. The solution was stirred at 0° C. The reaction was stirred for 30 minutes at 0° C., then the ice bath was removed and the mixture was warmed to RT where stirring was continued for a further 2 h. The reaction mixture was concentrated in vacuo. The residue was taken up in 10 ml MeOH and concentrated and the process was repeated twice. The resultant glass was placed under high vacuum for 1 h. The crude residue was diluted with 7 ml MeOH, treated with 150 mg K$_2$CO$_3$ and 10 drops of H$_2$O and allowed to stir at RT till the solution was basic by pH paper. The mixture was filtered and the solids were washed with 10 ml MeOH. The solution was concentrated to a residue that was placed under high vacuum. The crude material was purified by flash chromatography (SiO$_2$, eluting with 10-15% 7N NH$_3$ in CH$_3$OH/CH$_2$Cl$_2$) to give the desired compound as a glass/stiff foam (66%). $^1$H NMR (400 MHz, MeOD) δ$_H$ ppm 8.28 (m, 1H), 8.20 (m, 1H), 7.38 (d, J=8.29 Hz, 1H), 7.23 (s, 1H), 7.00 (dd, J=8.40, 1.55 Hz, 1H), 5.98 (t, J=3.21 Hz, 1H), 4.70 (m, 1H), 4.24 (q, J=5.18 Hz, 1H), 4.17 (m, 1H), 3.10 (m, 0.4H), 2.80 (m, 3H), 2.71 (d, J=5.60 Hz, 2H), 2.43 (m, 2H), 2.23 (dd, J=11.71, 6.12 Hz, 1H), 2.19 (m, 3H), 2.12 (m, 4H), 1.99 (m, 1H), 1.85 (m, 4H), 1.48 (s, 3H), 1.48 (m, 1H).

Compound 34: (2R,3R,4S,5R)-2-(6-amino-9H-purin-9-yl)-5-((methyl((1s,3R)-3-(2-(5-(1-methylcyclobutyl)-1H-benzo[d]imidazol-2-yl)ethyl)cyclobutyl)amino)methyl)tetrahydrofuran-3,4-diol

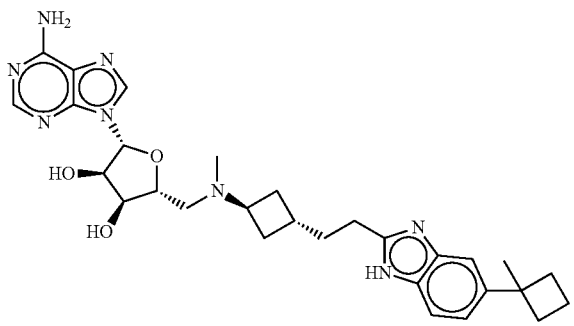

The diastereomers were separated by SFC. The material was taken up in MeOH/H$_2$O and lyophilized to a white powder (30 mg) $^1$H NMR (400 MHz, MeOD) δ$_H$ ppm 8.28 (s, 1H), 8.19 (s, J=4.15 Hz, 1H), 4.69 (m, 1H), 4.23 (t, J=5.49 Hz, 1H), 4.17 (m, 1H), 3.07 (m, 1H), 2.81 (t, J=7.57 Hz, 2H), 2.68 (m, 2H), 2.42 (m, 2H), 2.17 (s, 3H), 2.09 (m, 6H), 1.97 (m, 2H), 1.84 (m, 3H), 1.47 (s, 3H).

35: (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(methyl)amino)methyl)cyclopentane-1,2-diol

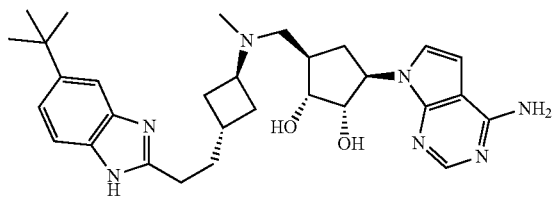 [SMILES: CN(C[C@H]1C[C@@H](n2ccc3c(N)ncnc32)[C@H](O)[C@@H]1O)[C@H]1C[C@H](CCc2nc3cc(C(C)(C)C)ccc3[nH]2)C1]

The diastereoisomers were separated by SFC The following SFC separation (120 mg).

Preparative Method: IC (2×15 cm), 35% isopropanol (0.2% DEA))/CO$_2$, 100 bar, 60 mL/min, 220 nm., inj vol.: 0.75 mL, 4 mg/mL methanol. Peak 2: 6.24 minutes. $^1$H NMR (400 MHz, d$_4$-MeOH) δ$_H$ 8.078 (s, 1H), 7.501 (s, 1H), 7.422-7.401 (m, 1H), 7.310-7.285 (m, 1H), 7.228-7.219 (m, 1H), 6.618-6.609 (m, 1H), 4.355-4.320 (m, 1H), 3.053-2.977 (m, 1H), 2.874-2.836 (m, 2H), 2.535-2.268 (m, 4H), 2.177-2.003 (m, 8H), 1.909-1.869 (m, 2H), 1.677-1.595 (m, 1H), 1.381 (s, 9H).

Compound 36: (1R,2S,3R,5R)-3-(4-amino-7H-pyrrolo[2,3-d]pyrimidin-7-yl)-5-((methyl((1r,3S)-3-(2-(5-(1-methylcyclobutyl)-1H-benzo[d]imidazol-2-yl)ethyl)cyclobutyl)amino)methyl)cyclopentane-1,2-diol

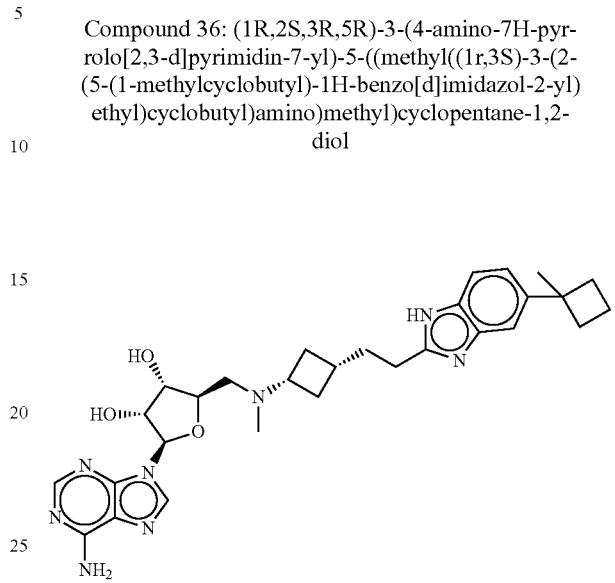

The diastereoisomers were separated by SFC. The material was taken up in MeOH/H$_2$O and lyophilized to a white solid (15 mg). $^1$H NMR (400 MHz, MeOD) δ$_H$ ppm 8.06 (s, 1H), 7.38 (d, J=8.09 Hz, 1H), 7.23 (br. s., 1H), 7.20 (d, J=3.32 Hz, 1H), 6.99 (m, 1H), 6.60 (d, J=3.52 Hz, 1H), 4.95 (m, 1H), 4.31 (t, J=6.74 Hz, 1H), 3.88 (m, 1H), 2.81 (m, 2H), 2.66 (m, 1H), 2.40 (m, 5H), 2.25 (m, 3H), 2.14 (br. s., 3H), 2.11 (m, 3H), 1.91 (m, 2H), 1.83 (m, 1H), 1.61 (m, 1H), 1.51 (m, 1H), 1.47 (s, 3H).

Compound 37: (1R,2S,3R,5R)-3-(4-amino-7H-pyrrolo[2,3-d]pyrimidin-7-yl)-5-((methyl((1r,3S)-3-(2-(5-(trifluoromethoxy)-1H-benzo[d]imidazol-2-yl)ethyl)cyclobutyl)amino)methyl)cyclopentane-1,2-diol

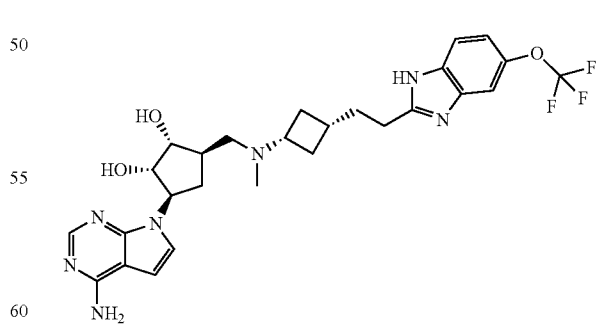

The diastereoisomers were separated by SFC. Lyophilization gave the desired product as a colorless solid (0.060 g). $^1$H NMR (400 MHz, d$_4$-MeOH) δ$_H$ 8.079 (s, 1H), 7.546-7.524 (m, 1H), 7.409 (s, 1H), 7.226-7.217 (m, 1H), 7.150-7.124 (m, 1H), 6.619-6.610 (m, 1H), 4.355-4.320 (m, 1H), 3.912-3.885

(m, 1H), 2.881-2.845 (m, 2H), 2.727-2.674 (m, 1H), 2.538-2.262 (m, 6H), 2.172 (s, 3H), 1.955-1.916 (m, 3H), 1.670-1.492 (m, 3H).

Compound 38: (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(ethyl)amino)methyl)cyclopentane-1,2-diol

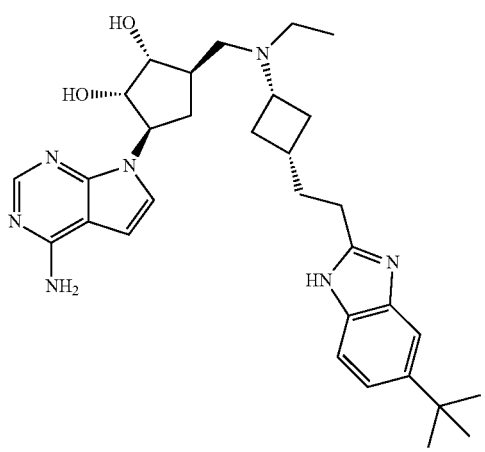 [SMILES: CCN(C[C@H]1C[C@@H](n2ccc3c(N)ncnc32)[C@H](O)[C@@H]1O)[C@H]1C[C@@H](CCc2nc3cc(C(C)(C)C)ccc3[nH]2)C1]

The diastereoisiomers were separated by SFC. After lyophilization the desired product was recovered as a colorless solid (32 mg).
Preparative Method: Lux-3 (2×15 cm),30% ethanol (0.2% DEA))/CO$_2$, 100 bar, 65 mL/min, 220 nm., inj vol.: 0.4 mL, 6.2 mg/mL methanol. $^1$H NMR (400 MHz, d$_4$-MeOH) δ$_H$ 8.082 (s, 1H), 7.493 (s, 1H), 7.415-7.393 (m, 1H), 7.295-7.270 (m, 1H), 7.215-7.206 (m, 1H), 6.621-6.612 (m, 1H), 4.343-4.309 (m, 1H), 3.924-3.897 (m, 1H), 3.044-2.962 (m, 1H), 2.834-2.798 (m, 2H), 2.728-2.695 (m, 1H), 2.660-2.607 (m, 2H), 2.543-2.380 (m, 2H), 2.281-2.257 (m, 3H), 1.932-1.906 (m, 3H), 1.660-1.523 (m, 3H), 1.368 (s, 9H), 1.050-1.014 (t, J=7.2 Hz, 3H).

Compound 39: (1R,2S,3R,5R)-3-(4-amino-7H-pyrrolo[2,3-d]pyrimidin-7-yl)-5-((methyl((1s,3R)-3-(2-(5-(1-methylcyclobutyl)-1H-benzo[d]imidazol-2-yl)ethyl)cyclobutyl)amino)methyl)cyclopentane-1,2-diol

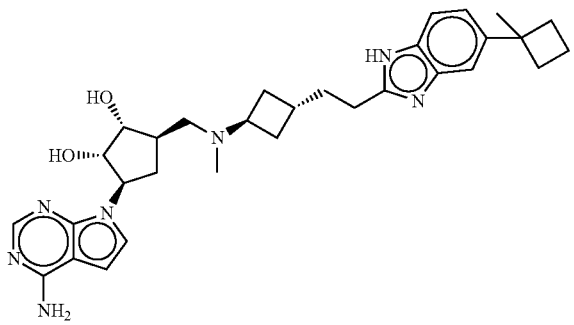

The diastereoisomers were separated by SFC. The material was taken up in MeOH/H$_2$O and lyophilized to a white powder (19 mg). $^1$H NMR (400 MHz, MeOD) δ$_H$ ppm 8 06 (s, 1H), 7.39 (d. J=8.50 Hz, 1H), 7.21 (m, 2H), 6.99 (dd, J=8.29, 1.45 Hz, 1H), 6.59 (d, J=3.52 Hz, 1H), 4.94 (m, 1H), 4.32 (dd, J=7.77, 5.91 Hz, 1H), 3.89 (m, 1H), 3.00 (m, 1H), 2.83 (t, J=7.57 Hz, 2H), 2.49 (m, 1H), 2.38 (m, 4H), 2.23 (m, 1H), 2.16 (s. 3H), 2.11 (m, 5H), 2 01 (m, 2H), 1.84 (m. 3H), 1.61 (m, 1H), 1.46 (s, 3H).

Compound 40: (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(cyclopropylmethyl)amino)methyl)cyclopentane-1,2-diol

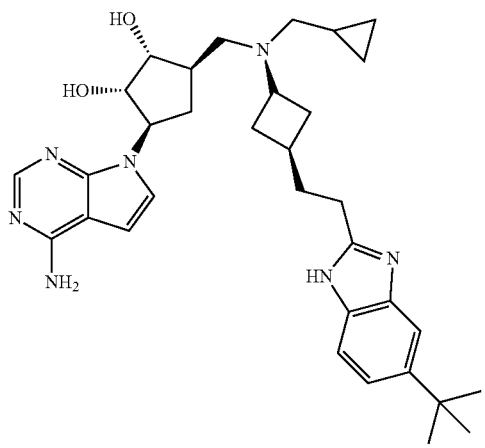

The diastereoisomers were separated by SFC. The material was taken up in MeOH/H$_2$O and lyophilized to yield a white powder (45 mg). $^1$H NMR (400 MHz, MeOD) δ$_H$ ppm 8.06 (s, 1H), 7.48 (br. s., 1H), 7.39 (d, J=8.29 Hz, 1H), 7.27 (m, 1H), 7.20 (d, J=3.73 Hz, 1H), 6.60 (d, J=3.52 Hz, 1H), 4.32 (dd, J=7.36, 6.12 Hz, 1H), 3.90 (m, 1H), 3.06 (m, 1H), 2.81 (t, J=6.84 Hz, 2H), 2.74 (m, 1H), 2.55 (dd, J=12.75, 7.77 Hz, 1H), 2.41 (m, 1H), 2.37 (d, J=6.84 Hz, 2H), 2.29 (m, 3H), 1.91 (m, 3H), 1.60 (m, 1H), 1.50 (m, 2H), 1.36 (s, 9H), 0.87 (m, 1H), 0.48 (d, J=8.09 Hz, 2H), 0.10 (m, 2H).

Compound 41: (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(isopropyl)amino)methyl)cyclopentane-1,2-diol The diastereoisomers were separated by SFC followed by lyophilization from H$_2$O/MeOH/CH$_3$CN to yield a white powder (100 mg). $^1$H NMR (400 MHz, MeOD) δ$_{14}$ ppm 8.06 (s, 1H), 7.48 (br. s., 1H), 7.39 (m, 1H), 7.27 (m, 1H), 7.20 (d, J=3.52 Hz, 1H), 6.60 (m, 1H), 4.32 (t, J=6.43 Hz, 1H), 3.93 (t, J=5.29 Hz, 1H), 3.54 (m, 0.2H), 3.11 (t, J=9.33 Hz, 1H), 3.02 (m, 1H), 2.82 (m, 2H), 2.66 (dd, J=13.68, 8.09 Hz, 1H), 2.46 (m, 1H), 2.36 (m, 1H), 2.23 (m, 3H), 2.05 (m, 1H), 1.91 (m, 3H), 1.59 (m, 3H), 1.36 (s, 9H), 1.02 (m, 6H).

Compound 42: (1R,2S,3R,5R)-3-(4-amino-7H-pyr-rolo[2,3-d]pyrimidin-7-yl)-5-(((((1r,3S)-3-(2-(5-(tert-butyl)-1H-benzo[d]imidazol-2-yl)ethyl)cyclobutyl)(cyclobutylmethyl)amino)methyl)cyclopentane-1,2-diol Step 1: ethyl 3-((1S,3r)-3-((cyclobutylmethyl)(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoate stalled. Another 1.3 equivalents of cyclobutanecarboxaldehyde was added and the reaction continued overnight. NaHCO$_3$ (saturated) was added to the reaction mixture which was then extracted 3 times with DCM. The combined organics were dried with MgSO$_4$ and concentrated to a yellow resin. Cis and trans isomers were separable on silica. Purification by FC (DCM/7N NH$_3$ in MeOH 96:4) yielded 2 separate batches of product, each enriched in one respective isomer to about 90%. Top isomer: 0.38 g (11:1 mixture, cis) Bottom isomer: 0.31 g (6:1 mixture, trans). MS (ESI$^+$) for

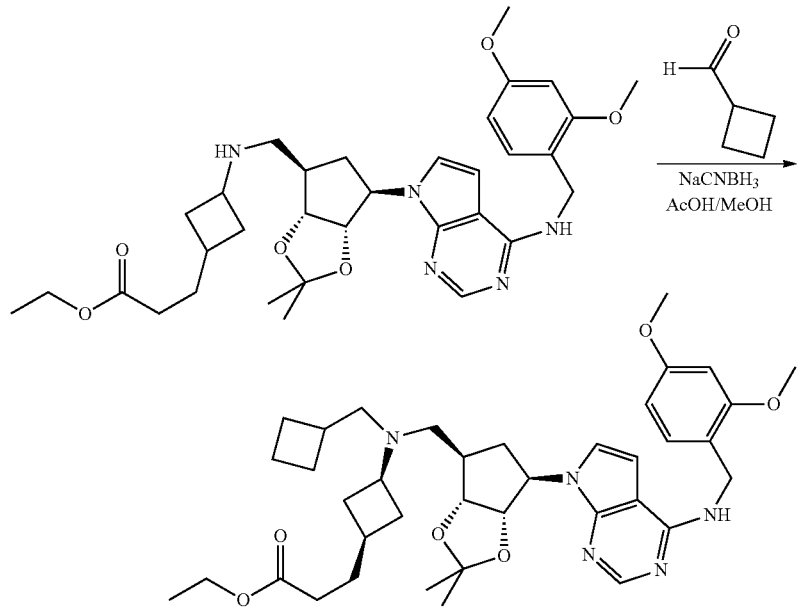

The amine ethyl 3-[3-({[(3aR,4R,6R,6aS)-6-{4-[(2,4-dimethoxybenzyl)amino]-7H-pyrrolo[2,3-d]pyrimidin-7-yl}-2,2-dimethyltetrahydro-3aH-cyclopenta[d][1,3]dioxol-4-yl]methyl}amino)cyclobutyl]propanoate (1.8 g, 3.0 mmol) was taken up in methanol (20 mL, 600 mmol) and sodium cyanoborohydride (0.37 g, 5.9 mmol) was added. The pH was adjusted to ca. 6 using a 10% solution of AcOH in methanol, then cyclobutanecarboxaldehyde (0.32 g, 3.8 mmol) was added in one portion. The reaction was allowed to proceed for 5 hours at which time HPLC indicated the reaction had $C_{35}H_{49}N_5O_6$ m/z 676.7 [M+H]$^+$; HPLC purity >69% (ret. time, 3.791).

Step 2: N-(2-amino-5-(tert-butyl)phenyl)-3-((1S,3r)-3-((cyclobutylmethyl)(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanamide

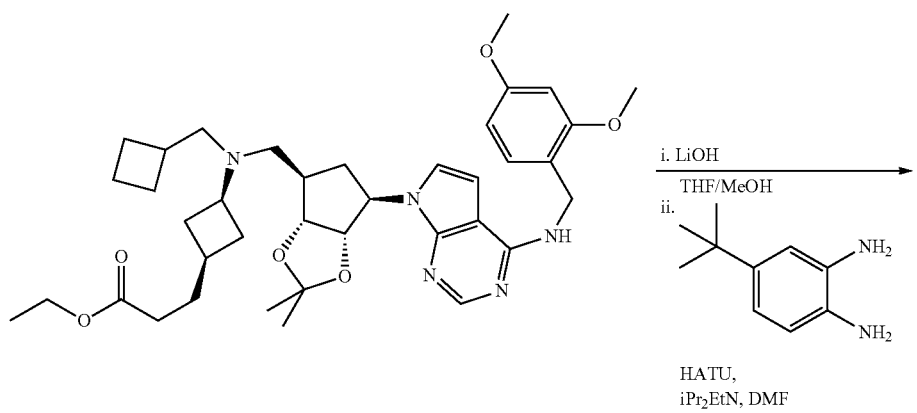

-continued

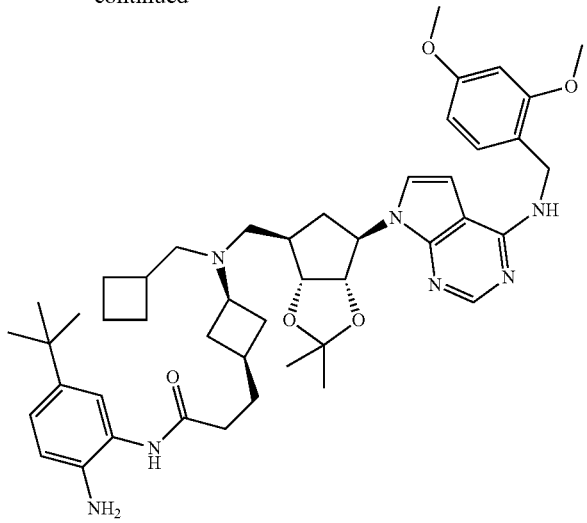

Top Isomer (cis): Lithium hydroxide monohydrate (0.236 g, 5.62 mmol) was added to a solution of ethyl 3-((1S,3r)-3-((cyclobutylmethyl)(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoate (6 mL, 70 mmol) and methanol (1.5 mL, 37 mmol). The reaction was stirred overnight at room temperature and by the next morning the starting material was consumed and had been transformed into the acid. The reaction was acidified with 1N HCl to pH=6. The volatiles were removed in vacuo and the remaining water was removed by azeotropic distillation with ethanol followed by 72 hours on the lyophilizer. The resulting off white solid was used without further purification. Retention time: 3.330 minutes MS (ESI$^+$) for $C_{36}H_{49}N_5O_6$ m/z 648.4 [M+H]$^+$; MS (ESI$^-$) for $C_{36}H_{49}N_5O_6$ m/z 646.4 [M–H]$^-$; HPLC purity >97% (ret. time, 3.329).

N,N,N',N'-Tetramethyl-O-(7-azabenzotriazol-1-yl)uronium hexafluorophosphate (0.334 g, 0.880 mmol) was added to a solution of 3-{cis-3-[(cyclobutylmethyl){[(3aR,4R,6R,6aS)-6-{4-[(2,4-dimethoxybenzyl)amino]-7H-pyrrolo[2,3-d]pyrimidin-7-yl}-2,2-dimethyltetrahydro-3aH-cyclopenta[d][1,3]dioxol-4-yl]methyl}amino]cyclobutyl}propanoic acid (0.38 g, 0.59 mmol) and N,N-diisopropylethylamine (0.337 mL, 1.94 mmol) and 4-tert-butylbenzene-1,2-diamine (0.116 g, 0.704 mmol) in N,N-dimethylformamide (3.63 mL, 46.9 mmol). The reaction was stirred overnight at room temperature and by the next morning the starting material was consumed. The reaction was partially concentrated to ca. 2 mLs and then NaHCO$_3$ (saturated) was added. The mixture was extracted with EtOAc 3 times and the combined organics were dried with MgSO$_4$ and concentrated. The resulting residue was purified by FC (DCM/7N NH$_3$ in MeOH 95:5) to yield N-(2-amino-5-(tert-butyl)phenyl)-3-((1S,3r)-3-((cyclobutylmethyl)(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanamide (0.30 g; 64%) as a purple-brown amorphous solid. HPLC purity >19% (ret. time, 3.574 min.)

Step 3: 7-((3aS,4R,6R,6aR)-6-((((1r,3S)-3-(2-(5-(tert-butyl)-1H-benzo[d]imidazol-2-yl)ethyl)cyclobutyl)(cyclobutylmethyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

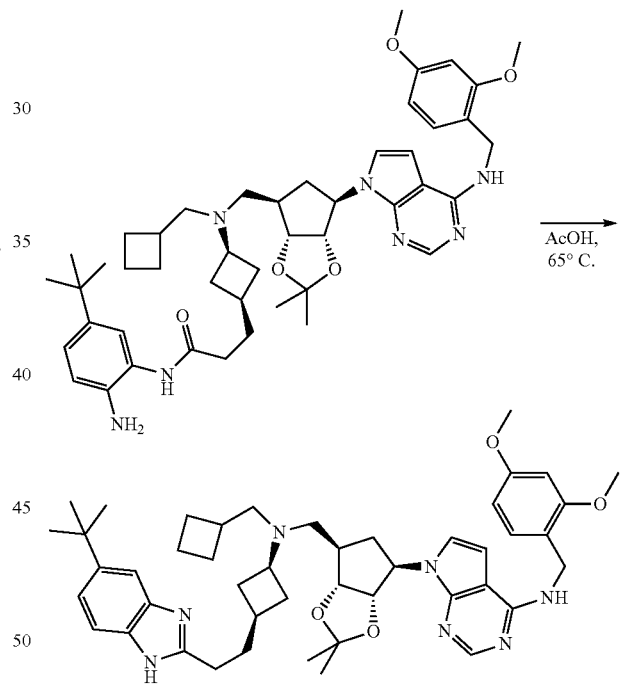

A solution of N-(2-amino-4-tert-butylphenyl)-3-{cis-3-[(cyclobutylmethyl){[(3aR,4R,6R,6aS)-6-{4-[(2,4-dimethoxybenzyl)amino]-7H-pyrrolo[2,3-d]pyrimidin-7-yl}-2,2-dimethyltetrahydro-3aH-cyclopenta[d][1,3]dioxol-4-yl]methyl}amino]cyclobutyl}propanamide (0.3 g, 0.4 mmol) in acetic acid (1.0 mL, 20 mmol) was stirred overnight at 65° C. and by next morning the starting material was consumed. The volatiles were removed in vacuo and the resulting residue purified by FC (DCM/7N NH$_3$ in MeOH 93:7) to yield 7-((3aS,4R,6R,6aR)-6-((((1r,3S)-3-(2-(5-(tert-butyl)-1H-benzo[d]imidazol-2-yl)ethyl)cyclobutyl)(cyclobutylmethyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine as a off white solid. MS (ESI$^+$) for $C_{46}H_{61}N_7O_4$ m/z 777.7 [M+H]$^+$; HPLC purity >64% (ret. time, 3.690 min.).

315

Step 4: (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(cyclobutylmethyl)amino)methyl)cyclopentane-1,2-diol

316

Compound 43: (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(cyclobutyl)amino)methyl)cyclopentane-1,2-diol

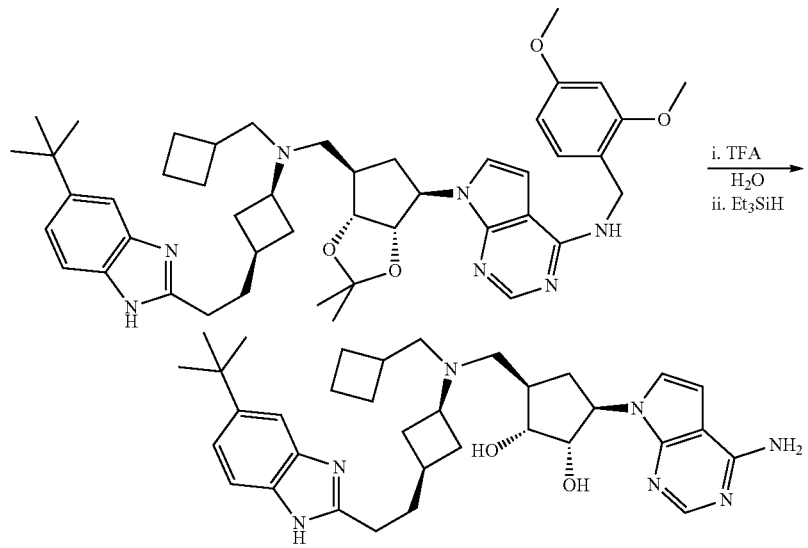

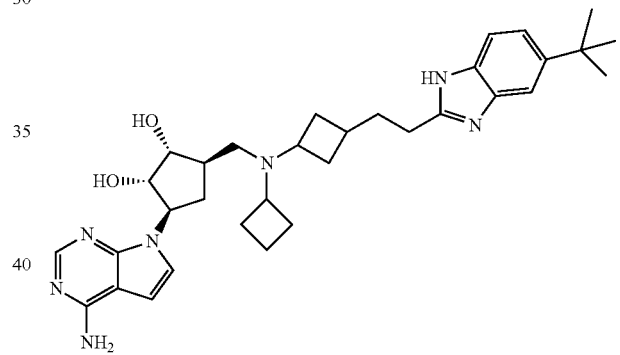

Trifluoroacetic acid (5 mL, 60 mmol) was added to a mixture of water (0.5 mL, 20 mmol) and 7-((3aS,4R,6R,6aR)-6-(((((1r,3S)-3-(2-(5-(tert-butyl)-1H-benzo[d]imidazol-2-yl)ethyl)cyclobutyl)(cyclobutylmethyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (0.2 g, 0.2 mmol) at room temperature. The reaction was allowed to proceed overnight at which time the bright pink suspension was quenched with triethylsilane (0.082 mL, 0.52 mmol). The volatiles were removed in vacuo and the resulting residue was taken up in methanol (15 mls). 500 mgs of $K_2CO_3$ and 8 drops $H_2O$ were added and the reaction was stirred at room temperature for 1 hour. The mixture was filtered and the filter cake washed with 10 mLs methanol. The filtrate was concentrated and the resulting residue was purified by FC (DCM/7N $NH_3$ in MeOH 90:10) to yield (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(cyclobutylmethyl)amino)methyl)cyclopentane-1,2-diol (0.037 g; 20%) as a colorless solid. MS (ESI$^+$) for $C_{34}H_{47}N_7O_2$ m/z 586.3 [M+H]$^+$; HPLC purity >89% (ret. time, 2.970 min.) $^1$H NMR (400 MHz, $d_4$-MeOH) $\delta_H$ 8.083 (s, 1H), 7.498 (s, 1H), 7.417-7.396 (m, 1H), 7.302-7.277 (m, 1H), 7.206-7.197 (m, 1H), 6.621-6.612 (m, 1H), 4.347-4.314 (m, 1H), 3.912-3.885 (m, 1H), 2.973-2.922 (m, 1H), 2.836-2.800 (m, 2H), 2.662-2.366 (m, 6H), 2.282-2.241 (m, 3H), 2.061-2.034 (m, 2H), 1.912-1.494 (m, 10H), 1.374 (s, 9H).

ethyl 3-(3-(cyclobutyl(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoate

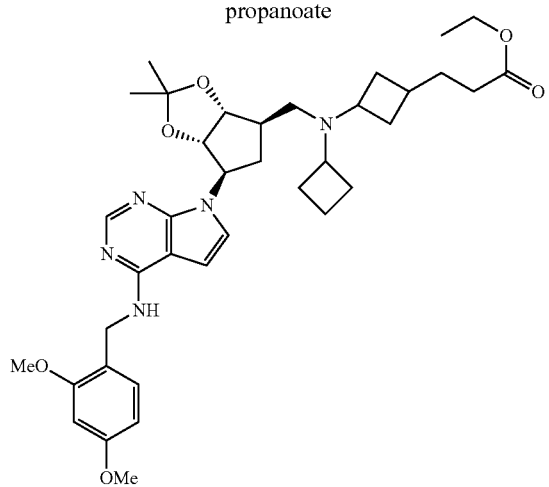

Ethyl 3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoate (0.84 g, 1.4 mmol) was taken up in methanol (10 ml) and Sodium cyanoborohydride (0.087 g, 1.4 mmol) was added. The pH was adjusted to ca. 6 using a 10% solution of AcOH in MeOH, then Cyclobutanone (0.15 ml, 2.1 mmol) added in one portion. The reaction was stirred at RT for 3 days. NaHCO₃ (sat'd) added to the reaction mixture which was then extracted (3×) with DCM. The combined organics were dried with MgSO₄, filtered and concentrated. The material was used without further purification.

3-(3-(cyclobutyl(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoic acid

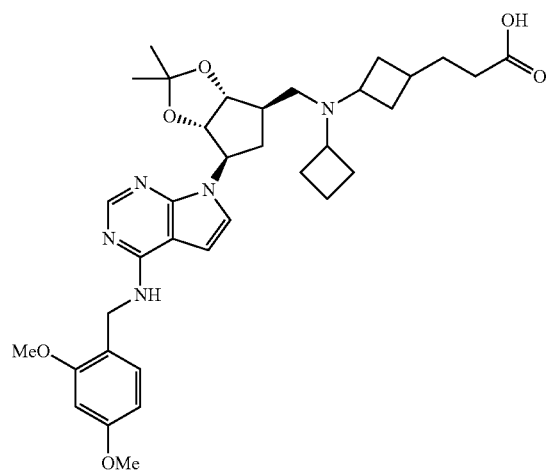 [SMILES: COc1ccc(CNc2ncnc3c2ccn3[C@@H]2C[C@H](CN(C3CCC3)C3CC(CCC(=O)O)C3)[C@H]3OC(C)(C)O[C@H]32)c(OC)c1]

Lithium hydroxide monohydrate (0.58 g, 14 mmol) added to a solution of ethyl 3-(3-(cyclobutyl(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoate (0.91 g, 1.4 mmol) in Tetrahydrofuran (12 ml, 150 mmol) and Methanol (3 ml, 60 mmol). The reaction mixture was stirred overnight at RT, upon which it was acidified with 1 N HCl to pH=6. The volatiles were removed in vacuo and the remaining water removed by azeotropic distillation with ethanol followed by 18 hours on lyophilizer. The resulting off white solid was used without further purification.

N-(2-amino-4-(tert-butyl)phenyl)-3-(3-(cyclobutyl(((3aR,4R,6R,6aS)-6-(4-((2,4-dimethoxybenzyl)amino)-7H-pyrrolo[2,3-d]pyrimidin-7-yl)-2,2-dimethyl tetrahydro-3aH-cyclopenta[d][1,3]dioxol-4-yl)methyl)amino)cyclobutyl)propanamide

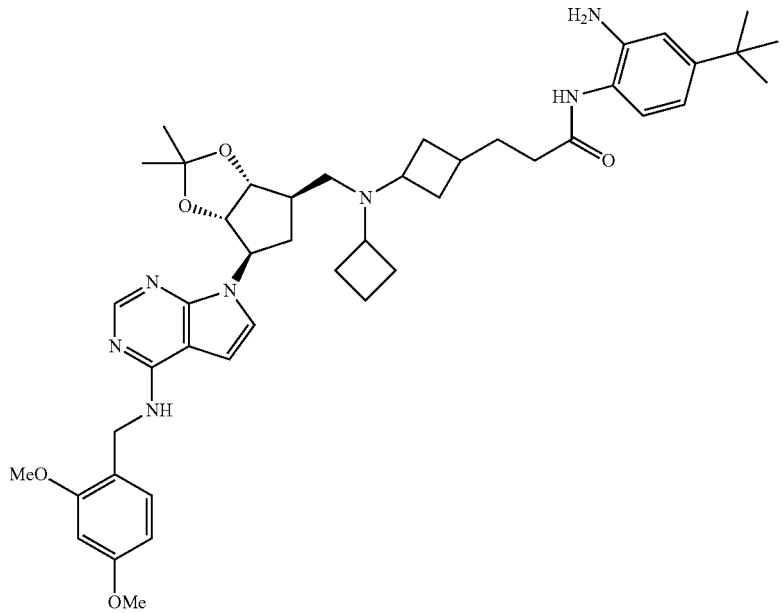 [SMILES: COc1ccc(CNc2ncnc3c2ccn3[C@@H]2C[C@H](CN(C3CCC3)C3CC(CCC(=O)Nc4ccc(C(C)(C)C)cc4N)C3)[C@H]3OC(C)(C)O[C@H]32)c(OC)c1]

319

N,N,N',N'-Tetramethyl-0-(7-azabenzotriazol-1-yl)uronium Hexafluorophosphate (0.783 g, 2.06 mmol) was added to a solution of 3-(3-(cyclobutyl(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoic acid (0.87 g, 1.4 mmol) and N,N-Diisopropylethylamine (0.789 ml, 4.53 mmol) and [8]4-tert-butylbenzene-1,2-diamine (0.270 g, 1.65 mmol) in N,N-Dimethylformamide (8.50 ml) The reaction was stirred overnight at RT, upon which the mixture was partially concentrated to ca. 2 mls and then NaHCO$_3$ (saturated) was added. The mixture was extracted with EtOAc (3×) and the combined organics were dried with MgSO$_4$, filtered and concentrated. The residue was purified by flash chromatography (DCM/7NNH$_3$ in MeOH 95:5) to give the desired compound (0.76 g) as a solid. 7-((3aS,4R,6R,6aR)-6-(((3-(2-(5-(tert-butyl)-1H-benzo[d]imidazol-2-yl)ethyl)cyclobutyl)(cyclobutyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

320

(1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(cyclobutyl)amino)methyl)cyclopentane-1,2-diol

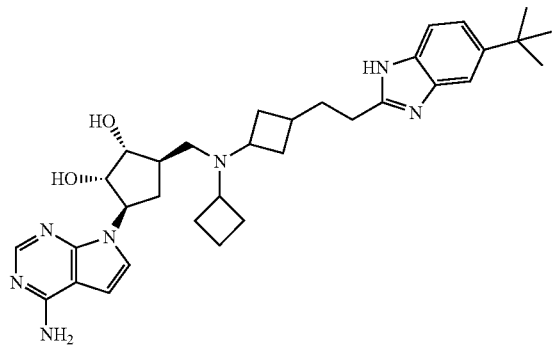

Trifluoroacetic Acid (10 ml, 200 mmol) added to a mixture of Water (1 ml, 80 mmol) and 7-((3aS,4R,6R,6aR)-6-(((3-(2-(5-(tert-butyl)-1H-benzo[d]imidazol-2-yl)ethyl)cyclobutyl)(cyclobutyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (0.61 g, 0.80 mmol) at RT.

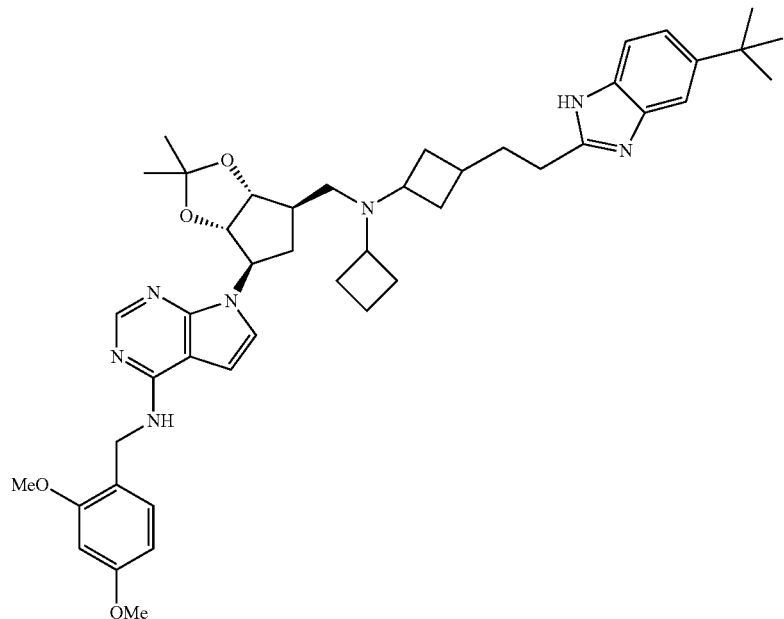 [SMILES: COc1ccc(CNc2ncnc3c2ccn3[C@@H]2C[C@H](CN(C3CCC3)C3CC(CCc4nc5cc(C(C)(C)C)ccc5[nH]4)C3)[C@H]3OC(C)(C)O[C@H]32)c(OC)c1]

A solution of N-(2-amino-4-(tert-butyl)phenyl)-3-(3-(cyclobutyl(43aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanamide (0.76 g, 0.97 mmol) in Acetic acid (2 ml) was stirred overnight at 60° C. The volatiles were removed in vacuo and the remaining residue purified directly by flash chromatography (DCM/7N NH$_3$ in MeOH 91:9) to give the desired compound (0.61 g) as a foam.

The reaction was stirred o/n at RT and was quenched by the addition of Triethylsilane (0.26 ml, 1.6 mmol). The volatiles were removed in vacuo and resulting and the residue was taken up in MeOH (15 mls),500 mg K$_2$CO$_3$ and 8 drops of water were added and the reaction was stirred at RT for 1 hour. The mixture was filtered and the filter cake was washed with MeOH (10 ml). The filtrate was concentrated and the resulting residue purified by flash chromatogrpahy (DCM/7N NH$_3$ in MeOH 90:10) to give the desired product (0.13 g) as a colorless foam. MS (ESI$^+$) for C$_{33}$H$_{45}$N$_7$O$_2$ m/z 572.2 [M+H]$^+$; MS (ESI$^-$) for C$_{33}$H$_{45}$N$_7$O$_2$ m/z 570.2 [M−H]$^-$; HPLC purity >90% (ret. time, 2.850 min.) $^1$H NMR (400

MHz, d₄-MeOH) δ_H 8.083 (s, 1H), 7.492 (s, 1H), 7.412-7.392 (m, 1H), 7.309-7.286 (m, 1H), 7.220-7.205 (m, 1H), 6.620-6.610 (d, J=4.0 Hz, 1H), 4.321-4.283 (m, 1H), 3.888-3.848 (m, 1H), 3.505-3.417 (m, 0.5H (methine of trans isomer)), 3.231-3.147 (m, 0.5H) (methine of cis isomer)), 3.051-2.953 (m, 1H), 2.871-2.732 (m, 3H), 2.583-2.501 (m, 1H), 2.441-2.368 (m, 1H), 2.244-2.205 (m, 3H), 2.170-1.833 (m, 9H), 1.695-1.560 (m, 4H), 1.384 (s, 9H).

Compound 44: (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(cyclopropylmethyl)amino)methyl)cyclopentane-1,2-diol ethyl 3-(3-((cyclopropylmethyl)(((3aR,4R,6R,6aS)-6-((4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoate

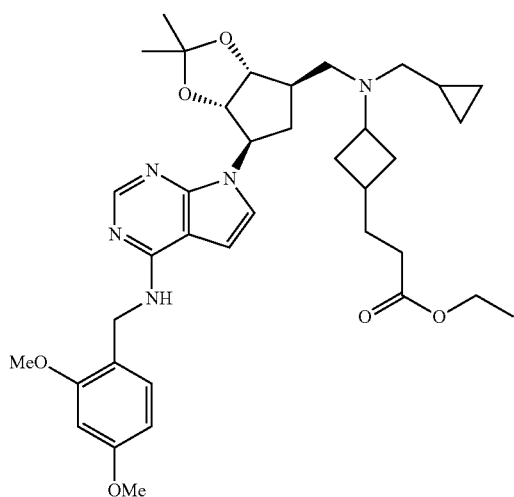 [SMILES: CCOC(=O)CCC1CC(N(CC2CC2)C[C@H]2C[C@@H](n3ccc4c(NCc5ccc(OC)cc5OC)ncnc43)[C@@H]3OC(C)(C)O[C@H]23)C1]

The amine ethyl 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoate (0.90 g, 1.5 mmol) was taken up in Methanol (10 mL) and Sodium cyanoborohydride (0.093 g, 1.5 mmol) was added. The pH was adjusted to ca. 6 using a 10% solution of AcOH in MeOH. The reaction was stirred o/n at RT. NaHCO₃ (sat'd) was added to rxn mixture which was then extracted (3×) with DCM. The combined organics were dried with MgSO₄, filtered and concentrated. The material was used without further purification.

322
3-(3-((cyclopropylmethyl)(((3 aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl) propanoic acid

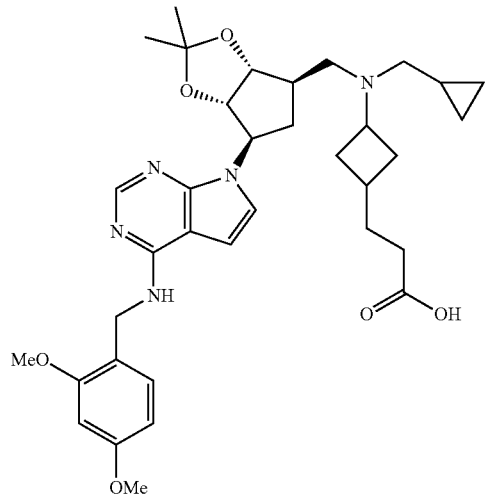 [SMILES: COc1ccc(CNc2ncnc3c2ccn3[C@@H]2C[C@H](CN(CC3CC3)C3CC(CCC(=O)O)C3)[C@H]3OC(C)(C)O[C@H]32)c(OC)c1]

Lithium hydroxide, monohydrate (0.62 g, 15 mmol) added to a solution of ethyl 3-(3-((cyclopropylmethyl)(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl) propanoate (0.98 g, 1.5 mmol) in Tetrahydrofuran (13 ml) and Methanol (3 ml). The reaction was stirred for 24 hours at RT, acidified with 1 N HCl to pH=6. The volatiles removed in vacuo and remaining water removed by azeotropic distillation with ethanol followed by 18 hours on lyophilizer. The resulting off white solid was used without further purification.

N-(2-amino-4-(tert-butyl)phenyl)-3-(3-((cyclopropylmethyl)(((3 aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanamide

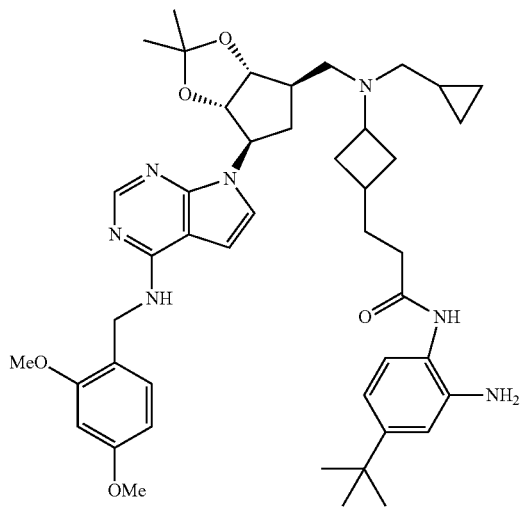 [SMILES: COc1ccc(CNc2ncnc3c2ccn3[C@@H]2C[C@H](CN(CC3CC3)C3CC(CCC(=O)Nc4ccc(C(C)(C)C)cc4N)C3)[C@H]3OC(C)(C)O[C@H]32)c(OC)c1]

323

N,N,N',N'-Tetramethyl-0-(7-azabenzotriazol-1-yl)uronium Hexafluorophosphate (0.846 g, 2.22 mmol) added to a solution of 3-(3-((cyclopropylmethyl)(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoic acid (0.94 g, 1.5 mmol) and N,N-Diisopropylethylamine (0.852 mL, 4.89 mmol) and [8]4-tert-butylbenzene-1,2-diamine (0.292 g, 1.78 mmol) in N,N-Dimethylformamide (9.19 mL, 119 mmol). The reaction was stirred overnight at RT, partially concentrated to ca. 2 mls and NaHCO$_3$ (saturated) was added. The mixture extracted with EtOAc (3×) and the combined organics were dried with MgSO$_4$, filtered and concentrated. The residue was purified by flash chromatography (DCM/7N NH$_3$ in MeOH 95:5) to give the desired compound (0.92 g) as a solid.

7-((3aS,4R,6R,6aR)-6-(((3-(2-(5-(tert-butyl)-1H-benzo[d]imidazol-2-yl)ethyl)cyclobutyl)(cyclopropylmethyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

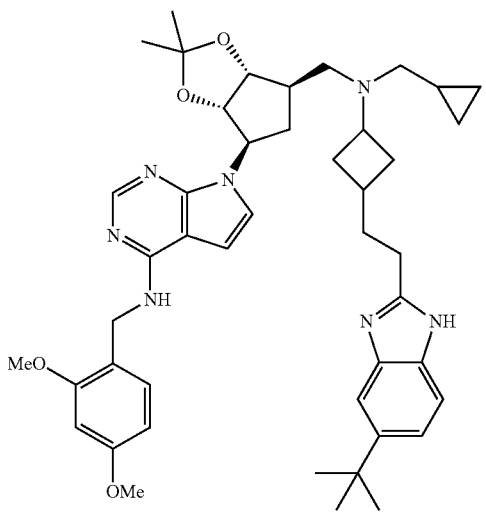 [SMILES: COc1ccc(CNc2ncnc3c2ccn3[C@@H]2C[C@H](CN(CC3CC3)C3CC(CCc4nc5cc(C(C)(C)C)ccc5[nH]4)C3)[C@H]3OC(C)(C)O[C@H]32)c(OC)c1]

N-(2-amino-4-(tert-butyl)phenyl)-3-(3-((cyclopropylmethyl)(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanamide (1.1 g, 1.4 mmol) in Acetic acid (5 ml) was heated at 60° C. overnight. The solution was concentrated and purified by flash chromatography (DCM/7N NH$_3$ ion MeOH 93:7) to yield the desired compound (0.57 g) as a colorless foam.

324

(1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(cyclopropylmethyl)amino)methyl)cyclopentane-1,2-diol

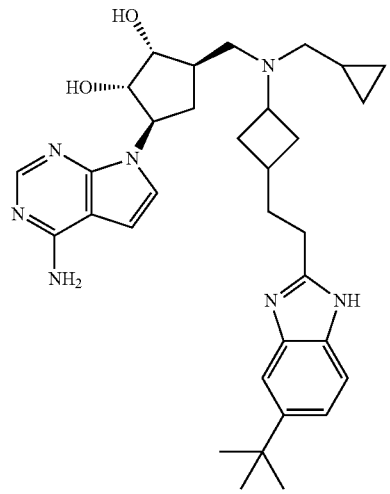 [SMILES: CC(C)(C)c1ccc2[nH]c(CCC3CC(N(CC4CC4)C[C@H]4C[C@@H](n5ccc6c(N)ncnc65)[C@H](O)[C@@H]4O)C3)nc2c1]

Trifluoroacetic Acid (10 mL) added to a mixture of Water (1 mL) and 7-((3aS,4R,6R,6aR)-6-(((3-(2-(5-(tert-butyl)-1H-benzo[d]imidazol-2-yl)ethyl)cyclobutyl)(cyclopropylmethyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (0.52 g, 0.68 mmol) at RT. The reaction was stirred overnight at RT and Triethylsilane (0.22 mL, 1.4 mmol) was added. The volatiles were removed in vacuo and resulting residue was taken up in MeOH (15 mls), 500 mgs of K$_2$CO$_3$ and 8 drops H$_2$O were added and the reaction stirred at RT for 1 hour. The mixture was filtered and the filter cake washed with 10 ml MeOH. The filtrate was concentrated and the resulting residue purified by flash chromatography (DCM I 7N NH$_3$ in MeOH 90:10) to give the desired product (0.196 g) as an off white foam. MS (ESI$^+$) for C$_{33}$H$_{45}$N$_7$O$_2$ m/z 572.6 [M+H]$^+$; MS (ESI$^-$) for C$_{33}$H$_{45}$N$_7$O$_2$ m/z 570.3 [M−H]$^-$; HPLC purity >90% (ret. time, 2.850 min.) $^1$H NMR (400 MHz, d$_4$-MeOH) δ$_H$ 7.944 (s, 1H), 7.361 (s, 1H), 7.280-7.259 (m, 1H), 7.172-7.150 (m, 1H), 7.092-7.078 (m, 1H), 6.484-6.475 (d, J=3.6 Hz, 1H), 4.222-4.185 (m, 1H), 3.815-3.779 (m, 1H), 3.329 (m, 0.5H (methine of trans isomer)), 2.961 (m, 0.5H (methine of cis isomer), 2.745-2.627 (m, 3H), 2.503-2.450 (m, 1H), 2.301-2.187 (m, 5H), 2.036-1.890 (m, 2H), 1.793-1.776 (m, 3H), 1.529-1.385 (m, 2H), 1.246 (s, 9H), 0.808-0.739 (m, 1H), 0.394-0.362 (m, 2H), 0.012-0.013 (m, 2H). Retention time: 2.850 minutes. HPLC Conditions: Agilent Zorbax Exlipse XDB-C18 column, 4.6×50 mm (1.8 um packing), Solvent A—Water (0.1% TFA), Solvent B—Acetonitrile (0.07% TFA) 6 min gradient from 5 to 95% B; 1 min hold; then recycle.

Compound 45: ethyl 3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isobutyl)amino)cyclobutyl)propanoate The amine ethyl 3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol- 4-yl)methyl)amino)cyclobutyl)propanoate (1.7 g, 2.8 mmol) was taken up in Methanol (20 ml) and Sodium cyanoborohydride (0.35 g, 5.6 mmol) was added. The pH was adjusted to ca. 6 using a 10% solution of AcOH in MeOH, then isobutyraldehyde (0.33 ml, 3.6 mmol) added in one portion. The reaction stirred at RT for 3 hours. Another 1.3 eq. of isobutyraldehyde was added and stirring was continued overnight. NaHCO₃ (sat'd) was added to reaction mixture which was then extracted (3×) with DCM. The combined organics was dried with MgSO₄ and concentrated. The residue was purified by flash chromatography (DCM/7N NH₃ in MeOH 97:3) to give the desired compound (1.75 g) as a colorless foam.

3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isobutyl)amino)cyclobutyl)propanoic acid

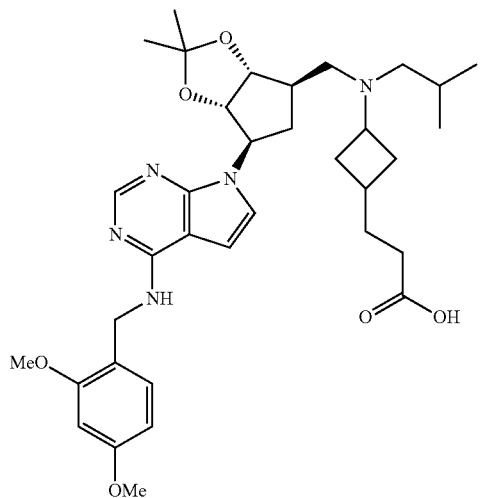 [SMILES: COc1ccc(CNc2ncnc3c2ccn3[C@@H]2C[C@H](CN(CC(C)C)C3CC(CCC(=O)O)C3)[C@H]3OC(C)(C)O[C@H]32)c(OC)c1]

Lithium hydroxide, monohydrate (1.11 g, 26.4 mmol) was added to a solution ethyl 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isobutyl)amino)cyclobutyl)propanoate (1.75 g, 2.64 mmol) in Tetrahydrofuran (13 ml, 160 mmol) and Methanol (3 ml, 70 mmol). The reaction was stirred for 24 hours at RT, acidified with 1 N HCl to pH=6, the volatiles removed in vacuo and remaining water removed by azeotropic distillation with ethanol followed by 18 hours on lyophilizer. The resulting off white solid was used without further purification.

N-(2-amino-4-(tert-butyl)phenyl)-3-(3-((((3 aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isobutyl)amino)cyclobutyl)propanamide

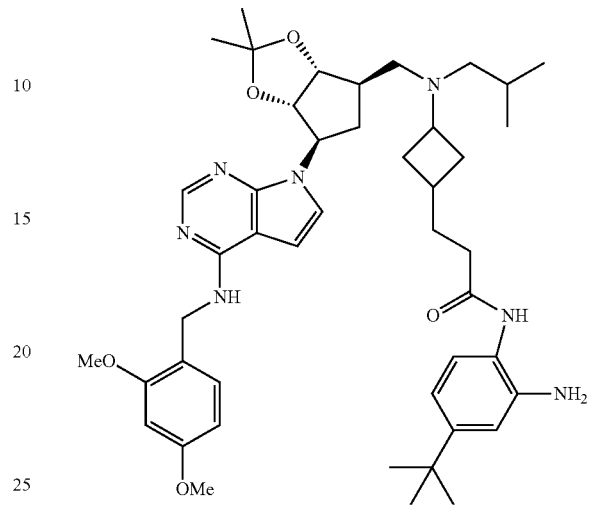

N,N,N',N'-Tetramethyl-O-(7-azabenzotriazol-1-yl)uronium Hexafluorophosphate (1.52 g, 4.01 mmol) added to a solution of 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isobutyl)amino)cyclobutyl)propanoic acid (1.7 g, 2.7 mmol) and N,N-Diisopropylethylamine (1.54 ml, 8.82 mmol) and 4-tert-butylbenzene-1,2-diamine (0.527 g, 3.21 mmol) in N,N-Dimethylformamide (16.6 ml). The reaction was stirred overnight at RT, partially concentrated to ca. 2 mls and then NaHCO₃ (saturated) added. Them mixture was extracted with EtOAc 3× and the combined organics were dried with MgSO₄ filtered, concentrated and purified by flash chromatography (DCM/7N NH₃ in MeOH 95:5) to yield the desired amide (1.71 g) as a solid.

7-((3aS,4R,6R,6aR)-6-(((3-(2-(5-(tert-butyl)-1H-benzo[d]imidazol-2-yl)ethyl)cyclobutyl)(isobutyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

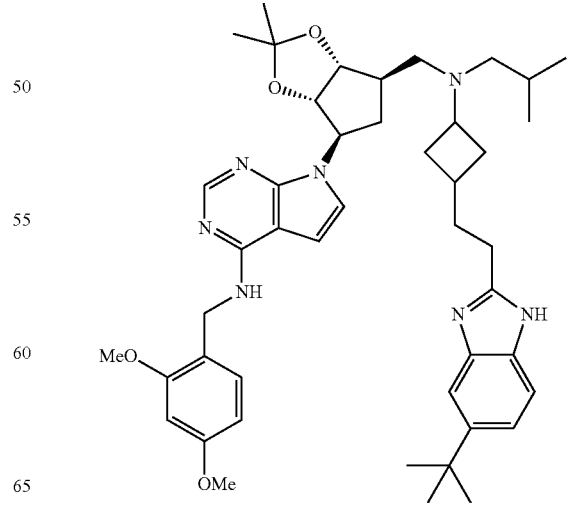

A solution of N-(2-amino-4-(tert-butyl)phenyl)-3-(3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isobutyl)amino)cyclobutyl)propanamide (1.71 g, 2.19 mmol) in Acetic acid (6 ml) was stirred overnight at 60° C., the volatiles were removed in vacuo and the remaining residue was purified by flash chromatography (SiO$_2$, DCM I 7N NH$_3$ in MeOH 94:6) to yield the desired compound (0.9 g) as a foam.

(1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(isobutyl)amino)methyl)cyclopentane-1,2-diol

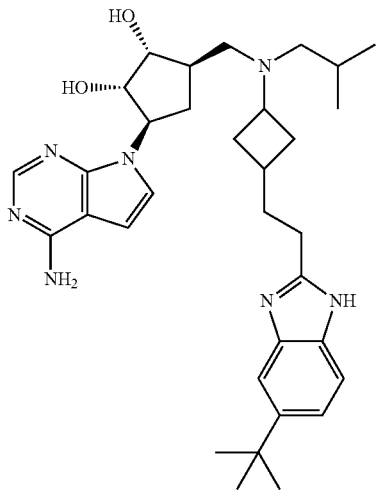 [SMILES: CC(C)CN(C[C@H]1C[C@@H](n2ccc3c(N)ncnc32)[C@H](O)[C@@H]1O)C1CC(CCc2nc3cc(C(C)(C)C)ccc3[nH]2)C1]

Trifluoroacetic Acid (20 ml, 300 mmol) added to a mixture of Water (2 ml, 100 mmol) and 7-((3aS,4R,6R,6aR)-6-(((3-(2-(5-(tert-butyl)-1H-benzo[d]imidazol-2-yl)ethyl)cyclobutyl)(isobutyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (0.9 g, 1 mmol) at RT. The reaction was stirred overnight and Triethylsilane (0.38 ml, 2.4 mmol) was added. The volatiles were removed in vacuo and resulting residue was taken up in MeOH (15 ml), 500 mgs of K$_2$CO$_3$ and 8 drops H$_2$O were added and reaction stirred at RT for 1 hour. The mixture was filtered and filter cake washed with 10 ml MeOH. The filtrate was concentrated and the resulting residue purified by flash chromatography (DCM/7N NH$_3$ in MeOH 90:10) to yield the desired product (0.274 g) as an off white foam. MS (ESI$^+$) for C$_{33}$H$_{47}$N$_7$O$_2$ m/z 574.6 [M+H]$^+$; MS (EST) for C$_{33}$H$_{45}$N$_7$O$_2$ m/z 572.4 [M−H]$^-$; HPLC purity >86% (ret. time, 2.918 min.) $^1$H NMR (400 MHz, d$_4$-MeOH) δ$_H$ 8.078 (s, 1H), 7.497 (s, 1H), 7.416-7.396 (m, 1H), 7.305-7.284 (m, 1H), 7.216-7.200 (m, 1H), 6.621-6.612 (d, J=3.6 Hz, 1H), 4.368-4.334 (m, 1H), 3.930-3.894 (m, 1H), 2.934-2.918 (m, 1H), 2.866-2.797 (m, 2H), 2.652-2.583 (m, 1H), 2.444-2.361 (m, 2H), 2.287-2.199 (m, 2H), 2.166-2.119 (m, 3.5H (contains methine of trans isomer)), 2.048-2.012 (m, 1H), 1.921-1.748 (m, 3.5H (contains methine of cis isomer)), 1.622-1.494 (m, 2H), 1.380 (s, 9H), 1.269-1.252 (m, 1H), 0.932-0.879 (m, 6H).

Compound 46: (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(cyclobutyl)amino)methyl)cyclopentane-1,2-diol The diastereoisomers were separated by SFC. The material was taken up in MeOH/H$_2$O and lyophilized to yield a white powder (23.7 mg). $^1$H NMR (400 MHZ, MeOD) δ$_H$ ppm 8.06 (s, 1H), 7.48 (br. s., 1H), 7.39 (d. J=8.71 Hz, 1H), 7.28 (dd, J=8.60, 1.76 Hz, 1H), 7.19 (d, J=3.52 Hz, 1H), 6.60 (d. J=3.52 Hz, 1H), 4.84 (m, 1H), 4.28 (dd, J=7.26, 6.22 Hz, 1H), 3.84 (t, J=5.70 Hz, 1H), 3.16 (m, 1H), 2.99 (m, 1H), 2.80 (t, J=7.15 Hz, 2H), 2.73 (dd, J=13.68, 6.22 Hz, 1H), 2.49 (dd, J=13.68, 7.67 Hz, 1H), 2.38 (m, 1H), 2.22 (m, 3H), 2.00 (m, 4H), 1.91 (m, 3H), 1.60 (m, 5H), 1.36 (s, 9H).

Compound 47: (1R,2S,3R,5R)-3-(4-amino-7H-pyrrolo[2,3-d]pyrimidin-7-yl)-5-((((1r,3S)-3-(2-(5-bromo-1H-benzo[d]imidazol-2-yl)ethyl)cyclobutyl)(methyl)amino)methyl)cyclopentane-1,2-diol Diastereoisomers were separated by SFC. The material was taken up in MeOH/H$_2$O and lyophilized to yield a white powder (21 mg). $^1$H NMR (400 MHz, MeOD) δ$_{14}$ ppm 8.06 (s. 1H), 7.63 (br. s., 1H), 7.39 (m, 1H), 7.30 (dd, J=8.50, 1.66 Hz, 1H), 7.20 (d. J=3.52 Hz, 1H), 6.60 (d, J=3.52 Hz, 1H), 4.32 (dd, J=7.67, 6.01 Hz, 1H). 3.88 (m, 1H), 2.82 (t, J=7.15 Hz, 2H), 2.71 (m, 1H), 2.52 (m, 1H), 2.41 (m, 2H), 2.25 (m, 2H), 2.18 (s, 3H), 2.03 (m, 1H), 1.92 (m, 3H), 1.62 (m, 1H), 1.51 (m, 2H).

Compound 48: (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(isobutyl)amino)methyl)cyclopentane-1,2-diol Diastereoisomers separated by SFC. After lyophilization (78 mg) obtained of a colorless solid.

Compound 49: (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(ethyl)amino)methyl)cyclopentane-1,2-diol The diastereoisomers were separated by SFC.
Lux-3 (2×15 cm), 30% ethanol (0.2% DEA))/CO$_2$, 100 bar, 65 mL/min, 220 nm. Inj vol.: 0.4 mL, 6.2 mg/mL methanol. $^1$H NMR (400 MHz, d$_4$-MeOH) δ$_H$ 8.081 (s, 1H), 7.499 (s, 1H), 7.416-7.395 (m, 1H), 7.308-7.282 (m, 1H), 7.226-7.216 (m, 1H), 6.619-6.610 (m, 1H), 4.344-4.310 (m, 1H), 3.922-3.895 (m, 1H), 3.410-3.329 (m, 1H), 2.875-2.837 (m, 2H), 2.738-2.689 (m, 1H), 2.659-2.607 (m, 2H), 2.535-2.483 (m, 1H), 2.452-2.380 (m, 1H), 2.311-2.224 (m, 1H), 2.158-2.121 (m, 3H), 2.061-2.030 (m, 2H), 1.913-1.863 (m, 2H), 1.674-1.590 (m, 1H), 1.381 (s, 9H), 1.056-1.020 (t, J=7.2 Hz, 3H).

Compound 50: (1R,2S,3R,5R)-3-(6-amino-9H-purin-9-yl)-5-(((3-(2-(5-(tert-butyl)-1H-benzo[d]imidazol-2-yl)ethyl)cyclobutyl)(isopropyl)amino)methyl)cyclopentane-1,2-diol ethyl 3-(3-((((1R,2R,3S,4R)-4-(6-((2,4-dimethoxybenzyl)amino)-9H-purin-9-yl)-2,3-dihydroxycyclopentyl)methyl)(isopropyl)amino)cyclobutyl)propanoate

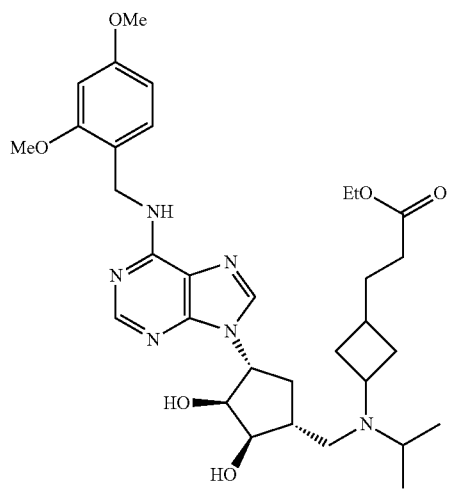 [SMILES: CCOC(=O)CCC1CC(N(C[C@H]2C[C@@H](n3cnc4c(NCc5ccc(OC)cc5OC)ncnc43)[C@H](O)[C@@H]2O)C(C)C)C1]

The amine ethyl 3-(3-((((1R,2R,3S,4R)-4-(6-((2,4-dimethoxybenzyl)amino)-9H-purin-9-yl)-2,3-dihydroxycyclopentyl)methyl)amino)cyclobutyl)propanoate (1.5 g, 2.5 mmol) was taken up in Acetonitrile (66 mL) and Isopropyl iodide (2.5 mL, 25 mmol) and Triethylamine (5.2 mL, 37 mmol) were added. The reaction was heated to 80° C. for 12 hours. Another 15 eq. TEA and another 15 eq iPrI were added and the reaction was continued for a further 8 hours. Another 15 equivalents each of iPrI and TEA were added and heating was continued overnight. The reaction was concentrated and saturated Na2CO3 (20 ml) and DCM (20 ml) were added. The layers were separated and the aqueous layer was further extracted 3 more times, the combined organics were dried and purified by flash chromatography (SiO$_2$, DCM/7N NH$_3$ in MeOH 97:3).

The residue obtained was dissolved in 30 ml DCM and washed with 20 ml saturated NaHCO$_3$ and 10 ms 1 N NaOH. The aqueous was extracted with DCM 3 times, the combined organics were dried over MgSO$_4$ and solvent removed to yield the desired product (1.3 g) as a foam/solid.

(3-((((1R,2R,3S,4R)-4-(6-((2,4-dimethoxybenzyl)amino)-9H-purin-9-yl)-2,3-dihydroxycyclopentyl)methyl)(isopropyl)amino)cyclobutyl)propanoic acid

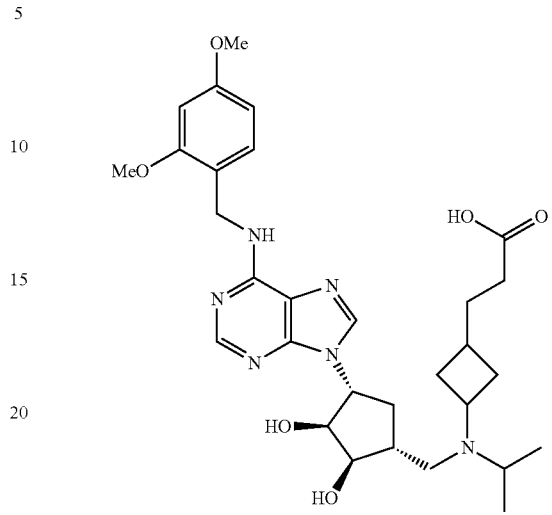

Lithium hydroxide, monohydrate (0.838 g, 20.0 mmol) added to a solution of ethyl 3-(3 (3-((((1R,2R,3 S,4R)-4-(6-((2,4-dimethoxybenzyl)amino)-9H-purin-9-yl)-2,3-dihydroxycyclopentyl)methyl)(isopropyl)amino)cyclobutyl)propanoic acid (1.3 g, 2.0 mmol) in Tetrahydrofuran (30 ml, 300 mmol) and Methanol (6.5 ml, 160 mmol). The reaction was stirred overnight at RT, acidified with 1 N HCl to pH=6. The volatiles were removed in vacuo and remaining water removed by azeotropic distillation with ethanol followed by lyophilization. The resulting solid was used without further purification.

N-(2-amino-4-(tert-butyl)phenyl)-3-(3-((((1R,2R,3S,4R)-4-(6-((2,4-dimethoxybenzyl)amino)-9H-purin-9-yl)-2,3-dihydroxycyclopentyl)methyl)(isopropyl)amino)cyclobutyl)propanamide

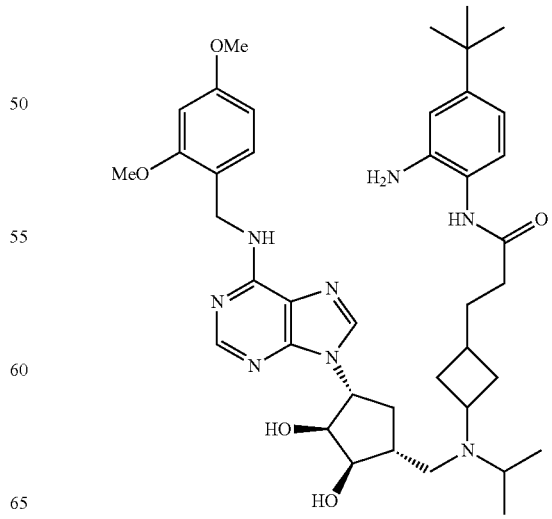

331

N,N,N',N'-Tetramethyl-0-(7-azabenzotriazol-1-yl)uronium Hexafluorophosphate (1.19 g, 3.13 mmol) added to a solution of 3-{3-[{[(3aR,4R,6R,6aS)-6-{6-[(2,4-dimethoxybenzyl)amino]-9H-purin-9-yl}-2,2-dimethyltetrahydro-3aH-cyclopenta[d][1,3]dioxol-4-yl]methyl}(isopropyl)amino]cyclobutyl}propanoic acid (1.30 g, 2.09 mmol) and N,N-Diisopropylethylamine (1.20 ml, 6.89 mmol) and 4-tert-butylbenzene-1,2-diamine (0.411 g, 2.50 mmol) in N,N-Dimethylformamide (12.9 ml). The reaction was stirred for 2 hours, NaHCO₃ (saturated) was added and the mixture extracted with EtOAc (3×) and the combined organics was dried over MgSO₄ filtered and concentrated. The residue was purified by flash chromatography (DCM→DCM/7N NH₃ in MeOH 95:5) to yield the desired amide (1.4 g) as a solid.

9-((3 aS,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydro-3aH-cyclopenta[d][1,3]dioxol-4-yl)-N-(2,4-dimethoxybenzyl)-9H-purin-6-amine

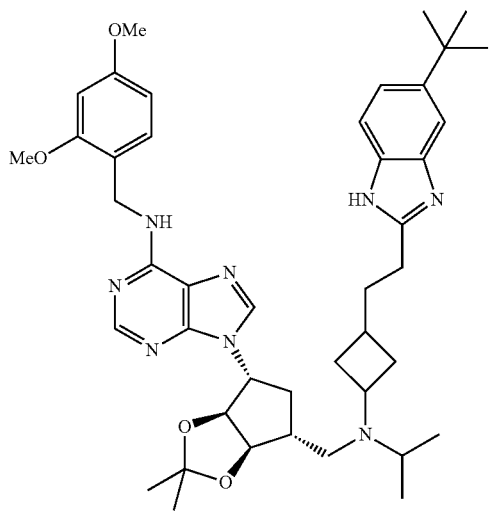 [SMILES: COc1ccc(CNc2ncnc3c2ncn3[C@@H]2C[C@H](CN(C(C)C)C3CC(CCc4nc5cc(C(C)(C)C)ccc5[nH]4)C3)[C@H]3OC(C)(C)O[C@H]32)c(OC)c1]

N-(2-amino-4-(tert-butyl)phenyl)-3-(3-(((((1R,2R,3S,4R)-4-(6-((2,4-dimethoxybenzyl)amino)-9H-purin-9-yl)-2,3-dihydroxycyclopentyl)methyl)(isopropyl)amino)cyclobutyl)propanamide (1.4 g, 1.8 mmol) in Acetic acid (5 ml, 90 mmol) stirred overnight at 60° C. The reaction was concentrated and purified by flash chromatography (DCM→DCM/7N NH₃ in MeOH 94:6) to yield the desired compound (0.91 g) as a foam.

332

(1R,2S,3R,5R)-3-(6-amino-9H-purin-9-yl)-5-(((3-(2-(5-(tert-butyl)-1H-benzo[d]imidazol-2-yl)ethyl)cyclobutyl)(isopropyl)amino)methyl)cyclopentane-1,2-diol

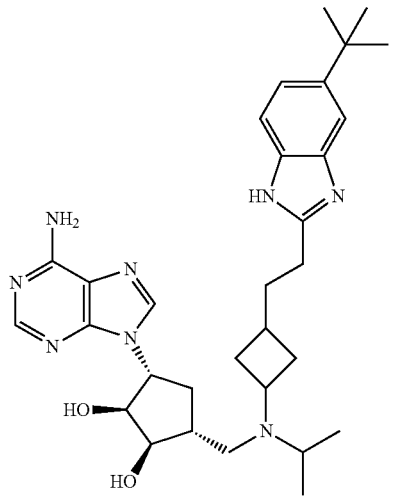 [SMILES: CC(C)N(C[C@H]1C[C@@H](n2cnc3c(N)ncnc32)[C@H](O)[C@@H]1O)C1CC(CCc2nc3cc(C(C)(C)C)ccc3[nH]2)C1]

Trifluoroacetic Acid (10 ml, 100 mmol) added to a mixture of Water (1 ml, 60 mmol) and 9-((3aS,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydro-3aH-cyclopenta[d][1,3]dioxol-4-yl)-N-(2,4-dimethoxybenzyl)-9H-purin-6-amine (0.91 g, 1.2 mmol) at RT. The reaction was stirred overnight at RT. The reaction was then heated to 35° C. and triethylsilane (0.39 ml, 2.4 mmol) was added. The reaction was stirred at 35° C. for a further 2 days. The volatiles were removed in vacuo and resulting residue was taken up in MeOH (15 mls). 500 mgs of K₂CO₃ and 8 drops H₂O were added and reaction stirred at RT for 1 hour. The mixture was filtered and filter cake washed with 10 mls MeOH. The filtrate was concentrated and the resulting residue was purified by flash chromatography (DCM/7N NH₃ in MeOH 90:10) to yield the desired product (0.142 g) as a colorless solid after several days of lyophilization.

Compound 51: (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(cyclobutyl)amino)methyl)cyclopentane-1,2-diol The diastereoisomers were separated by SFC (25 mg). ¹H NMR (400 MHz, MeOD) δ_H ppm 8.06 (s, 1H), 7.48 (br. s., 1H), 7.38 (d, J=7.88 Hz, 1H), 7.27 (dd, J=8.60, 1.55 Hz, 1H), 7.19 (d, J=3.52 Hz, 1H), 6.60 (d, J=3.73 Hz, 1H), 4.85 (m, 1H), 4.29 (m, 1H), 3.85 (t, J=5.60 Hz, 1H), 3.41 (m, 1H), 3.17 (m, 1H), 2.83 (t, J=7.36 Hz, 2H), 2.74 (dd, J=13.68, 6.63 Hz, 1H), 2.51 (dd, J=13.79, 7.57 Hz, 1H), 2.38 (m, 1H), 2.18 (m, 3H), 2.09 (m, 1H), 2.02 (m, 5H), 1 83 (m, 2H), 1.60 (m, 3H), 1.36 (s, 9H).

Compound 52: (1R,2S,3R,5R)-3-(4-amino-7H-pyrrolo[2,3-d]pyrimidin-7-yl)-5-(((((1r,3S)-3-(2-(5,6-dichloro-1H-benzo[d]imidazol-2-yl)ethyl)cyclobutyl)(methyl)amino)methyl)cyclopentane-1,2-diol The diastereoisomers were separated by SFC. The material was taken up in MeOH/H₂O and lyophilized to yield a cream colored solid (64 mg). ¹H NMR (400 MHz, MeOD) δ_H ppm 8.06 (s, 1H), 7.63 (s, 2H), 7.20 (d. J=3.52 Hz, 1H), 6.59 (d, J=3.73 Hz, 1H), 4.32 (dd. J=7.88, 6.01 Hz. 1H), 3.88 (dd, J=5.60, 4.77 Hz, 1H), 2.82 (t, J=7.26 Hz, 2H), 2.69 (m, 1H), 2.48 (m, 1H), 2.38 (m, 2H), 2.24 (m, 3H), 2.15 (s, 3H),1.91 (m, 3H), 1.61 (m, 1H), 1.50 (m, 2H).

Compound 53: (1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(isobutyl)amino)methyl)cyclopentane-1,2-diol Diastereisomers separated by SFC. After lyophilization of a colorless solid (85 mg) was recovered.

Compound 54: (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(cyclopropylmethyl)amino)methyl)cyclopentane-1,2-diol The diastereosiomers were separated by SFC. The material was taken up in MeOH/H₂O and lyophilized to yield a white powder (53 mg). ¹H NMR (400 MHz, MeOD) δ_H ppm 8.06 (s, 1H), 7.48 (br. s., 1H), 7.39 (d, J=8.50 Hz, 1H), 7.28 (dd, J=8.60, 1.76 Hz,1H), 7.21 (d, J=3.52 Hz, 1H), 6.60 (d, J=3.52 Hz, 1H), 4.32 (dd, J=7.67, 5.80 Hz, 1H), 3.91 (m, 1H), 3.44 (m, 1H), 2.84 (t, J=7.57 Hz, 2H), 2.78 (dd, J=13.27, 7.05 Hz, 1H), 2.58 (dd, J=13.06, 7.67 Hz, 1H), 2.40 (m, 3H), 2.11 (t, J=6.22 Hz, 3H), 2.02 (m, 2H). 1.87 (m, 2H), 1.62 (m, 1H), 1.37 (s, 9H), 0.87 (m, 1H), 0.49 (m, 2H), 0.12 (m, 2H).

Compound 55: (1R,2S,3R,5R)-3-(4-amino-7H-pyrrolo[2,3-d]pyrimidin-7-yl)-5-((((1s,3R)-3-(2-(5-bromo-1H-benzo[d]imidazol-2-yl)ethyl)cyclobutyl)(methyl)amino)methyl)cyclopentane-1,2-diol Diastereoisomers were separated SFC ¹H NMR (400 MHZ, MeOD) δ_H ppm 8.05 (s, 1H), 7.63 (s. 1H), 7.39 (m, 1H), 7.30 (dd, J=8.50, 1.66 Hz, 1H), 7.20 (d. J=3.52 Hz. 1H), 6.59 (d, J=3.73 Hz, 1H), 4.32 (dd, J=7.77, 5.91 Hz, 1H), 3.88 (dd, J=5.70, 4.66 Hz, 1H), 2.99 (m. 1H), 2.84 (t, J=7.57 Hz, 2H). 2.48 (m, 1H), 2.41 (dd, J=7.98, 4.87 Hz, 1H), 2.34 (m, 1H), 2.24 (m, 1H), 2.15 (s, 3H). 2.10 (m. 3H), 2.01 (m, 2H), 1.86 (t. J=8.19 Hz, 2H), 1.61 (m, 1H).

Compound 56: (1R,2S,3R,5R)-3-(4-amino-7H-pyrrolo[2,3-d]pyrimidin-7-yl)-5-((isopropyl(3-(2-(5-(trifluoromethoxy)-1H-benzo[d]imidazol-2-yl)ethyl)cyclobutyl)amino)methyl)cyclopentane-1,2-diol N-(2-amino-4-(trifluoromethoxy)phenyl)-3-(3-((((3 aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isopropyl)amino)cyclobutyl)propanamide

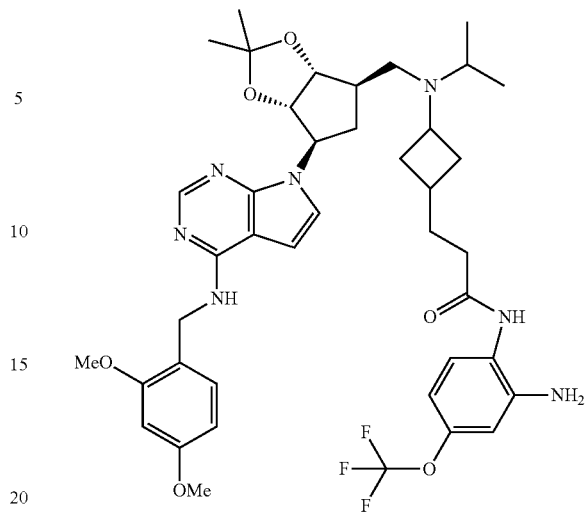

N,N,N',N'-Tetramethyl-0-(7-azabenzotriazol-1-yl)uronium Hexafluorophosphate (1.19 g, 3.14 mmol) added to a solution of 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(isopropyl)amino)cyclobutyl)propanoic acid (1.3 g, 2.1 mmol) and N,N-Diisopropylethylamine (1.20 mL, 6.90 mmol) and 4-(trifluoromethoxy)benzene-1,2-diamine (0.482 g, 2.51 mmol) in N,N-Dimethylformamide (13.0 mL, 167 mmol). The reaction was stirred overnight at RT and was partially concentrated to ca. 2 mls and then NaHCO₃ (saturated) was added. The mixture was extracted with EtOAc (3×) and the combined organics were dried with MgSO₄ filtered and concentrated. The residue was purified by flash chromatogrpahy (DCM/7N NH₃ in MeOH 95:5) to the desired amide (1.4 g) as a solid.

N-(2,4-dimethoxybenzyl)-7-((3 aS,4R,6R,6aR)-6-((isopropyl(3-(2-(5-(trifluoromethoxy)-1H-benzo[d]imidazol-2-yl)ethyl)cyclobutyl)amino)methyl)-2,2-dimethyltetrahydro-3aH-cyclopenta[d][1,3]dioxol-4-yl)-7H-pyrrolo[2,3-d]pyrimidin-4-amine

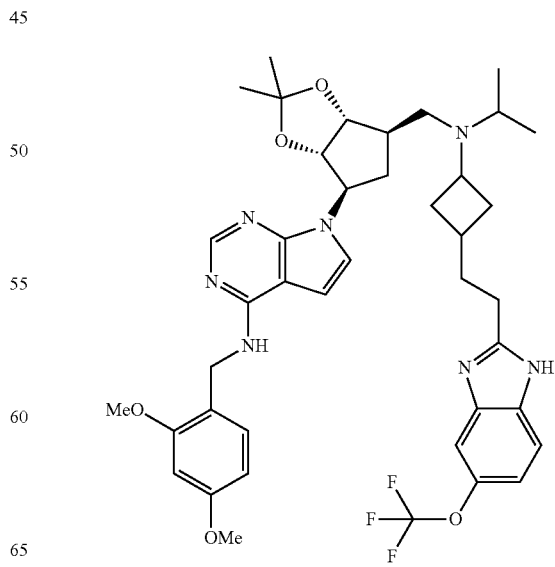

N-(2-amino-4-(trifluoromethoxy)phenyl)-3-(3-(((((3aR, 4R,6R,6aS)-6-(4-((2,4-dimethoxybenzyl)amino)-7H pyrrolo [2,3-d]pyrimidin-7-yl)-2,2-dimethyltetrahydro-3aH-cyclopenta[d][1,3]dioxol-4-yl)methyl)(isopropyl)amino) cyclobutyl)propanamide (1.4 g, 1.8 mmol) was heated in AcOH at 60° C. overnight. The reaction mixture was concentrated in vacuo giving the crude product.

(1R,2S,3R,5R)-3-(4-amino-7H-pyrrolo[2,3-d]pyrimidin-7-yl)-5-((isopropyl(3-(2-(5-(trifluoromethoxy)-1H-benzo[d]imidazol-2-yl)ethyl)cyclobutyl)amino)methyl)cyclopentane-1,2-diol

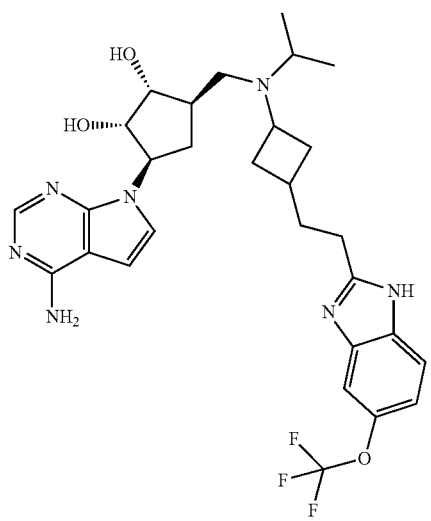

Trifluoroacetic Acid (10 mL, 100 mmol) added to a mixture of Water (1 mL, 60 mmol) and N-(2,4-dimethoxybenzyl)-7-((3aS,4R,6R,6aR)-6-((isopropyl(3-(2-(5-(trifluoromethoxy)-1H-benzo[d]imidazol-2-yl)ethyl)cyclobutyl) amino)methyl)-2,2-dimethyltetrahydro-3aH-cyclopenta[d] [1,3]dioxol-4-yl)-7H-pyrrolo[2,3-d]pyrimidin-4-amine (0.91 g, 1.2 mmol) at RT. The reaction was stirred overnight at RT then quenched by the addition of Triethylsilane (0.37 mL, 2.3 mmol). The volatiles were removed in vacuo and resulting residue was taken up in MeOH (15 mls). 500 mgs of $K_2CO_3$ and 8 drops $H_2O$ were added and reaction stirred at RT for 1 hour. Mixture was filtered and filter cake washed with 10 mls MeOH. The filtrate was concentrated and the resulting residue purified by flash chromatography (DCM/7N $NH_3$ in MeOH 90:10) to yield the desired product (0.232 g) as an off white foam. MS (ESI⁺) for $C_{29}H_{36}F_3N_7O_3$ m/z 588.2 [M+H]⁺; MS (ESI⁻) for $C_{29}H_{36}F_3N_7O_3$ m/z 586.2 [M–H]⁻;

HPLC purity >90% (ret. time, 2.570 min.) ¹H NMR (400 MHz, d₄-MeOH) δ_H 8.082 & 8.079 (s, 1H, overlapping peaks due to cis and trans isomers), 7.554-7.524 (m, 1H), 7.414 (s, 1H), 7.225-7.209 (m, 1H), 7.155-7.127 (m, 1H), 6.618-6.609 (m, 1H), 4.363-4.323 (m, 1H), 3.976-3.932 (m, 1H), 3.606-3.524 (m, 0.5H (methine from trans isomer)), 3.156-3.110 (m, 0.5H (methine from cis isomer), 3.089-3.006 (m, 1H), 2.731-2.679 (m, 1H), 2.544-2.360 (m, 2H), 2.256-2.239 (m, 3H), 2.093-2.061 (m, 2H), 1.987-1.861 (m, 3H), 1.648-1.568 (m, 2H), 1.072-1.006 (m, 6H).

Compound 57: (1R,2S,3R,5R)-3-(4-amino-7H-pyrrolo[2,3-d]pyrimidin-7-yl)-5-((methyl((1s,3R)-3-(2-(5-(trifluoromethoxy)-1H-benzo[d]imidazol-2-yl) ethyl)cyclobutyl)amino)methyl)cyclopentane-1,2-diol The diastereoisomers were separated by SFC. The material was lyophilized to give a solid (78 mg). ¹H NMR (400 MHz, d₄-MeOH) δ_H 8.076 (s, 1H), 7.548-7.527 (m, 1H), 7.414 (s, 1H), 7.227-7.218 (m, 1H), 7.148-7.123 (m, 1H), 6.616-6.607 (m, 1H), 4.361-4.327 (m, 1H), 3.926-3.899 (m, 1H), 3.037-3.000 (m, 1H), 2.907-2.870 (m, 2H), 2.538-2.283 (m, 4H), 2.178-2.013 (m, 8H), 1.913-1.872 (m, 2H), 1.680-1.599 (m, 1H).

Compound 58: (1R,2S,3R,5R)-3-(4-amino-7H-pyrrolo[2,3-d]pyrimidin-7-yl)-5-(((((1s,3R)-3-(2-(5,6-dichloro-1H-benzo[d]imidazol-2-yl)ethyl)cyclobutyl)(methyl)amino)methyl)cyclopentane-1,2-diol The diastereomers were separated by SFC. The material was taken up in MeOH/$H_2O$ and lyophilized to yield a tan powder (73 mg). ¹H NMR (400 MHz, MeOD) δ_H ppm 8.06 (s, 1H), 7.64 (s, 2H), 7.21 (d, J=3.73 Hz, 1H), 6.59 (d, J=3.52 Hz, 1H), 4.32 (dd, J=7.77, 6.12 Hz, 1H), 3.89 (m, 1H), 3.01 (m, 1H), 2.86 (t, J=7.67 Hz, 2H), 2.51 (m, 1H), 2.40 (m, 2H), 2.27 (m, 1H), 2.18 (s, 3H), 2.11 (m, 3H), 2.02 (q, J=6.43 Hz. 2H), 1.88 (t, J=8.19 Hz, 2H), 1.63 (m, 1H).

Compound 59: (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl) (cyclobutylmethyl)amino)methyl)cyclopentane-1,2-diol Step 1: ethyl 3-((1R,3s)-3-((cyclobutylmethyl) (((3aR,4R,6R,6aS)-6-(4-((2,4-dimethoxybenzyl) amino)-7H-pyrrolo[2,3-d]pyrimidin-7-yl)-2,2-dimethyltetrahydro-3aH-cyclopenta[d][1,3]dioxol-4-yl) methyl)amino)cyclobutyl)propanoate

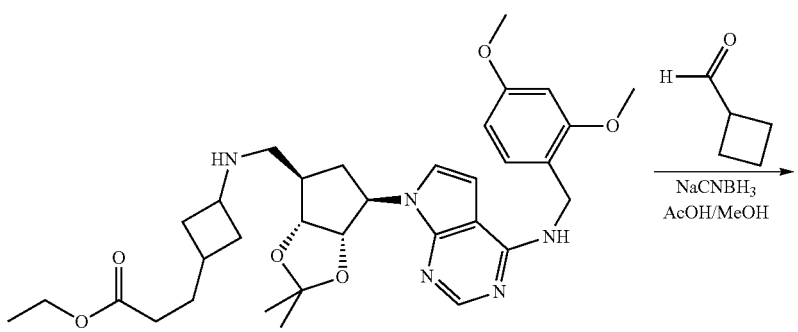

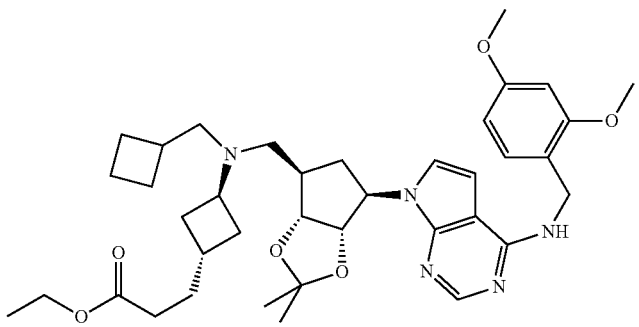

The amine ethyl 3-[3-({[(3aR,4R,6R,6aS)-6-{4-[(2,4-dimethoxybenzyl)amino]-7H-pyrrolo[2,3-d]pyrimidin-7-yl}-2,2-dimethyltetrahydro-3aH-cyclopenta[d][1,3]dioxol-4-yl]methyl}amino)cyclobutyl]propanoate (1.8 g, 3.0 mmol) was taken up in methanol (20 mL, 600 mmol) and sodium cyanoborohydride (0.37 g, 5.9 mmol) was added. The pH was adjusted to ca. 6 using a 10% solution of AcOH in methanol, then cyclobutanecarboxaldehyde (0.32 g, 3.8 mmol) was added in one portion. The reaction was allowed to proceed for 5 hours at which time HPLC indicated the reaction had stalled. Another 1.3 equivalents of cyclobutanecarboxaldehyde was added and the reaction continued overnight. NaHCO$_3$ (saturated) was added to the reaction mixture which was then extracted 3 times with DCM. The combined organics were dried with MgSO$_4$ and concentrated to a yellow resin. Cis and trans isomers were separable on silica. Purification by FC (DCM/7N NH$_3$ in MeOH 96:4) yielded 2 separate batches of product, each enriched in one respective isomer to about 90%. Top isomer: 0.38 g (5:1 mixture, cis) Bottom isomer: 0.31 g (7:1 mixture, trans). MS (ESI$^+$) for C$_{35}$H$_{49}$N$_5$O$_6$ m/z 676.7 [M+H]$^+$; HPLC purity >69% (ret. time, 3.791).

Step 2: N-(2-amino-5-(tert-butyl)phenyl)-3-((1R,3s)-3-((cyclobutylmethyl)(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanamide

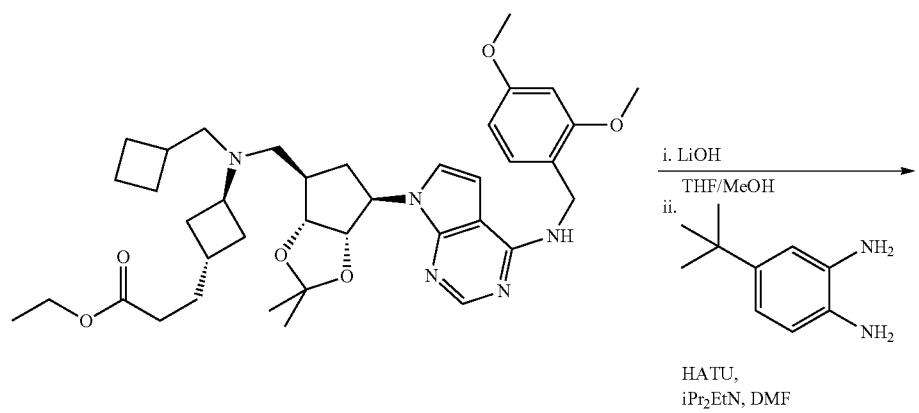

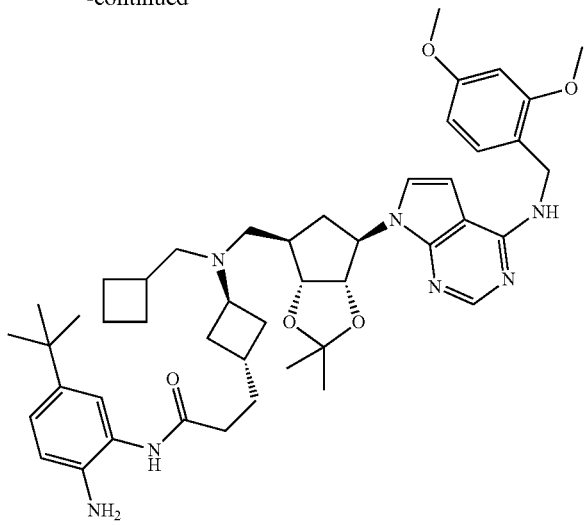

Bottom Isomer (trans): Lithium hydroxide monohydrate (0.192 g, 4.59 mmol) was added to a solution of ethyl 3-((1R,3s)-3-((cyclobutylmethyl)(((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoate (0.31 g, 0.46 mmol) in tetrahydrofuran (6 mL, 70 mmol) and methanol (1.5 mL, 37 mmol). The reaction was stirred overnight at room temperature and by the next morning the starting material was consumed and had been transformed into the acid. The reaction was acidified with 1N HCl to pH=6. The volatiles were removed in vacuo and the remaining water removed by azeotropic distillation with ethanol followed by 24 hours of lyophilization. The resulting off white solid was used without further purification. HPLC purity >94% (ret. time, 3.344).

N,N,N',N'-Tetramethyl-O-(7-azabenzotriazol-1-yl)uronium hexafluorophosphate (0.273 g, 0.718 mmol) added to a solution of 3-{trans-3-[(cyclobutylmethyl){[(3aR,4R,6R,6aS)-6-{4-[(2,4-dimethoxybenzyl)amino]-7H-pyrrolo[2,3-d]pyrimidin-7-yl}-2,2-dimethyltetrahydro-3aH-cyclopenta[d][1,3]dioxol-4-yl]methyl}amino]cyclobutyl}propanoic acid (0.31 g, 0.48 mmol) and N,N-diisopropylethylamine (0.275 mL, 1.58 mmol) and 4-tert-butylbenzene-1,2-diamine (0.0943 g, 0.574 mmol) in N,N-dimethylformamide (2.96 mL, 38.3 mmol). The reaction was stirred overnight at room temperature and by the next morning the starting material was consumed. The reaction was partially concentrated to ca. 2 mls and then NaHCO₃ (saturated) was added. The mixture was extracted with EtOAc 3 times and the combined organics were dried with MgSO₄ and concentrated. The resulting residue was purified by FC (DCM/7N NH₃ in MeOH 95:5) to yield N-(2-amino-5-(tert-butyl)phenyl)-3-((1R,3s)-3-((cyclobutylmethyl)(43aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanamide (0.29 g; 76%) as a purple-brown amorphous solid. HPLC purity >20% (ret. time, 3.650 min.)

Step 3: 7-((3aS,4R,6R,6aR)-6-((((1s,3R)-3-(2-(5-(tert-butyl)-1H-benzo[d]imidazol-2-yl)ethyl)cyclobutyl)(cyclobutylmethyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine

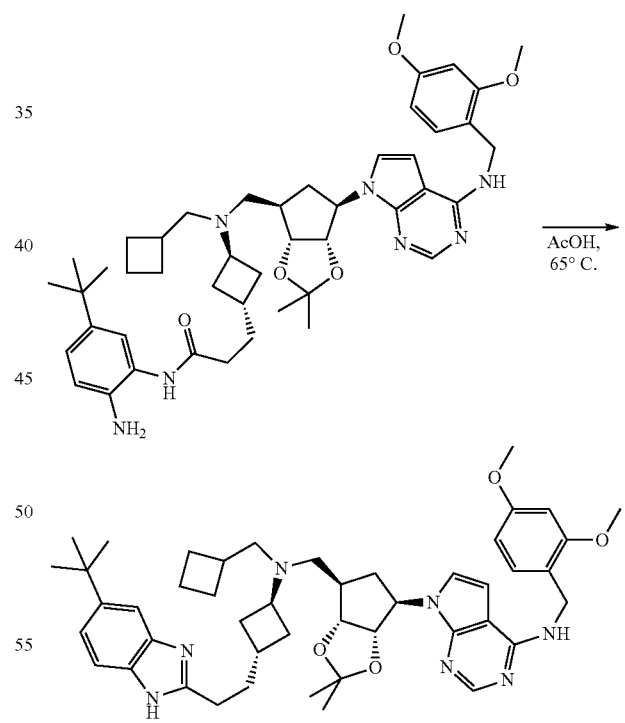

A solution of N-(2-amino-5-(tert-butyl)phenyl)-3-((1R,3s)-3-((cyclobutylmethyl)(((3 aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanamide (0.3 g, 0.4 mmol) in acetic acid (1.0 mL, 20 mmol) was stirred overnight at 65° C. and by next morning the starting material was consumed. The volatiles were removed in vacuo and the resulting residue purified by FC (DCM/7N NH₃ in MeOH 93:7) to yield 7-((3aS,4R,6R,6aR)-6-((((1s,3R)-3-(2-(5-(tert-butyl)-1H-benzo[d]imidazol-2-yl)ethyl)cyclobutyl)(cyclobutylmethyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine as an off white solid. HPLC purity >73% (ret. time, 3.709 min.).

Step 4: (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(cyclobutylmethyl)amino)methyl)cyclopentane-1,2-diol (5-(tert-butyl)-1H-benzo[d]imidazol-2-yl)ethyl)cyclobutyl)(cyclobutylmethyl)amino)methyl)cyclopentane-1,2-diol (0.018 g, 10%) as a colorless solid. MS (ESI⁺) for $C_{34}H_{47}N_7O_2$ m/z 586.4 [M+H]⁺; HPLC purity >93% (ret. time, 2.070 min.) ¹H NMR (400 MHz, d₄-MeOH) $\delta_H$ 8.083 (s, 1H), 7.501 (s, 1H), 7.421-7.400 (m, 1H), 7.315-7.290 (m, 1H), 7.218-7.209 (m, 1H), 6.621-6.612 (m, 1H), 4.350-4.317 (m, 1H), 3.930-3.903 (m, 1H), 3.403-3.367 (m, 1H), 2.880-2.843 (m, 2H), 2.722-2.360 (m, 6H), 2.323-2.241 (m, 2H), 2.173-1.606 (m, 13H), 1.387 (s, 9H).

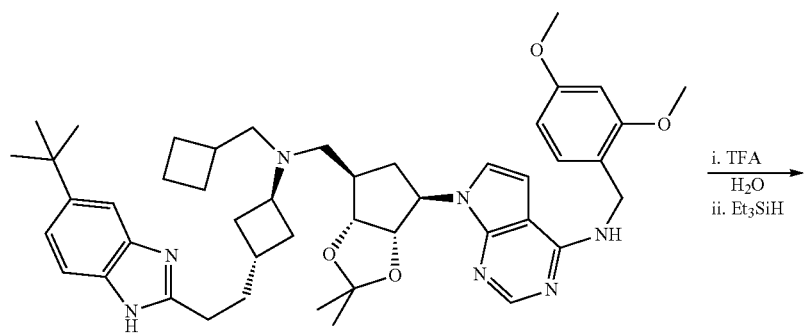

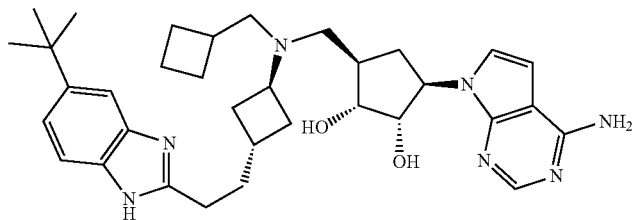

Trifluoroacetic acid (5 mL, 70 mmol) was added to a mixture of water (0.5 mL, 30 mmol) and 7-((3aS,4R,6R,6aR)-6-((((1s,3R)-3-(2-(5-(tert-butyl)-1H-benzo[d]imidazol-2-yl)ethyl)cyclobutyl)(cyclobutylmethyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (0.23 g, 0.30 mmol) at room temperature. The reaction was allowed to proceed overnight at which time the bright pink suspension was quenched with triethylsilane (0.095 mL, 0.59 mmol). The volatiles were removed in vacuo and the resulting residue was taken up in MeOH (15 mls). 500 mgs of K₂CO₃ and 8 drops H₂O were added and reaction stirred at room temperature for 1 hour. The mixture was filtered and the filter cake was washed with 10 mLs methanol. The filtrate was concentrated and the resulting residue purified by FC (DCM/7N NH₃ in MeOH 90:10) to yield (1R,2S,3R,5R)-3-(4-amino-7H-pyrrolo[2,3-d]pyrimidin-7-yl)-5-((((1s,3R)-3-(2-

Compound 60: (1R,2S,3R,5R)-3-(4-amino-7H-pyrrolo[2,3-d]pyrimidin-7-yl)-5-((isopropyl((1r,3S)-3-(2-(5-(trifluoromethoxy)-1H-benzo[d]imidazol-2-yl)ethyl)cyclobutyl)amino)methyl)cyclopentane-1,2-diol Diastereoisomers separated by SFC. After lyophilization, of a colorless solid (62 mg) was recovered.

Compound 61: (1R,2S,3R,5R)-3-(4-amino-7H-pyrrolo[2,3-d]pyrimidin-7-yl)-5-((isopropyl((1s,3R)-3-(2-(5-(trifluoromethoxy)-1H-benzo[d]imidazol-2-yl)ethyl)cyclobutyl)amino)methyl)cyclopentane-1,2-diol Diastereoisomers were separated SFC. The material was taken up in MeOH/H₂O and lyophilized to yield an off white powder (89 mg). ¹H NMR (400 MHz, MeOD) $\delta_H$ ppm 8.06 (s, 1H), 7.52 (d, J=8.71 Hz, 1H), 7.40 (s, 1H), 7.19 (d, J=3.52 Hz, 1H), 7.12 (m, 1H), 6.59 (d, J=3.52 Hz, 1H), 4.88 (m, 1H), 4.33 (m, 1H), 3.94 (t, J=5.39 Hz, 1H), 3.52 (m, 1H), 3.01 (m, 1H), 2.87 (t, J=7.15 Hz, 2H), 2.68 (dd, J=13.48, 7.88 Hz, 1H), 2.47 (dd, J=13.27, 7.46 Hz, 1H), 2.37 (m, 1H), 2.21 (m, 3H), 2.04 (m, 3H), 1.84 (m, 2H), 1.58 (m, 1H), 1.02 (d, J=6.63 Hz, 3H), 0.98 (d, J=6.43 Hz, 3H).

Compound 62: (1R,2S,3R,5R)-3-(4-amino-7H-pyrrolo[2,3-d]pyrimidin-7-yl)-5-((methyl(3-(2-(5-(oxetan-3-yl)-1H-benzo[d]imidazol-2-yl)ethyl)cyclobutyl)amino)methyl)cyclopentane-1,2-diol N-(4-(oxetan-3-yl)phenyl)acetamide

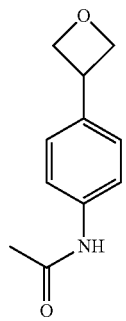

(4-Acetamidophenyeboronic acid {670 mg, 3.7 mmol), Nickel (II) iodide (35 mg, 0.11 mmol), trans-2-aminocyclohexanol (17 mg, 0.11 mmol), and Sodium hexamethyldisilazane (690 mg, 3.7 mmol) were weighed into a microwave reaction vial. A septum was placed over the top, nitrogen was purged and Isopropyl alcohol (5.7 ml, 75 mmol) was added. The vial was purged with nitrogen for 10 minutes and 3-iodooxetane (344 mg, 1.87 mmol) was added in 0.75 ml isopropyl alcohol. The septum was replaced with a microwave vial cap and the mixture was heated in a microwave reactor (microwave conditions: CEM Discovery Explorer microwave reactor; Ramp time: 10 min; 80° C. for 30 min; power: 300 W). The crude reaction mixture was diluted with 8 ml EtOH and the suspension was filtered through a pad of solka Floc®. The pad was washed with 35 ml EtOH and the filtrate was concentrated. The crude material was purified by flash chromatography (SiO$_2$, eluting with 40-60% EtOAc/CH$_2$Cl$_2$) to give the desired product as an oil (200 mg).

N-(2-nitro-4-(oxetan-3-yl)phenyl)acetamide

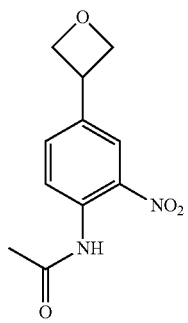 [SMILES: CC(=O)Nc1ccc(C2COC2)cc1[N+](=O)[O-]]

Sulfuric acid (9.4 ml, 180 mmol) was added carefully to 70% nitric acid (7:3, Nitric acid:Water, 11 ml, 170 mmol) which was cooled at 0° C. over about 5-10 minutes. The mixture was stirred for 10 minutes at 0° C., then allowed to warm to RT by removal of the ice bath. The acid solution was transferred to a separatory funnel and Methylene chloride (20 mL, 300 mmol) was added. The funnel was shaken for 5 minutes, and the phases were allowed to separate.

The organic phase (upper phase) was isolated and the process was repeated with an additional 20 ml CH$_2$Cl$_2$. The organic extracts were combined, it was assumed the organic phase contained about 5 g (~80 mmol) of anhydrous HNO$_3$. Using a 50 fold excess, this required about 25 ml of solution. The nitric acid solution was cooled in a ice bath. The N-(4-oxetan-3-ylphenyl)acetamide (21 0 mg, 0.70 mmol) was treated with 25 ml of the chilled HNO$_3$/CH$_2$Cl$_2$ solution and was allowed to stir about 30 minutes. The reaction mixture was carefully poured into 45 ml 1 0% NH$_4$OH solution and carefully shaken. The phases were separated and the aqueous phase was washed with 20 ml CH$_2$Cl$_2$. The combined organic phase was dried over Na$_2$SO$_4$, filtered and concentrated. The crude material was purified by flash chromatography (SiO$_2$, eluting with 25-35% EtOAc/CH$_2$Cl$_2$) to yield the desired product as a solid (170 mg).

2-nitro-4-(oxetan-3-yl)aniline

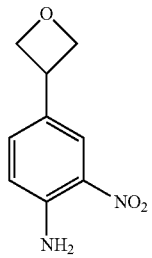

A suspension of N-(2-nitro-4-oxetan-3-ylphenyl)acetamide (125 mg, 0.529 mmo) in aqueous hydrazine (8 ml, 160 mmol) was heated at 70° C. for 2 h, the reaction mixture was cooled to 45° C. and the hydrazine was removed in vacuo to yield a solid. The crude material was purified by flash chromatography (SiO$_2$, eluting with 20% EtOAc/CH$_2$Cl$_2$ to yield the desired product (71 mg).

4-(oxetan-3-yl)benzene-1,2-diamine

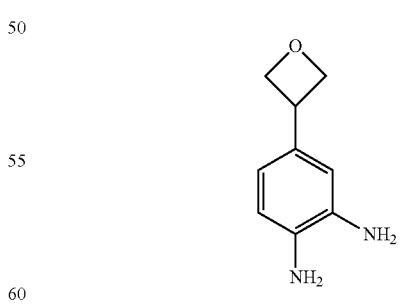

A solution of 2-nitro-4-oxetan-3-ylaniline (91 mg, 0.47 mmol) in Ethanol (6.1 ml) was carefully treated with 10% Palladium on carbon (10 mg, 0.009 mmol) as a slurry in ethanol. The reaction flask was evacuated and filled with hydrogen gas three times and the reaction was allowed to stir under an atmosphere of hydrogen for 2 h. The reaction mixture was filtered through a pad of solka Floc® and the pad was washed with 25 ml MeOH. The filtrated was concentrated to yield an oil that solidified under high vacuum overnight to give the desired compound (72 mg). The material was used as is in the next step. 1H NMR (400 MHZ, CDCl$_3$) $\delta_H$ ppm 6.81 (d, J=1.52 Hz, 1H), 6.70 (m, 2H), 5.02 (dd, 3=8.34, 5.81 Hz, 2H), 4.74 (m, 2H), 4.09 (m, 1H), 3.45 (br. s., 2H), 3.37 (br. s., 2H).

N-(2,4-dimethoxybenzyl)-7-((3aS,4R,6R,6aR)-2,2-dimethyl-6-((methyl(3-(2-(5-(oxetan-3-yl)-1H-benzo[d]imidazol-2-yl)ethyl)cyclobutyl)amino)methyl)tetrahydro-3aH-cyclopenta[d][1,3]dioxol-4-yl)-7H-pyrrolo[2,3-d]pyrimidin-4-amine the 2 aide regio-siomers. Each regio-siomer was processed separately in the next step.

The amide (130 mg) was taken up in 5 ml glacial acetic acid and heated at 65° C. for (2.25 h, the reaction was cooled and placed in the fridge overnight. The acetic acid was removed under high vacuum with the aid of a warm water bath. The two batches of crude product was taken up in 30 ml CH$_2$Cl$_2$ and the organic phase was washed with 10 ml portions of sat NaHCO$_3$ and 2% Na$_2$CO$_3$ solutions, dried over Na$_2$SO$_4$, filtered and concentrated. The crude material was purified by flash chromatography (SiO$_2$, eluting with 5.5-6.5% 7N NH$_3$ in CH$_3$OH/CH$_2$Cl$_2$ to give the desired compound (140 mg).

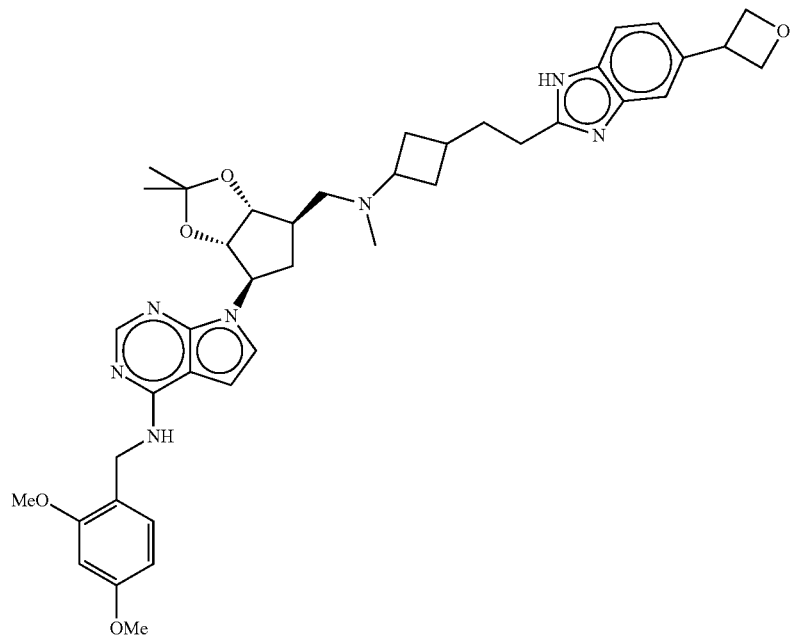

A solution of 3-(3-(((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanoic acid (250 mg. 0.42 mmol) and 4-oxetan-3-ylbenzene-1,2-diamine (72 mg, 0.44 mmol) in N,N-Dimethylformamide (4.3 ml, 56 mmol) was treated with N,N-Diisopropylethylamine (0.24 ml, 1.4 mmol) dropwise followed by N,N,N',N'-Tetramethyl-0-(7-azabenzotriazol-1-yl)uronium Hexafluorophosphate (240 mg, 0.632 mmol) in one portion. The reaction mixture was stirred at RT for 6 hours, upon which the reaction mixture was concentrated under high vacuum. The residue was partitioned between 30 ml EtOAc (some MeOH was added to aid in solublizing the product) and 30 ml 1/1 H$_2$O/sat NaHCO$_3$. The aqueous phase was extracted with 30 mL EtOAc and the combined organic phase was dried over Na$_2$SO$_4$, filtered and concentrated to a glass/stiff foam. The crude material was purified by flash chromatography (SiO$_2$, eluting with 6-7% 7N NH$_3$ in CH$_3$OH/CH$_2$Cl$_2$. Two sets of products were found, a less polar pair and a more polar pair corresponding to (1R,2S,3R,5R)-3-(4-amino-7H-pyrrolo[2,3-d]pyrimidin-7-yl)-5-((methyl(3-(2-(5-(oxetan-3-yl)-1H-benzo[d]imidazol-2-yl)ethyl)cyclobutyl)amino)methyl)cyclopentane-1,2-diol

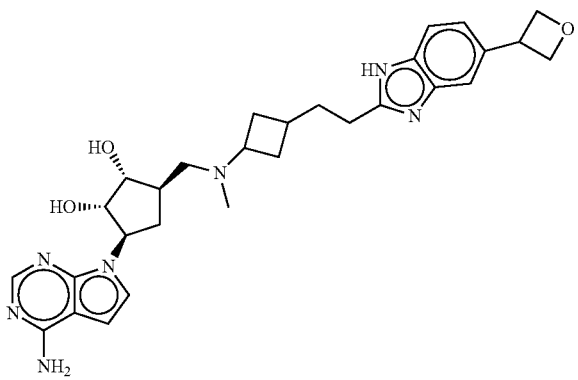

N-(2,4-dimethoxybenzyl)-7-((3aS,4R,6R,6aR)-2,2-dimethyl-6-((methyl(3-(2-(5-(oxetan-3-yl)-1H-benzo[d]imidazol-2-yl)ethyl)cyclobutyl)amino)methyl)tetrahydro-3aH-cyclopenta[d][1,3]dioxol-4-yl)-7H-pyrrolo[2,3-d]pyrimidin-4-amine (115 mg, 0.159 mmol) was dissolved in a mixture of Trifluoroacetic Acid (4.00 ml, 51.9 mmol) and Water (0.40 ml, 22 mmol) which had been pre-cooled at 0° C. in an ice bath. The solution was stirred at 0° C. for 2 h, the reaction mixture was allowed to warm to RT. After 1 the reaction mixture was concentrated in vacuo. The residue was taken up in 6 ml MeOH, concentrated and the process was repeated twice. The resultant residue was placed on high vacuum. The crude residue was diluted with 2 ml MeOH, treated with 140 mg $K_2CO_3$ and 10 drops of $H_2O$ and allowed to stir at RT until the solution was basic by pH paper. The solution was filtered through a fine frit and the solids washed with MeOH. The filtrate was concentrated to a solid that was placed on high vacuum overnight. The crude material was purified by prep TLC on two 20 cm×20 cm×1.0 mm prep TLC plate, eluting with 14% 7N $NH_3$ in $CH_3OH/CH_2Cl_2$ to ive the product as a colorless glass (37 mg) $^1H$ NMR (400 MHz, MeOD) $\delta_H$ ppm 8.06 (s, 1H), 7.52 (br. s., 1H), 7.48 (d, J=8.29 Hz, 1H), 7.28 (m, 1H), 7.20 (t, J=3.42 Hz, 1H), 6.60 (d, J=3.52 Hz, 1H), 5.12 (m, 2H), 4.80 (m, 2H), 4.38 (m, 1H), 4.32 (m, 1H), 3.89 (q, J=5.60 Hz, 1H), 3.04 (m, 1H), 2.85 (m, 2H), 2.70 (m, 1H), 2.52 (m, 1H), 2.41 (m. 2H), 2.27 (dd, J=10.99, 6.63 Hz, 2H), 2.19 (s, 3H), 2.17 (s, 3H), 2.14 (m, 1H), 2.03 (d, J=7.88 Hz, 1H), 1.91 (m, 3H), 1.62 (m, 1H), 1.51 (m, 1H).

Compound 63: (2R,3R,4S,5R)-2-(6-amino-9H-purin-9-yl)-5-((methyl((1r,3S)-3-(2-(5-(oxetan-3-yl)-1H-benzo[d]imidazol-2-yl)ethyl)cyclobutyl)amino)methyl)tetrahydrofuran-3,4-diol The diastereomers were separated by SFC. The material was taken up in MeOH/$H_2O$ and lyophilized to a tan powder (58 mg). $^1H$ NMR (400 MHz, MeOD) $\delta_H$ ppm 8.26 (s, 1H), 8.19 (s, 1H), 7.51 (s, 1H), 7.47 (d, J=8.29 Hz, 1H), 7.26 (dd, J=8.29, 1.45 Hz, 1H), 5.97 (d, J=3.94 Hz, 1H), 5.11 (dd, J=8.29, 6.01 Hz, 2H), 4.79 (t, J=6.32 Hz, 2H), 4.69 (m, 1H), 4.36 (m, 1H), 4.22 (t, J=5.60 Hz, 1H), 4.15 (m, 1H), 2.79 (t, J=7.15 Hz, 2H), 2.72 (m, 1H), 2.66 (m, 2H), 2.21 (m, 2H), 2.14 (s, 3H), 1.88 (m, 3H), 1.45 (m, 2H).

Compound 64: (2R,3R,4S,5R)-2-(6-amino-9H-purin-9-yl)-5-((methyl(3-(2-(5-(oxetan-3-yl)-1H-benzo[d]imidazol-2-yl)ethyl)cyclobutyl)amino)methyl)tetrahydrofuran-3,4-diol Step 1: 3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanoic acid

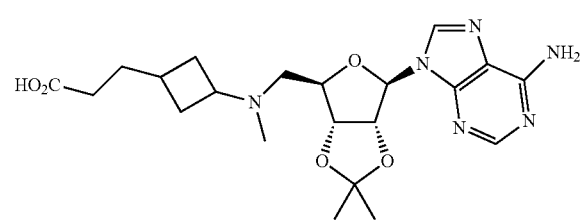 [SMILES: CN(C[C@H]1O[C@@H](n2cnc3c(N)ncnc32)[C@@H]2OC(C)(C)O[C@@H]21)C1CC(CCC(=O)O)C1]

A solution of ethyl 3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanoate (0.39 g, 0.82 mmol) in methanol (14 mL) was treated with a 1 M aqueous solution of sodium hydroxide (1.56 mL, 1.56 mmol) and the reaction mixture was heated at 50° C. with stirring for 3.5 h; HPLC/LC MS indicated conversion to the desired product. The reaction mixture was concentrated in vacuo and the aqueous residue was diluted with water (10 mL) and extracted with $CH_2Cl_2$ (3×5 mL). The aqueous layer was treated with a 1 M aqueous solution of hydrogen chloride (1.44 mL, 1.44 mmol) to adjust to pH 7. The clear, colorless solution was lyophilized to afford the crude title compound (0.487 g, 110%) as a slightly off-white solid, yield accounts for 1.56 mmol NaCl (91 mg): MS (ESI+) for $C_{21}H_{30}N_6O_5$ m/z 447.1 (M+H)$^+$; MS (ESI−) for $C_{21}H_{30}N_6O_5$ m/z 445.2 (M−H)$^-$; HPLC purity >95% (ret. time, 1.949 min).

Step 2: N-(2-amino-5-(oxetan-3-yl)phenyl)-3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanamide

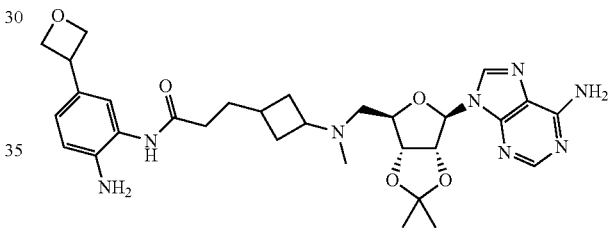

A suspension of the above crude 3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanoic acid and 4-(oxetan-3-yl)benzene-1,2-diamine (0.135 g, 0.822 mmol) in methylene chloride (8.0 mL) was treated with N,N-diisopropylethylamine (0.716 mL, 4.11 mmol) and cooled to −5° C. (ice/brine). N,N,N',N'-tetramethyl-O-(7-azabenzotriazol-1-yl)uronium hexafluorophosphate [HATU] (0.469 g, 1.23 mmol) was added and the reaction mixture was stirred for 5.25 h, warming to 15° C.; HPLC/LC MS indicated complete conversion. The reaction mixture was concentrated in vacuo and diluted with $CH_2Cl_2$ (15 mL) and water (7.5 mL). The separated aqueous layer was extracted with $CH_2Cl_2$ (2×10 mL). The combined organics were dried ($Na_2SO_4$) and concentrated in vacuo to afford a brown-purple semi-opaque oil/foam. Purification by column chromatography (2×8 cm silica; 0-5% 7 N methanolic $NH_3/CH_2Cl_2$) afforded both amide regioisomers of the title compound (0.45 g, 82%) as a semi-opaque pink foam: MS (ESI+) for $C_{30}H_{40}N_8O_5$ m/z 593.3 (M+H)$^+$; MS (ESI−) for $C_{30}H_{40}N_8O_5$ m/z 591.3 (M−H)$^-$ and 637.4 (M+HCO$_2$)$^-$; HPLC purity 90% (ret. time, 2.097 min).

Step 3: 9-((3aR,4R,6R,6aR)-2,2-dimethyl-6-((methyl (3-(2-(5-(oxetan-3-yl)-1H-benzo[d]imidazol-2-yl) ethyl)cyclobutyl)amino)methyl)tetrahydrofuro[3,4-d] [1,3]dioxol-4-yl)-9H-purin-6-amine

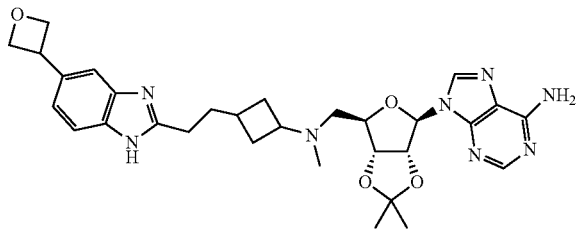 [SMILES: CN(C[C@H]1O[C@@H](n2cnc3c(N)ncnc32)[C@@H]2OC(C)(C)O[C@@H]21)C1CC(CCc2nc3cc(C4COC4)ccc3[nH]2)C1]

N-(2-amino-5-(oxetan-3-yl)phenyl)-3-(3-((((3aR,4R,6R, 6aR)-6-(6-amino-9H-purin-9-yl)-2,2-dimethyltetrahydrofuro[3,4-d][1,3]dioxol-4-yl)methyl)(methyl)amino)cyclobutyl)propanamide (0.446 g, 0.752 mmol) was taken up in acetic acid (7.7 mL, 140 mmol) and heated at 65° C. for 3.5 h; HPLC/LC MS indicated complete conversion. At 3.75 h the acetic acid was removed by distillation with minimal warming to afford an orange oil, which was taken up in $CH_2Cl_2$ (45 mL) and washed with saturated aqueous $NaHCO_3$ (2×30 mL). The aqueous layer was treated with NaCl until saturated and extracted with $CH_2Cl_2$ (2×20 mL). The combined organic layers were dried ($Na_2SO_4$) and concentrated in vacuo to afford a light orange oil. Purification by column chromatography (2×8 cm silica; 0-5% 7 N methanolic $NH_3/CH_2Cl_2$) afforded the title compound (0.28 g, 65%) as a light orange foam: MS (ESI+) for $C_{30}H_{38}N_8O_4$ m/z 575.3 (M+H)$^+$; MS (ESI−) for $C_{30}H_{38}N_8O_4$ m/z 573.3 (M−H)$^-$; HPLC purity >95% (ret. time 2.142 min).

Step 4: (2R,3R,4S,5R)-2-(6-amino-9H-purin-9-yl)-5-((methyl(3-(2-(5-(oxetan-3-yl)-1H-benzo[d]imidazol-2-yl)ethyl)cyclobutyl)amino)methyl)tetrahydrofuran-3,4-diol

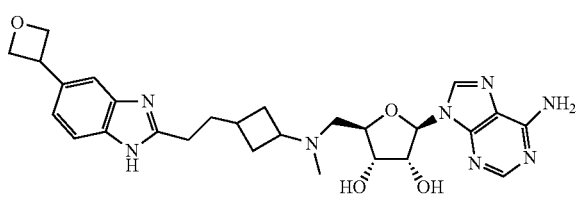 [SMILES: CN(C[C@H]1O[C@@H](n2cnc3c(N)ncnc32)[C@H](O)[C@@H]1O)C1CC(CCc2nc3cc(C4COC4)ccc3[nH]2)C1]

To a cooled (ice bath) flask containing 9-((3aR,4R,6R, 6aR)-2,2-dimethyl-6-((methyl(3-(2-(5-(oxetan-3-yl)-1H-benzo[d]imidazol-2-yl)ethyl)cyclobutyl)amino)methyl)tetrahydrofuro[3,4-d][1,3]dioxol-4-yl)-9H-purin-6-amine (0.28 g, 0.42 mmol) was added a precooled (ice bath) solution of trifluoroacetic acid (6.4 mL, 84 mmol) in water (0.75 mL, 42 mmol). The reaction mixture was stirred for 5.75 h at 0° C.; HPLC/LC MS indicated nearly complete consumption of starting material. At 6 h the flask was removed from the cold bath and the volatiles were removed by distillation at rt. The residue was diluted with MeOH (15 mL) and treated with potassium carbonate (0.32 g, 2.3 mmol) and water (1 mL) and the mixture was stirred for 20 min at rt; pH 2. Additional potassium carbonate (0.20 g, 1.4 mmol) was added and the mixture was stirred for 20 min; pH 8-9. The solution was filtered through a fine frit, rinsing with MeOH, and the filtrate was concentrated in vacuo to afford a tan semi-solid. Purification by column chromatography (3×8 cm silica; 10-20% 7 N methanolic $NH_3/CH_2Cl_2$) afforded the title compound (123 mg, 55%) as a nearly colorless glass: MS (ESI+) for $C_{27}H_{34}N_8O_4$ m/z 535.3 (M+H)$^+$; MS (ESI−) for $C_{27}H_{34}N_8O_4$ m/z 533.3 (M−H)$^-$; HPLC purity >95% (ret. time 1.765 min); $^1$H NMR (400 MHz, d$_4$-MeOH) mixture of cis/trans isomers $\delta_H$ 8.29-8.25 (m, 1H), 8.21-8.17 (m, 1H), 7.51 (s, 1H), 7.47 (d, J=8.3 Hz, 1H), 7.26 (dd, J=1.6, 8.3 Hz, 1H), 6.00-5.96 (m, 1H), 5.11 (dd, J=5.8, 8.3 Hz, 2H), 4.81-4.76 (m, 2H), 4.73-4.68 (m, 1H), 4.40-4.31 (m, 1H), 4.27-4.13 (series of m, 2H), 3.13-3.03 (m, 0.4H), 2.86-2.66 (series of m, 4.6H), 2.30-1.80 (series of m, 8.6H), 1.55-1.40 (m, 1.4H).

Compound 65: (2R,3R,4S,5R)-2-(6-amino-9H-purin-9-yl)-5-((methyl((1s,3R)-3-(2-(5-(oxetan-3-yl)-1H-benzo[d]imidazol-2-yl)ethyl)cyclobutyl)amino) methyl)tetrahydrofuran-3,4-diol The diastereomers were separated at by SFC. The material was taken up in MeOH/H$_2$O and lyophilized to a white powder (35 mg). $^1$H NMR (400 MHz, MeOD) $\delta_H$ ppm 8.28 (s, 1H), 8.19 (s, 1H), 7.51 (s, 1H), 7.48 (d, J=8.29 Hz, 1H), 7.27 (dd, J=8.29, 1.45 Hz, 1H), 5.98 (d, J=4.15 Hz, 1H), 5.12 (dd, J=8.40, 5.91 Hz, 2H), 4.79 (t, J=6.32 Hz, 2H), 4.69 (dd, J=5.39, 4.15 Hz, 1H), 4.36 (m, 1H), 4.23 (t, J=5.60 Hz, 1H), 4.17 (m, 1H), 3.05 (m. 1H), 2.83 (t, J=7.46 Hz, 2H), 2.67 (m. 2H), 2.16 (s, 3H), 2.08 (m, 2H), 1.98 (m, 3H), 1.83 (m, 2H).

Compound 67: (2R,3R,4S,5R)-2-(6-amino-9H-purin-9-A-5-[({3-[2-(5-cyclobutyl-1H-1,3-benzodiazol-2-yl)ethyl]cyclobutyl}(propan-2-yl)amino)methyl] oxolane-3,4-diol Step 1: Benzyl 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}amino)cyclobutyl]propanoate

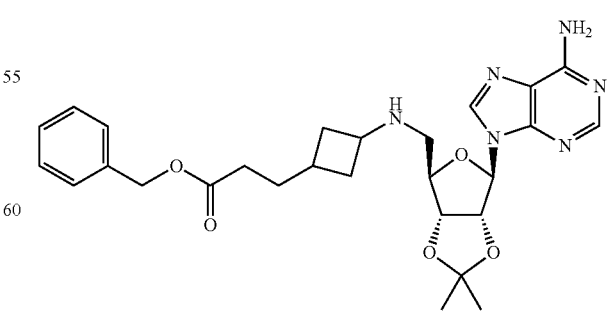

A suspension of the 9-[(3aR,4R,6R,6aR)-6-(aminomethyl)-2,2-dimethyl-tetrahydro-2H-furo[3,4-d][1,3]dioxol- 4-yl]-9H-purin-6-amine (1.45 g, 4.736 mmol), benzyl 3-(3-oxocyclobutyl)propanoate (1.21 g, 5.209 mmol) and acetic acid (246.45 µl, 4.31 mmol) in DCE:iPrOH (4:1, 50 ml) was stirred at RT for 1 h. A further aliquot of DCE (40 ml) and iPrOH (5 ml) was added to the reaction mixture and continued for 1 hour. STAB (1.28 g, 6.03 mmol) was then added and the reaction mixture was stirred for 18 hours. The reaction mixture was quenched with 1N $Na_2CO_3$ (10 ml), and the product was extracted with DCM (2×30 ml). This was dried over $Na_2SO_4$, filtered and evaporated to dryness. Purification by silica gel column chromatography, eluting with 7N $NH_3$ in MeOH:DCM (1:99-3:97) gave the desired product as a colourless oil, 1.51 g (58%); MS (ESI$^+$) for $C_{27}H_{34}N_6O_5$ m/z 523.65 [M+H]$^+$; HPLC purity 97% (ret. time, 1.43 min); $^1$H NMR (500 MHz, CHLOROFORM-d) $\delta_H$ ppm 8.35 (d, J=5.3 Hz, 1H), 7.87 (d, J=33.8 Hz, 1H), 7.40-7.29 (m, 5H), 6.08-5.94 (m, 1H), 5.59-5.42 (m, 3H), 5.10 (d, J=4.0 Hz, 2H), 5.03-4.96 (m, 1H), 4.33 (dq, J=7.3, 3.9 Hz, 1H), 3.12 (ddd, J=23.0, 14.6, 7.5 Hz, 1H), 2.85-2.77 (m, 1H), 2.74 (dd, J=12.5, 6.6 Hz, 1H), 2.39-2.07 (m, 4H), 1.90-1.64 (m, 5H), 1.61 (s, 4H), 1.38 (s, 3H), 1.28-1.06 (m, 1H).

Step 2. Benzyl 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}(propan-2-yl)amino)cyclobutyl]propanoate

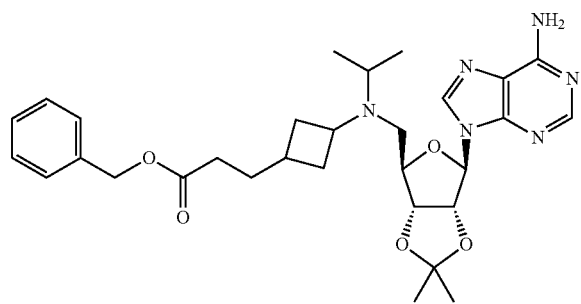 [SMILES: CC(C)N(C[C@H]1O[C@@H](n2cnc3c(N)ncnc32)[C@@H]2OC(C)(C)O[C@@H]21)C1CC(CCC(=O)OCc2ccccc2)C1]

$K_2CO_3$ (528.92 mg, 3.83 mmol) was added to a solution of benzyl 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}amino)cyclobutyl]propanoate (1.00 g, 1.91 mmol) and 2-iodopropane (0.57 ml, 5.74 mmol) in MeCN and stirred at 95° C. in a sealed tube for 18 hours. The reaction mixture was diluted with EtOAc (20 ml), filtered and evaporated to dryness. Purification by silica gel chromatography, eluting with 7N $NH_3$ in MeOH:DCM (1:99-5:95) gave the desired product as a colourless oil, 700 mg (65%); MS (ESI$^+$) for $C_{30}H_{40}N_6O_5$ m/z 565.70 [M+H]$^+$; HPLC purity 96% (ret. time, 1.48 min); $^1$H NMR (500 MHz, CHLOROFORM-d) $\delta_H$ ppm 8.35 (d, J=3.5 Hz, 1H), 7.88 (d, J=3.2 Hz, 1H), 7.44-7.29 (m, 5H), 6.03 (t, J=2.2 Hz, 1H), 5.62-5.42 (m, 3H), 5.10 (d, J=3.3 Hz, 2H), 5.06-4.92 (m, 1H), 4.26 (dt, J=9.9, 3.4 Hz, 1H), 3.46-2.84 (m, 2H), 2.88-2.61 (m, 1H), 2.51 (ddd, J=14.0, 9.1, 7.5 Hz, 1H), 2.33-2.15 (m, 2H), 2.50-2.13 (m, 2H), 2.16-1.74 (m, 4H), 1.60 (s, 3H), 1.43-1.35 (m, 4H), 0.96 (d, J=6.7 Hz, 3H), 0.79 (d, J=6.6 Hz, 3H).

Step 3. 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}(propan-2-yl)amino)cyclobutyl]propanoic acid

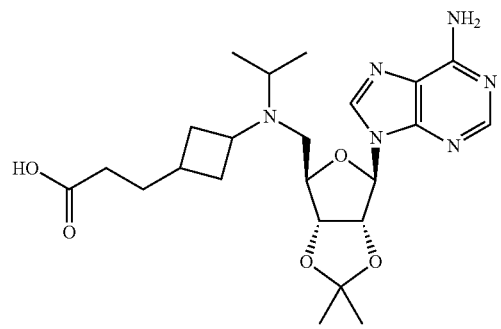 [SMILES: CC(C)N(C[C@H]1O[C@@H](n2cnc3c(N)ncnc32)[C@@H]2OC(C)(C)O[C@@H]21)C1CC(CCC(=O)O)C1]

10% Pd—C (70 mg) was added to a solution of benzyl 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}(propan-2-yl)amino)cyclobutyl]propanoate (790 mg, 1.40 mmol) in EtOH (20 ml) and stirred under an atmosphere of hydrogen for 18 hours at RT. A further aliquot of 10% Pd—C (70 mg) was added and the reaction was continued stirring under hydrogen for 4 hours. This was filtered and evaporated in vacuo, and then evaporated from DCM (2×20 ml) to give 680 mg (quant.) of a white foamy solid; MS (ESI$^+$) for $C_{23}H_{34}N_6O_5$ m/z 475.20 [M+H]$^+$; HPLC purity 100% (ret. time, 1.11 min); $^1$H NMR (500 MHz, CHLOROFORM-d) $\delta_H$ ppm 8.29 (d, J=16.3 Hz, 1H), 7.97 (d, J=16.2 Hz, 1H), 6.86 (s, 2H), 6.05 (dd, J=4.3, 1.7 Hz, 1H), 5.66-5.43 (m, 1H), 5.00 (ddd, J=19.3, 6.3, 3.2 Hz, 1H), 4.30 (s, 1H), 3.47-2.85 (m, 2H), 2.60 (ddd, J=38.8, 24.1, 13.5 Hz, 2H), 2.19 (ddd, J=14.7, 11.9, 7.1 Hz, 2H), 2.07-1.94 (m, 2H), 1.81 (dd, J=65.1, 6.9 Hz, 3H), 1.66-1.46 (m, 5H), 1.45-1.22 (m, 4H), 1.00 (d, J=6.4 Hz, 3H), 0.89 (dd, J=12.2, 6.6 Hz, 3H).

Step 4. 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}(propan-2-yl)amino)cyclobutyl]-N-(2-amino-4/5-cyclobutylphenyl)propanamide

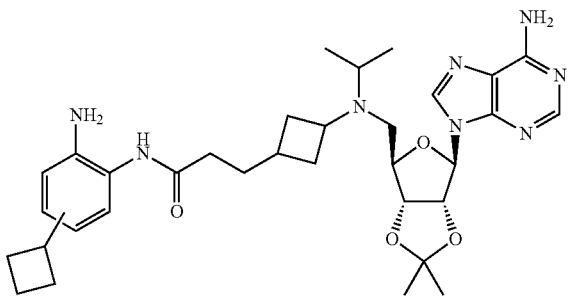

TEA (0.54 ml, 3.90 mmol) was added to a solution of 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}(propan-2-yl)amino)cyclobutyl]propanoic acid (308.46 mg, 0.65 mmol), 4-cyclobutylbenzene-1,2-diamine (210.90 mg, 1.30 mmol), ethyl (2E)-cyano(hydroxyimino)ethanoate (184.75 mg, 1.30 mmol), and EDC.HCl (249.21 mg, 1.30 mmol) in DCM (15 ml) at RT and stirred for two hours. The reaction mixture was concentrated in vacuo, then DCM (50 ml) was added. This was washed with sat. NaHCO$_3$ (2×30 ml). The aqueous was extracted with DCM (50 ml). The combined organics was dried over Na$_2$SO$_4$, filtered and evaporated. The product was purified by silica gel column chromatography eluting with EtOAc, and then 7N NH$_3$ in MeOH:DCM (5:95), to give a grey oil, 468 mg (93%); MS (ESI$^+$) for C$_{33}$H$_{46}$N$_8$O$_4$ m/z 619.35 [M+H]$^+$; HPLC purity 80% (ret. time, 1.44 min).

Step 5. 9-[(3aR,4R,6R,6aR)-6-[({3-[2-(5-cyclobutyl-1H-1,3-benzodiazol-2-yl)ethyl]cyclobutyl}(propan-2-yl)amino)methyl]-2,2-dimethyl-tetrahydro-2H-furo[3,4-d][1,3]dioxol-4-yl]-9H-purin-6-amine

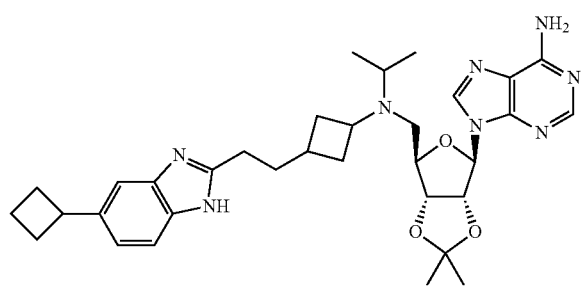 [SMILES: CC(C)N(C[C@H]1O[C@@H](n2cnc3c(N)ncnc32)[C@@H]2OC(C)(C)O[C@@H]21)C1CC(CCc2nc3cc(C4CCC4)ccc3[nH]2)C1]

AcOH (10 ml) was added to 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}(propan-2-yl)amino)cyclobutyl]-N-(2-amino-4/5-cyclobutylphenyl)propanamide (468 mg, 0.61 mmol) and heated to 65° C. whilst stirring for 4 hours. The reaction mixture was concentrated in vacuo, then dissolved in DCM (100 ml) and washed with sat. NaHCO$_3$ (2×80 ml), dried over Na$_2$SO$_4$, filtered and evaporated. Purification by flash silica gel chromatography (Biotage, Isolera, 25 g cartridge), eluting with 3N ammonia in MeOH:DCM (0-1:9) gave the desired product with purity approx 80%. Further purification by preparative HPLC afforded the desired product as a grey oil, 120 mg (27%); MS (ESI$^+$) for C$_{33}$H$_{44}$N$_8$O$_3$ m/z 601 [M+H]$^+$; HPLC purity 100% (ret. time, 1.43 min); $^1$H NMR (500 MHz, CHLOROFORM-d) δ$_H$ ppm 8.62 (d, J=53.1 Hz, 6H), 8.57 (s, 2H), 8.25 (d, J=19.3 Hz, 1H), 7.90 (d, J=20.3 Hz, 1H), 7.50 (dd, J=8.3, 3.9 Hz, 1H), 7.41 (d, J=4.5 Hz, 1H), 7.18-7.06 (m, 1H), 6.52 (d, J=96.3 Hz, 2H), 6.07 (dd, J=10.2, 1.3 Hz, 1H), 5.52-5.39 (m, 1H), 5.07 (dd, J=6.2, 3.4 Hz, 1H), 4.44 (td, J=9.3, 5.1 Hz, 1H), 3.59 (dq, J=17.4, 8.7 Hz, 1H), 3.36-3.10 (m, 2H), 3.08-2.92 (m, 2H), 2.87-2.72 (m, 2H), 2.43-2.27 (m, 2H), 2.24-1.65 (m, 10H), 1.57 (s, 4H), 1.37 (s, 3H), 1.10 (d, J=6.6 Hz, 3H), 0.91 (dd, J=8.9, 6.8 Hz, 3H).

Step 6. (2R,3R,4S,5R)-2-(6-amino-9H-purin-9-yl)-5-[({3-[2-(5-cyclobutyl-1H-1,3-benzodiazol-2-yl)ethyl]cyclobutyl}(propan-2-yl)amino)methyl]oxolane-3,4-diol

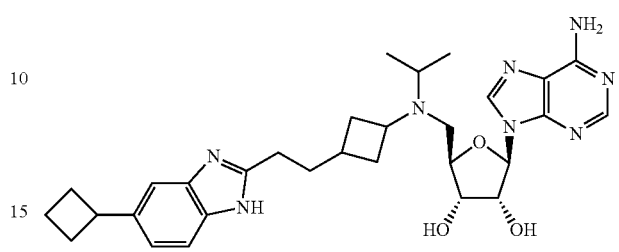

12N HCl (24 mmol, 2 ml) was added dropwise to a solution of 9-[(3aR,4R,6R,6aR)-6-[({3-[2-(5-cyclobutyl-1H-1,3-benzodiazol-2-yl)ethyl]cyclobutyl}(propan-2-yl)amino)methyl]-2,2-dimethyl-tetrahydro-2H-furo[3,4-d][1,3]dioxol-4-yl]-9H-purin-6-amine (120 mg, 0.164 mmol) in MeOH (2 ml) at 0° C. whilst stirring. This was then allowed to warm to RT and continued for 6 hours. The reaction mixture was cooled to 0° C. and basified with 7N NH$_3$ in MeOH (10 ml). This was then evaporated in vacuo. The crude product was absorbed onto silica gel (1 ml), placed onto an isolute flash Si cartridge (10 g) and purified, eluting with 7N NH$_3$ in MeOH:DCM (1:9) to give a white solid, 36 mg (38%); MS (ESI$^+$) for C$_{30}$H$_{40}$N$_8$O$_3$ m/z 561.45 [M+H]$^+$; HPLC purity 100% (ret. time, 1.13 min); $^1$H NMR (500 MHz, CHLOROFORM-d) δ$_H$ ppm 8.29 (d, J=4.6 Hz, 1H), 8.20 (d, J=1.6 Hz, 1H), 7.50-7.18 (m, 2H), 7.06 (ddd, J=8.3, 4.6, 1.3 Hz, 1H), 6.01-5.90 (m, 1H), 4.73 (dd, J=9.8, 5.1 Hz, 1H), 4.26 (q, J=5.4 Hz, 1H), 4.14-4.03 (m, 1H), 3.60-3.15 (m, 2H), 3.07-2.86 (m, 2H), 2.84-2.67 (m, 3H), 2.42-2.31 (m, 2H), 2.25-2.11 (m, 4H), 2.10-1.95 (m, 2H), 1.92-1.74 (m, 4H), 1.57 (dd, J=12.2, 6.2 Hz, 1H), 1.02 (dd, J=6.6, 4.0 Hz, 3H), 0.95 (dd, J=6.6, 2.3 Hz, 3H).

Compound 68: (2R,3R,4S,5R)-2-(6-Amino-9H-purin-9-yl)-5-{[(3-{2-[5-(1-methoxy-2-methylpropan-2-yl)-1H-1,3-benzodiazol-2-yl]ethyl}cyclobutyl)(methyl)amino]methyl}oxolane-3,4-diol Step 1: Benzyl 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}amino)cyclobutyl]propanoate

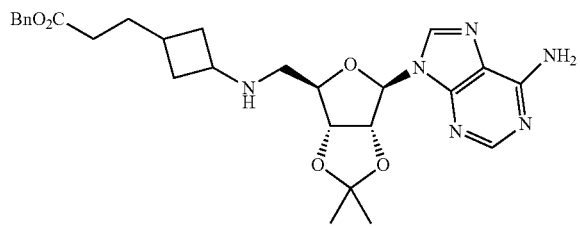

A suspension of 9-[(3aR,4R,6R,6aR)-6-(aminomethyl)-2,2-dimethyl-tetrahydro-2H-furo[3,4-d][1,3]dioxol-4-yl]-9H-purin-6-amine (5.00 g, 16.3 mmol), benzyl 3-(3-oxocyclobutyl)-propanoate (4.17 g, 18.0 mmol) and acetic acid (0.85 ml, 14.8 mmol) in DCE:iPrOH (7:2) (90 ml) was stirred at r.t. for 2 h. Sodium triacetoxyborohydride (4.40 g, 20.8 mmol) was added in portions and the mixture left to stir for 18 h at r.t. The reaction mixture was quenched with 1M Na$_2$CO$_3$ solution (10 ml) and the product was extracted with DCM (3×30 ml). The combined organic layers were dried over Na$_2$SO$_4$, filtered and evaporated to dryness. Purification by silica gel flash column chromatography eluting with 1% 7M NH$_3$ in MeOH:99% DCM gave the product as a yellow oil (5.25 g, 55%, 89% pure): MS (ESI$^+$) for C$_{27}$H$_{34}$N$_6$O$_5$ m/z 523.6 [M+H]$^+$; LC purity 89% (ret. time, 1.60 min); $^1$H NMR (500 MHz, CDCl$_3$) δ$_H$ 8.35 (d, J=6.0 Hz, 1H), 7.91 (s, 1H), 7.30-7.39 (m, 5H), 6.01 (dd, J=3.0 Hz, 1.6, 1H), 5.72 (br. s., 2H), 5.50 (dt, J=6.4 Hz, 3.3, 1H), 5.10 (d, J=3.8 Hz, 2H), 4.98-5.04 (m, 1H), 4.31-4.38 (m, 1H), 2.97-3.34 (m, 1H), 2.72-2.85 (m, 2H), 2.22-2.35 (m, 3H), 2.14 (td, J=8.3, 4.3 Hz, 1H), 1.73-1.90 (m, 4H), 1.64-1.71 (m, 1H), 1.62 (d, J=1.4 Hz, 3H), 1.39 (s, 3H), 1.10-1.27 (m, 1H).

Step 2: Benzyl 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}(methyl)amino)cyclobutyl]propanoate

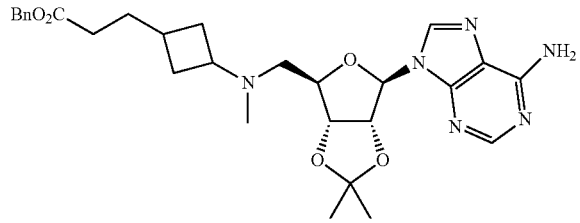

Benzyl 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}amino)cyclobutyl]propanoate (3.2 g, 6.12 mmol) was dissolved in methanol (32 ml). Formaldehyde in water (37%) (0.92 ml, 12.3 mmol) was added and stirred for 45 min before adding sodium cyanoborohydride (0.54 g, 8.57 mmol) portionwise. The reaction was stirred for 2 h at r.t. before adding water (1 ml) and evaporating off the solvent at r.t. The residue was purified by chromatography with 7M ammonia in methanol/DCM to give the desired compound as a yellow oil (mix of diastereomers) (2.05 g, 62%, 82% pure): MS (ESI$^+$) for C$_{28}$H$_{36}$N$_6$O$_5$ m/z 537.6 [M+H]$^+$; LC purity 82% (ret. time, 1.60 min); $^1$H NMR (500 MHz, CDCl$_3$) δ$_H$ 8.32-8.38 (m, 1H), 7.91-7.97 (m, 1H), 7.32-7.39 (m, 5H), 6.05-6.10 (m, 1H), 5.61 (br. s., 2H), 5.53 (ddd, J=16.5, 6.4, 1.8 Hz, 1H), 5.11 (m, 2H), 4.93-5.00 (m, 1H), 4.32-4.40 (m, 1H), 2.50-2.88 (m, 1H), 2.37-2.49 (m, 2H), 2.21-2.30 (m, 2H), 2.10 (m, 3H), 1.91-2.04 (m, 1H), 1.73-1.79 (m, 2H), 1.64-1.72 (m, 2H), 1.56-1.63 (m, 4H), 1.41 (s, 3H), 1.15 (q, J=9.7 Hz, 1H).

Step 3: 3-[3-({[(3aR,4R,6R,6aR)-6-(6-Amino-9H-purin-9-yl)-2,2-dimethyl-tetrahydro-2H-furo[3,4-d][1,3]dioxol-4-yl]methyl}(methyl)amino)cyclobutyl]propanoic acid

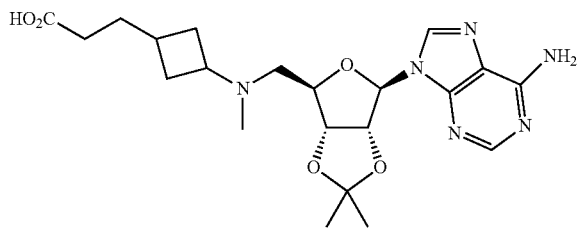 [SMILES: CN(C[C@H]1O[C@@H](n2cnc3c(N)ncnc32)[C@@H]2OC(C)(C)O[C@@H]21)C1CC(CCC(=O)O)C1]

Benzyl 3-[3-({[(3aR,4R,6R,6aR)-6-(6-amino-9H-purin-9-yl)-2,2-dimethyl-tetrahydro-2H-furo[3,4-d][1,3]dioxol-4-yl]methyl}(methyl)amino)cyclobutyl]propanoate (1.19 g, 2.22 mmol) was dissolved in ethanol (24 ml) and 10% palladium on charcoal (50% wet paste) (0.24 g) added. The suspension was stirred under an atmosphere of hydrogen for 18 h. It was then filtered and the solid washed with ethanol (10 ml). As the reaction was incomplete, further palladium on charcoal (0.21 g) was added and the reaction continued under hydrogen for a further 24 h. Filtered through double glass fibre, washed with ethanol and evaporated to dryness to give the desired compound as a white foam (mix of diastereomers) (0.85 g, 86%): MS (ESI$^+$) for C$_{21}$H$_{30}$N$_6$O$_5$ m/z 447.5 [M+H]$^+$; LC purity 86% (ret. time, 1.08 min); $^1$H NMR (500 MHz, d$_4$-MeOD) δ$_H$ 8.18-8.35 (m, 2H), 6.14-6.30 (m, 1H), 5.25-5.56 (m, 1H), 5.01-5.11 (m, 1H), 4.35-4.52 (m, 1H), 3.63-3.81 (m, 1H), 3.24-3.30 (m, 1H), 2.98-3.16 (m, 1H), 2.89 (ddd, J=17.2, 13.4, 3.7 Hz, 1H), 2.36 (m, 2H), 2.17-2.26 (m, 1H), 1.98-2.17 (m, 3H), 1.67-1.92 (m, 3H), 1.49-1.64 (m, 4H), 1.39 (s, 3H), 1.20-1.33 (m, 1H).

Step 4: Methyl 2-(4-fluorophenyl)-2-methylpropanoate

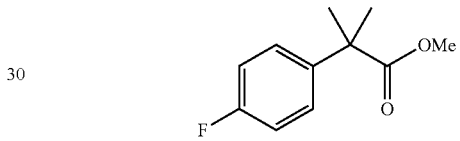

Sodium hydride (60% suspension in mineral oil) (2.64 g, 66 mmol) was washed with heptanes (2×20 ml) and suspended in THF (40 ml). A solution of methyl 2-(4-fluorophenyl)acetate (5.05 g, 30 mmol) in THF (10 ml) was added and stirred for 30 mins. Methyl iodide (5.6 ml, 90 mmol) was added in 1 ml portions over 30 mins, initially with cooling to 10° C. then gentle warming to 50° C. as the gas evolution ceased. After 4.5 h, water (50 ml) was added and the mixture extracted with EtOAc (2×50 ml). The combined organic phases were washed with brine (30 ml) and dried over MgSO$_4$ before filtering and evaporating to dryness to leave an orange oil (5.08 g, 79%, 91% pure by $^1$H NMR): MS (ESI$^+$) for C$_{11}$H$_{13}$FO$_2$ m/z 196.2 [M+H]$^+$; LC purity 80% (ret. time, 1.94 min); $^1$H NMR (500 MHz, CDCl$_3$) δ$_H$ 7.29-7.34 (m, 2H), 6.98-7.05 (m, 2H), 3.66 (s, 3H), 1.58 (s, 6H).

Step 5: 2-(4-Fluorophenyl)-2-methylpropan-1-ol

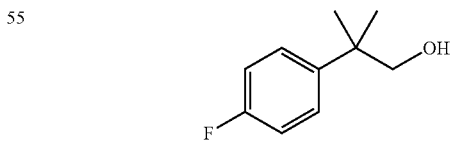

Methyl 2-(4-fluorophenyl)-2-methylpropanoate (5.08 g, 26.9 mmol) was dissolved in THF (51 ml) and cooled to 0° C. before adding a solution of lithium aluminium hydride (1M in THF) (38.8 ml, 38.8 mmol) dropwise over 30 mins. When the addition was complete, the reaction was warmed to r.t. and stirred for 3 h. After recooling on ice, water (1.35 ml) was added cautiously followed by 15% NaOH in water (1.35 ml) and more water (4.05 ml). The suspension was stirred at r.t. for 30 mins before the solid was filtered off and washed with THF (2×30 ml). The solvent was evaporated and the product purified by chromatography with EtOAc/heptanes to give a clear oil (3.48 g, 80%): MS (ESI$^+$) for $C_{10}H_{13}FO$ m/z 168.2 [M+H]$^+$; LC purity 94% (ret. time, 1.76 min); $^1$H NMR (500 MHz, CDCl$_3$) $\delta_H$ 7.41-7.32 (m, 2H), 7.15-7.00 (m, 2H), 3.62 (d, J=6.4 Hz, 2H), 1.35 (s, 6H).

Step 6:
1-Fluoro-4-(1-methoxy-2-methylpropan-2-yl)benzene

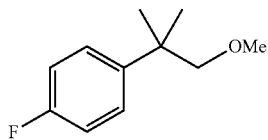

Sodium hydride (1.664 g, 41.6 mmol, 60% dispersion in mineral oil) was suspended in dry THF (18 ml) under N$_2$ and 2-(4-fluorophenyl)-2-methylpropan-1-ol (3.500 g, 20.8 mmol) in dry THF (18 ml) was slowly added to the suspension at 0° C. After complete addition the reaction was warmed to r.t. and left for 1 h. Iodomethane (6.5 ml, 0.104 mmol) was slowly added at r.t. and the reaction left for 3 h. The reaction was quenched by slow addition of H$_2$O (35 ml). The layers were separated and the aqueous layer was extracted with EtOAc (3×35 ml). The combined organic layers were dried over MgSO$_4$, filtered and concentrated in vacuo to give the crude product. The product was purified by silica flash column chromatography using between 100% heptane to 10% EtOAc:90% heptane as eluent to give the product as a colourless oil (2.991 g, 79%): LC purity 98% (ret. time, 2.16 min); $^1$H NMR (500 MHz, CDCl$_3$) $\delta_H$ 7.40-7.32 (m, 2H), 7.11-6.96 (m, 2H), 3.39 (s, 2H), 3.33 (s, 3H), 1.33 (s, 6H).

Step 7: 1-Fluoro-4-(1-methoxy-2-methylpropan-2-yl)-2-nitrobenzene

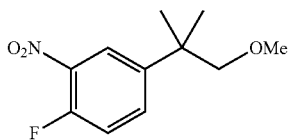 [SMILES: COCC(C)(C)c1ccc(F)c([N+](=O)[O-])c1]

Fluoro-4-(1-methoxy-2-methylpropan-2-yl)benzene (2.987 g, 16.4 mmol) was cooled in a salt ice/water bath to −20° C. and sulfuric acid (27 ml) was slowly added dropwise with stirring. On addition of sulfuric acid the solution turned a bright orange. Nitric acid (3 ml) was slowly added dropwise over 15-20 mins. On addition of nitric acid the solution turned dark yellow/brown and some white solid precipitated. The reaction was left for 30 mins then poured over ice (450 g). The mixture was extracted with DCM (2×225 ml) and the combined organic extracts were dried over MgSO$_4$, filtered and concentrated in vacuo to give the crude product. The product was purified by silica flash column chromatography using between 100% heptanes to 20% EtOAc:80% heptanes to give the product as a yellow oil (2.239 g, 60%): LC purity 96% (ret. time, 2.18 min); $^1$H NMR (500 MHz, CDCl$_3$) $\delta_H$ 8.08 (dd, J=7.1, 2.5 Hz, 1H), 7.67 (ddd, J=8.7, 4.1, 2.5 Hz, 1H), 7.23 (dd, J=10.6, 8.8 Hz, 1H), 3.41 (s, 2H), 3.33 (s, 3H), 1.37 (s, 6H).

Step 8: 1-Azido-4-(1-methoxy-2-methylpropan-2-yl)-2-nitrobenzene

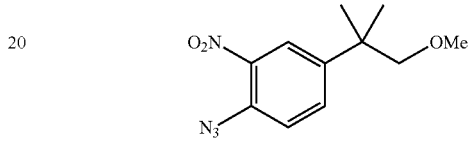

Fluoro-4-(1-methoxy-2-methylpropan-2-yl)-2-nitrobenzene (2.227 g, 9.80 mmol) was dissolved in DMF (25 ml) and sodium azide (1.274 g, 19.6 mmol) was added at r.t. and the reaction stirred overnight. The reaction was quenched with water (75 ml) and the mixture was extracted with TBME (3×75 ml). The combined organic layers were dried over MgSO$_4$, filtered and concentrated in vacuo to give the crude product. The product was purified by silica flash column chromatography using between 100% heptane to 15% EtOAc:85% heptane as eluent to give the product as a yellow oil (2.301 g, 75%, 80% pure): LC purity 79% (ret. time, 2.15 min); $^1$H NMR (500 MHz, CDCl$_3$) $\delta_H$ 7.97 (d, J=2.2 Hz, 1H), 7.66 (dd, J=8.5, 2.2 Hz, 1H), 7.33-7.22 (m, 1H), 3.40 (s, 2H), 3.33 (s, 3H), 1.36 (s, 6H).

Step 9: 4-(1-Methoxy-2-methylpropan-2-yl)benzene-1,2-diamine

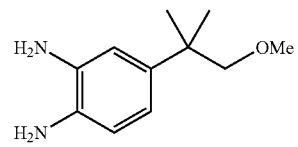

Azido-4-(1-methoxy-2-methylpropan-2-yl)-2-nitrobenzene (1.102 g, 3.52 mmol) was dissolved in EtOH (30 ml) and Pd/C (10% wt.) (0.110 g, 10% wt.) was added. The reaction was purged 3 times with N$_2$ then 3 times with H$_2$ and the reaction stirred at r.t. overnight. The mixture was filtered through Celite and the filtrate was concentrated in vacuo to give the crude product. The product was purified by silica flash column chromatography using between 100% heptane to 100% EtOAc as eluent to give the product as a pale brown oil which solidified into a dark orange solid (0.481 g, 63%, 90% pure): MS (ESI$^+$) for $C_{11}H_{18}N_2O$ m/z 195.1 [M+H]$^+$; LC purity 87% (ret. time, 0.99 min); $^1$H NMR (500 MHz, CDCl$_3$) $\delta_H$ 6.65 (dd, J=11.2, 1.9 Hz, 2H), 6.58 (d, J=7.9 Hz, 1H), 3.26 (s, 2H), 3.24 (s, 3H), 1.20 (s, 6H).

Step 10: 3-[3-({[(3aR,4R,6R,6aR)-6-(6-Amino-9H-purin-9-yl)-2,2-dimethyl-tetrahydro-2H-furo[3,4-d][1,3]dioxol-4-yl]methyl}(methyl)amino)cyclobutyl]-N-[2-amino-4-(1-methoxy-2-methylpropan-2-yl)phenyl]propanamide

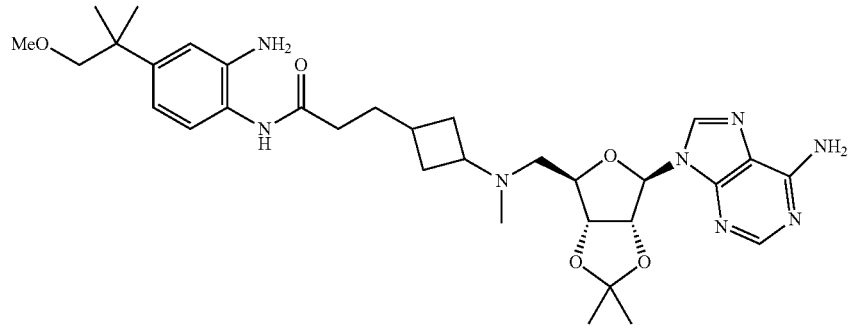 [SMILES: COCC(C)(C)c1ccc(NC(=O)CCC2CC(N(C)C[C@H]3O[C@@H](n4cnc5c(N)ncnc54)[C@@H]4OC(C)(C)O[C@@H]43)C2)c(N)c1]

3-[3-({[(3aR,4R,6R,6aR)-6-(6-Amino-9H-purin-9-yl)-2,2-dimethyl-tetrahydro-2H-furo[3,4-d][1,3]dioxol-4-yl]methyl}(methyl)amino)cyclobutyl]propanoic acid (0.620 g, 1.39 mmol), 4-(1-methoxy-2-methylpropan-2-yl)benzene-1,2-diamine (0.466 g, 2.08 mmol, 87% pure), EDC.HCl (0.532 g, 2.78 mmol) and OXYMA (ethyl-cyano(hydroxyimino)acetate) (0.395 g, 2.78 mmol) were added to a flask with a stirrer then purged with $N_2$. Dry DCM (22 ml) and dry $Et_3N$ (1.2 ml, 8.33 mmol) were added at r.t. and the reaction left overnight. The reaction was quenched by the addition of sat. $NaHCO_3$ solution (25 ml) and the organic layer separated. The aqueous layer was extracted with DCM (2×25 ml) and the combined organic layers were dried over $MgSO_4$, filtered and concentrated in vacuo to give the crude product. The product was purified by silica flash column chromatography using first 100% EtOAc to elute the dianiline then between 100% DCM to 20% 2M $NH_3$ in MeOH:80% DCM as eluent to give the product as a brown oil (1.081 g, quant.): MS (ESI$^+$) for $C_{32}H_{46}N_8O_5$ m/z 623.4 [M+H]$^+$; LC purity 98% (ret. time, 1.36 min); $^1$H NMR (500 MHz, CDCl$_3$) $\delta_H$ 8.39 (d, J=7.8 Hz, 1H), 7.99 (s, 1H), 7.42-7.30 (m, 1H), 7.24-7.00 (m, 1H), 6.96-6.81 (m, 1H), 6.12 (d, J=12.6 Hz, 1H), 5.77 (d, J=6.7 Hz, 1H), 5.63 (d, J=5.0 Hz, 1H), 5.14-4.93 (m, 1H), 4.60-4.31 (m, 1H), 4.28-3.69 (m, 2H), 3.48-3.03 (m, 5H), 2.65-2.48 (m, 1H), 2.46-2.33 (m, 1H), 2.34-2.10 (m, 7H), 2.10-1.98 (m, 1H), 2.00-1.66 (m, 4H), 1.62 (d, J=15.7 Hz, 13H), 1.44 (d, J=6.5 Hz, 4H), 1.30 (t, J=3.3 Hz, 7H), 1.12 (d, J=52.3 Hz, 1H).

3-[3-({[(3aR,4R,6R,6aR)-6-(6-Amino-9H-purin-9-yl)-2,2-dimethyl-tetrahydro-2H-furo[3,4-d][1,3]dioxol-4-yl]methyl}(methyl)amino)cyclobutyl]-N-[2-amino-4-(1-methoxy-2-methylpropan-2-yl)phenyl]propanamide (1.036 g, 1.66 mmol) was dissolved in AcOH (17 ml) and heated to 50° C. for 5 h. The reaction was concentrated in vacuo and the residue was dissolved in DCM (75 ml) and sat. $NaHCO_3$ solution (75 ml) was added. The organic layer was separated and the aqueous layer was extracted with DCM (2×75 ml). The combined organic layers were dried over $MgSO_4$, filtered and concentrated in vacuo to give the crude product as a dark orange oil (0.850 g, 94%). The product was purified using neutral prep-HPLC to give the product as a pale yellow oil (0.485 g, 47%, 88% pure): MS (ESI$^+$) for $C_{32}H_{44}N_8O_4$ m/z 605.4 [M+H]$^+$; LC purity 88% (ret. time, 1.25 min); $^1$H NMR (500 MHz, CDCl$_3$) $\delta_H$ 10.44 (dd, J=207.7, 22.9 Hz, 1H), 8.41 (d, J=17.1 Hz, 1H), 8.16 (d, J=13.8 Hz, 1H), 7.89-7.58 (m, 1H), 7.54-7.29 (m, 2H), 6.15 (d, J=10.9 Hz, 1H), 5.92-5.56 (m, 3H), 4.98 (d, J=12.5 Hz, 1H), 4.76-4.39 (m, 1H), 3.47 (d, J=6.2 Hz, 2H), 3.33 (d, J=4.8 Hz, 3H), 2.98-2.43 (m, 4H), 2.42-2.00 (m, 6H), 1.99-1.88 (m, 2H), 1.77-1.66 (m, 1H), 1.64 (s, 3H), 1.61-1.48 (m, 1H), 1.44 (d, J=8.1 Hz, 3H), 1.40 (d, J=7.9 Hz, 6H), 1.28 (dd, J=16.0, 9.0 Hz, 1H).

Step 11: 9-[(3aR,4R,6R,6aR)-6-{[(3-{2-[5-(1-Methoxy-2-methylpropan-2-yl)-1H-1,3-benzodiazol-2-yl]ethyl}cyclobutyl)(methyl)amino]methyl}-2,2-dimethyl-tetrahydro-2H-furo[3,4-d][1,3]dioxol-4-yl]-9H-purin-6-amine

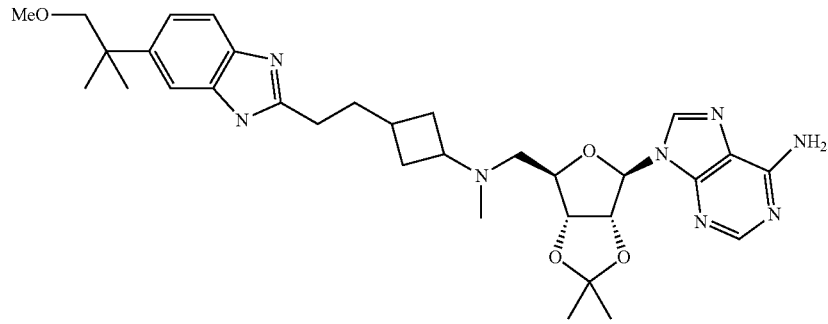 [SMILES: COCC(C)(C)c1ccc2nc(CCC3CC(N(C)C[C@H]4O[C@@H](n5cnc6c(N)ncnc65)[C@@H]5OC(C)(C)O[C@@H]54)C3)[nH]c2c1]

Step 12: (2R,3R,4S,5R)-2-(6-Amino-9H-purin-9-yl)-5-{[(3-{2-[5-(1-methoxy-2-ethylpropan-2-yl)-1H-1,3-benzodiazol-2-yl]ethyl}cyclobutyl)(methyl)amino]methyl}oxolane-3,4-diol

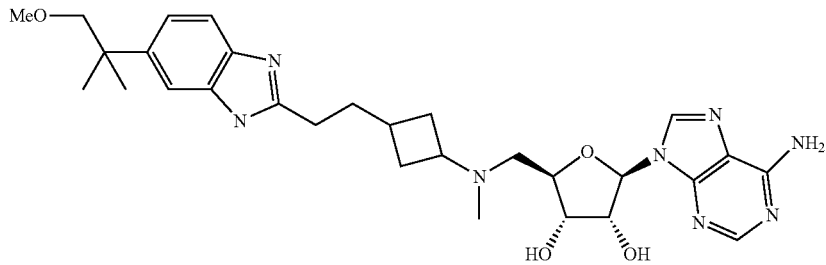 [SMILES: COCC(C)(C)c1ccc2nc(CCC3CC(N(C)C[C@H]4O[C@@H](n5cnc6c(N)ncnc65)[C@H](O)[C@@H]4O)C3)[nH]c2c1]

9-[(3aR,4R,6R,6aR)-6-{[(3-{2-[5-(1-Methoxy-2-methylpropan-2-yl)-1H-1,3-benzodiazol-2-yl]ethyl}cyclobutyl)(methyl)amino]methyl}-2,2-dimethyl-tetrahydro-2H-furo[3,4-d][1,3]dioxol-4-yl]-9H-purin-6-amine (0.485 g, 0.706 mmol, 88% pure) was dissolved in MeOH (20 ml) and conc. HCl (4.9 ml, 10 vol) was added at r.t. and the reaction left for 2.5 h. The reaction was concentrated in vacuo and the residue dissolved in the minimum amount of MeOH (~2 ml). The reaction was quenched by addition of sat. NaHCO₃ solution (10 ml) and EtOAc (30 ml). The layers were separated and the aqueous layer was extracted with EtOAc (2×30 ml). The combined organic layers were dried over MgSO₄, filtered and concentrated in vacuo to give the crude product. The product was purified by silica flash column chromatography using between 100% DCM and 20% 2M NH₃ in MeOH:80% DCM as eluent to give the product as a white foam (0.213 g, 53%): MS (ESI⁺) for C$_{29}$H$_{40}$N$_{8}$O$_{4}$ m/z 565.4 [M+H]⁺; LC purity 100% (ret. time, 2.11 min) (7 min); ¹H NMR (500 MHz, d$_4$-MeOD) δ$_H$ 8.28 (d, J=4.1 Hz, 1H), 8.22 (d, J=3.2 Hz, 1H), 7.51 (s, 1H), 7.42 (dd, J=8.5, 2.1 Hz, 1H), 7.29 (dd, J=8.5, 1.5 Hz, 1H), 6.01 (t, J=3.9 Hz, 1H), 4.84-4.74 (m, 1H), 4.41-4.29 (m, 1H), 4.29-4.19 (m, 1H), 3.48 (s, 2H), 3.30 (s, 3H), 3.14-2.98 (m, 1H), 2.99-2.89 (m, 1H), 2.90-2.73 (m, 2H), 2.39 (s, 3H), 2.37-2.30 (m, 1H), 2.28-2.10 (m, 2H), 2.08-1.86 (m, 4H), 1.70-1.51 (m, 1H), 1.38 (s, 6H).

Compound 69: (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(methyl)amino)methyl)cyclopentane-1,2-diol

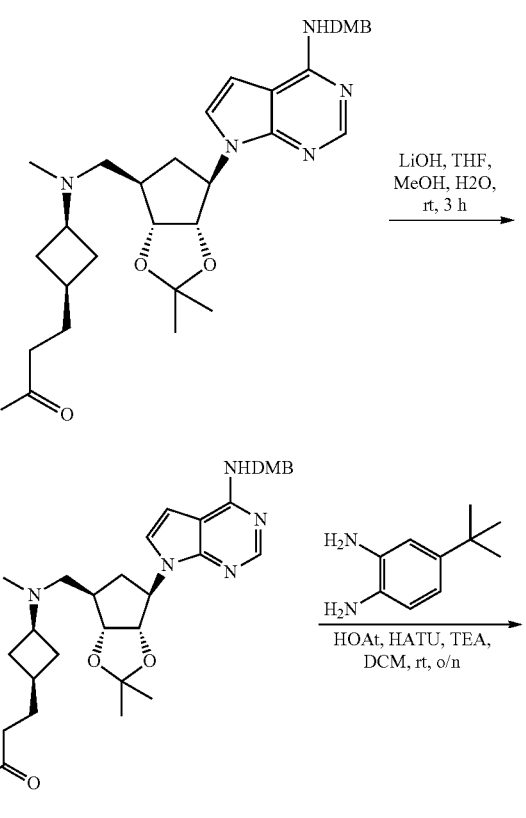

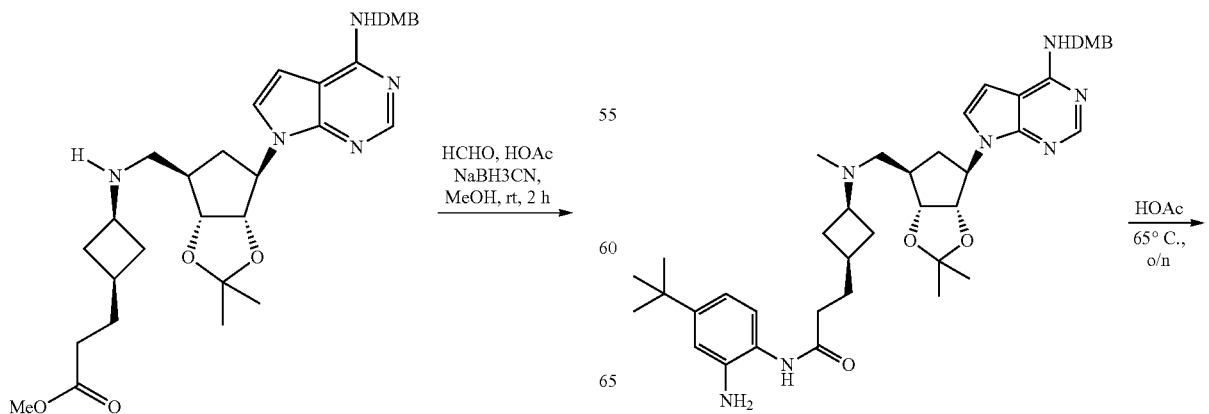

-continued

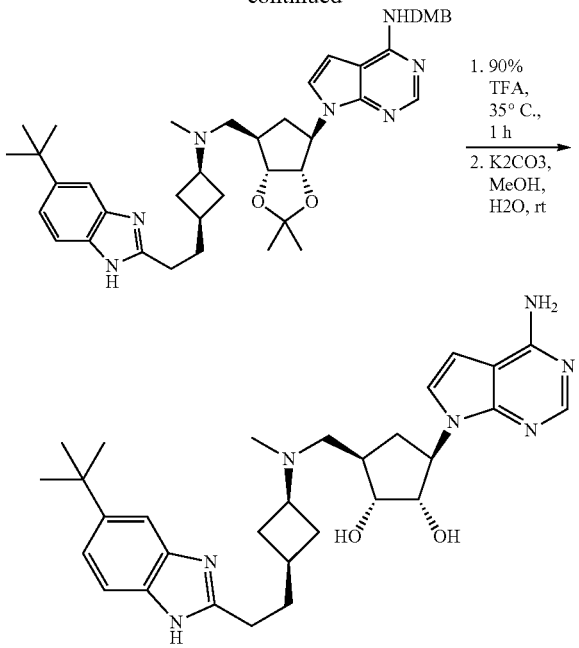

(1R,2S,3R,5R)-3-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(methyl)amino)methyl)cyclopentane-1,2-diol $^1$H NMR (500 MHz, MeOD): $\delta_H$ 8.06 (s, 1H), 7.47 (brs, 1H), 7.38 (d, J=8.0 HZ, 1H), 7.27 (d, J=8.0 Hz, 1H), 7.19 (s, 1H), 6.60 (s, 1H), 4.32 (s, 1H), 3.88 (s, 1H), 2.80 (brs, 2H), 2.68 (brs, 1H), 2.49-2.10 (m, 9H), 1.90 (brs, 2H), 1.62-1.49 (m, 3H), 1.35 (s, 9H) ppm; ESI-MS (m/z): 532.3 [M+1]$^+$.

benzyl 3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)amino)cyclobutyl)propanoate A solution of 7-((3aR,4R,6R,6aR)-6-(aminomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (20 g, 43.91 mmol), benzyl 3-(3-oxocyclobutyl)propanoate (12.2 g, 52.69 mmol) and HOAc (15 mL) in DCE (200 mL) was stirred at 30° C. for 3 h. NaBH(OAc)$_3$ (18.6 g, 87.81 mmol) was added and the reaction mixture was stirred at 30° C. for another 1 h. The mixture was washed with water (100 mL×2) and brine (100 mL), dried over Na$_2$SO$_4$, filtered and concentrated. The residue was purified by silica gel column chromatography using EA:DCM:MeOH=10:10:1 as eluent to afford the desired compound (21 g, yield: 65%, cis/trans=52/47) as a yellow solid. $^1$H NMR (500 MHz, MeOD): $\delta_H$ 8.16 (brs, 1H), 7.36-7.29 (m, 5H), 7.22 (d, J=3.5 Hz, 1H), 7.15 (d, J=8.5 Hz, 1H), 6.66 (brs, 1H), 6.54 (d, J=2.0 Hz, 1H), 6.43 (dd, J=8.5 and 2.0 Hz, 1H), 6.20 (brs, 1H), 5.41-5.39 (m, 1H), 5.08 (d, J=3.0 Hz, 1H), 4.99-4.95 (m, 1H), 4.66 (s, 2H), 4.30-4.25 (m, 1H), 3.83 (s, 3H), 3.76 (s, 3H), 3.38-3.35 (m, 0.5H), 3.11-3.06 (m, 0.5H), 2.92-2.82 (m, 2H), 2.29-2.18 (m, 3H), 2.12-2.05 (m, 0.5H), 1.90-1.68 (m, 4H), 1.63-1.61 (m, 1H), 1.60 (s, 3H), 1.38 (s, 3H), 1.35-1.28 (m, 0.5H), 1.25 (t, J=6.5 Hz, 2H), 1.15-1.12 (m, 0.5H) ppm; ESI-MS (negative mode, m/z): 670.3 [M−1]$^+$.

benzyl 3-(3-((((3 aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)cyclobutyl)propanoate A mixture of benzyl 3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)amino)cyclobutyl)propanoate (4 g, 5.95 mmol), 2-iodopropane (6 g, 35.72 mmol) and K$_2$CO$_3$ (2.5 g, 17.86 mmol) in CH$_3$CN (50 mL) was stirred at reflux for 2 days. The mixture was cooled to rt, filtered and the filtered cake was washed with CH$_3$CN (20 mL). The filtrate was concentrated and the residue was purified by Combi-Flash (80 g silica gel, start EA:DCM:MeOH=10:10:0 to 10:10:1 by gradient, 60 mL/min, 40 min, 2.4 L total solvent volume) to afford the desired compound (3 g, yield: 71%) as a yellow solid. $^1$H NMR (500 MHz, MeOD): $\delta_H$ 8.15 (s, 1H), 7.38-7.29 (m, 5H), 7.19 (d, J=4.0 Hz, 1H), 7.14 (d, J=8.0 Hz, 1H), 6.65 (d, J=3.0 Hz, 1H), 6.53 (d, J=2.0 Hz, 1H), 6.41 (dd, J=8.5 and 2.0 Hz, 1H), 6.20 (d, J=2.5 Hz, 1H), 5.36-5.32 (m, 1H), 5.09 (s, 1H), 5.07 (s, 1H), 4.94-4.89 (m, 3H), 4.65 (s, 2H), 4.17-4.14 (m, 1H), 3.82 (s, 3H), 3.75 (s, 3H), 3.41-3.35 (m, 0.5H), 3.04-2.95 (m, 0.5H), 2.94-2.86 (m, 1H), 2.72-2.52 (m, 2H), 2.25 (t, J=7.5 Hz, 1H), 2.21 (t, J=8.0 Hz, 1H), 2.05-1.90 (m, 2H), 1.90-1.82 (m, 0.5H), 1.76-1.70 (m, 0.5H), 1.65-1.55 (m, 5H), 1.42-1.34 (m, 4H), 0.95 (d, J=6.5 Hz, 3H), 0.83-0.80 (m, 3H) ppm; ESI-MS (m/z): 714.4 [M+1]$^+$.

3-(3-((((3 aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)cyclobutyl)propanoic acid To a solution of benzyl 3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)cyclobutyl)propanoate (2.7 g, 3.78 mmol) in THF/MeOH (15 mL/15 mL) was added a solution of LiOH.H$_2$O (1.6 g, 37.82 mmol) in water (5 mL). The mixture was stirred at 30° C. for 2 h. The volatiles were removed under reduced pressure. To the residue was diluted with water (10 mL) and extracted with EA (15 mL×2). The suspension water layers were adjusted to pH=3-4 with 1 N HCl solution and extracted with EA (30 mL×3). The combined organic layers were washed with brine (50 in L). The organic phase was dried over Na$_2$SO$_4$, filtered and concentrated to afford the desired compound as a yellow solid (2.9 g). $^1$H NMR (500 MHz, MeOD): $\delta_H$ 8.20 (s, 1H), 7.92 (s, 0.5H), 7.38-7.32 (m, 3H), 7.28-7.23 (m, 1.5H), 7.14 (d, J=8.5 Hz, 1H), 6.68 (brs, 1H), 6.56 (d, J=2.0 Hz, 1H), 6.44 (d, J=8.5 Hz, 1H), 6.25 (s, 1H), 5.51-5.47 (m, 1H), 5.18-5.13 (m, 1H), 4.66 (s, 2H), 4.61 (s, 1H), 4.43-4.40 (m, 1H), 3.96-3.90 (m, 0.5H), 3.85 (s, 3H), 3.77 (s, 3H), 3.65-3.58 (m, 0.5H), 3.50-3.40 (m, 2H), 2.46-2.36 (m, 1H), 2.20-2.00 (m, 4H), 1.98-1.70 (m, 2.5H), 1.70-1.58 (m, 4.5H), 1.40 (s, 3H), 1.18 (d, J=5.0 Hz, 3H), 0.90 (t, J=6.0 Hz, 3H) ppm; ESI-MS (m/z): 624.3 [M+1]$^+$.

N-(2-amino-4-(tert-butyl)phenyl)-3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)cyclobutyl)propan amide To a solution of 3-(3-((((3aR,4R,6R,6aR)-6-(4-((2,4-dimethoxybenzyl)amino)-7H-pyrrolo[2,3-d]pyrimidin-7- yl)-2,2-dimethyltetrahydrofuro[3,4-d][1,3]dioxol-4-yl)methyl)(isopropyl)amino)cyclobutyl)propanoic acid (2.7 g, 4.33 mmol), 4-(trifluoromethoxy)benzene-1,2-diamine (1.23 g, 6.49 mmol), HATU (2.5 g, 6.49 mmol) and HOAT (0.88 g, 6.49 mmol) in DCM (30 mL) was added TEA (1.8 mL, 12.99 mmol). The mixture was stirred at rt for 2 h. The mixture was added DCM (70 mL) and washed with water (20 mL×2) and brine (50 mL). The organic phase was dried over $Na_2SO_4$, filtered and concentrated. The residue was purified by Combi-Flash (80 g silica gel, start EA:DCM:MeOH=10:10:0 to 10:10:2 by gradient, 60 mL/min, 40 min, 2.4 L total solvent volume) to afford to afford the desired compound (2.2 g, yield: 67% (two steps) as a brown solid. $^1$H NMR (500 MHz, MeOD): $\delta_H$ 8.21 (s, 1H), 7.28-7.12 (m, 3H), 6.73 (brs, 1H), 6.69 (brs, 1H), 6.56-6.52 (m, 2H), 6.42 (dd, J=8.0 and 2.5 Hz, 1H), 6.26 (d, J=1.5 Hz, 1H), 5.48 (d, J=6.0 Hz, 1H), 5.20-5.16 (m, 1H), 4.66 (s, 2H), 4.46-4.42 (m, 1H), 4.08-3.98 (m, 0.5H), 3.84 (s, 3H), 3.76 (s, 3H), 3.75-3.69 (m, 0.5H), 3.60-3.38 (m, 2H), 2.60-2.30 (m, 3H), 1.92-1.86 (m, 1H), 1.80-1.70 (m, 1H), 1.59 (d, J=3.5 Hz, 3H), 1.40 (s, 3H), 1.25 (t, J=7.5 Hz, 3H),), 1.00-0.80 (m, 2H) ppm; ESI-MS (m/z): 798.3 [M+1]$^+$.

N-(2,4-dimethoxybenzyl)-7-((3aR,4R,6R,6aR)-6-((isopropyl(3-(2-(5-(trifluoromethoxy)-1H-benzo[d]imidazol-2-yl)ethyl)cyclobutyl)amino)methyl)-2,2-dimethyltetrahydrofuro[3,4-d][1,3]dioxol-4-yl)-7H-pyrrolo[2,3-d]pyrimidin-4-amine A solution of N-(2-amino-4-(tert-butyl)phenyl)-3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)cyclobutyl)propanamide (2.2 g, 2.5 mmol) in HOAc (20 mL) was stirred at 65° C. for 5 h. The mixture was cooled to rt and concentrated. The residue was dissolved in DCM (50 mL), washed with 15% $Na_2CO_3$ solution (20 mL×2), water (20 mL) and brine (30 mL). The organic phase was dried over $Na_2SO_4$, filtered and concentrated. The residue was purified by Combi-Flash (80 g silica gel, start EA:DCM:MeOH=10:10:0 to 10:10:2 by gradient, 60 mL/min, 35 min, 2.1 L total solvent volume) to afford to afford the desired compound (1.4 g) as a brown solid, which was separated by chiral HPLC to afford cis-isomer (600 mg, yield: 28%) and the trans isomer (480 mg, yield: 22%).

cis-isomer: $^1$H NMR (500 MHz, MeOD): $\delta_H$ 8.17 (s, 1H), 7.52 (d, J=9.0 Hz, 1H), 7.39 (s, 1H), 7.20 (d, J=4.0 Hz, 1H), 7.12 (d, J=8.0 Hz, 1H), 6.68 (brs, 1H), 6.49 (d, J=2.5 Hz, 1H), 6.39 (dd, J=8.5 and 2.0 Hz, 1H), 6.19 (d, J=2.0 Hz, 1H), 5.35 (dd, J=6.0 and 2.0 Hz, 1H), 4.68-4.60 (m, 2H), 4.18-4.13 (m, 1H), 3.78 (s, 3H), 3.73 (s, 3H), 3.10-3.02 (m, 1H), 2.95-2.88 (m, 1H), 2.78-2.72 (m, 2H), 2.69-2.57 (m, 2H), 2.12-2.02 (m, 2H), 1.86-1.76 (m, 2H), 1.57 (s, 3H), 1.52-1.40 (m, 2H), 1.37 (s, 3H), 0.96 (d, J=6.5 Hz, 3H), 0.82 (d, J=6.5 Hz, 3H) ppm; ESI-MS (m/z): 780.4 [M+1]$^+$.

trans-isomer: $^1$H NMR (500 MHz, MeOD): $\delta_H$ 8.15 (s, 1H), 7.52 (d, J=9.0 Hz, 1H), 7.40 (s, 1H), 7.20 (d, J=3.5 Hz, 1H), 7.12 (d, J=8.0 Hz, 1H), 6.68 (brs, 1H), 6.51 (d, J=2.0 Hz, 1H), 6.40 (dd, J=8.0 and 2.5 Hz, 1H), 6.20 (d, J=2.5 Hz, 1H), 5.35 (dd, J=6.0 and 2.0 Hz, 1H), 4.64 (s, 2H), 4.20-4.16 (m, 1H), 3.82 (s, 3H), 3.73 (s, 3H), 3.50-3.42 (m, 1H), 2.95-2.90 (m, 1H), 2.80 (t, J=6.0 Hz, 2H), 2.75-2.58 (m, 2H), 2.12-1.95 (m, 4H), 1.75-1.65 (m, 2H), 1.58 (s, 3H), 1.38 (s, 3H), 0.97 (d, J=6.5 Hz, 3H), 0.83 (d, J=6.5 Hz, 3H) ppm; ESI-MS (m/z): 780.4 [M+1]$^+$.

Compound 70: (1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(methyl)amino)methyl)cyclopentane-1,2-diol

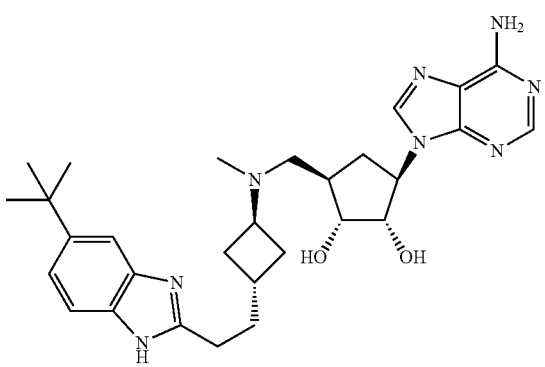 [SMILES: CN(C[C@H]1C[C@@H](n2cnc3c(N)ncnc32)[C@H](O)[C@@H]1O)[C@H]1C[C@H](CCc2nc3cc(C(C)(C)C)ccc3[nH]2)C1]

methyl 3-((1R,3s)-3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl) propanoate A solution of methyl 3-((1R,3s)-3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)amino)cyclobutyl)propanoate (1.85 g, 3.12 mmol) and $NaBH_3CN$ (590 mg, 9.36 mmol) in MeOH (25 mL) was adjusted pH=6 with AcOH, then formaldehyde (936 mg, 31.2 mmol) added. The reaction was stirred at 25° C. overnight. The reaction was quenched with sat. $NaHCO_3$ (5 mL), evaporated, added water (10 mL), extracted with DCM (150 mL×3), washed with brine (80 mL), dried and concentrated. The residue was purified by SGC to obtain the desired compound (1.85 g, Yield 97%) as white solid. $^1$H NMR (500 MHz, MeOD): $\delta_H$ 8.12 (s, 1H), 7.22 (d, J=3.5 Hz, 1H), 7.14 (d, J=8.5 Hz, 1H), 6.64 (d, J=3.0 Hz, 1H), 6.55 (d, J=2.5 Hz, 1H), 6.44 (dd, J=8.5 and 2.5 Hz, 1H), 5.01-4.98 (m, 2H), 4.65 (s, 2H), 4.60-4.58 (m, 1H), 4.30 (s, 1H), 3.84 (s, 3H), 3.76 (s, 3H), 3.66 (s, 3H), 3.44-3.38 (m, 1H), 2.80-2.73 (m, 2H), 2.48-2.43 (m, 4H), 2.32 (t, J=7.5 Hz, 2H), 2.20-2.16 (m, 4H), 1.95-1.94 (m, 2H), 1.82-1.81 (m, 2H), 1.56 (s, 3H), 1.31 (s, 3H) ppm; ESI-MS (m/z): 608.3 [M+1]$^+$.

3-((1R,3s)-3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl) propanoic acid A solution of methyl 3-((1R,3s)-3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanoate (1.85 g, 3.04 mmol) and LiOH (382 mg, 15.24 mmol) in THF/MeOH/$H_2O$ (1:1:1, 30 mL) were stirred at 50° C. for 2 h. The reaction was concentrated to obtain the desired compound (2.25 g, salt, purity 85%) as white solid. The crude was used directly next step without further purification. $^1$H NMR (500 MHz, MeOD): $\delta_H$ 8.11 (s, 1H), 7.92 (s, 1H), 7.30 (d, J=3.0 Hz, 1H), 7.14 (d, J=8.0 Hz, 1H), 6.67 (d, J=3.0 Hz, 1H), 6.54 (d, J=2.0 Hz, 1H), 6.44 (dd, J=10.0 and 2.5 Hz, 1H), 5.05-5.03 (m, 2H), 4.73 (d, J=6.0 Hz, 1H), 4.65 (s, 2H), 3.90-3.85 (m, 1H), 3.85 (s, 3H), 3.77 (s, 3H), 3.30-3.18 (m, 2H), 2.82 (s, 3H), 2.65-2.55 (m, 1H), 2.53-2.46 (m, 3H), 2.27-2.20 (m, 3H), 2.12-2.11 (m, 2H), 1.83-1.82 (m, 2H), 1.57 (s, 3H), 1.32 (s, 3H) ppm; ESI-MS (m/z): 594.3 [M+1]$^+$.

N-(2-amino-4-(tert-butyl)phenyl)-3-((1R,3s)-3-((((3 aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanamide A solution of 3-((1R,3s)-3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanoic acid (2.25 g, 3.8 mmol) HOAt (680 mg, 5 mmol) and HATU (1.9 g, 5 mmol) in DCM (60 mL) was stirred at room temperature for 1 h, then 4-tert-butylbenzendiamine (656 mg, 4 mmol) and TEA (1.21 g, 12 mmol) in DCM (3 mL) were added dropwise. The reaction was stirred at rt overnight. The reaction was added water (20 mL) and DCM (60 mL), extracted with DCM (60 mL×2), washed with brine (10 mL), dried and concentrated. The residue was purified by SGC to obtain the desired compound (1.1 g, Yield 46%) as yellowish solid. $^1$H NMR (500 MHz, MeOD): $\delta_H$ 8.11 (s, 1H), 7.21 (d, J=4.0 Hz, 1H), 7.13 (d, J=8.5 Hz, 1H), 6.98 (d, J=8.5 Hz, 1H), 6.92 (d, J=2.0 Hz, 1H), 6.77 (dd, J=8.0 and 1.5 Hz, 1H), 6.64 (d, J=3.5 Hz, 1H), 6.54 (d, J=2.0 Hz, 1H), 6.43 (dd, J=8.0 and 1.5 Hz, 1H), 5.02-4.99 (m, 2H), 4.65-4.61 (m, 3H), 3.83 (s, 3H), 3.75 (s, 3H), 3.60-3.52 (m, 1H), 2.97-2.83 (m, 2H), 2.58 (s, 3H), 2.54-2.38 (m, 4H), 2.33-2.29 (m, 2H), 2.18-2.04 (m, 3H), 1.94-1.91 (m, 2H), 1.55 (s, 3H), 1.30 (s, 3H), 1.25 (s, 9H) ppm; ESI-MS (m/z): 740.5 [M+1]$^+$.

7-((3aS,4R,6R,6aR)-6-((((1s,3R)-3-(2-(5-(tert-butyl)-1H-benzo[d]imidazol-2-yl)ethyl)cyclobutyl)(methyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine A solution of N-(2-amino-4-(tert-butyl)phenyl)-3-((1R, 3s)-3-((((3aR,4R,6R,6aS)-6-(4-((2,4-dimethoxybenzyl)amino)-7H-pyrrolo[2,3-d]pyrimidin-7-yl)-2,2-dimethyltetrahydro-3aH-cyclopenta[d][1,3]dioxol-4-yl)methyl)(methyl)amino)cyclobutyl)propanamide (1.1 g, 1.49 mmol) in AcOH (8 mL) were heated to 65° C. for 3 h. The reaction was evaporated, dissolved in MeOH (5 mL) adjusted pH=8 with saturated NaHCO$_3$ solution, concentrated and purified by Prep-TLC to obtain the desired compound (620 mg, 58%) as white solid. $^1$H NMR (500 MHz, MeOD): $\delta_H$ 8.10 (s, 1H), 7.48 (brs, 1H), 7.38 (brs, 1H), 7.28 (d, J=8.5 Hz, 1H), 7.21 (d, J=3.0 Hz, 1H), 7.13 (d, J=8.5 Hz, 1H), 6.62 (brs, 1H), 6.53 (s, 1H), 6.42 (d, J=8.5 Hz, 1H), 4.98-4.90 (m, 2H), 4.64 (s, 2H), 4.50 (brs, 1H), 3.83 (s, 3H), 3.75 (s, 3H), 3.01-2.98 (m, 1H), 2.83 (d, J=7.5 Hz, 1H), 2.44-2.34 (m, 4H), 2.16 (s, 3H), 2.12-1.96 (m, 6H), 1.84 (t, J=7.5 Hz, 2H), 1.53 (s, 3H), 1.36 (s, 9H), 1.28 (s, 3H) ppm; ESI-MS (m/z): 722.4 [M+1]$^+$.

(1R,2S,3R,5R)-3-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(methyl)amino)methyl)cyclopentane-1,2-diol A solution of 7-((3aS,4R,6R,6aR)-6-((((1s,3R)-3-(2-(5-(tert-butyl)-1H-benzo[d]imidazol-2-yl)ethyl)cyclobutyl)(methyl)amino)methyl)-2,2-dimethyltetrahydro-3aH-cyclopenta[d][1,3]dioxol-4-yl)-N-(2,4-dimethoxybenzyl)-7H-pyrrolo[2,3-d]pyrimidin-4-amine (620 mg, 0.86 mmol) in TFA (5 mL, 90%) was stirred at 25° C. for 1 hour. The reaction was concentrated to dryness, dissolved in MeOH (5 mL) and adjusted pH=8 with saturated K$_2$CO$_3$ solution. The mixture was stirred at rt for 0.5 h. Then the reaction was concentrated to obtain the residue. The residue was purified by Prep-HPLC to obtain the desired compound (330 mg, Yield 73%) as white solid. $^1$H NMR (500 MHz, MeOD): $\delta_H$ 8.07 (s, 1H), 7.49 (d, J=1.5 Hz, 1H), 7.40 (d, J=11.0 Hz, 1H), 7.29 (dd, J=11.0 and 2.5 Hz, 1H), 7.21 (d, J=5.0 Hz, 1H), 6.60 (d, J=4.0 Hz, 1H), 4.92-4.89 (m, 1H), 4.33 (dd, J=9.5 and 8.5 Hz, 1H), 3.90 (d, J=5.5 Hz, 1H), 3.03-2.99 (m, 1H), 2.85 (d, J=9.5 Hz, 1H), 2.50-2.22 (m, 4H), 2.16 (s, 3H), 2.15-1.98 (m, 5H), 1.88 (t, J=10.0 Hz, 2H), 1.68-1.59 (m, 1H), 1.37 (s, 9H) ppm; ESI-MS (m/z): 532.3 [M+1]$^+$.

Compound 71: (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(methyl)amino)methyl)tetrahydrofuran-3,4-diol

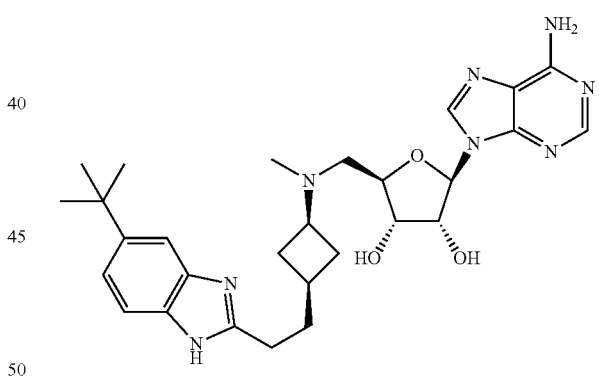

A mixture of cis-9-((3aR,4R,6R,6aR)-6-((((1r,3S)-3-(2-(5-(tert-butyl)-1H-benzo[d]imidazol-2-yl)ethyl)cyclobutyl)(methyl)amino)methyl)-2,2-dimethyltetrahydrofuro[3,4-d][1,3]dioxol-4-yl)-9H-purin-6-amine (920 mg, 1.60 mmol) in 3 M HCl/MeOH (20 mL) was stirred at 35° C. for 2 h and evaporated to dryness. The residue was dissolved in MeOH (15 mL) and saturated K$_2$CO$_3$ solution was added to adjust the solution to pH 8. Then, the mixture was stirred for 5 min and filtered. The filtrate was concentrated and the crude was purified by Prep-HPLC to obtain the target (400 mg, yield: 47%) as a white solid. $^1$H NMR (500 MHz, MeOD): $\delta_H$ 8.27 (s, 1H), 8.20 (s, 1H), 7.47 (s, 1H), 7.47 (s, 1H), 7.40-7.37 (m, 1H), 7.29-7.26 (m, 1H), 5.98 (d, J=4.5 Hz, 1H), 4.69 (t, J=4.5 Hz, 1H), 4.24-4.20 (m, 1H), 4.18-4.15 (m, 1H), 2.81-2.76 (m, 2H), 2.75-2.69 (m, 1H), 2.67-2.62 (m, 2H), 2.25-2.18 (m, 1H), 2.14 (s, 3H), 1.90-1.85 (m, 3H), 1.49-1.41 (m, 2H), 1.36 (s, 9H) ppm; ESI-MS (m/z): 535.3 [M+1]+.

Compound 72: (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(methyl)amino)methyl)tetrahydrofuran-3,4-diol

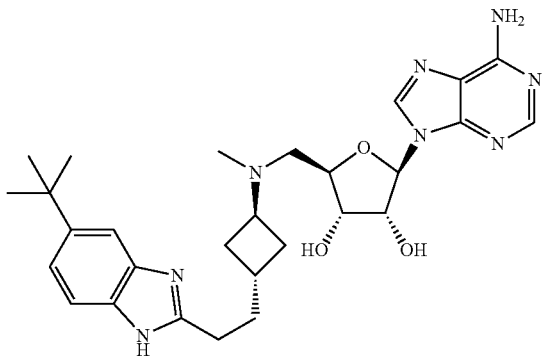 [SMILES: CN(C[C@H]1O[C@@H](n2cnc3c(N)ncnc32)[C@H](O)[C@@H]1O)[C@H]1C[C@H](CCc2nc3cc(C(C)(C)C)ccc3[nH]2)C1]

A mixture of trans-9-((3aR,4R,6R,6aR)-6-((((1r,3S)-3-(2-(5-(tert-butyl)-1H-benzo[d]imidazol-2-yl)ethyl)cyclobutyl)(methyl)amino)methyl)-2,2-dimethyltetrahydrofuro[3,4-d][1,3]dioxol-4-yl)-9H-purin-6-amine (420 mg, 0.73 mmol) in 3 M HCl/MeOH (20 mL) was stirred at 35° C. for 2 h and evaporated to dryness. The residue was dissolved in MeOH (15 mL) and saturated K$_2$CO$_3$ solution was added to adjust the solution to pH 8. Then, the mixture was stirred for 5 min and filtered. The filtrate was concentrated and the crude was purified by Prep-HPLC to obtain the target (198 mg, yield: 51%) as a white solid. $^1$H NMR (500 MHz, MeOD): δ$_H$ 8.28 (s, 1H), 8.19 (s, 1H), 7.48 (s, 1H), 7.38 (d, J=8.0 Hz, 1H), 7.28-7.26 (m, 1H), 5.98 (d, J=4.0 Hz, 1H), 4.69 (t, J=5.5 Hz, 1H), 4.23 (t, J=5.0 Hz, 1H), 4.19-4.16 (m, 1H), 3.06-3.03 (m, 1H), 2.80 (t, J=7.5 Hz, 2H), 2.68-2.64 (m, 2H), 2.16 (s, 3H), 2.09-1.95 (m, 5H), 1.85-1.80 (m, 2H), 1.36 (s, 9H) ppm; ESI-MS (m/z): 535.3 [M+1]+.

Benzyl 3-(3-(((((3aR,4R,6R,6aR)-6-(6-amino-9H-purin-9-yl)-2,2-dimethyltetrahydrofuro[3,4-d][1,3]dioxol-4-yl)methyl)(ethyl)amino)cyclobutyl)propanoate To a mixture of benzyl 3-(3-((((3aR,4R,6R,6aR)-6-(6-amino-9H-purin-9-yl)-2,2-dimethyltetrahydrofuro[3,4-d][1,3]dioxol-4-yl)methyl)amino)cyclobutyl)propanoate (3.76 g, 7.2 mmol) and NaBH$_3$CN (5.9 g, 93.6 mmol) in MeOH (40 mL) was added AcOH to adjust to pH=6. Then, 40% MeCHO (8.7 mL, 122.5 mmol) was added and the mixture was stirred at 30° C. for 1.5 h. Water (15 mL) was added and the mixture was concentrated in vacuo. Then, the mixture was extracted with DCM (30 mL×3). The combined organic phase was washed with brine, dried over Na$_2$SO$_4$, filtered and concentrated. The crude was purified by SGC (DCM: MeOH=100:1-20:1) to obtain the target (2.6 g, yield: 66%) as a white solid. $^1$H NMR (500 MHz, MeOD): δ$_H$ 8.26 (s, 1H), 8.23 (m, 1H), 7.37-7.28 (m, 5H), 6.24 (s, 1H), 5.52-5.49 (m, 1H), 5.10-5.06 (m, 3H), 4.41-4.40 (m, 1H), 3.20-2.90 (m, 2H), 2.80-2.60 (m, 2H), 2.12-1.77 (m, 4H), 1.74-1.60 (m, 3H), 1.39 (s, 3H), 1.26-1.22 (m, 3H), 0.94-0.89 (m, 3H) ppm; ESI-MS (m/z): 551.3 [M+1]+.

3-(3-(((((3aR,4R,6R,6aR)-6-(6-amino-9H-purin-9-yl)-2,2-dimethyltetrahydrofuro[3,4-d][1,3]dioxol-4-yl)methyl)(ethyl)amino)cyclobutyl)propanoic acid To a solution of Benzyl 3-(3-((((3aR,4R,6R,6aR)-6-(6-amino-9H-purin-9-yl)-2,2-dimethyltetrahydrofuro[3,4-d][1,3]dioxol-4-yl)methyl)(ethyl)amino)cyclobutyl)propanoate (2.6 g, 4.73 mmol) in MeOH (40 mL) was added 10% Pd/C (2.3 g) and the mixture was stirred under H$_2$ atmosphere at 50° C. for 20 h. The mixture was filtered and the filtrate was concentrated to obtain the target (2 g, yield: 92%) as a white solid. $^1$H NMR (500 MHz, MeOD): δ$_H$ 8.27 (s, 1H), 8.25 (s, 1H), 6.30 (s, 1H), 5.52-5.49 (m, 1H), 5.14-5.12 (m, 1H), 4.51-4.47 (m, 1H), 3.43-3.36 (m, 2H), 3.22-3.15 (m, 1H), 2.94-2.89 (m, 2H), 2.28-2.05 (m, 4H), 1.96-1.80 (m, 2H), 1.74-1.69 (m, 1H), 1.65-1.59 (m, 5H), 1.41-1.36 (m, 4H), 1.03-0.99 (m, 3H) ppm; ESI-MS (m/z): 461.3 [M+1]+.

N-(2-amino-4-(tert-butyl)phenyl)-3-(3-((((3aR,4R,6R,6aR)-6-(6-amino-9H-purin-9-yl)-2,2-dimethyltetrahydrofuro[3,4-d][1,3]dioxol-4-yl)methyl)(ethyl)amino)cyclobutyl)propanamide To a solution of 3-(3-((((3aR,4R,6R,6aR)-6-(6-amino-9H-purin-9-yl)-2,2-dimethyltetrahydrofuro[3,4-d][1,3]dioxol-4-yl)methyl)(ethyl)amino)cyclobutyl)propanoic acid (2 g, 4.35 mmol), HOAT (768 mg, 5.65 mmol), HATU (2.2 g, 5.65 mmol) and TEA (3 mL, 21.3 mmol) in DCM (40 mL) was added 4-tert-butylbenzene-1,2-diamine (785 mg, 4.79 mmol) and the mixture was stirred at rt for 2 h. Water (15 mL) was added and the mixture was extracted with DCM (30 mL×2). The combined organic phase was washed with H$_2$O (20 mL×2). The combined organic layers were dried over Na$_2$SO$_4$, filtered and concentrated. The crude was purified by SGC (DCM: MeOH-70:1-20:1) to obtain the target (1.6 g, yield: 61%) as a white solid. $^1$H NMR (500 MHz, MeOD): δ$_H$ 8.28-8.27 (m, 1H), 8.24-8.23 (m, 1H), 7.10-6.92 (m, 2H), 6.81-6.76 (m, 1H), 6.22 (s, 1H), 5.54-5.52 (m, 1H), 5.03 (s, 1H), 4.36 (s, 1H), 3.03-2.50 (m, 5H), 2.32-2.26 (m, 2H), 2.16-1.80 (m, 4H), 1.73-1.69 (m, 2H), 1.59 (s, 3H), 1.39 (s, 3H), 1.28-1.24 (m, 9H), 0.94-0.85 (m, 3H) ppm; ESI-MS (m/z): 607.3 [M+1]+.

9-((3aR,4R,6R,6aR)-6-(((3-(2-(5-(tert-butyl)-1H-benzo[d]imidazol-2-yl)ethyl)cyclobutyl)(ethyl)amino)methyl)-2,2-dimethyltetrahydrofuro[3,4-d][1,3]dioxol-4-yl)-9H-purin-6-amine A solution of N-(2-amino-4-(tert-butyl)phenyl)-3-(3-((((3aR,4R,6R,6aR)-6-(6-amino-9H-purin-9-yl)-2,2-dimethyltetrahydrofuro[3,4-d][1,3]dioxol-4-yl)methyl)(ethyl)amino)cyclobutyl)propanamide (1.6 g, 2.64 mmol) in AcOH (20 mL) was stirred at 65° C. for 15 h. The solution was concentrated in vacuo and diluted with DCM (30 mL). The mixture was washed with saturated NaHCO$_3$ solution (20 mL×2) and brine (20 mL×1). The combined organic phase was dried over Na$_2$SO$_4$, filtered and concentrated to obtain the target 1.5 g (yield: 97%) as a white solid. $^1$H NMR (500 MHz, MeOD): δ$_H$ 8.28-8.26 (m, 1H), 8.22 (s, 1H), 7.48 (s, 1H), 7.40-7.38 (m, 1H), 7.30-7.27 (m, 1H), 6.20-6.18 (m, 1H), 5.52-5.49 (m, 1H), 5.02-4.98 (m, 1H), 4.34-4.31 (m, 1H), 2.95-2.92 (m, 1H), 2.79-2.68 (m, 4H), 2.56-2.50 (m, 2H), 2.09-1.81 (m, 5H), 1.71-1.63 (m, 1H), 1.58 (s, 3H), 1.38 (s, 3H), 1.36 (s, 9H), 1.35-1.28 (m, 1H), 0.89-0.85 (m, 3H) ppm; ESI-MS (m/z): 589.3 [M+1]+.

A mixture of 9-((3aR,4R,6R,6aR)-6-(((3-(2-(5-(tert-butyl)-1H-benzo[d]imidazol-2-yl)ethyl)cyclobutyl)(ethyl)

amino)methyl)-2,2-dimethyltetrahydrofuro[3,4-d][1,3]dioxol-4-yl)-9H-purin-6-amine (1.35 g, 2.30 mmol) in 3 M HCl/MeOH (20 mL) was stirred at 35° C. for 2 h and evaporated to dryness. The residue was dissolved in MeOH (15 mL) and saturated K$_2$CO$_3$ solution was added to adjust the solution to pH 8. Then, the mixture was stirred for 5 min and filtered. The filtrate was concentrated and the crude was separated by chiral HPLC and purified by Prep-HPLC to obtain the cis product (280 mg, total yield: 22%) and trans product (150 mg, total yield: 12%) as a white solids.

Compound 73: (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(ethyl)amino)methyl)tetrahydrofuran-3,4-diol

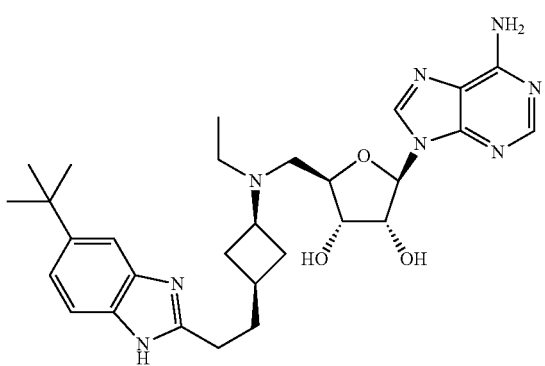 [SMILES: CCN(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

Cis-isomer: $^1$H NMR (500 MHz, MeOD): δ$_H$ 8.27 (s, 1H), 8.20 (s, 1H), 7.47 (s, 1H), 7.39-7.37 (m, 1H), 7.29-7.26 (m, 1H), 5.97 (d, J=4.5 Hz, 1H), 4.67 (t, J=5.0 Hz, 1H), 4.24 (t, J=5.5 Hz, 1H), 4.18-4.14 (m, 1H), 3.06-3.03 (m, 1H), 2.91-2.81 (m, 2H), 2.79-2.75 (m, 2H), 2.64-2.58 (m, 2H), 2.25-2.19 (m, 1H), 1.89-1.86 (m, 3H), 1.52-1.47 (m, 2H), 1.36 (s, 9H), 0.98 (t, J=7.0 Hz, 3H) ppm; ESI-MS (m/z): 549.3 [M+1]$^+$.

Compound 74: (2R,3R,4S,5R)-2-(6-amino-9H-purin-9-yl)-5-(((((1s,3R)-3-(2-(5-(tert-butyl)-1H-benzo[d]imidazol-2-yl)ethyl)cyclobutyl)(ethyl)amino)methyl)tetrahydrofuran-3,4-diol

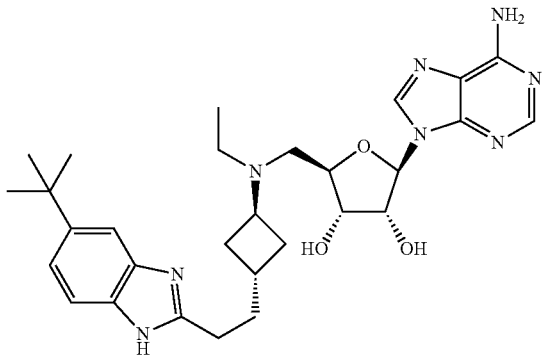 [SMILES: CCN(C[C@H]1O[C@@H](n2cnc3c(N)ncnc32)[C@H](O)[C@@H]1O)[C@H]1C[C@H](CCc2nc3cc(C(C)(C)C)ccc3[nH]2)C1]

Trans-isomer: $^1$H NMR (500 MHz, MeOD): δ$_H$ 8.28 (s, 1H), 8.20 (s, 1H), 7.48 (s, 1H), 7.39-7.37 (m, 1H), 7.29-7.26 (m, 1H), 5.97 (d, J=4.0 Hz, 1H), 4.67 (t, J=5.0 Hz, 1H), 4.24 (t, J=6.0 Hz, 1H), 4.18-4.14 (m, 1H), 3.42-3.35 (m, 1H), 2.91-2.78 (m, 4H), 2.64-2.58 (m, 2H), 2.10-2.07 (m, 3H), 1.99-1.96 (m, 2H), 1.85-1.79 (m, 2H), 1.35 (m, 9H), 0.98 (t, J=6.5 Hz, 3H) ppm; ESI-MS (m/z): 549.3 [M+1]$^+$.

Compound 76: (2R,3R,4S,5R)-2-(4-amino-7H-pyrrolo[2,3-d]pyrimidin-7-yl)-5-((isopropyl((1s,3R)-3-(2-(5-(trifluoromethoxy)-1H-benzo[d]imidazol-2-yl)ethyl)cyclobutyl)amino)methyl)tetrahydrofuran-3,4-diol

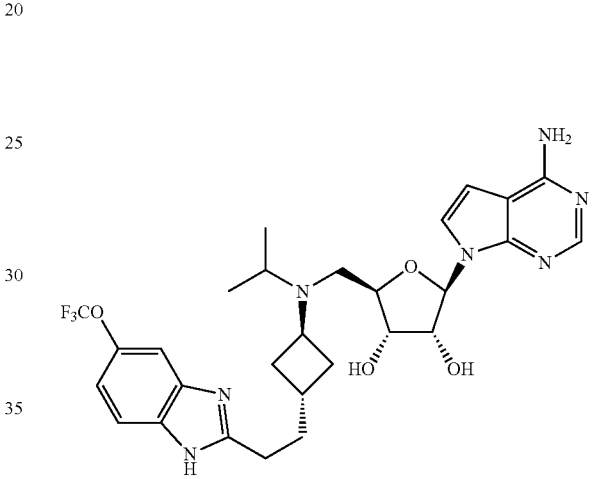

A solution of trans-N-(2,4-dimethoxybenzyl)-7-((3aR,4R,6R,6aR)-6-((isopropyl(3-(2-(5-(trifluoromethoxy)-1H-benzo[d]imidazol-2-yl)ethyl)cyclobutyl)amino)methyl)-2,2-dimethyltetrahydrofuro[3,4-d][1,3]dioxol-4-yl)-7H-pyrrolo[2,3-d]pyrimidin-4-amine (480 mg, 0.62 mmol) in 90% TFA (5 mL) was stirred at 30° C. for 2 h. The volatiles were removed under reduced pressure. To the residue was added MeOH (6 mL) and adjusted to pH=9~10 with NH$_3$.H$_2$O. The mixture was stirred at rt for 30 min and concentrated. The residue was purified by Prep-HPLC to afford the desired compound (182 mg, yield: 50%) as a white solid. $^1$H NMR (400 MHz, MeOD): δ$_H$ 8.09 (s, 1H), 7.52 (d, J=8.8 Hz, 1H), 7.39 (s, 1H), 7.27 (d, J=3.6 Hz, 1H), 7.12 (d, J=8.8 Hz, 1H), 6.64 (d, J=3.2 Hz, 1H), 6.11 (d, J=4.0 Hz, 1H), 4.44 (t, J=4.8 Hz, 1H), 4.12 (t, J=6.0 Hz, 1H), 4.06-4.01 (m, 1H), 3.62-3.53 (m, 1H), 3.10-3.00 (m, 1H), 2.92-2.65 (m, 4H), 2.25-2.15 (m, 2H), 2.10-1.98 (m, 3H), 1.85-1.76 (m, 2H), 1.03 (d, J=6.4 Hz, 3H), 0.98 (d, J=6.4 Hz, 3H) ppm; $^{19}$F NMR (400 MHz, MeOD): δ −59.80 ppm; ESI-MS (m/z): 590.3 [M+1]$^+$.

373
Compounds 77 and 78
374
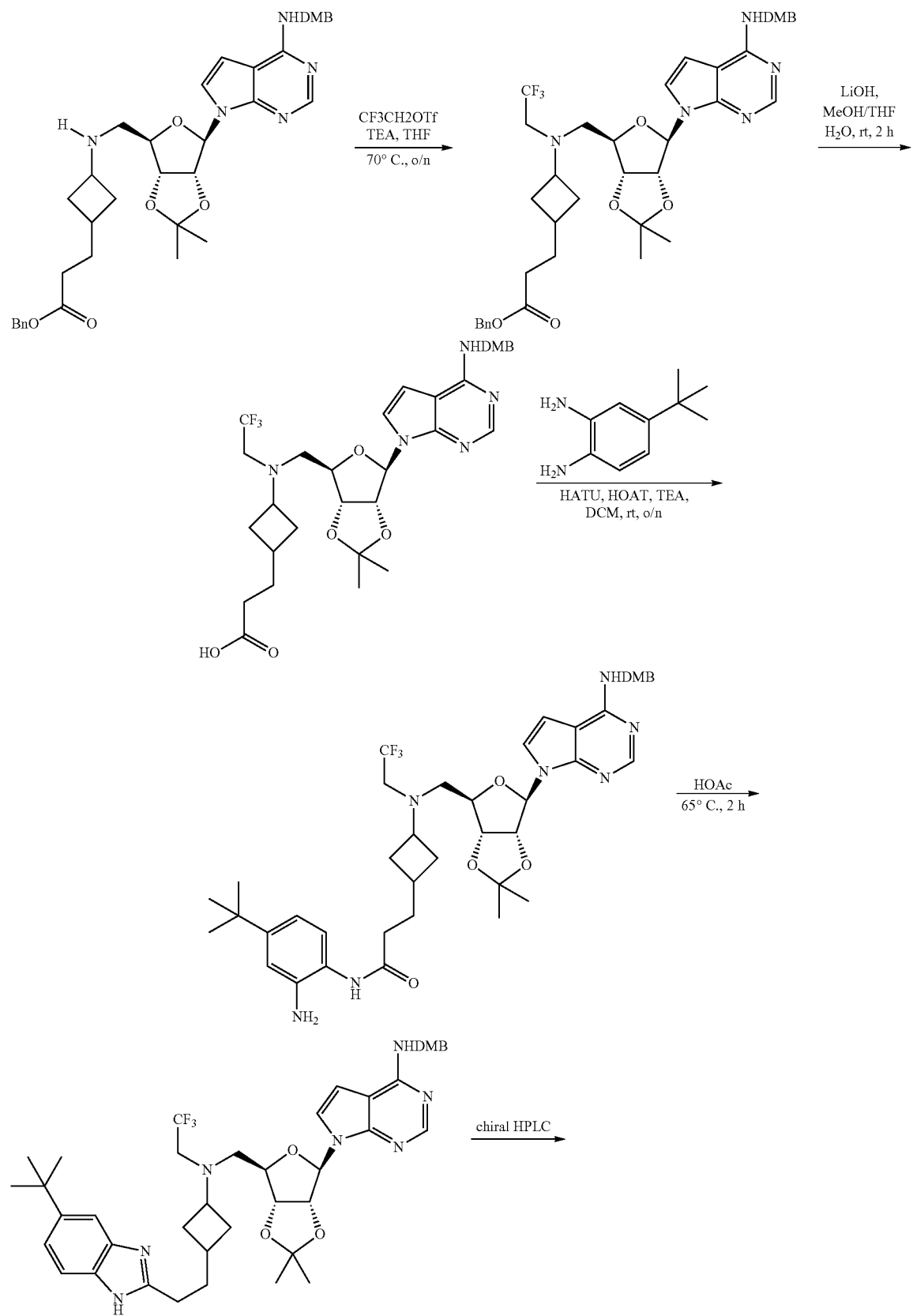

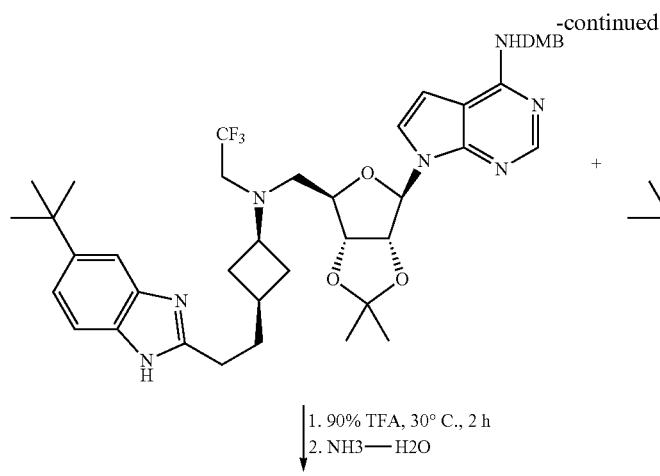
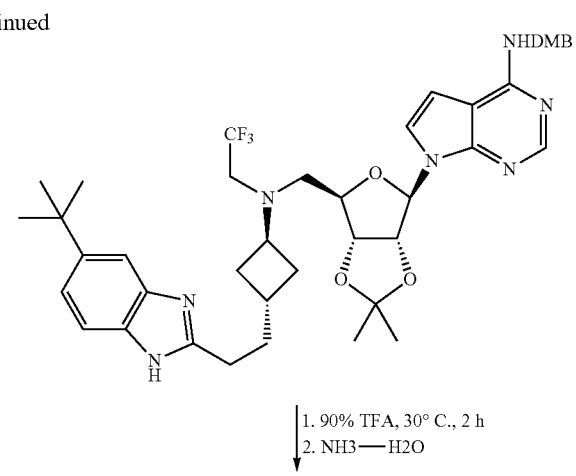

Compound 78: (2R,3R,4S,5R)-2-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol Compound 77: (2R,3R,4S,5R)-2-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol

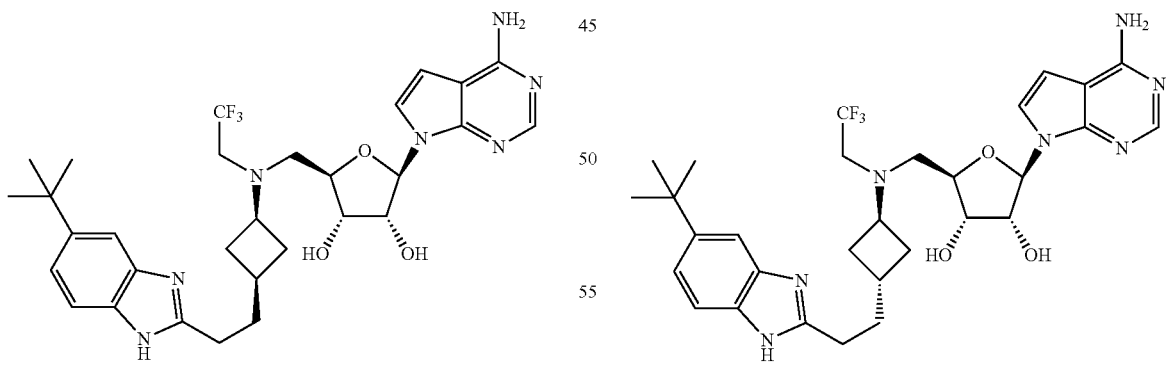

$^1$H NMR (500 MHz, MeOD): $\delta_H$ 8.09 (s, 1H), 7.48 (brs, 1H), 7.40-7.37 (m, 1H), 7.28 (dd, J=10.5 and 1.5 Hz, 1H), 7.21 (d, J=4.5 Hz, 1H), 6.65 (d, J=4.5 Hz, 1H), 6.11 (d, J=5.0 Hz, 1H), 4.44 (t, J=6.0 Hz, 1H), 4.13-4.08 (m, 2H), 3.30-3.15 (m, 3H), 3.09-3.03 (m, 1H), 2.97-2.90 (m, 1H), 2.78 (t, J=9.0 Hz, 2H), 2.28-2.20 (m, 2H), 1.92-1.78 (m, 3H), 1.55-1.45 (m, 2H), 1.37 (s, 9H) ppm; LC-MS (m/z): 602.3 [M+1]$^+$.

$^1$H NMR (500 MHz, MeOD): $\delta_H$ 8.09 (s, 1H), 7.48 (brs, 1H), 7.39 (d, J=10.5 Hz, 1H), 7.28 (dd, J=10.5 and 2.0 Hz, 1H), 7.21 (d, J=5.0 Hz, 1H), 6.64 (d, J=4.5 Hz, 1H), 6.12 (d, J=6.0 Hz, 1H), 4.45 (t, J=6.0 Hz, 1H), 4.14-4.09 (m, 2H), 3.68-3.60 (m, 1H), 3.30-3.15 (m, 2H), 3.11-3.04 (m, 1H), 2.97-2.90 (m, 1H), 2.80 (t, J=9.5 Hz, 2H), 2.12-2.03 (m, 3H), 2.00-1.90 (m, 2H), 1.90-1.80 (m, 2H), 1.36 (s, 9H) ppm; LC-MS (m/z): 602.3 [M+1]$^+$.

Benzyl 3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanoate To a mixture of benzyl 3-(3-((((3aR,4R,6R,6aR)-6-(6-amino-9H-purin-9-yl)-2,2-dimethyltetrahydrofuro[3,4-d][1,3]dioxol-4-yl)methyl)amino)cyclobutyl)propanoate (3.76 g, 7.2 mmol) and NaBH$_3$CN (5.9 g, 93.6 mmol) in MeOH (40 mL) was added AcOH to adjust to pH=6. Then, 37% HCHO (8.7 mL, 122.4 mmol) was added and the mixture was stirred at 30° C. for 1.5 h. Water (15 mL) was added and the mixture was concentrated in vacuo. Then, the mixture was extracted with DCM (30 mL×3). The combined organic phase was washed with brine, dried over Na$_2$SO$_4$, filtered and concentrated. The crude was purified by SGC (DCM: MeOH=100:1-20:1) to obtain the target (2.4 g, yield: 67%) as a white solid. $^1$H NMR (500 MHz, MeOD): $\delta_H$ 8.27 (s, 1H), 8.22 (d, J=2.5 Hz, 1H), 7.35-7.30 (m, 5H), 6.22 (s, 1H), 5.55-5.52 (m, 1H), 5.09 (s, 2H), 5.04-5.01 (m, 1H), 4.40-4.38 (m, 1H), 2.76-2.65 (m, 3H), 2.29-2.22 (m, 2H), 2.18 (s, 3H), 2.11-1.95 (m, 2H), 1.78-1.71 (m, 2H), 1.64-1.61 (m, 2H), 1.59 (s, 3H), 1.41-1.39 (m, 1H), 1.38 (s, 3H) ppm; ESI-MS (m/z): 537.3 [M+1]$^+$.

3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanoic acid To a solution of benzyl 3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanoate (2.4 g, 4.48 mmol) in MeOH (40 mL) was added 10% Pd/C (2.3 g) and the mixture was stirred under H$_2$ atmosphere at 50° C. for 15 h. The mixture was filtered and the filtrate was concentrated to obtain the target (1.9 g, yield: 95%) as a white solid. $^1$H NMR (500 MHz, MeOD): $\delta_H$ 8.27 (s, 1H), 8.24 (s, 1H), 6.27 (s, 1H), 5.54-5.52 (m, 1H), 5.09-5.07 (m, 1H), 4.50-4.47 (m, 1H), 3.17-3.07 (m, 2H), 3.02-2.90 (m, 1H), 2.39-2.35 (m, 3H), 2.31-2.05 (m, 4H), 1.91-1.70 (m, 2H), 1.64-1.51 (m, 5H), 1.39 (s, 3H), 1.23-1.15 (m, 1H) ppm; ESI-MS (m/z): 447.2 [M+1]$^+$.

N-(2-amino-4-(tert-butyl)phenyl)-3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanamide To a solution of 3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanoic acid (1.9 g, 4.26 mmol), HOAT (753 mg, 5.54 mmol), HATU (2.1 g, 5.54 mmol) and TEA (3 mL, 21.3 mmol) in DCM (40 mL) was added 4-tert-butylbenzene-1,2-diamine (769 mg, 4.69 mmol) and the mixture was stirred at rt for 2 h. Water (15 mL) was added and the mixture was extracted with DCM (30 mL×2). The combined organic phase was washed with H$_2$O (20 mL×2). The combined organic layers were dried over Na$_2$SO$_4$, filtered and concentrated. The crude was purified by SGC (DCM: MeOH=70:1-20:1) to obtain the target (1.8 g, yield: 72%) as a white solid. $^1$H NMR (500 MHz, MeOD): $\delta_H$ 8.28 (s, 1H), 8.23 (d, J=3.0 Hz, 1H), 7.10-6.92 (m, 2H), 6.81-6.76 (m, 1H), 6.21 (s, 1H), 5.56 (s, 1H), 5.49 (d, J=3.0 Hz, 1H), 5.01 (s, 1H), 4.36 (s, 1H), 2.69-2.49 (m, 3H), 2.31-2.27 (m, 2H), 2.13-2.00 (m, 5H), 1.88-1.81 (m, 2H), 1.75-1.65 (m, 2H), 1.60 (s, 3H), 1.41-1.35 (m, 4H), 1.28-1.25 (m, 9H) ppm; ESI-MS (m/z): 593.4 [M+1]$^+$.

9-((3aR,4R,6R,6aR)-6-((((1r,3S)-3-(2-(5-(tert-butyl)-1H-benzo[d]imidazol-2-yl)ethyl)cyclobutyl)(methyl)amino)methyl)-2,2-dimethyltetrahydrofuro[3,4-d][1,3]dioxol-4-yl)-9H-purin-6-amine A solution of N-(2-amino-4-(tert-butyl)phenyl)-3-(3-((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanamide (1.8 g, 3.04 mmol) in AcOH (20 mL) was stirred at 65° C. for 15 h. The solution was concentrated in vacuo and diluted with DCM (30 mL). The mixture was washed with saturated NaHCO$_3$ solution (20 mL×2) and brine (20 mL×1). The combined organic phase was dried over Na$_2$SO$_4$, filtered and concentrated to obtain 1.7 g (yield: 97%) of the desired product.

The product was separated by chiral HPLC to obtain 920 mg of cis-isomer and 420 mg of trans-isomer.

Cis-Isomer: $^1$H NMR (500 MHz, MeOD): $\delta_H$ 8.27 (s, 1H), 8.21 (s, 1H), 7.48 (s, 1H), 7.40-7.38 (m, 1H), 7.29-7.26 (m, 1H), 6.19 (d, J=2.5 Hz, 1H), 5.55-5.52 (m, 1H), 4.99-4.97 (m, 1H), 4.35-4.31 (m, 1H), 2.77-2.73 (m, 2H), 2.62-2.46 (m, 3H), 2.10-2.01 (m, 4H), 1.84-1.81 (m, 3H), 1.58 (s, 3H), 1.38-1.36 (m, 12H), 1.19-1.14 (m, 3H) ppm; ESI-MS (m/z): 575.3 [M+1]$^+$.

Trans-isomer: $^1$H NMR (500 MHz, MeOD): $\delta_H$ 8.28 (s, 1H), 8.21 (s, 1H), 7.48 (s, 1H), 7.40-7.38 (m, 1H), 7.30-7.27 (m, 1H), 6.19 (d, J=1.5 Hz, 1H), 5.55-5.52 (m, 1H), 5.01-4.98 (m, 1H), 4.36-4.34 (m, 1H), 2.96-2.92 (m, 2H), 2.77 (t, J=7.5 Hz, 2H), 2.58-2.50 (m, 2H), 2.09 (s, 3H), 2.04-1.90 (m, 4H), 1.82-1.79 (m, 1H), 1.70-1.66 (m, 2H), 1.59 (s, 3H), 1.38 (s, 3H), 1.36 (s, 9H) ppm; ESI-MS (m/z): 575.3 [M+1]$^+$.

Compound 87: (2R,3R,4S,5R)-2-(4-amino-7H-pyrrolo[2,3-d]pyrimidin-7-yl)-5-((isopropyl((1r,3S)-3-(2-(5-(trifluoromethoxy)-1H-benzo[d]imidazol-2-yl)ethyl)cyclobutyl)amino)methyl)tetrahydrofuran-3,4-diol

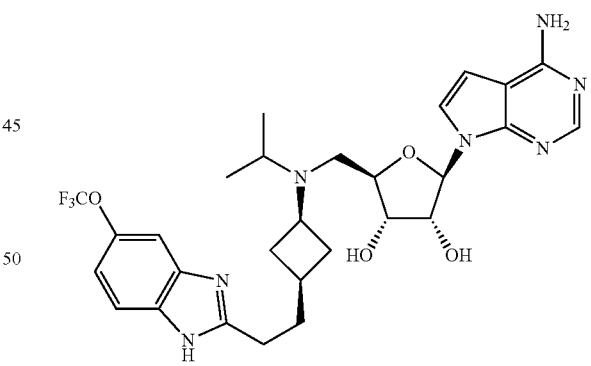

A solution of cis-N-(2,4-dimethoxybenzyl)-7-((3aR,4R,6R,6aR)-6-((isopropyl(3-(2-(5-(trifluoromethoxy)-1H-benzo[d]imidazol-2-yl)ethyl)cyclobutyl)amino)methyl)-2,2-dimethyltetrahydrofuro[3,4-d][1,3]dioxol-4-yl)-7H-pyrrolo[2,3-d]pyrimidin-4-amine (600 mg, 0.77 mmol) in 90% TFA (5 mL) was stirred at 30° C. for 2 h. The volatiles were removed under reduced pressure. To the residue was added MeOH (6 mL) and adjusted to pH=9-10 with NH$_3$·H$_2$O. The mixture was stirred at rt for 30 min and concentrated. The residue was purified by Prep-HPLC to afford the desired compound (260 mg, yield: 57%) as a white solid. $^1$H NMR (400 MHz, MeOD): $\delta_H$ 8.09 (s, 1H), 7.52 (d, J=8.8

Hz, 1H), 7.39 (s, 1H), 7.27 (d, J=4.0 Hz, 1H), 7.12 (dd, J=8.4 and 0.8 Hz, 1H), 6.64 (d, J=4.0 Hz, 1H), 6.12 (d, J=4.4 Hz, 1H), 4.43 (t, J=5.2 Hz, 1H), 4.11 (t, J=5.2 Hz, 1H), 4.05-4.01 (m, 1H), 3.20-3.10 (m, 1H), 3.08-3.00 (m, 1H), 2.88-2.65 (m, 4H), 2.25-2.15 (m, 2H), 1.92-1.82 (m, 3H), 1.65-1.55 (m, 2H), 1.02 (d, J=6.4 Hz, 3H), 0.98 (d, J=6.4 Hz, 3H) ppm; $^{19}$F NMR (400 MHz, MeOD): δ −59.80 ppm; ESI-MS (m/z): 590.3 [M+1]$^+$.

Compounds 90 and 75: benzyl 3-(3-((((3 aR,4R,6R, 6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)amino) cyclobutyl)propanoate To a solution of 7-43aR,4R,6R,6aR)-6-(aminomethyl)-2, 2-dimethyltetrahydrofuro[3,4-d][1,3]dioxol-4-yl)-N-(2,4-dimethoxybenzyl)-7H-pyrrolo[2,3-d]pyrimidin-4-amine (2.5 g, 5.49 mmol), benzyl 3-(3-oxocyclobutyl)propanoate (1.66 g, 7.14 mmol) and HOAc (329 mg, 5.49 mmol) in DCE (40 mL) was added NaB(OAc)$_3$H (2.33 g, 11 mmol) in one portion. Then the resulting reaction mixture was stirred at rt overnight. Saturated aqueous NaHCO$_3$ (40 mL) was added to quench the reaction, then was extracted with DCM (50 mL×3), dried over anhydrous Na$_2$SO$_4$ and concentrated. The crude was purified by SGC (DCM:MeOH=100:1 to 50:1) to afford the desired compound (2.3 g, yield: 64%) as a white solid. $^1$H NMR (500 MHz, MeOD): δ$_H$ 8.14 (d, J=2.5 Hz, 1H), 7.35-7.28 (m, 5H), 7.20 (d, J=4.0 Hz, 1H), 7.13 (d, J=8.0 Hz, 1H), 6.64 (d, J=3.0 Hz, 1H), 6.53 (d, J=2.0 Hz, 1H), 6.42 (d, J=8.5 Hz, 1H), 6.18 (d, J=2.5 Hz, 1H), 5.40-5.39 (m, 1H), 5.08-5.07 (m, 2H), 4.96-4.94 (m, 1H), 4.64 (s, 2H), 4.26-4.24 (m, 1H), 3.82 (s, 3H), 3.75 (s, 3H), 3.10-3.05 (m, 0.55H), 2.86-2.82 (m, 2H), 2.26-2.20 (m, 3H), 2.10-1.59 (m, 5H), 1.58 (s, 3H), 1.37 (s, 3H), 1.35-1.25 (m, 0.6H), 1.15-1.08 (m, 0.5H) ppm; LC-MS (m/z): 672.4 [M+1]$^+$.

benzyl 3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)cyclobutyl) propanoate Benzyl 3-(3-((((3 aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)amino) cyclobutyl)propanoate (2.3 g, 3.43 mmol) was mixed with K$_2$CO$_3$ (3.3 g, 24 mmol) and 2-iodopropane (5.8 g, 34.3 mmol) in MeCN (25 mL) in a sealed tube, then heated to 95° C. with stirring for 20 h. The reaction mixture was filtered and rinsed with MeCN (30 mL), the filtrate was evaporated in vacuo to afford the desired compound (2.1 g, yield: 88%) as a white solid, which was used for next step without further purification. $^1$H NMR (500 MHz, MeOD): δ$_H$ 8.13 (s, 1H), 7.35-7.29 (m, 5H), 7.18 (d, J=3.0 Hz, 1H), 7.13 (d, J=8.5 Hz, 1H), 6.64 (d, J=3.0 Hz, 1H), 6.53 (d, J=2.5 Hz, 1H), 6.41 (dd, J=8.5 and 2.5 Hz, 1H), 6.18 (d, J=2.5 Hz, 1H), 5.33-5.32 (m, 1H), 5.08-5.06 (m, 2H), 4.90-4.89 (m, 1H), 4.64 (s, 2H), 4.15-4.14 (m, 1H), 3.83 (s, 3H), 3.75 (s, 3H), 3.37-3.36 (m, 0.43H), 3.01-2.98 (m, 0.59H), 2.92-2.88 (m, 1H), 2.70-2.40 (m, 3H), 2.24-2.18 (m, 2H), 2.10-1.80 (m, 3H), 1.75-1.69 (m, 2H), 1.61-1.52 (m, 5H), 1.38 (s, 3H), 0.94 (d, J=6.5 Hz, 3H), 0.81-0.79 (m, 3H) ppm; LC-MS (m/z): 714.0 [M+1]$^+$.

3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)cyclobutyl)propanoic acid Benzyl 3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)cyclobutyl) propanoate (1.5 g, 2.1 mmol) was dissolved in MeOH (25 mL), Pd/C (10% on carbon, 70% water, 742 mg) was added and the resultant mixture was stirred at 35° C. under 1 atm H$_2$ overnight. The mixture was then filtered and rinsed with MeOH (15 mL×3), the filtrate was evaporated in vacuo to afford the desired compound (1.12 g, yield: 85%) as a white solid, which was used for next step without further purification. $^1$H NMR (500 MHz, MeOD): δ$_H$ 8.18 (s, 1H), 7.90 (s, 1H), 7.35-7.32 (m, 1H), 7.23-7.22 (m, 1H), 7.12 (d, J=8.5 Hz, 1H), 6.66 (brs, 1H), 6.54 (d, J=2.0 Hz, 1H), 6.43-6.41 (m, 1H), 6.24-6.23 (m, 1H), 5.47-5.46 (m, 1H), 5.13-5.12 (m, 2H), 4.64 (s, 2H), 4.41-4.37 (m, 1H), 3.84 (s, 3H), 3.75 (s, 3H), 3.64-3.58 (0.6H), 3.46-3.40 (m, 1.7H), 2.45-1.60 (m, 9H), 1.57 (s, 3H), 1.38 (s, 3H), 1.11 (d, J=7.0 Hz, 3H), 0.87 (d, J=6.5 Hz, 3H) ppm; LC-MS (m/z): 624.0 [M+1]$^+$.

N-(2-amino-4-(tert-butyl)phenyl)-3-(3-((((3aR,4R, 6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl) amino)cyclobutyl)propanamide To a solution of 3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)cyclobutyl)propanoic acid (1.1 g, 1.76 mmol), HATU (1 g, 2.64 mmol), HOAT (359 mg, 2.64 mmol) in DCM (30 mL) was added a solution of 4-tert-butylbenzene-1,2-diamine (433 mg, 2.64 mmol) and TEA (533 mg, 5.28 mmol) in DCM (10 mL) dropwise, then the resultant reaction mixture was stirred at rt overnight. After diluted with DCM (50 mL), the mixture was washed water (30 mL×3), dried and concentrated. The crude was purified by SGC (DCM:MeOH=100:1 to 40:1) to afford the desired compound (680 mg, yield: 50%) as a white solid. $^1$H NMR (500 MHz, MeOD): δ$_H$ 8.16 (s, 1H), 7.19 (d, J=3.5 Hz, 1H), 7.14-7.10 (m, 1.7H), 6.99-6.97 (m, 0.6H), 6.92 (s, 0.6H), 6.77 (dd, J=8.0, 2.0 Hz, 1H), 6.66-6.65 (m, 1H), 6.54-6.53 (m, 1H), 6.42 (d, J=8.0 Hz, 1H), 6.20 (d, J=2.0 Hz, 1H), 5.36-5.35 (m, 1H), 4.96-4.95 (m, 1H), 4.65 (s, 2H), 3.83 (s, 3H), 3.75 (s, 3H), 3.17-2.73 (m, 4H), 2.33-1.71 (m, 8H), 1.58 (s, 3H), 1.53-1.50 (m, 1H), 1.38 (s, 3H), 1.28 (s, 9H), 1.0 (d, J=5.5 Hz, 3H), 0.84 (d, J=5.0 Hz, 3H) ppm; LC-MS (m/z): 770.0 [M+1]$^+$.

7-((3aR,4R,6R,6aR)-6-(((3-(2-(5-(tert-butyl)-1H-benzo[d]imidazol-2-yl)ethyl)cyclobutyl)(isopropyl) amino)methyl)-2,2-dimethyltetrahydrofuro[3,4-d][1, 3]dioxol-4-yl)-N-(2,4-dimethoxybenzyl)-7H-pyrrolo [2,3-d]pyrimidin-4-amine N-(2-Amino-4-(tert-butyl)phenyl)-3-(3-((((3aR,4R,6R, 6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)cyclobutyl) propanamide (670 mg, 0.87 mmol) was dissolved in HOAc (8 mL) and then heated to 65° C. with stirring overnight. Solvent was removed in vacuo. The residue was dissolved in DCM (60 mL), then washed with NaHCO₃ (sat. 20 mL) and water (20 mL), the organic phase was dried and concentrated. The crude was purified by Prep-TLC (DCM:MeOH=10:1) to afford the desired compound (470 mg, yield: 73%) as a white solid, which was then separated by Chiral HPLC to afford cis (243 mg) and trans isomers (180 mg) as a white solids.

Cis-isomer: $^1$H NMR (500 MHz, MeOD): $\delta_H$ 8.15 (s, 1H), 7.47 (s, 1H), 7.38-7.37 (m, 1H), 7.27 (dd, J=8.5 and 1.5 Hz, 1H), 7.17 (d, J=4.0 Hz, 1H), 7.10 (d, J=8.5 Hz, 1H), 6.65 (d, J=3.0 Hz, 1H), 6.49 (d, J=2.5 Hz, 1H), 6.38 (dd, J=8.0 and 2.5 Hz, 1H), 6.18 (d, J=2.5 Hz, 1H), 5.33 (dd, J=6.5 and 2.5 Hz, 1H), 4.92-4.91 (m, 1H), 4.63 (s, 2H), 4.16-4.15 (m, 1H), 3.78 (s, 3H), 3.72 (s, 3H), 3.08-3.07 (m, 1H), 2.97-2.96 (m, 1H), 2.72-2.66 (m, 4H), 2.09-2.03 (m, 2H), 1.82-1.78 (m, 3H), 1.56 (s, 3H), 1.48-1.40 (m, 2H), 1.38 (s, 3H), 1.36 (s, 9H), 0.95 (d, J=7.0 Hz, 3H), 0.81 (d, J=6.5 Hz, 3H) ppm; LC-MS (m/z): 752.0 [M+1]⁺.

Trans-isomer: $^1$H NMR (500 MHz, MeOD): $\delta_H$ 8.14 (s, 1H), 7.47 (s, 1H), 7.38-7.37 (m, 1H), 7.27 (dd, J=8.5 and 1.5 Hz, 1H), 7.18 (d, J=3.5 Hz, 1H), 7.10 (d, J=8.0 Hz, 1H), 6.64 (d, J=4.0 Hz, 1H), 6.50 (d, J=2.0 Hz, 1H), 6.39-6.37 (m, 1H), 6.18 (d, J=2.0 Hz, 1H), 5.33 (dd, J=6.0 and 2.5 Hz, 1H), 4.90 (dd, J=6.5 and 3.5 Hz, 1H), 4.62 (s, 2H), 4.17-4.15 (m, 1H), 3.80 (s, 3H), 3.71 (s, 3H), 3.44-3.43 (m, 1H), 2.93-2.90 (m, 1H), 2.77-2.68 (m, 3H), 2.62-2.60 (m, 1H), 2.05-1.93 (m, 5H), 1.68-1.67 (m, 2H), 1.56 (s, 3H), 1.36 (s, 12H), 0.95 (d, J=7.0 Hz, 3H), 0.81 (d, J=6.5 Hz, 3H) ppm; LC-MS (m/z): 752.0 [M+1]⁺.

Compound 90: (2R,3R,4S,5R)-2-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol

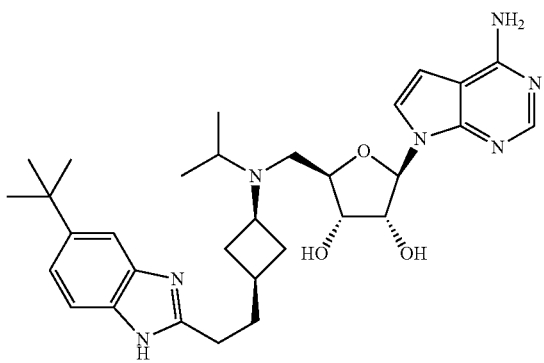 [SMILES: CC(C)N(C[C@H]1O[C@@H](n2ccc3c(N)ncnc32)[C@H](O)[C@@H]1O)[C@H]1C[C@@H](CCc2nc3cc(C(C)(C)C)ccc3[nH]2)C1]

To a mixture of TFA (2.7 mL) and water (0.3 mL) was added cis isomer-7-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (235 mg, 0.31 mmol). The solution was allowed to stand at 35° C. for 2 h and evaporated to dryness. The residue was co-evaporated with methanol twice. Then the residue was dissolved in MeOH (20 mL). The solution was neutralized by K₂CO₃ (124 mg, dissolved in 1 mL of H₂O) with stirring at rt for 1 h. Solvent was removed in vacuo, then the crude was purified by Prep-HPLC to afford the desired compound (90 mg, yield: 51%) as a white solid. $^1$H NMR (500 MHz, MeOD): $\delta_H$ 8.08 (s, 1H), 7.47 (s, 1H), 7.39-7.37 (m, 1H), 7.28 (d, J=2.5 Hz, 1H), 7.26 (d, J=4.5 Hz, 1H), 6.62 (d, J=4.5 Hz, 1H), 6.10 (d, J=5.5 Hz, 1H), 4.43-4.41 (m, 1H), 4.12-4.09 (m, 1H), 4.04-4.01 (m, 1H), 3.15-3.13 (m, 1H), 3.04-3.01 (m, 1H), 2.86-2.68 (m, 4H), 2.21-2.17 (m, 2H), 1.88-1.85 (m, 3H), 1.60-1.57 (m, 2H), 1.36 (s, 9H), 1.01 (d, J=8.0 Hz, 3H), 0.97 (d, J=8.0 Hz, 3H) ppm; LC-MS (m/z): 562.5 [M+1]⁺.

Compound 75: (2R,3R,4S,5R)-2-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(isopropyl)amino)methyl)tetrahydrofuran-3,4-diol

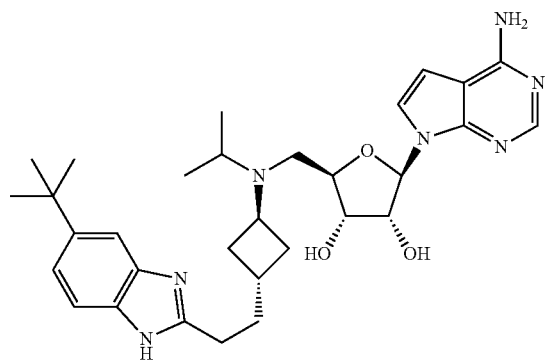 [SMILES: CC(C)N(C[C@H]1O[C@@H](n2ccc3c(N)ncnc32)[C@H](O)[C@@H]1O)[C@H]1C[C@H](CCc2nc3cc(C(C)(C)C)ccc3[nH]2)C1]

To a mixture of TFA (2.7 mL) and water (0.3 mL) was added trans isomer 7-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (175 mg, 0.23 mmol). The solution was allowed to stand at 35° C. for 2 h and evaporated to dryness. The residue was co-evaporated with methanol twice. Then the residue was dissolved in MeOH (20 mL). The solution was neutralized by K₂CO₃ (97 mg, dissolved in 1 mL of H₂O) with stirring at rt for 1 h. Solvent was removed in vacuo, then the crude was purified by Prep-HPLC to afford the desired compound (95 mg, yield: 71%) as a white solid. $^1$H NMR (500 MHz, MeOD): $\delta_H$ 8.09 (s, 1H), 7.49 (s, 1H), 7.41-7.39 (m, 1H), 7.30-7.27 (m, 2H), 6.64 (d, J=4.0 Hz, 1H), 6.12 (d, J=5.5 Hz, 1H), 4.45-4.42 (m, 1H), 4.13-4.11 (m, 1H), 4.05-4.03 (m, 1H), 3.58-3.54 (m, 1H), 3.06-3.02 (m, 1H), 2.89-2.80 (m, 3H), 2.74-2.70 (m, 1H), 2.20-2.17 (m, 2H), 2.03-1.99 (m, 3H), 1.84-1.81 (m, 3H), 1.38 (s, 9H), 1.03 (d, J=8.5 Hz, 3H), 0.98 (d, J=8.0 Hz, 3H) ppm; LC-MS (m/z): 562.5 [M+1]⁺.

Compound 96: (2R,3R,4S,5R)-2-(6-amino-9H-purin-9-yl)-5-((methyl((1r,3S)-3-(2-(5-(trifluoromethoxy)-1H-benzo[d]imidazol-2-yl)ethyl)cyclobutyl)amino)methyl)tetrahydrofuran-3,4-diol

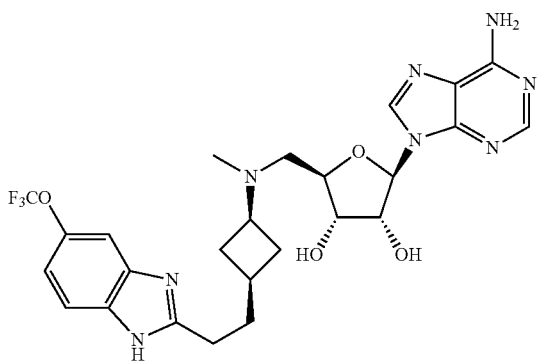 [SMILES: CN(C[C@H]1O[C@@H](n2cnc3c(N)ncnc32)[C@H](O)[C@@H]1O)[C@H]1C[C@@H](CCc2nc3cc(OC(F)(F)F)ccc3[nH]2)C1]

N-(2-amino-4-(trifluoromethoxy)phenyl)-3-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanamide To a solution of 3-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanoic acid (1.2 g, 2.91 mmol), HATU (2.17 g, 5.83 mmol) and HOAT (0.91 g, 5.83 mmol) in DCM (17 mL) were added 4-(trifluoromethoxy)benzene-1,2-diamine (1.1 g, 5.83 mmol) and TEA (2.05 mL, 14.56 mmol). The mixture was stirred at rt overnight. The mixture was diluted with DCM (50 mL) and washed with water (15 mL×3) and brine (30 mL). The organic phase was dried over Na$_2$SO$_4$, filtered and concentrated. The residue was purified by Combi-Flash (40 g silica gel, start EA:DCM:MeOH=10:10:0 to 10:10:8 by gradient, 40 mL/min, 50 min, 2.0 L total solvent volume) to afford the desired compound (1.0 g, yield: 60%) as a yellow solid. $^1$H NMR (500 MHz, MeOD): δ$_H$ 8.29 (s, 1H), 8.25-8.24 (m, 1H), 7.20-7.13 (m, 1H), 6.95-6.85 (m, 0.4H), 6.73 (brs, 0.8H), 6.54 (d, J=7.5 Hz, 0.8H), 6.22 (d, J=2.0 Hz, 1H), 5.60-5.55 (m, 1H), 5.03-5.00 (m, 1H), 4.40-4.35 (m, 1H), 3.40-3.35 (m, 0.3H), 3.00-2.92 (m, 0.7H), 2.70-2.47 (m, 3H), 2.36-2.28 (m, 2H), 2.20-1.80 (m, 6H), 1.76-1.66 (m, 2H), 1.60 (s, 3H), 1.40 (s, 3H), 1.26-1.16 (m, 1H) ppm; ESI-MS (m/z): 621.3 [M+1]$^+$.

9-((3aR,4R,6R,6aR)-2,2-dimethyl-6-((methyl(3-(2-(5-(trifluoromethoxy)-1H-benzo[d]imidazol-2-yl)ethyl)cyclobutyl)amino)methyl)tetrahydrofuro[3,4-d][1,3]dioxol-4-yl)-9H-purin-6-amine A solution of N-(2-amino-4-(trifluoromethoxy)phenyl)-3-(3-(((((3aR,4R,6R,6aR)-6-(6-amino-9H-purin-9-yl)-2,2-dimethyltetrahydrofuro[3,4-d][1,3]dioxol-4-yl)methyl)(methyl)amino)cyclobutyl)propanamide (1.0 g, 1.61 mmol) in HOAc (10 mL) was stirred at 65° C. overnight. The mixture was cooled to rt and concentrated. The residue was dissolved in DCM (50 mL), washed wth saturation NaHCO$_3$ solution (10 mL×2), water (20 mL) and brine (30 mL). The residue was separated by chiral HPLC to afford the cis isomer (460 mg, yield: 47%) and the trans isomer (220 mg, yield: 23%).

cis-isomer: $^1$H NMR (500 MHz, MeOD): δ$_H$ 8.28 (s, 1H), 8.23 (s, 1H), 7.53 (d, J=9.0 Hz, 1H), 7.40 (s, 1H), 7.13 (dd, J=8.5 and 1.0 Hz, 1H), 6.21 (d, J=2.0 Hz, 1H), 5.55 (dd, J=6.5, 2.5 Hz, 1H), 5.01 (q, J=3.5 Hz, 1H), 4.33-4.37 (m, 1H), 2.81-2.78 (m, 2H), 2.66-2.58 (m, 2H), 2.53-2.49 (m, 1H), 2.13-2.03 (m, 5H), 1.86-1.84 (m, 3H), 1.59 (s, 3H), 1.43-1.39 (m, 4H), 1.22-1.17 (m, 1H) ppm; LC-MS (m/z): 603.3 [M+1]$^+$.

trans-isomer: $^1$H NMR (500 MHz, MeOD): δ$_H$ 8.29 (s, 1H), 8.22 (s, 1H), 7.52 (brs, 1H), 7.40 (s, 1H), 7.13 (d, J=9.0 Hz, 1H), 6.21 (d, J=2.0 Hz, 1H), 5.55 (dd, J=6.5 and 2.0 Hz, 1H), 5.01 (q, J=3.0 Hz, 1H), 4.38-4.34 (m, 1H), 2.96-2.92 (m, 1H), 2.84-2.81 (m, 2H), 2.59-2.49 (m, 2H), 2.10 (s, 3H), 2.05-1.91 (m, 4H), 1.85-1.79 (m, 1H), 1.73-1.66 (m, 3H), 1.60 (s, 3H), 1.39 (s, 3H) ppm; LC-MS (m/z): 603.3 [M+1]$^+$.

Compound 96

A solution of cis-9-((3aR,4R,6R,6aR)-2,2-dimethyl-6-((methyl(3-(2-(5-(trifluoromethoxy)-1H-benzo[d]imidazol-2-yl)ethyl)cyclobutyl)amino)methyl)tetrahydrofuro[3,4-d][1,3]dioxol-4-yl)-9H-purin-6-amine (460 mg, 0.77 mmol) in 1 N HCl/MeOH (10 mL) was stirred at 30° C. for 4 h. The volatiles were removed under reduced pressure. To the residue was added MeOH (10 mL) and adjusted to pH=10~11 with NH$_3$.H$_2$O. The mixture was stirred at rt for 30 min and concentrated. The residue was purified by Prep-HPLC to afford the desired compound (215 mg, yield: 43%) as a white solid. $^1$H NMR (500 MHz, MeOD): δ$_H$ 8.28 (s, 1H), 8.21 (s, 1H), 7.52 (d, J=8.0 Hz, 1H), 7.40 (s, 1H), 7.12 (dd, J=8.5 and 0.5 Hz, 1H), 6.00 (d, J=4.0 Hz, 1H), 4.71 (t, J=4.5 Hz, 1H), 4.24 (t, J=5.5 Hz, 1H), 4.18 (t, J=6.0 Hz, 1H), 2.84-2.81 (m, 2H), 2.77-2.68 (m, 3H), 2.25-2.22 (m, 2H), 2.17 (s, 3H), 1.91-1.89 (m, 3H), 1.51-1.45 (m, 2H) ppm; LC-MS (m/z): 563.3 [M+1]$^+$.

Compound 97: (2R,3R,4S,5R)-2-(6-amino-9H-purin-9-yl)-5-((methyl((1s,3R)-3-(2-(5-(trifluoromethoxy)-1H-benzo[d]imidazol-2-yl)ethyl)cyclobutyl)amino)methyl)tetrahydrofuran-3,4-diol

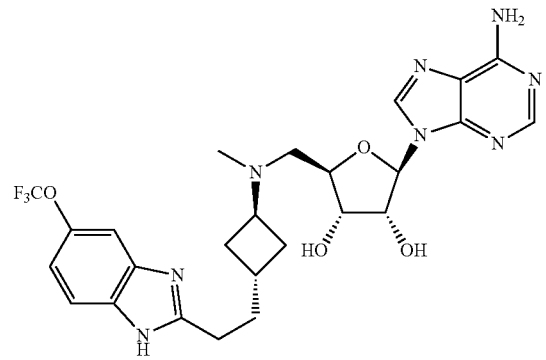 [SMILES: CN(C[C@H]1O[C@@H](n2cnc3c(N)ncnc32)[C@H](O)[C@@H]1O)[C@H]1C[C@H](CCc2nc3cc(OC(F)(F)F)ccc3[nH]2)C1]

A solution of trans-9-((3aR,4R,6R,6aR)-2,2-dimethyl-6-((methyl(3-(2-(5-(trifluoromethoxy)-1H-benzo[d]imidazol-2-yl)ethyl)cyclobutyl)amino)methyl)tetrahydrofuro[3,4-d][1,3]dioxol-4-yl)-9H-purin-6-amine (220 mg, 0.37 mmol) in 1 N HCl/MeOH (5 mL) was stirred at 30° C. for 4 h. The volatiles were removed under reduced pressure. To the residue was added MeOH (10 mL) and adjusted to pH=10~11 with NH$_3$.H$_2$O. The mixture was stirred at rt for 30 min and concentrated. The residue was purified by Prep-HPLC to afford the desired compound (80 mg, yield: 39%) as a white solid. $^1$H NMR (500 MHz, MeOD): $\delta_H$ 8.29 (s, 1H), 8.20 (s, 1H), 7.52 (d, J=8.5 Hz, 1H), 7.40 (s, 1H), 7.11 (d, J=8.5 Hz, 1H), 6.00 (d, J=4.0 Hz, 1H), 4.72 (t, J=4.5 Hz, 1H), 4.25 (t, J=5.5 Hz, 1H), 4.18-4.20 (m, 1H), 3.04-3.08 (m, 1H), 2.83-2.86 (m, 2H), 2.64-2.72 (m, 2H), 2.17 (s, 3H), 1.97-2.10 (m, 5H), 1.82-1.85 (m, 2H) ppm; LC-MS (m/z): 563.3 [M+1]$^+$.

Compound 106

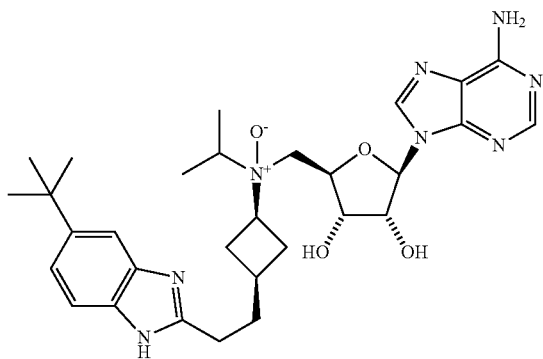 [SMILES: CC(C)[N+]([O-])(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

To a solution of (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol (300 mg, 0.53 mmol) in 30% aqueous dioxane (20 mL) was added MCPBA (91 mg, 0.53 mmol). The mixture was stirred at rt for 3 h and was then concentrated. The crude was purified by Prep-HPLC to obtain the desired product (160 mg, Yield: 45%) as a white solid. $^1$H NMR (500 MHz, MeOD): $\delta_H$ 8.24 (s, 1H), 8.22 (s, 1H), 7.49 (brs, 1H), 7.42-7.38 (m, 1H), 7.31-7.29 (m, 1H), 6.00-5.96 (m, 1H), 4.68-4.65 (m, 2H), 4.43-4.36 (m, 1H), 4.05-4.00 (m, 1H), 3.88-3.76 (m, 1H), 3.68-3.49 (m, 1H), 3.46-3.37 (m, 1H), 2.84-2.81 (m, 2H), 2.42-2.15 (m, 4H), 1.95-1.89 (m, 3H), 1.39 (s, 1H), 1.35-1.27 (m, 3H), 1.25-1.21 (m, 3H) ppm; ESI-MS (m/z): 579.4 [M+1]$^+$.

Compound 107

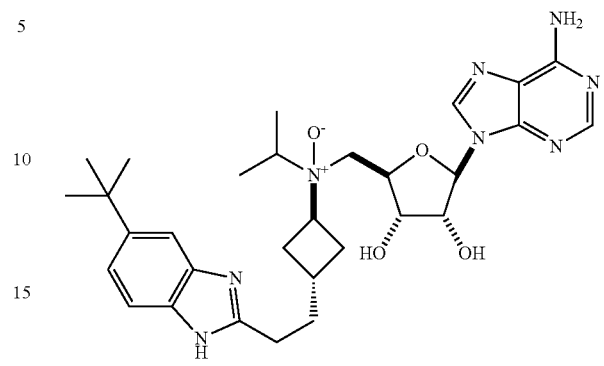

To a solution of (2R,3R,4S,5R)-2-(6-amino-9H-purin-9-yl)-5-(((((1s,3R)-3-(2-(5-(tert-butyl)-1H-benzo[d]imidazol-2-yl)ethyl)cyclobutyl)(isopropyl)amino)methyl)tetrahydrofuran-3,4-diol (300 mg, 0.53 mmol) in 30% aqueous dioxane (20 mL) was added MCPBA (91 mg, 0.53 mmol). The mixture was stirred at rt for 3 h and was then concentrated. The crude was purified by Prep-HPLC to obtain the desired product (80 mg, Yield: 26%) as a white solid. $^1$H NMR (500 MHz, MeOD): $\delta_H$ 8.25-8.22 (m, 2H), 7.49 (brs, 1H), 7.42-7.38 (m, 1H), 7.31-7.28 (m, 1H), 6.02-5.97 (m, 1H), 4.69-4.60 (m, 2H), 4.47-4.32 (m, 2H), 3.86-3.74 (m, 1H), 3.70-3.54 (m, 1H), 3.45-3.35 (m, 1H), 2.97-2.72 (m, 4H), 2.15-1.75 (m, 5H), 1.39 (s, 1H), 1.34-1.28 (m, 3H), 1.26-1.22 (m, 3H) ppm; ESI-MS (m/z): 579.7 [M+1]$^+$.

Example 9

Supercritical Fluid Chromatography

Compounds were purified by Supercritical Fluid Chromatography (SFC) using known techniques. Such as methods employed by Lotus Separations, LLC, Princeton, N.J. See, e.g. http://www.lotussep.com. See also, http://www.greenchemistrygroup.org/Program2009.html.

SFC separation conditions for certain examples are listed below. Other compounds described herein can be separated by similar methods.

| Cmpd | Lotus prep separation conditions | Lotus analytical separation conditions |
|---|---|---|
| 28 | AD-H (2 × 15 cm) 40% isopropanol(0.1% DEA))/CO2, 100 bar 70 mL/min, 220 nm. inj vol.: 1 mL, 2.5 mg/mL methanol | AD-H(15 × 0.46 cm) 40% isopropanol(DEA)/CO2, 100 bar 5 mL/min, 220 and 254 nm |
| 30 | AD-H (2 × 15 cm) 35% isopropanol(0.1% DEA))/CO2, 100 bar 70 mL/min, 220 nm. inj vol.: 0.5-2 mL, 13 mg/mL ethanol | AD-H(15 × 0.46 cm) 40% isopropanol(DEA)/CO2, 100 bar 3 mL/min, 220 and 254 nm |
| 31 | AD-H (2 × 15 cm) 40% isopropanol(0.1% DEA))/CO2, 100 bar 70 mL/min, 220 nm. inj vol.: 1 mL, 2.5 mg/mL methanol | AD-H(15 × 0.46 cm) 40% isopropanol(DEA)/CO2, 100 bar 5 mL/min, 220 and 254 nm |
| 34 | AD-H (2 × 15 cm) 35% isopropanol(0.1% DEA))/CO2, 100 bar 70 mL/min, 220 nm. inj vol.: 0.5-2 mL, 13 mg/mL ethanol | AD-H(15 × 0.46 cm) 40% isopropanol(DEA)/CO2, 100 bar 3 mL/min, 220 and 254 nm |
| 35 | IC (2 × 15 cm) 35% isopropanol(0.2% DEA))/CO2, 100 bar 60 mL/min, 220 nm. inj vol.: 0.75 mL, 4 mg/mL methanol | IC (15 × 0.46 cm) 40% isopropanol(DEA)/CO2, 100 bar 3 mL/min, 220 nm |
| 36 | AD-H (2 × 15 cm) 35% isopropanol(0.1% DEA))/CO2, 100 bar 70 mL/min, 220 nm. inj vol.: | AD-H(15 × 0.46 cm) 40% isopropanol(DEA)/CO2, 100 bar 3 mL/min, 220 nm |

-continued

| Cmpd | Lotus prep separation conditions | Lotus analytical separation conditions |
|---|---|---|
|  | 0.5 mL, 6.7 mg/mL 9:1 methanol:DCM | |
| 37 | IC (2 × 15 cm) 30% isopropanol(0.2% DEA)/CO2, 100 bar 65 mL/min, 220 nm. inj vol.: 1 mL, 2.6 mg/mL methanol | IC(15 × 0.46 cm) 30% isopropanol(DEA)/CO2, 100 bar 3 mL/min, 280 nm |
| 38 | Lux-3 (2 × 15 cm) 30% ethanol(0.2% DEA))/CO2, 100 bar 65 mL/min, 220 nm. inj vol.: 0.4 mL, 6.2 mg/mL methanol | Lux-3 (15 × 0.46 cm) 25% ethanol(NH4OH)/CO2, 100 bar 3 mL/min, 220 nm |
| 39 | AD-H (2 × 15 cm) 35% isopropanol(0.1% DEA))/CO2, 100 bar 70 mL/min, 220 nm. inj vol.: 0.5 mL, 6.7 mg/mL 9:1 methanol:DCM | AD-H(15 × 0.46 cm) 40% isopropanol(DEA)/CO2, 100 bar 3 mL/min, 220 nm |
| 40 | AD-H (2 × 15 cm) 40% isopropanol(0.1% DEA))/CO2, 100 bar 65 mL/min, 220 nm. inj vol.: 0.5-1 mL, 8.1 mg/mL methanol | AD-H (15 × 0.46 cm) 40% isopropanol(DEA)/CO2, 100 bar 3 mL/min, 280 nm |
| 41 | Premier (2 × 25 cm) 30% methanol(0.1% DEA))CO2, 100 bar 60 ml/min, 220 nm. Inj vol.: 1 mL, 20 mg/mL methanol | Premier (25 × 0.46 cm) 25% methanol(DEA)/CO2, 100 bar 3 mL/min, 220 nm |
| 46 | Lux-3 (2 × 15 cm) 25% ethanol(0.1% NH4OH))/CO2, 100 bar 65 mL/min, 220 nm. inj vol.: 0.3 mL, 2 mg/mL methanol | Lux-3 (15 × 0.46 cm) 30% ethanol(NH4OH)/CO2, 100 bar 3 mL/min, 220 nm |
| 47 | AD-H (2 × 15 cm) 30% ethanol(0.1% DEA))/CO2, 100 bar 65 mL/min, 220 nm. inj vol.: 0.5 mL, 12 mg/mL methanol | AD-H (15 × 0.46 cm) 40% ethanol(DEA)/CO2, 100 bar 3 mL/min, 280 nm |
| 48 | AD-H (2 × 15 cm) 40% 1:1 heptane:ethanol(0.1% DEA))/CO2, 100 bar 65 mL/min, 220 nm. inj vol.: 0.5 mL, 25 mg/mL ethanol | AD-H(15 × 0.46 cm) 50% 1:1 heptane:ethanol(DEA)/CO2, 100 bar 3 mL/min, 280 nm |
| 49 | Lux-3 (2 × 15 cm) 30% ethanol(0.2% DEA))/CO2, 100 bar 65 mL/min, 220 nm. inj vol.: 0.4 mL, 6.2 mg/mL methanol | Lux-3 (15 × 0.46 cm) 25% ethanol(NH4OH)/CO2, 100 bar 3 mL/min, 220 nm |
| 51 | Lux-3 (2 × 15 cm) 25% ethanol(0.1% NH4OH))/CO2, 100 bar 65 mL/min, 220 nm. inj vol.: 0.3 mL, 2 mg/mL methanol | Lux-3 (15 × 0.46 cm) 30% ethanol(NH4OH)/CO2, 100 bar 3 mL/min, 220 nm |
| 52 | AD-H (2 × 15 cm) 40% ethanol(0.2% DEA))/CO2, 100 bar 60 mL/min, 220 nm. inj vol.: 0.5 mL, 10 mg/mL methanol | AD-H (15 × 0.46 cm) 40% ethanol(DEA)/CO2, 100 bar 3 mL/min, 280 nm |
| 53 | AD-H (2 × 15 cm) 40% 1:1 heptane:ethanol(0.1% DEA))/CO2, 100 bar 65 mL/min, 220 nm. inj vol.: 0.5 mL, 25 mg/mL ethanol | AD-H(15 × 0.46 cm) 50% 1:1 heptane:ethanol(DEA)/CO2, 100 bar 3 mL/min, 280 nm |
| 54 | AD-H (2 × 15 cm) 40% isopropanol(0.1% DEA))/CO2, 100 bar 65 mL/min, 220 nm. inj vol.: 0.5-1 mL, 8.1 mg/mL methanol | AD-H (15 × 0.46 cm) 40% isopropanol(DEA)/CO2, 100 bar 3 mL/min, 280 nm |
| 55 | AD-H (2 × 15 cm) 30% ethanol(0.1% DEA))/CO2, 100 bar 65 mL/min, 220 nm. inj vol.: 0.5 mL, 12 mg/mL methanol | AD-H(15 × 0.46 cm) 40% ethanol(DEA)/CO2, 100 bar 3 mL/min, 280 nm |
| 57 | IC (2 × 15 cm) 30% isopropanol(0.2% DEA))/CO2, 100 bar 65 mL/min, 220 nm. inj vol.: 1 mL, 2.6 mg/mL methanol | IC(15 × 0.46 cm) 30% isopropanol(DEA)/CO2, 100 bar 3 mL/min, 280 nm |
| 58 | AD-H (2 × 15 cm) 40% ethanol(0.2% DEA))/CO2, 100 bar 60 mL/min, 220 nm. inj vol.: 0.5 mL, 10 mg/mL methanol | AD-H (15 × 0.46 cm) 40% ethanol(DEA)/CO2, 100 bar 3 mL/min, 280 nm |
| 60 | AD-H (2 × 15 cm) 30% ethanol(0.1% DEA))/CO2, 100 bar 60 mL/min, 220 nm, inj vol.: 0.5 mL, 10 mg/mL methanol | AD-H(15 × 0.46 cm) 25% ethanol(DEA)/CO2, 100 bar 3 mL/min, 280 nm |
| 61 | AD-H (2 × 15 cm) 30% ethanol(0.1% DEA))/CO2, 100 bar 60 mL/min, 220 nm. inj vol.: 0.5 mL, 10 mg/mL methanol | AD-H(15 × 0.46 cm) 25% ethanol(DEA)/CO2, 100 bar 3 mL/min, 280 nm |
| 63 | AD-H (2 × 15 cm) 38% methanol(0.1% DEA))/CO2, 100 | AD-H(15 × 0.46 cm) 40% methanol(DEA)/CO2, 100 bar 3 |

-continued

| Cmpd | Lotus prep separation conditions | Lotus analytical separation conditions |
|---|---|---|
| | bar 70 mL/min, 220 nm. inj vol.: 1.5 mL, 11.8 mg/mL methanol | mL/min, 220 and 254 nm |
| 65 | AD-H (2 × 15 cm) 38% methanol(0.1% DEA))/CO2, 100 bar 70 mL/min, 220 nm. inj vol.: 1.5 mL, 11.8 mg/mL methanol | AD-H(15 × 0.46 cm) 40% methanol(DEA)/CO2, 100 bar 3 mL/min, 220 and 254 nm |
| 69 | IC (2 × 15 cm) 35% isopropanol(0.2% DEA)/CO2, 100 bar 60 mL/min, 220 nm. inj vol.: 0.75 mL, 4 mg/mL methanol | IC (15 × 0.46 cm) 40% isopropanol(DEA)/CO2, 100 bar 3 mL/min, 220 nm |
| 114 | LUX2 (2 × 15 cm) 45% methanol(0.1% DEA))/CO2, 100 bar 60 mL/min, 220 nm. inj vol.: 0.75 mL, 5.6 mg/mL methanol:DCM | LUX2 (15 × 0.46 cm) 45% methanol(DEA)/CO2, 100 bar 5 mL/min, 220 and 254 nm |
| 114 | OZ-H (3 × 25 cm) 40% methanol(0.1% DEA)/CO2, 100 bar 65 mL/min, 220 nm. inj vol.: 1.75 mL, 10 mg/mL methanol | OZ-H(15 × 0.46 cm) 40% methanol(DEA)/CO2, 100 bar 3 mL/min, 220 and 254 nm |
| 115 | LUX2 (2 × 15 cm) 45% methanol(0.1% DEA))/CO2, 100 bar 60 mL/min, 220 nm. inj vol.: 0.75 mL, 5.6 mg/mL methanol:DCM | LUX2 (15 × 0.46 cm) 45% methanol(DEA)/CO2, 100 bar 5 mL/min, 220 and 254 nm |
| 115 | OZ-H (3 × 25 cm) 40% methanol(0.1% DEA))/CO2, 100 bar 65 mL/min, 220 nm. inj vol.: 1.75 mL, 10 mg/mL methanol | OZ-H(15 × 0.46 cm) 40% methanol(DEA)/CO2, 100 bar 3 mL/min, 220 and 254 nm |
| 116 | LUX-2 (2 × 15 cm) 35% methanol(0.1% DEA)/CO2, 100 bar 70 mL/min, 220 nm. inj vol.: 1 mL, 8.5 mg/mL methanol | LUX-2(15 × 0.46 cm) 45% methanol(DEA)/CO2, 100 bar 3 mL/min, 220 nm |
| 119 | LUX-2 (2 × 15 cm) 35% methanol(0.1% DEA)/CO2, 100 bar 70 mL/min, 220 nm. inj vol.: 1 mL, 8.5 mg/mL methanol | LUX-2(15 × 0.46 cm) 45% methanol(DEA)/CO2, 100 bar 3 mL/min, 220 nm |
| 121 | OZ-H (3 × 25 cm) 40% methanol(0.1% DEA)/CO2, 100 bar 65 mL/min, 220 nm. inj vol.: 2 mL, 14 mg/mL methanol | OZ-H(15 × 0.46 cm) 40% methanol(DEA)/CO2, 100 bar 3 mL/min, 220 and 254 nm |
| 122 | OZ-H (3 × 25 cm) 40% methanol(0.1% DEA)/CO2, 100 bar 65 mL/min, 220 nm. inj vol.: 2 mL, 14 mg/mL methanol | OZ-H(15 × 0.46 cm) 40% methanol(DEA)/CO2, 100 bar 3 mL/min, 220 and 254 nm |
| 123 | OZ-H (3 × 25 cm) 40% methanol(0.1% DEA)/CO2, 100 bar 65 mL/min, 220 nm. inj vol.: 0.8 mL, 19 mg/mL methanol | OZ-H(15 × 0.46 cm) 40% methanol(DEA)/CO2, 100 bar 3 mL/min, 220 and 254 nm |
| 124 | OZ-H (3 × 25 cm) 40% methanol(0.1% DEA)/CO2, 100 bar 65 mL/min, 220 nm. inj vol.: 0.8 mL, 19 mg/mL methanol | OZ-H(15 × 0.46 cm) 40% methanol(DEA)/CO2, 100 bar 3 mL/min, 220 and 254 nm |
| 128 | AD-H (2 × 15 cm) 30% isopropanol(0.1% DEA))/CO2, 100 bar 65 mL/min, 220 nm. inj vol.: 0.5-2 mL, 20 mg/mL methanol | AD-H(15 × 0.46 cm) 40% isopropanol(DEA)/CO2, 100 bar 3 mL/min, 220 and 254 nm |
| 129 | AD-H (2 × 15 cm) 30% isopropanol(0.1% DEA))/CO2, 100 bar 65 mL/min, 220 nm. inj vol.: 0.5-2 mL, 20 mg/mL methanol | AD-H(15 × 0.46 cm) 40% isopropanol(DEA)/CO2, 100 bar 3 mL/min, 220 and 254 nm |
| 131 | AD-H (2 × 15 cm) 30% methanol(0.1% DEA))/CO2, 100 bar 70 mL/min, 220 nm. inj vol.: 1 mL, 15 mg/mL methanol | AD-H(15 × 0.46 cm) 30% isopropanol(DEA)/CO2, 100 bar 3 mL/min, 220 and 254 nm |
| 132 | AD-H (2 × 15 cm) 30% methanol(0.1% DEA))/CO2, 100 bar 70 mL/min, 220 nm. inj vol.: 1 mL, 15 mg/mL methanol | AD-H(15 × 0.46 cm) 30% isopropanol(DEA)/CO2, 100 bar 3 mL/min, 220 and 254 nm |
| 133 | AD-H (2 × 15 cm) 30% methanol(0.1% DEA))/CO2, 100 bar 70 mL/min, 220 nm. inj vol.: 0.5 mL, 7.7 mg/mL methanol | AD-H(15 × 0.46 cm) 30% methanol(DEA)/CO2, 100 bar 4 mL/min, 220 and 254 nm |
| 134 | AD-H (2 × 15 cm) 30% methanol(0.1% DEA))/CO2, 100 bar 70 mL/min, 220 nm. inj vol.: 0.5 mL, 7.7 mg/mL methanol | AD-H(15 × 0.46 cm) 30% methanol(DEA)/CO2, 100 bar 4 mL/min, 220 and 254 nm |

-continued

| Cmpd | Lotus prep separation conditions | Lotus analytical separation conditions |
|---|---|---|
| 135 | AD-H (2 × 15 cm) 30% isopropanol(0.1% DEA))/CO2, 100 bar 70 mL/min, 220 nm. inj vol.: 0.75 mL, 15 mg/mL methanol | AD-H(15 × 0.46 cm) 30% isopropanol(DEA)/CO2, 100 bar 3 mL/min, 220 and 254 nm |
| 136 | AD-H (2 × 15 cm) 30% isopropanol(0.1% DEA))/CO2, 100 bar 70 mL/min, 220 nm. inj vol.: 0.75 mL, 15 mg/mL methanol | AD-H(15 × 0.46 cm) 30% isopropanol(DEA)/CO2, 100 bar 3 mL/min, 220 and 254 nm |
| 137 | IC (2 × 15 cm) 35% isopropanol(0.1% DEA))/CO2, 100 bar 60 mL/min, 220 nm. inj vol.: 0.5 mL, 10 mg/mL methanol | IC(15 × 0.46 cm) 35% isopropanol(DEA)/CO2, 100 bar 3 mL/min, 220 and 254nm |
| 138 | IC (2 × 15 cm) 35% isopropanol(0.1% DEA))/CO2, 100 bar 60 mL/min, 220 nm. inj vol.: 0.5 mL, 10 mg/mL methanol | IC(15 × 0.46 cm) 35% isopropanol(DEA)/CO2, 100 bar 3 mL/min, 220 and 254 nm |

Example 10

Bioassay Protocol and General Methods

Cell Culture.

Human hematological tumor cell lines THP-1, RS4;11, and MV4-11 were obtained from ATCC, MOLM-13 cells were obtained from DSMZ. All lines were grown in RPMI 1640 containing 10% FBS and maintained using the vendors recommended cell densities and environmental conditions. Media was supplemented with non essential amino acids and L-Glutamine. THP-1 cells were also supplemented with 0.05 mM β-Mercaptoethanol.

Methylation Analysis.

Cells were seeded at $5 \times 10^5$ cells/mL in a 12 well plate at a final volume of 2 mLs. Cells were dosed with compounds to the appropriate concentration from a 50 mM DMSO stock solution. Compound and media were refreshed every two days over the course of seven day incubation by counting cells using trypan blue exclusion (Vicell), pelleting at 200 g for 5 minutes and resuspending in fresh media containing compound at a final cell concentration of $5 \times 10^5$ cells/mL. Following compound incubation, histones were extracted from $1 \times 10^6$ cells using a commercial histone extraction kit (Active Motif). Purified histones were quantitated using the BCA protein assay (Pierce) with a BSA standard curve. 400 ng of isolated histones were fractionated by SDS-PAGE on a 4-20% gel and transferred to nitrocellulose membranes. Membranes were incubated with various primary and secondary antibodies and imaged on the Licor imaging system (Odyssey). The H3K79-Me2 rabbit polyclonal was purchased from Abcam. Other rabbit polyclonal antibodies including H3K4-Me3, H3K9-Me3, H3K27-Me2, and H3K27-Me3 were purchased from Cell Signaling Technologies (CST). A mouse monoclonal total H3 antibody was used as a loading control (CST). Fluorescently labeled secondary antibodies were purchased from Odyssey.

Cell Growth and Viability Analysis.

Cells were harvested from exponentially growing cell cultures and seeded at $3 \times 10^4$ cells per well. Samples were maintained in a 96 well black walled clear bottom plate (Corning). A final concentration of 50 uM compound in 0.2% DMSO was added to the appropriate wells on Day 0. Treatment of MV4-11 and MOLM-13 lasted 14 days, while THP-1 cells were treated for 18 days. Compound and media were replaced every two days during incubation by transferring samples to a V-bottom plate (Corning), spinning at 200 g for 5 minutes in a room temperature rotor, resuspending in fresh media containing compound and transferring back to the assay plate. Cells were counted periodically using the Guava Viacount assay and read on the EasyCyte Plus instrument (Millipore). Assay plates were split when necessary to within recommended cell densities. Final cell counts were adjusted to take cell splits into account and reported as total viable cells/well.

HOXA9 (qPCR).

Cells were treated with compound for 7 days similar to methylation assay. Cell were pelleted at 200 g in a room temperature rotor and total RNA isolated using the Qiagen RNeasy kit. RNA concentration and quality was determined by using the Nanovue (GE Healthcare). Total RNA was reverse transcribed using a high capacity cDNA reverse transcription kit (Applied Biosystems). A predesigned labeled primer set for HOXA9 was purchased from Applied Biosystems. qPCR reactions contained 50 ng cDNA, 1× labeled primer and 1× Taqman universal PCR master mix (Applied Biosystems). Samples were run on a 7900 HT Fast Real Time PCR machine (Applied Biosystems) with PCR conditions of 2 min 50° C., 10 min 95° C., 40 cycles at 15 sec 95° C. and 1 min 60° C. HOXA9 cycle numbers were normalized to the house keeping gene B2 microglobulin (B2M predesigned control from Applied Biosystems). Percent of DMSO control was calculated with the equation, percent control=$(2^{-\Delta\Delta CT})$ *100 where the ΔΔCT is the difference between normalized HOXA9 sample and control (ΔCT sample−ΔCT control=ΔΔCT).

Determination of $IC_{50}$.

Test compounds were serially diluted 3 fold in DMSO for 10 points and 1 μl was plated in a 384 well microtiter plate. Positive control (100% inhibition standard) was 2.5 uM final concentration of S-adenosyl-L-homocysteine and negative control (0% inhibition standard) contained 1 μl of DMSO. Compound was then incubated for 30 minutes with 40 μl per well of DOT1L(1-416) (0.25 nM final concentration in assay buffer: 20 mM TRIS, pH 8.0, 10 mM NaCl, 0.002% Tween20, 0.005% Bovine Skin Gelatin, 100 mM KCl, and 0.5 mM DTT). 10 μl per well of substrate mix (same assay buffer with 200 nM S-[methyl-$^3$H]-adenosyl-L methionine, 600 nM of unlabeled S-[methyl-$^3$H]-adenosyl-L methionine, and 20 nM oligonucleosome) was added to initiate the reaction. Reaction was incubated for 120 minutes at room temperature and quenched with 10 μl per well of 100 μM 5-methyl-adenosyl-L methionine. For detection, substrate from 50 μl of reaction was immobilized on a 384 well Streptavidin coated Flashplate (Perkin Elmer) (also coated with 0.2% polyethyleneimine) and read on a Top Count scintillation counter (Perkin Elmer). $IC_{50}$ values are presented in the table below. In this table, "A" indicates IC$_{50}$ values of <0.1 µM; "B" indicates IC$_{50}$ values of >0.1 µM and <1 µM; "C" indicates IC$_{50}$ values of >1 µM and <10 µM; and "D" indicates IC$_{50}$ values of >10 µM and <50 µM

| Compound# | DOT1L IC$_{50}$ |
|---|---|
| 2 | A |
| 3 | A |
| 4 | A |
| 5 | A |
| 6 | A |
| 7 | A |
| 8 | D |
| 9 | A |
| 10 | A |
| 11 | A |
| 12 | A |
| 13 | A |
| 14 | A |
| 15 | C |
| 16 | C |
| 17 | B |
| 18 | B |
| 19 | A |
| 20 | A |
| 21 | C |
| 22 | B |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | B |
| 62 | B |
| 63 | B |
| 64 | B |
| 65 | B |
| 66 | B |
| 67 | A |
| 68 | A |
| 69 | A |
| 70 | A |
| 71 | A |
| 72 | A |
| 73 | A |

-continued

| Compound# | DOT1L IC$_{50}$ |
|---|---|
| 74 | A |
| 75 | A |
| 76 | A |
| 77 | B |
| 78 | C |
| 79 | A |
| 80 | B |
| 81 | B |
| 82 | B |
| 83 | B |
| 84 | C |
| 85 | D |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | B |
| 102 | B |
| 103 | C |
| 104 | C |
| 105 | C |
| 106 | A |
| 107 | A |
| 110 | A |
| 111 | A |
| 112 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |

Example 11

Tumor Anti-Proliferation Assays

In Vitro Anti-Proliferative Assay.

The potency and selectivity of the anti-proliferative activity of the compounds of the present invention were assessed using a panel of MLL-rearranged and non-MLL-rearranged human leukemia cell lines. The cell lines used in the study are listed in FIG. 1A. The MLL-rearranged panel included cell lines derived from ALL, AML and biphenotypic leukemias harboring MLL-AF4, MLL-AF9 or MLL-ENL fusions. These cell lines recruit DOT1L. The panel also included five cell lines that do not possess an MLL-rearrangement, and one cell line that bears a partial tandem duplication of the MLL gene (MLL-PTD).

Exponentially growing cells were plated, in triplicate, in 96-well plates at a density of $3 \times 10^4$ cells/well in a final volume of 150 µl. Cells were incubated in the presence of increasing concentrations of Compound 2. Anti-proliferative activity was determined by cell viability measurements every 3-4 days for up to 14 days. On days of cell counts, growth media and Compound 2 were replaced and cells split back to a density of $5 \times 10^4$ cells/well.

The half maximal inhibitory concentration ($IC_{50}$) results in FIG. 1 show that Compound 2 demonstrates potent nanomolar anti-proliferative activity against three of four MLL-rearranged cell lines tested (MV4;11 (MLL-AF4), MOLM-13 (MLL-AF9), and KOPN-8 (MLL-ENL). EOL-1 cells which express an MLL-PTD were also highly sensitive to Compound 2 ($IC_{50}=11$ nM). RS4;11 cells and two non MLL-rearranged cells (Reh and Kasumi-1) were 1-3 log orders less sensitive, and two non-MLL-rearranged cells (Jurkat and HL-60) showed no activity. Overall, the results indicate that Compound 2 potently and selectively inhibits the proliferation of MLL-rearranged leukemia cell lines and a subset of non-MLL-rearranged leukemia cell lines.

In Vivo Anti-Proliferative Assay.

The in vivo anti-tumor activity of the compounds of the present invention were assessed in a mouse xenograft model of MLL-rearranged leukemia.

Four groups of 20 (Groups 1, 3, 4 and 5), and one group of 8 (Group 2) female nude mice (average weight of 0.023 kg) bearing MV4-11 xenograft tumors of sizes ranging from 80-120 mm³ were implanted subcutaneously with minipumps (Alzet Model 2001). Group 1 received vehicle only from the pump. Group 2 received vehicle only from the pump plus ip injections tid (8 hours apart) of vehicle. Group 3 received 112 mg/kg/day from the pump plus ip injections tid (8 hours apart) of 20 mg/kg of Compound 2 for a total daily dose of 172 mg/kg/day. Group 4 and 5 received 112 and 56 mg/kg/day of Compound 2 from the pumps, respectively. Pumps were designed to last for 7 days and were exchanged twice to give total infusion duration of 21 days exposure.

A single blood sample was taken from all animals in Groups 4 and 5 on days 7, 14, and 21 and assayed for plasma levels of Compound 2. Blood samples were taken from Group 3 on days 7 and 14 at the following time points (3 animals per time point): 5 minutes pre-ip dose, and 15 min, 30 min, 1, 2, and 4 hours post ip dose. On day 21 three hours after the last ip injection, a single blood sample was taken from Group 3. Tumor size was measured every 4 days. After 21 days the study was terminated, and mean TGI calculated.

Figure 2:
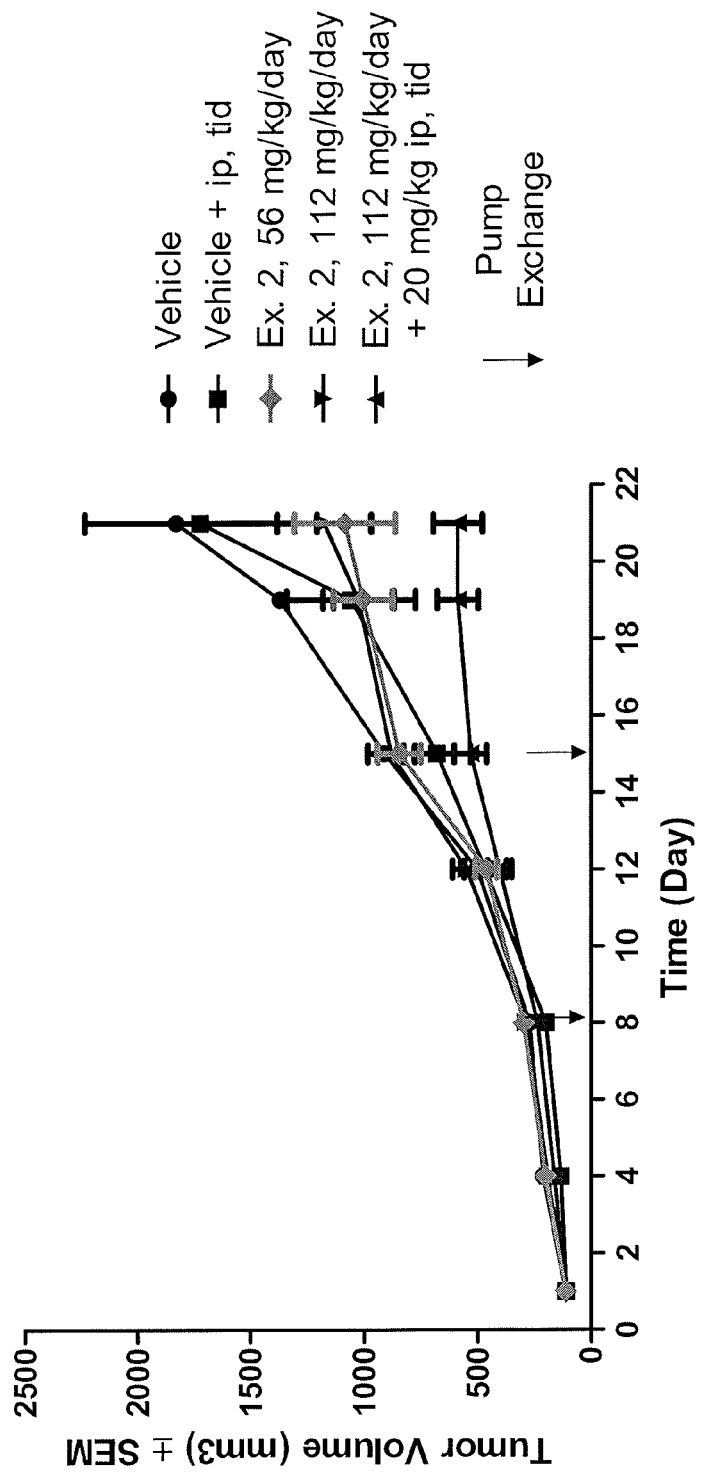
FIG. 2 is a plot showing the tumor growth over 21 days of dosing.

FIG. 2 shows the tumor growth over the 21 days of dosing. There was no difference in tumor size between the two vehicle control groups. The high dose minipump group supplemented with ip dosing showed a statistically significant TGI of >70% compared to the controls. The 56 and 112 mg/kg/day groups showed non-statistically significant TGI values of 43 and 38%, respectively, compared to controls. Compound 2 is referred to as Ex. 2 in FIG. 2.

Figure 3:
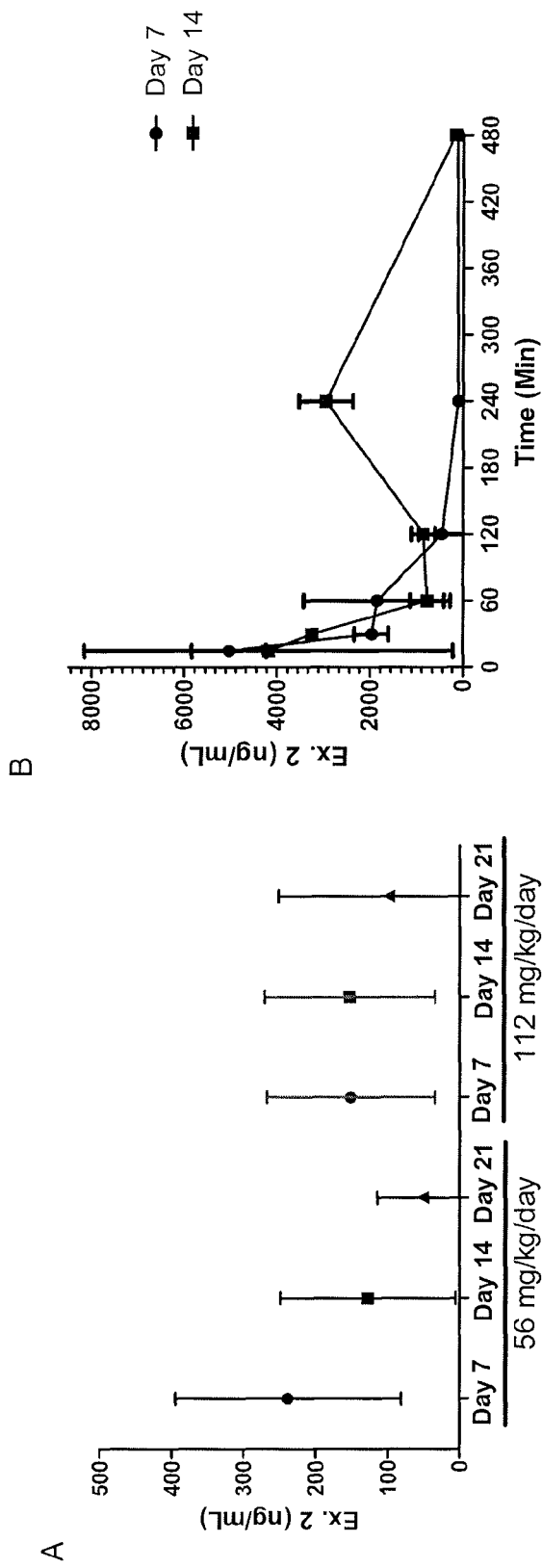
FIG. 3A is a plot showing the estimated steady state plasma concentrations of Compound 2 in Groups 4 and 5 as determined by the averaged blood samples taken on days 7, 14 and 21.
FIG. 3B is a plot showing the Compound 2 plasma concentrations plotted against time after ip injection.

FIG. 3A shows the estimated steady state plasma concentrations of Compound 2 in Groups 4 and 5 as determined by the averaged blood samples taken on days 7, 14, and 21. The data suggest that the average steady state Compound 2 plasma levels ranged from 99 to 152 ng/ml for Group 4, and 52 to 238 ng/ml for Group 5. The average plasma level from the last sampling on day 21 was 99 ng/ml for Group 4 and 52 ng/ml for Group 5.

FIG. 3B shows the Compound 2 plasma concentrations plotted against time after ip injection. The ip injections produced a significant increase in plasma exposure to Compound 2 in turns of both the $C_{max}$(4200 to 5000 ng/ml) after each of the tid injections and the daily AUCs over those produced by the steady state plasma level resulting from the continuous infusion. Overall, the results indicate that Compound 2 demonstrated significant anti-tumor activity in a mouse xenograft model of MLL-rearranged leukemia.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula (IV) or its N-oxide or a pharmaceutically acceptable salt thereof:

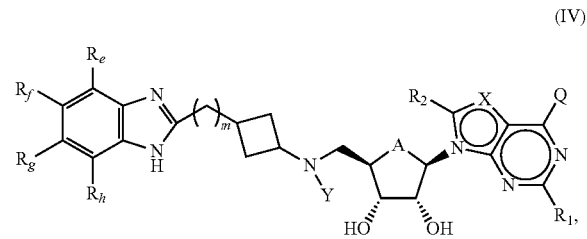

(IV)

wherein
A is O or $CH_2$;
Q is H, $NH_2$, $NHR_b$, $NR_bR_c$, OH, $R_b$, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

Y is H, $R_d$, $SO_2R_d$, or $COR_d$, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and each of which $C_3$-$C_8$ cycloalkyl, $C_6$-$C_{10}$ aryl, 4 to 6-membered heterocycloalkyl, and 5 to 6-membered heteroaryl substituents on $R_d$ is further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$ and $R_2$ independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O-$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, and m is 0, 1, or 2.

2. The compound of claim 1, wherein A is O.

3. The compound of claim 1, wherein A is O and m is 2.

4. The compound of claim 1, wherein X is N.

5. The compound of claim 1, wherein Q is $NH_2$ or $NHR_b$, in which $R_b$ is -$M_1$-$T_1$, $M_1$ being a bond or $C_1$-$C_6$ alkyl linker and $T_1$ being $C_3$-$C_8$ cycloalkyl.

6. The compound of claim 1, wherein $R_1$ and $R_2$, are each H.

7. The compound of claim 1, wherein Y is $R_d$.

8. The compound of claim 7, wherein $R_d$ is $C_1$-$C_6$ alkyl optionally substituted with $C_3$-$C_8$ cycloalkyl or halo.

9. The compound of claim 7, wherein $R_d$ is $C_3$-$C_8$ cycloalkyl optionally substituted with $C_1$-$C_6$ alkyl or halo.

10. The compound of claim 1, wherein at least one of $R_e$, $R_f$, $R_g$, and $R_h$ is halo, $C_1$-$C_6$ alkoxyl optionally substituted with one or more halo; $C_1$-$C_6$ alkylsulfonyl optionally substituted with one or more halo; $C_1$-$C_6$ alkyl optionally substituted with one or more substituents selected from CN, halo, $C_3$-$C_8$ cycloalkyl, hydroxy, and $C_1$-$C_6$ alkoxyl; $C_3$-$C_8$ cycloalkyl optionally substituted with one or more $C_1$-$C_6$ alkyl or CN; or 4 to 8-membered heterocycloalkyl optionally substituted with one or more substituents selected from CN, halo, hydroxy, $C_1$-$C_6$ alkyl and $C_1$-$C_6$ alkoxyl.

11. The compound of claim 10, wherein at least one of $R_e$, $R_f$, $R_g$, and $R_h$ is selected from the group consisting of F; Cl; Br; $CF_3$; $OCF_3$; $SO_2CF_3$; oxetanyl optionally substituted with one or more substituents selected from CN, halo, hydroxy, $C_1$-$C_6$ alkyl and $C_1$-$C_6$ alkoxyl; $C_3$-$C_8$ cycloalkyl optionally substituted with one or more substituents selected from $C_1$-$C_4$ alkyl; and $C_1$-$C_4$ alkyl optionally substituted with one or more substituents selected from halo, $C_3$-$C_8$ cycloalkyl, hydroxy and $C_1$-$C_6$ alkoxyl.

12. A compound selected from

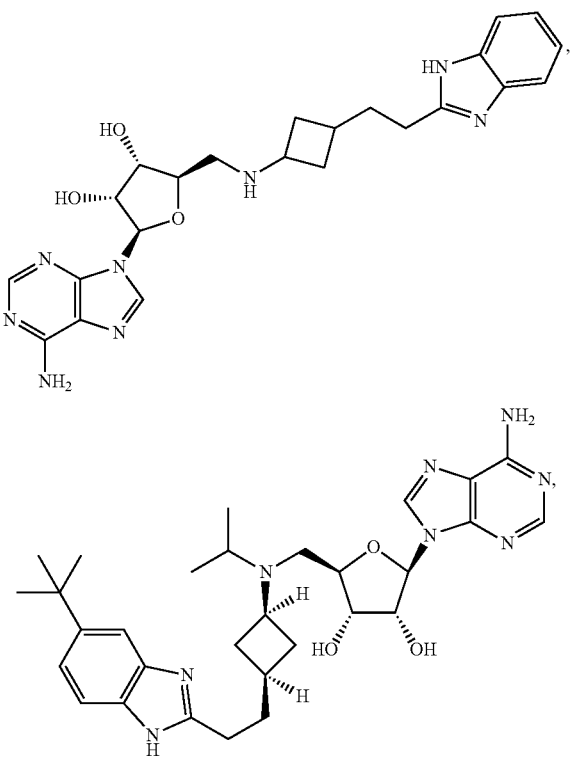

399
-continued
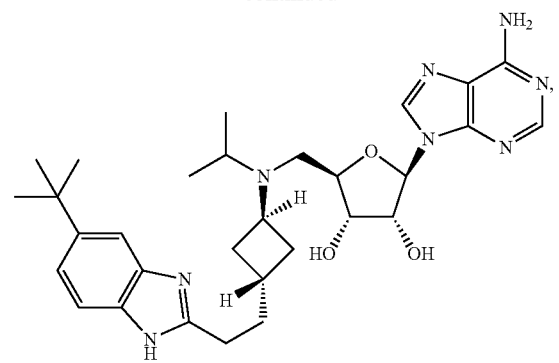
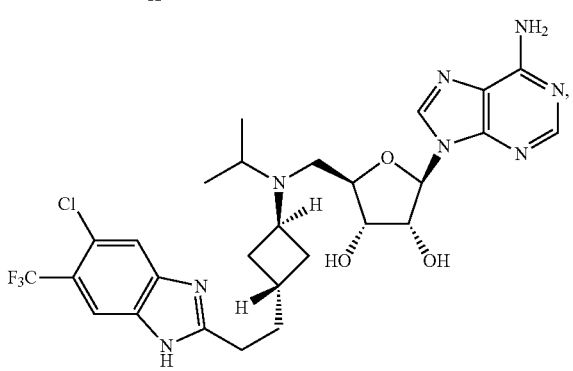
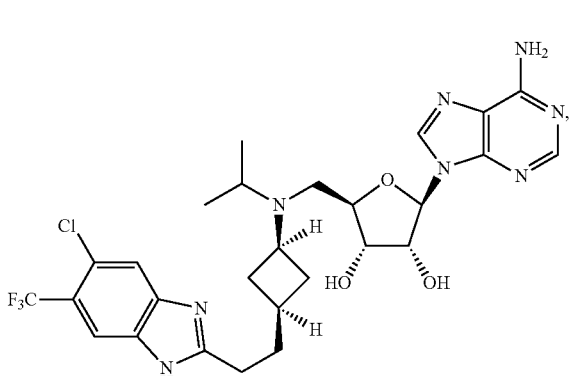
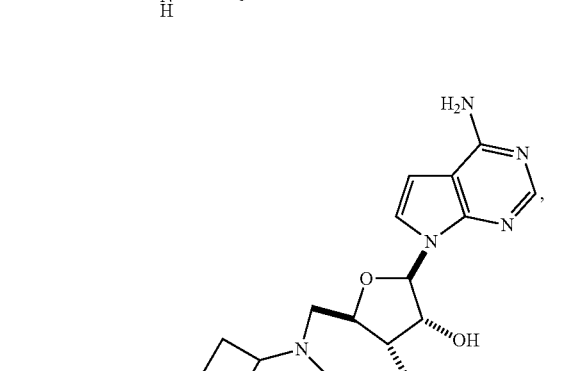
400
-continued
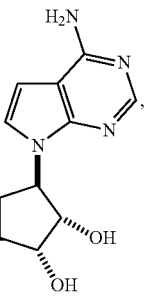

401
-continued
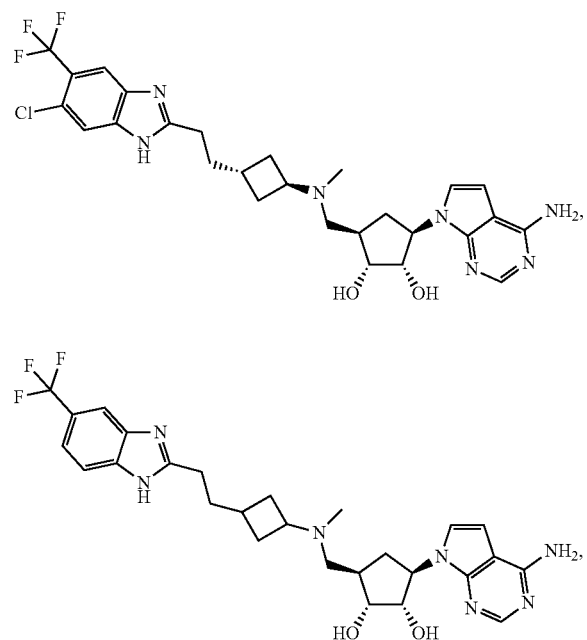
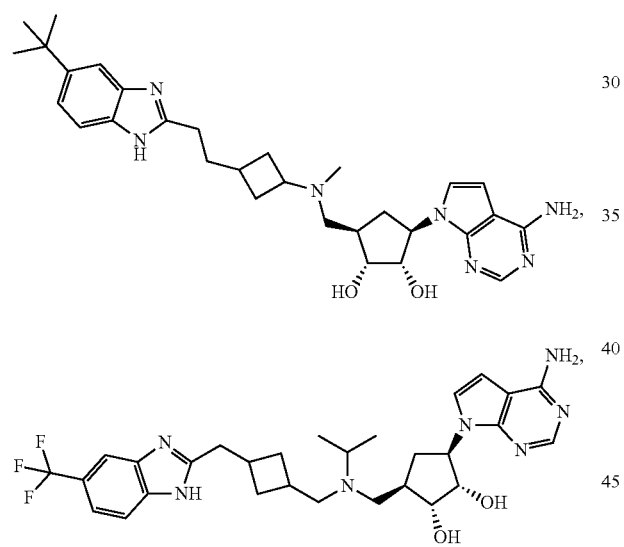
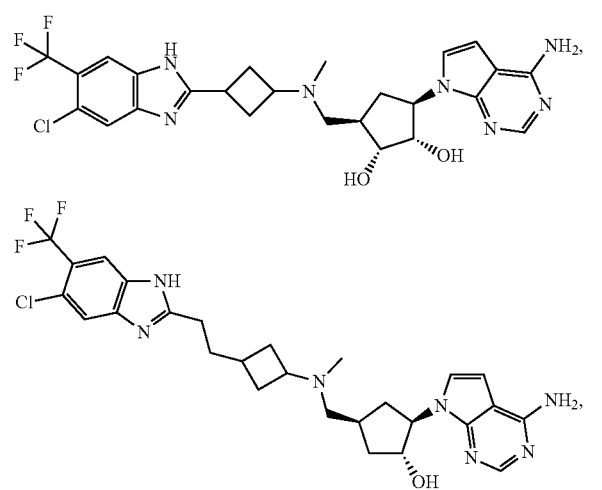
402
-continued
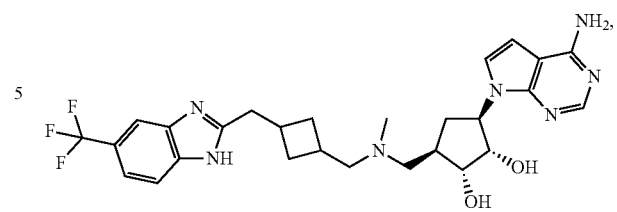
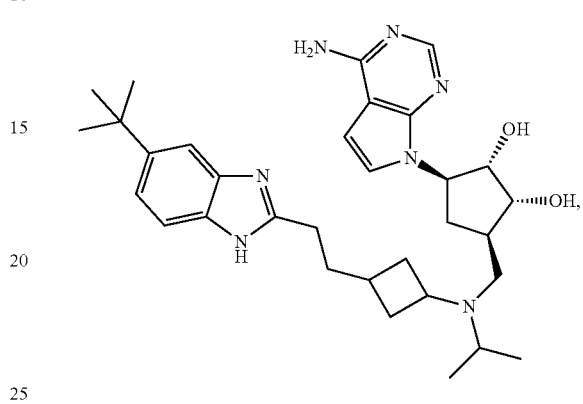
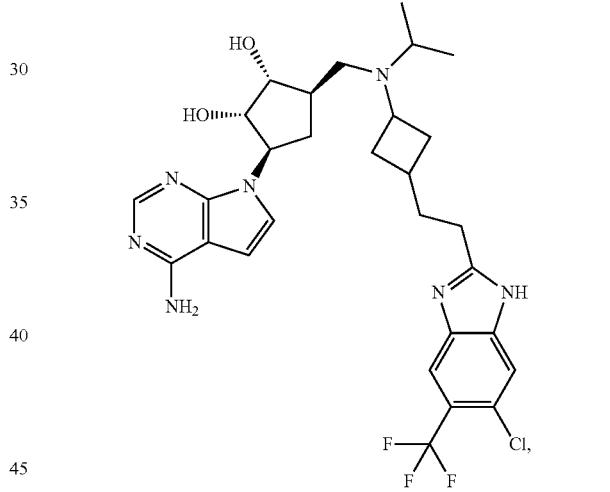
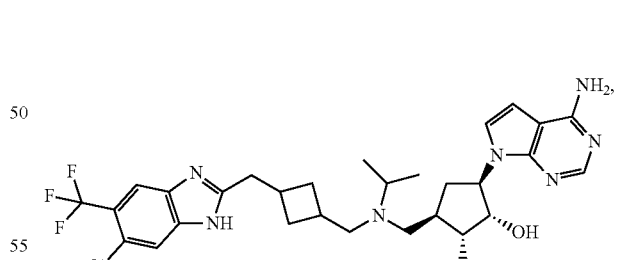
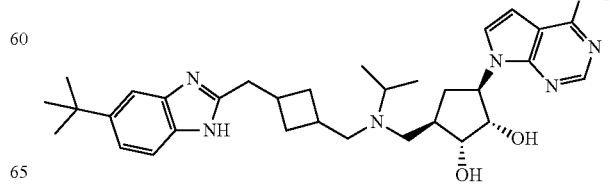

403
-continued
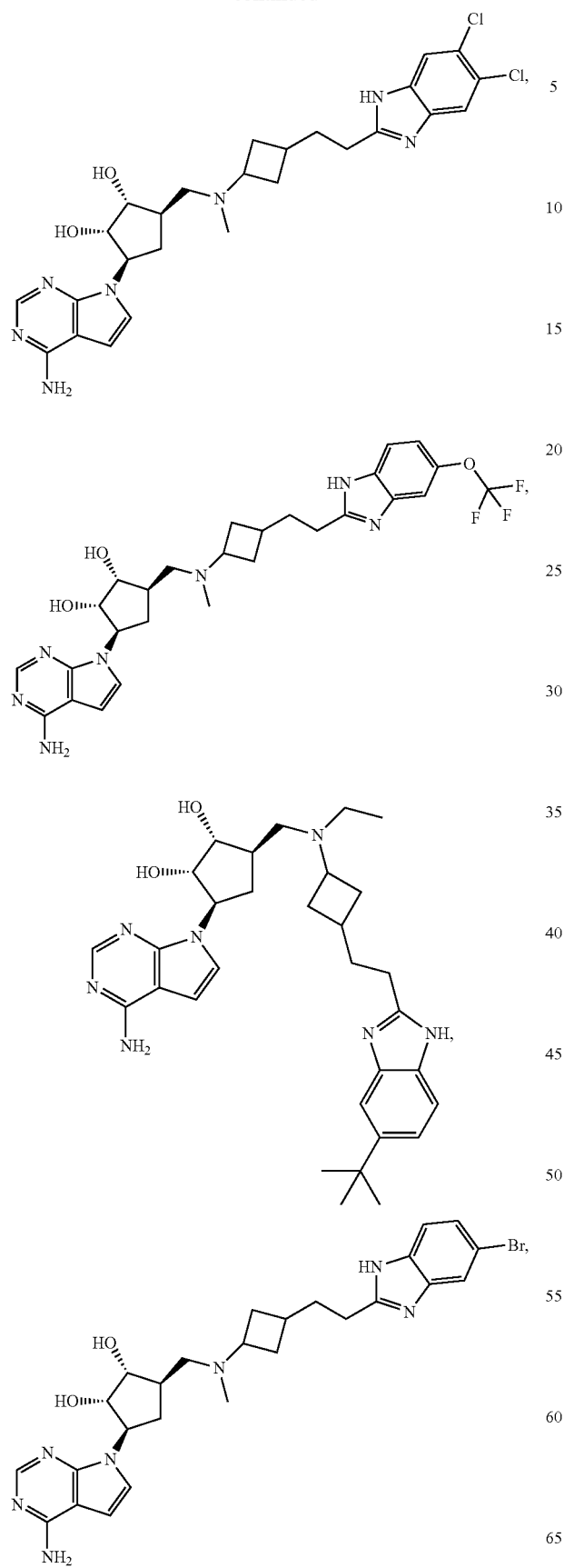
404
-continued
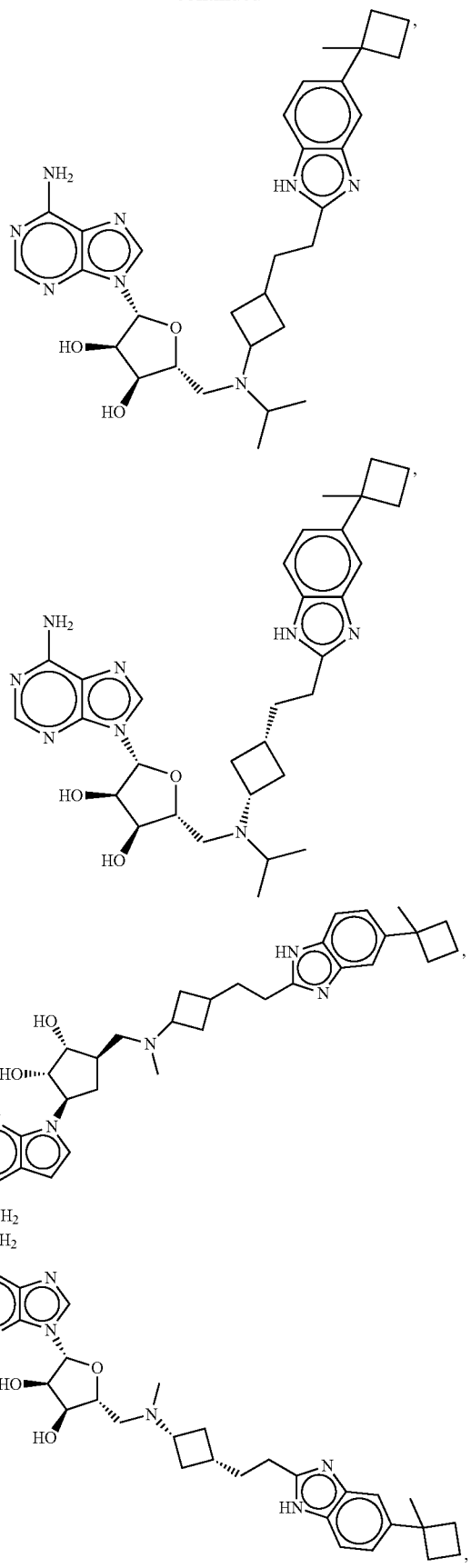

405
-continued
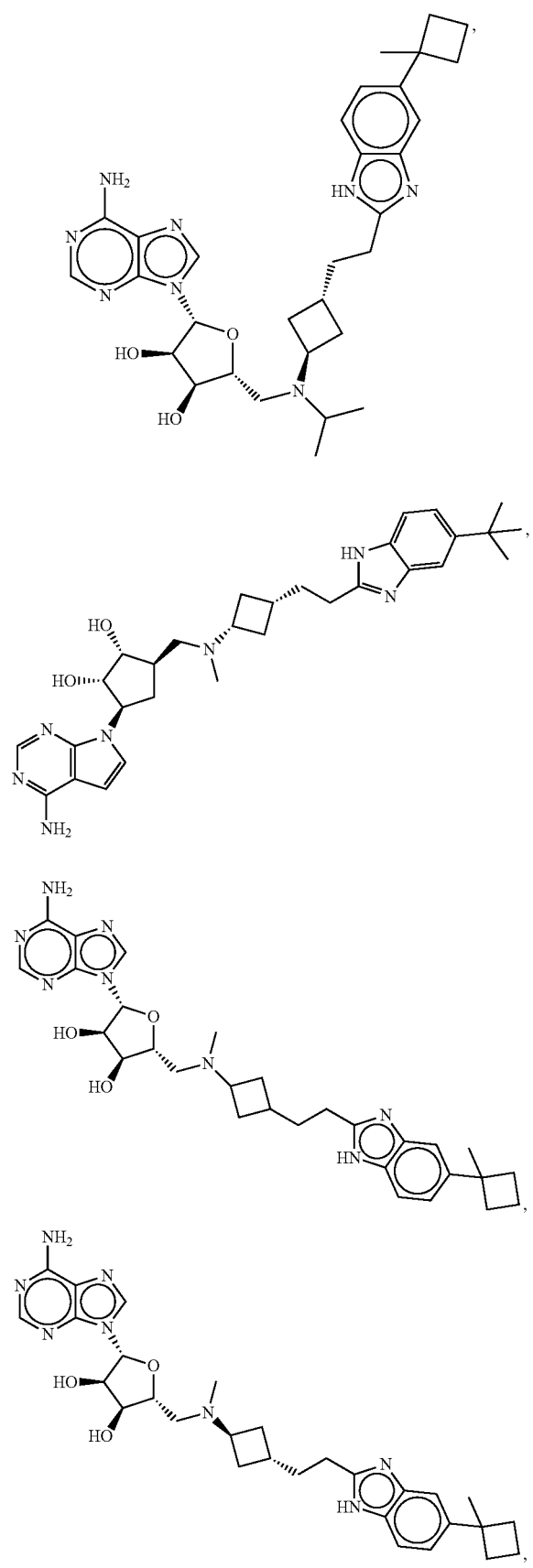
406
-continued
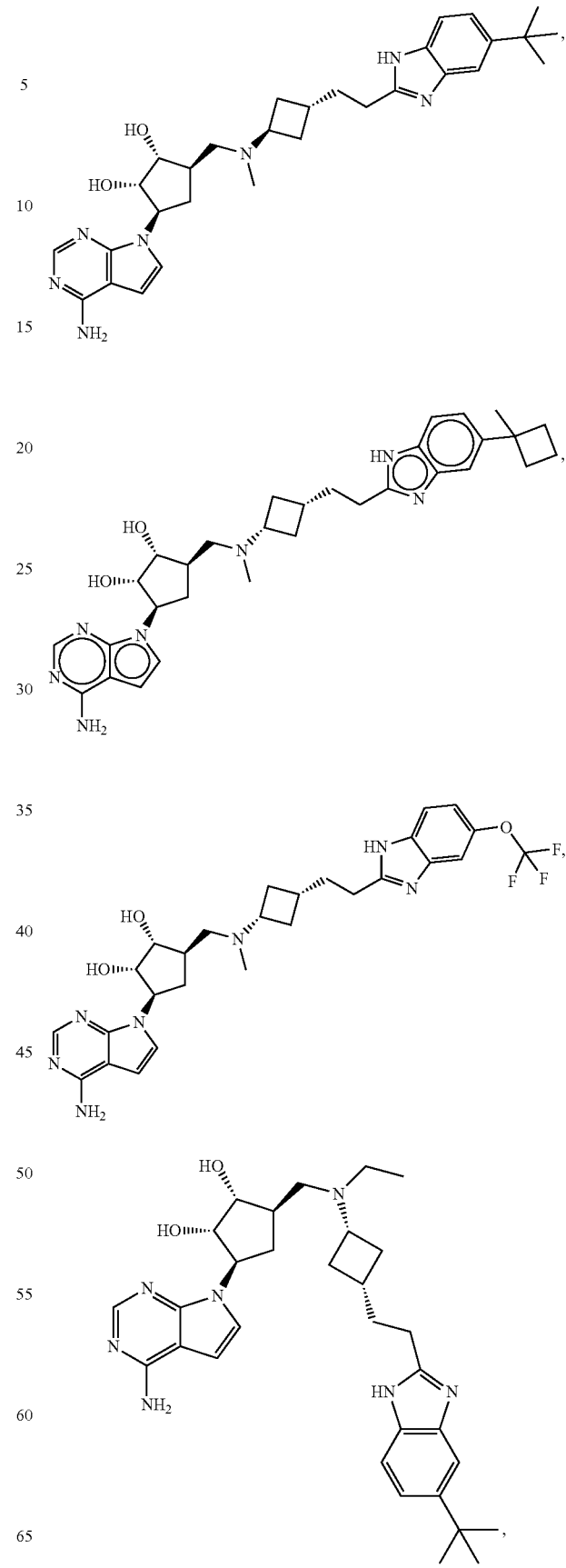

407
-continued
408
-continued
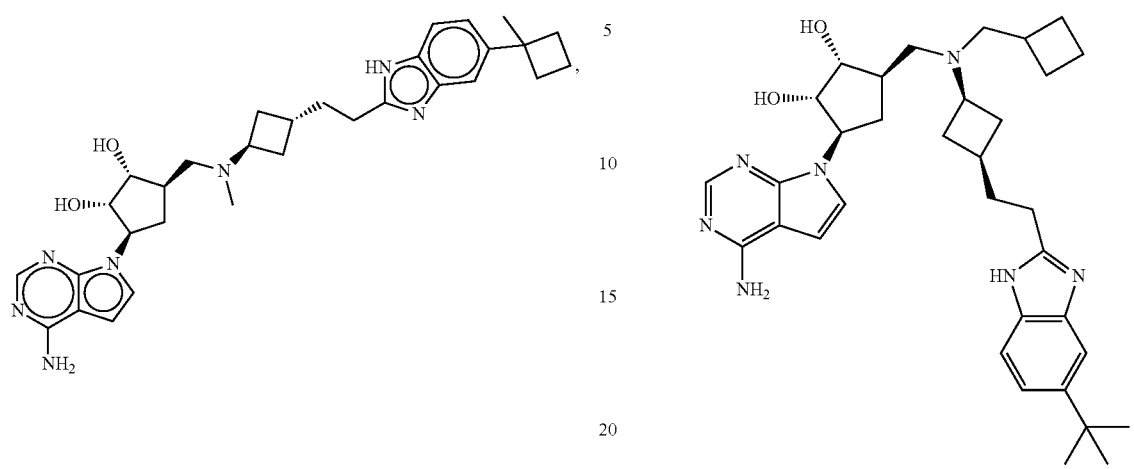
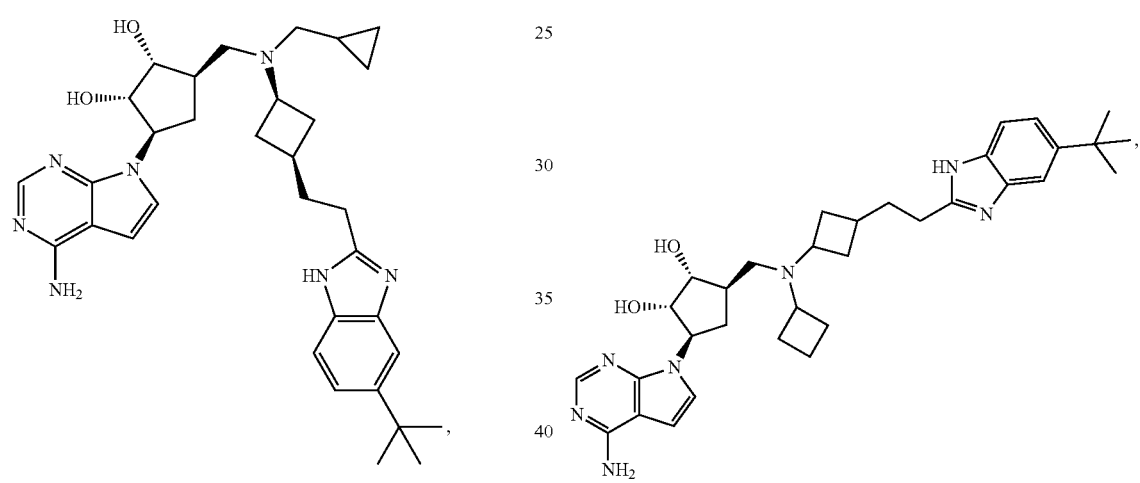
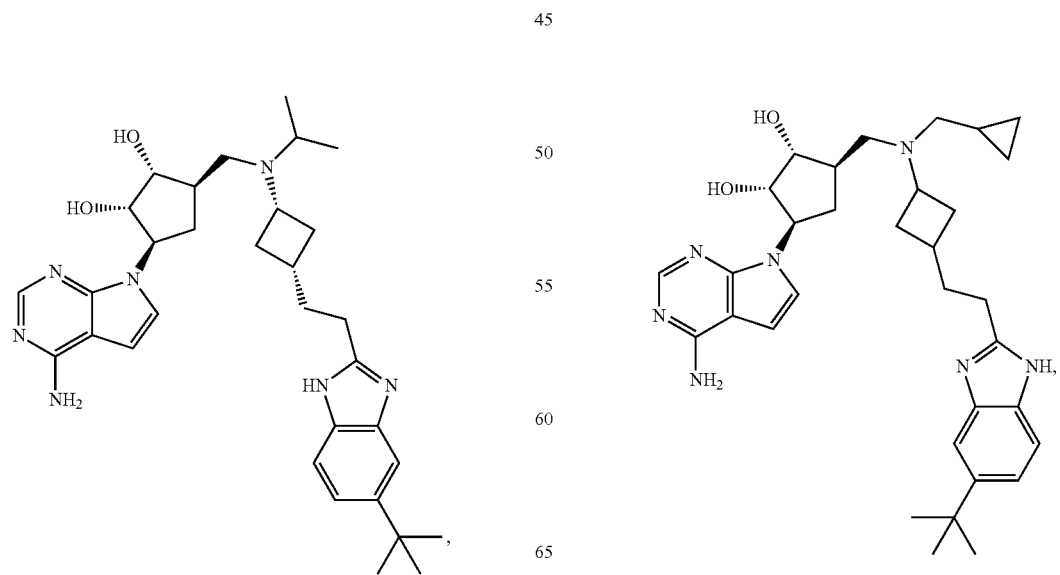

409
-continued
410
-continued
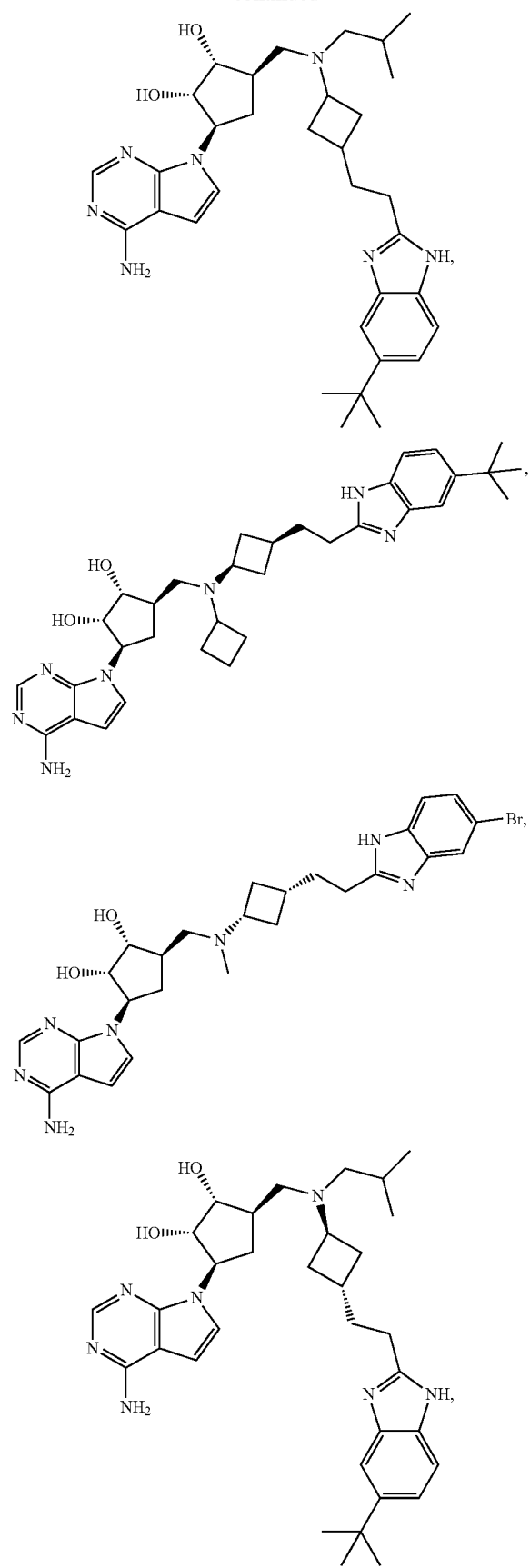
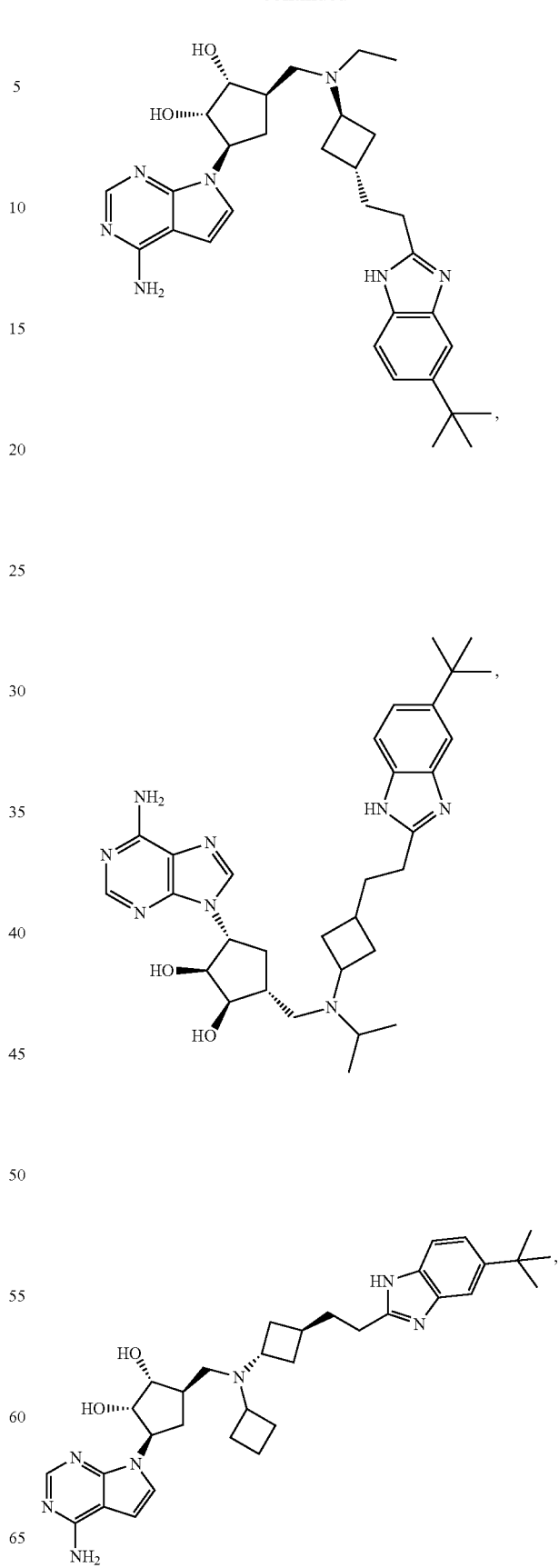

411
-continued
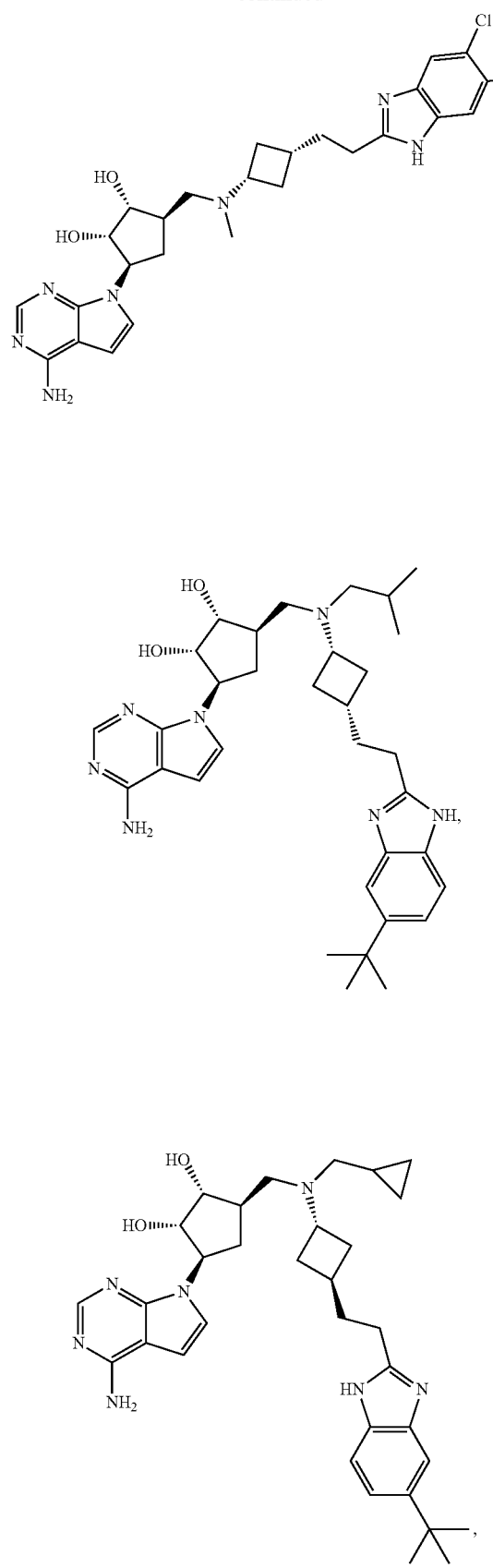
412
-continued
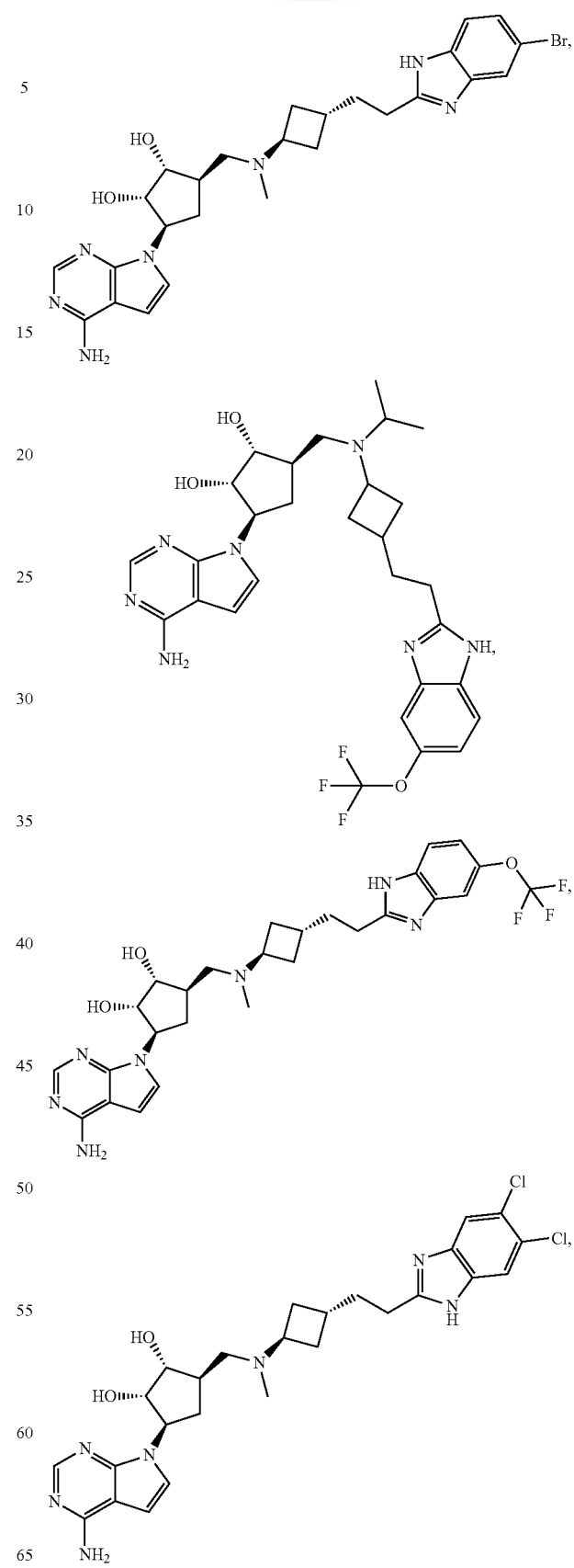

413
-continued
414
-continued
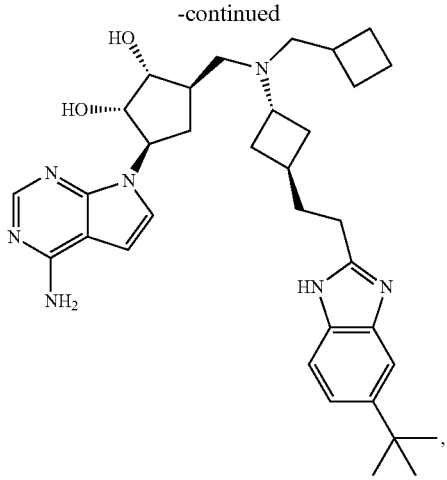
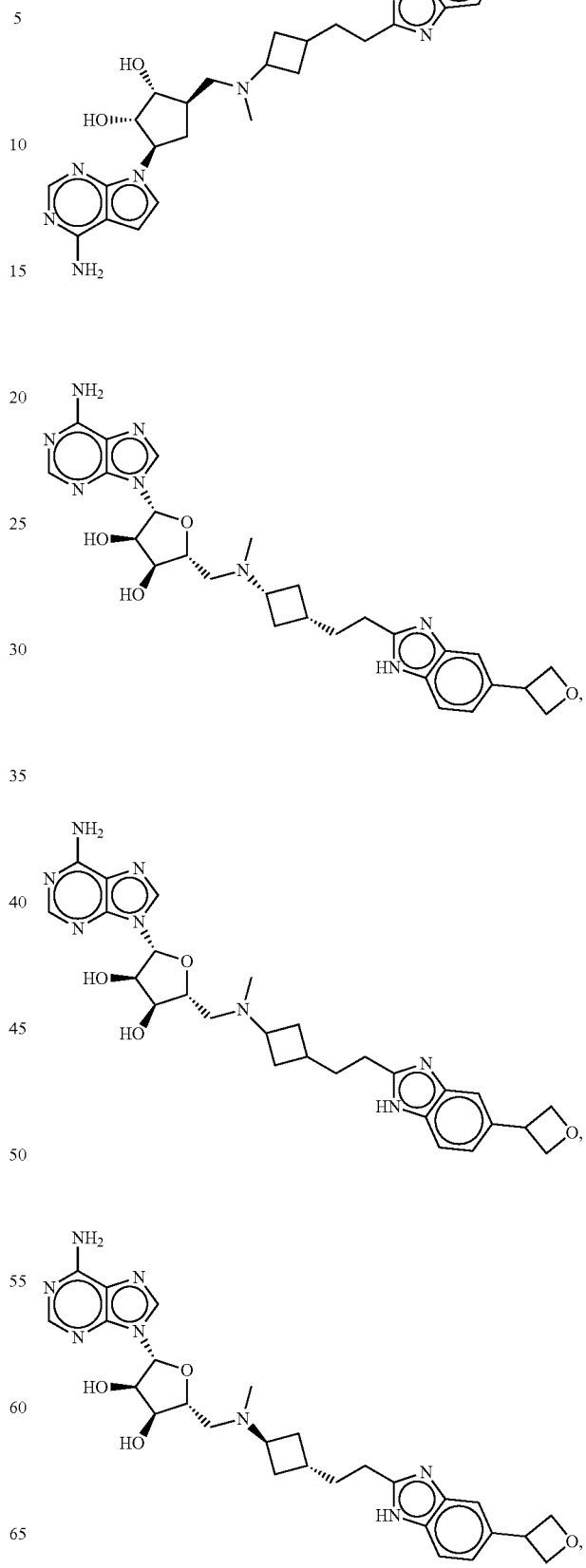

415
-continued
416
-continued
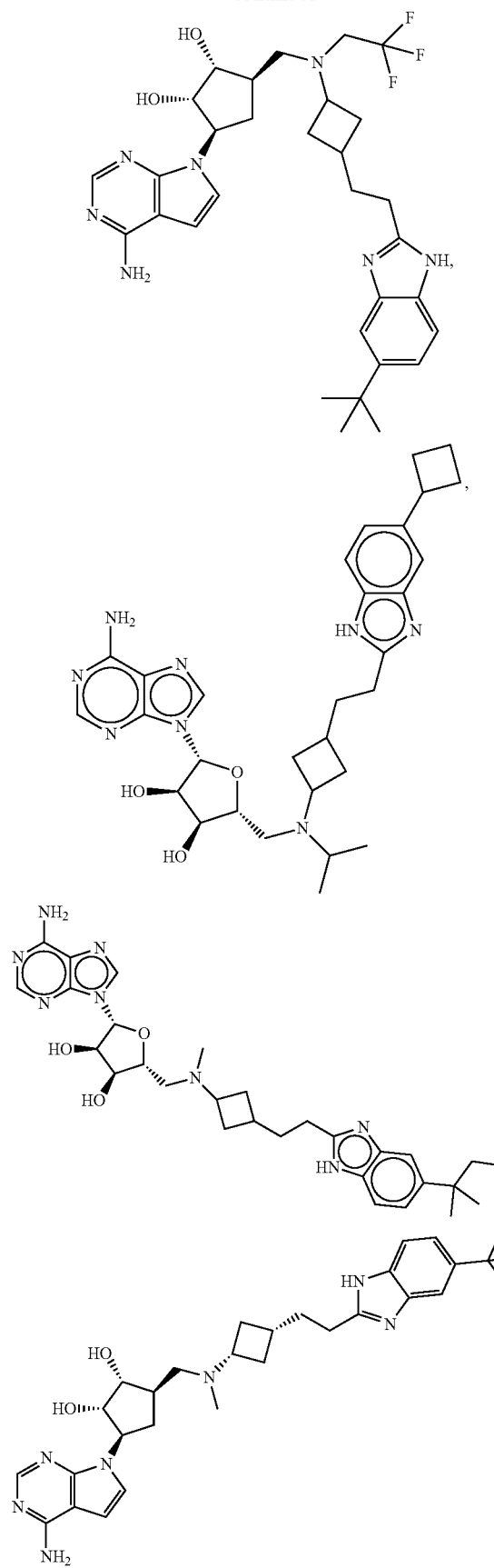
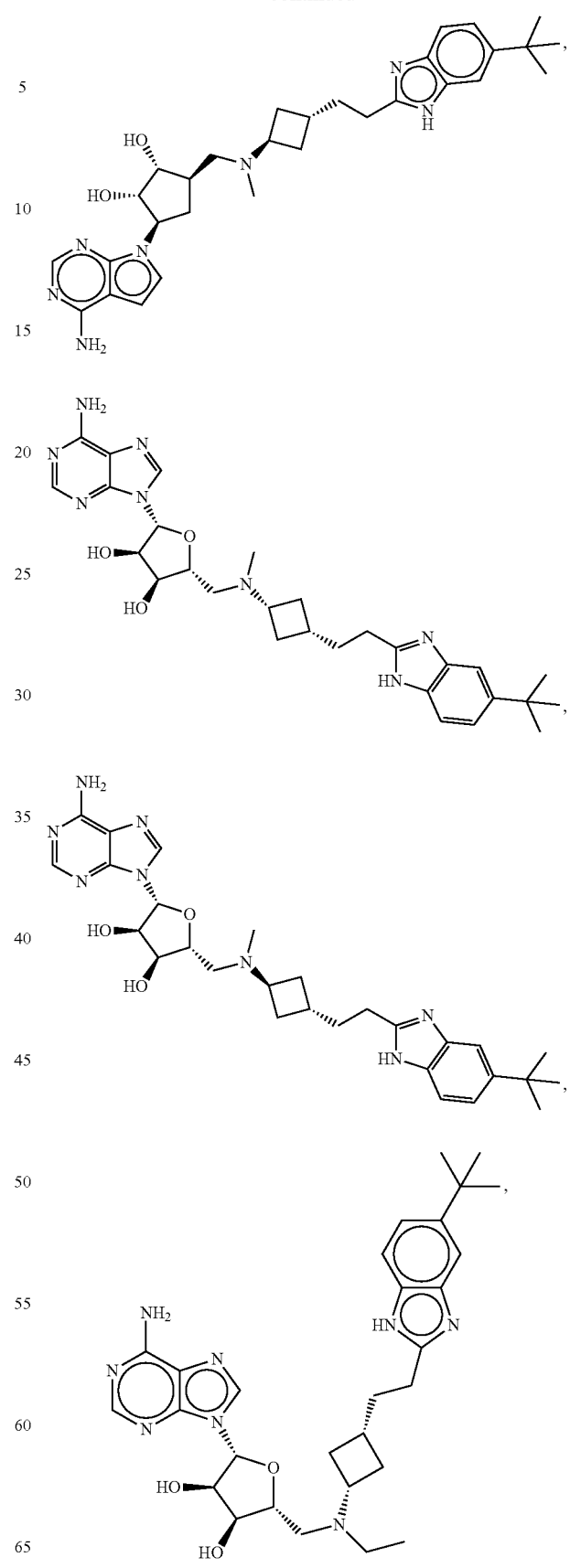

417
-continued
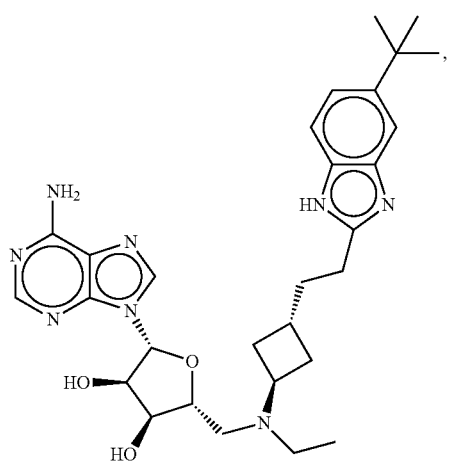
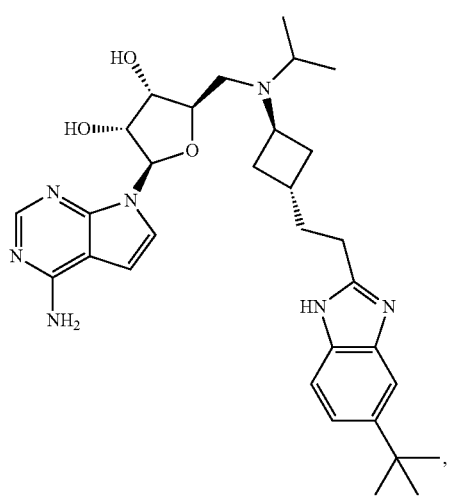
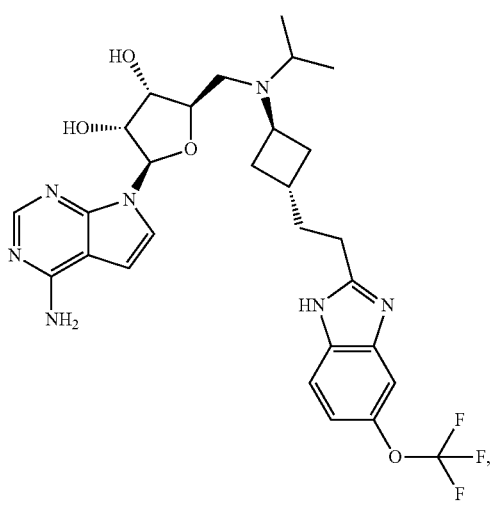
418
-continued
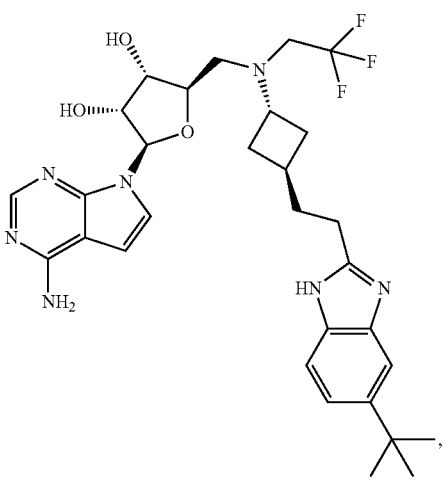
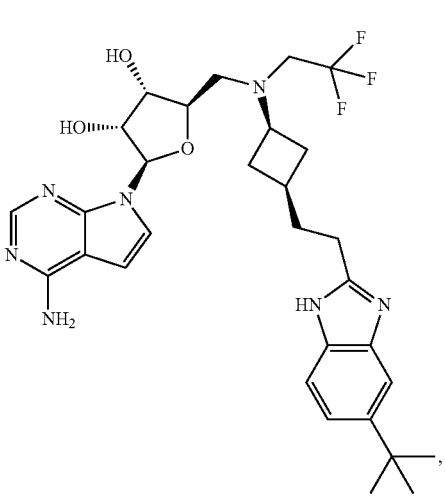
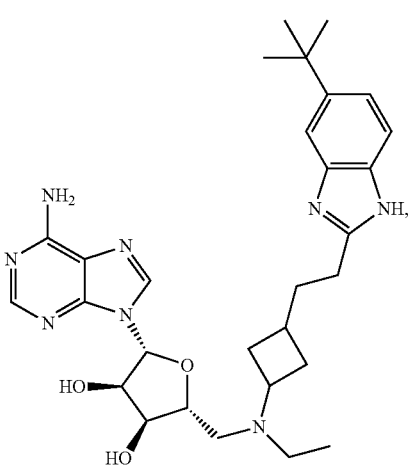

419  
-continued
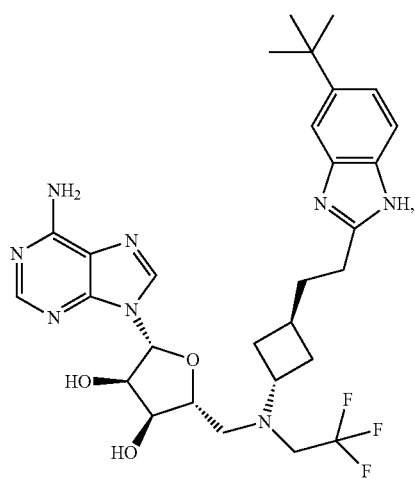
420  
-continued
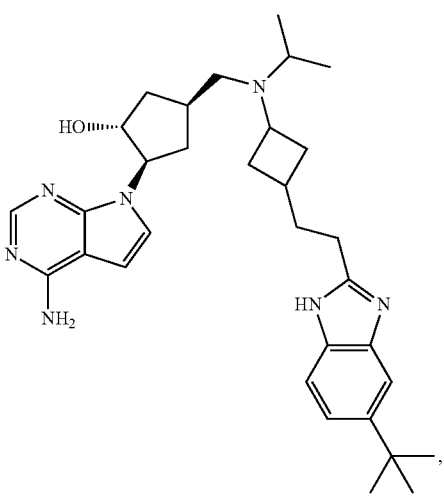
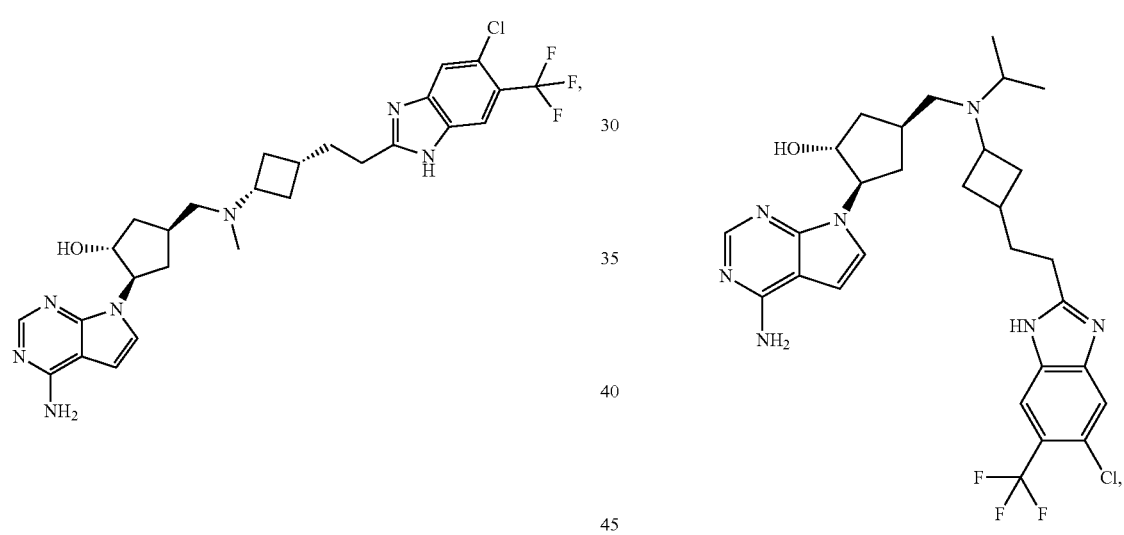
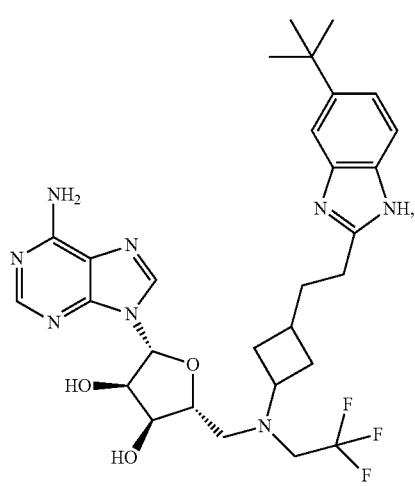
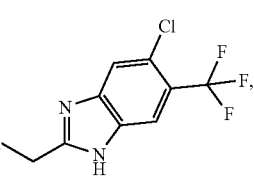

421
-continued
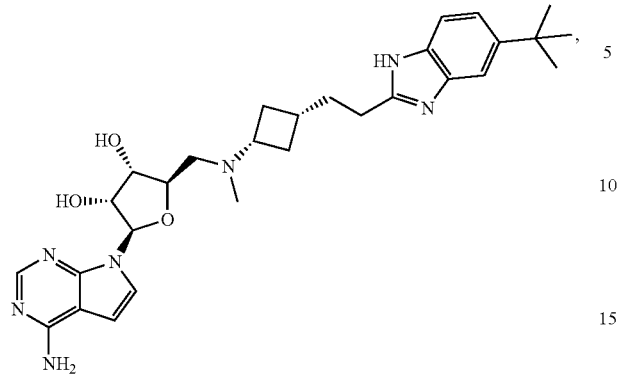
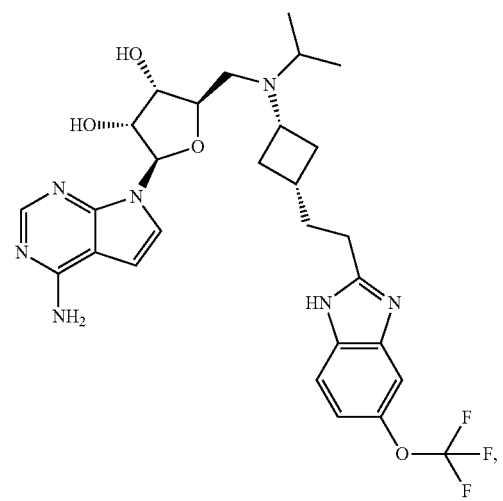
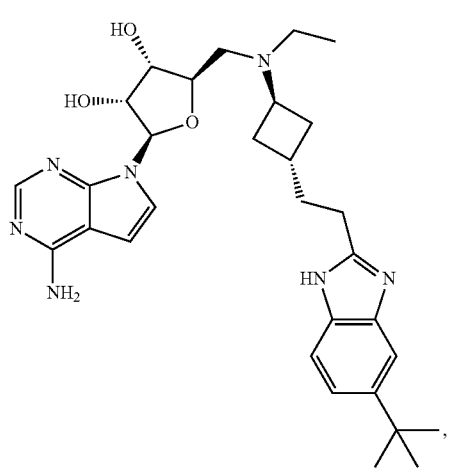
422
-continued
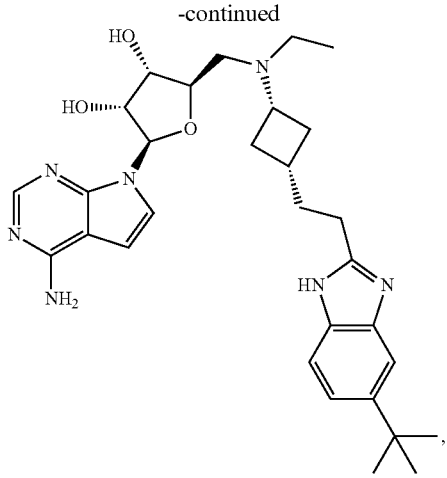
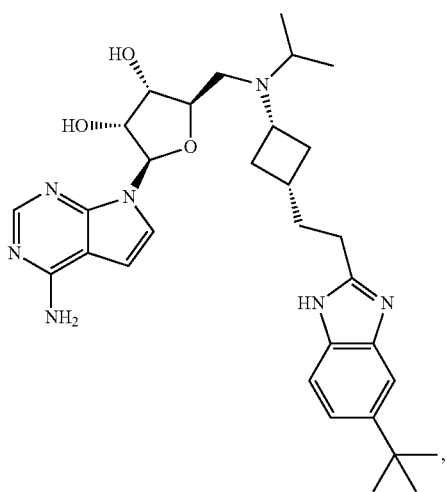
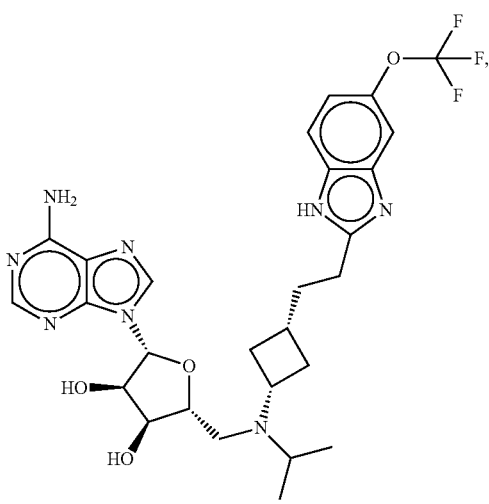

423
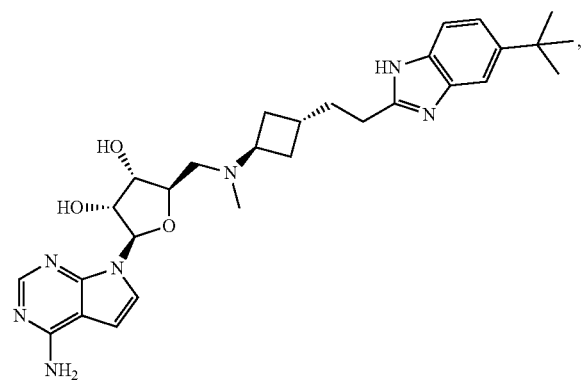
424
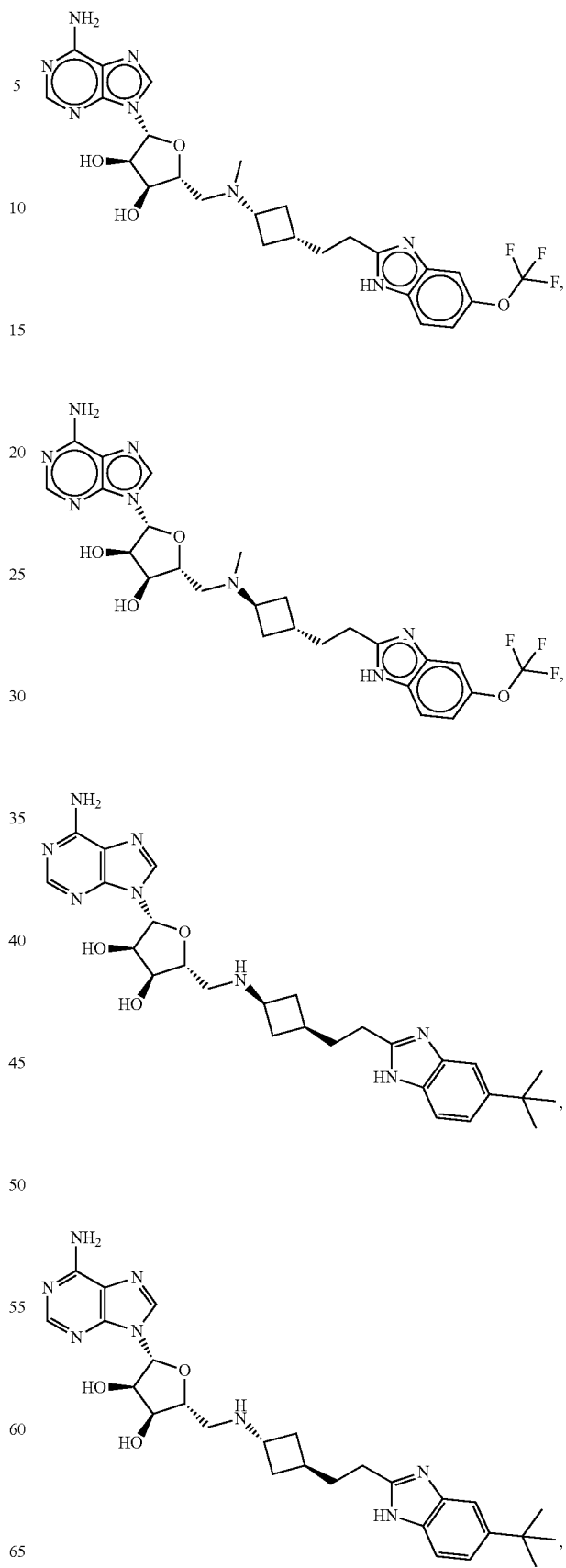

425
-continued
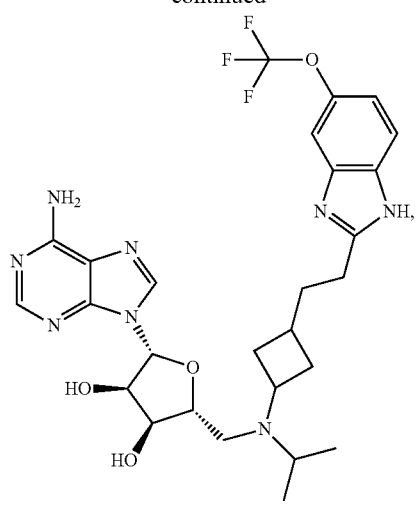
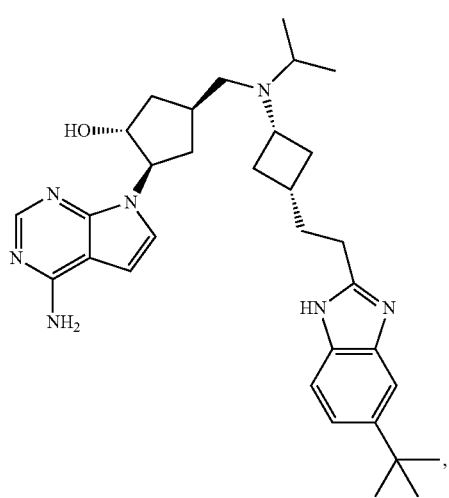
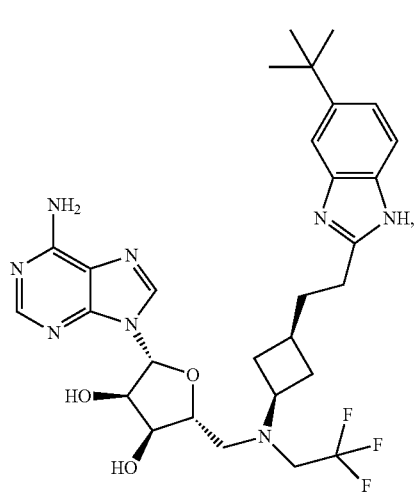
426
-continued
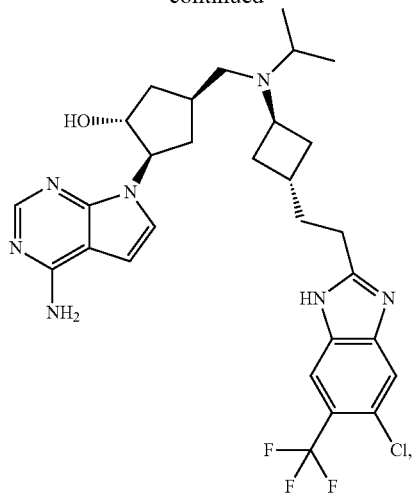
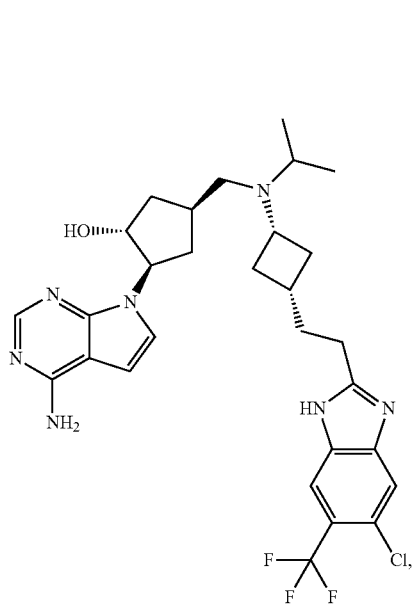

427
-continued
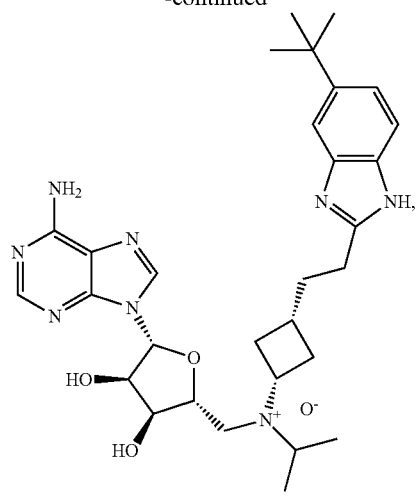
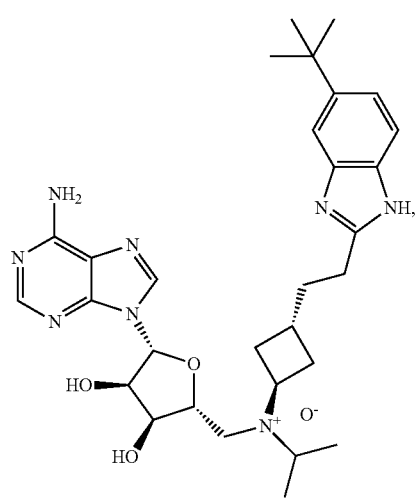
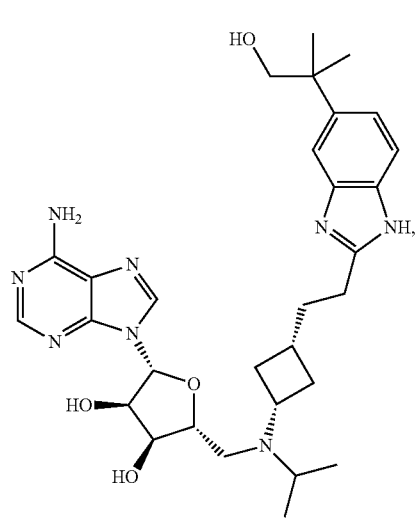
428
-continued
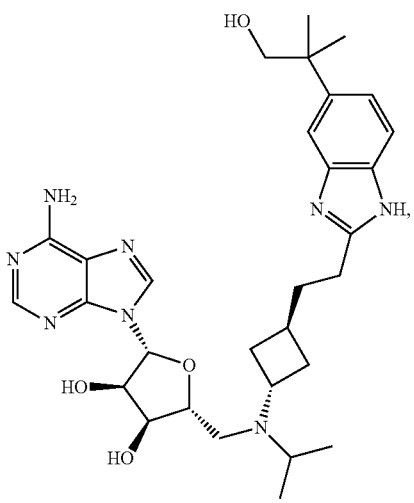
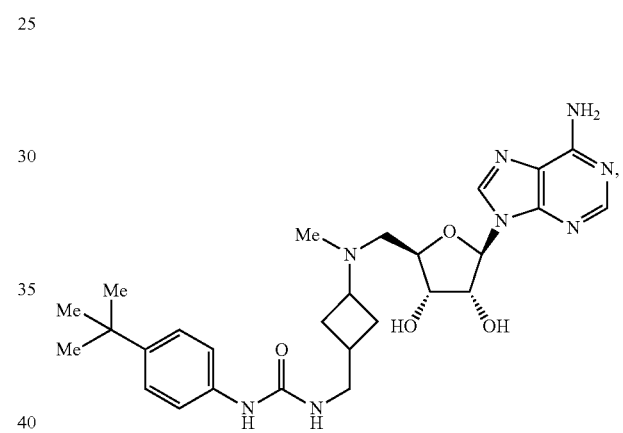
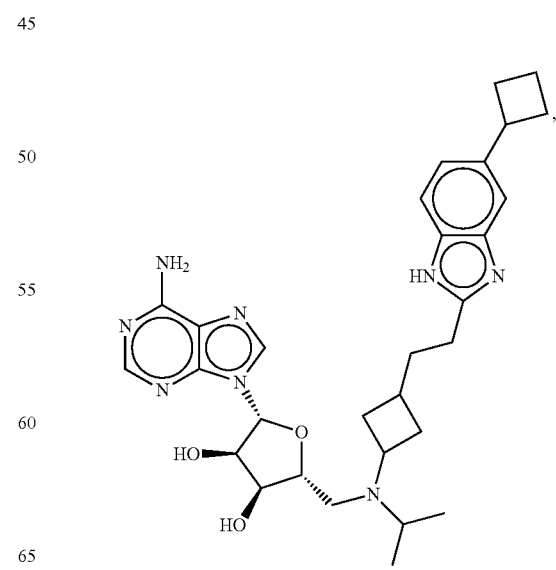

429
-continued
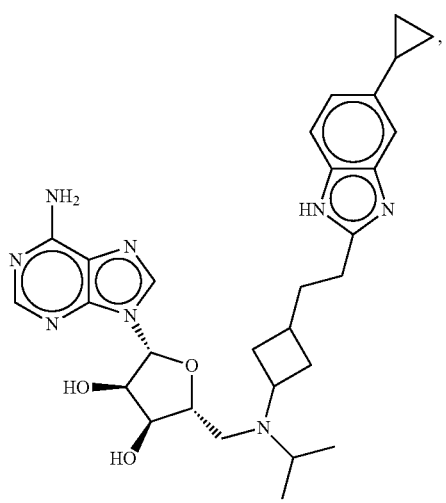
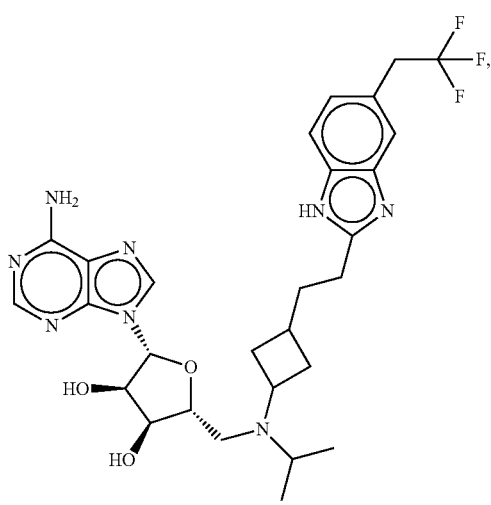
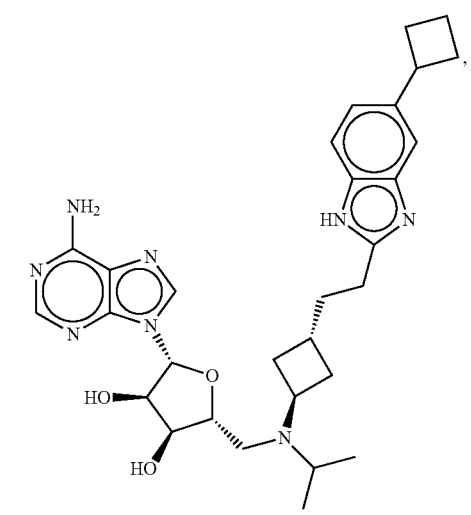
430
-continued
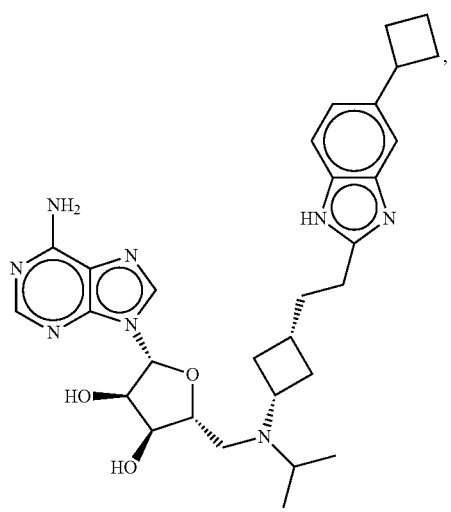
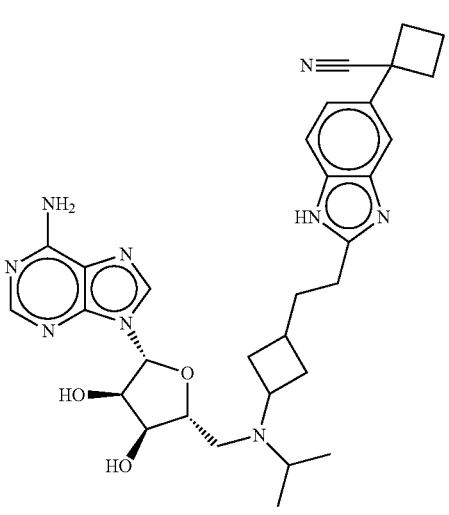

431
-continued
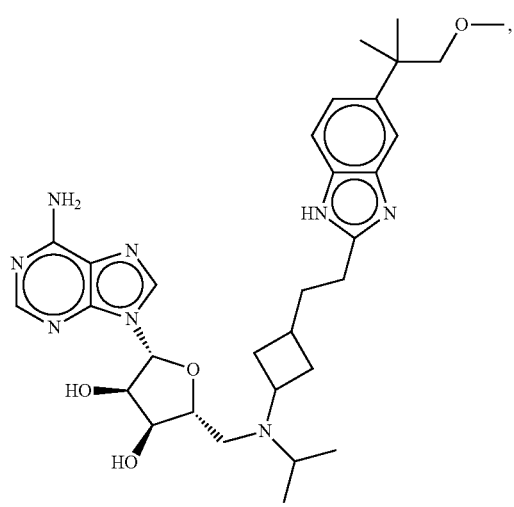
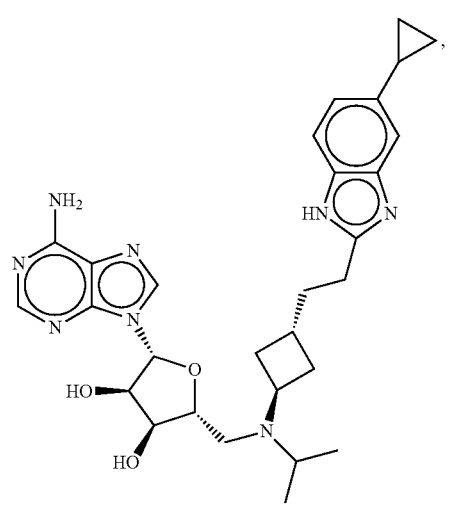
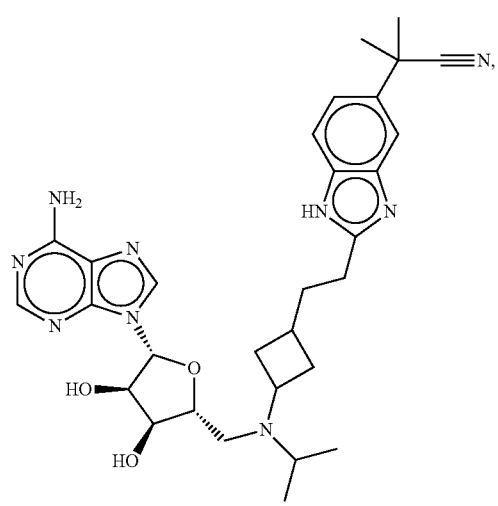
432
-continued
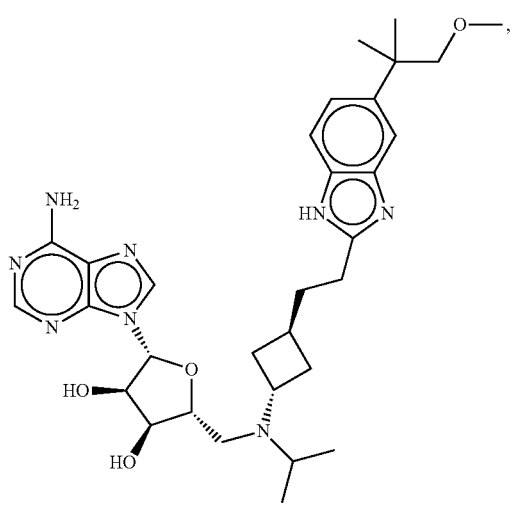
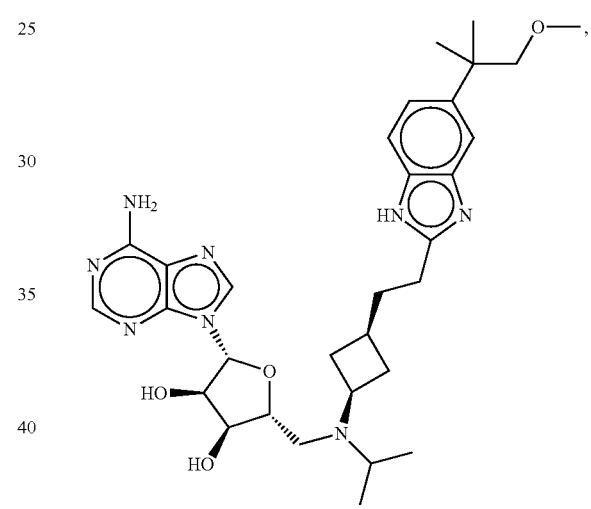
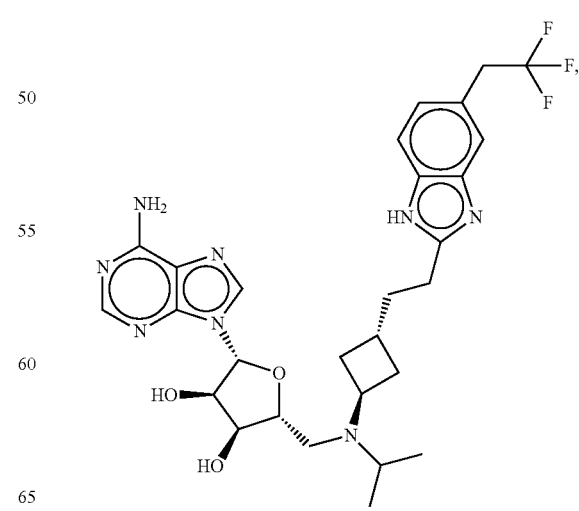

433
-continued
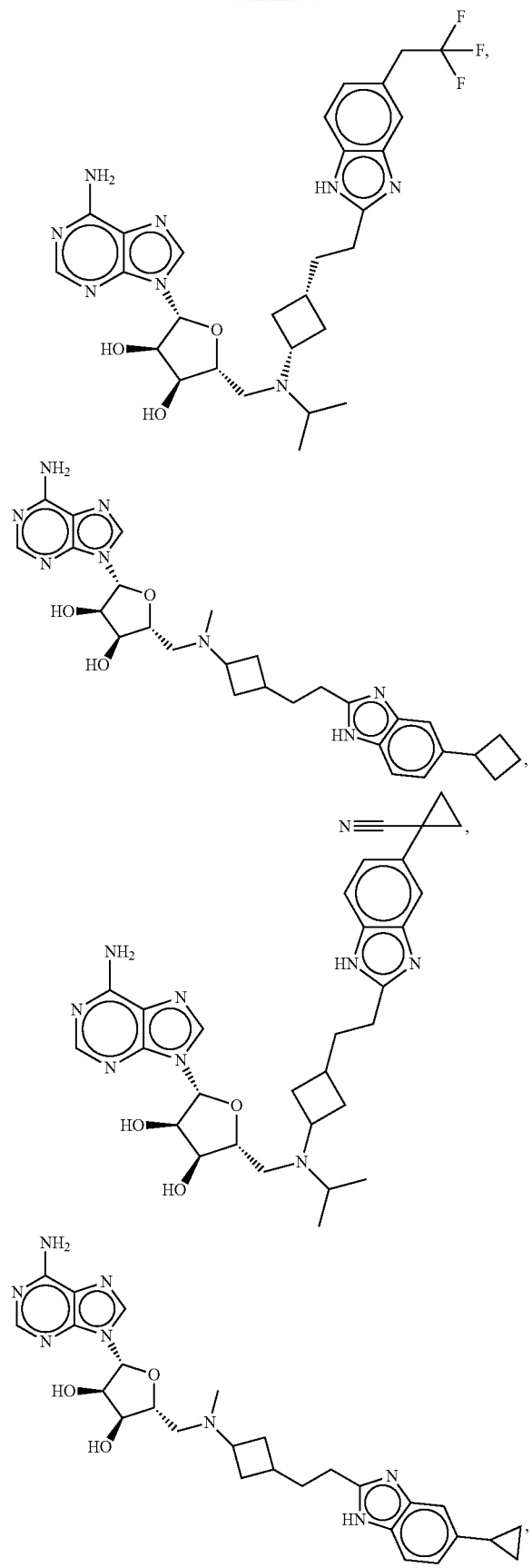
434
-continued
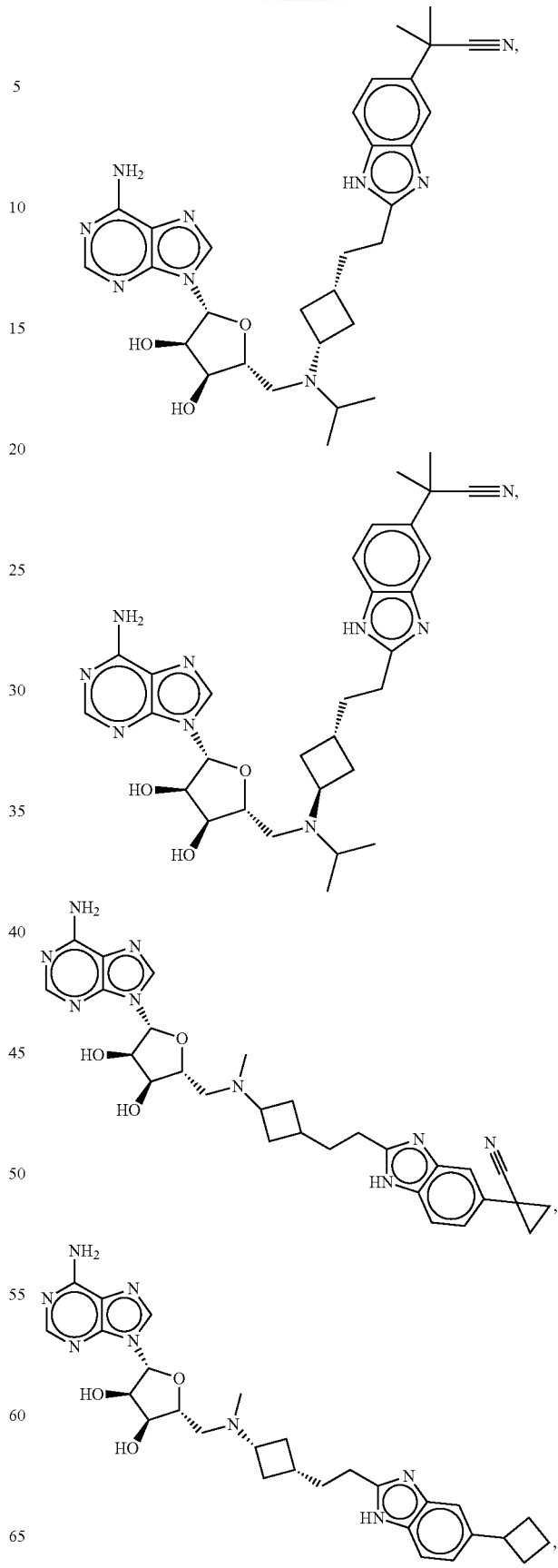

435
-continued
436
-continued
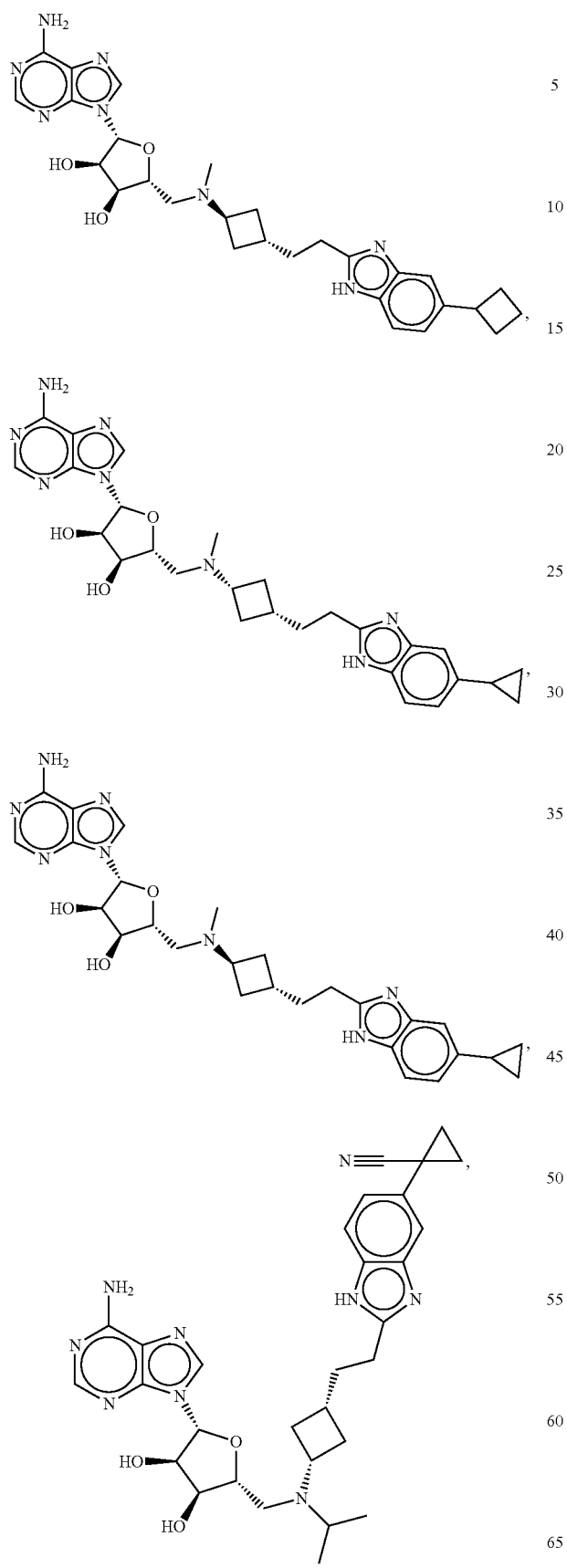
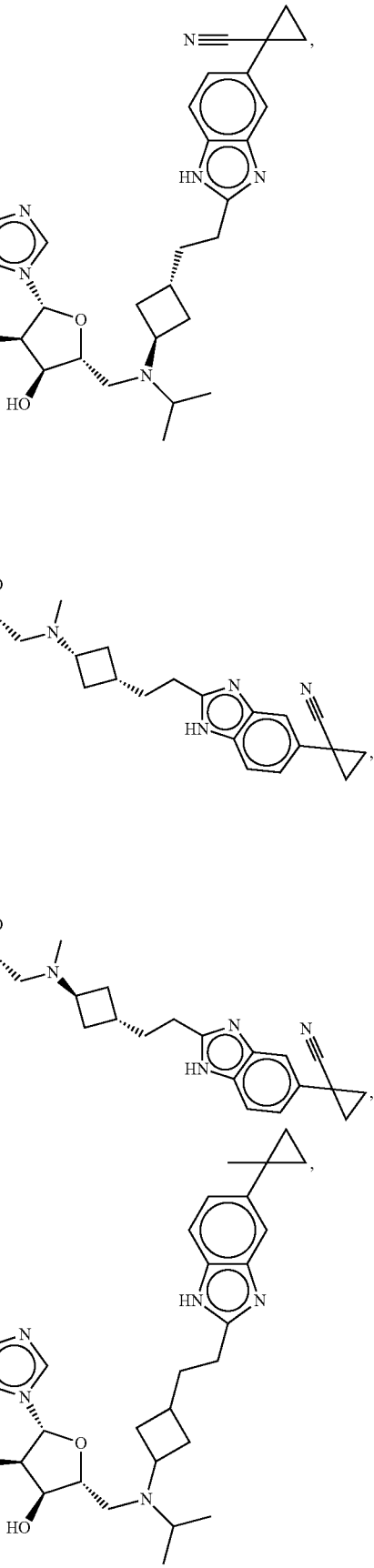

-continued

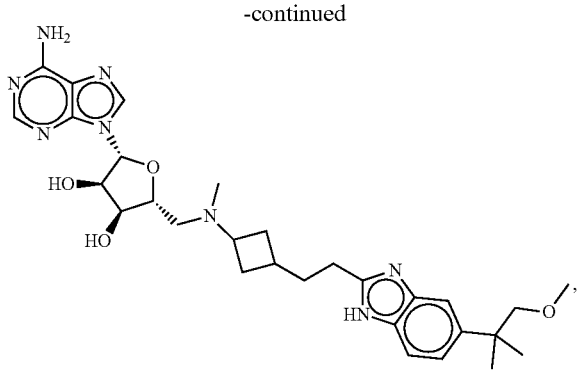

and pharmaceutically acceptable salts thereof.

13. A pharmaceutical composition comprising a therapeutically effective amount of a compound of claim 1 and a pharmaceutically acceptable carrier.

14. A pharmaceutical composition comprising a therapeutically effective amount of a compound of claim 12 and a pharmaceutically acceptable carrier.

15. A method of treating cancer comprising administering to a subject in need thereof a therapeutically effective amount of the composition of claim 13.

16. A method of treating hematological cancer comprising administering to a subject in need thereof a therapeutically effective amount of the composition of claim 13.

17. A method of treating leukemia comprising administering to a subject in need thereof a therapeutically effective amount of the composition of claim 13.

18. A method of claim 17, wherein the leukemia is acute myeloid leukemia, acute lymphocytic leukemia or mixed lineage leukemia.

19. A method of treating a MLL-rearranged leukemia, comprising administering to a subject in need thereof a therapeutically effective amount of the composition of claim 13.

20. A method of treating a leukemia characterized by a partial tandem duplication of the MLL gene (MLL-PTD), comprising administering to a subject in need thereof a therapeutically effective amount of the composition of claim 13.

* * * * *